United States Patent
Rodriguez et al.

(10) Patent No.: US 8,809,538 B2
(45) Date of Patent: Aug. 19, 2014

(54) PIPERIDINE-CONTAINING COMPOUNDS AND USE THEREOF

(75) Inventors: Martha E. Rodriguez, Boudler, CO (US); David A. Mareska, Boulder, CO (US); Jeremy J. Hans, Saint Louis, MO (US); Darren M. Harvey, Boulder, CO (US); Robert D. Groneberg, Boulder, CO (US); Michael O'Sullivan, Denver, CO (US)

(73) Assignee: Array BioPharma Inc., Boulder, CO (US)

( * ) Notice: Subject to any disclaimer, the term of this patent is extended or adjusted under 35 U.S.C. 154(b) by 230 days.

(21) Appl. No.: 13/143,998

(22) PCT Filed: Jan. 7, 2010

(86) PCT No.: PCT/US2010/020304
§ 371 (c)(1),
(2), (4) Date: Jul. 11, 2011

(87) PCT Pub. No.: WO2010/080864
PCT Pub. Date: Jul. 15, 2010

(65) Prior Publication Data
US 2011/0275608 A1 Nov. 10, 2011

Related U.S. Application Data

(60) Provisional application No. 61/143,868, filed on Jan. 12, 2009.

(51) Int. Cl.
*C07D 403/00* (2006.01)
*C07D 403/14* (2006.01)
*A61K 31/454* (2006.01)
*A61K 31/4545* (2006.01)

(52) U.S. Cl.
USPC ............ 546/193; 546/194; 546/208; 546/209; 514/318; 514/326

(58) Field of Classification Search
USPC ............ 546/193, 194, 208, 209; 514/318, 326
See application file for complete search history.

(56) References Cited

U.S. PATENT DOCUMENTS

| | | | |
|---|---|---|---|
| 6,395,753 B1 | 5/2002 | Kodama et al. | |
| 2006/0052416 A1 | 3/2006 | Dickson, Jr. et al. | |
| 2006/0079556 A1 | 4/2006 | Sher et al. | |
| 2006/0100224 A1* | 5/2006 | Svenstrup et al. | 514/269 |
| 2006/0173050 A1* | 8/2006 | Liu et al. | 514/344 |
| 2008/0064726 A1 | 3/2008 | Hayakawa et al. | |

FOREIGN PATENT DOCUMENTS

| | | |
|---|---|---|
| EP | 1015447 | 7/2000 |
| EP | 1676844 A1 | 7/2006 |
| WO | 97/36876 A1 | 10/1997 |
| WO | 97/36897 A1 | 10/1997 |
| WO | 98/27080 A1 | 6/1998 |
| WO | 99/12924 A1 | 3/1999 |
| WO | 00/61557 A1 | 10/2000 |
| WO | 03/020703 A1 | 3/2003 |
| WO | 03/040107 A1 | 5/2003 |
| WO | 03/042174 A1 | 5/2003 |
| WO | 03/049736 A1 | 6/2003 |
| WO | 03/086397 A1 | 10/2003 |
| WO | 2004/046110 A1 | 6/2004 |
| WO | 2004/052859 A1 | 6/2004 |
| WO | 2004/054974 A2 | 7/2004 |
| WO | 2005/097750 A1 | 10/2005 |
| WO | 2005/116009 A1 | 12/2005 |

(Continued)

OTHER PUBLICATIONS

Vu et. al. "Discovery of benzothiazole derivatives as efficacious and enterocyte-specific MTP inhibitors" Bioorganic & Medicinal Chemistry Letters 19 (2009) 1416-1420.*

(Continued)

*Primary Examiner* — David K O Dell
(74) *Attorney, Agent, or Firm* — Sughrue Mion, PLLC

(57) ABSTRACT

A method for preventing and/or treating a metabolic disease, cerebrovascular disease, etc. which comprises administering to a mammal an effective amount of the compound of the formula (I):

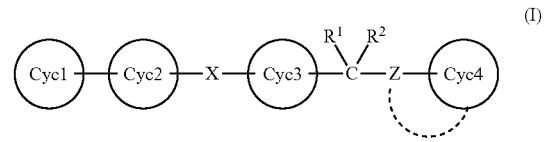

wherein all symbols have the same meanings as defined in the specification; a salt thereof, an N-oxide thereof, a solvate thereof, or a prodrug thereof. And a novel compound of the formula (I-1):

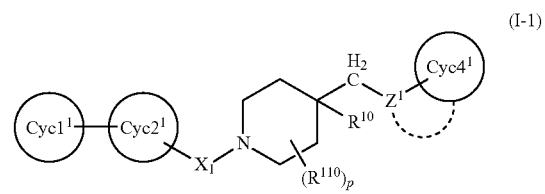

wherein all symbols have the same meanings as defined in the specification; a salt thereof, an N-oxide thereof, a solvate thereof, or a prodrug thereof has an anti-diabetic effect and a neuroprotective effect. Accordingly, the compound of the formula (I) and the compound of the formula (I-1) are useful in a method for preventing and/or treating for a metabolic disease such as diabetes, cerebrovascular disease such as stroke, etc.

6 Claims, No Drawings

(56) References Cited

FOREIGN PATENT DOCUMENTS

| WO | 2006/083673 A2 | 8/2006 | |
|---|---|---|---|
| WO | 2006/129199 A1 | 12/2006 | |
| WO | WO 2008103351 A2 * | 8/2008 | ............ C07D 409/04 |

OTHER PUBLICATIONS

Martin, Yvonne C. et. al. "Do Structurally Similar Molecules Have Similar Biological Activity?" Journal of Medicinal Chemistry 2002, 45, 4350-4358.*

Banker (Modern Pharmaceutics) Banker, G.S. et al, "Modern Pharmaceutics, 3ed.", Marcel Dekker, New York, 1996, pp. 451 and 596.*

Wolff, Manfred E. "Burger's Medicinal Chemistry, 5ed, Part I", John Wiley & Sons, 1995, pp. 975-977.*

Communication issued May 8, 2012 by the European Patent Office in counterpart European Application No. 10729483.7.

Kim, Dooseop et al. "Potent 1,3,4-trisubstituted pyrrolidine CCR5 receptor antagonists: effects of fused heterocycles on antiviral activity and pharmacokinetic properties". Bioorganic & Medicinal Chemistry Letters, Pergamon, Elsevier Science, GB, vol. 15, No. 8, Apr. 15, 2005. pp. 2129-2134, XP004829188.

Mamolo, Maria G. et al. "Antimycobacterial activity of new 3-substituted 5-(pyridin-4-yl)-3H-1,3,4-oxadiazol-2-one and 2-thione derivatives. Preliminary molecular modeling investigations". Bioorganic & Medicinal Chemistry, Pergamon, GB, vol. 13, No. 11, Jun. 1, 2005, pp. 3797-3809, XP004873538.

Cramer, Richard D. et al. "'Lead Hopping'. Validation of Topomer Similarity as a Superior Predictor of Similar Biological Activities". J. Med. Chem. vol. 47, 2004, pp. 6777-6791, XP002674311.

Mach, Robert H. et al. "Synthesis of 2-(5-Bromo-2,3-dimethoxyphenyl)-5-(aminomethyl)-IH-pyrrole Analogues and Their Binding Affinities for Dopamine D2, D3, and D4 Receptors". Bioorganic & Medicinal Chemistry, Pergamon, GB, vol. 11, No. 2, Jan. 1, 2003, pp. 225-233, XP002999779.

Huang, Yunsheng et al. Synthesis of 2-(2,3-dimethoxyphenyl)-4-(aminomethyl)imidazole Analogues and their Binding Affinities for Dopamine D2 and D3 Receptors. Bioorganic & Medicinal Chemistry, vol. 9, May 7, 2001, pp. 3113-3122, XP002674312.

Salvino, Joseph M. et al. "Polymer-Supported Tetrafluorophenol: A New Activated Resin for Chemical Library Synthesis". Journal of Combinatorial Chemistry, American Chemical Society, vol. 2, No. 6, Jan. 1, 2000, pp. 691-697, XP001018460.

Ryndina, S. A. et al. "Torp-Ziegler Cyclization in the Synthesis of 3-Amino-4-Cyanopyrrole Derivatives". Chemistry of Heterocyclic Compounds, vol. 36, No. 12, 2000, p. 1409-1420, XP002395104.

International Search Report dated Mar. 10, 2010 issued in Application No. PCT/US10/20304.

Office Action dated May 23, 2013 issued by the European Patent Office in counterpart European Application No. 10729483.7.

* cited by examiner

PIPERIDINE-CONTAINING COMPOUNDS AND USE THEREOF

TECHNICAL FIELD

The present invention relates to piperidine-containing compounds which is useful as medicaments, and use thereof. For more detail, the present invention relates to a method for preventing and/or treating a metabolic disease, cerebrovascular disease, etc., which comprises administering to a mammal an effective amount of the compound represented by formula (I):

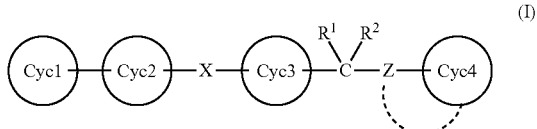

wherein all symbols have the same meanings as described below;
a salt thereof, an N-oxide thereof, a solvate thereof, or a prodrug thereof, and a novel compound of formula (I-1):

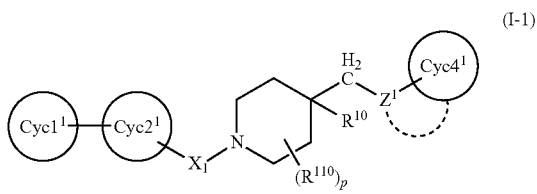

wherein all symbols have the same meanings as described below;
a salt thereof, an N-oxide thereof, a solvate thereof, or a prodrug thereof.

BACKGROUND ART

Diabetes is one of the most prevalent chronic diseases, characterized by impaired glucose metabolism and elevating blood glucose level. Diabetes is classified into two groups. Type 1 diabetes, or insulin dependent diabetes mellitus (IDDM), is caused by lack of insulin secreted from pancreatic beta-cells. Type 2 diabetes, or non-insulin dependent diabetes mellitus (NIDDM), is due to short of insulin action following both reduction of insulin secretion and insulin resistance. Insulin resistance is characterized by impaired insulin signaling in the insulin-target tissues such as liver, muscle, fat and pancreas itself. The Western diet with high-fat content leads to weight gain and obesity, which accelerates the development of insulin resistance and type 2 diabetes.

Presently, type 2 diabetes is treated with several medications that stimulate or replace the pancreatic beta-cell function, or enhance the insulin sensitivity of target tissues. However, the efficacy of these therapies often attenuates in the course of disease progression. Besides, the present agents for diabetes have several undesirable side effects such as hepatotoxicity, hypoglycemia, weight gain, gastrointestinal discomfort, lactic acidosis, and edema and so on. Accordingly, the more effective antidiabetic agent without these side effects has been desired earnestly.

On the other hand, the brain tissues are subject to ischemia over a long period of time in cerebrovascular disease, resulting in neuron cells necrosis and failure of regeneration, finally, cell deaths cause cerebral infarction. Although ischemic stroke is the third most common cause of death in the United States and Europe, the only currently approved medicinal treatment is administration of intravenous recombinant tissue plasminogen activator (rt-PA). Other than rt-PA, examples of the currently and mainly used as cerebral infarction treating agents include thrombolytic agents such as urokinase, anticoagulants such as warfarin and heparin, and free radical scavengers such as Radicut (edalabon) (product name: manufactured by Mitsubishi Pharma Corporation).

However, rt-PA shows its efficacy only when it is administered within 3 hours after onset of cerebral infarction, and with respect to anticoagulants, since it takes several days to express the anticoagulation action, the effects could hardly be said to be sufficient. In addition, since Radicut (product name: manufactured by Mitsubishi Pharma Corporation) sometimes causes serious side effects such as nephropathy, its use requires sufficient precautions. Thus, since the currently used cerebral infarction treating agents have problems in terms of their effect or toxicity and also have many limitations regarding their use, the development of useful therapeutic agents has been desired earnestly.

It was described that a compound represented by formula (K):

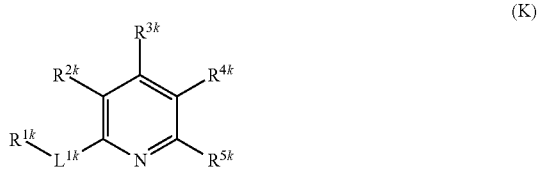

wherein $L^{1k}$ represents —C(O)—NH—, etc.; $R^{1k}$ represents heterocyclealkyl, etc.; $R^{2k}$ and $R^{4k}$ each independently represents cyano, etc.; $R^{1k}$ represents halogen, etc.; $R^{5k}$ represents alkoxy, etc.; is useful in antidiabetic agent and cerebral infarction treating agent as c-jun N-terminal kinase inhibitor (see reference such as patent literature 1).

Furthermore, it was described that a compound represented by formula (U):

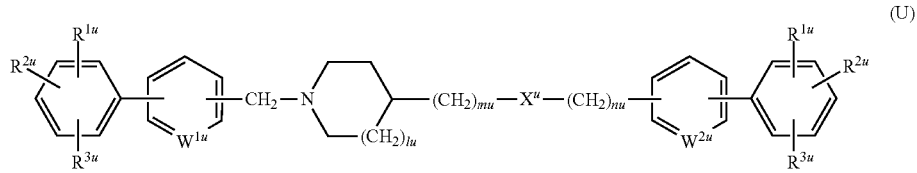

wherein $R^{1u}$, $R^{2u}$ and $R^{3u}$ each independently represents a hydrogen atom, alkoxy, etc.; $W^{1u}$ and $W^{2u}$ each independently represents N or CH; $X^u$ represents $NR^{4u}CO$, etc.; $R^{4u}$ represents a hydrogen, etc.; lu, mu and nu each independently represents a number of 0 or 1; is useful in an antasthmatic agent (see reference such as patent literature 2).

Furthermore, it has been described that a compound represented by formula (V):

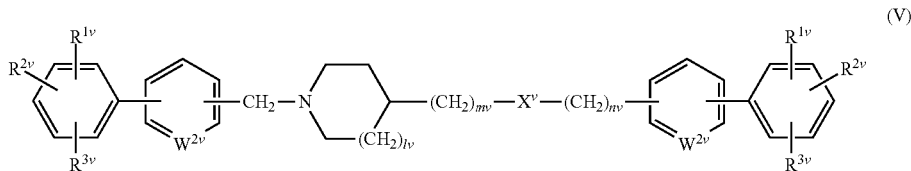

(V)

wherein $R^{1v}$, $R^{2v}$ and $R^{3v}$ each independently represents a hydrogen atom, alkoxy, etc.; $W^{1v}$ and $W^{2v}$ each independently represents N or CH; $X^v$ represents $NR^{4v}CO$, etc.; $R^{4v}$ represents a hydrogen, etc.; lv, mv and nv each independently represents a number of 0 or 1; is useful in an anti-inflammatory agent (see reference such as patent literature 3).

Furthermore, it has been described that a compound represented by formula (W):

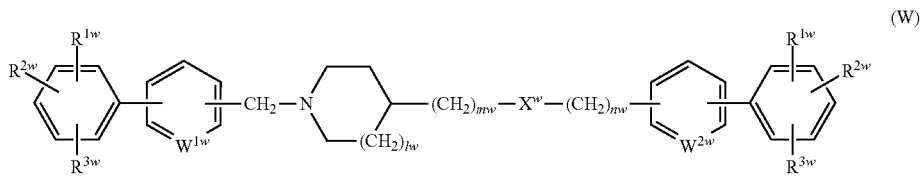

(W)

wherein $R^{1w}$, $R^{2w}$ and $R^{3w}$ each independently represents a hydrogen atom, alkoxy, etc.; $W^{1w}$ and $W^{2w}$ each independently represents N or CH; $X^w$ represents $NR^{4w}CO$, etc.; $R^{4W}$ represents a hydrogen, etc.; lw, mw and nw each independently represents a number of 0 or 1; is useful in an HDAC inhibitor (see reference such as patent literature 4).

Furthermore, it has been described that a compound represented by formula (Y):

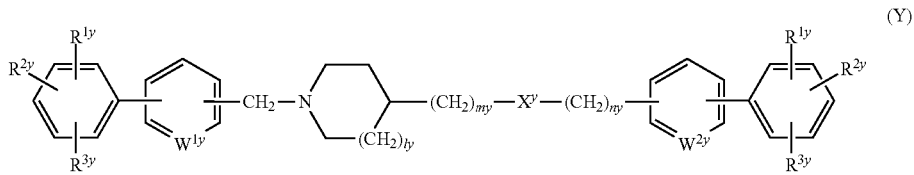

(Y)

wherein $R^{1y}$, $R^{2y}$ and $R^{3y}$ each independently represents a hydrogen atom, alkoxy, etc.; $W^{1y}$ and $W^{2y}$ each independently represents N or CH; XY represents $NR^{4y}CO$, etc.; $R^{4Y}$ represents a hydrogen, etc.; ly, my and ny each independently represents a number of 0 or 1; is useful in a preventive/therapeutic agent for diseases attributable to erythropoietin production depression (see reference such as patent literature 5).

Furthermore, it has been described that a compound represented by formula (B):

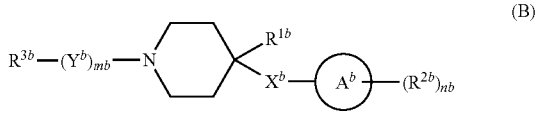

(B)

wherein $R^{1b}$ represents carbocyclyl which may have a substituent(s), etc.; $R^{2b}$ represents heteroaryl which may have a substituent(s), etc.; $R^{ab}$ represents heteroaryl which may have a substituent(s), etc.; $X^b$ represents C1-5 alkylene chain, etc.; $Y^b$ represents —C(O)—, etc.; Ring $A^b$ represents aromatic 5-6 membered monocyclic ring which may have a substituent(s), etc.; mb represents a number of 0 or 1; nb represents a number of 0-5; is useful in CCR5 antagonists as therapeutic agents (see reference such as patent literature 6)

Furthermore, it has been described that a compound represented by formula (C):

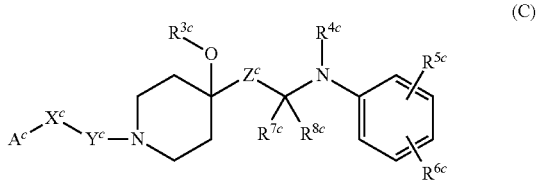

(C)

wherein $R^{3c}$ represents alkyl, etc.; $R^{4c}$ represents alkyl, etc.; $R^{5c}$ and $R^{6c}$ each independently represents alkoxy which may have a substituent, etc.; $R^{7c}$ and $R^{8c}$ each independently represents alkyl, etc.; $A^c$ represents phenyl substituted by phenyl or unsubstituted thienyl, etc.; $X^c$ represents a bond, etc.; $Y^c$ represents alkylene, etc.; $Z^c$ represents alkylene, etc.; is useful in antiarrhythmic agent (see reference such as patent literature 7)

Furthermore, it has been described that a compound represented by formula (D):

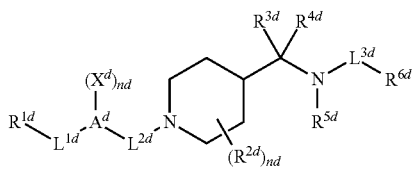

wherein $R^{1d}$ represents heteroaryl which may have a substituent(s), etc.; $R^{2d}$ represents alkyl, etc.; $R^{3d}$ and $R^{4d}$ each independently represents hydrogen, etc.; $R^{5d}$ represents hydrogen, etc.; $R^{6d}$ represents heteroaryl which may have a substituent(s), etc.; $A^d$ represents phenyl, etc.; $L^{1d}$ represents a bond, etc.; $L^{2d}$ represents methylene, etc.; $L^{3d}$ represents —C(O)—, etc.; $X^d$ represents halogen, etc.; nd represents a number of 0-3; is useful in cannabinoid receptor ligands (see reference such as patent literature 8)

Furthermore, it has been described that a compound represented by formula (E):

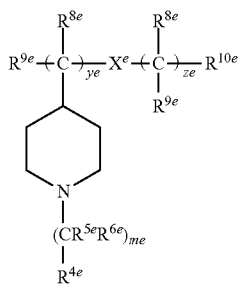

wherein $R^{4e}$ represents heteroaryl, etc.; $R^{5e}$ and $R^{6e}$ each independently represents hydrogen, etc.; $R^{8e}$ and $R^{9e}$ each independently represents alkyl, etc.; $R^{10e}$ represents heteroaryl, etc.; $X^e$ represents oxygen, etc.; me represents a number of 0-4; ye represents a number of 0-2; ze represents a number of 0-2; is useful in a preventive/therapeutic agent for Alzheimer's diseases (see reference such as patent literature 9)

Furthermore, it has been described that a compound represented by formula (F):

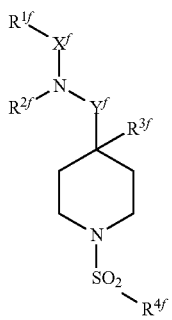

wherein $R^{1f}$ represents heteroaryl which may have a substituent(s), etc.; $R^{2f}$ represents alkyl which may have a substituent(s), etc.; $R^{3f}$ represents hydroxy, etc.; $R^{4f}$ represents heteroaryl which may have a substituent(s), etc.; $X^f$ represents —C(O)— or —S(O)$_2$—; $Y^f$ represents —CR$^{5f}$R$^{6f}$— or —CR$^{5f}$R$^{6f}$CR$^{7f}$R$^{8f}$—; $R^{5f}$, $R^{6f}$, $R^{7f}$ and $R^{8f}$ each independently represents alkyl, etc.; is useful in cannabinoid receptor 1 antagonists (see reference such as patent literature 10)

Furthermore, it has been described that a compound represented by formula (G):

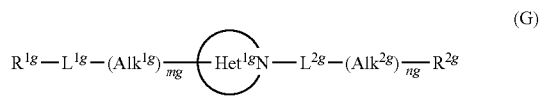

wherein $R^{1g}$ and each independently represents heterocyclic ring which may have a substituent(s), etc.; Alk$^{1g}$ and Alk$^{2g}$ each independently represents bivalent hydrocarbon which may have a substituent(s), etc.; $L^{1g}$ represents 1-6 linker group, etc.; $L^{2g}$ represents a bond or 1-6 linker group, etc.; Het$^{1g}$ represents optionally substituted saturated heterocyclic ring containing nitrogen; mg and ng each independently represents a number of 0 or 1; is useful in a melanin concentrating hormone receptor antagonist (see reference such as patent literature 11)

Furthermore, it has been described that a compound represented by formula (J):

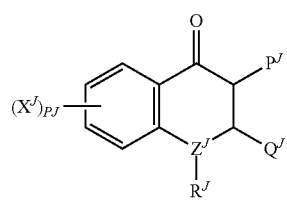

wherein, $P^J$ represents alkyl which may have a substituent(s), etc.; $Q^J$ represents heterocyclyl ring which may have a substituent(s), etc.; $Z^J$ represents nitrogen, oxygen or sulfur which may be oxidized; $R^J$ represents phenyl which may have a substituent(s), etc.; $X^J$ represents halogene, etc.; PJ is 0 to 4; is useful in a fungicides (see reference such as patent literature 12).

Furthermore, it has been described that a compound represented by formula (H):

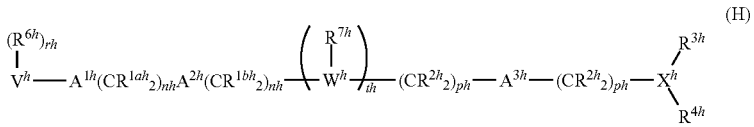

wherein, $R^{1ah}$, $R^{1bh}$, $R^{2h}$ and $R^{7h}$ each independently represents hydrogen, etc; $R^{3h}$ and $R^{4h}$ each independently represents hydrogen, pyridine, etc; $R^{6h}$ represents alkoxy, amino, nitrile, etc; $A^{1h}$ and $A^{2h}$ each independently represents bond, —CONH—, etc; $A^{3h}$ represents bond, etc; $V^h$ represents pyridine, etc; $W^h$ represents piperidine, etc; $X^h$ represents thiazole, etc; nh and ph each independently represents 0 to 4; rh represents 0 to 5; is useful in a farnesyl-protein transferase inhibitor (see reference such as patent literature 13)

Furthermore, it has been described that a compound represented by formula (L):

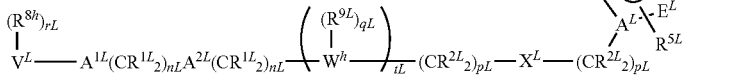

wherein, $R^{1L}$, $R^{2L}$, $R^{3L}$, $R^{4L}$, $R^{5L}$ and $R^{7L}$ each independently represents hydrogen, etc; $R^{8L}$ represents alkoxy, amino, nitrile, etc; $A^L$ represents carbon or nitrogen; $B^L$, $C^L$, $D^L$ and $E^L$ each independently represents carbon, nitrogen, oxygen or sulfur; $F^L$ each independently represents carbon or nitrogen; $A^{1L}$ and $A^{2L}$ each independently represents bond, —CONH—, etc; $V^L$ represents pyridine, etc; $W^L$ represents piperidine, etc; $X^L$ represents bond, etc; rL represents 0 to 5; nL and pL each independently represents 0 to 4; tL represents 0 or 1; qL represents 0 to 3; is useful in a farnesyl-protein transferase inhibitor (see reference such as patent literature 14) Furthermore, it has been described that a compound represented by formula (N):

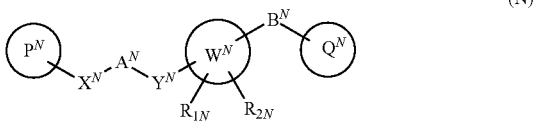

wherein, $W^N$ represents piperidine, etc; $R_{1N}$ and $R_{2N}$ each independently represents hydrogen, etc; $B^N$ represents —CONH—(C0-2 alkylene)-, etc; $Q^N$ and $P^N$ each independently represents pyridine which may have a substituent(s) such as alkoxy, amine, nitrile, etc; $A^N$ represents thiazole, etc; $X^N$ and $Y^N$ each independently represents bond, C1-6 alkyl, etc; is useful in a mGluR5 positive allosteric modulator (see reference such as patent literature 15).

[Patent literature 1] WO2006083673
[Patent literature 2] WO2003020703

[Patent literature 3] U.S. Pat. No. 6,395,753
[Patent literature 4] WO2003086397
[Patent literature 5] WO2004052859
[Patent literature 6] WO2004054974
[Patent literature 7] WO2000061557
[Patent literature 8] WO2003042174
[Patent literature 9] WO2003049736
[Patent literature 10] US20060079556
[Patent literature 11] WO2004046110
[Patent literature 12] WO1998027080
[Patent literature 13] WO1997036876

[Patent literature 14] WO1997036897
[Patent literature 15] WO2006129199

DISCLOSURE OF THE INVENTION

Although many therapeutic agents for metabolic diseases and cerebrovascular disease have developed for a long time, some therapeutic agents have undesirable side effects.

As an example, it is noted that the compound represented by formula (K) is useful for an antidiabetic agent and a cerebral infarction treating agent in PCT publication WO2006083673, the compounds was, however, found to have undesirable side effects such as hepatotoxicity in our assay described below.

Accordingly, it is desired to develop an agent for the prevention and/or treatment of metabolic diseases such as diabetes and cerebrovascular disease such as stroke with high-safety and sufficient pharmacological activity.

The present inventors have made extensive studies to find a compound that can become a therapeutic agent for metabolic diseases and cerebrovascular disease without undesirable side effects such as hepatotoxicity. As a result, we have found that the object is achieved by the compounds of the present invention represented by the formula (I) having an equivalent anti-diabetic effect and unexpected advantageous properties which avoid undesirable side effects such as hepatotoxicity, when compared to the compound represented by (K) reported in PCT publication WO2006083673, and then we have completed the present invention.

Namely, the present invention relates to the followings.
(1) A compound of the formula (I-1):

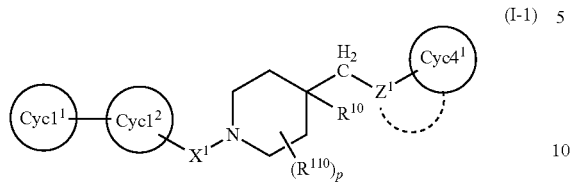
(I-1)

wherein Cyc1¹ is 5- to 6-membered mono-cyclic carbocyclic ring which may have a substituent(s) or 5- to 6-membered mono-cyclic heterocyclic ring which may have a substituent(s);
Cyc2¹ is 5-membered mono-cyclic heterocyclic ring which may have a substituent(s);
Cyc4¹ is 5- to 10-membered mono-cyclic or bi-cyclic carbocyclic ring which may have a substituent(s) or 5- to 10-membered mono-cyclic or bi-cyclic heterocyclic ring which may have a substituent(s);
$X^1$ is —CH$_2$—, —CO— or —SO$_2$—;
$Z^1$ is —N(R$^{51}$)—CO—, —CO—N(R$^{51}$)—, —N(R$^{51}$)—, bond or —O—,
wherein R$^{51}$ is hydrogen or C1-4 alkyl which may have a substituent(s), or R$^{51}$ and the substituent of Cyc4¹ may be taken together to form C1-4 alkylene which may have a substituent(s) or C2-4 alkenylene which may have a substituent(s);
R$^{10}$ is hydrogen or a substituent;
R$^{110}$ is a substituent;
p is an integer of 0 to 8,
wherein p is an integer of 2 to 8, each R$^{110}$ may be same or different; and
wherein the compound of the formula (I-1) is not a compound of formula (I-2):

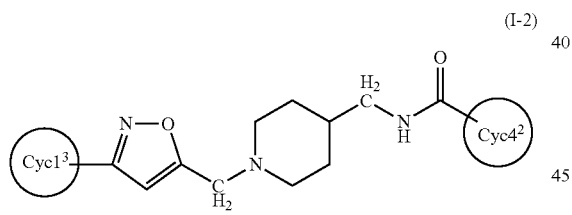
(I-2)

wherein Cyc1³ is

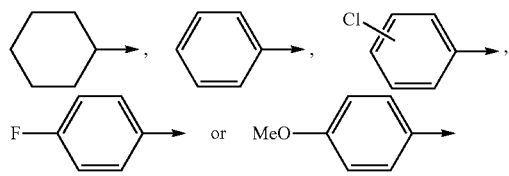

wherein the arrow represents a binding position to isoxazolyl carbon;
Cyc4² is

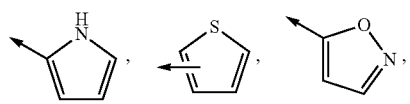

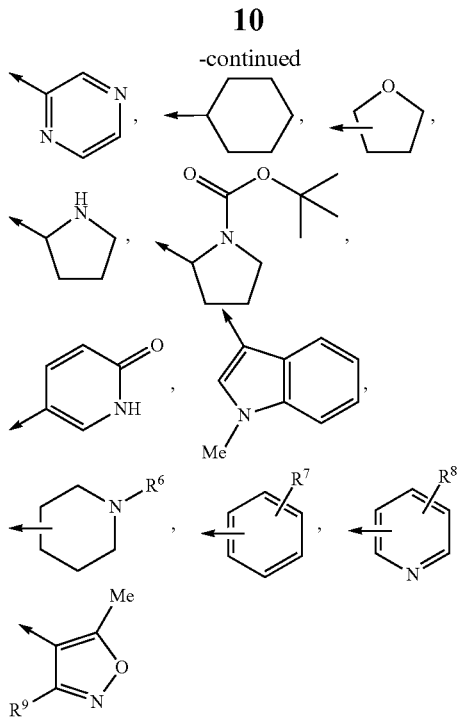

wherein the arrow represents a binding position to carbonyl carbon;
R⁶ is hydrogen, acetyl, tert-butoxycarbonyl, methylsulfonyl or phenylsulfonyl;
R⁷ is hydrogen, chlorine, phenyl, trifluoromethyl, methoxy, phenoxy, cyano or N-acetylamino;
R⁸ is hydrogen, N,N-dimethylamino or N-morpholinyl; and
R⁹ is hydrogen, methyl or phenyl, a salt thereof, an N-oxide thereof, a solvate thereof, or a prodrug thereof,
(2) The compound according to (1) above, wherein

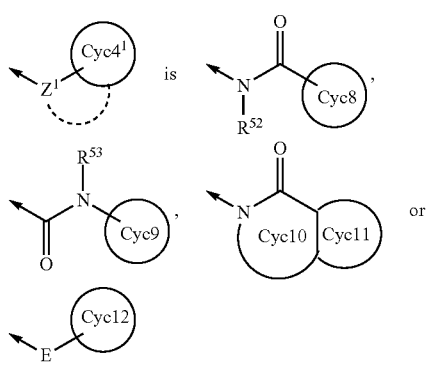

wherein the arrow represents a binding position to methylene carbon;
Cyc8 is (1) 5- to 6-membered mono-cyclic carbocyclic ring which may have a substituent(s) or 5- to 6-membered mono-cyclic heterocyclic ring which may have a substituent(s) or (2) 8- to 10-membered bi-cyclic carbocyclic ring which may have a substituent(s) or 8- to 10-membered bi-cyclic heterocyclic ring which may have a substituent(s);
Cyc9 is (1) 5- to 6-membered mono-cyclic carbocyclic ring which may have a substituent(s) or 5- to 6-membered mono-cyclic heterocyclic ring which may have a substituent(s) or (2) 8- to 10-membered bi-cyclic carbocyclic ring which may have a substituent(s) or 8- to 10-membered bi-cyclic heterocyclic ring which may have a substituent(s);

Cyc10 is 5- to 6-membered mono-cyclic heterocyclic ring which may have a substituent(s);

Cyc11 is 6-membered mono-cyclic carbocyclic ring which may have a substituent(s) or 6-membered mono-cyclic heterocyclic ring which may have a substituent(s);

Cyc12 is 5- to 10-membered mono-cyclic or bi-cyclic carbocyclic ring which may have a substituent(s) or 5- to 10-membered mono-cyclic or bi-cyclic heterocyclic ring which may have a substituent(s);

E is —O— or —N($R^{54}$)—, wherein $R^{54}$ is hydrogen or C1-4 alkyl which may have a substituent(s);

$R^{52}$ is hydrogen or C1-4 alkyl which may have a substituent(s);

$R^{53}$ is hydrogen or C1-4 alkyl which may have a substituent(s); and wherein the compound of the formula (I-1) is not the compound of formula (I-2) described in (1) above; and the other symbols have the same meanings as described in (1) above, (3) The compound according to (2) above, wherein Cyc8 is (1) 5- to 6-membered mono-cyclic carbocyclic ring which have at least two substituents or 6-membered mono-cyclic heterocyclic ring which have at least two substituents or (2) 8- to 10-membered bi-cyclic carbocyclic ring which may have a substituent(s) or 8- to 10-membered bi-cyclic heterocyclic ring which may have a substituent(s);

Cyc9 is (1) 5- to 6-membered mono-cyclic carbocyclic ring which have at least two substituents or 5- to 6-membered mono-cyclic heterocyclic ring which have at least two substituents or (2) 8- to 10-membered bi-cyclic carbocyclic ring which may have a substituent(s) or 8- to 10-membered bi-cyclic heterocyclic ring which may have a substituent(s); and wherein the compound of the formula (I-1) is not the compound of formula (I-2) described in (1) above, (4) The compound according to (2) above, wherein Cyc8 is (1)(a) imidazolyl, triazolyl, pyrazolyl, furanyl, oxazolyl, thiazolyl, isothiazolyl, furazanyl, oxadiazolyl or thiadiazolyl which may have a substituent(s) or (1)(b) pyrrolyl or thienyl which have a substituent(s), (5) The compound according to (1) above, wherein the compound of the formula (I-1) is a compound of the formula (I-1-1):

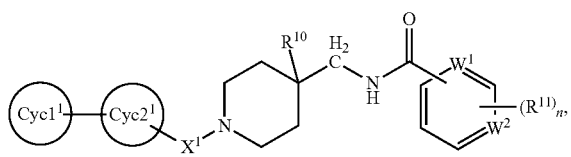

(I-1-1)

a compound of the formula (I-1-2):

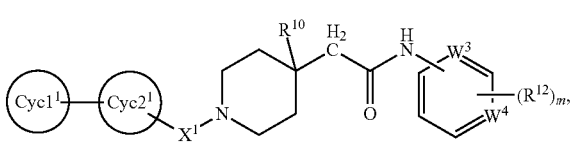

(I-1-2)

a compound of the formula (I-1-3):

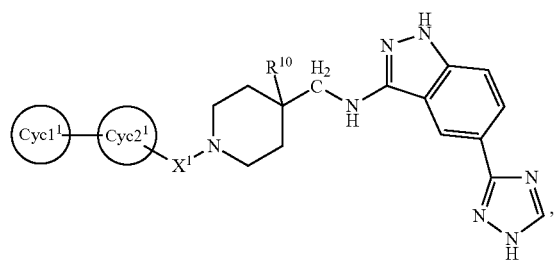

(I-1-3)

or a compound of the formula (I-1-4):

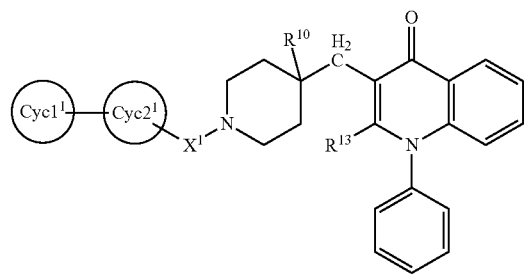

(I-1-4)

wherein $W^1$ and $W^2$ are each independently CH or N;

$W^3$ and $W^4$ are each independently CH or N;

$R^{11}$ is halogen, hydroxy, C1-4 alkoxy which may have a substituent(s), C1-4 alkyl which may have a substituent(s), cyano or amino, and each $R^{11}$ may be same or different;

$R^{12}$ is halogen, hydroxy, C1-4 alkoxy which may have a substituent(s), C1-4 alkyl which may have a substituent(s), cyano or amino;

$R^{13}$ is C1-4 alkyl which may have a substitutent(s);

n is an integer of 2 to 4;

m is an integer of 0 to 4, wherein m is an integer of 2 to 4, each $R^{12}$ may be same or different; and the other symbols have the same meanings as described in (1) above, (6) A compound of the formula (I-1-5):

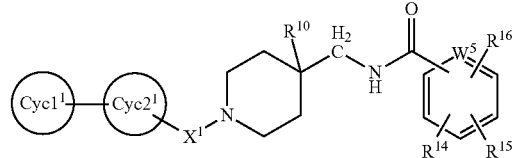

(I-1-5)

wherein $Cyc1^1$ is 5- to 6-membered mono-cyclic carbocyclic ring which may have a substituent(s) or 5- to 6-membered mono-cyclic heterocyclic ring which may have a substituent(s);

$Cyc2^1$ is 5-membered mono-cyclic heterocyclic ring which may have a substituent(s);

$X^1$ is —$CH_2$—, —CO— or —$SO_2$—;

$R^{10}$ is hydrogen or a substituent;

$W^5$ is CH or N;

$R^{14}$ is cyano or amino;

$R^{15}$ is halogen, cyano or amino; and $R^{16}$ is halogen, hydroxy, C1-4 alkoxy which may have a substituent(s), C1-4 alkyl which may have a substituent(s), cyano or amino, a salt thereof, an N-oxide thereof, a solvate thereof, or a prodrug thereof, (7) The compound according to (5) above or (6) above, wherein $Cyc1^1$ is pyrrolidinyl, phenyl, N-morpholinyl or pyridyl which may have a substituent(s); and $Cyc2^1$ is thiazolyl, isoxazolyl, thienyl or oxadiazolyl which may have a substituent(s), (8) The compound according to (7) above, wherein

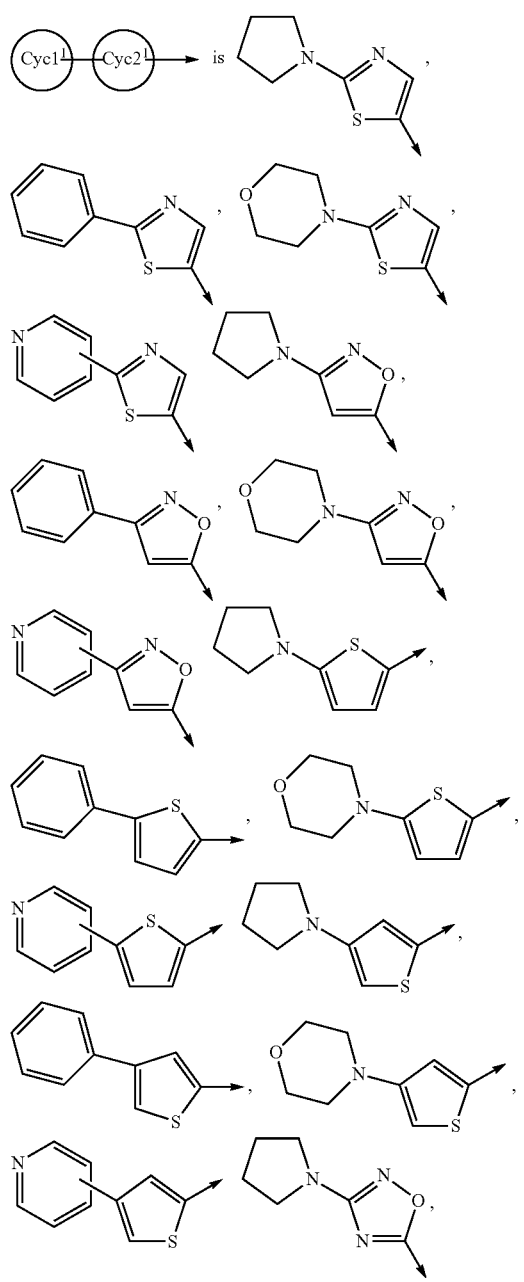

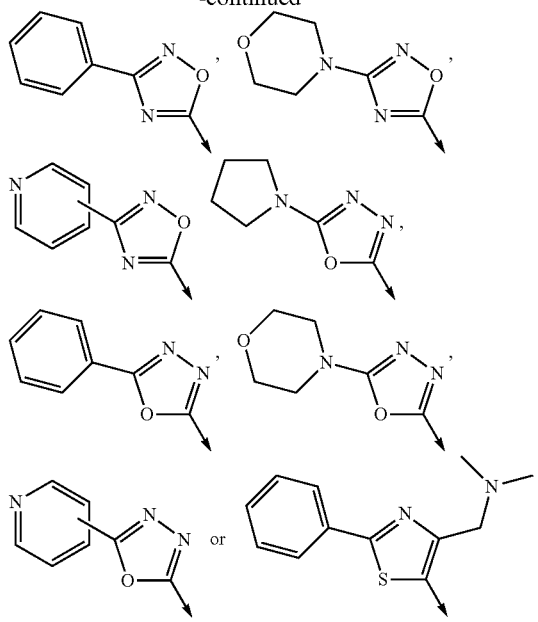

wherein the arrow represents a binding position to $X^1$, (9) The compound according to (5) above or (6) above, wherein

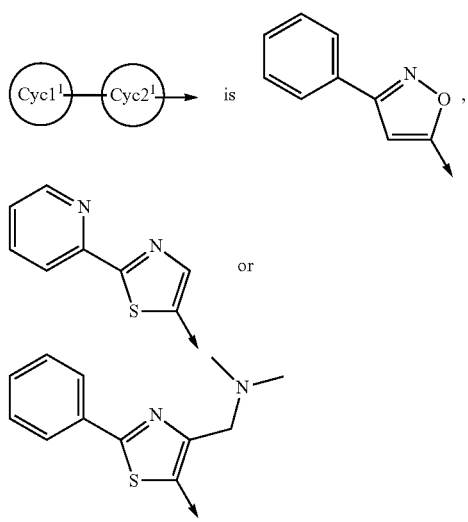

wherein the arrow represents a binding position to $X^1$;

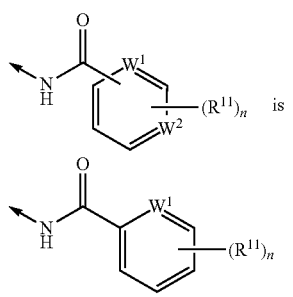

wherein the arrow represents a binding position to methylene carbon;

[Structures showing amide compounds with $W^3$, $W^4$, $(R^{12})_m$]

wherein the arrow represents a binding position to methylene carbon;

[Structures showing amide compounds with $W^5$, $R^{14}$, $R^{15}$, $R^{16}$, and a pyridine with $R^{16}$, CN, $NH_2$]

wherein the arrow represents a binding position to methylene carbon;

$X^1$ is —$CH_2$—;

$R^{10}$ is hydrogen; and $R^{16}$ is chlorine, hydroxy, methoxy or ethoxy which may have a substituent(s), methyl or ethyl which may have a substituent(s), cyano or amino; and the other symbols have the same meanings as described in (5) above or (6) above,

(10) The compound according to (6) above, which is selected from the group consisting of (1) 4-amino-5-chloro-6-ethoxy-N-({1-[(3-phenyl-5-isoxazolyl)methyl]-4-piperidinyl}methyl)-2-pyridinecarboxamide, (2) 4-amino-5-cyano-6-ethoxy-N-({1-[(3-phenyl-5-isoxazolyl)methyl]-4-piperidinyl}methyl)-2-pyridinecarboxamide, (3) 4-amino-5-cyano-6-ethoxy-N-((1-((2-(pyridin-2-yl)thiazol-5-yl)methyl)piperidin-4-yl)methyl)picolinamide, and (4) 4-Amino-5-cyano-N-((1-((4-((dimethylamino)methyl)-2-phenylthiazol-5-yl)methyl)piperidin-4-yl)methyl)-6-ethoxypicolinamide,

(11) A pharmaceutical composition which comprises the compound of the formula (I-1-5) according to (6) above, a salt thereof, an N-oxide thereof, a solvate thereof, or a prodrug thereof,

(12) A method for preventing and/or treating an insulin-resistant diabetes mellitus, which comprises administering to a mammal an effective amount of a compound of formula (I):

[Structure: Cyc1—Cyc2—X—Cyc3—C($R^1$)($R^2$)—Z—Cyc4]  (I)

wherein Cyc1 is a cyclic ring which may have a substituent(s);

Cyc2 is a cyclic ring which may have a substituent(s);

Cyc3 is a cyclic ring which may have a substituent(s);

Cyc4 is a cyclic ring which may have a substituent(s);

X is —$CR^3R^4$—, —CO— or —$SO_2$—, wherein $R^3$ and $R^4$ are each independently hydrogen or C1-4 alkyl which may have a substituent(s);

$R^1$ and $R^2$ are each independently hydrogen or C1-4 alkyl which may have a substituent(s); and Z is —N($R^5$)—CO—, —CO—N($R^5$)—, —N($R^5$)—, bond or —O—, wherein $R^5$ is hydrogen or C1-4 alkyl which may have a substituent(s), or $R^5$ and the substituent of Cyc4 may be taken together to form C1-4 alkylene which may have a substituent(s) or C2-4 alkenylene which may have a substituent(s), a salt thereof, an N-oxide thereof, a solvate thereof, or a prodrug thereof,

(13) The method according to (12) above, wherein $R^1$ and $R^2$ are each hydrogen;

Cyc1 is 5- to 7-membered mono-cyclic carbocyclic ring which may have a substituent(s) or 5- to 7-membered mono-cyclic heterocyclic ring which may have a substituent(s);

Cyc2 is 5- to 7-membered mono-cyclic carbocyclic ring which may have a substituent(s) or 5- to 7-membered mono-cyclic heterocyclic ring which may have a substituent(s);

Cyc3 is 5- to 6-membered mono-cyclic heterocyclic ring which may have a substituent(s); and Cyc4 is 5- to 10-membered mono-cyclic or bi-cyclic carbocyclic ring which may have a substituent(s) or 5- to 10-membered mono-cyclic or bi-cyclic heterocyclic ring which may have a substituent(s),

(14) The method according to (13) above, wherein the compound of the formula (I) is a compound of formula (I-1-5):

[Structure: Cyc1¹—Cyc2¹—$X^1$—N-piperidine-C($R^{10}$)($H_2$)—NH—CO—aromatic ring with $W^5$, $R^{14}$, $R^{15}$, $R^{16}$]  (I-1-5)

wherein Cyc1¹ is 5- to 6-membered mono-cyclic carbocyclic ring which may have a substituent(s) or 5- to 6-membered mono-cyclic heterocyclic ring which may have a substituent(s);

Cyc2¹ is 5-membered mono-cyclic heterocyclic ring which may have a substituent(s);

$X^1$ is —$CH_2$—, —CO— or —$SO_2$—;

$R^{10}$ is hydrogen or a substituent;

$W^5$ is CH or N;

$R^{14}$ is cyano or amino;

$R^{15}$ is halogen, cyano or amino; and $R^{16}$ is halogen, hydroxy, C1-4 alkoxy which may have a substituent(s), C1-4 alkyl which may have a substituent(s), cyano or amino,

(15) Use of the compound of the formula (I) according to (12) above, a salt thereof, an N-oxide thereof, a solvate thereof, or a prodrug thereof, for the manufacture of an agent for preventing and/or treating an insulin-resistant diabetes mellitus.

(16) A method for preventing and/or treating a stroke, which comprises administering to a mammal an effective amount of a compound of formula (I):

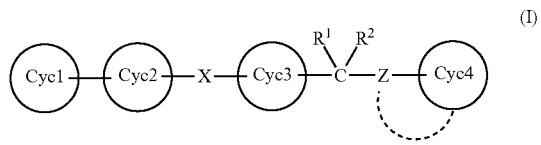

(I)

wherein Cyc1 is a cyclic ring which may have a substituent(s);
Cyc2 is a cyclic ring which may have a substituent(s);
Cyc3 is a cyclic ring which may have a substituent(s);
Cyc4 is a cyclic ring which may have a substituent(s);
X is —$CR^3R^4$—, —CO— or —$SO_2$—,
wherein $R^3$ and $R^4$ are each independently hydrogen or C1-4 alkyl which may have a substituent(s);
$R^1$ and $R^2$ are each independently hydrogen or C1-4 alkyl which may have a substituent(s); and
Z is —$N(R^5)$—CO—, —CO—$N(R^5)$—, —$N(R^5)$—, bond or —O—,
wherein $R^5$ is hydrogen or C1-4 alkyl which may have a substituent(s), or $R^5$ and the substituent of Cyc4 may be taken together to form C1-4 alkylene which may have a substituent(s) or C2-4 alkenylene which may have a substituent(s),
a salt thereof, an N-oxide thereof, a solvate thereof, or a prodrug thereof,

(17) The method according to (16) above,
wherein $R^1$ and $R^2$ are hydrogen;
Cyc1 is 5- to 7-membered mono-cyclic carbocyclic ring which may have a substituent(s) or 5- to 7-membered mono-cyclic heterocyclic ring which may have a substituent(s);
Cyc2 is 5- to 7-membered mono-cyclic carbocyclic ring which may have a substituent(s) or 5- to 7-membered mono-cyclic heterocyclic ring which may have a substituent(s);
Cyc3 is 5- to 6-membered mono-cyclic heterocyclic ring which may have a substituent(s); and
Cyc4 is 5- to 10-membered mono-cyclic or bi-cyclic carbocyclic ring which may have a substituent(s) or 5- to 10-membered mono-cyclic or bi-cyclic heterocyclic ring which may have a substituent(s),

(18) The method according to (17) above, wherein the compound of the formula (I) is a compound of formula (I-1-5):

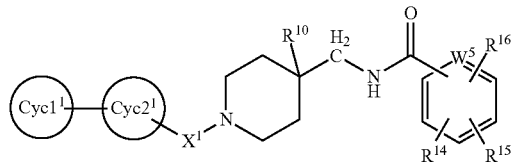

(I-1-5)

wherein $Cyc1'$ is 5- to 6-membered mono-cyclic carbocyclic ring which may have a substituent(s) or 5- to 6-membered mono-cyclic heterocyclic ring which may have a substituent(s);
Cyc2' is 5-membered mono-cyclic heterocyclic ring which may have a substituent(s);
$X^1$ is —$CH_2$—, —CO— or —$SO_2$—;
$R^{10}$ is hydrogen or a substituent;
$W^5$ is CH or N;
$R^{14}$ is cyano or amino;
$R^{15}$ is halogen, cyano or amino; and
$R^{16}$ is halogen, hydroxy, C1-4 alkoxy which may have a substituent(s), C1-4 alkyl which may have a substituent(s), cyano or amino, and

(19) Use of the compound of the formula (I) according to (16) above, a salt thereof, an N-oxide thereof, a solvate thereof, or a prodrug thereof, for the manufacture of an agent for preventing and/or treating a stroke.

In the present specification, Cyc1 represents a cyclic ring which may have a substituent(s).

The "cyclic ring" in the "cyclic ring which may have a substituent(s)" represented by Cyc1 includes, for example, a "carbocyclic ring", a "heterocyclic ring", and the like.

The "carbocyclic ring" represented by Cyc1 includes, for example, a "3- to 15-membered mono-cyclic, bi-cyclic or tri-cyclic carbocyclic ring", and the like. The "3- to 15-membered mono-cyclic, bi-cyclic or tri-cyclic carbocyclic ring" represented by Cyc1 includes a "3- to 15-membered mono-cyclic, bi-cyclic or tri-cyclic unsaturated carbocyclic ring, partially or completely saturated carbocyclic ring", a "spiro-bound bi-cyclic carbocyclic ring, and a crosslinked bi-cyclic carbocyclic ring", and the like.

The "3- to 15-membered mono-cyclic, bi-cyclic or tri-cyclic partially or completely saturated carbocyclic ring" represented by Cyc1 includes, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, and the like. The "spiro-bound bi-cyclic carbocyclic ring" represented by Cyc1 includes, for example, spiro[4.4]nonane, spiro[4.5]decane, spiro[5.5]undecane rings and the like. The "crosslinked bi-cyclic carbocyclic ring" represented by Cyc1 includes, for example, bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane, noradamantane rings and the like. Among the "3- to 15-membered mono-cyclic, bi-cyclic or tri-cyclic unsaturated carbocyclic ring" represented by Cyc1, a "3- to 15-membered mono-cyclic, bi-cyclic or tri-cyclic aromatic carbocyclic ring" represented by Cyc1 includes, for example, benzene, azulene, naphthalene, phenanthrene, anthracene rings and the like.

The "heterocyclic ring" represented by Cyc1 includes, for example, a "3- to 15-membered mono-cyclic, bi-cyclic or tri-cyclic heterocyclic ring having 1 to 4 nitrogen atom(s), 1 or 2 oxygen atom(s) and/or 1 or 2 sulfur atom(s) as a hetero atom(s)", and the like. Herein, the "3- to 15-membered mono-cyclic, bi-cyclic or tri-cyclic heterocyclic ring having 1 to 4 nitrogen atom(s), 1 or 2 oxygen atom(s) and/or 1 or 2 sulfur atom(s) as a hetero atom(s)" represented by Cyc1 includes a "3- to 15-membered mono-cyclic, bi-cyclic or tri-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof", a "spiro-bound bi-cyclic heterocyclic ring and a crosslinked bi-cyclic heterocyclic ring".

The "3- to 15-membered mono-cyclic, bi-cyclic or tri-cyclic unsaturated heterocyclic ring having 1 to 4 nitrogen atom(s), 1 or 2 oxygen atom(s) and/or 1 or 2 sulfur atom(s) as a hetero atom(s), or a partially or completely saturated one thereof" represented by Cyc1 includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, imidazo[1,2-a]pyridine, chromene, benzoxepine, benzoxazepine, benzoxadiazepine, benzothiepine, benzothiazepine, benzothiadiazepine, benzoazepine, benzodiazepine, benzofurazan, benzothiadiazole, benzotriazole, isoxazolo[4,5-d]pyridazine, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydroxepine, tetrahydroxepine, perhydroxepine, thiirane, thietane, dihydrothiophene, tetrahydrothiophene, dihydrothiopyran, tetrahydrothiopyran, dihydrothiepin, tetrahydrothiepin, perhydrothiepin, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydroxazine, tetrahydroxazine, dihydroxadiazine, tetrahydroxadiazine, dihydroxazepine, tetrahydroxazepine, perhydroxazepine, dihydroxadiazepine, tetrahydroxadiazepine, perhydroxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, 1,4-dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chroman, benzodithiolane, benzodithiane, 6,7-dihydro-5H-cyclopenta[b]pyrazine, 5H-cyclopenta[b]pyrazine, imidazo[2,1-b][1,3]thiazole rings and the like. The "spiro-bound bi-cyclic heterocyclic ring" represented by Cyc1 includes, for example, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane rings and the like. The "crosslinked bi-cyclic heterocyclic ring" represented by Cyc1 includes, for example, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane rings and the like. Among the "3- to 15-membered mono-cyclic, bi-cyclic or tri-cyclic unsaturated heterocyclic ring having 1 to 4 nitrogen atom(s), 1 or 2 oxygen atom(s) and/or 1 or 2 sulfur atom(s) as a hetero atom(s)" represented by Cyc1, a "3- to 15-membered mono-cyclic, bi-cyclic or tri-cyclic aromatic heterocyclic ring having 1 to 4 nitrogen atom(s), 1 or 2 oxygen atom(s) and/or 1 or 2 sulfur atom(s) as a hetero atom(s)" represented by Cyc1 includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzooxazole, benzothiazole, benzimidazole, imidazo[1,2-a]pyridine, benzofurazan, benzothiadiazole, benzotriazole, isoxazolo[4,5-d]pyridazine, carbazole, β-carboline, acridine, phenazine, dibenzofuran, dibenzothiophene, phenanthridine, phenanthroline, perimidine rings and the like.

Moreover, Cyc1 also represents 5- to 7-membered mono-cyclic carbocyclic ring which may have a substituent(s) or 5- to 7-membered mono-cyclic heterocyclic ring which may have a substituent(s).

The "5- to 7-membered mono-cyclic carbocyclic ring" in the "5- to 7-membered mono-cyclic carbocyclic ring which may have a substituent(s)" represented by Cyc1 includes, for example, a "5- to 7-membered mono-cyclic carbocyclic ring" and the like. The "5- to 7-membered mono-cyclic carbocyclic ring" represented by Cyc1 includes a "5- to 7-membered mono-cyclic unsaturated carbocyclic ring, partially or completely saturated carbocyclic ring" and the like.

The "5- to 7-membered mono-cyclic unsaturated carbocyclic ring, partially or completely saturated carbocyclic ring" represented by Cyc1 includes, for example, cyclopentane, cyclohexane, cyclopentene, cyclohexene, cycloheptane, cyclopentadiene, cyclohexadiene, benzene, cycloheptadiene and the like. Among the "5- to 7-membered mono-cyclic unsaturated carbocyclic ring" represented by Cyc1, a "5- to 7-membered mono-cyclic aromatic carbocyclic ring" represented by Cyc1 includes, for example, benzene.

The "substituent" in the "5- to 7-membered mono-cyclic carbocyclic ring which may have a substituent(s)" represented by Cyc1 includes the same example of such as the "substituent" in the "cyclic ring which may have a substituent(s)" represented by Cyc1 described above.

The "5- to 7-membered mono-cyclic heterocyclic ring" in the "5- to 7-membered mono-cyclic heterocyclic ring which may have a substituent(s)" represented by Cyc1 includes, for example, a "5- to 7-membered mono-cyclic heterocyclic ring having 1 to 4 nitrogen atom(s), 1 or 2 oxygen atom(s) and/or 1 or 2 sulfur atom(s) as a hetero atom(s)" and the like. Herein, the "5- to 7-membered mono-cyclic heterocyclic ring having 1 to 4 nitrogen atom(s), 1 or 2 oxygen atom(s) and/or 1 or 2 sulfur atom(s) as a hetero atom(s)" represented by Cyc1 includes a "5- to 7-membered mono-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof".

The "5- to 7-membered mono-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof" represented by Cyc1 includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydroxepine, tetrahydroxepine, perhydroxepine, dihydrothiophene, tetrahydrothiophene, dihydrothiopyran, tetrahydrothiopyran, dihydrothiepin, tetrahydrothiepin, perhydrothiepin, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydroxazine, tetrahydroxazine, dihydroxadiazine, tetrahydroxadiazine, dihydroxazepine, tetrahydroxazepine, perhydroxazepine, dihydroxadiazepine, tetrahydroxadiazepine, perhydroxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine and the like. Among the "5- to 7-membered mono-cyclic unsaturated heterocyclic ring having 1 to 4 nitrogen atom(s), 1 or 2 oxygen atom(s) and/or 1 or 2 sulfur atom(s) as a hetero atom(s)" represented by Cyc1, a "5- to 7-membered mono-cyclic aromatic heterocyclic ring having 1 to 4 nitrogen atom(s), 1 or 2 oxygen atom(s) and/or 1 or 2 sulfur atom(s) as a hetero atom(s)" represented by Cyc1 includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole rings and the like.

The "substituent" in the "5- to 7-membered mono-cyclic heterocyclic ring which may have a substituent(s)" represented by Cyc1 includes the same example of such as the "substituent" in the "cyclic ring which may have a substituent(s)" represented by Cyc1 described above.

The "substituent" in the "cyclic ring which may have a substituent(s)" represented by Cyc1 is not particularly limited, so long as it is a substituent. The "substituent" in the "cyclic ring which may have a substituent(s)" represented by Cyc1 includes, for example, (1) carboxyl, (2) sulfo, (3) sulfino, (4) phosphono, (5) nitro, (6) oxo, (7) thioxo, (8) cyano, (9) amidino, (10) dihydroxyboryl(—$B(OH)_2$), (11) halogen (fluorine, chlorine, bromine and iodine), (12) alkoxycarbonyl (for example, C1-6 alkoxycarbonyl, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, isopentoxycarbonyl, hexyloxycarbonyl, etc.), (13) alkylsulfinyl (for example, C1-6 alkylsulfinyl, such as methylsulfinyl, ethylsulfinyl, propylsulfinyl, butylsulfinyl, pentylsulfinyl, hexylsulfinyl, tert-butylsulfinyl, etc.), (14) arylsulfinyl (C6-10 aromatic carbocyclic sulfinyl, such as phenylsulfinyl, naphthylsulfinyl, etc.), (15) alkylsulfonyl (for example, C1-6 alkylsulfonyl, such as methylsulfonyl, ethylsulfonyl, propylsulfonyl, butylsulfonyl, pentylsulfonyl, hexylsulfonyl, tert-butylsulfonyl, etc.), and the like, (16) arylsulfonyl (for example, C6-10 aromatic carbocyclic sulfonyl, such as phenylsulfonyl, naphthylsulfonyl, etc.), (17) alkylcarbonylhydrazino (for example, C1-6 alkylcarbonylhydrazino (—NH—NH—CO—(C1-6 alkyl), such as methylcarbonylhydrazino, ethylcarbonylhydrazino, tert-butylcarbonylhydrazino, etc.), (18) arylhydrazone (for example, C6-10 aromatic carbo cyclic hydrazone which may have a substituent(s), such as benzaldehyde hydrazone, p-methoxybenzaldehyde hydrazone, etc.), (19) acyl (for example, C1-6 alkanoyl, such as formyl, acetyl, propanoyl, pivaloyl, etc., C3-8 cycloalkanoyl, such as cyclopentylcarbonyl, cyclohexylcarbonyl, etc., C6-10 aromatic carbocyclic carbonyl, such as, benzoyl, etc., heterocyclic carbonyl which may have a substituent(s), such as morpholin-4-ylcarbonyl, piperidin-1-ylcarbonyl, 1-methylpiperazin-4-ylcarbonyl etc., C6-10 aromatic carbocyclic alkanoyl which may have a substituent(s), such as phenylmethylcarbonyl, 2-phenylethylcarbonyl, etc.), and the like, (20) optionally protected hydroxy, (21) optionally protected thiol, (22) optionally protected amino, (23) carbamoyl which may have a substituent(s), (24) sulfamoyl which may have a substituent(s), (25) imino which may have a substituent(s), (26) alkyl which may have a substituent(s), (27) alkenyl which may have a substituent(s), (28) alkynyl which may have a substituent(s), (29) carbocyclic ring which may have a substituent(s), (30) heterocyclic ring which may have a substituent(s), and the like. And these substituent(s) may exist on the substitutable position and the number of substituents may be from 1 to 5, if the number of substituents is two or more, each substituent may be same or different.

The "alkyl" in the "alkyl which may have a substituent(s)" as the "substituent" in the "cyclic ring which may have a substituent(s)" represented by Cyc1 includes, for example, a straight or branched C1-10 alkyl such as methyl, ethyl, propyl, isopropyl, butyl, isobutyl, sec-butyl, tert-butyl, pentyl, hexyl, heptyl, octyl, nonyl, decyl, and the like. The "substituent" in the "alkyl which may have a substituent(s)" is not particularly limited, so long as it is a substituent. The "substituent" in the "alkyl which may have a substituent(s)" as the "substituent" in the "cyclic ring which may have a substituent(s)" represented by Cyc1 includes, for example, straight or branched C1-10 alkyl (such as methyl, ethyl, propyl, isopropyl, butyl, isobutyl, sec-butyl, tert-butyl, pentyl, hexyl, heptyl, octyl, nonyl, decyl, etc.), straight or branched C2-6 alkenyl (such as ethenyl, propenyl, butenyl, butadienyl, pentenyl, pentadienyl, hexenyl, hexadienyl, etc.), straight or branched C2-6 alkynyl (such as ethynyl, propynyl, butynyl, butadiynyl, pentynyl, pentadiynyl, hexynyl, hexadiynyl, etc.), hydroxy, C1-4 alkoxy (such as methoxy, ethoxy, propoxy, isopropoxy, butoxy, isobutoxy, sec-butoxy, tert-butoxy, etc.), C6-10 aryloxy (such as phenoxy, benzyloxy, etc.), thiol, C1-6 alkylthio (such as methylthio, ethylthio, propylthio, isopropylthio, butylthio, isobutylthio, tert-butylthio, pentylthio, hexylthio, etc.), C6-10 arylthio (such as phenylthio), amino, mono- or di-(C1-6 alkyl)amino (such as methylamino, ethylamino, propylamino, dimethylamino, diethylamino, etc.), mono- or di-(C6-10 aryl)amino (such as phenyamino, diphenylamino, etc.), mono-(C1-6 alkyl)-mono-(C6-10 aryl)amino (such as N-phenyl-N-methylamino, N-phenyl-N-ethylamino, etc.), mono- or di-(C1-6 alkyl)aminoalkoxy (such as methylaminoethoxy, ethylaminoethoxy, propylaminoethoxy, dimethylaminoethoxy, diethylaminoethoxy, etc.), heterocyclealkoxy (such as 2-(4-morpholinyl)ethoxy, 2-(4-morpholinyl)propoxy, etc.), heterocyclic ring (such as imidazolyl, morpholinyl, piperazinyl, etc.), tert-butoxycarboxylpiperazine, carboxyl, C1-6 alkylcarbonyloxy (such as acetoxy, ethylcarbonyloxy, etc.), halogen (for example, fluorine, chlorine, bromine and iodine, etc.), cyano, nitro, oxo, and the like. And these substituent(s) may exist on the substitutable position and the number of substituents may be from 1 to 5, if the number of substituents is two or more, each substituent may be same or different.

The "alkenyl" in the "alkenyl which may have a substituent(s)" as the "substituent" in the "cyclic ring which may have a substituent(s)" represented by Cyc1 includes, for example a straight or branched C2-6 alkenyl such as ethenyl, propenyl, butenyl, butadienyl, pentenyl, pentadienyl, hexenyl, hexadienyl, and the like. The "substituent" in the "alkenyl which may have a substituent(s)" is not particularly limited, so long as it is a substituent. The "substituent" in the "alkenyl which may have a substituent(s)" as the "substituent" in the "cyclic ring which may have a substituent(s)" represented by Cyc1 includes the same example of such as the "substituent" in the "alkyl which may have a substituent(s)" as the "substituent" in the "cyclic ring which may have a substituent(s)" represented by Cyc1 described above. And these substituent(s) may exist on the substitutable position and the number of substituents may be from 1 to 4, if the number of substituents is two or more, each substituent may be same or different.

The "alkynyl" in the "alkynyl which may have a substituent(s)" as the "substituent" in the "cyclic ring which may have a substituent(s)" represented by Cyc1 includes, for example, a straight or branched C2-6 alkynyl such as ethynyl, propynyl, butynyl, butadiynyl, pentynyl, pentadiynyl, hexynyl, hexadiynyl, and the like. The "substituent" in the "alkynyl which may have a substituent(s)" is not particularly limited, so long as it is a substituent. The "substituent" in the "alkynyl which may have a substituent(s)" as the "substituent" in the "cyclic ring which may have a substituent(s)" represented by Cyc1 includes the same example of such as the "substituent" in the "alkyl which may have a substituent(s)" as the "substituent" in the "cyclic ring which may have a substituent(s)" represented by Cyc1 described above. And these substituent(s) may exist on the substitutable position and the number of substituents may be from 1 to 4, if the number of substituents is two or more, each substituent may be same or different.

The "carbocyclic ring" in the "carbocyclic ring which may have a substituent(s)" as the "substituent" in the "cyclic ring which may have a substituent(s)" represented by Cyc1 includes, for example, a "3- to 15-membered mono-cyclic, bi-cyclic or tri-cyclic carbocyclic ring" represented by Cyc1 described above, and the like. The "substituent" in the "carbocyclic ring which may have a substituent(s)" is not particularly limited, so long as it is a substituent. The "substituent" in the "carbocyclic ring which may have a substituent(s)" as the "substituent" in the "cyclic ring which may have a substituent(s)" represented by Cyc1 includes the same example of such as the "substituent" in the "alkyl which may have a substituent(s)" as the "substituent" in the "cyclic ring which may have a substituent(s)" represented by Cyc1 described above. And these substituent(s) may exist on the substitutable position and the number of substituents may be from 1 to 4, if the number of substituents is two or more, each substituent may be same or different.

The "heterocyclic ring" in the "heterocyclic ring which may have a substituent(s)" as the "substituent" in the "cyclic ring which may have a substituent(s)" represented by Cyc1 includes, for example, a "3- to 15-membered mono-cyclic, bi-cyclic or tri-cyclic heterocyclic ring having 1 to 4 nitrogen atom(s), 1 or 2 oxygen atom(s) and/or 1 or 2 sulfur atom(s) as a hetero atom(s)" represented by Cyc1 described above, and the like. The "substituent" in the "heterocyclic ring which may have a substituent(s)" is not particularly limited, so long as it is a substituent. The "substituent" in the "heterocyclic ring which may have a substituent(s)" as the "substituent" in the "cyclic ring which may have a substituent(s)" represented by Cyc1 includes the same example of such as the "substituent" in the "alkyl which may have a substituent(s)" as the "substituent" in the "cyclic ring which may have a substituent(s)" represented by Cyc1 described above. And these substituent(s) may exist on the substitutable position and the number of substituents may be from 1 to 5, if the number of substituents is two or more, each substituent may be same or different.

The "imino which may have a substituent(s)" as the "substituent" in the "cyclic ring which may have a substituent(s)" represented by Cyc1 includes, for example, non-substituted imino and imino substituted by C1-10 alkyl (such as methylimino, ethylimino, etc.), imino substituted by C6-10 aromatic carbocyclic which may have a substituent(s) (such as phenylimino, p-fluorophenylimino, p-chlorophenylimino, etc.), imino substituted by hydroxy (such as hydroxyimino, etc.), imino substituted by C1-6 alkoxy (such as methoxyimino, ethoxyimino, etc.), imino substituted by C6-10 aromatic carbocyclic which may have a substituent(s) (such as phenoxyimino, p-fluorophenoxyimino, p-chlorophenoxyimino, etc.) and the like.

The "optionally protected hydroxy" as the "substituent" in the "cyclic ring which may have a substituent(s)" represented by Cyc1 includes, for example, non-substituted hydroxy, hydroxy substituted by arbitrary "protecting group" and the like. Herein, the "protecting group" of hydroxy as the "substituent" in the "cyclic ring which may have a substituent(s)" represented by Cyc1 includes, for example, (i) alkyl which may have a substituent(s) (which has the same meaning as the "alkyl which may have a substituent(s)" as the "substituent" in the "cyclic ring which may have a substituent(s)" represented by Cyc1 described above), (ii) carbocyclic ring which may have a substituent(s) (which has the same meaning as the "carbocyclic ring which may have a substituent(s)" as the "substituent" in the "cyclic ring which may have a substituent(s)" represented by Cyc1 described above), (iii) heterocyclic ring which may have a substituent(s) (which has the same meaning as the "heterocyclic ring which may have a substituent(s)" as the "substituent" in the "cyclic ring which may have a substituent(s)" represented by Cyc1 described above), (iv) acyl (for example, C1-6 alkanoyl, such as formyl, acetyl, propanoyl, pivaloyl, etc., C3-8 cycloalkanoyl, such as cyclopentylcarbonyl, cyclohexylcarbonyl, etc., C6-10 aromatic carbocyclic carbonyl, such as benzoyl, etc., heterocyclic carbonyl which may have a substituent(s), such as morpholin-4-ylcarbonyl, piperidin-1-ylcarbonyl, 1-methylpiperazin-4-ylcarbonyl etc., C6-10 aromatic carbocyclic alkanoyl which may have a substituent(s), such as phenylmethylcarbonyl, 2-phenylethylcarbonyl, etc.), (v) sulfonyl (such as alkylsulfonyl (for example, C1-6 alkylsulfonyl, such as methylsulfonyl, ethylsulfonyl, propylsulfonyl, butylsulfonyl, pentylsulfonyl, hexylsulfonyl, tert-butylsulfonyl, etc.), (vi) arylsulfonyl (for example, C6-10 aromatic carbocyclic sulfonyl, such as phenylsulfonyl, naphthylsulfonyl, etc.) and the like.

The "optionally protected thiol" as the "substituent" in the "cyclic ring which may have a substituent(s)" represented by Cyc1 includes, for example, non-substituted thiol, thiol substituted by arbitrary "protecting group" and the like. Herein, the "protecting group" of thiol as the "substituent" in the "cyclic ring which may have a substituent(s)" represented by Cyc1 includes the same example of the "protecting group" in the "optionally protected hydroxy" as the "substituent" in the "cyclic ring which may have a substituent(s)" represented by Cyc1 described above and the like.

The "optionally protected amino" as the "substituent" in the "cyclic ring which may have a substituent(s)" represented by Cyc1 includes, for example, non-substituted amino, amino substituted by arbitrary one or two "protecting groups" and the like. Herein, the "protecting group" of amino as the "substituent" in the "cyclic ring which may have a substituent(s)" represented by Cyc1 includes the same example of the "protecting group" in the "optionally protected hydroxy" as the "substituent" in the "cyclic ring which may have a substituent(s)" represented by Cyc1 described above and the like.

The "optionally protected carbamoyl" as the "substituent" in the "cyclic ring which may have a substituent(s)" represented by Cyc1 includes, for example, non-substituted carbamoyl, carbamoyl substituted by arbitrary one or two "protecting groups" and the like. Herein, the carbamoyl protecting group includes, for example, alkyl which may have a substituent(s) (which has the same meaning as the "alkyl which may have a substituent(s)" as the "substituent" in the "cyclic ring which may have a substituent(s)" represented by Cyc1 described above), carbocyclic ring which may have a substituent(s) (which has the same meaning as the "carbocyclic ring which may have a substituent(s)" as the "substituent" in the "cyclic ring which may have a substituent(s)" represented by Cyc1 described above), heterocyclic ring which may have a substituent(s) (which has the same meaning as the "heterocyclic ring which may have a substituent(s)" as the "substituent" in the "cyclic ring which may have a substituent(s)" represented by Cyc1 described above) and the like. More concretely, the carbamoyl protecting group includes, for example, N-mono-C1-6 alkylcarbamoyl (such as N-methylcarbamoyl, N-ethylcarbamoyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl, and the like), N-mono-(C1-6alkyl substituted by hydroxy)carbamoyl (such as N-hydroxymethylcarbamoyl, N-(2-hydroxyethyl)carbamoyl, N-(3-hydroxypropyl)carbamoyl, N-(4-hydroxybutyl)carbamoyl, and the like), N-mono-(C1-6 alkyl substituted by amino)carbamoyl (such as N-aminomethylcarbamoyl, N-(2-aminoethyl)carbamoyl, N-(3-aminopropyl)carbamoyl, N-(4-aminobutyl)carbamoyl, and the like), N-mono-(C1-6 alkyl substituted by dimethylamino)carbamoyl (such as N-(dimethylamino)methylcarbamoyl, N-(2-dimethylaminoethyl)carbamoyl, N-(3-dimethylaminopropyl)carbamoyl, N-(4-dimethylaminobutyl)carbamoyl, and the like), N-mono(carbocyclic which may have a substituent(s))carbamoyl (such as N-cyclopropylcarbamoyl, N-cyclopentylcarbamoyl, N-cyclohexylcarbamoyl, N-phenylcarbamoyl, and the like), N,N-di-C1-6 alkylcarbamoyl (such as N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl, and the like) and the like.

The "optionally protected sulfamoyl" as the "substituent" in the "cyclic ring which may have a substituent(s)" represented by Cyc1 includes, for example, non-substituted sulfamoyl, sulfamoyl substituted by arbitrary one or two "protection group(s)" and the like. Herein, the "protecting group" of sulfamoyl as the "substituent" in the "cyclic ring which may have a substituent(s)" represented by Cyc1 includes, for example, alkyl which may have a substituent(s) (which has the same meaning as the "alkyl which may have a substituent(s)" as the "substituent" in the "cyclic ring which may have a substituent(s)" represented by Cyc1 described above) and the like. More concretely, the protecting group of sulfamoyl include, for example, N-mono-C1-6 alkylsulfamoyl (such as N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl, and the like), N,N-di-C1-6 alkylsulfamoyl (such as N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl, and the like) and the like.

Cyc2 represents a cyclic ring which may have a substituent(s).

The "cyclic ring" in the "cyclic ring which may have a substituent(s)" represented by Cyc2 includes the same example of the "cyclic ring" in the "cyclic ring which may have a substituent(s)" represented by Cyc1. The "substituent" in the "cyclic ring which may have a substituent(s)" represented by Cyc2 includes the same example of such as the "substituent" in the "cyclic ring which may have a substituent(s)" represented by Cyc1 described above.

Moreover, Cyc2 also represents 5- to 7-membered monocyclic carbocyclic ring which may have a substituent(s) or 5- to 7-membered mono-cyclic heterocyclic ring which may have a substituent(s).

The "5- to 7-membered mono-cyclic carbocyclic ring" in the "5- to 7-membered mono-cyclic carbocyclic ring which may have a substituent(s)" represented by Cyc2 includes the same example of the "5- to 7-membered mono-cyclic carbocyclic ring" in the "5- to 7-membered mono-cyclic carbocyclic ring which may have a substituent(s)" represented by Cyc1. The "substituent" in the "5- to 7-membered monocyclic carbocyclic ring which may have a substituent(s)" represented by Cyc2 includes the same example of such as the "substituent" in the "cyclic ring which may have a substituent(s)" represented by Cyc1 described above.

The "5- to 7-membered mono-cyclic heterocyclic ring" in the "5- to 7-membered mono-cyclic heterocyclic ring which may have a substituent(s)" represented by Cyc2 includes the same example of the "5- to 7-membered mono-cyclic heterocyclic ring" in the "5- to 7-membered mono-cyclic heterocyclic ring which may have a substituent(s)" represented by Cyc1. The "substituent" in the "5- to 7-membered mono-cyclic heterocyclic ring which may have a substituent(s)" represented by Cyc2 includes the same example of such as the "substituent" in the "cyclic ring which may have a substituent(s)" represented by Cyc1 described above.

Cyc3 represents a cyclic ring which may have a substituent(s).

The "cyclic ring" in the "cyclic ring which may have a substituent(s)" represented by Cyc3 includes the same example of the "cyclic ring" in the "cyclic ring which may have a substituent(s)" represented by Cyc1. The "substituent" in the "cyclic ring which may have a substituent(s)" represented by Cyc3 includes the same example of such as the "substituent" in the "cyclic ring which may have a substituent(s)" represented by Cyc1 described above.

Moreover, Cyc3 also represents 5- to 6-membered mono-cyclic heterocyclic ring which may have a substituent(s).

The "5- to 6-membered mono-cyclic heterocyclic ring" in the "5- to 6-membered mono-cyclic heterocyclic ring which may have a substituent(s)" represented by Cyc3 includes, for example, a "5- to 6-membered mono-cyclic heterocyclic ring having 1 to 4 nitrogen atom(s), 1 or 2 oxygen atom(s) and/or 1 or 2 sulfur atom(s) as a hetero atom(s)" and the like. Herein, the "5- to 6-membered mono-cyclic heterocyclic ring having 1 to 4 nitrogen atom(s), 1 or 2 oxygen atom(s) and/or 1 or 2 sulfur atom(s) as a hetero atom(s)" represented by Cyc3 includes a "5- to 6-membered mono-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof".

The "5- to 6-membered mono-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof" represented by Cyc3 includes, for example, pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydroxazine, tetrahydroxazine, dihydroxadiazine, tetrahydroxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine and the like. Among the "5- to 6-membered mono-cyclic unsaturated heterocyclic ring having 1 to 4 nitrogen atom(s), 1 or 2 oxygen atom(s) and/or 1 or 2 sulfur atom(s) as a hetero atom(s)" represented by Cyc3, a "5- to 6-membered mono-cyclic aromatic heterocyclic ring having 1 to 4 nitrogen atom(s), 1 or 2 oxygen atom(s) and/or 1 or 2 sulfur atom(s) as a hetero atom(s)" represented by Cyc3 includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole rings and the like.

The "substituent" in the "5- to 6-membered mono-cyclic heterocyclic ring which may have a substituent(s)" represented by Cyc3 includes the same example of such as the "substituent" in the "cyclic ring which may have a substituent(s)" represented by Cyc1 described above.

Cyc4 represents a cyclic ring which may have a substituent(s).

The "cyclic ring" in the "cyclic ring which may have a substituent(s)" represented by Cyc4 includes the same example of the "cyclic ring" in the "cyclic ring which may have a substituent(s)" represented by Cyc1. The "substituent" in the "cyclic ring which may have a substituent(s)" represented by Cyc4 includes the same example of such as the "substituent" in the "cyclic ring which may have a substituent(s)" represented by Cyc1 described above.

Moreover, Cyc4 also represents 5- to 10-membered mono-cyclic or bi-cyclic carbocyclic ring which may have a substituent(s) or 5- to 10-membered mono-cyclic or bi-cyclic heterocyclic ring which may have a substituent(s).

The "5- to 10-membered mono-cyclic or bi-cyclic carbocyclic ring" in the "5- to 10-membered mono-cyclic or bi-cyclic carbocyclic ring which may have a substituent(s)" represented by Cyc4 includes, for example, a "5- to 10-membered mono-cyclic or bi-cyclic carbocyclic ring" and the like. The "5- to 10-membered mono-cyclic or bi-cyclic carbocyclic ring" represented by Cyc4 includes a "5- to 10-membered mono-cyclic or bi-cyclic unsaturated carbocyclic ring, partially or completely saturated carbocyclic ring", a "spiro-bound bi-cyclic carbocyclic ring, and crosslinked bi-cyclic carbocyclic ring" and the like.

The "5- to 10-membered mono-cyclic or bi-cyclic unsaturated carbocyclic ring, partially or completely saturated carbocyclic ring" represented by Cyc4 includes, for example, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene rings and the like. The "spiro-bound bi-cyclic carbocyclic ring" represented by Cyc4 includes, for example, spiro[4.4]nonane, spiro[4.5]decane rings and the like. The "crosslinked bi-cyclic carbocyclic ring" represented by Cyc4 includes, for example, bicyclo[2.2.1]heptane, bicyclo[2.2.1]hepta-2-ene, bicyclo[3.1.1]heptane, bicyclo[3.1.1]hepta-2-ene, bicyclo[3.2.1]octane, bicyclo[2.2.2]octane, bicyclo[2.2.2]octa-2-ene, adamantane, noradamantane rings and the like. Among the "5- to 10-membered mono-cyclic or bi-cyclic unsaturated carbocyclic ring" represented by Cyc4, a "5- to 10-membered mono-cyclic or bi-cyclic aromatic carbocyclic ring" represented by Cyc4 includes, for example, benzene, azulene, naphthalene rings and the like. The "substituent" in the "5- to 10-membered mono-cyclic or bi-cyclic carbocyclic ring which may have a substituent(s)" represented by Cyc4 includes the same example of such as the "substituent" in the "cyclic ring which may have a substituent(s)" represented by Cyc1 described above.

The "5- to 10-membered mono-cyclic or bi-cyclic heterocyclic ring" in the "5- to 10-membered mono-cyclic or bi-cyclic heterocyclic ring which may have a substituent(s)" represented by Cyc4 includes, for example, a "5- to 10-membered mono-cyclic or bi-cyclic heterocyclic ring having 1 to 4 nitrogen atom(s), 1 or 2 oxygen atom(s) and/or 1 or 2 sulfur atom(s) as a hetero atom(s)" and the like. Herein, the "5- to 10-membered mono-cyclic or bi-cyclic heterocyclic ring having 1 to 4 nitrogen atom(s), 1 or 2 oxygen atom(s) and/or 1 or 2 sulfur atom(s) as a hetero atom(s)" represented by Cyc4 includes a "5- to 10-membered mono-cyclic or bi-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof", a "spiro-bound bi-cyclic heterocyclic ring and crosslinked bi-cyclic heterocyclic ring".

The "5- to 10-membered mono-cyclic or bi-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof" represented by Cyc4 includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, isoxazolo[4,5-d]pyridazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydroxepine, tetrahydroxepine, perhydroxepine, dihydrothiophene, tetrahydrothiophene, dihydrothiopyran, tetrahydrothiopyran, dihydrothiepin, tetrahydrothiepin, perhydrothiepin, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydroxazine, tetrahydroxazine, dihydroxadiazine, tetrahydroxadiazine, dihydroxazepine, tetrahydroxazepine, perhydroxazepine, dihydroxadiazepine, tetrahydroxadiazepine, perhydroxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindane, benzodioxane, chroman, benzodithiolane, benzodithiane, 6,7-dihydro-5H-cyclopenta[b]pyrazine, 5H-cyclopenta[b]pyrazine, imidazo[2,1-b][1,3]thiazole rings and the like. The "spiro-bound bi-cyclic heterocyclic ring" represented by Cyc4 includes, for example, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane rings and the like. The "crosslinked bi-cyclic heterocyclic ring" represented by Cyc4 includes, for example, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane rings and the like. Among the "5- to 10-membered mono-cyclic or bi-cyclic unsaturated heterocyclic ring having 1 to 4 nitrogen atom(s), 1 or 2 oxygen atom(s) and/or 1 or 2 sulfur atom(s) as a hetero atom(s)" represented by Cyc4, a "5- to 10-membered mono-cyclic or bi-cyclic aromatic heterocyclic ring having 1 to 4 nitrogen atom(s), 1 or 2 oxygen atom(s) and/or 1 or 2 sulfur atom(s) as a hetero atom(s)" represented by Cyc4 includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, isoxazolo[4,5-d]pyridazine rings and the like.

The "substituent" in the "5- to 10-membered mono-cyclic or bi-cyclic heterocyclic ring which may have a substituent(s)" represented by Cyc4 includes the same example of such as the "substituent" in the "cyclic ring which may have a substituent(s)" represented by Cyc1 described above.

Cyc1$^1$ represents 5- to 6-membered mono-cyclic carbocyclic ring which may have a substituent(s) or 5- to 6-membered mono-cyclic heterocyclic ring which may have a substituent(s).

The "5- to 6-membered mono-cyclic carbocyclic ring" in the "5- to 6-membered mono-cyclic carbocyclic ring which may have a substituent(s)" represented by Cyc1$^1$ includes, for example, a "5- to 6-membered mono-cyclic carbocyclic ring" and the like. The "5- to 6-membered mono-cyclic carbocyclic ring" represented by Cyc1$^1$ includes a "5- to 6-membered mono-cyclic unsaturated carbocyclic ring, partially or completely saturated carbocyclic ring" and the like.

The "5- to 6-membered mono-cyclic unsaturated carbocyclic ring, partially or completely saturated carbocyclic ring" represented by Cyc1$^1$ includes, for example, cyclopentane, cyclohexane, cyclopentene, cyclohexene, cyclopentadiene, cyclohexadiene, benzene and the like. Among the "5- to 6-membered mono-cyclic unsaturated carbocyclic ring" represented by Cyc1$^1$, a "5- to 6-membered mono-cyclic aromatic carbocyclic ring" represented by Cyc1$^1$ includes, for example, benzene.

The "substituent" in the "5- to 6-membered mono-cyclic carbocyclic ring which may have a substituent(s)" represented by Cyc1$^1$ includes the same example of such as the "substituent" in the "cyclic ring which may have a substituent(s)" represented by Cyc1 described above.

The "5- to 6-membered mono-cyclic heterocyclic ring" in the "5- to 6-membered mono-cyclic heterocyclic ring which may have a substituent(s)" represented by Cyc1¹ includes the same example of the "5- to 6-membered mono-cyclic heterocyclic ring" in the "5- to 6-membered mono-cyclic heterocyclic ring which may have a substituent(s)" represented by Cyc3. The "substituent" in the "5- to 6-membered mono-cyclic heterocyclic ring which may have a substituent(s)" represented by Cyc1¹ includes the same example of such as the "substituent" in the "cyclic ring which may have a substituent(s)" represented by Cyc1 described above.

Cyc1³ represents

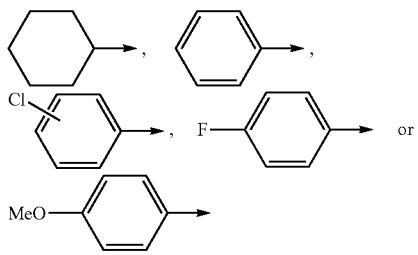

wherein the arrow represents a binding position to isoxazolyl carbon.

Cyc2¹ represents 5-membered mono-cyclic heterocyclic ring which may have a substituent(s).

The "5-membered mono-cyclic heterocyclic ring" in the "5-membered mono-cyclic heterocyclic ring which may have a substituent(s)" represented by Cyc2¹ includes, for example, a "5-membered mono-cyclic heterocyclic ring having 1 to 4 nitrogen atom(s), 1 or 2 oxygen atom(s) and/or 1 or 2 sulfur atom(s) as a hetero atom(s)" and the like. Herein, the "5-membered mono-cyclic heterocyclic ring having 1 to 4 nitrogen atom(s), 1 or 2 oxygen atom(s) and/or 1 or 2 sulfur atom(s) as a hetero atom(s)" represented by Cyc2¹ includes a "5-membered mono-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof".

The "5-membered mono-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof" represented by Cyc2¹ includes, for example, pyrrole, imidazole, triazole, pyrazole, furan, thiophene, oxazole, isoxazole, thiazole, isothiazole, furazan, oxadiazole, thiadiazole, pyrroline, pyrrolidine, imidazoline, imidazolidine, triazoline, triazolidine, pyrazoline, pyrazolidine, dihydrofuran, tetrahydrofuran, dihydrothiophene, tetrahydrothiophene, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydrothiadiazole, tetrahydrothiadiazole (thiadiazolidine), and the like. Among the "5-membered mono-cyclic unsaturated heterocyclic ring having 1 to 4 nitrogen atom(s), 1 or 2 oxygen atom(s) and/or 1 or 2 sulfur atom(s) as a hetero atom(s)" represented by Cyc2¹, a "5-membered mono-cyclic aromatic heterocyclic ring having 1 to 4 nitrogen atom(s), 1 or 2 oxygen atom(s) and/or 1 or 2 sulfur atom(s) as a hetero atom(s)" represented by Cyc2¹ includes, for example, pyrrole, imidazole, triazole, pyrazole, furan, thiophene, oxazole, isoxazole, thiazole, isothiazole, furazan, oxadiazole, thiadiazole, and the like.

The "substituent" in the "5-membered mono-cyclic heterocyclic ring which may have a substituent(s)" represented by Cyc2¹ includes the same example of such as the "substituent" in the "cyclic ring which may have a substituent(s)" represented by Cyc1 described above.

Cyc4¹ represents 5- to 10-membered mono-cyclic or bi-cyclic carbocyclic ring which may have a substituent(s) or 5- to 10-membered mono-cyclic or bi-cyclic heterocyclic ring which may have a substituent(s).

The "5- to 10-membered mono-cyclic or bi-cyclic carbocyclic ring" in the "5- to 10-membered mono-cyclic or bi-cyclic carbocyclic ring which may have a substituent(s)" represented by Cyc4¹ includes the same example of the "5- to 10-membered mono-cyclic or bi-cyclic carbocyclic ring" in the "5- to 10-membered mono-cyclic or bi-cyclic carbocyclic ring which may have a substituent(s)" represented by Cyc4. The "substituent" in the "5- to 10-membered mono-cyclic or bi-cyclic carbocyclic ring which may have a substituent(s)" represented by Cyc4¹ includes the same example of such as the "substituent" in the "cyclic ring which may have a substituent(s)" represented by Cyc1 described above.

The "5- to 10-membered mono-cyclic or bi-cyclic heterocyclic ring" in the "5- to 10-membered mono-cyclic or bi-cyclic heterocyclic ring which may have a substituent(s)" represented by Cyc4¹ includes the same example of the "5- to 10-membered mono-cyclic or bi-cyclic heterocyclic ring" in the "5- to 10-membered mono-cyclic or bi-cyclic heterocyclic ring which may have a substituent(s)" represented by Cyc4. The "substituent" in the "5- to 10-membered mono-cyclic or bi-cyclic heterocyclic ring which may have a substituent(s)" represented by Cyc4¹ includes the same example of such as the "substituent" in the "cyclic ring which may have a substituent(s)" represented by Cyc1 described above.

Cyc4² represents

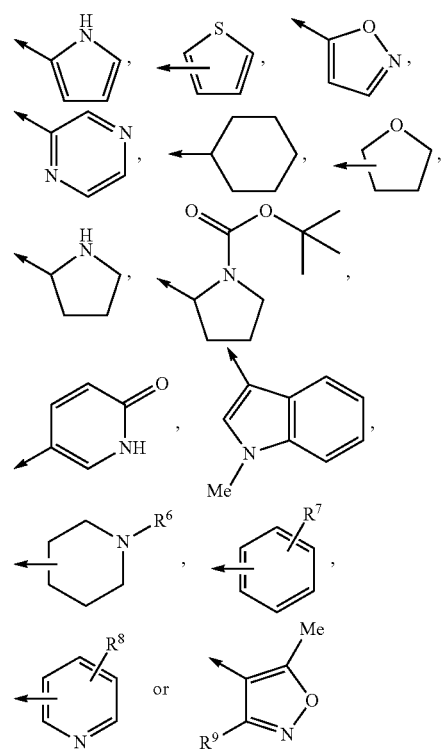

wherein the arrow represents a binding position to carbonyl carbon.

X represents —CR³R⁴—, —CO— or —SO₂—.

X¹ represents —CH₂—, —CO— or —SO₂—.

R¹ represents hydrogen or C1-4 alkyl which may have a substituent(s).

The "C1-4 alkyl" in the "C1-4 alkyl which may have a substituent(s)" represented by $R^1$ includes, for example, a straight or branched C1-4 alkyl such as methyl, ethyl, propyl, isopropyl, butyl, isobutyl, sec-butyl, tert-butyl, and the like.

The "substituent" in the "C1-4 alkyl which may have a substituent(s)" represented by $R^1$ includes the same example of such as the "substituent" in the "alkyl which may have a substituent(s)" as the "substituent" in the "cyclic ring which may have a substituent(s)" represented by Cyc1 described above.

$R^2$ represents hydrogen or C1-4 alkyl which may have a substituent(s).

The "C1-4 alkyl" in the "C1-4 alkyl which may have a substituent(s)" represented by $R^2$ includes the same example of the "C1-4 alkyl which may have a substituent(s)" represented by $R^1$. The "substituent" in the "C1-4 alkyl which may have a substituent(s)" represented by $R^2$ includes the same example of such as the "substituent" in the "alkyl which may have a substituent(s)" as the "substituent" in the "cyclic ring which may have a substituent(s)" represented by Cyc1 described above.

$R^3$ represents hydrogen or C1-4 alkyl which may have a substituent(s).

The "C1-4 alkyl" in the "C1-4 alkyl which may have a substituent(s)" represented by $R^3$ includes the same example of the "C1-4 alkyl which may have a substituent(s)" represented by $R^1$. The "substituent" in the "C1-4 alkyl which may have a substituent(s)" represented by $R^3$ includes the same example of such as the "substituent" in the "alkyl which may have a substituent(s)" as the "substituent" in the "cyclic ring which may have a substituent(s)" represented by Cyc1 described above.

$R^4$ represents hydrogen or C1-4 alkyl which may have a substituent(s).

The "C1-4 alkyl" in the "C1-4 alkyl which may have a substituent(s)" represented by $R^4$ includes the same example of the "C1-4 alkyl which may have a substituent(s)" represented by $R^1$. The "substituent" in the "C1-4 alkyl which may have a substituent(s)" represented by $R^4$ includes the same example of such as the "substituent" in the "alkyl which may have a substituent(s)" as the "substituent" in the "cyclic ring which may have a substituent(s)" represented by Cyc1 described above.

$R^5$ represents hydrogen or C1-4 alkyl which may have a substituent(s).

The "C1-4 alkyl" in the "C1-4 alkyl which may have a substituent(s)" represented by $R^5$ includes the same example of the "C1-4 alkyl which may have a substituent(s)" represented by $R^1$. The "substituent" in the "C1-4 alkyl which may have a substituent(s)" represented by $R^5$ includes the same example of such as the "substituent" in the "alkyl which may have a substituent(s)" as the "substituent" in the "cyclic ring which may have a substituent(s)" represented by Cyc1 described above.

Z represents —N(R⁵)—CO—, —CO—N(R⁵)—, —N(R⁵)—, bond or —O—.

The "C1-4 alkylene" in the "C1-4 alkylene which may have a substituent(s)" represented by the term "$R^5$ and the substituent of Cyc4 may be taken together to form" as herein defined includes, for example, methylene, ethylene, propylene, buthylene, and the like. The "substituent" in the "C1-4 alkylene which may have a substituent(s)" represented by the term "$R^5$ and the substituent of Cyc4 may be taken together to form" as herein defined includes the same example of such as the "substituent" in the "alkyl which may have a substituent(s)" as the "substituent" in the "cyclic ring which may have a substituent(s)" represented by Cyc1 described above.

The "C2-4 alkenylene" in the "C2-4 alkenylene which may have a substituent(s)" represented by the term "$R^5$ and the substituent of Cyc4 may be taken together to form" as herein defined includes, for example, vinylene, propenylene, butenylene, and the like. The "substituent" in the "C2-4 alkenylene which may have a substituent(s)" represented by the term "$R^5$ and the substituent of Cyc4 may be taken together to form" as herein defined includes the same example of such as the "substituent" in the "alkyl which may have a substituent(s)" as the "substituent" in the "cyclic ring which may have a substituent(s)" represented by Cyc1 described above.

$R^{51}$ represents hydrogen or C1-4 alkyl which may have a substituent(s).

The "C1-4 alkyl" in the "C1-4 alkyl which may have a substituent(s)" represented by $R^{51}$ includes the same example of the "C1-4 alkyl which may have a substituent(s)" represented by $R^1$. The "substituent" in the "C1-4 alkyl which may have a substituent(s)" represented by $R^{51}$ includes the same example of such as the "substituent" in the "alkyl which may have a substituent(s)" as the "substituent" in the "cyclic ring which may have a substituent(s)" represented by Cyc1 described above.

$Z^1$ represents —N(R⁵¹)—CO—, —CO—N(R⁵¹)—, —N(R⁵¹)—, bond or —O—.

The "C1-4 alkylene" in the "C1-4 alkylene which may have a substituent(s)" represented by the term "$R^{51}$ and the substituent of Cyc4¹ may be taken together to form" as herein defined includes the same example of the "C1-4 alkylene" in the "C1-4 alkylene which may have a substituent(s)" represented by the term "$R^5$ and the substituent of Cyc4 may be taken together to form" as herein defined. The "substituent" in the "C1-4 alkylene which may have a substituent(s)" represented by the term "$R^{51}$ and the substituent of Cyc4¹ may be taken together to form" as herein defined includes the same example of such as the "substituent" in the "alkyl which may have a substituent(s)" as the "substituent" in the "cyclic ring which may have a substituent(s)" represented by Cyc1 described above.

The "C2-4 alkenylene" in the "C2-4 alkenylene which may have a substituent(s)" represented by the term "$R^{51}$ and the substituent of Cyc4¹ may be taken together to form" as herein defined includes the same example of the "C2-4 alkenylene" in the "C2-4 alkenylene which may have a substituent(s)" represented by the term "$R^5$ and the substituent of Cyc4 may be taken together to form" as herein defined. The "substituent" in the "C2-4 alkenylene which may have a substituent(s)" represented by the term "$R^{51}$ and the substituent of Cyc4¹ may be taken together to form" as herein defined includes the same example of such as the "substituent" in the "alkyl which may have a substituent(s)" as the "substituent" in the "cyclic ring which may have a substituent(s)" represented by Cyc1 described above.

$R^{10}$ represents hydrogen or a substituent.

The "substituent" represented by $R^{10}$ includes the same example of such as the "substituent" in the "cyclic ring which may have a substituent(s)" represented by Cyc1 described above.

$R^{110}$ represents a substituent.

The "substituent" represented by $R^{110}$ includes the same example of such as the "substituent" in the "cyclic ring which may have a substituent(s)" represented by Cyc1 described above.

p represents an integer of 0 to 8; when p is an integer of 2 to 8, then each $R^{110}$ may be same or different.

$R^6$ represents hydrogen, acetyl, tert-butoxycarbonyl, methylsulfonyl or phenylsulfonyl.

$R^7$ represents hydrogen, chlorine, phenyl, trifluoromethyl, methoxy, phenoxy, cyano or N-acetylamino.

$R^8$ represents hydrogen, N,N-dimethylamino or N-morpholinyl.

$R^9$ represents hydrogen, methyl or phenyl.

Cyc8 represents (1) 5- to 6-membered mono-cyclic carbocyclic ring which may have a substituent(s), 5- to 6-membered mono-cyclic heterocyclic ring which may have a substituent(s) or (2) 8- to 10-membered bi-cyclic carbocyclic ring which may have a substituent(s) or 8- to 10-membered bi-cyclic heterocyclic ring which may have a substituent(s).

The "5- to 6-membered mono-cyclic carbocyclic ring" in the "5- to 6-membered mono-cyclic carbocyclic ring which may have a substituent(s)" represented by Cyc8 includes the same example of the "5- to 6-membered mono-cyclic carbocyclic ring" in the "5- to 6-membered mono-cyclic carbocyclic ring which may have a substituent(s)" represented by Cyc1$^1$. The "substituent" in the "5- to 6-membered mono-cyclic carbocyclic ring which may have a substituent(s)" represented by Cyc8 includes the same example of such as the "substituent" in the "cyclic ring which may have a substituent(s)" represented by Cyc1 described above.

The "5- to 6-membered mono-cyclic heterocyclic ring" in the "5- to 6-membered mono-cyclic heterocyclic ring which may have a substituent(s)" represented by Cyc8 includes the same example of the "5- to 6-membered mono-cyclic heterocyclic ring" in the "5- to 6-membered mono-cyclic heterocyclic ring which may have a substituent(s)" represented by Cyc1$^1$. The "substituent" in the "5- to 6-membered mono-cyclic heterocyclic ring which may have a substituent(s)" represented by Cyc8 includes the same example of such as the "substituent" in the "cyclic ring which may have a substituent(s)" represented by Cyc1 described above.

The "8- to 10-membered bi-cyclic carbocyclic ring" in the "8- to 10-membered bi-cyclic carbocyclic ring which may have a substituent(s)" represented by Cyc8 includes, for example, a "8- to 10-membered bi-cyclic carbocyclic ring", and the like. The "8- to 10-membered bi-cyclic carbocyclic ring" represented by Cyc8 includes a "8- to 10-membered bi-cyclic unsaturated carbocyclic ring, partially or completely saturated carbocyclic ring", and the like.

The "8- to 10-membered bi-cyclic unsaturated carbocyclic ring, partially or completely saturated carbocyclic ring" represented by Cyc8 includes, for example, perhydropentalene, perhydroazulene, indene, perhydroindene, indane, dihydronaphthalene, tetrahydronaphthalene, perhydronaphthalene rings and the like. Among the "8- to 10-membered bi-cyclic unsaturated carbocyclic ring" represented by Cyc8, a "8- to 10-membered bi-cyclic aromatic carbocyclic ring" represented by Cyc8 includes, for example, pentalene, azulene, naphthalene rings and the like.

The "substituent" in the "8- to 10-membered bi-cyclic carbocyclic ring which may have a substituent(s)" represented by Cyc8 includes the same example of such as the "substituent" in the "cyclic ring which may have a substituent(s)" represented by Cyc1 described above.

The "8- to 10-membered bi-cyclic heterocyclic ring" in the "8- to 10-membered bi-cyclic heterocyclic ring which may have a substituent(s)" represented by Cyc8 includes, for example, a "8- to 10-membered bi-cyclic heterocyclic ring having 1 to 4 nitrogen atom(s), 1 or 2 oxygen atom(s) and/or 1 or 2 sulfur atom(s) as a hetero atom(s)", and the like. Herein, the "8- to 10-membered bi-cyclic heterocyclic ring having 1 to 4 nitrogen atom(s), 1 or 2 oxygen atom(s) and/or 1 or 2 sulfur atom(s) as a hetero atom(s)" represented by Cyc8 includes a "8- to 10-membered bi-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof".

The "8- to 10-membered bi-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof" represented by Cyc8 includes, for example, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, isoxazolo[4,5-d]pyridazine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, benzodioxepane, dihydrobenzoxazepine, tetrahydrobenzoxazepine, dioxaindane, benzodioxane, chroman, benzodithiolane, benzodithiane, 6,7-dihydro-5H-cyclopenta[b]pyrazine, 5H-cyclopenta[b]pyrazine, imidazo[2,1-b][1,3]thiazole rings and the like. Among the "8- to 10-membered bi-cyclic unsaturated heterocyclic ring having 1 to 4 nitrogen atom(s), 1 or 2 oxygen atom(s) and/or 1 or 2 sulfur atom(s) as a hetero atom(s)" represented by Cyc8, a "8- to 10-membered bi-cyclic aromatic heterocyclic ring having 1 to 4 nitrogen atom(s), 1 or 2 oxygen atom(s) and/or 1 or 2 sulfur atom(s) as a hetero atom(s)" represented by Cyc8 includes, for example, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, isoxazolo[4,5-d]pyridazine rings and the like.

The "substituent" in the "8- to 10-membered bi-cyclic heterocyclic ring which may have a substituent(s)" represented by Cyc8 includes the same example of such as the "substituent" in the "cyclic ring which may have a substituent(s)" represented by Cyc1 described above.

Moreover, Cyc8 also represents 5- to 6-membered mono-cyclic carbocyclic ring which have at least two substituents or 6-membered mono-cyclic heterocyclic ring which have at least two substituents.

The "5- to 6-membered mono-cyclic carbocyclic ring" in the "5- to 6-membered mono-cyclic carbocyclic ring which have at least two substituents" represented by Cyc8 includes the same example of the "5- to 6-membered mono-cyclic carbocyclic ring which may have a substituent(s)" represented by Cyc1¹. The "substituent" in the "5- to 6-membered mono-cyclic carbocyclic ring which have at least two substituents" represented by Cyc8 includes the same example of such as the "substituent" in the "cyclic ring which may have a substituent(s)" represented by Cyc1 described above.

The "6-membered mono-cyclic heterocyclic ring" in the "6-membered mono-cyclic heterocyclic ring which have at least two substituents" represented by Cyc8 includes, for example, a "6-membered mono-cyclic heterocyclic ring having 1 to 4 nitrogen atom(s), 1 or 2 oxygen atom(s) and/or 1 or 2 sulfur atom(s) as a hetero atom(s)" and the like. Herein, the "6-membered mono-cyclic heterocyclic ring having 1 to 4 nitrogen atom(s), 1 or 2 oxygen atom(s) and/or 1 or 2 sulfur atom(s) as a hetero atom(s)" represented by Cyc8 includes a "6-membered mono-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof".

The "6-membered mono-cyclic unsaturated heterocyclic ring having 1 to 4 nitrogen atom(s), 1 or 2 oxygen atom(s) and/or 1 or 2 sulfur atom(s) as a hetero atom(s), or partially or completely saturated one thereof" represented by Cyc8 includes, for example, pyridine, pyrazine, pyrimidine, pyridazine, pyran, thiopyran, oxazine, oxadiazine, thiazine, thiadiazine, dihydropyridine, tetrahydropyridine, piperidine, dihydropyrazine, tetrahydropyrazine, dihydropyrimidine, tetrahydropyrimidine, perhydropyrimidine, dihydropyridazine, tetrahydropyridazine, perhydropyridazine, dihydropyran, tetrahydropyran, dihydroxazine, tetrahydroxazine, dihydroxadiazine, tetrahydroxadiazine, dihydrothiazine, tetrahydrothiazine, dihydrothiadiazine, tetrahydrothiadiazine, morpholine, thiomorpholine rings and the like. Among the "6-membered mono-cyclic unsaturated heterocyclic ring having 1 to 4 nitrogen atom(s), 1 or 2 oxygen atom(s) and/or 1 or 2 sulfur atom(s) as a hetero atom(s)" represented by Cyc8, a "6-membered mono-cyclic aromatic heterocyclic ring having 1 to 4 nitrogen atom(s), 1 or 2 oxygen atom(s) and/or 1 or 2 sulfur atom(s) as a hetero atom(s)" represented by Cyc8 includes, for example, pyridine, pyrazine, pyrimidine, pyridazine rings and the like.

The "substituent" in the "6-membered mono-cyclic heterocyclic ring which have two substituents" represented by Cyc8 includes the same example of such as the "substituent" in the "cyclic ring which may have a substituent(s)" represented by Cyc1 described above.

Cyc9 represents (1) 5- to 6-membered mono-cyclic carbocyclic ring which may have a substituent(s) or 5- to 6-membered mono-cyclic heterocyclic ring which may have a substituent(s) or (2) 8- to 10-membered bi-cyclic carbocyclic ring which may have a substituent(s) or 8- to 10-membered bi-cyclic heterocyclic ring which may have a substituent(s);

The "5- to 6-membered mono-cyclic carbocyclic ring" in the "5- to 6-membered mono-cyclic carbocyclic ring which may have a substituent(s)" represented by Cyc9 includes the same example of the "5- to 6-membered mono-cyclic carbocyclic ring" in the "5- to 6-membered mono-cyclic carbocyclic ring which may have a substituent(s)" represented by Cyc1¹. The "substituent" in the "5- to 6-membered mono-cyclic carbocyclic ring which may have a substituent(s)" represented by Cyc9 includes the same example of such as the "substituent" in the "cyclic ring which may have a substituent(s)" represented by Cyc1 described above.

The "5- to 6-membered mono-cyclic heterocyclic ring" in the "5- to 6-membered mono-cyclic heterocyclic ring which may have a substituent(s)" represented by Cyc9 includes the same example of the "5- to 6-membered mono-cyclic heterocyclic ring" in the "5- to 6-membered mono-cyclic heterocyclic ring which may have a substituent(s)" represented by Cyc1¹. The "substituent" in the "5- to 6-membered mono-cyclic heterocyclic ring which may have a substituent(s)" represented by Cyc9 includes the same example of such as the "substituent" in the "cyclic ring which may have a substituent(s)" represented by Cyc1 described above.

The "8- to 10-membered bi-cyclic carbocyclic ring" in the "8- to 10-membered bi-cyclic carbocyclic ring which may have a substituent(s)" represented by Cyc9 includes the same example of the "8- to 10-membered bi-cyclic carbocyclic ring" in the "8- to 10-membered bi-cyclic carbocyclic ring which may have a substituent(s)" represented by Cyc8. The "substituent" in the "8- to 10-membered bi-cyclic carbocyclic ring which may have a substituent(s)" represented by Cyc9 includes the same example of such as the "substituent" in the "cyclic ring which may have a substituent(s)" represented by Cyc1 described above.

The "8- to 10-membered bi-cyclic heterocyclic ring" in the "8- to 10-membered bi-cyclic heterocyclic ring which may have a substituent(s)" represented by Cyc9 includes the same example of the "8- to 10-membered bi-cyclic heterocyclic ring" in the "8- to 10-membered bi-cyclic heterocyclic ring which may have a substituent(s)" represented by Cyc8. The "substituent" in the "8- to 10-membered bi-cyclic heterocyclic ring which may have a substituent(s)" represented by Cyc9 includes the same example of such as the "substituent" in the "cyclic ring which may have a substituent(s)" represented by Cyc1 described above.

Moreover, Cyc9 also represents 5- to 6-membered mono-cyclic carbocyclic ring which have at least two substituents or 5- to 6-membered mono-cyclic heterocyclic ring which have at least two substituents.

The "5- to 6-membered mono-cyclic carbocyclic ring" in the "5- to 6-membered mono-cyclic carbocyclic ring which have at least two substituents" represented by Cyc9 includes the same example of the "5- to 6-membered mono-cyclic carbocyclic ring which may have a substituent(s)" represented by Cyc1¹. The "substituent" in the "5- to 6-membered mono-cyclic carbocyclic ring which have at least two substituents" represented by Cyc9 includes the same example of such as the "substituent" in the "cyclic ring which may have a substituent(s)" represented by Cyc1 described above.

The "5- to 6-membered mono-cyclic heterocyclic ring" in the "5- to 6-membered mono-cyclic heterocyclic ring which have at least two substituents" represented by Cyc9 includes the same example of the "5- to 6-membered mono-cyclic heterocyclic ring" in the "5- to 6-membered mono-cyclic heterocyclic ring which may have a substituent(s)" represented by Cyc1¹. The "substituent" in the "5- to 6-membered mono-cyclic heterocyclic ring which have at least two substituents" represented by Cyc9 includes the same example of such as the "substituent" in the "cyclic ring which may have a substituent(s)" represented by Cyc1 described above.

Cyc10 represents 5- to 6-membered mono-cyclic heterocyclic ring which may have a substituent(s).

The "5- to 6-membered mono-cyclic heterocyclic ring" in the "5- to 6-membered mono-cyclic heterocyclic ring which may have a substituent(s)" represented by Cyc10 includes pyrrolidine, pyrroline, piperidine, tetrahydropyridine rings and the like. The "substituent" in the "5- to 6-membered mono-cyclic heterocyclic ring which may have a substituent(s)" represented by Cyc10 includes the same example of such as the "substituent" in the "cyclic ring which may have a substituent(s)" represented by Cyc1 described above.

Cyc11 represents 6-membered mono-cyclic carbocyclic ring which may have a substituent(s) or 6-membered mono-cyclic heterocyclic ring which may have a substituent(s).

The "6-membered mono-cyclic carbocyclic ring" in the "6-membered mono-cyclic carbocyclic ring which may have a substituent(s)" represented by Cyc11 includes, for example, a "6-membered mono-cyclic carbocyclic ring" and the like. The "6-membered mono-cyclic carbocyclic ring" represented by Cyc11 includes, for example, a "6-membered mono-cyclic unsaturated carbocyclic ring, partially or completely saturated carbocyclic ring" and the like.

The "6-membered mono-cyclic unsaturated carbocyclic ring, partially or completely saturated carbocyclic ring" represented by Cyc11 includes, for example, cyclohexane, cyclohexene, cyclohexadiene, benzene. Among the "6-membered mono-cyclic unsaturated carbocyclic ring" represented by Cyc11, a "6-membered mono-cyclic aromatic carbocyclic ring" represented by Cyc11 includes, for example, benzene.

The "substituent" in the "6-membered mono-cyclic carbocyclic ring which may have a substituent(s)" represented by Cyc11 includes the same example of such as the "substituent" in the "cyclic ring which may have a substituent(s)" represented by Cyc1 described above.

The "6-membered mono-cyclic heterocyclic ring" in the "6-membered mono-cyclic heterocyclic ring which may have a substituent(s)" represented by Cyc11 includes the same example of the "6-membered mono-cyclic heterocyclic ring which have at least two substituents" represented by Cyc8. The "substituent" in the "6-membered mono-cyclic heterocyclic ring which may have a substituent(s)" represented by Cyc11 includes the same example of such as the "substituent" in the "cyclic ring which may have a substituent(s)" represented by Cyc1 described above.

Cyc12 represents 5- to 10-membered mono-cyclic or bi-cyclic carbocyclic ring which may have a substituent(s) or 5- to 10-membered mono-cyclic or bi-cyclic heterocyclic ring which may have a substituent(s).

The "5- to 10-membered mono-cyclic or bi-cyclic carbocyclic ring" in the "5- to 10-membered mono-cyclic or bi-cyclic carbocyclic ring which may have a substituent(s)" represented by Cyc12 includes the same example of the "5- to 10-membered mono-cyclic or bi-cyclic carbocyclic ring" in the "5- to 10-membered mono-cyclic or bi-cyclic carbocyclic ring which may have a substituent(s)" represented by Cyc4$^1$. The "substituent" in the "5- to 10-membered mono-cyclic or bi-cyclic carbocyclic ring which may have a substituent(s)" represented by Cyc12 includes the same example of such as the "substituent" in the "cyclic ring which may have a substituent(s)" represented by Cyc1 described above.

The "5- to 10-membered mono-cyclic or bi-cyclic heterocyclic ring" in the "5- to 10-membered mono-cyclic or bi-cyclic heterocyclic ring which may have a substituent(s)" represented by Cyc12 includes the same example of the "5- to 10-membered mono-cyclic or bi-cyclic heterocyclic ring" in the "5- to 10-membered mono-cyclic or bi-cyclic heterocyclic ring which may have a substituent(s)" represented by Cyc4$^1$. The "substituent" in the "5- to 10-membered mono-cyclic or bi-cyclic heterocyclic ring which may have a substituent(s)" represented by Cyc12 includes the same example of such as the "substituent" in the "cyclic ring which may have a substituent(s)" represented by Cyc1 described above.

E represents —O— or —N(R$^{54}$)—.

R$^{52}$ represents hydrogen or C1-4 alkyl which may have a substituent(s).

The "C1-4 alkyl" in the "C1-4 alkyl which may have a substituent(s)" represented by R$^{52}$ includes the same example of the "C1-4 alkyl which may have a substituent(s)" represented by R$^1$. The "substituent" in the "C1-4 alkyl which may have a substituent(s)" represented by R$^{52}$ includes the same example of such as the "substituent" in the "alkyl which may have a substituent(s)" as the "substituent" in the "cyclic ring which may have a substituent(s)" represented by Cyc1 described above.

R$^{53}$ represents hydrogen or C1-4 alkyl which may have a substituent(s).

The "C1-4 alkyl" in the "C1-4 alkyl which may have a substituent(s)" represented by R$^{53}$ includes the same example of the "C1-4 alkyl which may have a substituent(s)" represented by R$^1$. The "substituent" in the "C1-4 alkyl which may have a substituent(s)" represented by R$^{53}$ includes, for example, the same example of such as the "substituent" in the "alkyl which may have a substituent(s)" as the "substituent" in the "cyclic ring which may have a substituent(s)" represented by Cyc1 described above.

R$^{54}$ represents hydrogen or C1-4 alkyl which may have a substituent(s).

The "C1-4 alkyl" in the "C1-4 alkyl which may have a substituent(s)" represented by R$^{54}$ includes the same example of the "C1-4 alkyl which may have a substituent(s)" represented by R$^1$. The "substituent" in the "C1-4 alkyl which may have a substituent(s)" represented by R$^{54}$ includes the same example of such as the "substituent" in the "alkyl which may have a substituent(s)" as the "substituent" in the "cyclic ring which may have a substituent(s)" represented by Cyc1 described above.

W$^1$ represents CH or N;
when W$^1$ represents CH, then the hydrogen of CH is optionally substituted with R$^{11}$.

W$^2$ represents CH or N;
when W$^2$ represents CH, then the hydrogen of CH is optionally substituted with R$^{11}$.

W$^3$ represents CH or N.
when W$^3$ represents CH, then the hydrogen of CH is optionally substituted with R$^{12}$.

W$^4$ represents CH or N.
when W$^4$ represents CH, then the hydrogen of CH is optionally substituted with R$^{12}$.

W$^5$ represents CH or N.
when W$^5$ represents CH, then the hydrogen of CH is optionally substituted with R$^{14}$, R$^{15}$ or R$^{16}$.

R$^{11}$ represents halogen, OH, C1-4 alkoxy which may have a substituent(s), C1-4 alkyl which may have a substituent(s), cyano or amino.

The "halogen" represented by R$^{11}$ includes, for example, fluorine, chlorine, bromine and iodine, and the like.

The "C1-4 alkoxy" in the "C1-4 alkoxy which may have a substituent(s)" represented by R$^{11}$ includes, for example, a straight or branched C1-4 alkoxy such as methoxy, ethoxy, propoxy, isopropoxy, butoxy, isobutoxy, sec-butoxy, tert-butoxy, and the like. The "substituent" in the "C1-4 alkoxy which may have a substituent(s)" represented by R$^{11}$ includes the same example of such as the "substituent" in the "alkyl which may have a substituent(s)" as the "substituent" in the "cyclic ring which may have a substituent(s)" represented by Cyc1 described above.

The "C1-4 alkyl" in the "C1-4 alkyl which may have a substituent(s)" represented by R$^1$ the same example of the "C1-4 alkyl which may have a substituent(s)" represented by R$^1$. The "substituent" in the "C1-4 alkyl which may have a substituent(s)" represented by R$^{11}$ includes the same example of such as the "substituent" in the "alkyl which may have a substituent(s)" as the "substituent" in the "cyclic ring which may have a substituent(s)" represented by Cyc1 described above.

n represents an integer of 2 to 4.

$R^{12}$ represents halogen, OH, C1-4 alkoxy which may have a substituent(s), C1-4 alkyl which may have a substituent(s), cyano or amino.

The "halogen" represented by $R^{12}$ includes the same example of the "halogen" represented by $R^{11}$.

The "C1-4 alkoxy" in the "C1-4 alkoxy which may have a substituent(s)" represented by $R^{12}$ includes the same example of the "C1-4 alkoxy" in the "C1-4 alkoxy which may have a substituent(s)" represented by $R^{11}$. The "substituent" in the "C1-4 alkoxy which may have a substituent(s)" represented by $R^{12}$ includes the same example of such as the "substituent" in the "alkyl which may have a substituent(s)" as the "substituent" in the "cyclic ring which may have a substituent(s)" represented by Cyc1 described above.

The "C1-4 alkyl" in the "C1-4 alkyl which may have a substituent(s)" represented by $R^{12}$ includes the same example of the "C1-4 alkyl which may have a substituent(s)" represented by $R^1$. The "substituent" in the "C1-4 alkyl which may have a substituent(s)" represented by $R^{12}$ includes the same example of such as the "substituent" in the "alkyl which may have a substituent(s)" as the "substituent" in the "cyclic ring which may have a substituent(s)" represented by Cyc1 described above.

m represents an integer of 0 to 4;
when m is an integer of 2 to 4, then each $R^{12}$ may be same or different.

$R^{13}$ is C1-4 alkyl which may have a substitutent(s).

The "C1-4 alkyl" in the "C1-4 alkyl which may have a substituent(s)" represented by $R^{13}$ includes the same example of the "C1-4 alkyl which may have a substituent(s)" represented by $R^1$. The "substituent" in the "C1-4 alkyl which may have a substituent(s)" represented by $R^{13}$ includes the same example of such as the "substituent" in the "alkyl which may have a substituent(s)" as the "substituent" in the "cyclic ring which may have a substituent(s)" represented by Cyc1 described above.

$R^{14}$ represents cyano or amino.

$R^{15}$ represents halogen, cyano or amino.

The "halogen" represented by $R^{15}$ includes the same example of the "halogen" represented by $R^{11}$.

$R^{16}$ represents halogen, OH, C1-4 alkoxy which may have a substituent(s), C1-4 alkyl which may have a substituent(s), cyano or amino.

The "halogen" represented by $R^{16}$ includes the same example of the "halogen" represented by $R^{11}$.

The "C1-4 alkoxy" in the "C1-4 alkoxy which may have a substituent(s)" represented by $R^{16}$ includes the same example of the "C1-4 alkoxy" in the "C1-4 alkoxy which may have a substituent(s)" represented by $R^{11}$. The "substituent" in the "C1-4 alkoxy which may have a substituent(s)" represented by $R^{16}$ includes the same example of such as the "substituent" in the "alkyl which may have a substituent(s)" as the "substituent" in the "cyclic ring which may have a substituent(s)" represented by Cyc1 described above.

The "C1-4 alkyl" in the "C1-4 alkyl which may have a substituent(s)" represented by $R^{16}$ includes the same example of the "C1-4 alkyl which may have a substituent(s)" represented by $R^1$. The "substituent" in the "C1-4 alkyl which may have a substituent(s)" represented by $R^{16}$ includes the same example of such as the "substituent" in the "alkyl which may have a substituent(s)" as the "substituent" in the "cyclic ring which may have a substituent(s)" represented by Cyc1 described above.

A prodrug of the compound of the formula (I) means a compound which is converted to the compound represented by the formula (I) by the reaction with an enzyme, a gastric acid, or the like, in the living body. Examples of the prodrug for the compound represented by the formula (I) include a compound wherein the amino group of the compound represented by the formula (I) is acylated, alkylated, phosphorylated, or the like (for example, a compound wherein the amino group of the compound represented by the formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); a compound wherein the hydroxy group of the compound represented by the formula (I) is acylated, alkylated, phosphorylated, borated, or the like (for example, a compound wherein the hydroxy group of the compound represented by the formula (I) is modified by acetylation, palmitoylation, propanoylation, pivaloylation, succinylation, fumaration, alanylation, dimethylaminomethylcarbonylation, etc.); a compound wherein the carboxyl of the compound represented by the formula (I) is modified by esterification, amidation, or the like (for example, a compound wherein the carboxyl of the compound represented by the formula (I) is esterified or amidated with ethyl ester, phenyl ester, carboxymethyl ester, dimethylaminomethyl ester, pivaloyloxymethyl ester, 1-((ethoxycarbonyl)oxy)ethyl ester, phthalidyl ester, (5-methyl-2-oxo-1,3-dioxolen-4-yl)methyl ester, 1-((cyclohexyloxy)carbonyl)oxy)ethyl ester, methyl amide, etc.), and the like. These compounds may be prepared by known method. In addition, the prodrug for the compound represented by the formula (I) may take a hydrate form or a non-hydrate form. In addition, the prodrug of the compound represented by the formula (I) may be a compound which is converted into the compound represented by the formula (I) under the physiological conditions as described in *Pharmaceutical Research and Development*, Vol. 7 "Molecular Design", pages 163-198 published in 1990 by Hirokawa Publishing Co. In addition, a compound (1) may be labeled with an isotope (for example, $^3H$, $^{14}C$, $^{35}S$, $^{125}I$, etc.) and the like.

In the present invention, each group represented by Cyc1, Cyc2, Cyc3, Cyc4, Cyc1$^1$, Cyc2$^1$, Cyc4$^1$, X, X$^1$, R$^1$, R$^2$, R$^3$, R$^4$, R$^5$, Z, R$^{51}$, Z$^1$, R$^{10}$, R$^{110}$, p, Cyc8, Cyc9, Cyc10, Cyc11, Cyc12, E, R$^{52}$, R$^{53}$, R$^{54}$, W$^1$, W$^2$, W$^3$, W$^4$, W$^5$, R$^{11}$, n, R$^{12}$, m, R$^{13}$, R$^{14}$, R$^{15}$, and R$^{16}$ is all preferred. In particular, the compounds described in Examples are more preferred. In the following, preferred groups and preferred rings will be listed. All symbols used herein have the same meanings as described above.

In the present invention, Cyc1 is preferably, for example, 5- to 7-membered mono-cyclic carbocyclic ring which may have a substituent(s), 5- to 7-membered mono-cyclic heterocyclic ring which may have a substituent(s), and the like, and more preferably, pyrrolidinyl, phenyl, N-morpholinyl, pyridyl which may have a substituent(s), and the like, and especially preferably phenyl, pyridyl which may have a substituent(s), and the like.

In the present invention, Cyc2 is preferably, for example, 5- to 7-membered mono-cyclic carbocyclic ring which may have a substituent(s), 5- to 7-membered mono-cyclic heterocyclic ring which may have a substituent(s), and the like, and more preferably, 5-membered mono-cyclic heterocyclic ring which may have a substituent(s), and the like, and especially preferably isoxazolyl, oxadiazolyl, thiazolyl, furanyl, thienyl, which may have a substituent(s), and the like.

In the present invention, Cyc3 is preferably, for example, 5- to 6-membered mono-cyclic heterocyclic ring which may have a substituent(s), and the like, and more preferably, for example, piperidyl, piperazinyl which may have a substituent(s), and the like.

In the present invention, Cyc4 is preferably, for example, 5- to 10-membered mono- or bi-cyclic carbocyclic ring which may have a substituent(s), 5- to 10-membered mono- or bi-cyclic heterocyclic ring which may have a substituent(s), and the like, and more preferably, 5- to 6-membered mono-cyclic carbocyclic ring which may have a substituent(s), 5- to 6-membered mono-cyclic heterocyclic ring which may have a substituent(s), 8- to 10-membered bi-cyclic carbocyclic ring which may have a substituent(s), 8- to 10-membered bi-cyclic heterocyclic ring which may have a substituent(s), and the like.

In the present invention, Cyc1¹ is preferably 5- to 6-membered mono-cyclic carbocyclic ring which may have a substituent(s) or 5- to 6-membered mono-cyclic heterocyclic ring which may have a substituent(s), and more preferably, for example, pyrrolidinyl, phenyl, N-morpholinyl, pyridyl which may have a substituent(s), and the like, and especially preferably, for example, phenyl, pyridyl which may have a substituent(s), and the like.

In the present invention, Cyc2¹ is preferably 5-membered mono-cyclic heterocyclic ring which may have a substituent(s), and more preferably, isoxazolyl, oxadiazolyl, thiazolyl, thienyl, which may have a substituent(s), and the like, and especially preferably, isoxazolyl, thiazolyl which may have a substituent(s), and the like.

In the present invention,

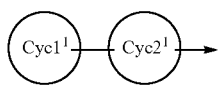

is preferably, for example,

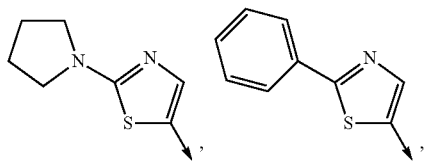

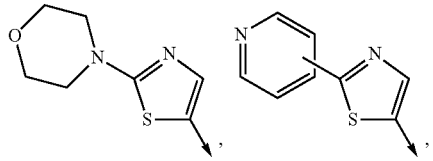

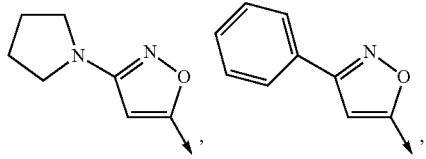

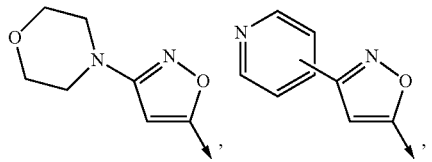

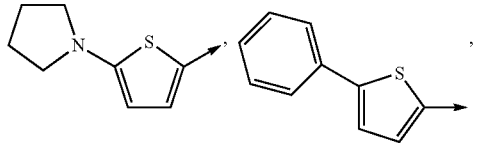

-continued

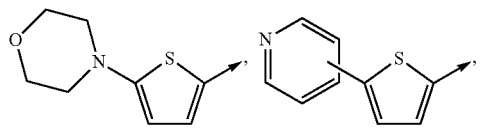

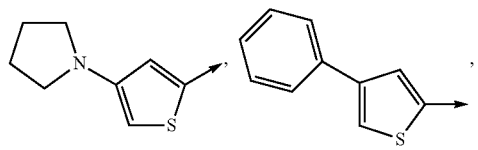

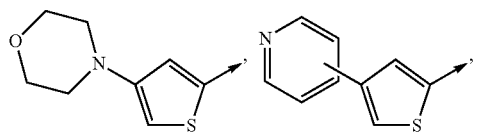

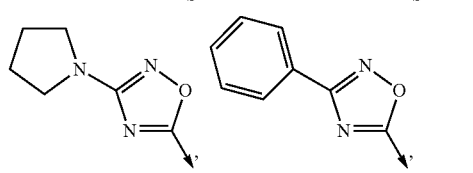

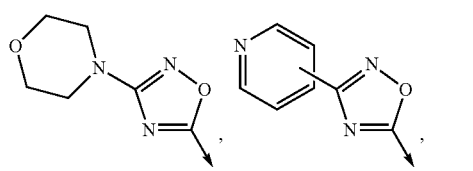

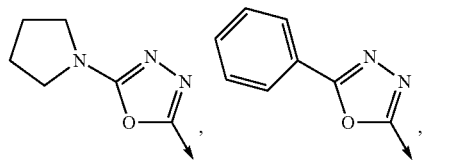

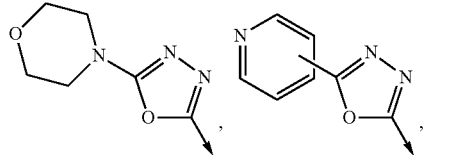

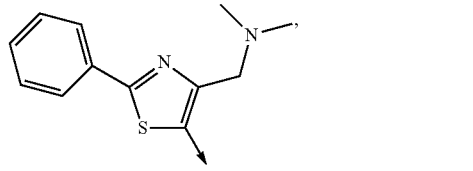

and the like, and more preferably, for example,

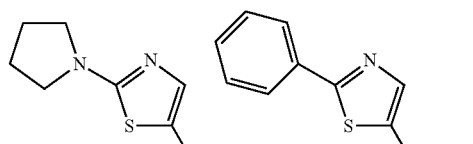

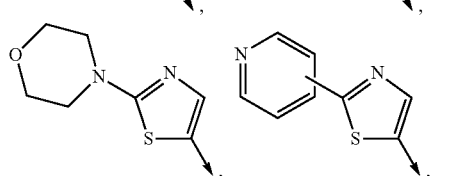

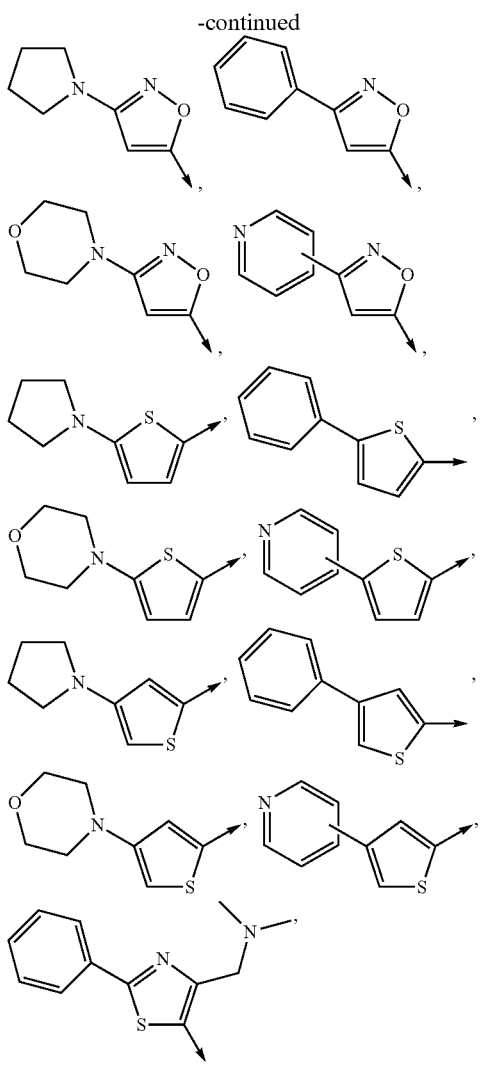

and the like, and especially preferably, for example,

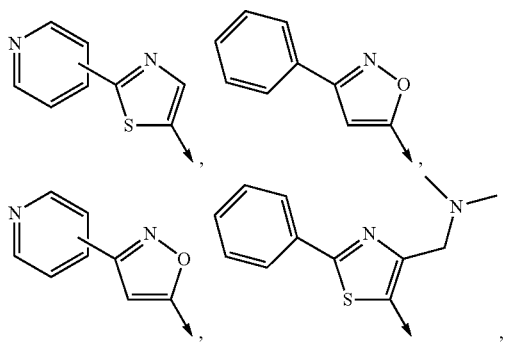

and the like.

In the present invention, Cyc4¹ is preferably 5- to 10-membered mono- or bi-cyclic carbocyclic ring which may have a substituent(s) or 5- to 10-membered mono- or bi-cyclic heterocyclic ring which may have a substituent(s), and more preferably, 5- to 6-membered mono-cyclic carbocyclic ring which may have a substituent(s), 5- to 6-membered mono-cyclic heterocyclic ring which may have a substituent(s), 8- to 10-membered bi-cyclic carbocyclic ring which may have a substituent(s), 8- to 10-membered bi-cyclic heterocyclic ring which may have a substituent(s), and the like, and especially preferably phenyl, pyridyl, pyrimidinyl, indazolyl, which may have a substituent(s), and the like.

In the present invention, X is preferably, for example, —$CH_2$—, —CO—, —$SO_2$—, and the like, and more preferably, for example, —$CH_2$—, —$SO_2$—, and the like, and especially preferably —$CH_2$—, and the like.

In the present invention, $X^1$ is preferably —$CH_2$—, —CO—, or —$SO_2$—, and more preferably, for example, —$CH_2$—, —$SO_2$—, and the like, and especially preferably —$CH_2$—, and the like.

In the present invention, $R^1$ is preferably, for example, hydrogen, C1-4 alkyl, and the like, and more preferably, for example, hydrogen, methyl, and the like.

In the present invention, $R^2$ is preferably, for example, hydrogen, C1-4 alkyl, and the like, and more preferably, for example, hydrogen, methyl, and the like.

In the present invention, $R^3$ is preferably, for example, hydrogen, C1-4 alkyl, and the like, and more preferably, for example, hydrogen, methyl, and the like.

In the present invention, $R^4$ is preferably, for example, hydrogen, C1-4 alkyl, and the like, and more preferably, for example, hydrogen, methyl, and the like.

In the present invention, $R^5$ is preferably, for example, hydrogen, C1-4 alkyl, and the like, and more preferably, for example, hydrogen, methyl, and the like.

In the present invention, Z is preferably —N($R^5$)—CO—, —CO—N($R^5$)—, —N($R^5$)—, bond, or —O—, and more preferably, for example, —NH—CO—, —CO—NH—, —NH—, bond, —O—, and the like, and especially preferably —NH—CO—, —CO—NH—, —NH—, bond and the like.

In the present invention, C1-4 alkylene which may have a substituent(s) or C2-4 alkenylene which may have a substituent(s) represented by the term "$R^5$ and the substituent of Cyc4 may be taken together to form" as herein defined is preferably, for example, methylene, ethylene, propylene which may have a substituent(s), vinylene, propenylene which may have a substituent(s), and the like, and more preferably, for example, ethylene which may have a substituent(s), vinylene which may have a substituent(s), and the like.

In the present invention, $R^{51}$ is preferably, for example, hydrogen, C1-4 alkyl, and the like, and more preferably, for example, hydrogen, methyl, and the like.

In the present invention, $Z^1$ is preferably —N($R^{51}$)—CO—, —CO—N($R^{51}$)—, —N($R^{51}$)—, bond or —O—, and more preferably, for example, —NH—CO—, —CO—NH—, —NH—, bond, —O—, and the like, and especially preferably —NH—CO—, —CO—NH—, —NH—, bond, and the like.

In the present invention, C1-4 alkylene which may have a substituent(s), C2-4 alkenylene which may have a substituent(s) represented by the term "$R^{51}$ and the substituent of Cyc4¹ may be taken together to form" as herein defined is preferably, for example, methylene, ethylene, propylene which may have a substituent(s), vinylene, propenylene which may have a substituent(s) and the like, and more preferably, for example, ethylene which may have a substituent(s), vinylene which may have a substituent(s), and the like.

In the present invention, $R^{10}$ is preferably hydrogen or substituent, and more preferably, for example, hydrogen, C1-4 alkyl, hydroxy, phenyl, cyano, and the like, and especially preferably hydrogen, hydroxy, and the like.

In the present invention, $R^{110}$ is preferably substituent, and more preferably, for example, methyl, ethyl, methoxy, ethoxy, propoxy, hydroxy, phenyl, cyano, amino and the like, and especially preferably, for example, hydroxy, and the like.

In the present invention, p is preferably an integer of 0 to 8, more preferably, for example, an integer of 0 to 1, and the like.

In the present invention, Cyc8 is preferably 5- to 6-membered mono-cyclic carbocyclic ring which may have a substituent(s), 5- to 6-membered mono-cyclic heterocyclic ring which may have a substituent(s), 8- to 10-membered bi-cyclic carbocyclic ring which may have a substituent(s) or 8- to 10-membered bi-cyclic heterocyclic ring which may have a substituent(s), and more preferably, for example, 5- to 6-membered mono-cyclic carbocyclic ring which have at least two substituents, 6-membered mono-cyclic heterocyclic ring which have at least two substituents, 8- to 10-membered bi-cyclic carbocyclic ring which may have a substituent(s), 8- to 10-membered bi-cyclic heterocyclic ring which may have a substituent(s), imidazolyl, triazolyl, pyrazolyl, furanyl, oxazolyl, thiazolyl, isothiazolyl, furazanyl, oxadiazolyl, thiadiazolyl which may have a substituent(s), pyrrolyl, thienyl which have a substituent(s), and the like, and especially preferably phenyl, pyridyl which have at least two substituents, and the like.

In the present invention, Cyc9 is preferably 5- to 6-membered mono-cyclic carbocyclic ring which may have a substituent(s), 5- to 6-membered mono-cyclic heterocyclic ring which may have a substituent(s), 8- to 10-membered bi-cyclic carbocyclic ring which may have a substituent(s) or 8- to 10-membered bi-cyclic heterocyclic ring which may have a substituent(s), and more preferably, for example, 5- to 6-membered mono-cyclic carbocyclic ring which have at least two substituents, 5- to 6-membered mono-cyclic heterocyclic ring which have at least two substituents, 8- to 10-membered bi-cyclic carbocyclic ring which may have a substituent(s), 8- to 10-membered bi-cyclic heterocyclic ring which may have a substituent(s), and the like, and especially preferably phenyl, pyridyl which may have a substituent(s), and the like.

In the present invention, Cyc10 is preferably 5- to 6-membered mono-cyclic heterocyclic ring which may have a substituent(s), and more preferably, for example, piperidine, tetrahydropyridine, and the like.

In the present invention, Cyc11 is preferably 6-membered mono-cyclic carbocyclic ring which may have a substituent(s) or 6-membered mono-cyclic heterocyclic ring which may have a substituent(s), and more preferably, for example, 6-membered mono-cyclic carbocyclic ring which may have a substituent(s), and the like.

In the present invention, Cyc12 is preferably 5- to 10-membered mono- or bi-cyclic carbocyclic ring which may have a substituent(s) or 5- to 10-membered mono- or bi-cyclic heterocyclic ring which may have a substituent(s), and more preferably, 5- to 6-membered mono-cyclic carbocyclic ring which may have a substituent(s), 5- to 6-membered mono-cyclic heterocyclic ring which may have a substituent(s), 8- to 10-membered bi-cyclic carbocyclic ring which may have a substituent(s), 8- to 10-membered bi-cyclic heterocyclic ring which may have a substituent(s), and the like, and especially preferably indazolyl which may have a substituent(s), and the like.

In the present invention, E is preferably —O— or —N($R^{54}$)—, and more preferably, for example, —O—, —NH—, and the like, and especially preferably —NH—, and the like.

In the present invention, $R^{52}$ is preferably, for example, hydrogen, C1-4 alkyl, and the like, and more preferably, for example, hydrogen, methyl, and the like.

In the present invention, $R^{53}$ is preferably, for example, hydrogen, C1-4 alkyl, and the like, and more preferably, for example, hydrogen, methyl, and the like.

In the present invention, $R^{54}$ is preferably, for example, hydrogen, C1-4 alkyl, and the like, and more preferably, for example, hydrogen, methyl, and the like.

In the present invention, $W^1$ is preferably CH or N, more preferably, for example, N.

In the present invention, $W^2$ is preferably CH or N, more preferably, for example, CH.

In the present invention, $W^3$ is preferably CH or N, more preferably, for example, N.

In the present invention, $W^4$ is preferably CH or N, more preferably, for example, CH.

In the present invention, $W^5$ is preferably CH or N, more preferably, for example, N.

In the present invention, $R^{11}$ is preferably halogen, hydroxy, C1-4 alkoxy which may have a substituent(s), C1-4 alkyl which may have a substituent(s), cyano or amino, and more preferably, for example, chlorine, hydroxy, methoxy, ethoxy, propoxy, isopropoxy which may have a substituent(s), methyl, ethyl, propyl, isopropyl which may have a substituent(s), cyano, amino, and the like, and especially preferably chlorine, ethoxy which may have a substituent(s), ethyl which may have a substituent(s), cyano, amino, and the like.

In the present invention, n is preferably an integer of 2 to 4, more preferably, for example, an integer of 2 to 3, and the like.

In the present invention, $R^{12}$ is preferably halogen, hydroxy, C1-4 alkoxy which may have a substituent(s), C1-4 alkyl which may have a substituent(s), cyano or amino, and more preferably, for example, chlorine, hydroxy, methoxy, ethoxy, propoxy, isopropoxy which may have a substituent(s), methyl, ethyl, propyl, isopropyl which may have a substituent(s), cyano, amino, and the like, and especially preferably chlorine, ethoxy which may have a substituent(s), ethyl which may have a substituent(s), cyano, amino, and the like.

In the present invention, m is preferably an integer of 0 to 4, more preferably, for example, an integer of 2 to 3, and the like.

In the present invention, $R^{13}$ is preferably, for example, C1-4 alkyl which may have a substituent(s), and the like, and more preferably, for example, methyl, ethyl, which may have a substituent(s), and the like, and especially preferably methyl which may have a substituent(s), and the like.

In the present invention, $R^{14}$ is preferably cyano or amino, and more preferably, for example, amino.

In the present invention, $R^{15}$ is preferably halogen, cyano or amino, and more preferably, for example, chloro or cyano, and the like, and especially preferably cyano.

In the present invention, $R^{16}$ is preferably halogen, hydroxy, C1-4 alkoxy which may have a substituent(s), C1-4 alkyl which may have a substituent(s), cyano or amino, and more preferably, for example, chlorine, hydroxy, methoxy, ethoxy, propoxy, isopropoxy which may have a substituent(s), methyl, ethyl, propyl, isopropyl which may have a substituent(s), cyano, amino, and the like, and especially preferably methoxy, ethoxy, propoxy, and the like.

In the present invention, the compound represented by the formula (I) including the combination of the above-described preferable group and ring is preferred. For example, a compound represented by formula (I-P):

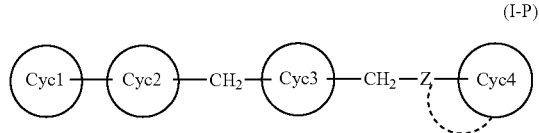

(I-P)

wherein all symbols have the same meanings as described above, is preferred.

Furthermore, the preferred compound represented by the formula (I-P) is, for example, a compound represented by formula (I-P-1):

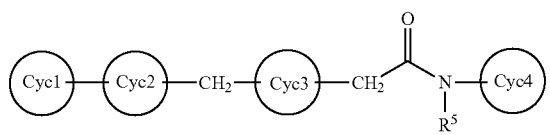

(I-P-1)

wherein all symbols have the same meanings as described above, a compound represented by formula (I-P-1-1):

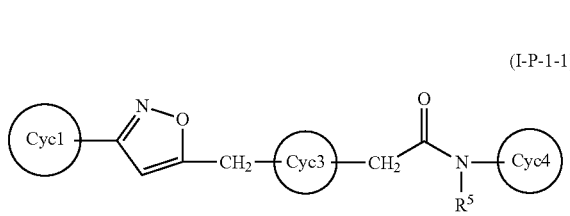

(I-P-1-1)

wherein all symbols have the same meanings as described above, a compound represented by formula (I-P-1-2):

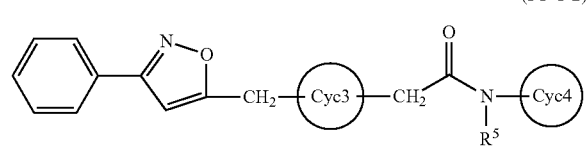

(I-P-1-2)

wherein all symbols have the same meanings as described above, a compound represented by formula (I-P-1-2-1):

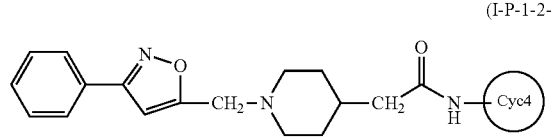

(I-P-1-2-1)

wherein all symbols have the same meanings as described above, a compound represented by formula (I-P-4-1):

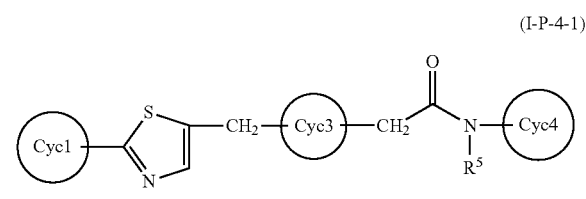

(I-P-4-1)

wherein all symbols have the same meanings as described above, a compound represented by formula (I-P-4-2):

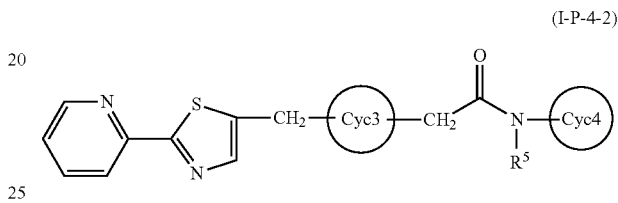

(I-P-4-2)

wherein all symbols have the same meanings as described above, a compound represented by formula (I-P-4-2-1):

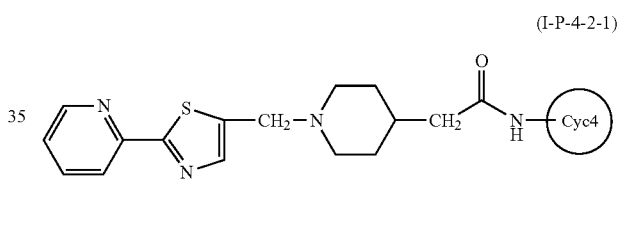

(I-P-4-2-1)

wherein all symbols have the same meanings as described above, a compound represented by formula (I-P-2):

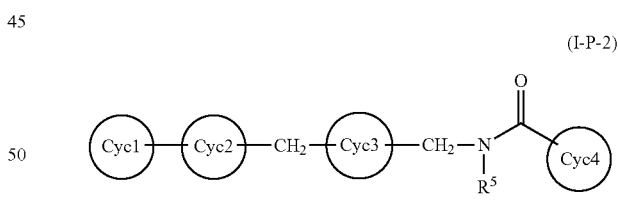

(I-P-2)

wherein all symbols have the same meanings as described above, a compound represented by formula (I-P-2-1):

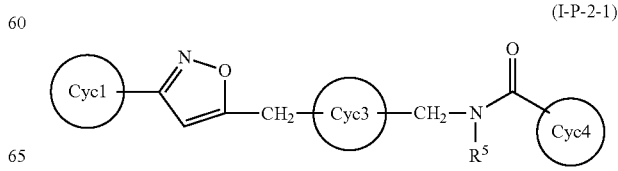

(I-P-2-1)

wherein all symbols have the same meanings as described above, a compound represented by formula (I-P-2-2):

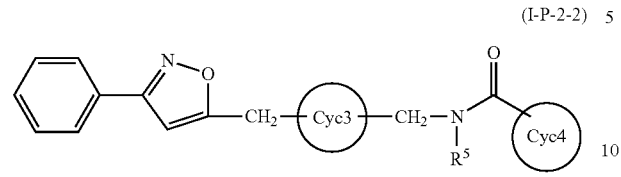
(I-P-2-2)

wherein all symbols have the same meanings as described above, a compound represented by formula (I-P-2-2-1):

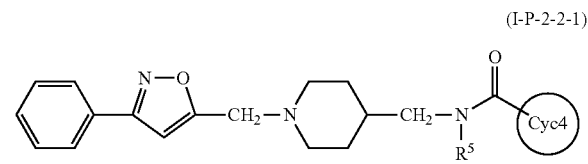
(I-P-2-2-1)

wherein all symbols have the same meanings as described above, a compound represented by formula (I-P-5-1):

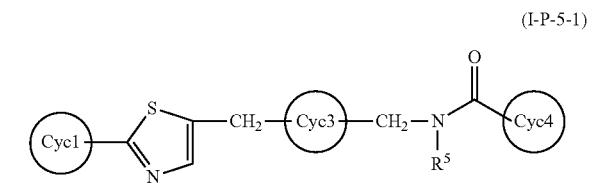
(I-P-5-1)

wherein all symbols have the same meanings as described above, a compound represented by formula (I-P-5-2):

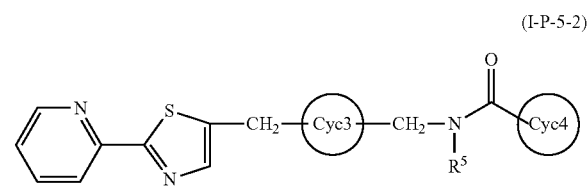
(I-P-5-2)

wherein all symbols have the same meanings as described above, a compound represented by formula (I-P-5-2-1):

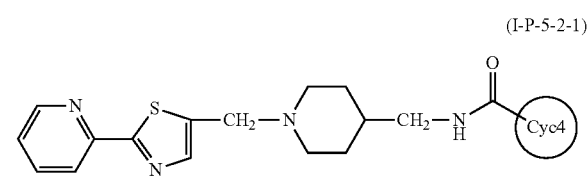
(I-P-5-2-1)

wherein all symbols have the same meanings as described above, a compound represented by formula (I-P-3):

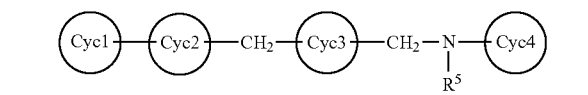
(I-P-3)

wherein all symbols have the same meanings as described above, and a compound represented by formula (I-P-3-1):

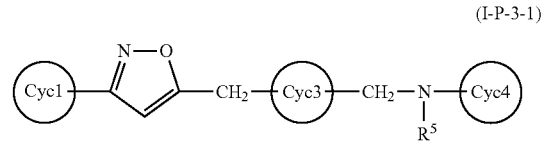
(I-P-3-1)

wherein all symbols have the same meanings as described above, and a compound represented by formula (I-P-3-2):

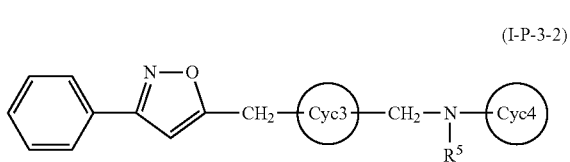
(I-P-3-2)

wherein all symbols have the same meanings as described above, and a compound represented by formula (I-P-3-2-1):

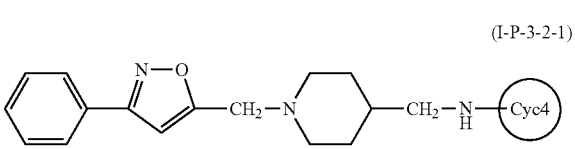
(I-P-3-2-1)

wherein all symbols have the same meanings as described above, and the like.

And the compound represented by the formula (I) is also preferably, for example, a compound represented by the formula (I-1):

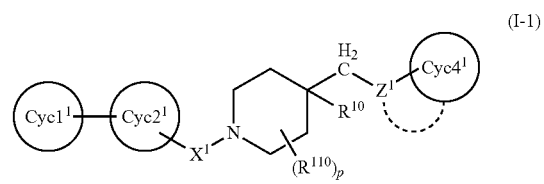
(I-1)

wherein all symbols have the same meanings as described above.

Furthermore, the preferred compound represented by the formula (I-1) is, for example, a compound represented by formula (I-1-A):

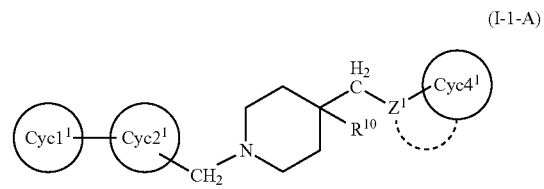
(I-1-A)

wherein all symbols have the same meanings as described above.

The compound represented by formula (I-1-A) is preferably, for example, a compound represented by formula (I-1-B):

(I-1-B)

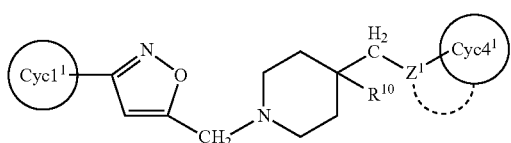

wherein all symbols have the same meanings as described above, a compound represented by formula (I-1-B-1):

(I-1-B-1)

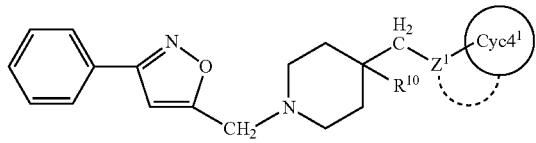

wherein all symbols have the same meanings as described above, a compound represented by formula (I-1-C):

(I-1-C)

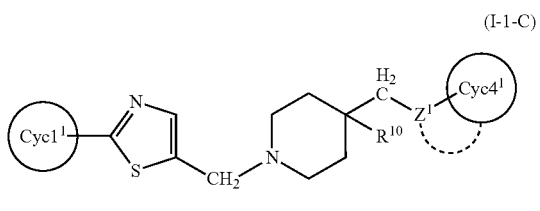

wherein all symbols have the same meanings as described above, a compound represented by formula (I-C-1):

(I-1-C-1)

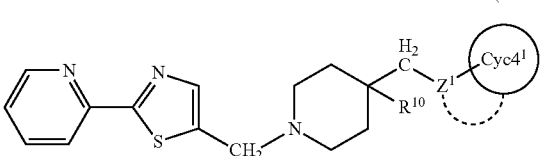

wherein all symbols have the same meanings as described above, and the like.

Furthermore, the preferred compound represented by the formula (I-1-A) is, for example, a compound represented by formula (I-1-A-1):

(I-1-A-1)

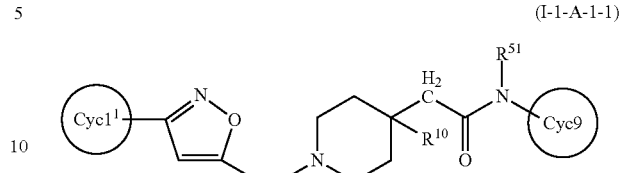

wherein all symbols have the same meanings as described above, a compound represented by formula (I-1-A-1-1):

(I-1-A-1-1)

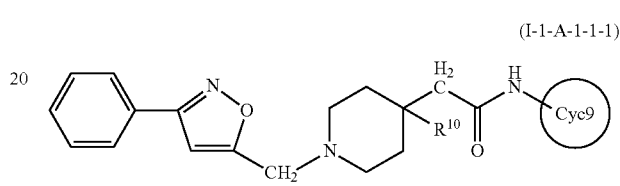

wherein all symbols have the same meanings as described above, a compound represented by formula (I-1-A-1-1-1):

(I-1-A-1-1-1)

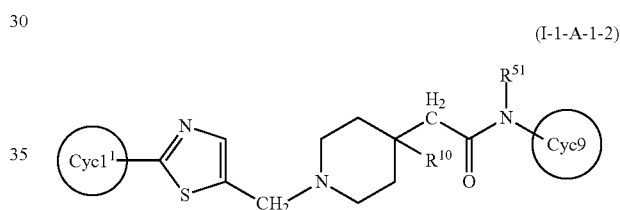

wherein all symbols have the same meanings as described above, a compound represented by formula (I-1-A-1-2):

(I-1-A-1-2)


wherein all symbols have the same meanings as described above, a compound represented by formula (I-1-A-1-2-1):

(I-1-A-2-1)

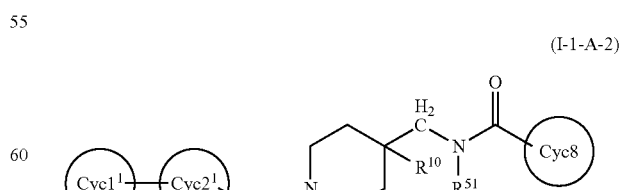

wherein all symbols have the same meanings as described above, a compound represented by formula (I-1-A-2):

(I-1-A-2)

wherein all symbols have the same meanings as described above; and wherein the compound of the formula (I-1-A-2) is not a compound of formula (I-2):

(I-2)

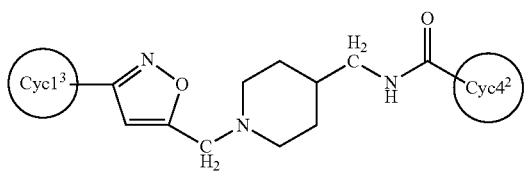

wherein all symbols have the same meanings as described above, a compound represented by formula (I-1-A-2-1):

(I-1-A-2-1)

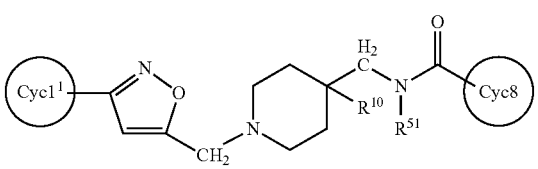

wherein all symbols have the same meanings as described above; and wherein the compound of the formula (I-1-A-2-1) is not a compound of formula (I-2):

(I-2)

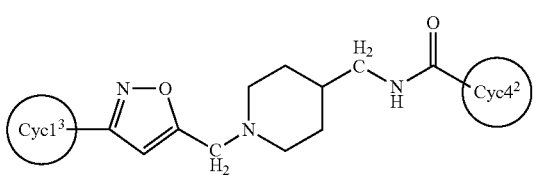

wherein all symbols have the same meanings as described above, a compound represented by formula (I-1-A-2-1-1):

(I-1-A-2-1-1)

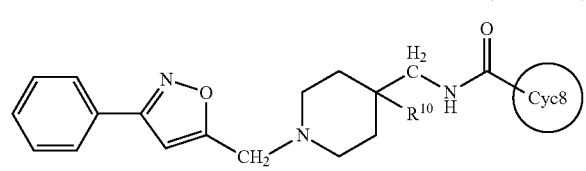

wherein all symbols have the same meanings as described above; and
wherein the compound of the formula (I-1-A-2-1-1) is not a compound of formula (I-2-1):

(I-2-1)

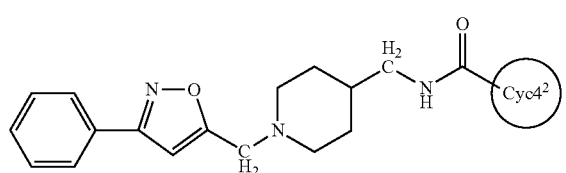

wherein all symbols have the same meanings as described above, a compound represented by formula (I-1-A-2-2):

(I-1-A-2-2)

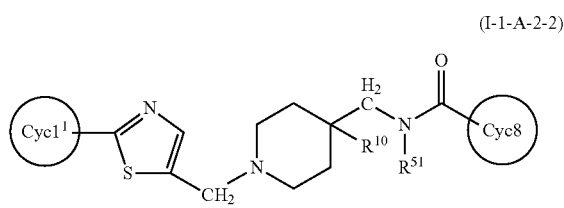

wherein all symbols have the same meanings as described above, a compound represented by formula (I-1-A-2-2-1):

(I-1-A-2-2-1)

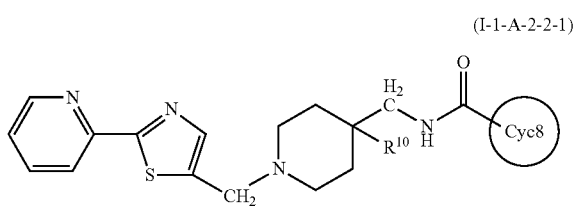

wherein all symbols have the same meanings as described above, a compound represented by formula (I-1-A-3):

(I-1-A-3)

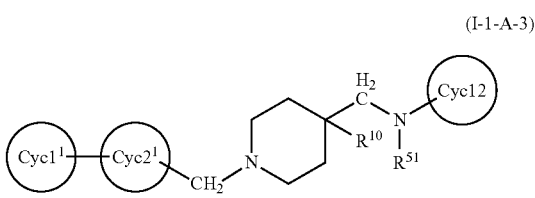

wherein all symbols have the same meanings as described above, a compound represented by formula (I-1-A-3-1):

(I-1-A-3-1)

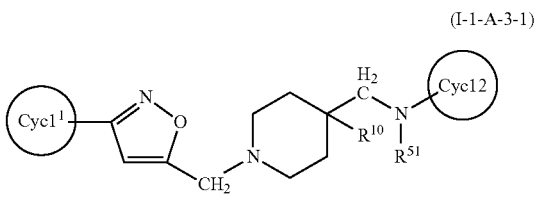

wherein all symbols have the same meanings as described above, a compound represented by formula (I-1-A-3-1-1):

(I-1-A-3-1-1)

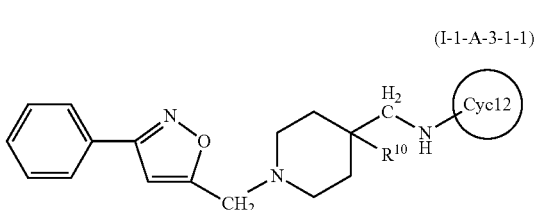

wherein all symbols have the same meanings as described above, a compound represented by formula (I-1-A-3-2):

(I-1-A-3-2)

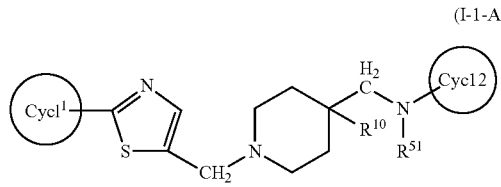

wherein all symbols have the same meanings as described above, a compound represented by formula (I-1-A-3-2-1):

(I-1-A-3-2-1)

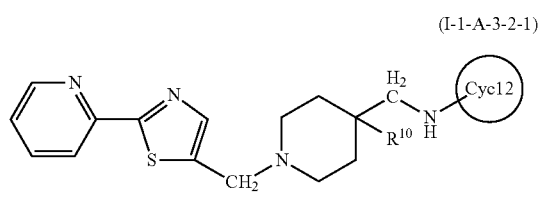

wherein all symbols have the same meanings as described above, and the like.

Furthermore, the preferred compound represented by the formula (I-1) is, for example, a compound represented by formula (I-1-1):

(I-1-1)

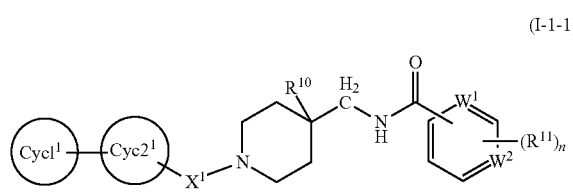

wherein all symbols have the same meanings as described above.

The compound represented by the formula (I-1-1) is preferably, for example, a compound represented by the formula (I-1-1-1):

(I-1-1-1)

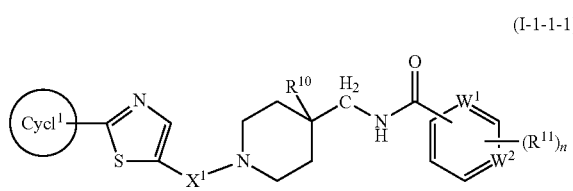

wherein all symbols have the same meanings as described above, a compound represented by formula (I-1-1-2):

(I-1-1-2)

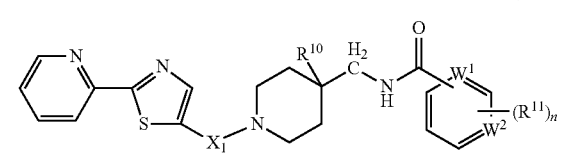

wherein all symbols have the same meanings as described above, a compound represented by formula (I-1-1-3):

(I-1-1-3)

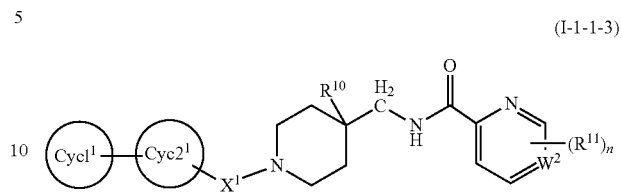

wherein all symbols have the same meanings as described above, a compound represented by formula (I-1-1-3-1):

(I-1-1-3-1)

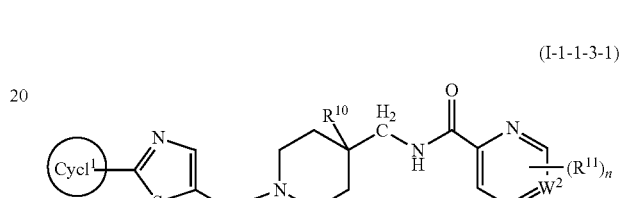

wherein all symbols have the same meanings as described above, a compound represented by formula (I-1-1-3-2):

(I-1-1-3-2)

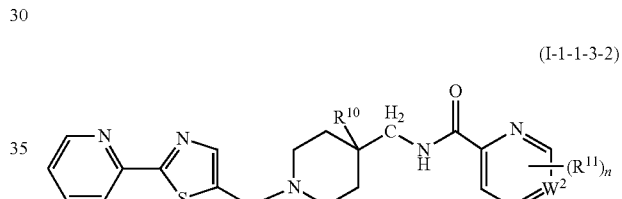

wherein all symbols have the same meanings as described above, a compound represented by formula (I-1-1-4):

(I-1-1-4)

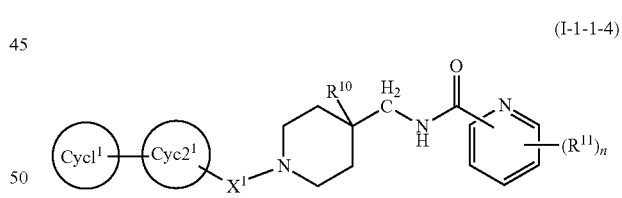

wherein all symbols have the same meanings as described above, a compound represented by formula (I-1-1-4-1):

(1-1-1-4-1)

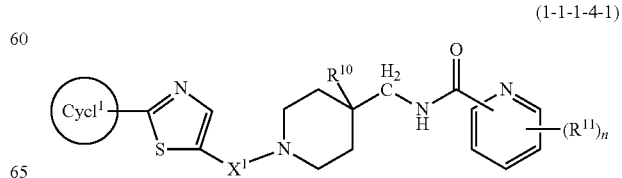

wherein all symbols have the same meanings as described above, a compound represented by formula (I-1-1-4-2):

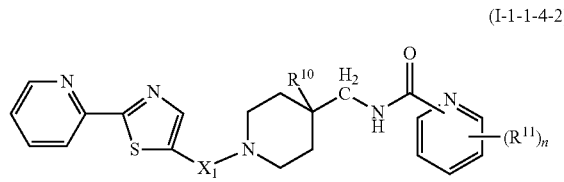
(I-1-1-4-2)

wherein all symbols have the same meanings as described above, and the like.

Furthermore, the preferred compound represented by the formula (I-1) is, for example, a compound represented by formula (I-1-2):

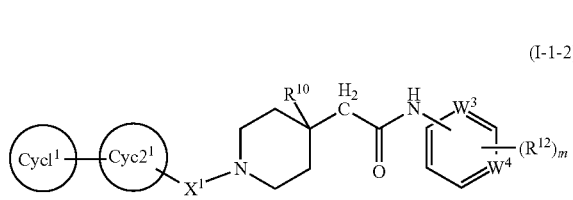
(I-1-2)

wherein all symbols have the same meanings as described above.

The compound represented by the formula (I-1-2) is preferably, for example, a compound represented by the formula (I-1-2-1):

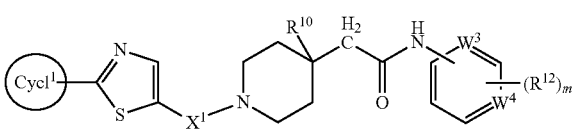
(I-1-2-1)

wherein all symbols have the same meanings as described above, a compound represented by formula (I-1-2-2):

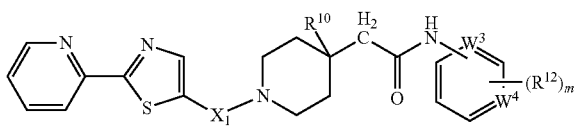
(I-1-2-2)

wherein all symbols have the same meanings as described above, a compound represented by formula (I-1-2-3):

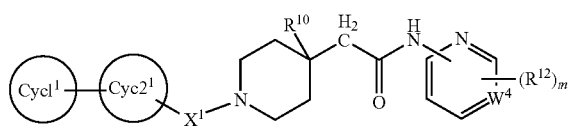
(I-1-2-3)

wherein all symbols have the same meanings as described above, a compound represented by formula (I-1-2-3-1):

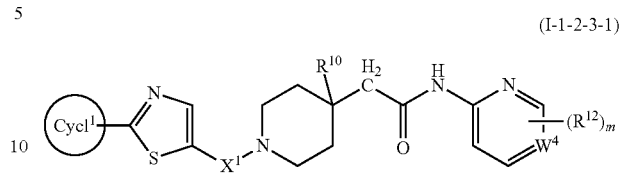
(I-1-2-3-1)

wherein all symbols have the same meanings as described above, a compound represented by formula (I-1-2-3-2):

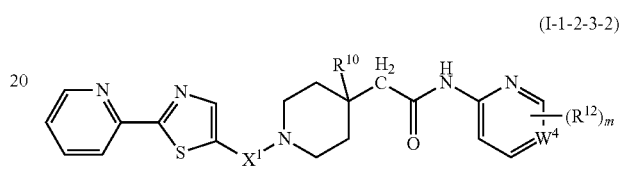
(I-1-2-3-2)

wherein all symbols have the same meanings as described above, a compound represented by formula (I-1-2-4):

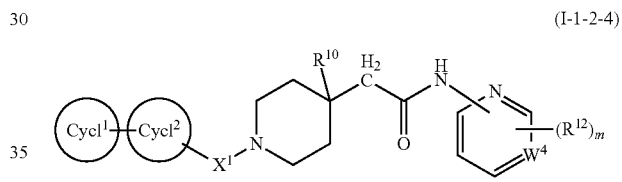
(I-1-2-4)

wherein all symbols have the same meanings as described above, a compound represented by formula (I-1-2-4-1):

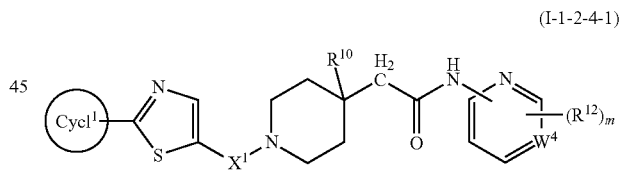
(I-1-2-4-1)

wherein all symbols have the same meanings as described above, and a compound represented by formula (I-1-2-4-2):

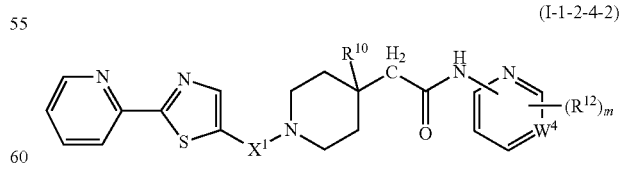
(I-1-2-4-2)

wherein all symbols have the same meanings as described above, and the like.

Furthermore, the preferred compound represented by the formula (I-1) is, for example, a compound represented by formula (I-1-3):

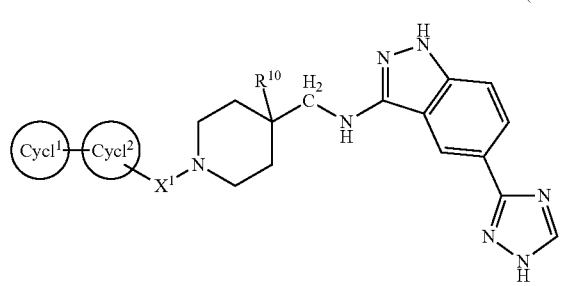

(I-1-3)

wherein all symbols have the same meanings as described above, and the like.

The compound represented by the formula (I-1-3) is preferably, for example, a compound represented by the formula (I-1-3-1):

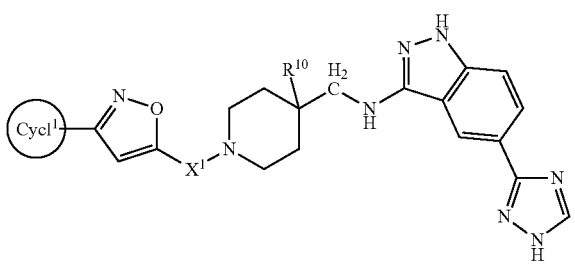

(I-1-3-1)

wherein all symbols have the same meanings as described above, a compound represented by formula (I-1-3-2):

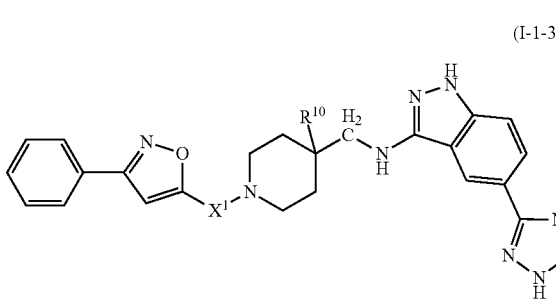

(I-1-3-2)

wherein all symbols have the same meanings as described above, and the like.

Furthermore, the preferred compound represented by the formula (I-1) is, for example, a compound represented by formula (I-1-4):

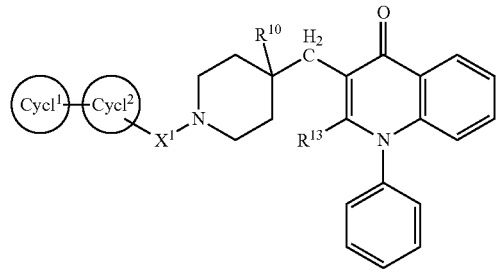

(I-1-4)

wherein all symbols have the same meanings as described above, and the like.

The compound represented by the formula (I-1-4) is preferably, for example, a compound represented by the formula (I-1-4-1):

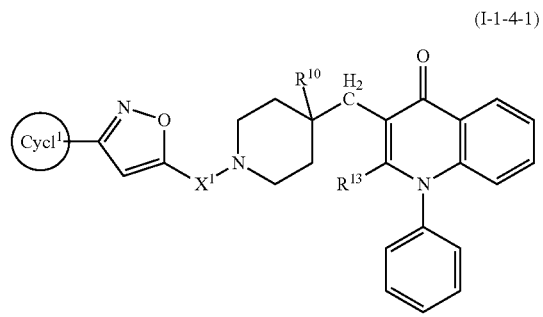

(I-1-4-1)

wherein all symbols have the same meanings as described above, a compound represented by formula (I-1-4-2):

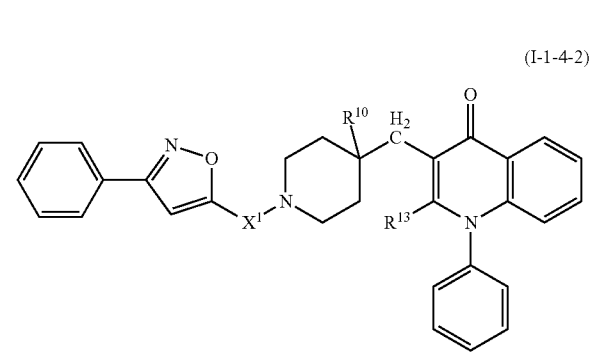

(I-1-4-2)

wherein all symbols have the same meanings as described above, and the like.

Furthermore, the preferred compound represented by the formula (I-1) is, for example, a compound represented by formula (I-1-5):

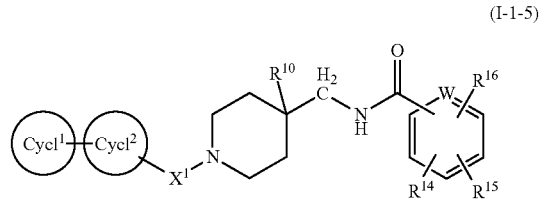

(I-1-5)

wherein all symbols have the same meanings as described above, and the like.

The compound represented by the formula (I-1-5) is preferably, for example, a compound represented by the formula (I-1-5-1):

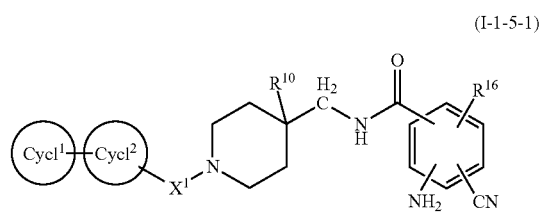

(I-1-5-1)

wherein all symbols have the same meanings as described above, a compound represented by formula (I-1-5-1-1):

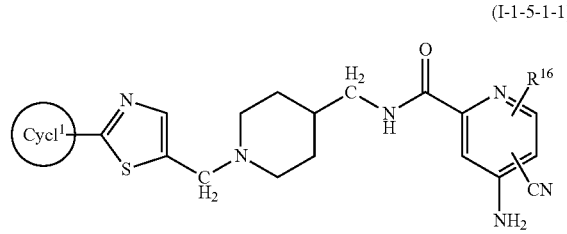

(I-1-5-1-1)

wherein all symbols have the same meanings as described above, a compound represented by formula (I-1-5-1-1-1):

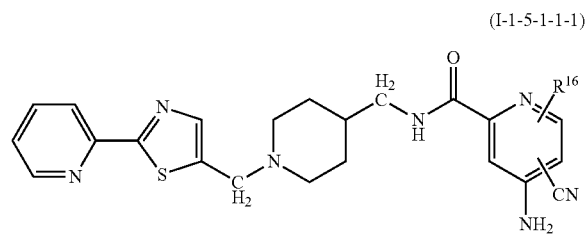

(I-1-5-1-1-1)

wherein all symbols have the same meanings as described above, a compound represented by formula (I-1-5-1-2):

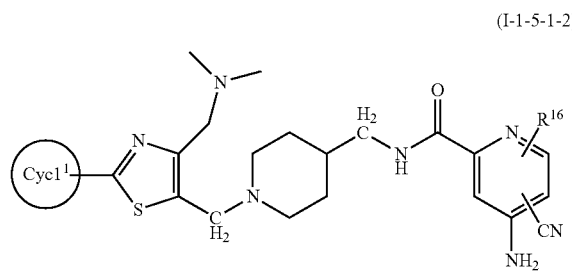

(I-1-5-1-2)

wherein all symbols have the same meanings as described above, a compound represented by formula (I-1-5-1-2-1):

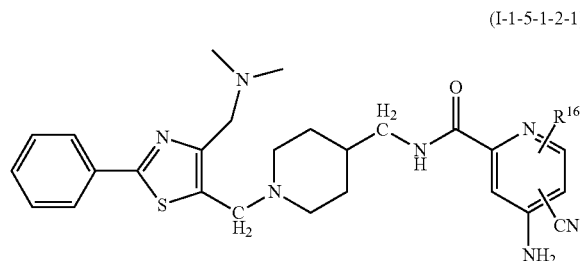

(I-1-5-1-2-1)

wherein all symbols have the same meanings as described above, and the like.

In the present invention, the compound represented by the formula (I-1) is preferably, the compound represented by the formula (I-1-1), (I-1-2), (I-1-3), (I-1-4), (I-1-5), and the like, more preferably, for example, the compound represented by the formula (I-1-1), (I-1-5), and the like, and especially preferably, the compound represented by the formula (I-1-5).

In the present invention, the compound represented by the formula (I-1) including the combination of the above-described preferable group and ring is preferred. The combination includes the same example of such as the above-described, for example, the compound represented by the formulae (I-1-A), (I-1-B), (I-1-B-1), (I-1-C), (I-1-C-1), (I-1-A-1), (I-1-A-1-1), (I-1-A-1-1-1), (I-1-A-1-2), (I-1-A-1-2-1), (I-1-A-2), (I-1-A-2-1), (I-1-A-2-1-1), (I-1-A-2-2), (I-1-A-3), (I-1-A-3-1), (I-1-A-3-1-1), (I-1-A-3-2), (I-1-A-3-2-1), (I-1-1), (I-1-1-1), (I-1-1-2), (I-1-1-3), (I-1-1-3-1), (I-1-1-3-2), (I-1-1-4), (I-1-1-4-1), (I-1-1-4-2), (I-1-2), (I-1-2-1), (I-1-2-2), (I-1-2-3), (I-1-2-3-1), (I-1-2-3-2), (I-1-2-4), (I-1-2-4-1), (I-1-2-4-2), (I-1-3), (I-1-3-1), (I-1-3-2), (I-1-4), (I-1-4-1), (I-1-4-2), (I-1-5), (I-1-5-1), (I-1-5-1-1), (I-1-5-1-1-1), (I-1-5-1-2), (I-1-5-1-2-1) and the like.

In the present invention, examples of the preferable compound of the formula (I-1) include, for example, 5-(3-hydroxyphenyl)-N-({1-[(3-phenyl-5-isoxazolyl)methyl]-4-piperidinyl}methyl)-2-furamide, 4-chloro-3-methoxy-N-({1-[(2-phenyl-1,3-thiazol-5-yl)methyl]-4-piperidinyl}methyl)benzamide, 4-chloro-N-[(1-{[3-(2-chlorophenyl)-5-isoxazolyl]methyl}-4-piperidinyl)methyl]-3-methoxybenzamide, 4-chloro-3-methoxy-N-({1-[(5-phenyl-2-thienyl)methyl]-4-piperidinyl}methyl)benzamide, 4-chloro-N-[(1-{[3-(4-fluorophenyl)-5-isoxazolyl]methyl}-4-piperidinyl)methyl]-3-methoxybenzamide, 4-chloro-N-[(1-{[2-(2-chlorophenyl)-1,3-thiazol-5-yl]methyl}-4-piperidinyl)methyl]-3-methoxybenzamide, 4-chloro-3-methoxy-N-[(1-{[5-(2-pyridinyl)-2-thienyl]methyl}-4-piperidinyl)methyl]benzamide, 4-chloro-3-methoxy-N-({1-[(4-phenyl-2-furyl)methyl]-4-piperidinyl}methyl)benzamide, 4-chloro-3-methoxy-N-({1-[(3-phenyl-1,2,4-oxadiazol-5-yl)methyl]-4-piperidinyl}methyl)benzamide, 4-chloro-3-methoxy-N-[(1-{[5-(2-pyridinyl)-2-thienyl]sulfonyl}-4-piperidinyl)methyl]benzamide, 5,6-dichloro-2-({1-[(3-phenyl-5-isoxazolyl)methyl]-4-piperidinyl}methyl)-1(2H)-isoquinolinone, 3-phenyl-N-({1-[(3-phenyl-5-isoxazolyl)methyl]-4-piperidinyl}methyl)isoxazolo[4,5-d]pyridazin-4-amine, N-[(1-{[3-(4-chlorophenyl)-5-isoxazolyl]methyl}-4-piperidinyl)methyl]-3-phenylisoxazolo[4,5-d]pyridazin-4-amine, N-[(1-{[3-(3-chlorophenyl)-5-isoxazolyl]methyl}-4-piperidinyl)methyl]-3-phenylisoxazolo[4,5-d]pyridazin-4-amine, N-[(1-{[3-(2-chlorophenyl)-5-isoxazolyl]methyl}-4-piperidinyl)methyl]-3-phenylisoxazolo[4,5-d]pyridazin-4-amine, 3-phenyl-4-({1-[(3-phenyl-5-isoxazolyl)methyl]-4-piperidinyl}methoxy)isoxazolo[4,5-d]pyridazine, 4-anilino-2-[({1-[(3-phenyl-5-isoxazolyl)methyl]-4-piperidinyl}methyl)amino]-5-pyrimidinecarboxamide, methyl 6-bromo-1-oxo-4-phenyl-2-({1-[(3-phenyl-5-isoxazolyl)methyl]-4-piperidinyl}methyl)-1,2-dihydro-3-isoquinolinecarboxylate, methyl 6-chloro-1-oxo-4-phenyl-2-({1-[(3-phenyl-5-isoxazolyl)methyl]-4-piperidinyl}methyl)-1,2-dihydro-3-isoquinolinecarboxylate, 4-amino-5-cyano-6-ethoxy-N-((1-((5-(pyridin-2-yl)-1,3,4-thiadiazol-2-yl)methyl)piperidin-4-yl)methyl)picolinamide, (R)-4-Amino-5-cyano-6-(1-hydroxypropan-2-ylamino)-N-((1-((2-(pyridin-2-yl)thiazol-5-yl)methyl)piperidin-4-yl)methyl)picolinamide, 4-chloro-3-methoxy-N-({1-[(3-phenyl-5-isoxazolyl)methyl]-4-piperidinyl}methyl)benzamide,
4-amino-5-chloro-6-ethoxy-N-({1-[(3-phenyl-5-isoxazolyl)methyl]-4-piperidinyl}methyl)-2-pyridinecarboxamide,
4-amino-3,5-dichloro-6-ethoxy-N-({1-[(3-phenyl-5-isoxazolyl)methyl]-4-piperidinyl}methyl)-2-pyridinecarboxamide,
4-amino-5-cyano-6-ethoxy-N-({1-[(3-phenyl-5-isoxazolyl)methyl]-4-piperidinyl}methyl)-2-pyridinecarboxamide,
3,4-dichloro-N-({1-[(3-phenyl-5-isoxazolyl)methyl]-4-piperidinyl}methyl)benzamide,
4-chloro-3-(2-hydroxyethoxy)-N-({1-[(3-phenyl-5-isoxazolyl)methyl]-4-piperidinyl}methyl)benzamide,
N-(4-amino-5-cyano-6-ethoxy-2-pyridinyl)-2-{1-[(3-phenyl-5-isoxazolyl)methyl]-4-piperidinyl}acetamide,
N-({1-[(3-phenyl-5-isoxazolyl)methyl]-4-piperidinyl}methyl)-5-(1H-1,2,4-triazol-3-yl)-1H-indazol-3-amine,
methyl 1-oxo-4-phenyl-2-({1-[(3-phenyl-5-isoxazolyl)methyl]-4-piperidinyl}methyl)-1,2-dihydro-3-isoquinolinecarboxylate,
4-amino-5-cyano-6-ethoxy-N-((1-((2-(pyridin-2-yl)thiazol-5-yl)methyl)piperidin-4-yl)methyl)picolinamide,
4-Amino-5-cyano-N-((1-((4-((dimethylamino)methyl)-2-phenylthiazol-5-yl)methyl)piperidin-4-yl)methyl)-6-ethoxypicolinamide, and the like.

All isomers are included in the present invention, unless otherwise specified. For example, alkyl, alkoxy and alkynylene includes straight or branched one. In addition, isomers on double bond, ring, fused ring (E-, Z-, cis-, trans-isomers), isomers generated due to asymmetric carbon atom(s) (R-form, S-form, α-configuration, β-configuration, enantiomer, diastereomer), optically active isomers with optical rotation (D-, L-, d-, l-isomers), polar compounds generated by chromatographic separation (more polar compound, less polar compound), equilibrium compounds, mixtures thereof with arbitrary ratio and racemic mixtures are also included in the present invention. Further, isomers due to the tautomerism are all included in the present invention.

Salts

In the present invention, the compound represented by the formula (I) may form a salt thereof, and may be N-oxide form thereof or quaternary ammonium salt thereof. Furthermore, these compounds may be a solvate thereof. The compounds of the present invention include all pharmacologically acceptable salts of the compound represented by the formula (I). As pharmacologically acceptable salts, water-soluble salts with little toxicity are preferred. Suitable pharmacologically acceptable salts in the compound of the present invention include, for example, salts of alkali metals (such as potassium, sodium, lithium, and the like); salts of alkaline earth metals (such as calcium, magnesium, and the like); ammonium salts (such as tetramethylammonium salts, tetrabutylammonium salts, and the like); salts of organic amines (such as triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, and the like); and acid addition salts such as salts of inorganic acid (such as hydrochloride, hydrobromide, hydroiodide, sulfate, phosphate, nitrate, and the like), and salts of organic acid (such as, acetate, trifluoroacetate, lactate, tartrate, oxalate, fumarate, maleate, benzoate, citrate, methansulfonate, ethansulfonate, benzenesulfonate, toluenesulfonate, isethionate, gulcuronate, gluconate and the like), and the like. The N-oxide form of the compound represented by the formula (I) means the compound wherein the nitrogen atom was oxidized. The N-oxide form of the compound represented by the formula (I) may additionally form a salt described above. The quaternary ammonium salt of the compound represented by the formula (I) means the compound wherein the nitrogen atom of the compound represented by the formula (I) is quaternized by $R^0$ ($R^0$ represents alkyl, alkenyl, alkynyl (which has the same meaning as described above) which each may have a substituent(s), and cyclic ring (which has the same meaning as described above) which may have a substituent(s).) The quaternary ammonium salt of the compound represented by the formula (I) may additionally form the salt described above and the N-oxide form described above. The appropriate solvate of the compound represented by the formula (I), a salt thereof, an N-oxide form thereof, and a quaternary ammonium salt thereof, include water, alcohol solvate (such as ethanol) and the like. The solvates are preferably nontoxic and water-soluble. The compounds represented by the formula (I) can be converted into the salt described above, the N-oxide form described above thereof, the solvates described above by conventional means.

The nomenclature and numbering of the compounds used in the present invention is performed using a computer program conducting designation generally according to IUPAC regulations, ACD/Name (registered trademark, version 5.08/17, Advanced Chemistry Development Inc.). For example, the compound:

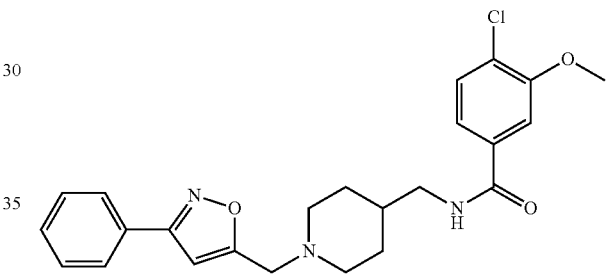

is named as 4-chloro-3-methoxy-N-({1-[(3-phenyl-5-isoxazolyl)methyl]-4-piperidinyl}methyl)benzamide.

Production Process of the Compound of the Present Invention

A compound represented by the formula (I) may be prepared by modifying or combining known methods, for example, methods shown below, methods described in Examples, or methods described in *Comprehensive Organic Transformations: A Guide to Functional Group Preparations*, 2nd Edition (Richard C. Larock, John Wiley & Sons Inc., 1999, or other methods. Furthermore, the starting compound may be used in the form of a salt. An example of the salt used includes a salt of the compound of the formula (I) described above. The compound of the present invention can be produced, for example, by the following processes.

a) The compound of the formula (I) wherein Cyc3 is heterocyclic ring containing nitrogen atom which may have a substituent(s), X is methylene, Z is —N($R^5$)CO—, that is, the compound of the formula (I-A):

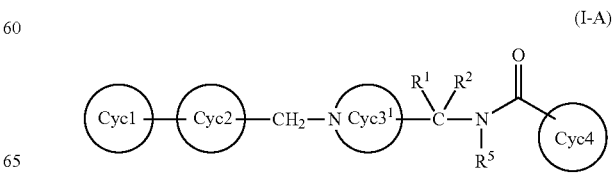

(I-A)

wherein Cyc3[1] is saturated heterocyclic ring containing nitrogen atom which may have a substituent(s), the "substituent" in the "saturated heterocyclic ring containing nitrogen atom which may have a substituent(s)" represented by Cyc3[2] have the same example of such as the "substituent" in the "cyclic ring which may have a substituent(s)" represented by Cyc3 and all other symbols have the same meanings as described above, can be prepared by amidation reaction of a compound represented by formula (I-B):

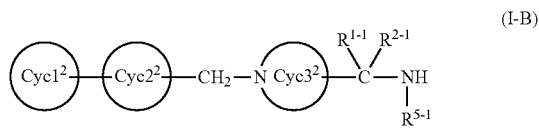

wherein Cyc1[2], Cyc2[2], Cyc3[2], $R^{1-1}$, $R^{2-1}$ and $R^{5-1}$ have the same meanings as Cyc1, Cyc2, Cyc3[1], $R^1$, $R^2$ and $R^5$ respectively, with the proviso that, carboxyl, hydroxy, amino or thiol in Cyc1[2], Cyc2[2], Cyc3[2], $R^{1-1}$, $R^{2-1}$ and $R^{5-1}$ may be protected, if necessary, and a compound represented by formula (I-C):

wherein Cyc4[3] have the same meanings as Cyc4. With the proviso that carboxyl, hydroxy, amino or thiol in Cyc4[3] may be protected, if necessary, followed by removal of the protecting group.

The amidation is known. For example, it includes the method
(1) via an acyl halide,
(2) via a mixed acid anhydride,
(3) using a condensing agent.

These methods are explained as follows.
(1) The method via an acyl halide may be carried out, for example, by reacting a carboxylic acid with an acyl halide (for example, oxalyl chloride or thionyl chloride) in an organic solvent (for example, chloroform, dichloromethane, diethyl ether or tetrahydrofuran) or without a solvent at about −20° C. to reflux temperature. And then, the obtained acyl halide derivative may be reacted with an amine in an organic solvent (for example, chloroform, dichloromethane, diethyl ether or tetrahydrofuran) in the presence of a base (for example, pyridine, triethylamine, dimethylaniline, dimethylaminopyridine or diisopropylethylamine etc.) at about 0 to 40° C. As an alternative, the obtained acyl halide derivative may be reacted with an amine in an organic solvent (for example, dioxane, tetrahydrofuran) using an alkaline aqueous solution (for example, sodium hydrogen carbonate, sodium hydroxide) at about −78 to 40° C.
(2) The method via a mixed acid anhydride may be carried out, for example, by reacting a carboxylic acid with an acyl halide (for example, pivaloyl chloride, p-toluenesulfonyl chloride or methanesulfonyl chloride) or an acid derivative (for example, ethyl chloroformate or isobutyl chloroformate) in an organic solvent (for example, chloroform, dichloromethane, diethyl ether, tetrahydrofuran) or without a solvent, in the presence of a base (for example, pyridine, triethylamine, dimethylaniline, dimethylaminopyridine or diisopropylethylamine) at about 0 to 40° C. And then the obtained mixed acid anhydride derivative may be reacted with an amine in an organic solvent (for example, chloroform, methylene chloride, diethyl ether or tetrahydrofuran), at about 0 to 40° C.
(3) The method using a condensing agent may be carried out, for example, by reacting a carboxylic acid with amine in an organic solvent (for example, chloroform, dichloromethane, dimethylformamide, diethyl ether or tetrahydrofuran) or without a solvent, in the presence or absence of a base (for example, pyridine, triethylamine, dimethylaniline or dimethylaminopyridine), using a condensing agent (for example, 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide, or 1-propanephosphonic acid cyclic anhydride (PPA)), in the presence or absence of 1-hydroxybenzothiazole (HOBt), at about 0 to 40° C.

The reaction described in (1), (2) and (3) may be carried out under an inert gas (for example, argon, nitrogen) to avoid water in order to obtain a preferable result.

The removal of the protecting group is known and may be carried out by following method.

The protecting group of carboxyl includes, for example, methyl, ethyl, allyl, tert-butyl, trichloroethyl, benzyl (Bn) or phenacyl etc.

The protecting group of hydroxy includes, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaloyl, benzoyl, benzyl (Bn), p-methoxybenzyl, allyloxycarbonyl (Alloc), and 2,2,2-trichloroethoxycarbonyl (Troc) etc.

The protecting group of amino includes such as benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl (Fmoc), benzyl (Bn), p-methoxybenzyl, benzyloxymethyl (BOM) or 2-(trimethylsilyl)ethoxymethyl (SEM) etc.

The protective group of thiol includes, for example, benzyl, methoxybenzyl, methoxymethyl (MOM), 2-tetrahydropyranyl (THP), diphenylmethyl and acetyl (Ac) etc.

With regard to the protective group for carboxyl, hydroxy, amino and thiol, there is no particular limitation to the above ones so far as it is a group which is able to be easily and selectively detached. For example, a deprotection reaction may be carried out by a method mentioned in "T. W. Greene, *Protective Groups in Organic Synthesis*, John Wiley & Sons Inc, 1999".

The reaction for removing the protective group for carboxyl, hydroxy, amino or thiol is known and its examples are as follows.
(1) a deprotection reaction by hydrolysis with an alkali;
(2) a deprotection reaction under an acidic condition;
(3) a deprotection reaction by hydrogenolysis;
(4) a deprotection reaction of silyl;
(5) a deprotection reaction using a metal; and
(6) a deprotection reaction using a metal complex.

Those methods will be specifically illustrated as follows.
(1) A deprotection reaction by hydrolysis with an alkali is carried out, for example, at about 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and dioxane etc.).

(2) A deprotection reaction under an acidic condition is carried out, for example, at about 0 to 100° C. in an organic acid (for example, acetic acid, trifluoroacetic acid, methanesulfonic acid or para-toluenesulfonic acid), an inorganic acid (for example, hydrochloric acid and sulfuric acid) or a mixture thereof (such as hydrogen bromide/acetic acid) in an organic solvent (such as dichloromethane, chloroform, dioxane, ethyl acetate and anisole etc.).

(3) A deprotection reaction by hydrogenolysis is carried out, for example, at about 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent [such as an ether type (such as tetrahydrofuran, dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as dimethylformamide), water, ethyl acetate, acetic acid or a mixed solvent comprising two or more thereof].

(4) A deprotection reaction of silyl is carried out, for example, at about 0 to 40° C. using tetrabutylammonium fluoride in an organic solvent miscible with water (such as tetrahydrofuran and acetonitrile etc.).

(5) A deprotection reaction using a metal is carried out, for example, at about 0 to 40° C. with or without ultrasonic wave in the presence of powdery zinc in an acidic solvent (such as acetic acid, a buffer of pH 4.2 to 7.2 and a mixed solution of a solution thereof with an organic solvent such as tetrahydrofuran).

(6) A deprotection reaction using a metal complex is carried out, for example, at about 0 to 40° C. using a metal complex [such as tetrakis(triphenylphosphine) palladium (0), bis(triphenylphosphine) palladium (II) dichloride, palladium (II) acetate and tris(triphenylphosphine) rhodium (I) chloride] in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, dimethylformamide, tetrahydrofuran, ethyl acetate, acetonitrile, dioxane and ethanol), water or a mixed solvent thereof.

Apart from the above, the deprotection may also be effected, for example, according to the methods described in T. W. Greene, *Protective Groups in Organic Synthesis*, Wiley, New York, 1999.

As persons skilled in the art can easily understand that the aimed compound of the present invention is able to be easily produced by using appropriate ones among those deprotection reactions.

The compound of the formula (I-B) can be produced by the method as illustrated in the Reaction Scheme1, wherein $P^N$ is a protective group for amino group, and all other symbols have the same meaning as described above.

Reaction Scheme 1:

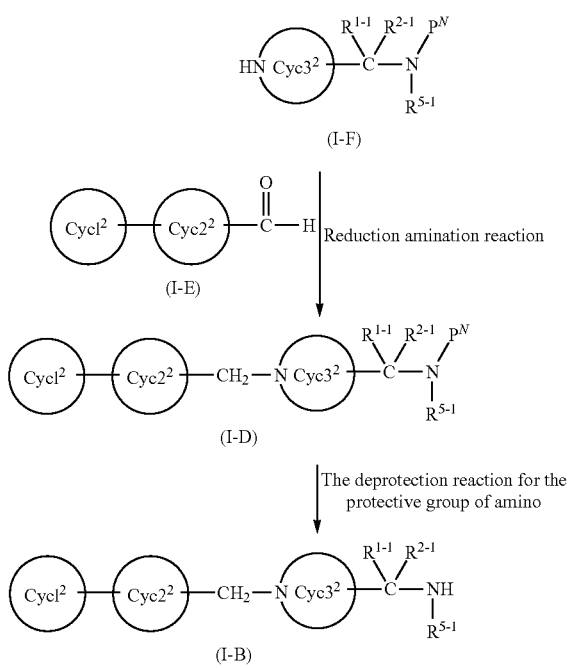

In the Reaction Scheme 1, the reaction from the compound of the formula (I-F) to the compound of the formula (I-D) is a reductive amination reaction.

The reductive amination is well known. For example, it may be carried out with reducing agent (for example, sodium triacetoxyborohydride, tetramethylammonium triacetoxyborohydride or sodium cyanoborohydride) at about 0 to 40° C. in an organic solvent (for example, acetonitrile dichloroethane, dichloromethane or dimethylformamide) in the presence or absence of tertiary amine (for example, triethylamine or diisopropylethylamine), in the presence or absence of acetic acid.

In the Reaction Scheme 1, the reaction from the compound of the formula (I-D) to the compound of the formula (I-B) is a deprotection reaction for the protecting group of amino.

The protecting group of amino includes such as benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl (Fmoc), benzyl (Bn), p-methoxybenzyl, benzyloxymethyl (BOM) or 2-(trimethylsilyl)ethoxymethyl (SEM) etc.

The deprotection reaction for the protecting group of amino can be carried out by the same methods as described above.

b) Among the compound of the formula (I), the compound of the formula (I-G):

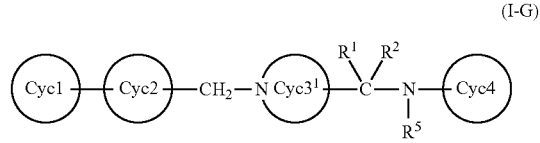

wherein all symbols have the same meanings as described above, can be prepared by substituent-introduction reaction of the compound represented by the formula (I-B):

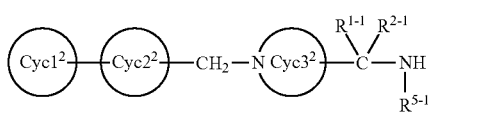 (I-B)

wherein all symbols have the same meanings as described above, and a compound represented by formula (I-H):

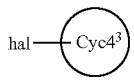 (I-H)

wherein hal is halogen and all other symbols have the same meaning as described above, if necessary, followed by removal of the protecting group.

The substituent-introduction reaction is well known. For example, the method is conducted into practice by reacting the compound of the formula (I-B) and the compound of the formula (I-H) in an organic solvent (for example, benzene, toluene, dimethylformamide, dioxane, tetrahydrofuran, methanol, acetonitrile, dimethoxyethane, acetone, etc.) in the presence of base (for example, sodium ethylate, sodium hydroxide, potassium hydroxide, triethylamine, sodium carbonate, sodium hydrogencarbonate, potassium carbonate, cesium carbonate, thallium carbonate, tripotassium phosphate, cesium fluoride, cesium hydroxide, tetrabutyl ammonium fluoride, sodium tert-butoxide, potassium tert-butoxide etc.) or aqueous solutions thereof, or their mixtures, and a catalyst (tetrakis(triphenylphosphine)palladium (Pd(PPh$_3$)$_4$), bis(triphenylphosphine)palladium dichloride (PdCl$_2$(PPh)$_2$), palladium acetate (Pd(OAc)$_2$), bis(dibenzylideneacetone)palladium, palladium black, 1,1'-bis(diphenylphoshineferrocene)dichloropalladium (PdCl$_2$(dppf)$_2$), diallyl palladium dichloride (PdCl$_2$(allyl)$_2$), phenylbis(triphenylphosphine)palladium iodide (PhPdI(PPh$_3$)$_2$), tris(dibenzylideneacetone)dipalladium (0), etc.) in the presence or absence of (S)-2,2'-bis(diphenylphosphino)-1,1'-binaphthyl or 4,5-bis(diphenylphosphino)-9,9-dimethyl-9H-xanthene at a temperature of room temperature to about 120° C.

The compound represented by the formula (I-B) can be produced by the same method as described above.

c) Among the compound of the formula (I-J):

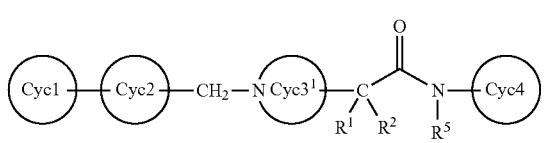 (I-J)

wherein all symbols have the same meanings as described above, can be prepared by amidation reaction of the compound represented by formula (I-K):

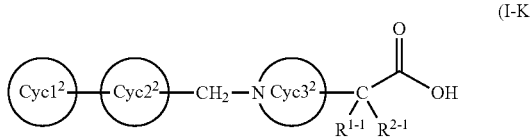 (I-K)

wherein all symbols have the same meanings as described above, and a compound of formula (I-L):

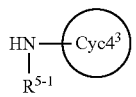 (I-L)

wherein all symbols have the same meanings as described above, if necessary, followed by removal of the protecting group.

The amidation reaction can be carried out by the same method as described above for the amidation reaction.

The compound of the formula (I-K) can be produced by the methods as illustrated in the Reaction Scheme 2, wherein P$^M$ is a protecting group of carboxyl, and all other symbols have the same meanings as described above.

Reaction Scheme 2:

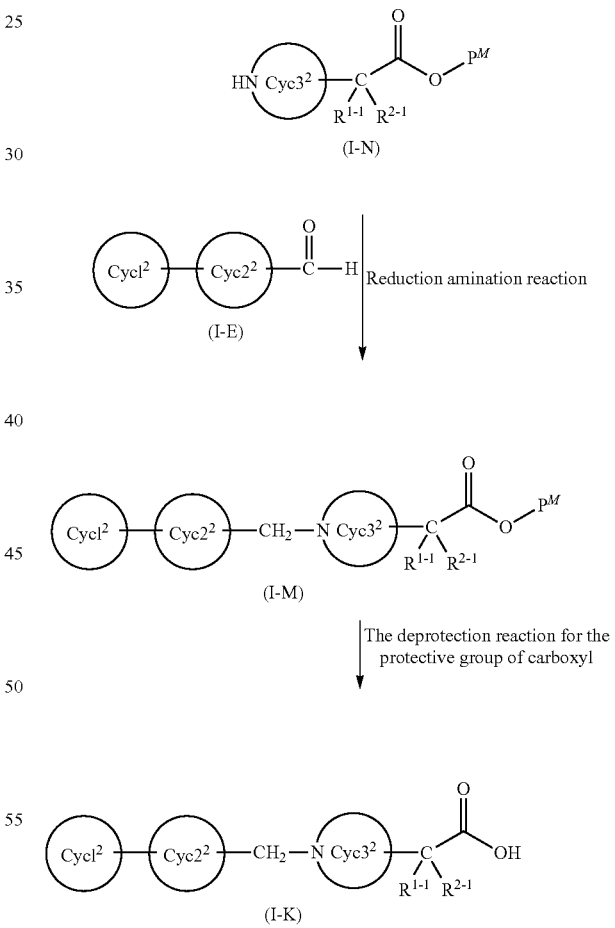

In the Reaction Scheme 2, the reaction from the compound of the formula (I-N) to the compound of the formula (I-M) is a reductive amination reaction.

The reductive amination reaction can be carried out by the same method as described above for the reductive amination reaction.

In the Reaction Scheme 2, the reaction from the compound of the formula (I-M) to the compound of the formula (I-K) is a deprotection reaction for the protecting group of carboxyl.

The deprotection reaction for the protecting group of carboxyl can be carried out by the same method as described above for the deprotection reaction for the protecting group of carboxyl.

Protective group for the carboxyl group include, for example, methyl, ethyl, allyl, tert-butoxy, trichloroethyl, benzyl (Bn), phenacyl, methoxybenzyl, trityl or 2-chlorotrityl group, and the like.

d) The compound of the formula (I) wherein Cyc3 is heterocyclic ring containing nitrogen atom which may have a substituent(s), X is methylene, $R^1$ and $R^2$ are each hydrogen, Z is —N($R^5$)CO—, $R^5$ and the substituent of Cyc4 is taken together to form C1-4 alkylene which may have a substituent(s) or C2-4 alkenylene which may have a substituent(s), that is, the compound of the formula (I-O):

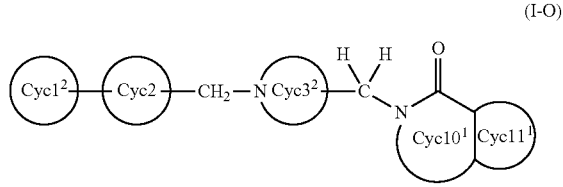

wherein $Cyc10^1$ and $Cyc11^1$ have the same meanings as $Cyc10^1$ and $Cyc11^1$ respectively, with the proviso that, carboxyl, hydroxy, amino or thiol in $Cyc10^1$ and $Cyc11^1$ may be protected, if necessary and all other symbols have the same meaning as described above, can be produced by the methods as illustrated in the Reaction Scheme 3, wherein all symbols have the same meaning as described above.

Reaction Scheme 3:

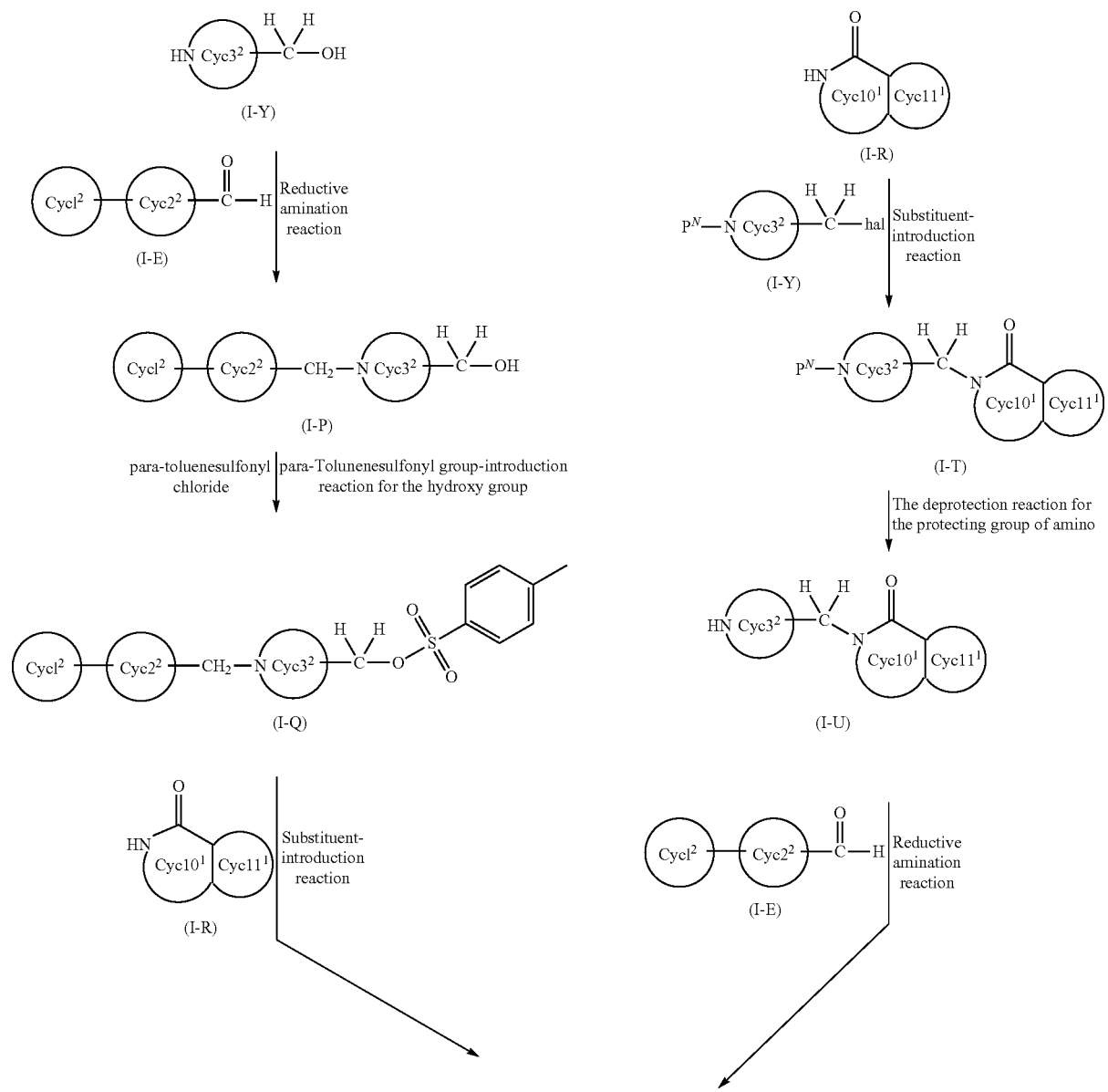

-continued

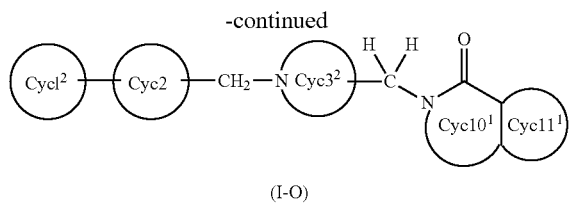

(I-O)

In the Reaction Scheme 3, the reaction from the compound of the formula (I-Y) to the compound of the formula (I-P) is a reductive amination reaction.

The reductive amination reaction can be carried out by the same method as described above for the reductive amination reaction.

In the Reaction Scheme 3, the reaction from the compound of the formula (I-P) to the compound of the formula (I-Q) is a para-toluenesulfonyl group-introduction reaction for the hydroxy group.

The para-toluenesulfonyl group-introduction reaction for the hydroxy group is well known. For example, it may be carried out by reacting para-toluenesulfonyl chloride in an organic solvent (for example, toluene, dichloromethane, benzene, diethyl ether, tetrahydrofuran) in the presence of a base (for example, pyridine, triethylamine, dimethylaniline, dimethylaminopyridine or diisopropylethylamine) at about 0 to 40° C.

In the Reaction Scheme 3, the reaction from the compound of the formula (I-Q) to the compound of the formula (I-O) is a substituent-introduction reaction.

The substituent-introduction reaction can be carried out by the same method as described above for the substituent-introduction reaction.

In the Reaction Scheme 3, the reaction from the compound of the formula (I-R) to the compound of the formula (I-T) is a substituent-introduction reaction.

The substituent-introduction reaction can be carried out by the same method as described above for the substituent-introduction reaction.

In the Reaction Scheme 3, the reaction from the compound of the formula (I-T) to the compound of the formula (I-U) is a deprotection reaction for the protecting group of amino.

The deprotection reaction for the protecting group of amino can be carried out by the same method as described above for the deprotection reaction for the protecting group of amino.

In the Reaction Scheme 3, the reaction from the compound of the formula (I-U) to the compound of the formula (I-O) is a reductive amination reaction.

The reductive amination reaction can be carried out by the same method as described above for the reductive amination reaction.

e) The compound of the formula (I) wherein Cyc3 is heterocyclic ring containing nitrogen atom which may have a substituent(s), X is methylene, Z is —N(R$^5$)CO—, R$^5$ and the substituent of Cyc4 is taken together to form vinylene which have a methoxycarbonyl and a phenyl, that is, the compound of the formula (I-Y):

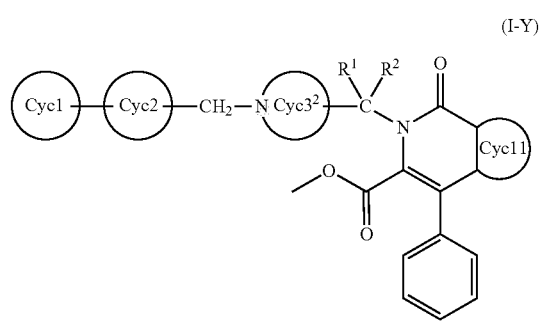

(I-Y)

wherein all symbols have the same meanings as described above, can be produced by the methods as illustrated in the Reaction Scheme 4.

Reaction Scheme 4:

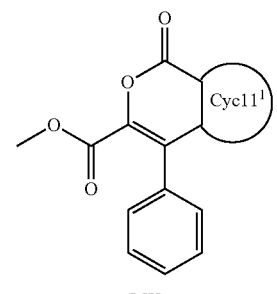

(I-W)

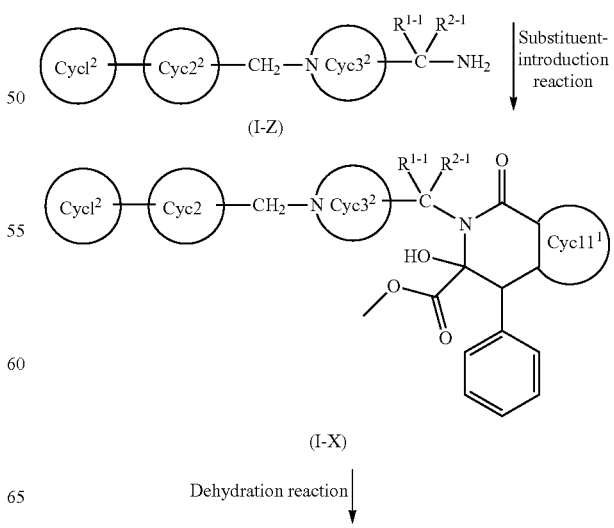

Dehydration reaction

-continued

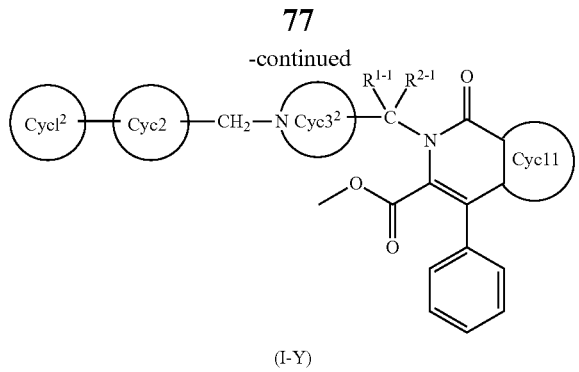

(I-Y)

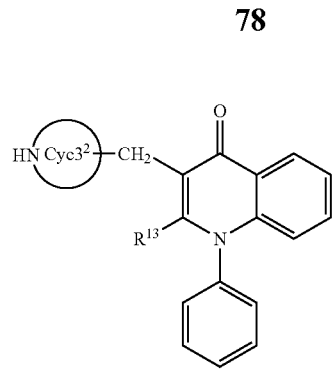

(I-A-B)

In the Reaction Scheme 4, the reaction from the compound of the formula (I-W) to the compound of the formula (I-X) is a substituent-introduction reaction.

The compound represented by formula (I-Z) can be produced by the same method as the compound represented by the formula (I-B) described above in the scheme 1.

The substituent-introduction reaction can be carried out by the same method as described above for the substituent-introduction reaction.

In the Reaction Scheme 4, the reaction from the compound of the formula (I-X) to the compound of the formula (I-Y) is a dehydration reaction.

The dehydration reaction is known and may be carried out by heating in the presence of an organic acid (for example, acetic acid, trifluoroacetic acid, methanesulfonic acid, para-toluenesulfonic acid, etc.), an inorganic acid (for example, hydrochloric acid, sulfuric acid, etc.) or an organic base (for example, piperidine, pyridine, triethylamine, diisopropylethylamine, 1,8-diazabicyclo[5.4.0]undec-7-ene, etc.), an inorganic base (for example, sodium hydrogen carbonate, sodium carbonate, potassium carbonate, etc.) in the absence or presence of an organic solvent [for example, a benzene solvent (for example, benzene, toluene, xylene, chlorobenzene, etc.), an ether solvent (for example, tetrahydrofuran, dioxane, etc.), an alcohol solvent (for example, methanol, ethanol, isopropanol, butanol, etc.), at room temperature to reflux temperature.

f) The compound of the formula (I) wherein Cyc3 is heterocyclic ring containing nitrogen atom which may have a substituent(s), X is methylene, Z is bond, $R^1$ and $R^2$ are each hydrogen, Cyc4 is 1,4-dihydroquinoline which have $R^{13}$, phenyl and oxo as substituents, that is, the compound of the formula (I-A-A):

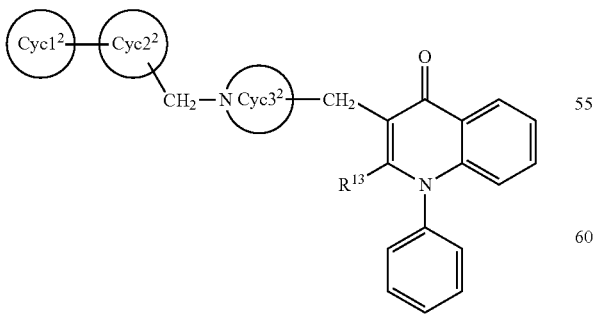

(I-A-A)

wherein all symbols have the same meanings as described above, can be prepared by reductive amination reaction of the compound represented by formula (I-A-B):

wherein all symbols have the same meanings as described above, and a compound represented by the formula (I-E):

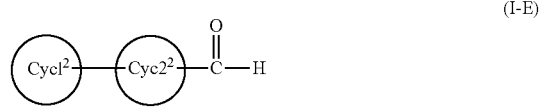

(I-E)

wherein all symbols have the same meanings as described above, to the reaction and if necessary to the deprotection reaction of a protecting group.

The reductive amination reaction can be carried out by the same method as described above for the reductive amination reaction.

The compound represented by formula (I-A-B) can be produced by the methods as illustrated in the Reaction Scheme 5, wherein all symbols have the same meanings as described above.

Reaction Scheme 5:

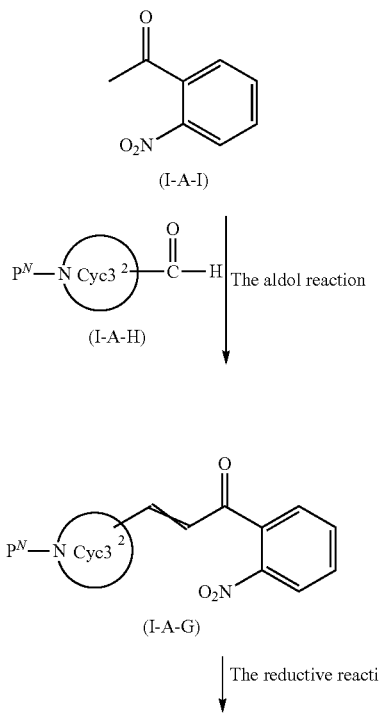

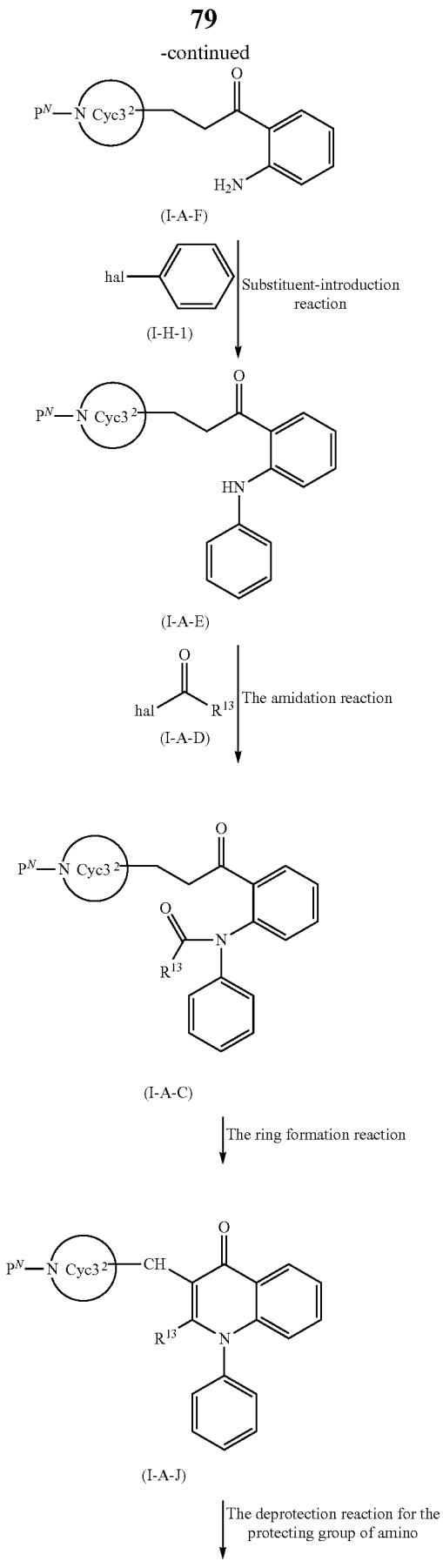

(I-A-F)

(I-H-1)

(I-A-E)

(I-A-D)

(I-A-C)

The ring formation reaction (I-A-J)

The deprotection reaction for the protecting group of amino

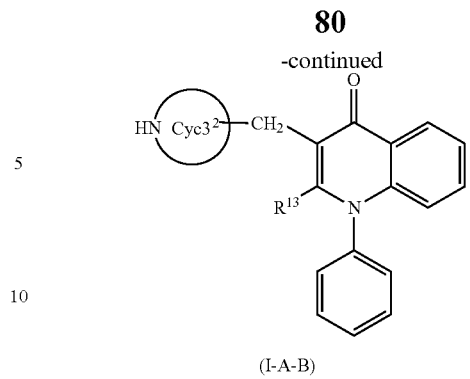

(I-A-B)

In the Reaction Scheme 5, the reaction from the compound represented by the formula (I-A-I) to the compound represented by the formula (I-A-G) is an aldol reaction.

The aldol reaction is well known and may be carried out by heating in the presence of an organic acid (for example, acetic acid, trifluoroacetic acid, methanesulfonic acid, para-toluenesulfonic acid, etc.), an inorganic acid (for example, hydrochloric acid, sulfuric acid, etc.) or an organic base (for example, piperidine, pyridine, triethylamine, diisopropylethylamine, 1,8-diazabicyclo[5.4.0]undec-7-ene, etc.), an inorganic base (for example, sodium hydrogen carbonate, sodium carbonate, potassium carbonate, sodium hydroxide, potassium hydroxide, sodium tert-butoxide, potassium tert-butoxide, etc.) in the absence or presence of an organic solvent [for example, a benzene solvent (for example, benzene, toluene, xylene, chrolobenzene, etc.), an ether solvent (for example, tetrahydrofuran, dioxane, etc.), an alcohol solvent (for example, methanol, ethanol, isopropanol, butanol, etc.), at room temperature to reflux temperature.

In the Reaction Scheme 5, the reaction from the compound represented by the formula (I-A-G) to the compound represented by the formula (I-A-F) is a reductive reaction.

The reductive reaction is well known and may be carried by hydrogenolysis, for example, at about 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent [such as an ether type (such as tetrahydrofuran, dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as dimethylformamide), water, ethyl acetate, acetic acid or a mixed solvent comprising two or more thereof].

In the Reaction Scheme 5, the reaction from the compound represented by (I-A-F) to the compound represented by the formula (I-A-E) is a substituent-introduction reaction.

The substituent-introduction reaction can be carried out by the same method as described above for the substituent-introduction reaction.

In the Reaction Scheme 5, the reaction from the compound represented by (I-A-E) to the compound represented by the formula (I-A-C) is an amidation reaction.

The amidation reaction can be carried out by the same method as described above for the amidation reaction.

In the Reaction Scheme 5, the reaction from the compound represented by (I-A-C) to the compound represented by the formula (I-A-J) is a ring formation reaction.

The ring formation reaction is well known and may be carried out by heating in the presence of an organic base (for example, piperidine, pyridine, triethylamine, diisopropylethylamine, 1,8-diazabicyclo[5.4.0]undec-7-ene, etc.), an inorganic base (for example, sodium hydrogen carbonate, sodium carbonate, potassium carbonate, sodium hydroxide, potassium hydroxide, sodium tert-butoxide, potassium tert-butoxide, etc.) in the absence or presence of an organic solvent [for example, a benzene solvent (for example, benzene, toluene, xylene, chrolobenzene, etc.), an ether solvent (for example, tetrahydrofuran, dioxane, etc.), an alcohol solvent (for example, methanol, ethanol, isopropanol, butanol, etc.), at room temperature to reflux temperature.

In the Reaction Scheme 5, the reaction from the compound represented by (I-A-J) to the compound represented by the formula (I-A-B) is a deprotection reaction for the protecting group of amino.

The deprotection reaction for the protecting group of amino can be carried out by the same method as described above the deprotection reaction for the protecting group of amino.

g) The compound of the formula (I) wherein Cyc3 is piperidine ring which have a $R^{10}$, X is methylene, $R^1$ and $R^2$ are each hydrogen, Z is —NHCO—, Cyc4 is benzene or pyridine ring which have a $R^{14}$, a $R^{15}$ and a $R^{16}$, that is, the compound of the formula (I-1-5-A):

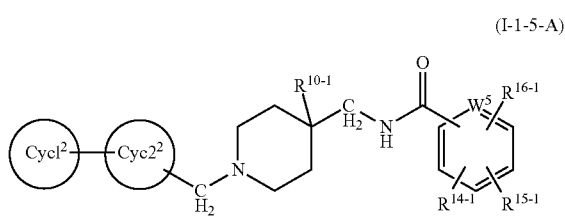

(I-1-5-A)

wherein $R^{10-1}$, $R^{14-}$, $R^{15-1}$ and $R^{16-1}$ have the same meanings as $R^{10}$, $R^{14}$, $R^{15}$ and $R^{16}$ respectively, with the proviso that, carboxyl, hydroxy, amino or thiol in $R^{10-1}$ may be protected, amino in $R^{14-1}$ and $R^{15-1}$ may be protected, and hydroxy or amino in $R^{16-1}$ may be protected, if necessary, and all other symbols have the same meaning as described above, can be produced by the methods as illustrated in the Reaction Scheme 6, wherein all symbols have the same meaning as described above.

Reaction Scheme 6:

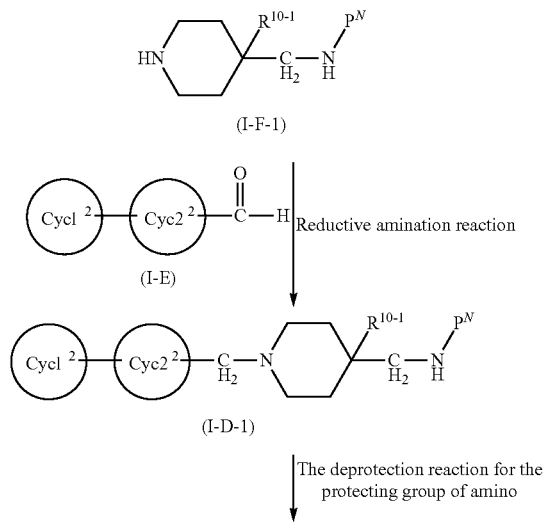

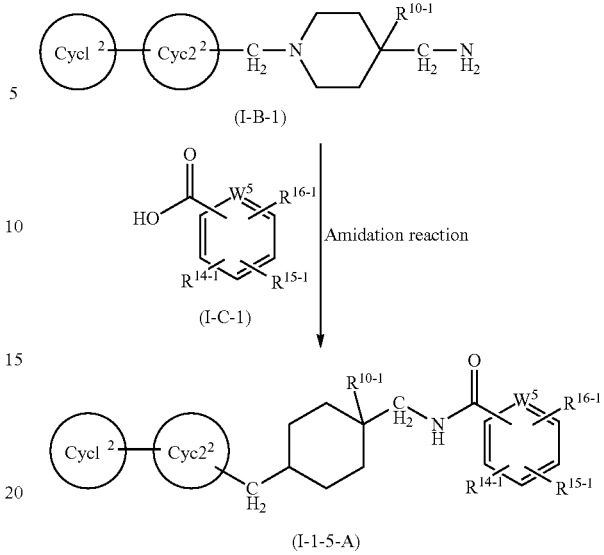

wherein all symbols have the same meaning as described above.

In the Reaction Scheme 6, the reaction from the compound of the formula (I-F-1) to the compound of the formula (I-D-1) is a reductive amination reaction.

The reductive amination reaction can be carried out by the same method as described above for the reductive amination reaction.

In the Reaction Scheme 6, the reaction from the compound of the formula (I-D-1) to the compound of the formula (I-B-1) is a deprotection reaction for the protecting group of amino.

The deprotection reaction for the protecting group of amino can be carried out by the same method as described above the deprotection reaction for the protecting group of amino.

In the Reaction Scheme 6, the reaction from the compound of the formula (I-B-1) to the compound of the formula (I-1-5-A) is an amidation reaction.

The amidation reaction can be carried out by the same method as described above for the amidation reaction.

The compound of the present invention can be prepared by these reactions or reactions modified a part of them.

Other starting compounds or compounds used as reagent are known compounds can be prepared easily by combination of known methods, for example, the methods described in *Comprehensive Organic Transformations: A Guide to Functional Group Preparations,* 2nd Edition (Richard C. Larock, John Willey & Sons Inc, 1999) or Elmer J. Rauckman et al., *J. Org. Chem.,* vol. 41, No. 3, 1976, p 564-565 etc.

In each reaction of the specification, the reactions with heating, as will be apparent to those skilled in the art, it may be carried with water bath, oil bath, sand bath and microwave.

In each reaction of the specification, it may be used a solid phase reagent which is supported by polymer (for example, polystyrene, polyacrylamide, polypropylene or polyethyleneglycol etc.).

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing or by recrystallization. The purification may be done each reaction or after several reactions.

In a reaction using polystyrene resin of the specification, the obtained products may be purified by conventional techniques. For example, the purification may be carried out by rinsing them with a solvent (for example, dimethylformamide, dichloromethane, methanol, tetrahydrofuran, toluene, acetic acid/toluene, etc.) more than once.

Pharmacological Activity

A pharmacological test except for the Biological Examples hereinafter described includes, for example, the following method. By the method shown below, the in vivo effect of the compound represented by the formula (I) can be proved. A vehicle used for the administration of the compound represented by the formula (I) to an animal may be any material so long as it can suspend or dissolve the compound into safe and administrable state. For example, it is possible to appropriately select and use vehicles which those skilled in the art use for the administration to an animal, and examples of such vehicles are methylcellulose, carboxymethyl cellulose, hydroxypropyl cellulose, hydroxypropylmethyl cellulose, propylene glycol, polyethylene glycol, sugar, sugar alcohol, edible oil, distilled water, physiological saline solution, and a mixture thereof and the like.

(1) Consideration of the Improvement in Insulin-Resistance on Diabetes Model of KKAy Mice Male, 8-weeks old KKAy/Ta Jcl mice are pre-breaded individually in single cages for approximately one week. During pre-breaded and test term, mice are provided pellet diet and tap water from bottle of feed water ad libitum. On the first day of the experiment (Day 0), the body weight of mice are measured. Blood samples are collected from coccygeal vein using a microcapillary to measure plasma glucose concentration. Based on plasma glucose concentration, mice are divided into some groups (five mice per group) using a stratified randomization method and started dosing. The dosing can be carried out by oral gavage administration compulsorily or parenteral administration by subcutaneous injection, after suspending or dissolving the test compound in the above described vehicle. The control group receives preferably only the vehicle. The doses and the administration frequency can be increased or decreased appropriately by the effect of the test compound, preferably, for example, about 0.1 mg/kg body weight to 100 mg/kg body weight, about 1 to 3 times par day, every day. The endpoints of the efficacy on the present model include body weight, food intakes, blood glucose level, triglycereide of plasma, insulin, weight of liver. These endpoints can be measured after arbitrary days from starting the dosing. For example, on the second day (Day 2) to seventh day (Day 7) from starting dosing, the efficacy on the model can be confirmed by measuring these endpoints. On the model, pioglitazone can show the efficacy such as body weight gain, decline of blood glucose level and insulin level, and the like, by oral administration one time per day and from 50 mg/kg body weight.

Toxicity

Because the compound represented by the formula (I) of the present invention does not have undesirable side effects such as hepatotoxicity, the toxicity of the compound is very low. Therefore, it is considered that the compound represented by the formula (I) of the present invention is sufficiently safe to be used as a pharmaceutical.

Application to Pharmaceuticals

The compound represented by the formula (I), a salt thereof, an N-oxide thereof, a solvate thereof, or a prodrug thereof (hereinafter, which may be abbreviated to the compound of the present invention) can be used as an agent for prevention and/or treatment of metabolic diseases (for example, diabetes mellitus such as insulin-resistant diabetes mellitus or non-insulin-resistant diabetes mellitus, hyperlipemia, other insulin-resistant diseases, etc.), cerebrovascular disease (for example, stroke, cerebral bleeding, subarachnoid hemorrhage, spontaneous occlusion of circle of Willis, chronic subdural hematoma, etc.), and the like.

Metabolic diseases and cerebrovascular disease are not limited the diseases described above, and the diseases include all diseases in which the involvement of those diseases has so far been suggested or will be found afterward. Other than metabolic diseases and cerebrovascular disease described above, the compound of the present invention can be used as an agent for prevention and/or treatment of inflammatory diseases (for example, diabetic complication (for example, retinopathy, nephropathy, nervous disorder, macrovascular disease, etc.), inflammation, dermatitis, atopic dermatitis, hepatic inflammation, inflammation of the kidneys, glomerulonephritis, pancreatitis, psoriasis, gout, Addison's disease, osteitis syndrome (for example, osteitis such as osteomyelitis, osteomalacia, periostitis, etc.), arthritis (for example, rheumatoid arthritis, osteoarthritis, rheumatoid spondylitis, gouty arthritis, synovitis, etc.), inflammatory eye disease, inflammatory pulmonary disease (for example, chronic pneumonia, pulmonary silicosis, pulmonary sarcoidosis, lung tuberculosis, adult respiratory distress syndrome (ARDS), severe acute respiratory syndrome (SARS), etc.), inflammatory enteropathy (for example, Crohn's disease, chronic ulcerative colitis, etc.), allergy disease (for example, allergic dermatitis, allergic rhinitis, etc.), autoimmune diseases, autoimmune hemolytic anemia, systemic erythematosus, rheumatism, Castleman's disease, immune rejection accompanied with implanting (for example, graft-versus-host reaction, etc.); nervous disorder (for example, central nervous system damage (for example, cerebral hemorrhage, head injury, spinal cord injury, brain edema, multiple sclerosis, etc.), neurodegenerative disease (for example, Alzheimer disease, Parkinson's disease, amyotrophic lateral sclerosis (ALS), acquired immunodeficiency syndrome (AIDS) encephalosis, etc.), cerebral meningitis, Creutzfeldt-Jakob disease etc.); pulmonary problems (for example, asthma, chronic obstructive pulmonary disease (COPD), etc.); circulatory system disease (for example, angina pectoris, cardiac failure, congestive cardiac failure, acute cardiac failure, chronic cardiac failure, cardiac infarction, acute cardiac infarction, cardiac infarction prognosis, intraatrial myxoma, arterial sclerosis, hypertension, dialysis hypotension, thrombosis, diffuse intravascular coagulation syndrome (DIC), reperfusion injury, post-percutaneous transluminal coronary angioplasty (PTCA) restenosis, etc.); urinary system disease (for example, renal failure, etc.); bone disease (for example, osteoporosis, etc.); cancer disease (for example, malignancy such as growth and metastasis of malignant tumor, etc.), multiple myeloma, plasma cell leukemia, cancerous cachexia, etc.; infectious disease (for example, virus infection caused by cytomegalovirus, influenza virus, herpes virus, corona virus, etc., cachexia accompanied with infection, cachexia related to AIDS, blood poisoning such as sepsis, septic shock, endotoxic shock, gram-negative sepsis, toxic shock syndrome, severe acute respiratory syndrome (SARS) accompanied with virus infection, etc.); and the like.

When the compound of the present invention is used for the aforementioned purposes, normally it is administered systemically or locally by oral route or parenteral route.

The compound of the present invention is safe and low in toxicity so that it may be administered to a mammal including human or a non-human animal (for example, monkey, sheep, cattle, horse, dog, cat, rabbit, rat, mouse, etc.).

The doses to be administered are determined depending upon, for example, age, body weight, symptom, the desired therapeutic effect, the route of administration, the duration of the treatment, and the like. For a human adult, generally 1 mg to 1000 mg per dose is orally administered once to several times a day, or 0.1 mg to 100 mg per dose is parenterally (preferably intravenously) administered once to several times a day, or intravenously administered continuously for 1 to 24 hours a day.

As mentioned above, the doses to be administered depend upon various conditions. Therefore, there may be cases where doses lower than or greater than the ranges specified above are applied.

The compound of the present invention may be safely administered orally or parenterally (for example, local, rectal, intravenous administration) alone or by mixing with a pharmaceutically acceptable carrier to be made into a medicinal preparation, for example, solid agents for oral administration (for example, tablets including those coated with sugar or film, powder, pills, granules, capsules, etc.), liquid agents for oral administration, injections, suppositories, sustained release drug, etc., in accordance with a known method generally used as a manufacturing method of a medicinal preparation. The amount of the compound of the present invention in such preparations is about 0.01% of part weight to about 100% of part weight, preferably about 0.1% of part weight to about 50% of part weight, and more preferably, about 0.5% of part weight to about 20% of part weight, relative to the whole of the preparation.

The compound of the present invention used in the production of those medicinal preparations is not limited to substantially pure and single substance, and may include impurities (for example, by-product, solvent, raw material, etc. which is derived from the production steps) as far as they are pharmaceutically acceptable as pharmaceutical bulk.

The carrier which is used in the production of the medicinal preparation includes various conventional organic or inorganic carrier materials, such as vehicles, lubricants, binders and disintegrants of solid preparation, or solvents, solution adjuvants, suspending or emulsifying agents, tonicity agent, buffering agents and soothing agents, etc. of liquid preparation. If necessary, conventional preservatives, antioxidants, coloring agents, sweetening agents, absorbents and humectants can be used appropriately on adequate dose.

Solid agents for oral administration include tablets, pills, capsules, dispersible powders and granules. Capsules include hard capsules and soft capsules. In such solid agents, one or more of the active compound(s) may be alone, or admixed with vehicles (such as lactose, mannitol, glucose, microcrystalline cellulose, starch, corn starch, light anhydrous silicic acid, etc.), binders (such as hydroxypropyl cellulose, polyvinylpyrrolidone, magnesium metasilicate aluminate, crystalline cellulose, white sugar, D-mannitol, dextrin, hydroxypropylmethyl cellulose, starch, sucrose, gelatin, methylcellulose, sodium carboxymethyl cellulose, etc.), disintegrants (such as cellulose calcium glycolate, starch, carboxymethyl cellulose, carboxymethyl cellulose calcium, sodium carboxymethyl starch, L-hydroxypropyl cellulose, etc.), lubricants (such as magnesium stearate, calcium stearate, talc, colloidal silica, etc.), and formulated according to common methods. The solid agents may, if desired, be coated with coating agents (such as white sugar, gelatin, hydroxypropyl cellulose or hydroxypropylmethyl cellulose phthalate), or be coated with two or more films. And further, coating may include containment within capsules of absorbable materials such as gelatin.

Liquid agents for oral administration include pharmaceutically acceptable solutions, suspensions, emulsions, syrups, elixirs, etc. In such liquid agents, one or more of the active compound(s) may be dissolved, suspended or emulsified into diluent(s) commonly used in the art (such as purified water, ethanol or a mixture thereof). The liquid agents may further comprise some additives, such as wetting agents, suspending agents, emulsifying agents, sweetening agents, flavoring agents, aroma, preservatives or buffering agents.

Injections for parenteral administration include any types of injections including drops. Examples of injections include intramuscular injections, subcutaneous injections, intradermal injections, intraarterial injections, intravenous injections, intraabdominal injections, intraspinal injections, intravenous drips, etc. Injections for parenteral administration also include sterile aqueous, suspensions, emulsions and solid forms which are dissolved or suspended into solvent(s) for injection immediately before use. In injections, one or more of the active compound(s) may be dissolved, suspended or emulsified into solvent(s). Examples of the solvents include distilled water for injection, physiological saline, macrogol, vegetable oil (for example, sesame-seed oil, corn oil, olive oil, etc.), propylene glycol, polyethylene glycol, alcohol such as ethanol, or a mixture thereof.

Injections may comprise some additives, such as stabilizing agents (for example, D-sorbitol, D-mannitol, L-alanine, ascorbic acid, albumin, inositol, sodium gluconic acid, sodium thioglycolate, polyoxyethylene hardened castor oil, etc.), solution adjuvants (for example, glutamic acid, aspartic acid, POLYSORBATE 80 (registered trade mark), polyethylene glycol, propylene glycol, D-mannitol, benzyl benzoate, ethanol, trisaminomethane, cholesterol, triethanolamine, sodium carbonate, sodium citrate, etc.), emulsifying agents or emulsifying agents (for example, surface-active agents such as stearyltriethanolamine, sodium lauryl sulfate, laurylaminopropionic acid, lecithin, benzalkonium chloride, benzetonium chloride, glycerin monostearate, etc.; hydrophilic polymer such as polyvinyl alcohol, polyvinylpyrrolidone, sodium carboxymethylcellulose, methylcellulose, hydroxymethylcellulose, hydroxyethylcellulose, hydroxypropylcellulose, etc.; and the like), soothing agents (for example, benzyl alcohol, etc.), tonicity agents (for example, glucose, D-sorbitol, sodium chloride, glycerin, D-mannitol, etc.), buffering agents (for example, phosphate buffer, acetate buffer, carbonate buffer, citrate buffer, etc.), preservatives (for example, parahydroxybenzoate esters, chlorobutanol, benzylalcohol, phenethyl alcohol, dehydroacetate, sorbic acid, etc.), antioxidants (for example, sulfite salt, ascorbic acid, α-tocopherol, etc.), and the like. They may be sterilized at a final step, or may be prepared and compensated according to aseptic manipulations. They may also be manufactured into sterile solid agents, for example, freeze-dried products, which may be dissolved in sterile water or some other sterile diluent(s) for injection immediately before use.

Freeze drying can be carried out by the known method. Generally, a preferable method is to dry by freezing at −25° C. or below, and then raising the temperature of a drying rack to 25° C. to 40° C., while holding the vacuum pressure of a dry warehouse at about 13.3 Pa or below.

The other preparations for parenteral administration include liquids for external use, ointments, liniments, insufflations, spray preparations, suppositories and pessaries for vaginal administration which comprise one or more of the active substance(s) and may be prepared by methods known per se.

The compound of the present invention may be administered as a combination preparation by combining with other pharmaceuticals for the purpose of 1) supplementation and/or enhancement of the preventive and/or therapeutic effects of the compound, 2) improvement of pharmacokinetics and absorption of the compound and reduction of the dosage, and/or 3) reduction of side effects of the compound.

In addition, the compound of the present invention may be combined and administered as a combination preparation for the purpose of 1) supplementing and/or enhancing the preventive and/or treatment effect of the other pharmaceuticals to be combined (hereinafter, which may be abbreviated to a concomitant drug(s)), 2) improving pharmacokinetics and absorption of the concomitant drug(s) and reducing the dose of the concomitant drug(s), and/or 3) reducing side effect of the concomitant drug(s).

The combination preparations of the compound of the present invention and a concomitant drug(s) may be administered as one combination preparation comprising these components, or may be administered separately. When they are administered separately as independent preparations, they may be administered simultaneously or with time lag. Administration with time lag includes the method of administering the compound of the present invention before other drugs and vice versa, and each administration route may be the same or different. There is no limitation on a disease on which the combination preparations of the compound of the present invention and a concomitant drug(s) have preventive and/or treatment effects, so long as the preventive and/or treatment effect of the combination preparation is supplemented and/or enhanced in the disease. There is no limitation on the weight ratio between the compound of the present invention and the concomitant drug(s) in a combined preparation by combining the compound of the present invention with the concomitant drug(s).

Furthermore, the concomitant drug(s) is not limited to a low molecular weight compound, and may be a macromolecule protein, polypeptide, polynucleotide (DNA, RNA, gene), antisense, decoy, antibody, vaccine, and the like. The dosage of the concomitant drug(s) can be properly selected according to the clinical dosage. The compounding ratio of the compound of the present invention and the concomitant drug(s) can be properly selected by the age and body weight of the object, administration route, administration term, target disease, symptom, combination, and the like. For example, the amount of the concomitant drug(s) may be used 0.01 parts by weight to 100 parts by weight relative to 1 part by weight of the compound of the present invention.

The concomitant drug(s) may be administered in the proper combination of arbitrary one or two or more member(s) selected from the same or different groups in arbitrary proportion.

Examples of the concomitant drug(s) of the compound of the present invention as a preventive and/or therapeutic agent for hyperlipemia includes, for example, a MTP (Microsomal Triglyceride Transfer Protein) inhibitor, an HMG-CoA reductase inhibitor, a squalene synthetase inhibitor, a fibrate preparation, an ACAT (Acyl-CoA: cholesterol O-acyltransferase) inhibitor, a 5-lipoxygenase inhibitor, a cholesterol absorption inhibitor, a bile acid absorption inhibitor, a ileum Na$^+$/bile acid cotransporter (IBAT) inhibitor, an LDL receptor activator/enhanced expression, a lipase inhibitor, a probucol preparation, a niacin preparation.

Examples of the concomitant drug(s) of the compound of the present invention as a preventive and/or therapeutic agent for diabetes mellitus (insulin-resistant diabetes mellitus or non-insulin-resistant diabetes mellitus), diabetes complication and the like, include a hypoglycemic sulfonylurea agent, a biguanide preparation, an α-glucosidase inhibitor, a rapid-acting insulin secretagogue, an insulin preparation, a GPR 40 agonist(G protein coupled receptor 40 agonist), a SGLT (sodium-dependent glucose transporter, for example, SGLT1, SGLT2) inhibitor, a GLP-1 (hormone Glucagon-Like Peptide-1)/GLP-1 analog, a DPP4 (dipeptidyl peptidase) inhibitor, a PTP1B inhibitor, a β3 adrenoceptor agonist, a PPAR (for example, PPARα, PPARγ, PPARδ) agonist, and diabetes complication therapeutic agent and the like.

Examples of the concomitant drug(s) of the compound of the present invention as a preventive and/or therapeutic agent for cerebrovascular disease include an anti-thrombus agent, an oral anticoagulant, an anti-platelet agent, a thrombolytic agent, a cerebral circulation metabolism improving agent, an HMG-CoA reductase inhibitor, and the like.

Examples of the MTP inhibitor include BMS-201038, BMS-212122, BMS-200150, GW-328713, R-103757, and the like.

Examples of the HMG-CoA reductase inhibitor include atorvastatin, fluvastatin, lovastatin, pitavastatin, pravastatin, rosuvastatin, simvastatin, and the like.

Examples of the squalene synthetase inhibitor include TAK-475 and the like.

Examples of the fibrate preparation include gemfibrozil, clofibrate, bezafibrate, fenofibrate, and the like.

Examples of the ACAT inhibitor include F-12511, F-1394, CI-1011, melinamide, FCE27677, RP73163, and the like.

Examples of the 5-lipoxygenase inhibitor include zileuton, and the like.

Examples of the cholesterol absorption inhibitor include SCH48461 and the like.

Examples of the bile acid absorption inhibitor include cholestyramine, cholestagel, and the like.

Examples of the ileum Na$^+$/bile acid cotransporter (IBAT) inhibitor include S-8921, and the like.

Examples of the LDL receptor activator/enhanced expression agent include MD-700, LY295427, and the like.

Examples of the lipase inhibitor include orlistat and the like.

Examples of the hypoglycemic sulfonylurea agent include acetohexamide, glibenclamide, gliclazide, glyclopyramide, chlorpropamide, tolazamide, tolbutamide, glimepiride, and the like.

Examples of the biguanide preparation include buformin hydrochloride, metformin hydrochloride, and the like.

Examples of the α-glucosidase inhibitor include acarbose, voglibose, and the like.

Examples of the rapid-acting insulin secretagogue include nateglinide, repaglinide, and the like.

Examples of the GPR 40 agonist include the compounds described in WO04/41266, WO04/106276, WO05/51890, WO05/63725, WO06/83612, WO07/13689 and the like.

Examples of the SGLT inhibitor include T-1095, AVE-2268, KGT-1251/KGT-1681, and the like.

Examples of the GLP-1/GLP-1 analog include Liraglutide (NN2211), exenatide (trade name Byetta), and the like.

Examples of the DPP4 inhibitor include NVP-DPP728A, vildagliptin, and the like.

Examples of the β3 adrenoceptor agonist include AJ9677, L750355, CP331648, and the like.

Examples of the PPAR agonist include pioglitazone, troglitazone, rosiglitazone, JTT-501, and the like.

Examples of the diabetes complication therapeutic agent include epalrestat, and the like.

Examples of the anti-thrombus agent include tissue plasminogen activator (t-PA), rt-PA, heparin, and the like.

Examples of the oral anticoagulant include warfarin, and the like.

Examples of the anti-platelet agent include aspirin, dipyridamole, ticlopidine hydrochloride, beraprost sodium, cilostazol, ozagrel sodium, and the like.

Examples of the thrombolytic agent include urokinase, tisokinase, alteplase, and the like.

Examples of the cerebral circulation metabolism improving agent include idebenone, calcium hopantenate, amantadine hydrochloride, meclofenoxate hydrochloride, dihydroergotoxin mesylate, pyrithioxine hydrochloride, γ-aminobutyric acid, bifemelane hydrochloride, lisuride maleate, indeloxazine hydrochloride, nicergoline, propentofylline, and the like.

The following excellent effects can be obtained by combining the compound of the present invention with the concomitant drug(s).

(1) The concomitant use can decrease the dose compared to administration of the compound alone of the present invention or the concomitant drug(s) alone;

(2) The compound of the present invention and the concomitant drug can be selected according to a patient's symptom (mild case, severe case, etc.);

(3) The selection of the concomitant drug(s) of which mechanism of the action is different from that of the compound of the present invention can decrease the dose in patients and extend the therapeutic period;

(4) The selection of the concomitant drug(s) of which mechanism of the action is different from that of the compound of the present invention can maintain the therapeutic effect;

(5) The combination of the compound of the present invention with the concomitant drug(s) can obtain the synergistic effect.

Especially, in the case that the concomitant drug(s) is a steroid drug, it is possible to take a steroid drug of weak action as compared with administration of the steroid drug alone.

Generally, in the case of the combination of fibrate preparations with a HMG-CoA reductase inhibitor, it is known that rhabdmyolysis may occur as a side effect. However, the incidence and the degree of rhabdmyolysis can be decreased by using the above described concomitant drugs.

Hereinafter, to use the compound of the present invention in conjunction with a concomitant drug(s) is termed "the combination preparation of the present invention". In the case of using the combination preparation of the present invention, there is no particular limitation for administration time of the compound of the present invention or and a concomitant drug(s). The administration of the compound of the present invention or pharmaceutical composition thereof and a concomitant drug(s) or pharmaceutical composition thereof to the administration object includes a simultaneous administration and administrations with time difference. The dose of a concomitant drug can be properly selected according to object of the administration, route of the administration, disease, combination, etc., as far as it conforms to the clinical dose. There is no particular limitation on the way of administration, as far as the compound of the present invention and a concomitant drug(s) are combined in vivo. The way of administration includes, for example, (1) administration of a single preparation obtained by preparing the compound of the present invention and a concomitant drug(s) simultaneously, (2) simultaneous administration of two kind of preparation obtained by preparing the compound of the present invention and a concomitant drug(s) separately by the same route of administration, (3) administrations with time difference of two kind of preparation obtained by preparing the compound of the present invention and a concomitant drug(s) separately by the same route of administration, (4) simultaneous administration of two kind of preparation obtained by preparing the compound of the present invention and a concomitant drug(s) separately by different route of administration, (5) administrations with time difference of two kind of preparation obtained by preparing the compound of the present invention and a concomitant drug(s) separately by different route of administration (such as, administration in the order of the compound of the present invention and a concomitant drug(s), or vice-versa, etc.

In the administration of the combination preparation of the present invention, the concomitant drug(s) of the present invention and/or the concomitant drug(s) can be safely administered as they are or after being mixed with a pharmaceutically acceptable carrier according to a per se known method usually employed in the production of pharmaceutical preparations, orally or parenterally (for example, topical administration, rectal administration, intravenous administration, etc.) in the form of solid preparations for internal use (for example, tablets including sugar coated tablets and film-coating tablets), powders, pills, granules, capsules, etc.), liquid preparations for internal use, liquid preparations for external use, injections, suppositories, delayed-release preparations or the like.

The carrier which is used in the production of the pharmaceutical preparation includes various conventional organic or inorganic carrier materials, such as excipients, lubricants, binders and disintegrators for solid preparations, solvents, solubilizers, suspending or emulsifying agents, isotonic agents, buffers and soothing agents, etc. If necessary, conventional preservatives, antioxidants, coloring agents, sweetening agents, adsorbents, wetting agents, and the like can be used appropriately in a suitable amount.

The excipient includes, for example, lactose, mannitol, glucose, microcrystalline cellulose, starch, corn starch, light anhydrous silicic acid, and the like. The binder includes, for example, hydroxypropyl cellulose, polyvinylpyrrolidone, magnesium metasilicate aluminate, crystalline cellulose, white soft sugar, D-mannitol, dextrin, hydroxypropylmethyl cellulose starch, sucrose, gelatin, methylcellulose, sodium carboxymethylcellulose, and the like. The disintegrator includes, for example, cellulose calcium glycolate, starch, carboxymethylcellulose, carboxymethylcellulose calcium, sodium carboxymethylstarch, L-hydroxypropyl cellulose, and the like. The lubricant includes, for example, magnesium stearate, calcium stearate, talc, colloid silica, and the like. The solvent medium includes, for example, distilled water for injection, physiological saline solution, macrogol, vegetable oil (such as sesame oil, corn oil, olive oil), alcohols (for example, propylene glycol, polyethylene glycol, ethanol, etc.) or a mixture thereof.

The stabilizer includes, for example, D-sorbitol, D-mannitol, L-alanine, ascorbic acid, albumin, inositol, sodium gluconate, sodium thioglycolate, polyoxyethylene hardened caster oil, etc. The solubilizer includes, for example, glutamic acid, aspartic acid, Polysolbate 80 (trade name), polyethylene glycol, propylene glycol, D-mannitol, benzyl benzoate, ethanol, trisaminomethane, cholesterol, triethanolamine, sodium carbonate, citric sodium, etc. The emulsifying or suspending agent includes, for example, surfactants (for example, stearyl triethanolamine, sodium lauryl sulfate, laurylaminopropionate, lecithin, benzalkonium chloride, benzethonium chloride, glyceryl monostearate, etc.), hydrophilic polymers (for example, polyvinyl alcohol, polyvinylpyrrolidone, sodium carboxymethylcellulose, methylcellulose, hydroxymethylcellulose, hydroxyethylcellulose, hydroxypropylcellulose, etc.) and the like. The soothing agents include, for example, benzyl alcohol, and the like. The isotonic agents include, for example, glucose, D-sorbitol, sodium chloride, glycerin, D-mannitol, and the like. The buffers include, for example, a buffer solution of phosphates, acetates, carbonates, citrates, or the like. The preservative includes, for example, p-hydroxybenzoic acid ester, chlorobutanol, benzyl alcohol, phenethyl alcohol, dehydroacetic acid, sorbic acid, and the like. The antioxidant includes, for example, sulfites, ascorbic acid, α-tocopherol, and the like.

The compounding ratio of the compound of the present invention in a combination preparation varies depending on the dosage form. It is usually about 0.01% by weight to 100% by weight relative to the whole preparation, preferably about 0.1% by weight to 50% by weight relative to the whole preparation, more preferably about 0.5% by weight to 20% by weight relative to the whole preparation.

The compounding ratio of the concomitant drug(s) in the combination preparation of the present invention varies depending on the dosage form. It is usually about 0.01% by weight to 100% by weight, preferably about 0.1% by weight to 50% by weight relative to the whole preparation, more preferably about 0.5% by weight to 20% by weight relative to the whole preparation.

The content of the additive such as carrier, etc. in the combination preparation of the present invention varies depending on the dosage form. It is usually about 1% by weight to 99.99% by weight, preferably about 10% by weight to 90% by weight relative to the whole preparation. In addition, it may be the same in the formulation of the compound of the present invention and the concomitant drug(s) independently.

These drug preparations can be prepared by the usual method (such as the method described in Japanese Pharmacopoeia, etc.). The tablet can be prepared by mixing uniformly the compound of the present invention and/or the concomitant drug(s) in the presence or absence of excipients, disintegrators, or other appropriate additives to prepare granulated powder in an appropriate manner, and then compacting with a lubricant, etc.; by mixing uniformly the compound of the present invention and/or the concomitant drug(s), in the presence or absence of excipients, disintegrators, or other appropriate additives in an appropriate manner, and then compacting the mixture directly; or by optionally adding an appropriate additive to previously granulated powder, mixing the mixture uniformly and then compacting into tablets. If necessary, the tablet may be prepared with coloring agents, flavoring substance, etc. Furthermore, it can be coated by using appropriate coating agents.

The injection preparation can be prepared by the following method. A certain amount of the compounds of the present invention and/or a concomitant drug(s) is dissolved, suspended or emulsified usually in an aqueous medium such as distilled water for injection, physiological saline solution, and Ringer solution, or in a non-aqueous medium such as vegetable oil, etc.; or a certain amount of the compound of the present invention and/or a concomitant drug(s) is sealed in a container for injection. The carrier for the preparation for oral administration includes a conventional material used in the field of pharmaceutical formulation, such as starch, mannitol, crystalline cellulose, sodium carboxymethylcellulose, etc.

The carrier for injections includes, for example, distilled water, physiological saline solution, glucose solution, infusion, and the like.

Although the dose of the combination preparation of the present invention depends on the age, weight, disease symptom, therapeutic effect, administration route, therapy period, and the like, the compound of the present invention and the concomitant drug(s) are usually administered orally once or several times per day at a dose per administration of from 0.1 mg to 1000 mg per human adult, or parenterally (preferably intravenous administration once or several times per day at a dose per administration of from 0.1 mg to 100 mg per human adult, or continuously administered intravenously for 1 hour to 24 hours per day.

It goes without saying that the dose of these compounds may be less than the aforementioned value or may need to exceed the aforementioned range because the dose varies under various conditions as mentioned above. The concomitant drug(s) can be administrated at arbitrary dose as far as the side effect is not a serious problem and the purpose of the present invention can be achieved. The daily dose as a concomitant drug(s) differs depending on age, sex, body weight, different sensitivity, time and interval of administration object, characteristics of pharmaceutical preparation, dispensing, kind, and type of active ingredient of medicinal preparation; and the like, so that it is not particularly limited.

In the mode of administration of the combination preparation of the present invention, the compound of the present invention may be administered simultaneously, or the combination preparation may be administered firstly followed by administering the compound of the present invention, or the compound of the present invention may be administered firstly, followed by administering the concomitant drug(s). In the case of time difference administration, time difference differs depending on active ingredient to be administered, dosage form, and administration route. For example, in the case where the concomitant drug(s) may be administered firstly, the compound of the present invention can be administered within 1 minute to 3 days, preferably 10 minutes to 1 day, more preferably 15 minutes to 1 hour after the administration of the concomitant drug(s) of the present invention.

In the case where the compound of the present invention is administered firstly, the concomitant drug(s) of the present invention can be administered within 1 minute to 1 day, preferably 10 minutes to 6 hours, more preferably 15 minutes to 1 hour after the administration of the compound of the present invention, and the like.

EFFECT OF THE INVENTION

The antidiabetic agent and the cerebral infarction treating agent of the present invention comprising the compound represented by the formula (I), a salt thereof, or an N-oxide thereof, or a solvate thereof, or a prodrug thereof can be very useful in a preventing and/or treatment for various diseases including, for example, metabolic diseases such as diabetes, cerebrovascular disease such as stroke, and the like, because of an anti-diabetic effect and a neuroprotective effect, and they are low toxicity because they don't have undesirable side effects such as hepatotoxicity.

BEST MODE FOR CARRYING OUT THE INVENTION

Now, the present invention is described in greater detail by reference to the following Examples, although the present invention is not construed as being restricted thereto.

Example 1

5-(3-hydroxyphenyl)-2-furoic Acid

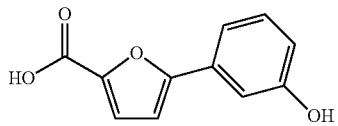 [SMILES: O=C(O)c1ccc(-c2cccc(O)c2)o1]

A solution of methyl 5-(3-hydroxyphenyl)furan-2-carboxylate (500 mg) in ethanol (11 mL) was treated with aqueous 3 mol/L sodium hydroxide (3.8 mL) at room temperature and refluxed for three hours. The reaction was brought to room temperature and concentrated. The residue was dissolved in water and brought to pH 2 via the addition of 1 N hydrochloric acid. The precipitated beige solids were collected by filtration to obtain the title compound (175 mg) having the following physical data.

$^1$H NMR (DMSO-d$_6$): δ 9.73 (s, 1H), 7.33-7.13 (m, 4H), 7.02 (d, J=2.4 Hz, 1H), 6.78 (d, J=7.7 Hz, 1H);

Mass data (APCI, Neg.): m/z 203 (M−H)$^-$.

Example 2 methyl 4-amino-3,5-dichloro-6-ethoxy-2-pyridinecarboxylate

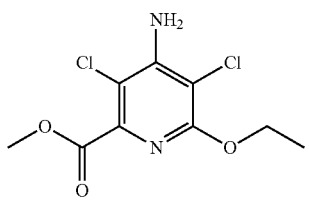 [SMILES: CCOc1nc(C(=O)OC)c(Cl)c(N)c1Cl]

N-Chlorosuccinimide (0.667 g) was added to a room temperature solution of methyl 4-amino-6-ethoxypicolinate (0.980 g, prepared according to the reported preparation in Zhao, H.; et al. *J. Med. Chem.* 2006, 49, 4455) in N,N-dimethylformamide (10 mL). After the reaction was stirred for 18 hours, water was added and the resulting mixture was extracted with dichloromethane. The mixture was dried over anhydrous magnesium sulfate and concentrated. The residue was purified by column chromatography on silica gel (dichloromethane:diethyl ether=5:3) to obtain the title compound (0.176 g) having the following physical data.

$^1$H NMR (DMSO-d$_6$): δ 6.79 (s, 2H), 4.28 (q, J=7.0 Hz, 2H), 3.86 (s, 3H), 1.29 (t, J=7.0 Hz, 3H).

Example 3

4-amino-3,5-dichloro-6-ethoxy-2-pyridinecarboxylic Acid

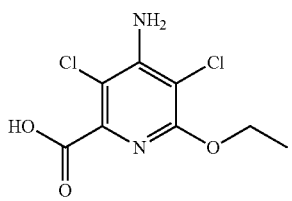

Lithium hydroxide monohydrate (0.027 g) was added to a room temperature solution of the compound prepared in Example 2 (0.172 g) in ethanol (0.5 mL)-water (0.3 mL). The mixture was stirred for two hours and then brought to pH 3 via the addition of 1 N hydrochloric acid. The precipitated solids were collected by filtration to obtain the title compound (0.110 g) having the following physical data.

$^1$H NMR (DMSO-d$_6$): δ 6.85 (s, 2H), 4.28 (q, J=7.0 Hz, 2H), 1.29 (t, J=7.0 Hz, 3H);

Mass data (APCI, Neg.): m/z 249 (M−H)$^-$.

Example 4

2-chlorobenzaldehyde Oxime

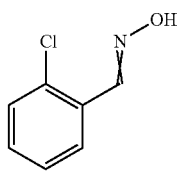

Hydroxylamine hydrochloride (35.6 g) was added to a 0° C. mixture of 2-chlorobenzaldehyde (60.0 g) and sodium carbonate (22.6 g) in methanol (1.0 L)-water (1.0 L). The reaction was stirred overnight and then concentrated to half volume. The mixture was extracted twice with ethyl acetate. The organics were combined, washed with brine, dried over anhydrous magnesium sulfate and concentrated to obtain the title compound (65.4 g) having the following physical data.

$^1$H NMR (CDCl$_3$): δ 8.57 (s, 1H), 8.18-8.03 (bs, 1H), 7.83 (dd, J=2.3, 7.8 Hz, 1H), 7.40 (dd, J=1.6, 7.8 Hz, 1H), 7.35-7.25 (m, 2H).

Example 5

2-chloro-N-hydroxybenzenecarboximidoyl Chloride

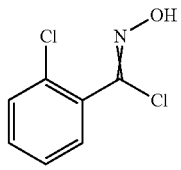 [SMILES: ON=C(Cl)c1ccccc1Cl]

N-Chlorosuccinimide (56.1 g) was added slowly to a 0° C. solution of the compound prepared in Example 4 (65.4 g) in N,N-dimethylformamide (1.2 L). The reaction was stirred at room temperature overnight and then diluted with ice water and methyl tert-butyl ether. The layers were separated and the aqueous phase was extracted once more with methyl tert-butyl ether. The organic phases were combined, washed with brine, dried over anhydrous magnesium sulfate and concentrated to obtain the title compound (79.5 g) having the following physical data.

$^1$H NMR (CDCl$_3$): δ 9.02 (s, 1H), 7.49-7.43 (m, 2H), 7.41-7.36 (m, 1H), 7.34-7.29 (m, 1H).

Example 6

[3-(2-chlorophenyl)-5-isoxazolyl]methanol

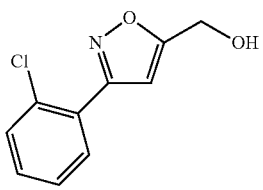 [SMILES: OCc1cc(-c2ccccc2Cl)no1]

A solution of triethylamine (48 mL) in diethyl ether (0.5 L) was added over two hours to a 0° C. solution of the compound prepared in Example 5 (50.0 g) and propargyl alcohol (31 mL) in diethyl ether (1.2 L). The reaction was stirred at room temperature overnight, washed with water, dried over anhydrous magnesium sulfate and concentrated to obtain the title compound (50.0 g) having the following physical data.

$^1$H NMR (CDCl$_3$): δ 7.74-7.69 (m, 1H), 7.48 (d, J=7.8 Hz, 1H), 7.42-7.32 (s, 2H), 6.72 (s, 1H), 4.84 (s, 2H).

Example 7

3-phenyl-5-isoxazolecarbaldehyde

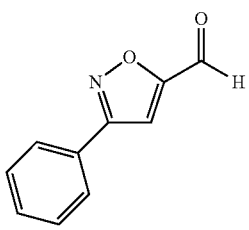 [SMILES: O=Cc1cc(-c2ccccc2)no1]

A solution of (3-phenylisoxazol-5-yl) methanol (10.0 g) and 2-iodoxybenzoic acid (24.0 g) in ethyl acetate (350 mL) was refluxed overnight. The mixture was cooled to room temperature, filtered and concentrated. The resulting solids were triturated (hexane:diethyl ether=1:1) to obtain the title compound (8.22 g) having the following physical data.

$^1$H NMR (DMSO-d$_6$): δ 9.97 (s, 1H), 8.06-7.91 (m, 3H), 7.64-7.47 (m, 3H).

Example 8 tert-butyl ({1-[(3-phenyl-5-isoxazolyl)methyl]-4-piperidinyl}methyl)carbamate

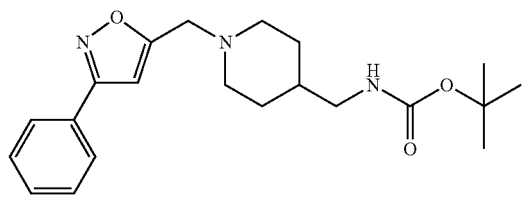 [SMILES: CC(C)(C)OC(=O)NCC1CCN(Cc2cc(-c3ccccc3)no2)CC1]

A solution of the compound prepared in Example 7 (2.00 g), tert-butyl piperidin-4-ylmethylcarbamate (2.72 g) and acetic acid (0.66 mL) in acetonitrile (60 mL) was stirred at room temperature for 30 minutes. Tetramethylammonium triacetoxyborohydride (9.12 g) was added and the reaction was stirred overnight. The reaction was then poured into a saturated aqueous sodium bicarbonate solution and the resulting mixture was extracted three times with ethyl acetate. The combined organics were dried with anhydrous magnesium sulfate and concentrated to a white solid. The solid was triturated with hexane to obtain the title compound (3.90 g) having the following physical data.

$^1$H NMR (CDCl$_3$): δ 7.83-7.79 (m, 2H), 7.48-7.43 (m, 3H), 6.49 (s, 1H), 4.66-4.57 (m, 1H), 3.73 (s, 2H), 3.06-2.93 (m, 4H), 2.16-2.07 (m, 2H), 1.74-1.66 (m, 2H), 1.52-1.39 (m, 10H), 1.38-1.24 (m, 2H);

Mass data (ESI, Pos.): m/z 372 (M+H)$^+$.

Example 9

1-{1-[(3-phenyl-5-isoxazolyl)methyl]-4-piperidinyl}methanamine

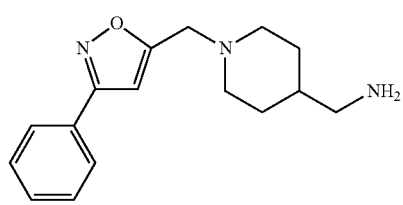 [SMILES: NCC1CCN(Cc2cc(-c3ccccc3)no2)CC1]

Trifluoroacetic acid (2.1 mL) was added to a room temperature solution of the compound prepared in Example 8 (0.99 g) in dichloromethane (10 mL). The reaction was stirred overnight and then concentrated. The crude residue was azeotroped with a solution of hexane and toluene, diluted with ethyl acetate and washed with an aqueous 10% sodium carbonate solution. The organics were dried over anhydrous magnesium sulfate and concentrated to obtain the title compound (0.60 g) having the following physical data.

$^1$H NMR (CDCl$_3$): δ 7.84-7.78 (m, 2H), 7.49-7.42 (m, 3H), 6.50 (s, 1H), 3.74 (s, 2H), 3.03-2.95 (m, 2H), 2.60-2.57 (m, 2H), 2.18-2.07 (m, 2H), 1.79-1.70 (m, 2H), 1.35-1.23 (m, 3H), 1.21-1.10 (m, 2H);

Mass data (ESI, Pos.): m/z 272 (M+H)$^+$.

Example 10 tert-butyl 4-{[(4-chloro-3-methoxybenzoyl)amino]methyl}-1-piperidinecarboxylate

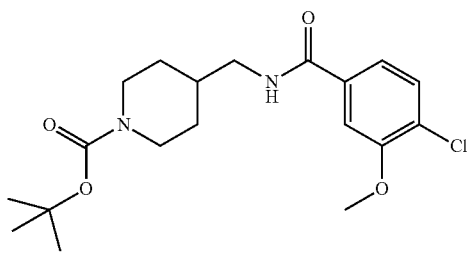 [SMILES: COc1cc(C(=O)NCC2CCN(C(=O)OC(C)(C)C)CC2)ccc1Cl]

1-Ethyl-3-(3'-dimethylaminopropyl)carbodiimide hydrochloride (2.26 g) and diisopropylethylamine (2.05 mL) were added to a room temperature solution of 4-chloro-3-methoxybenzoic acid (2.00 g) and 1-hydroxybenzotriazole hydrate (1.81 g) in dichloromethane (53 mL). After the reaction was stirred for five minutes, tert-butyl 4-(aminomethyl)piperidine-1-carboxylate (2.53 g) was added and the mixture was stirred overnight. The reaction was then partitioned between 1 N hydrochloric acid and dichloromethane. The organic layer was separated, dried over anhydrous magnesium sulfate and concentrated and purified by column chromatography on silica gel (dichloromethane:methanol=19:1). The resulting residue was triturated in diethyl ether and the solids were collected by filtration to obtain the title compound (3.56 g) having the following physical data. $^1$H NMR (DMSO-d$_6$): δ 8.60 (t, J=5.7 Hz, 1H), 7.61-7.39 (m, 3H), 3.91 (m, 5H), 3.15 (t, J=6.0 Hz, 2H), 2.81-2.62 (m, 2H), 1.72-1.51 (m, 3H), 1.39 (s, 9H), 1.12-0.92 (m, 2H)$^+$;

Mass data (ESI, Pos.): m/z 283 (M-tert-butoxycarbonyl+H)$^+$.

Example 11

4-chloro-3-methoxy-N-(4-piperidinylmethyl)benzamide Trifluoroacetate

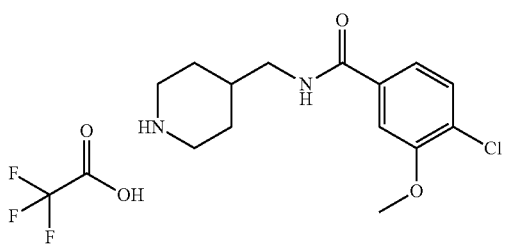 [SMILES: O=C(O)C(F)(F)F ; COc1cc(C(=O)NCC2CCNCC2)ccc1Cl]

A solution of the compound prepared in Example 10 (1.44 g) in dichloromethane (8.04 mL)-trifluoroacetic acid (1.46 mL) was stirred for 18 hours. The reaction was concentrated and the excess trifluoroacetic acid was removed via azeotropic distillation from toluene and diethyl ether. The resulting oil solidified upon treatment with (diethyl ether:hexane=5:1) and the solids were collected by filtration to obtain the title compound (1.36 g) having the following physical data.

$^1$H NMR (DMSO-d$_6$): δ 8.68 (t, J=5.8 Hz, 1H), 8.58-8.42 (m, 1H), 8.22-8.08 (m, 1H), 7.53-7.44 (m, 3H), 3.91 (s, 3H), 3.28-3.16 (m, 4H), 2.87-2.75 (m, 2H), 1.83-1.75 (m, 3H), 1.32 (d, J=11.9 Hz, 2H);

Mass data (ESI, Pos.): m/z 283 (M+H)$^+$.

Example 12

2-(4-chlorophenol)-1,3-thiazole-5-carbaldehyde

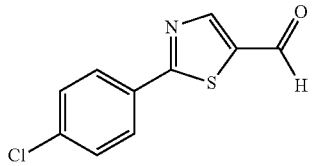 [SMILES: O=Cc1cnc(-c2ccc(Cl)cc2)s1]

A mixture of 4-chlorobenzothioamide (100 mg) and 2-bromomalonaldehyde (88 mg) in ethanol (1.2 mL) was heated to 60° C. overnight. The reaction was cooled to room temperature and concentrated. The residue was dissolved in ethyl acetate and washed with a saturated aqueous sodium bicarbonate solution. The organics were dried over anhydrous magnesium sulfate and concentrated. The crude product was purified by column chromatography on silica gel (ethyl acetate:hexane=1:6) to obtain the title compound (0.60 g) having the following physical data.

$^1$H NMR (CDCl$_3$): δ 10.06 (s, 1H), 8.43 (s, 1H), 8.00-7.95 (m, 2H), 7.50-7.45 (m, 2H).

Example 13

2-(2-chlorophenyl)-1,3-thiazole-5-carbaldehyde

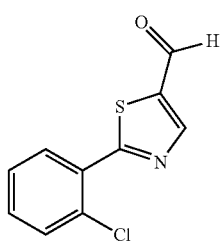 [SMILES: O=Cc1cnc(-c2ccccc2Cl)s1]

According to the same procedure described in Example 12, using the corresponding thioamide instead of 4-chlorobenzothioamide, the title compound having the following physical data was obtained. $^1$H NMR (DMSO-d$_6$): δ 10.1 (s, 1H), 8.52 (s, 1H), 8.40-8.31 (m, 1H), 7.59-7.51 (m, 1H), 7.48-7.39 (m, 2H).

Example 14

4-phenyl-2-furaldehyde

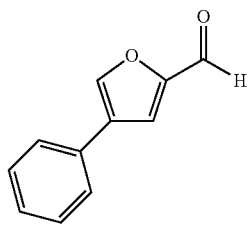 [SMILES: O=Cc1cc(-c2ccccc2)co1]

Phenylboronic acid (1.46 g) was added to a stirred mixture of 4-bromofuran-2-carbaldehyde (2.00 g) and tetrakis(triphenylphosphine)palladium(0) (0.396 g) in N,N-dimethylformamide (57 mL) and a solution of sodium carbonate (3.03 g) in water (7 mL). The reaction was heated at 110° C. overnight. The resulting mixture was filtered and the filtrate was partitioned between water and diethyl ether. The layers were separated and the aqueous phase was extracted with diethyl ether. The organics were combined, washed with brine, dried over anhydrous magnesium sulfate and concentrated. The residue was purified by column chromatography on silica gel (dichloromethane:hexane=9:1) to obtain the title compound (1.55 g) having the following physical data.

$^1$H NMR (DMSO-$d_6$): δ 9.66 (s, 1H), 8.64 (s, 1H), 8.05 (s, 1H), 7.72-7.61 (m, 2H), 7.40-7.28 (m, 3H).

Example 15

5-(2-pyridinyl)-2-thiophenecarbaldehyde

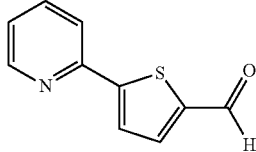 [SMILES: O=Cc1ccc(-c2ccccn2)s1]

A solution of (5-(pyridin-2-yl)thien-2-yl) methanol (0.100 g) and manganese dioxide (0.136 g) in tetrahydrofuran (3.5 mL) was refluxed overnight. The mixture was cooled to room temperature and the solids were filtered. The filtrate was concentrated and the residue was triturated (hexane:diethyl ether=1:1) to obtain the title compound (8.22 g) having the following physical data.

$^1$H NMR (DMSO-$d_6$): δ 9.94 (s, 1H), 8.62 (d, J=4.0 Hz, 1H), 8.17-7.86 (m, 1H), 8.15-7.92 (m, 3H), 7.42 (dd, J=4.8, 7.5 Hz, 1H).

Example 16

4-chloro-3-methoxy-N-({1-[(3-phenyl-5-isoxazolyl)methyl]-4-piperidinyl}methyl)benzamide

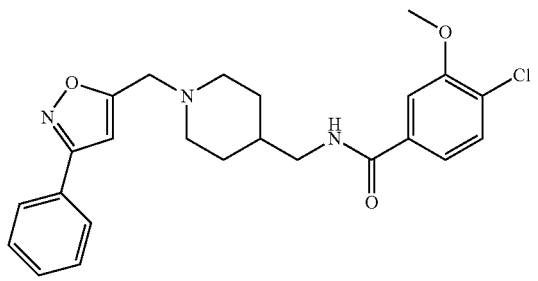 [SMILES: COc1cc(C(=O)NCC2CCN(Cc3cc(-c4ccccc4)no3)CC2)ccc1Cl]

To a solution of 4-chloro-3-methoxybenzoic acid (65 mg) in dichloromethane (4 mL) was added 1-ethyl-3-(3'-dimethylaminopropyl)carbodiimide (67 mg), 1-hydroxybenzotriazole hydrate (58 mg), and diisopropylethylamine (0.25 mL). The mixture was stirred at room temperature for five minutes and then the hydrochloride salt of the compound prepared in Example 9 (100 mg) was added. The reaction mixture was stirred at room temperature for 16 hours. The organic phase was diluted with ethyl acetate, washed with a saturated aqueous sodium bicarbonate solution, dried over anhydrous magnesium sulfate and concentrated. The residue was purified by column chromatography on silica gel (ethyl acetate:hexane=1:1, then ethyl acetate) to obtain the title compound (70 mg) having the following physical data.

$^1$H NMR (CDCl$_3$): δ 7.87-7.74 (m, 2H), 7.53-7.33 (m, 5H), 7.18-7.11 (m, 1H), 6.49 (s, 1H), 6.23-6.13 (m, 1H), 3.96 (s, 3H), 3.74 (s, 2H), 3.41-3.32 (m, 2H), 3.03-2.94 (m, 2H), 2.20-2.09 (m, 2H), 1.82-1.72 (m, 2H), 1.69-1.61 (m, 1H), 1.47-1.32 (m, 2H);

Mass data (ESI, Pos.): m/z 440 (M+H)$^+$.

Example 17

2-anilino-N-({1-[(3-phenyl-5-isoxazolyl)methyl]-4-piperidinyl}methyl)-1,3-thiazole-4-carboxamide

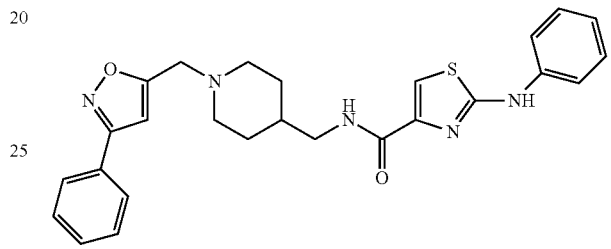

According to the same procedure described in Example 16, using the corresponding carboxylic acid instead of 4-chloro-3-methoxybenzoic acid, the title compound having the following physical data was obtained.

$^1$H NMR (CDCl$_3$): δ 7.87-7.75 (m, 2H), 7.48-7.42 (m, 4H), 7.41-7.31 (m, 4H), 7.29-7.20 (m, 1H), 7.15-7.08 (m, 2H), 6.49 (s, 1H), 3.73 (s, 2H), 3.34 (t, J=6.5 Hz, 2H), 2.99 (d, J=11.2 Hz, 2H), 2.14 (t, J=11.4 Hz, 2H), 1.82-1.73 (m, 2H), 1.69-1.58 (m, 1H), 1.48-1.35 (m, 2H);

Mass data (ESI, Pos.): m/z 474 (M+H)$^+$.

Example 18

4-chloro-2-methoxy-N-({1-[(3-phenyl-5-isoxazolyl)methyl]-4-piperidinyl}methyl)benzamide

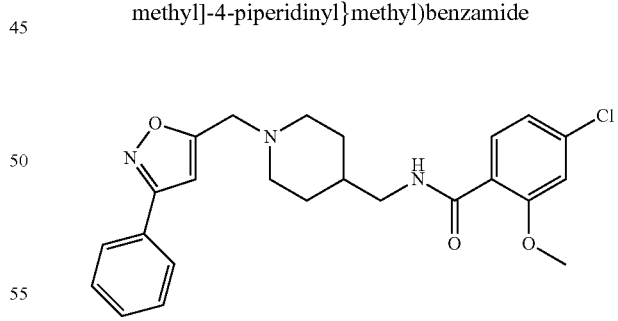

According to the same procedure described in Example 16, using the corresponding carboxylic acid instead of 4-chloro-3-methoxybenzoic acid, the title compound having the following physical data was obtained.

$^1$H NMR (CDCl$_3$): δ 8.14 (d, J=8.4 Hz, 1H), 7.87-7.71 (m, 3H), 7.53-7.39 (m, 3H), 7.09-7.04 (m, 1H), 6.97 (s, 1H), 6.49 (s, 1H), 3.97 (s, 3H), 3.74 (s, 2H), 3.37 (t, J=6.3 Hz, 2H), 2.99 (d, J=11.3 Hz, 2H), 2.15 (t, J=11.5 Hz, 2H), 1.77 (d, J=12.7 Hz, 2H), 1.69-1.55 (m, 1H), 1.47-1.33 (m, 2H);

Mass data (ESI, Pos.): m/z 440 (M+H)$^+$.

Example 19

5-(4-chlorophenyl)-N-({1-[(3-phenyl-5-isoxazolyl)methyl]-4-piperidinyl}methyl)-2-furamide

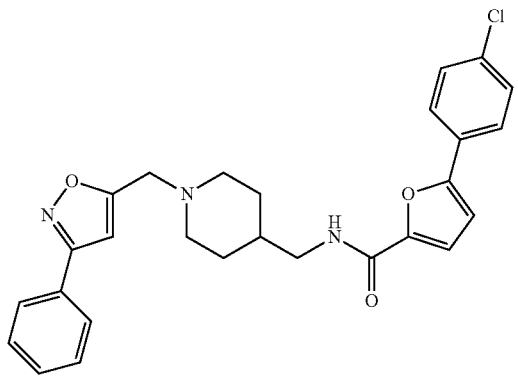 [SMILES: O=C(NCC1CCN(Cc2cc(-c3ccccc3)no2)CC1)c1ccc(-c2ccc(Cl)cc2)o1]

According to the same procedure described in Example 16, using the corresponding carboxylic acid instead of 4-chloro-3-methoxybenzoic acid, the title compound having the following physical data was obtained.

¹H NMR (DMSO-d₆): δ 7.94-7.83 (m, 2H), 7.63 (d, J=8.6 Hz, 2H) 7.42-7.12 (m, 6H), 6.73 (d, J=3.6 Hz, 1H), 6.28 (m, 2H), 3.74 (s, 2H), 3.38 (t, J=6.4 Hz, 2H), 3.00 (d, J=11.4 Hz, 2H), 2.21-2.08 (m, 2H), 1.80 (d, J=12.7 Hz, 2H), 1.71-1.61 (m, 1H), 1.43 (dd, J=12.02, 3.04 Hz, 2H);

Mass data (ESI, Pos.): m/z 476 (M+H)⁺.

Example 20

N-({1-[(3-phenyl-5-isoxazolyl)methyl]-4-piperidinyl}methyl)-1H-indole-6-carboxamide

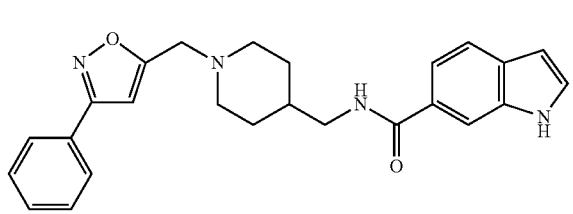 [SMILES: O=C(NCC1CCN(Cc2cc(-c3ccccc3)no2)CC1)c1ccc2cc[nH]c2c1]

According to the same procedure described in Example 16, using the corresponding carboxylic acid instead of 4-chloro-3-methoxybenzoic acid and the compound prepared in Example 9, the title compound having the following physical data was obtained.

¹H NMR (CDCl₃): δ 8.49-8.37 (m, 1H), 7.99 (s, 1H), 7.87-7.74 (m, 2H), 7.68-7.62 (m, 1H), 7.49-7.38 (m, 4H), 7.36-7.30 (s, 1H), 6.59 (s, 1H), 6.50 (s, 1H), 6.32-6.19 (m, 1H), 3.74 (s, 2H), 3.46-3.36 (m, 2H), 3.03-2.94 (m, 2H), 2.23-2.09 (m, 2H), 1.85-1.76 (m, 2H), 1.74-1.61 (m, 1H), 1.50-1.35 (m, 2H);

Mass data (ESI, Pos.): m/z 415 (M+H)⁺.

Example 21

5-(3-hydroxyphenyl)-N-({1-[(3-phenyl-5-isoxazolyl)methyl]-4-piperidinyl}methyl)-2-furamide

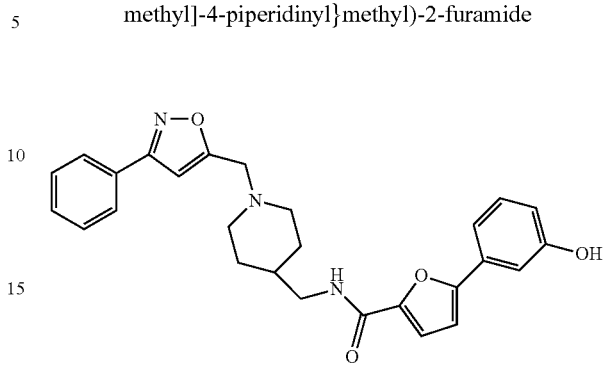

According to the same procedure described in Example 16, using the corresponding carboxylic acid instead of 4-chloro-3-methoxybenzoic acid and the compound prepared in Example 9, the title compound having the following physical data was obtained.

¹H NMR (CD₃OD): δ 7.83 (dd, J=2.5, 6.2 Hz, 2H), 7.53-7.41 (m, 3H), 7.34-7.16 (m, 4H), 6.89-6.72 (m, 3H), 3.78 (s, 2H), 3.40-3.31 (m, 2H), 3.01 (d, J=11.5 Hz, 2H), 2.20 (t, J=10.1 Hz, 2H), 1.87-1.62 (m, 3H), 1.49-1.33 (m, 2H);

Mass data (APCI, Pos.): m/z 458 (M+H)⁺.

Example 22

5-phenyl-N-({1-[(3-phenyl-5-isoxazolyl)methyl]-4-piperidinyl}methyl)-2-furamide

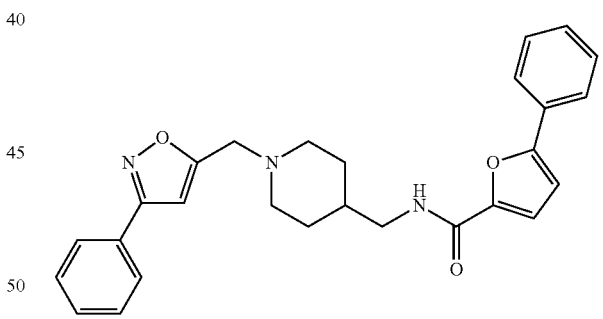

According to the same procedure described in Example 16, using the corresponding carboxylic acid instead of 4-chloro-3-methoxybenzoic acid and the compound prepared in Example 9, the title compound having the following physical data was obtained.

¹H NMR (CDCl₃): δ 7.84-7.76 (m, 2H), 7.74-7.67 (m, 2H), 7.47-7.38 (m, 5H), 7.36-7.31 (m, 1H), 7.20-7.15 (m, 1H), 6.76-6.71 (m, 1H), 6.52-6.42 (m, 2H), 3.76-3.71 (m, 2H), 3.42-3.34 (m, 2H), 3.04-2.95 (m, 2H), 2.21-2.10 (m, 2H), 1.85-1.76 (m, 2H), 1.72-1.61 (m, 1H), 1.49-1.37 (m, 2H);

Mass data (ESI, Pos.): m/z 442 (M+H)⁺.

Example 23

N-({1-[(3-phenyl-5-isoxazolyl)methyl]-4-piperidinyl}methyl)-3-(3-pyridinyl)benzamide

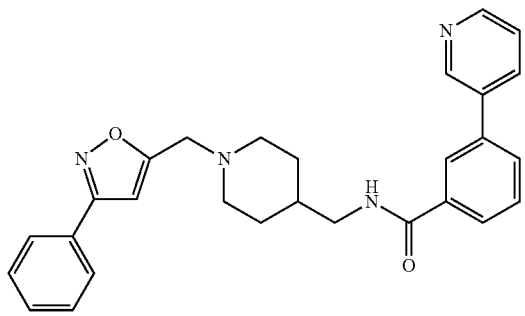 [SMILES: O=C(NCC1CCN(Cc2cc(-c3ccccc3)no2)CC1)c1cccc(-c2cccnc2)c1]

According to the same procedure described in Example 16, using the corresponding carboxylic acid instead of 4-chloro-3-methoxybenzoic acid and the compound prepared in Example 9, the title compound having the following physical data was obtained.

$^1$H NMR (DMSO-$d_6$): δ 8.87 (s, 1H), 8.60-8.52 (m, 1H), 8.18-8.01 (m, 2H), 7.91-7.79 (m, 4H), 7.64-7.43 (m, 5H), 6.50 (s, 1H), 6.79 (s, 1H), 3.78 (s, 2H), 3.37-3.31 (m, 2H), 3.07-2.97 (m, 2H), 2.25-2.13 (m, 2H), 1.86-1.63 (m, 3H), 1.48-1.34 (m, 2H);

Mass data (ESI, Pos.): m/z 453 (M+H)$^+$.

Example 24

4-amino-5-chloro-6-ethoxy-N-({1-[(3-phenyl-5-isoxazolyl)methyl]-4-piperidinyl}methyl)-2-pyridinecarboxamide

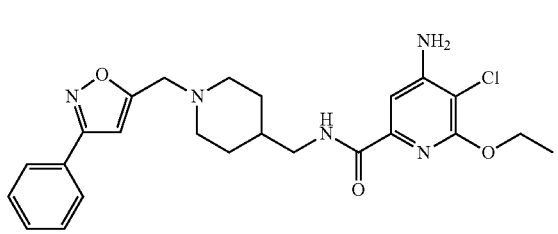 [SMILES: CCOc1nc(C(=O)NCC2CCN(Cc3cc(-c4ccccc4)no3)CC2)cc(N)c1Cl]

According to the same procedure described in Example 16, using the corresponding carboxylic acid instead of 4-chloro-3-methoxybenzoic acid, the title compound having the following physical data was obtained.

$^1$H NMR (DMSO-$d_6$): δ 8.34 (t, J=6.2 Hz, 1H), 7.87 (dd, J=2.9, 6.4 Hz, 2H), 7.52-7.47 (m, 3H), 7.09 (s, 1H), 6.94 (s, 1H), 6.68-6.59 (br s, 2H), 4.42 (q, J=7.0 Hz, 2H), 3.70 (s, 2H), 3.28-3.09 (m, 2H), 2.87 (d, J=11.1 Hz, 1H), 2.03 (t, J=10.7 Hz, 2H), 1.62 (d, J=11.7 Hz, 2H), 1.57-1.48 (m, 1H), 1.34-1.17 (m, 5H);

Mass data (APCI, Pos.): m/z 470 (M+H)$^+$.

Example 25

4-amino-3,5-dichloro-6-ethoxy-N-({1-[(3-phenyl-5-isoxazolyl)methyl]-4-piperidinyl}methyl)-2-pyridinecarboxamide

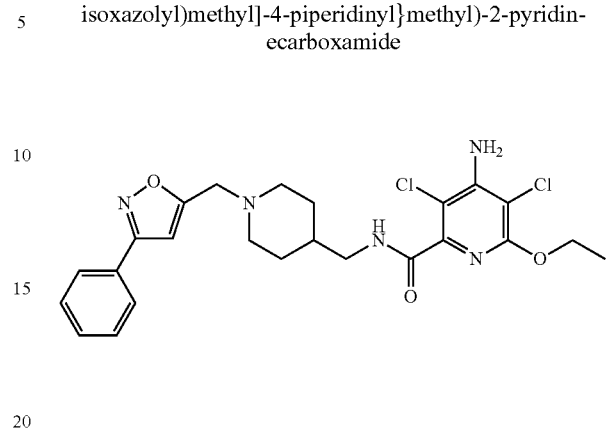

According to the same procedure described in Example 16, using the corresponding carboxylic acid instead of 4-chloro-3-methoxybenzoic acid, the title compound having the following physical data was obtained.

$^1$H NMR (DMSO-$d_6$): δ 8.36 (t, J=6.2 Hz, 1H), 7.87 (dd, J=2.9, 6.5 Hz, 2H), 7.61-7.44 (m, 3H), 6.94 (s, 1H), 6.64-6.58 (br s, 2H), 4.31 (q, J=7.0 Hz, 2H), 3.71 (s, 2H), 3.10 (t, J=6.3 Hz, 2H), 2.88 (d, J=11.5 Hz, 2H), 2.04 (t, J=10.6 Hz, 2H), 1.69 (d, J=10.9 Hz, 2H), 1.55-1.45 (m, 1H), 1.31-1.21 (m, 5H);

Mass data (APCI, Pos.): m/z 504 (M+H)$^+$.

Example 26

4-amino-5-cyano-6-ethoxy-N-({1-[(3-phenyl-5-isoxazolyl)methyl]-4-piperidinyl}methyl)-2-pyridinecarboxamide

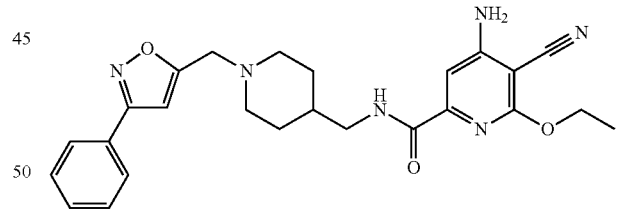

According to the same procedure described in Example 16, using the corresponding carboxylic acid instead of 4-chloro-3-methoxybenzoic acid, the title compound having the following physical data was obtained.

$^1$H NMR (CDCl$_3$): δ 7.84-7.76 (m, 3H), 7.50-7.41 (m, 3H), 7.19 (s, 1H), 6.48 (s, 1H), 5.11 (s, 2H), 4.43 (q, J=7.1 Hz, 2H), 3.74 (s, 2H), 3.38-3.31 (m, 2H), 3.02-2.95 (m, 2H), 2.19-2.09 (m, 2H), 1.80-1.70 (m, 2H), 1.66-1.54 (m, 1H), 1.47-1.34 (m, 5H);

Mass data (ESI, Pos.): m/z 461 (M+H)$^+$.

Example 27

5-chloro-N-({1-[(3-phenyl-5-isoxazolyl)methyl]-4-piperidinyl}methyl)-2-pyridinecarboxamide

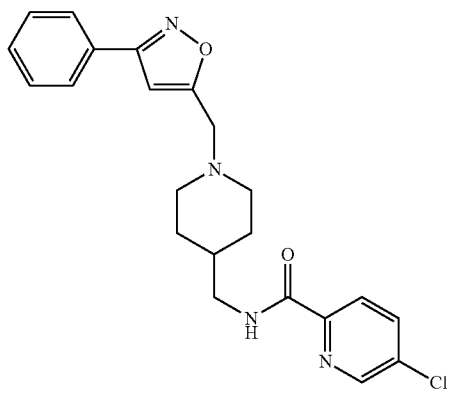 [SMILES: O=C(NCC1CCN(Cc2cc(-c3ccccc3)no2)CC1)c1ccc(Cl)cn1]

A mixture of 5-chloropicolinic acid (43 mg) and N-cyclohexylcarbodiimide-N'-propyloxymethyl polystyrene resin (PS-Carbodiimide: Argonaut Technologies catalog number 80,037-1; 354 mg) in dichloroethane (4 mL) was shaken for 45 minutes. The reaction was shaken for 45 minutes more after the addition of N,N-dimethylformamide (0.1 mL). The compound prepared in Example 9 (50 mg) was added and the mixture was shaken overnight. Benzaldehyde polystyrene resin (PS-benzaldehyde: Argonaut Technologies catalog number 80,036-2; 184 mg) was then added and the reaction was shaken for 3.5 hours. Macroporous triethylammonium methylpolystyrene carbonate (MP-carbonate: Argonaut Technologies catalog number 80,026-9; 202 mg) was added and the reaction was shaken for 1.5 hours more. The mixture was then filtered and concentrated to obtain the title compound (30 mg) having the following physical data.

$^1$H NMR (CDCl$_3$): δ 8.50-8.47 (m, 1H), 8.15 (d, J=8.6 Hz, 1H), 8.03-7.97 (m, 1H), 7.84-7.77 (m, 3H), 7.49-7.42 (m, 3H), 6.49 (s, 1H), 3.73 (s, 2H), 3.38 (t, J=6.3 Hz, 2H), 3.04-2.95 (m, 2H), 2.20-2.10 (m, 2H), 1.83-1.74 (m, 2H), 1.71-1.62 (m, 1H), 1.50-1.36 (m, 2H);

Mass data (ESI, Pos.): m/z 411 (M+H)$^+$.

Example 28

3,4-dichloro-N-({1-[(3-phenyl-5-isoxazolyl)methyl]-4-piperidinyl}methyl)benzamide

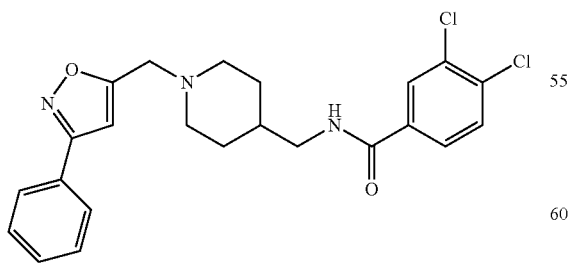

According to the same procedure described in Example 27, using the corresponding carboxylic acid instead of 5-chloropicolinic acid, the title compound having the following physical data was obtained.

$^1$H NMR (CDCl$_3$): δ 7.87 (m, 1H), 7.84-7.76 (m, 2H), 7.62-7.55 (m, 1H), 7.52-7.41 (m, 4H), 6.49 (s, 1H), 6.33-6.26 (m, 1H), 3.73 (s, 2H), 3.38-3.31 (m, 2H), 3.03-2.93 (m, 2H), 2.20-2.07 (m, 2H), 1.82-1.70 (m, 2H), 1.69-1.57 (m, 1H), 1.46-1.31 (m, 2H);

Mass data (ESI, Pos.): m/z 444 (M+H)$^+$.

Example 29

3,5-dichloro-N-({1-[(3-phenyl-5-isoxazolyl)methyl]-4-piperidinyl}methyl)benzamide

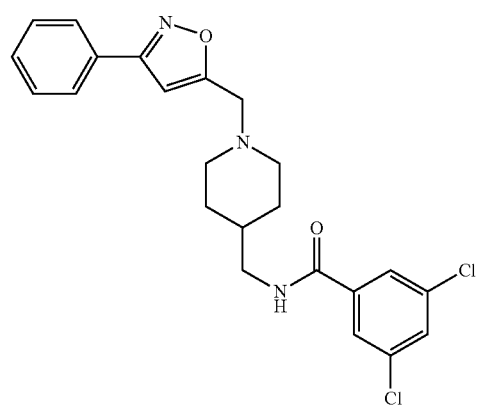 [SMILES: O=C(NCC1CCN(Cc2cc(-c3ccccc3)no2)CC1)c1cc(Cl)cc(Cl)c1]

According to the same procedure described in Example 27, using the corresponding acid instead of 5-chloropicolinic acid, the title compound (40 mg) having the following physical data was obtained.

$^1$H NMR (CDCl$_3$): δ 7.83-7.78 (m, 2H), 7.62-7.61 (m, 2H), 7.49-7.43 (m, 4H), 6.49 (s, 1H), 6.16-6.10 (m, 1H), 3.74 (s, 2H), 3.36 (t, J=6.4 Hz, 2H), 3.02-2.97 (m, 2H), 2.18-2.11 (m, 2H), 1.80-1.73 (m, 2H), 1.68-1.60 (m, 1H), 1.46-1.35 (m, 2H);

Mass data (APCI, Pos.): m/z 444 (M+H)$^+$.

Example 30

5-chloro-N-({1-[(3-phenyl-5-isoxazolyl)methyl]-4-piperidinyl}methyl)-2-thiophenecarboxamide

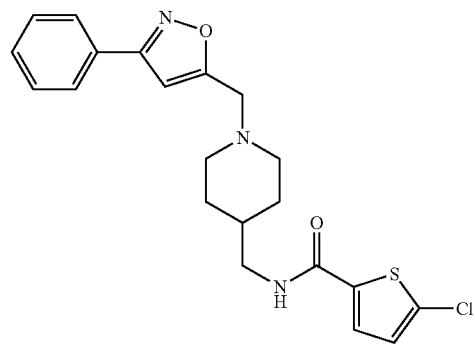 [SMILES: O=C(NCC1CCN(Cc2cc(-c3ccccc3)no2)CC1)c1ccc(Cl)s1]

According to the same procedure described in Example 27, using the corresponding acid instead of 5-chloropicolinic acid, the title compound (45 mg) having the following physical data was obtained.

$^1$H NMR (CDCl$_3$): δ 7.83-7.78 (m, 2H), 7.48-7.43 (m, 3H), 7.24 (d, J=3.9 Hz, 1H), 6.88 (d, J=3.9 Hz, 1H), 6.49 (s, 1H), 6.05-5.98 (m, 1H), 3.73 (s, 2H), 3.31 (t, J=6.2 Hz, 2H), 3.01-2.94 (m, 2H), 2.17-2.09 (m, 2H), 1.78-1.71 (m, 2H), 1.67-1.55 (m, 1H), 1.44-1.32 (m, 2H);

Mass data (APCI, Pos.): m/z 416 (M+H)$^+$.

Example 31

2-methyl-N-({1-[(3-phenyl-5-isoxazolyl)methyl]-4-piperidinyl}methyl)-1,3-benzothiazole-6-carboxamide

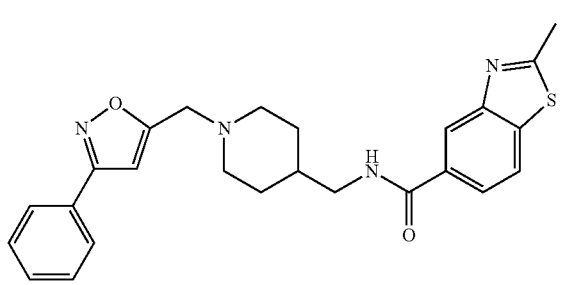 [SMILES: Cc1nc2cc(C(=O)NCC3CCN(Cc4cc(-c5ccccc5)no4)CC3)ccc2s1]

According to the same procedure described in Example 27, using the corresponding carboxylic acid instead of 5-chloropicolinic acid, the title compound having the following physical data was obtained.

$^1$H NMR (CDCl$_3$): δ 8.27 (s, 1H), 7.91-7.85 (m, 1H), 7.84-7.77 (m, 3H), 7.48-7.41 (m, 3H), 6.50 (s, 1H), 6.30-6.22 (m, 1H), 3.74 (s, 2H), 3.45-3.37 (m, 2H), 3.04-2.95 (m, 2H), 2.86 (s, 3H), 2.21-2.10 (m, 2H), 1.84-1.75 (m, 2H), 1.72-1.62 (m, 1H), 1.49-1.37 (m, 2H);

Mass data (ESI, Pos.): m/z 447 (M+H)$^+$.

Example 32

4-fluoro-N-({1-1-[(3-phenyl-5-isoxazolyl)methyl]-4-piperidinyl}methyl)benzamide

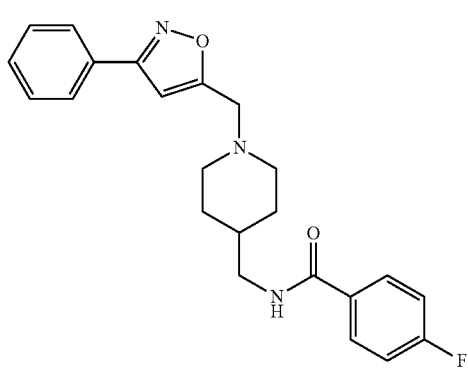 [SMILES: O=C(NCC1CCN(Cc2cc(-c3ccccc3)no2)CC1)c1ccc(F)cc1]

According to the same procedure described in Example 27, using the corresponding acid instead of 5-chloropicolinic acid, the title compound (25 mg) having the following physical data was obtained.

$^1$H NMR (CDCl$_3$): δ 7.83-7.73 (m, 4H), 7.48-7.42 (m, 3H), 7.10 (t, J=8.6 Hz, 2H), 6.49 (s, 1H), 6.20-6.10 (m, 1H), 3.74 (s, 2H), 3.36 (t, J=6.3 Hz, 2H), 3.03-2.94 (m, 2H), 2.20-2.08 (m, 2H), 1.82-1.73 (m, 2H), 1.71-1.58 (m, 1H), 1.47-1.35 (m, 2H);

Mass data (ESI, Pos.): m/z 394 (M+H)$^+$.

Example 33

N-({1-[(3-phenyl-5-isoxazolyl)methyl]-4-piperidinyl}methyl)-2-(3-pyridinyl)-1,3-thiazole-4-carboxamide

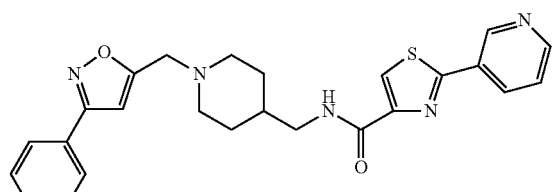

According to the same procedure described in Example 27, using the corresponding carboxylic acid instead of 5-chloropicolinic acid, the title compound having the following physical data was obtained.

$^1$H NMR (CDCl$_3$): δ 9.21-9.17 (m, 1H), 8.73-8.68 (m, 1H), 8.26-8.19 (m, 1H), 8.18-8.16 (m, 1H), 7.83-7.77 (m, 2H), 7.55-7.38 (m, 5H), 6.49 (s, 1H), 3.74 (s, 2H), 3.45-3.48 (m, 2H), 3.04-2.94 (m, 2H), 2.22-2.11 (m, 2H), 1.86-1.77 (m, 2H), 1.74-1.62 (m, 1H), 1.52-1.38 (m, 2H);

Mass data (ESI, Pos.): m/z 460 (M+H)$^+$.

Example 34

4-cyano-3-methoxy-N-({1-[(3-phenyl-5-isoxazolyl)methyl]-4-piperidinyl}methyl)benzamide

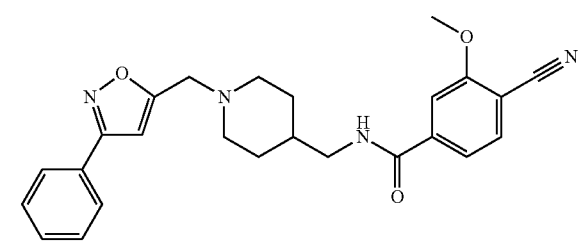 [SMILES: COc1cc(C(=O)NCC2CCN(Cc3cc(-c4ccccc4)no3)CC2)ccc1C#N]

According to the same procedure described in Example 27, using the corresponding carboxylic acid (prepared according to the reported preparation in WO 2005/105802) instead of 5-chloropicolinic acid, the title compound having the following physical data was obtained.

$^1$H NMR (CDCl$_3$): δ 7.84-7.77 (m, 2H), 7.63-7.58 (m, 1H), 7.51-7.41 (m, 4H), 7.24-7.20 (m, 1H), 6.48 (s, 1H), 6.26-6.13 (m, 1H), 3.99 (s, 3H), 3.74 (s, 2H), 3.42-3.34 (m, 2H), 3.04-2.92 (m, 2H), 2.20-2.10 (m, 2H), 1.81-1.72 (m, 2H), 1.71-1.60 (m, 1H), 1.49-1.35 (m, 2H);

Mass data (ESI, Pos.): m/z 431 (M+H)$^+$.

Example 35

4-chloro-3-methoxy-N-({1-[(4-phenyl-2-thienyl)methyl]-4-piperidinyl}methyl)benzamide

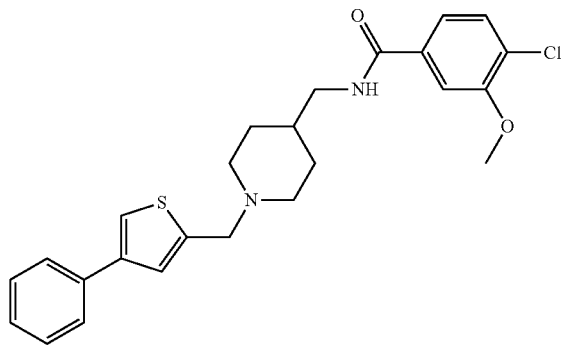 [SMILES: COc1cc(C(=O)NCC2CCN(Cc3cc(-c4ccccc4)cs3)CC2)ccc1Cl]

A mixture of 4-phenylthiophene-2-carbaldehyde (0.074 g) and the compound prepared in Example 11 (0.075 g) and acetic acid (0.023 mL) in acetonitrile (1 mL) was stirred at room temperature for 30 minutes. Tetramethylammonium triacetoxyborohydride (0.156 g) was added and the reaction was stirred for 18 hours. The mixture was partitioned between a saturated aqueous sodium bicarbonate solution and ethyl acetate. The organic layer was dried over anhydrous magnesium sulfate and concentrated. The residue was purified by column chromatography on silica gel (ethyl acetate:hexane=9:1) to obtain the title compound (0.066 g) having the following physical data.

$^1$H NMR (CDCl$_3$): δ 7.63-7.08 (m, 10H), 6.15 (s, 1H), 3.96 (s, 3H), 3.74 (s, 2H), 3.37 (t, J=6.3 Hz, 2H), 3.00 (d, J=11.5 Hz, 2H), 2.05 (t, J=11.6 Hz, 2H), 1.76-1.25 (m, 5H);

Mass data (ESI, Pos.): m/z 455 (M+H)$^+$.

Example 36

4-chloro-3-methoxy-N-({1-[(2-phenyl-1,3-thiazol-5-yl)methyl]-4-piperidinyl}methyl)benzamide

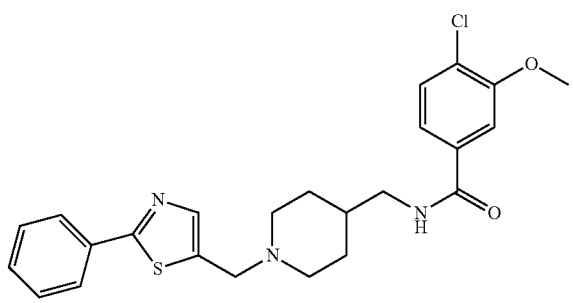 [SMILES: COc1cc(C(=O)NCC2CCN(Cc3cnc(-c4ccccc4)s3)CC2)ccc1Cl]

According to the same procedure described in Example 35, using the corresponding aldehyde instead of 4-phenylthiophene-2-carbaldehyde, the title compound having the following physical data was obtained.

$^1$H NMR (CD$_3$OD): δ 7.96-7.85 (m, 2H), 7.68 (s, 1H), 7.55-7.31 (m, 6H), 3.94 (s, 3H), 3.82 (s, 2H), 3.40-3.22 (m, 2H), 3.00 (d, J=11.4 Hz, 2H), 2.11 (t, J=10.9 Hz, 2H), 1.78 (d, J=13.5 Hz, 2H), 1.74-1.62 (m, 1H), 1.45-1.29 (m, 2H);

Mass data (APCI, Pos.): m/z 456 (M+H)$^+$.

Example 37

4-chloro-3-methoxy-N-({1-[(1-phenyl-1H-pyrazol-4-yl)methyl]-4-piperidinyl}methyl)benzamide

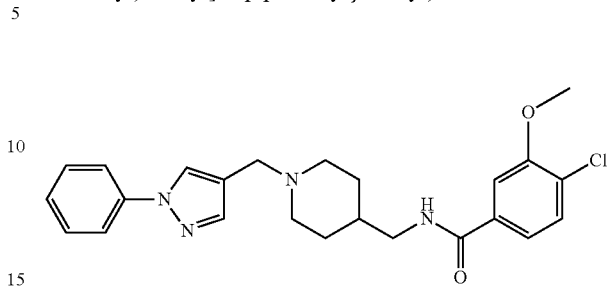

According to the same procedure described in Example 35, using the corresponding aldehyde instead of 4-phenylthiophene-2-carbaldehyde, the title compound having the following physical data was obtained.

$^1$H NMR (CD$_3$OD): δ 8.18 (s, 1H), 7.74-7.69 (m, 3H), 7.52-7.31 (m, 6H), 3.94 (s, 3H), 3.59 (s, 2H), 3.34-3.27 (m, 2H), 3.04 (d, J=11.5 Hz, 2H), 2.13 (t, J=11.2 Hz, 2H), 1.78 (d, J=11.2 Hz, 2H), 1.74-1.64 (m, 1H), 1.46-1.24 (m, 2H);

Mass data (APCI, Pos.): m/z 439 (M+H)$^+$.

Example 38

4-chloro-N-[(1-{[3-(4-chlorophenyl)-5-isoxazolyl]methyl}-4-piperidinyl)methyl]-3-methoxybenzamide

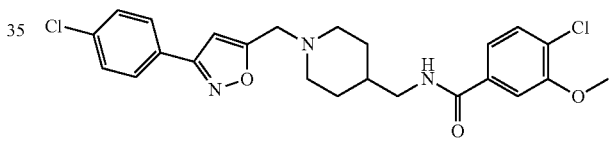

According to the same procedure described in Example 35, using the corresponding aldehyde instead of 4-phenylthiophene-2-carbaldehyde, the title compound having the following physical data was obtained.

$^1$H NMR (CD$_3$OD): δ 7.83 (d, J=8.6 Hz, 2H), 7.55-7.30 (m, 5H), 6.79 (s, 1H), 3.94 (s, 3H), 3.78 (s, 2H), 3.38-3.20 (m, 2H), 3.00 (d, J=11.6 Hz, 2H), 2.18 (t, J=11.5 Hz, 2H), 1.78 (d, J=11.9 Hz, 2H), 1.69-1.62 (m, 1H), 1.38 (dd, J=12.3, 3.4 Hz, 2H);

Mass data (APCI, Pos.): m/z 474 (M+H)$^+$.

Example 39

4-chloro-N-[(1-{[3-(3-chlorophenyl)-5-isoxazolyl]methyl}-4-piperidinyl)methyl]-3-methoxybenzamide

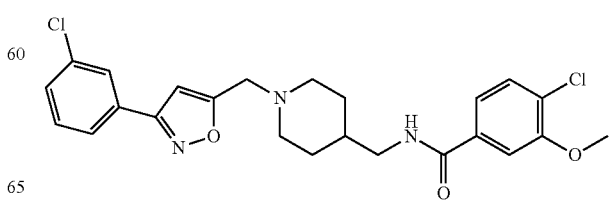

According to the same procedure described in Example 35, using the corresponding aldehyde instead of 4-phenylthiophene-2-carbaldehyde, the title compound having the following physical data was obtained.

¹H NMR (CD₃OD): δ 7.87 (s, 1H), 7.78-7.76 (m, 1H), 7.54-7.31 (m, 5H), 6.82 (s, 1H), 3.94 (s, 3H), 3.78 (s, 2H), 3.38-3.20 (m, 2H), 3.00 (d, J=11.6 Hz, 2H), 2.18 (t, J=2.1 Hz, 2H), 1.77 (d, J=11.3 Hz, 2H), 1.69-1.62 (m, 1H), 1.44-1.24 (m, 2H);

Mass data (APCI, Pos.): m/z 474 (M+H)⁺.

Example 40

4-chloro-N-[(1-{[3-(2-chlorophenyl)-5-isoxazolyl]methyl}-4-piperidinyl)methyl]-3-methoxybenzamide

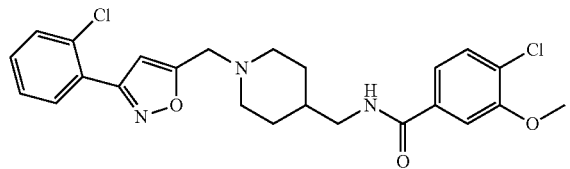 [SMILES: COc1cc(C(=O)NCC2CCN(Cc3cc(-c4ccccc4Cl)no3)CC2)ccc1Cl]

According to the same procedure described in Example 35, using the corresponding aldehyde instead of 4-phenylthiophene-2-carbaldehyde, the title compound having the following physical data was obtained.

¹H NMR (CD₃OD): δ 7.67 (dd, J=1.8, 7.5 Hz, 1H), 7.74-7.31 (m, 6H), 6.78 (s, 1H), 3.94 (s, 3H), 3.78 (s, 2H), 3.38-3.20 (m, 2H), 3.01 (d, J=11.6 Hz, 2H), 2.19 (t, J=2.1 Hz, 2H), 1.77 (d, J=11.3 Hz, 2H), 1.69-1.62 (m, 1H), 1.48-1.24 (m, 2H);

Mass data (APCI, Pos.): m/z 474 (M+H)⁺.

Example 41

4-chloro-3-methoxy-N-({1-[(5-phenyl-2-thienyl)methyl]-4-piperidinyl}methyl)benzamide

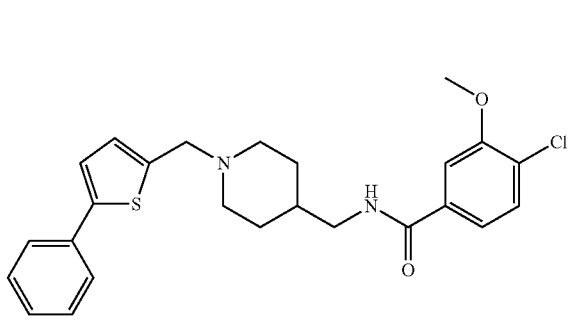 [SMILES: COc1cc(C(=O)NCC2CCN(Cc3ccc(-c4ccccc4)s3)CC2)ccc1Cl]

According to the same procedure described in Example 35, using the corresponding aldehyde instead of 4-phenylthiophene-2-carbaldehyde, the title compound having the following physical data was obtained.

¹H NMR (CDCl₃): δ 7.61-7.54 (m, 2H), 7.49-7.45 (m, 1H), 7.42-7.32 (m, 3H), 7.18-7.11 (m, 2H), 6.88-6.84 (m, 1H), 6.19-6.11 (m, 1H), 3.96 (s, 3H), 3.71 (s, 2H), 3.40-3.33 (m, 2H), 3.05-2.96 (m, 2H), 2.09-1.99 (m, 2H), 1.80-1.71 (m, 2H), 1.69-1.59 (m, 1H), 1.47-1.32 (m, 2H);

Mass data (ESI, Pos.): m/z 455 (M+H)⁺.

Example 42

4-chloro-3-methoxy-N-({1-[(5-methyl-4-phenyl-2-thienyl)methyl]-4-piperidinyl}methyl)benzamide

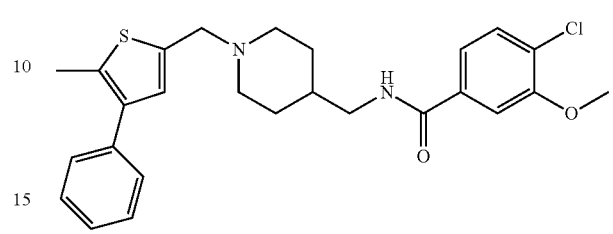

According to the same procedure described in Example 35, using the corresponding aldehyde instead of 4-phenylthiophene-2-carbaldehyde, the title compound having the following physical data was obtained.

¹H NMR (CD₃OD): δ 7.55-7.48 (m, 1H), 7.44-7.21 (m, 7H), 6.90 (s, 1H), 3.94 (s, 3H), 3.78 (s, 2H), 3.38-3.20 (m, 2H), 3.01 (d, J=11.5 Hz, 2H), 2.44 (s, 3H), 2.09 (t, J=11.1 Hz, 2H), 1.77 (d, J=12.3 Hz, 2H), 1.69-1.62 (m, 1H), 1.48-1.24 (m, 2H);

Mass data (APCI, Pos.): m/z 469 (M+H)⁺.

Example 43

4-chloro-N-[(1-{[3-(4-chlorophenyl)-1,3-thiazol-5-yl]methyl}-4-piperidinyl)methyl]-3-methoxybenzamide

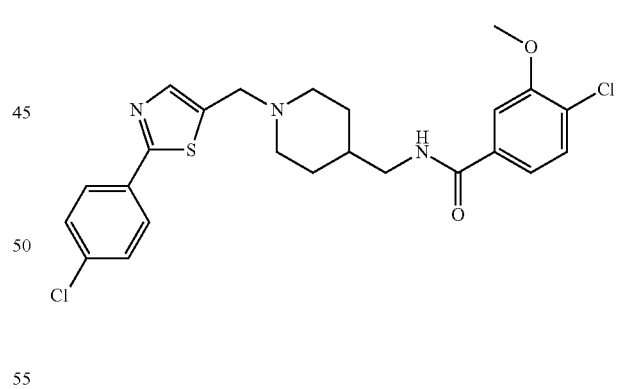

According to the same procedure described in Example 35, using the corresponding aldehyde instead of 4-phenylthiophene-2-carbaldehyde, the title compound having the following physical data was obtained.

¹H NMR (CDCl₃): δ 7.88-7.82 (m, 2H), 7.61 (s, 1H), 7.47 (s, 1H), 7.43-7.36 (m, 3H), 7.17-7.11 (m, 1H), 6.18-6.12 (m, 1H), 3.96 (s, 3H), 3.74 (s, 2H), 3.40-3.33 (m, 2H), 3.00-2.93 (m, 2H), 2.11-2.00 (m, 2H), 1.80-1.71 (m, 2H), 1.70-1.60 (m, 1H), 1.43-1.31 (m, 2H);

Mass data (ESI, Pos.): m/z 490 (M+H)⁺.

Example 44

4-chloro-N-[(1-{[3-(4-fluorophenyl)-5-isoxazolyl]methyl}-4-piperidinyl)methyl]-3-methoxybenzamide

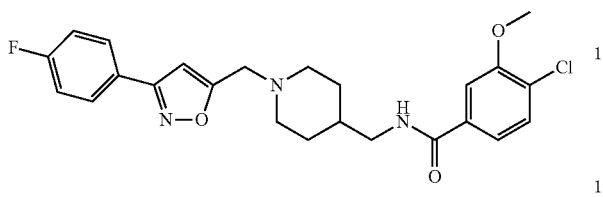

According to the same procedure described in Example 35, using the corresponding aldehyde instead of 4-phenylthiophene-2-carbaldehyde, the title compound having the following physical data was obtained.

$^1$H NMR (CD$_3$OD): δ 7.56 (dd, J=5.4, 8.2 Hz, 2H), 7.54-7.29 (m, 3H), 7.21 (t, J=8.6 Hz, 2H), 6.79 (s, 1H), 3.94 (s, 3H), 3.78 (s, 2H), 3.38-3.20 (m, 2H), 3.07 (d, J=11.3 Hz, 2H), 2.09 (t, J=11.1 Hz, 2H), 1.77 (d, J=12.3 Hz, 2H), 1.69-1.62 (m, 1H), 1.48-1.24 (m, 2H);

Mass data (APCI, Pos.): m/z 458 (M+H)$^+$.

Example 45

4-chloro-N-[(1-{[2-(2-chlorophenyl)-1,3-thiazol-5-yl]methyl}-4-piperidinyl)methyl]-3-methoxybenzamide

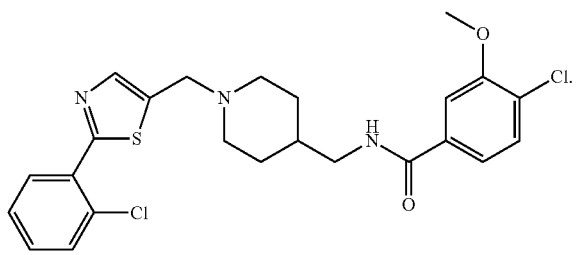 [SMILES: COc1cc(C(=O)NCC2CCN(Cc3cnc(-c4ccccc4Cl)s3)CC2)ccc1Cl]

According to the same procedure described in Example 35, using the corresponding aldehyde instead of 4-phenylthiophene-2-carbaldehyde, the title compound having the following physical data was obtained.

$^1$H NMR (CDCl$_3$): δ 8.21-8.16 (m, 1H), 7.71 (s, 1H), 7.52-7.45 (m, 2H), 7.43-7.30 (m, 3H), 7.17-7.11 (m, 1H), 6.19-6.12 (m, 1H), 3.96 (s, 3H), 3.80 (s, 2H), 3.40-3.33 (m, 2H), 3.03-2.94 (m, 2H), 2.12-2.02 (m, 2H), 1.80-1.71 (m, 2H), 1.70-1.58 (m, 1H), 1.46-1.32 (m, 2H);

Mass data (ESI, Pos.): m/z 490 (M+H)$^+$.

Example 46

4-chloro-3-methoxy-N-[(1-{[5-(2-pyridinyl)-2-thienyl]methyl}-4-piperidinyl)methyl]benzamide

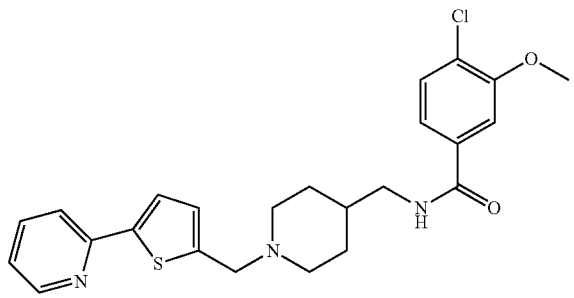 [SMILES: COc1cc(C(=O)NCC2CCN(Cc3ccc(-c4ccccn4)s3)CC2)ccc1Cl]

According to the same procedure described in Example 35, using the corresponding aldehyde instead of 4-phenylthiophene-2-carbaldehyde, the title compound having the following physical data was obtained.

$^1$H NMR (CD$_3$OD): δ 8.45 (d, J=4.9 Hz, 1H), 7.85-7.67 (m, 2H), 7.60-7.29 (m, 4H), 7.22 (t, J=5.8 Hz, 2H), 6.98 (d, J=3.6 Hz, 1H), 3.93 (s, 3H), 3.74 (s, 2H), 3.27 (d, J=6.7 Hz, 2H), 3.00 (d, J=11.5 Hz, 2H), 2.09 (t, J=10.9 Hz, 2H), 1.76 (d, J=6.7 Hz, 2H), 1.69-1.62 (m, 1H), 1.36 (m, 2H);

Mass data (APCI, Pos.): m/z 456 (M+H)$^+$.

Example 47

N-{[1-(4-biphenylylmethyl)-4-piperidinyl]methyl}-4-chloro-3-methoxybenzamide

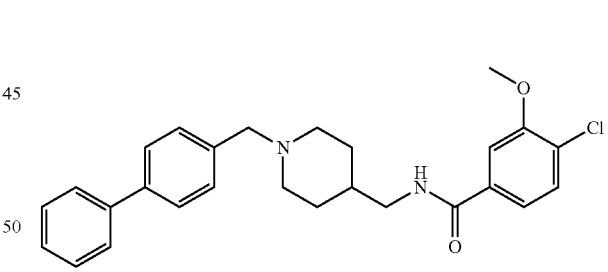

According to the same procedure described in Example 35, using the corresponding aldehyde instead of 4-phenylthiophene-2-carbaldehyde, the title compound having the following physical data was obtained.

$^1$H NMR (CDCl$_3$): δ 7.62-7.51 (m, 4H), 7.49-7.30 (m, 7H), 7.17-7.10 (m, 1H), 6.19-6.10 (m, 1H), 3.96 (s, 3H), 3.54 (s, 2H), 3.40-3.33 (m, 2H), 3.00-2.90 (m, 2H), 2.05-1.95 (m, 2H), 1.78-1.70 (m, 2H), 1.69-1.60 (m, 1H), 1.44-1.32 (m, 2H);

Mass data (ESI, Pos.): m/z 449 (M+H)$^+$.

Example 48

4-chloro-3-methoxy-N-({1-[4-(1-pyrrolidinyl)benzyl]-4-piperidinyl}methyl)benzamide

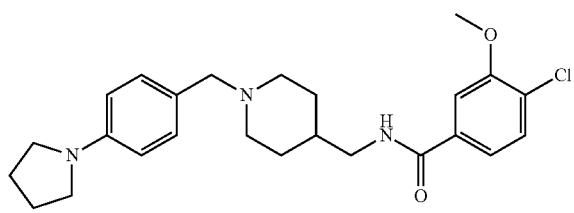 [SMILES: COc1cc(C(=O)NCC2CCN(Cc3ccc(N4CCCC4)cc3)CC2)ccc1Cl]

According to the same procedure described in Example 35, using the corresponding aldehyde instead of 4-phenylthiophene-2-carbaldehyde, the title compound having the following physical data was obtained.

$^1$H NMR (CDCl$_3$): δ 7.48-7.44 (m, 1H), 7.41-7.36 (m, 1H), 7.17-7.10 (m, 3H), 6.55-6.48 (m, 2H), 6.16-6.09 (m, 1H), 3.96 (s, 3H), 3.41 (s, 2H), 3.38-3.31 (m, 2H), 3.29-3.23 (m, 4H), 2.96-2.87 (m, 2H), 2.02-1.87 (m, 6H), 1.75-1.66 (m, 2H), 1.65-1.51 (m, 1H), 1.42-1.29 (m, 2H);

Mass data (ESI, Pos.): m/z 442 (M+H)$^+$.

Example 49

4-chloro-3-methoxy-N-({1-[(4-phenyl-2-furyl)methyl]-4-piperidinyl}methyl)benzamide

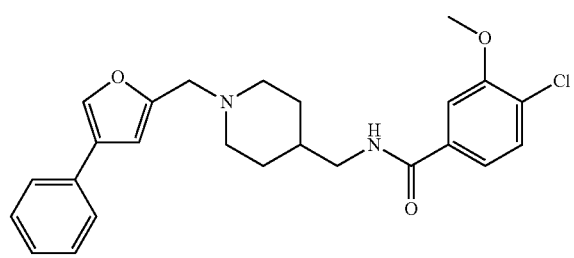 [SMILES: COc1cc(C(=O)NCC2CCN(Cc3cc(-c4ccccc4)co3)CC2)ccc1Cl]

According to the same procedure described in Example 35, using the corresponding aldehyde instead of 4-phenylthiophene-2-carbaldehyde, the title compound having the following physical data was obtained.

$^1$H NMR (DMSO-d$_6$): δ 8.56 (t, J=9.0 Hz, 1H), 8.09 (s, 1H), 7.60-7.54 (m, 3H), 7.51 (d, J=8.6 Hz, 1H), 7.46-7.42 (m, 1H), 7.39-7.34 (m, 2H), 7.27-7.21 (m, 1H), 6.74 (s, 1H), 3.91 (s, 3H), 3.48 (s, 2H), 3.17-3.11 (m, 2H), 2.88-2.80 (m, 2H), 1.99-1.90 (m, 2H), 1.69-1.61 (m, 2H), 1.58-1.47 (m, 1H), 1.24-1.12 (m, 2H);

Mass data (APCI, Pos.): m/z 439 (M+H)$^+$.

Example 50

4-chloro-3-methoxy-N-({1-[(5-phenyl-1,3,4-oxadiazol-2-yl)methyl]-4-piperidinyl}methyl)benzamide

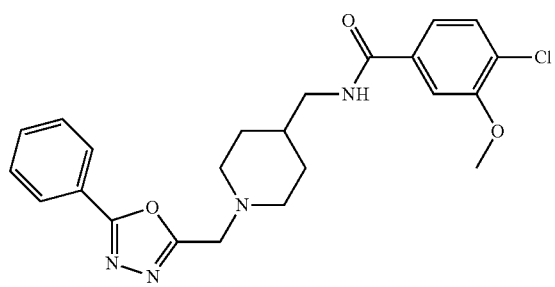 [SMILES: COc1cc(C(=O)NCC2CCN(Cc3nnc(-c4ccccc4)o3)CC2)ccc1Cl]

2-(Chloromethyl)-5-phenyl-1,3,4-oxadiazole (31 mg, prepared according to the reported preparation in Natero, R.; et al. *Synth. Commun.* 2004, 34, 2523) was added to a solution of the compound prepared in Example 11 (60 mg) and diisopropylethylamine (0.083 mL) in N,N-dimethylformamide (0.8 mL). The solution was heated to 100° C. overnight. The reaction was cooled to room temperature, diluted with ethyl acetate and washed twice with a saturated aqueous sodium bicarbonate solution. The organic phase was dried over anhydrous magnesium sulfate and concentrated. The residue was purified by column chromatography on silica gel (ethyl acetate:hexane=1:1, then ethyl acetate) to obtain the title compound (36 mg) having the following physical data.

$^1$H NMR (CDCl$_3$): δ 8.10-8.04 (m, 2H), 7.57-7.44 (m, 4H), 7.41-7.36 (m, 1H), 7.18-7.11 (m, 1H), 6.20-6.11 (m, 1H), 3.96 (s, 3H), 3.74 (s, 2H), 3.41-3.34 (m, 2H), 3.08-2.99 (m, 2H), 2.30-2.19 (m, 2H), 1.83-1.73 (m, 2H), 1.69-1.60 (m, 1H), 1.49-1.35 (m, 2H);

Mass data (ESI, Pos.): m/z 441 (M+H)$^+$.

Example 51

4-chloro-3-methoxy-N-({1-[(3-phenyl-1,2,4-oxadiazol-5-yl)methyl]-4-piperidinyl}methyl)benzamide

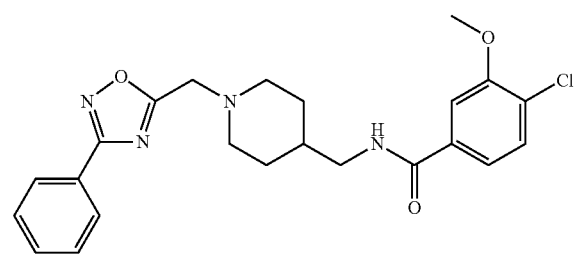 [SMILES: COc1cc(C(=O)NCC2CCN(Cc3nc(-c4ccccc4)no3)CC2)ccc1Cl]

According to the same procedure described in Example 50, using 5-(chloromethyl)-3-phenyl-1,2,4-oxadiazole instead of 2-(chloromethyl)-5-phenyl-1,3,4-oxadiazole, the title compound having the following physical data was obtained.

$^1$H NMR (CD$_3$OD): δ 8.18-8.12 (m, 2H), 7.70-7.63 (m, 1H), 7.62-7.55 (m, 2H), 7.52-7.47 (m, 1H), 7.46-7.40 (m, 1H), 7.39-7.34 (m, 1H), 3.94 (s, 3H), 3.77 (s, 2H), 3.34-3.24

(m, 2H), 3.11-3.02 (m, 2H), 2.30-2.19 (m, 2H), 1.83-1.74 (m, 2H), 1.73-1.63 (m, 1H), 1.46-1.32 (m, 2H);

Mass data (APCI, Pos.): m/z 441 (M+H)⁺.

Example 52

4-chloro-3-methoxy-N-({1-[(2-phenyl-1,3-thiazol-4-yl)methyl]-4-piperidinyl}methyl)benzamide

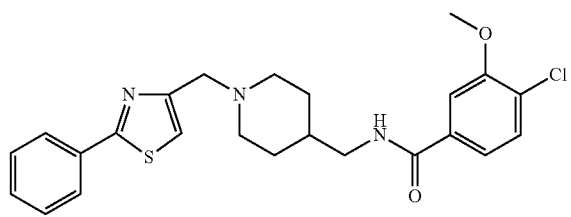 [SMILES: COc1cc(C(=O)NCC2CCN(Cc3csc(-c4ccccc4)n3)CC2)ccc1Cl]

According to the same procedure described in Example 50, using 4-(chloromethyl)-2-phenylthiazole instead of 2-(chloromethyl)-5-phenyl-1,3,4-oxadiazole, the title compound having the following physical data was obtained.

¹H NMR (CDCl₃): δ 7.97-7.92 (m, 2H), 7.49-7.36 (m, 5H), 7.18-7.11 (m, 2H), 6.19-6.12 (m, 1H), 3.96 (s, 3H), 3.75 (s, 2H), 3.40-3.33 (m, 2H), 3.10-3.02 (m, 2H), 2.18-2.07 (m, 2H), 1.80-1.72 (m, 2H), 1.70-1.55 (m, 1H), 1.50-1.36 (m, 2H);

Mass data (ESI, Pos.): m/z 456 (M+H)⁺.

Example 53

4-chloro-N-[(1-{[3-(2,6-dichlorophenyl)-5-isoxazolyl]methyl}-4-piperidinyl)methyl]-3-methoxybenzamide

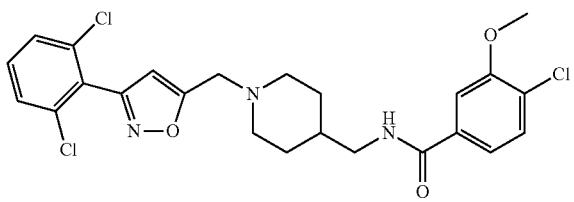 [SMILES: COc1cc(C(=O)NCC2CCN(Cc3cc(-c4c(Cl)cccc4Cl)no3)CC2)ccc1Cl]

According to the same procedure described in Example 50, using 5-(chloromethyl)-3-(2,6-dichlorophenyl)isoxazole instead of 2-(chloromethyl)-5-phenyl-1,3,4-oxadiazole, the title compound having the following physical data was obtained.

¹H NMR (DMSO-d₆): δ 8.57-8.50 (m, 1H), 7.68-7.62 (m, 2H), 7.60-7.40 (m, 4H), 6.61 (s, 1H), 3.91 (s, 3H), 3.77 (s, 2H), 3.19-3.13 (m, 2H), 2.91-2.83 (m, 2H), 2.09-2.00 (m, 2H), 1.71-1.64 (m, 2H), 1.59-1.47 (m, 1H), 1.29-1.16 (m, 2H);

Mass data (APCI, Pos.): m/z 508 (M+H)⁺.

Example 54

2-chloro-5-{[({1-[(3-phenyl-5-isoxazolyl)methyl]-4-piperidinyl}methyl)amino]carbonyl}phenyl Ethyl Carbonate

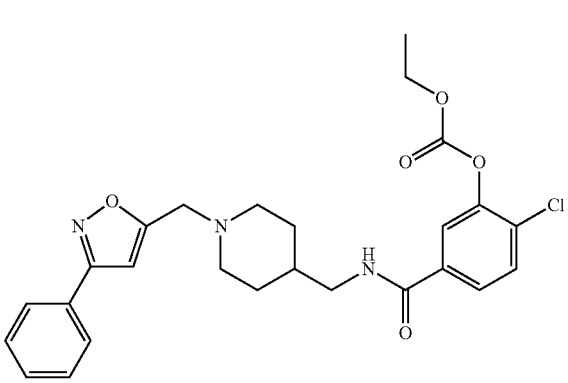 [SMILES: CCOC(=O)Oc1cc(C(=O)NCC2CCN(Cc3cc(-c4ccccc4)no3)CC2)ccc1Cl]

Ethyl chloroformate (0.029 mL) was added to a 0° C. solution of 4-chloro-3-hydroxybenzoic acid (50 mg) and 4-methylmorpholine (0.092 L) in dichloromethane (2 mL). The reaction was stirred for two hours and then was treated with the compound prepared in Example 9 (79 mg). The reaction was stirred overnight, then diluted with ethyl acetate and washed twice with a saturated aqueous sodium bicarbonate solution. The organic phase was dried over anhydrous magnesium sulfate and concentrated. The residue was purified by column chromatography on silica gel (ethyl acetate:hexane=1:9, then methanol:concentrated aqueous ammonia:ethyl acetate=2:3:95) to obtain the title compound (60 mg) having the following physical data.

¹H NMR (CDCl₃): δ 7.84-7.77 (m, 2H), 7.66-7.57 (m, 2H), 7.55-7.41 (m, 4H), 6.49 (s, 1H), 6.21-6.11 (m, 1H), 4.40-4.32 (m, 2H), 3.74 (s, 2H), 3.39-3.20 (m, 2H), 3.03-2.94 (m, 2H), 2.18-2.09 (m, 2H), 1.81-1.71 (m, 2H), 1.68-1.55 (m, 1H), 1.44-1.36 (m, 5H);

Mass data (APCI, Pos.): m/z 498 (M+H)⁺.

Example 55

4-chloro-3-hydroxy-N-({1-[(3-phenyl-5-isoxazolyl)methyl]-4-piperidinyl}methyl)benzamide

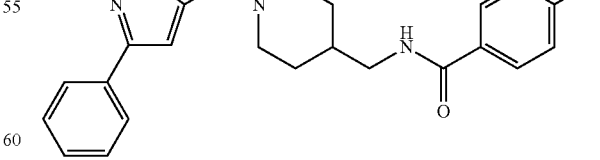

Aqueous 1 N sodium hydroxide (0.105 mL) was added to a room temperature solution of the compound prepared in Example 54 (35 mg) in tetrahydrofuran (1 mL). The mixture was stirred for two hours and was then adjusted to pH 7 via the addition of aqueous 3% hydrochloric acid. The mixture was then extracted with ethyl acetate three times. The organic phases were combined, dried over anhydrous magnesium sulfate and concentrated to obtain the title compound (10 mg) having the following physical data.

$^1$H NMR (CDCl$_3$): δ 7.84-7.78 (m, 2H), 7.48-7.36 (m, 7H), 6.50 (s, 1H), 6.18-6.09 (m, 1H), 3.75 (s, 2H), 3.39-3.33 (m, 2H), 3.05-2.95 (m, 2H), 2.21-2.07 (m, 2H), 1.81-1.71 (m, 2H), 1.69-1.58 (m, 1H), 1.48-1.35 (m, 2H);

Mass data (APCI, Pos.): m/z 426 (M+H)$^+$.

Example 56

4-chloro-3-(2-hydroxyethoxy)-N-({1-[(3-phenyl-5-isoxazolyl)methyl]-4-piperidinyl}methyl)benzamide

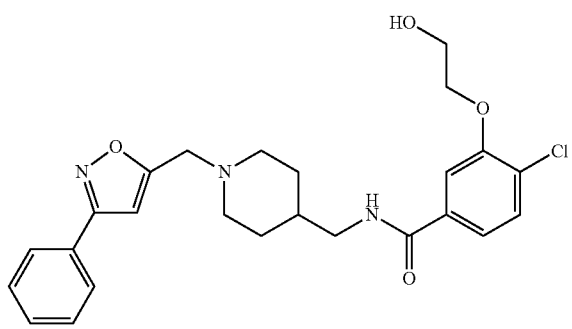 [SMILES: O=C(NCC1CCN(Cc2cc(-c3ccccc3)no2)CC1)c1ccc(Cl)c(OCCO)c1]

2-Bromoethanol (0.012 mL) was added to a mixture of the compound prepared in Example 55 (50 mg) and potassium carbonate (49 mg) in N,N-dimethylformamide (0.8 mL). The mixture was stirred at room temperature overnight, then 50° C. for six hours. The reaction was cooled to room temperature and was adjusted to pH 7 via the addition of aqueous 3% hydrochloric acid. The mixture was extracted twice with ethyl acetate and the organic phases were combined, dried over anhydrous magnesium sulfate and concentrated. The residue was purified by column chromatography on silica gel (methanol:ethyl acetate=1:19) to obtain the title compound (10 mg) having the following physical data.

$^1$H NMR (CDCl$_3$): δ 7.85-7.77 (m, 2H), 7.51-7.38 (m, 5H), 7.22-7.15 (m, 1H), 6.50 (s, 1H), 6.24-6.17 (m, 1H), 4.26-4.18 (m, 2H), 4.06-3.98 (m, 2H), 3.75 (s, 2H), 3.41-3.31 (m, 2H), 3.05-2.94 (m, 2H), 2.19-2.09 (m, 2H), 1.81-1.71 (m, 2H), 1.68-1.55 (m, 2H), 1.47-1.34 (m, 2H);

Mass data (APCI, Pos.): m/z 470 (M+H)$^+$.

Example 57

Ethyl {1-[(3-phenyl-5-isoxazolyl)methyl]-4-piperidinyl}acetate

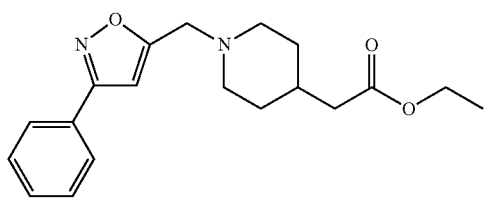 [SMILES: CCOC(=O)CC1CCN(Cc2cc(-c3ccccc3)no2)CC1]

A solution of the compound prepared in Example 7 (500 mg), ethyl 2-(piperidin-4-yl)acetate (494 mg) and acetic acid (0.33 mL) in acetonitrile (15 mL) was stirred for 30 minutes at room temperature. Tetramethylammonium triacetoxyborohydride (2.28 g) was added and the reaction was stirred overnight. The reaction was poured into a saturated aqueous sodium bicarbonate solution and was extracted three times with ethyl acetate. The organic phases were combined, dried over anhydrous magnesium sulfate and concentrated to obtain the title compound (675 mg) having the following physical data.

$^1$H NMR (CDCl$_3$): δ 7.86-7.76 (m, 2H), 7.50-7.40 (m, 3H), 6.49 (s, 1H), 4.12 (q, J=7.1 Hz, 1H), 3.73 (s, 2H), 3.00-2.90 (m, 2H), 2.27-2.11 (m, 4H), 2.09-2.01 (m, 1H), 1.86-1.67 (m, 3H), 1.44-1.30 (m, 2H), 1.29-1.20 (m, 3H);

Mass data (APCI, Pos.): m/z 329 (M+H)$^+$.

Example 58

{1-[(3-phenyl-5-isoxazolyl)methyl]-4-piperidinyl}acetic Acid Hydrochloride

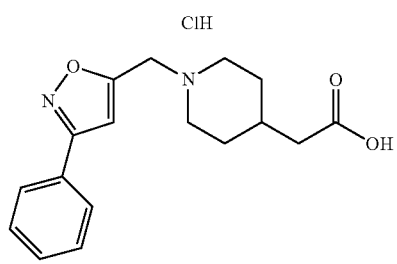 [SMILES: Cl ; O=C(O)CC1CCN(Cc2cc(-c3ccccc3)no2)CC1]

A solution of the compound prepared in Example 57 (600 mg) in trifluoroacetic acid (2 mL)-aqueous 18% hydrochloric acid (4 mL) was refluxed for two hours. The reaction was cooled to room temperature and concentrated to obtain the title compound (699 mg) having the following physical data.

$^1$H NMR (DMSO-d$_6$): δ 11.26-11.11 (m, 1H), 7.94-7.85 (m, 2H), 7.61-7.50 (m, 3H), 7.37 (s, 1H), 4.56 (s, 2H), 3.51-3.39 (m, 2H), 3.12-2.97 (m, 2H), 2.23-2.15 (m, 2H), 1.99-1.82 (m, 3H), 1.65-1.49 (m, 2H).

Example 59

{1-[(3-phenyl-5-isoxazolyl)methyl]-4-piperidinyl}acetyl Chloride Hydrochloride

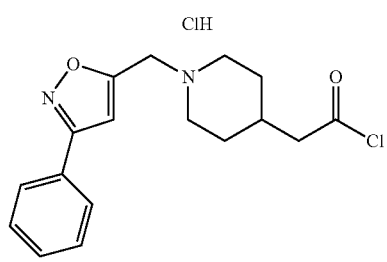 [SMILES: Cl ; O=C(Cl)CC1CCN(Cc2cc(-c3ccccc3)no2)CC1]

Oxalyl chloride (0.24 mL) was added dropwise to a 0° C. solution of the compound prepared in Example 58 (615 mg) in dichloromethane (8 mL). The reaction was stirred at room temperature for 30 minutes and then concentrated to obtain the title compound (600 mg) having the following physical data. $^1$H NMR (DMSO-d$_6$): δ 7.92-7.81 (m, 2H), 7.62-7.48

(m, 3H), 7.38 (s, 1H), 4.59 (s, 2H), 3.50-3.36 (m, 2H), 3.12-2.97 (m, 2H), 2.22-2.09 (m, 2H), 1.99-1.79 (m, 3H), 1.67-1.50 (m, 2H).

Example 60

N-(4-amino-5-cyano-6-ethoxy-2-pyridinyl)-2-{1-[(3-phenyl-5-isoxazolyl)methyl]-4-piperidinyl}acetamide

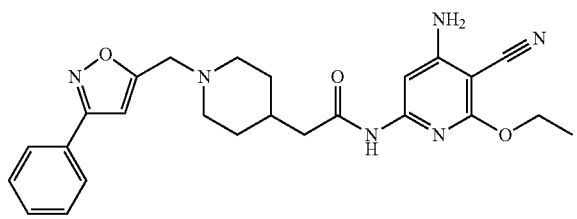 [SMILES: CCOc1nc(NC(=O)CC2CCN(Cc3cc(-c4ccccc4)no3)CC2)cc(N)c1C#N]

A mixture of the compound prepared in Example 59 (100 mg) and 4,6-diamino-2-ethoxynicotinonitrile (50 mg, prepared according to the preparation reported in Szczepankiewicz, B. G.; et al. *J. Med. Chem.* 2006, 49, 3563 and references therein) in pyridine (1.5 mL) was heated to 50° C. overnight and then 80° C. for six days. The mixture was cooled to room temperature, diluted with ethyl acetate and washed twice with a saturated aqueous sodium bicarbonate solution. The organic phase was dried over anhydrous magnesium sulfate and concentrated. The residue was purified by column chromatography on silica gel (ethyl acetate:hexane=4:1) to obtain the title compound (18 mg) having the following physical data.

$^1$H NMR (CDCl$_3$): δ 7.85-7.76 (m, 2H), 7.50-7.41 (m, 4H), 7.24 (s, 1H), 6.48 (s, 1H), 4.91-4.84 (m, 2H), 4.32 (q, J=6.7 Hz, 2H), 3.77-3.71 (m, 2H), 3.00-2.92 (m, 2H), 2.30-2.27 (m, 2H), 2.23-2.12 (m, 2H), 1.96-1.84 (m, 1H), 1.84-1.74 (m, 2H), 1.42-1.33 (m, 5H).

Mass data (APCI, Pos.): m/z 461 (M+H)$^+$.

Example 61 tert-butyl 4-[(6-chloro-1-oxo-3,4-dihydro-2(1H)-isoquinolinyl)methyl]-1-piperidinecarboxylate

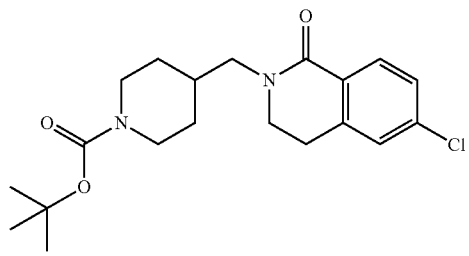 [SMILES: CC(C)(C)OC(=O)N1CCC(CN2CCc3cc(Cl)ccc3C2=O)CC1]

A room temperature solution of 6-chloro-3,4-dihydroisoquinolin-1(2H)-one (0.100 g) in N,N-dimethylformamide (3 mL) was treated with sodium hydride (95% dispersion in mineral oil, 0.028 g) and stirred for 20 minutes. tert-Butyl 4-(bromomethyl)piperidine-1-carboxylate (0.184 g) was added and the reaction was stirred at 40° C. overnight. The mixture was diluted with diethyl ether and washed sequentially with water, 1 N hydrochloric acid, a saturated aqueous sodium bicarbonate solution and brine. The organic phase was dried over anhydrous magnesium sulfate and concentrated. The residue was purified by column chromatography on silica gel (dichloromethane:methanol=47:3) to obtain the title compound (0.188 g) having the following physical data.

$^1$H NMR (CDCl$_3$): δ 8.00 (d, J=8.3 Hz, 1H), 7.31 (dd, J=8.3, 1.9 Hz, 1H), 7.18 (s, 1H), 3.57 (t, J=6.5 Hz, 1H), 3.44 (t, J=6.1 Hz, 2H), 3.30 (d, J=6.1 Hz, 2H), 2.98 (t, J=6.5 Hz, 1H), 2.72-2.62 (m, 2H), 2.28-2.18 (m, 2H), 1.83-1.73 (m, 2H), 1.68 (d, J=12.3 Hz, 1H), 1.46 (s, 9H), 1.22 (m, 2H);

Mass data (APCI, Pos.): m/z 379 (M+H)$^+$.

Example 62

6-chloro-2-(4-piperidinylmethyl)-3,4-dihydro-1(2H)-isoquinolinone Trifluoroacetate

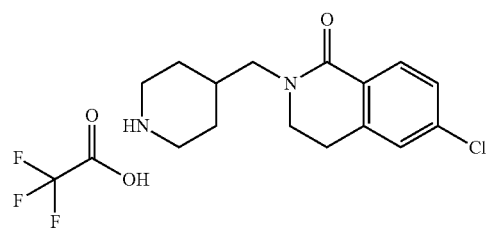

According to the same procedure described in Example 11, using the compound prepared in Example 61 instead of the compound prepared in Example 10, the title compound having the following physical data was obtained.

$^1$H NMR (DMSO-d$_6$): δ 8.44-8.21 (m, 1H), 7.84 (d, J=8.3 Hz, 1H), 7.49-7.35 (m, 2H), 3.52 (d, J=5.8 Hz, 2H), 3.45 (d, J=6.4 Hz, 2H), 3.16-3.12 (m, 2H), 2.87-2.81 (m, 2H), 2.36 (t, J=6.0 Hz, 2H), 2.06-1.81 (m, 3H), 1.50-1.19 (m, 2H);

Mass data (ESI, Pos.): m/z 279 (M+H)$^+$.

Example 63

6-chloro-2-({1-[(3-phenyl-5-isoxazolyl)methyl]-4-piperidinyl}methyl)-3,4-dihydro-1(2H)-isoquinolinone

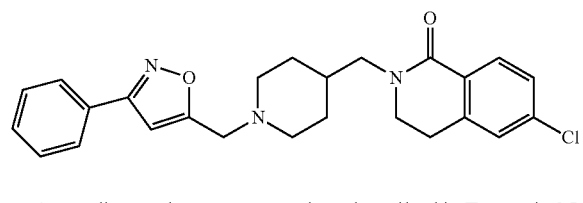

According to the same procedure described in Example 35, using the compound prepared in Example 62 instead of the compound prepared in Example 11 and the compound prepared in Example 7 instead of 4-phenylthiophene-2-carbaldehyde, the title compound having the following physical data was obtained.

$^1$H NMR (CD$_3$OD): δ 7.86-7.79 (m, 3H), 7.36-7.25 (m, 5H), 6.78 (s, 1H), 3.78-3.72 (m, 2H), 3.61 (t, J=6.6 Hz, 2H), 3.46 (d, J=7.3 Hz, 2H), 3.31-3.25 (m, 2H), 3.01 (t, J=6.2 Hz, 2H), 2.19 (t, J=10.8 Hz, 2H), 1.78-1.81 (m, 3H), 1.42-1.28 (m, 2H);

Mass data (APCI, Pos.): m/z 436 (M+H)$^+$.

Example 64

{1-[(3-phenyl-5-isoxazolyl)methyl]-4-piperidinyl}methanol

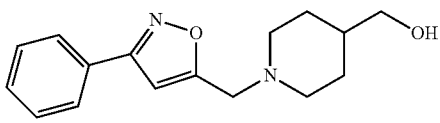 [SMILES: OCC1CCN(Cc2cc(-c3ccccc3)no2)CC1]

Sodium triacetoxyborohydride (12.2 g) was added portionwise to a room temperature mixture of the compound prepared in Example 7 (5.00 g) and piperidin-4-ylmethanol (4.99 g) in dichloromethane (150 mL). The reaction mixture was stirred at room temperature overnight. The reaction mixture was diluted with dichloromethane and washed sequentially with a saturated aqueous sodium bicarbonate solution and brine. The organics were dried over anhydrous magnesium sulfate and concentrated to obtain the crude title compound (8.05 g), which was used without further purification having the following physical data.

Mass data (ESI, Pos.): m/z 273 (M+H)+.

Example 65

{1-[(3-phenyl-5-isoxazolyl)methyl]-4-piperidinyl}methyl 4-methylbenzenesulfonate

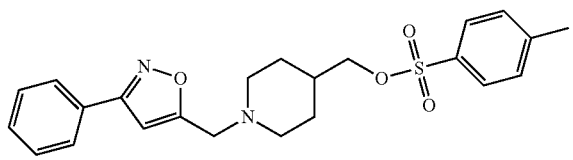 [SMILES: Cc1ccc(S(=O)(=O)OCC2CCN(Cc3cc(-c4ccccc4)no3)CC2)cc1]

Triethylamine (12.1 mL) and p-toluene sulfonylchloride (6.61 g) were added sequentially to a room temperature mixture of the compound prepared in Example 64 (7.86 g) in dichloromethane (100 mL). The reaction mixture was stirred at room temperature overnight. The reaction mixture was diluted with dichloromethane and washed sequentially with a saturated aqueous sodium bicarbonate solution and brine. The combined organics were dried over anhydrous magnesium sulfate and concentrated. The residue was purified by column chromatography on silica gel to obtain the title compound (1.52 g) having the following physical data.

$^1$H NMR (CDCl$_3$): δ 7.82-7.75 (m, 4H), 7.48-7.42 (m, 3H), 7.37-7.31 (m, 2H), 6.47 (s, 1H), 3.86 (d, J=6.2 Hz, 2H), 3.70 (s, 2H), 2.98-2.89 (m, 2H), 2.45 (s, 3H), 2.14-2.15 (m, 2H), 1.73-1.64 (m, 3H), 1.35-1.22 (m, 2H);

Mass data (APCI, Pos.): m/z 427 (M+H)+.

Example 66

4-phenyl-2-({1-[(3-phenyl-5-isoxazolyl)methyl]-4-piperidinyl}methyl)-3,4-dihydro-1(2H)-isoquinolinone

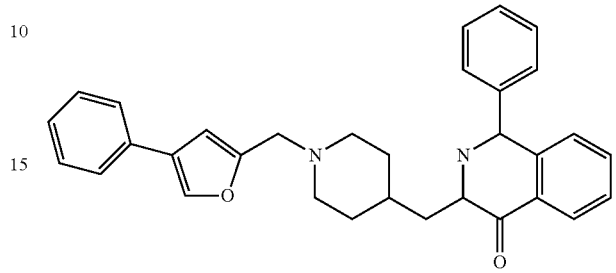

According to the same procedure described in Example 61, using the compound prepared in Example 65 instead of tert-butyl 4-(bromomethyl)piperidine-1-carboxylate and 4-phenyl-3,4-dihydroisoquinolin-1(2H)-one (prepared according to the reported preparation in Davies, R. V.; et al. J. Chem. Soc. Perkin Trans. 1 1978, 180) instead of 6-chloro-3,4-dihydroisoquinolin-1(2H)-one, the title compound having the following physical data was obtained.

$^1$H NMR (CD$_3$OD): δ 8.04 (d, J=6.7 Hz, 1H), 7.82-7.76 (m, 2H), 7.45-7.04 (m, 11H), 6.75 (d, J=7.1 Hz, 1H), 4.35 (d, J=4.3 Hz, 2H), 3.95 (t, J=11.5 Hz, 1H), 3.73-3.62 (m, 2H), 3.12-3.06 (m, 2H), 2.81-2.67 (m, 2H), 2.18-1.84 (m, 3H), 1.43-1.22 (m, 4H);

Mass data (APCI, Pos.): m/z 478 (M+H)+.

Example 67

4-chloro-3-methoxy-N-({1-[(3-phenyl-5-isoxazolyl)carbonyl]-4-piperidinyl}methyl)benzamide

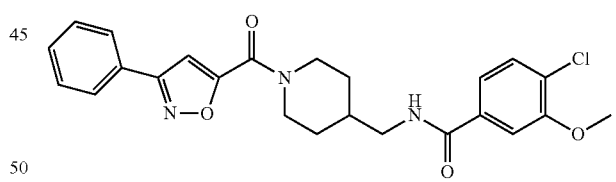

A solution of 3-phenylisoxazole-5-carboxylic acid (0.075 g) in dichloromethane (1.6 mL) was treated with 1-ethyl-3-(3'-dimethylaminopropyl)carbodiimide hydrochloride (0.084 g), 1-hyroxybenzotriazole hydrate (0.067 g) and diisopropylethylamine (0.21 mL) and stirred for five minutes. The product prepared in Example 11 (0.17 g) was added and the mixture was stirred at room temperature overnight. The mixture was partitioned between 1 N hydrochloric acid and dichloromethane. The organic phase was dried over anhydrous magnesium sulfate and concentrated. The residue was purified by column chromatography on silica gel (dichloromethane:methanol=9:1) to obtain the title compound (0.077 g) having the following physical data.

$^1$H NMR (DMSO-d$_6$): δ 8.63 (t, J=5.6 Hz, 1H), 7.92 (dd, J=1.9, 7.6 Hz, 2H), 7.63-7.42 (m, 5H), 7.27 (s, 1H), 4.49 (d,

J=12.8 Hz, 1H), 3.97 (d, J=13.3 Hz, 1H), 3.91 (s, 3H), 3.20 (d, J=6.3 Hz, 2H), 3.13 (t, J=12.2 Hz, 1H), 2.85 (t, J=11.3 Hz, 1H), 1.99-1.72 (m, 3H), 1.24-1.15 (m, 2H);

Mass data (APCI, Pos.): m/z 454 (M+H)+.

Example 68

N-{[1-(4-biphenylylsulfonyl)-4-piperidinyl]methyl}-4-chloro-3-methoxybenzamide

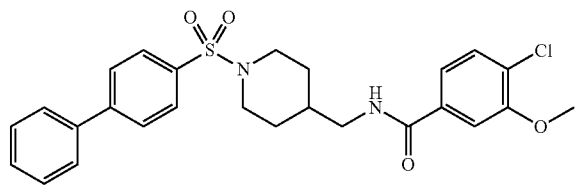 [SMILES: COc1cc(C(=O)NCC2CCN(S(=O)(=O)c3ccc(-c4ccccc4)cc3)CC2)ccc1Cl]

A solution of the compound prepared in Example 11 (0.050 g) and biphenylyl-4-sulfonyl chloride (0.033 g) in dichloromethane (0.7 mL) was treated with triethylamine (0.092 mL). The mixture was stirred at room temperature overnight and then was washed with 1 N hydrochloric acid. The organic phase was dried over anhydrous magnesium sulfate and concentrated. The residue was triturated with diethyl ether to obtain the title compound (0.039 g) having the following physical data.

$^1$H NMR (DMSO-$d_6$): δ 8.57 (t, J=5.3 Hz, 1H), 7.93 (d, J=8.2 Hz, 2H), 7.80 (d, J=7.8 Hz, 2H), 7.75 (d, J=7.8 Hz, 2H), 7.58-7.37 (m, 6H), 3.89 (s, 3H), 3.67 (d, J=11.5 Hz, 2H), 3.13 (t, J=6.0 Hz, 2H), 2.29 (t, J=11.3 Hz, 2H), 1.74 (d, J=12.4 Hz, 2H), 1.58-1.49 (m, 1H), 1.23 (d, J=9.4 Hz, 2H);

Mass data (APCI, Pos.): m/z 499 (M+H)+.

Example 69

N-{[1-(3-biphenylylsulfonyl)-4-piperidinyl]methyl}-4-chloro-3-methoxybenzamide

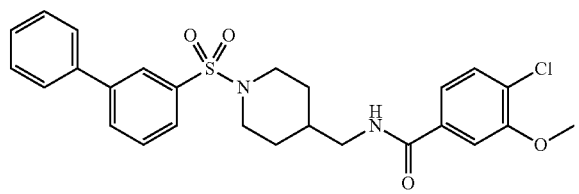 [SMILES: COc1cc(C(=O)NCC2CCN(S(=O)(=O)c3cccc(-c4ccccc4)c3)CC2)ccc1Cl]

According to the same procedure described in Example 68, using the corresponding sulfonyl chloride instead of biphenylyl-4-sulfonyl chloride, the title compound having the following physical data was obtained.

$^1$H NMR (DMSO-$d_6$): δ 8.61-8.52 (m, 1H), 8.07-7.51 (m, 12H), 3.90 (s, 3H), 3.78-3.64 (m, 2H), 3.19-3.07 (m, 2H), 2.34-2.25 (m, 2H), 1.82-1.70 (m, 2H), 1.55-1.51 (m, 1H), 1.29-1.21 (m, 2H);

Mass data (APCI, Pos.): m/z 499 (M+H)+.

Example 70

4-chloro-3-methoxy-N-[1-{[6-(4-morpholinyl)-3-pyridinyl]sulfonyl}-4-piperidinyl)methyl]benzamide

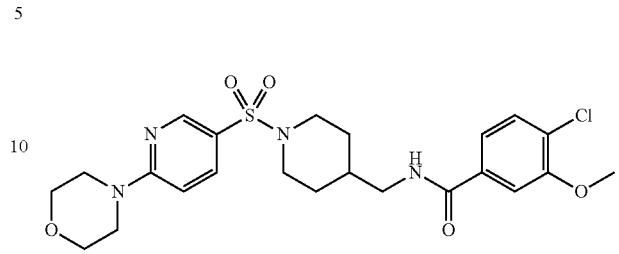

According to the same procedure described in Example 68, using the corresponding sulfonyl chloride instead of biphenylyl-4-sulfonyl chloride, the title compound having the following physical data was obtained.

$^1$H NMR (DMSO-$d_6$): δ 8.57 (t, J=5.5 Hz, 1H), 8.37 (d, J=2.3 Hz, 1H), 7.75 (dd, J=2.4, 9.1 Hz, 1H), 7.58-7.36 (m, 3H), 6.95 (d, J=9.2 Hz, 1H), 3.91 (s, 3H), 3.63-3.53 (m, 8H), 3.36-3.23 (m, 2H), 3.13 (t, J=6.0 Hz, 2H), 2.22 (t, J=10.9 Hz, 2H), 1.80-1.65 (m, 3H), 1.31-1.03 (m, 2H);

Mass data (APCI, Pos.): m/z 509 (M+H)+.

Example 71

4-chloro-3-methoxy-N-[(1-{[5-(2-pyridinyl)-2-thienyl]sulfonyl}-4-piperidinyl)methyl]benzamide

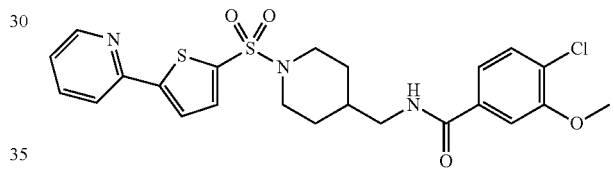

According to the same procedure described in Example 68, using the corresponding sulfonyl chloride instead of biphenylyl-4-sulfonyl chloride, the title compound having the following physical data was obtained.

$^1$H NMR (DMSO-$d_6$): δ 8.63-8.54 (m, 2H), 8.13-7.35 (m, 8H), 3.89 (s, 3H), 3.72-3.59 (m, 2H), 3.55-3.41 (m, 2H), 3.21-3.09 (m, 2H), 1.85-1.55 (m, 3H), 1.31-1.22 (m, 2H);

Mass data (APCI, Pos.): m/z 506 (M+H)+.

Example 72

N-({1-[(3-phenyl-5-isoxazolyl)methyl]-4-piperidinyl}methyl)-1-(tetrahydro-2H-pyran-2-yl)-5-(1-trityl-1H-1,2,4-triazol-3-yl)-1H-indazol-3-amine

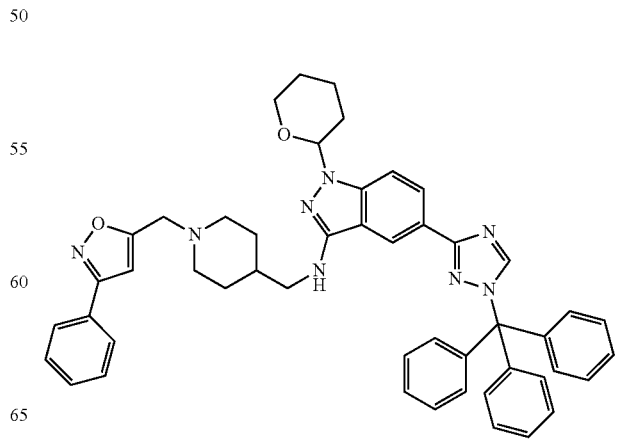

3-Bromo-1-(tetrahydro-2H-pyran-2-yl)-5-(1-trityl-1H-1,2,4-triazol-3-yl)-1H-indazole (0.25 g, prepared according to the reported preparation in US 2004/0127536), the compound prepared in Example 9 (0.29 g), racemic-2,2'-bis(diphenylphosphino)-1,1'-binaphthyl (0.040 g), and sodium tert-butoxide (0.20 g) were suspended in toluene (6 mL) and purged with argon. Tris(dibenzylideneacetone)dipalladium(0) (0.019 g) was added and the system was sealed and heated at 100° C. overnight. The reaction mixture was cooled to room temperature and partitioned between dichloromethane and a saturated aqueous sodium bicarbonate solution. The organics were dried over anhydrous magnesium sulfate and concentrated. The residue was purified by column chromatography on silica gel to obtain the title compound (0.13 g) having the following physical data.

$^1$H NMR (CDCl$_3$): δ 8.25 (s, 1H), 8.13-8.08 (m, 1H), 7.92 (s, 1H), 7.84-7.79 (m, 2H), 7.48-7.43 (m, 3H), 7.38-7.32 (m, 10H), 7.24-7.19 (m, 6H), 6.50 (s, 1H), 5.52-5.46 (m, 1H), 4.08-4.02 (m, 2H), 3.75-3.66 (m, 3H), 3.44-3.28 (m, 1H), 3.03-2.95 (m, 2H), 2.57-2.54 (m, 1H), 2.19-2.07 (m, 3H), 2.00-1.92 (m, 1H), 1.90-1.81 (m, 2H), 1.77-1.64 (m, 3H), 1.64-1.58 (m 1H), 1.49-1.36 (m, 2H);

Mass data (APCI, Pos.): m/z 781 (M+H)$^+$.

Example 73

N-({1-[(3-phenyl-5-isoxazolyl)methyl]-4-piperidinyl}methyl)-5-(1H-1,2,4-triazol-3-yl)-1H-indazol-3-amine

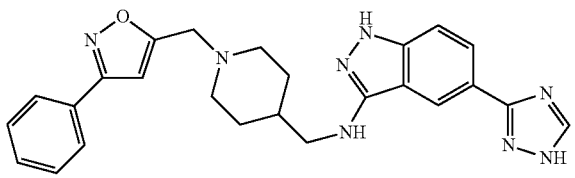 [SMILES: c1ccc(-c2cc(CN3CCC(CNc4n[nH]c5ccc(-c6nc[nH]n6)cc45)CC3)on2)cc1]

The compound prepared in Example 72 (0.13 g) was suspended in a mixture of tetrahydrofuran (6 mL), methanol (6 mL), water (1.5 mL) and concentrated hydrochloric acid (1.5 mL) and heated at reflux overnight. The reaction mixture was cooled to room temperature and poured into a saturated aqueous sodium bicarbonate solution and extracted into ethyl acetate. The organics were dried over anhydrous magnesium sulfate and concentrated. The residue was purified by column chromatography on silica gel to obtain the title compound (0.040 g) having the following physical data.

$^1$H NMR (DMSO-d$_6$): δ 13.90 (s, 1H), 11.62 (s, 1H), 11.42 (s, 1H), 8.51-8.46 (m, 1H), 7.98-7.77 (m, 3H), 7.55-7.47 (m, 3H), 7.36-7.22 (m, 1H), 6.95 (s, 1H), 6.26-6.18 (m, 1H), 3.71 (s, 2H), 3.19-3.11 (m, 2H), 2.95-2.86 (m, 2H), 2.06 (t, J=10.7 Hz, 2H), 1.84-1.76 (m, 2H), 1.75-1.64 (m, 1H), 1.35-1.20 (m, 2H);

Mass data (APCI, Pos.): m/z 455 (M+H)$^+$.

Example 74

(2E)-3-(2,3-dichlorophenyl)acryloyl Azide

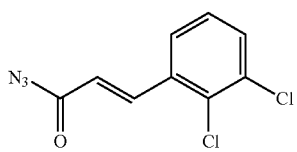 [SMILES: [N-]=[N+]=NC(=O)/C=C/c1cccc(Cl)c1Cl]

Diphenylphosphoryl azide (3.00 mL) was added 2,3-dichlorocinnamic acid (3.00 g) to a room temperature suspension in benzene (20 mL) and triethylamine (2.50 mL). The reaction mixture was stirred at room temperature overnight and then concentrated. The residue was purified by column chromatography on silica gel (ethyl acetate:hexane=1:9) to obtain the title compound (1.77 g) having the following physical data.

$^1$H NMR (CDCl$_3$): δ 8.16 (d, J=15.9 Hz, 1H), 7.52 (d, J=7.9 Hz, 2H), 7.28-7.22 (m, 1H), 6.41 (d, J=15.9 Hz, 1H).

Example 75

5,6-dichloro-1(2H)-isoquinolinone

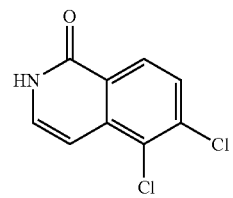 [SMILES: O=c1[nH]ccc2c(Cl)c(Cl)ccc12]

The compound prepared in Example 74 (1.00 g) was suspended in diphenylmethane (5 mL) and slowly heated to 250° C. The reaction mixture was cooled to room temperature and purified by column chromatography on silica gel to obtain the title compound (0.070 g) having the following physical data.

$^1$H NMR (CDCl$_3$): δ 11.66 (s, 1H), 8.15 (d, J=8.6 Hz, 1H), 7.70 (d, J=8.6 Hz, 1H), 7.44-7.38 (m, 1H), 6.73 (d, J=7.3 Hz).

Example 76 tert-butyl 4-[(5,6-dichloro-1-oxo-2(1H)-isoquinolinyl)methyl]-1-piperidinecarboxylate

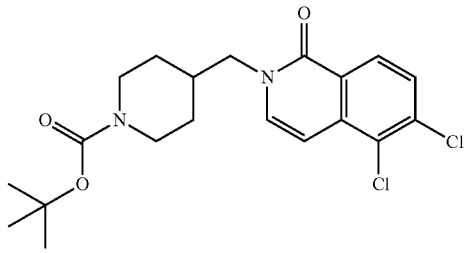 [SMILES: CC(C)(C)OC(=O)N1CCC(Cn2ccc3c(Cl)c(Cl)ccc3c2=O)CC1]

Sodium hydride (95% dispersion in mineral oil, 0.026 g) was added to a room temperature suspension of the compound prepared in Example 75 (0.07 g) in N,N-dimethylformamide (10 mL). The reaction mixture was stirred at room temperature for one hour and then tert-butyl 4-(bromomethyl)piperidine-1-carboxylate (0.14 g) added to the system. The reaction mixture was heated at 80° C. overnight, then cooled to room temperature, diluted with ethyl acetate and washed sequentially with a saturated aqueous sodium bicarbonate solution, water and brine. The organics were dried over anhydrous magnesium sulfate and concentrated. The residue was purified by column chromatography on silica gel (ethyl acetate:hexane=3:7) to obtain the title compound (0.05 g) having the following physical data.

¹H NMR (CDCl₃): δ 8.28 (d, J=8.7 Hz, 1H), 7.53 (d, J=8.7 Hz, 1H), 7.12 (d, J=7.6 Hz, 1H), 6.86 (d, J=7.6 Hz, 1H), 4.23-4.03 (m, 2H), 3.96-3.77 (m, 2H), 2.75-2.59 (m 2H), 2.15-2.05 (m, 1H), 1.72-1.59 (m, 2H), 1.48-1.40 (m, 11H);

Mass data (APCI, Pos.): m/z 311 (M-tert-butoxylcarbonyl+H)⁺.

Example 77

5,6-dichloro-2-(4-piperidinylmethyl)-1(2H)-isoquinolinone Hydrochloride

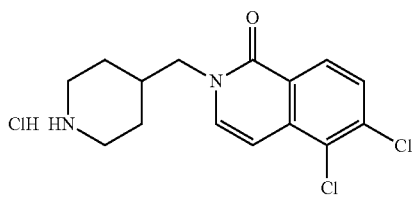 [SMILES: Cl ; O=c1c2ccc(Cl)c(Cl)c2ccn1CC1CCNCC1]

The compound prepared in Example 76 (0.05 g) was suspended in 1,4-dioxane (4 mL), hydrochloric acid (4 mol/L solution in 1,4-dioxane, 0.88 mL) was added and the reaction mixture was stirred at room temperature overnight. The reaction mixture was concentrated to obtain the title compound (0.04 g) having the following physical data.

Mass data (ESI, Pos.): m/z 311 (M+H)⁺.

Example 78

5,6-dichloro-2-({1-[(3-phenyl-5-isoxazolyl)methyl]-4-piperidinyl}methyl)-1(2H)-isoquinolinone

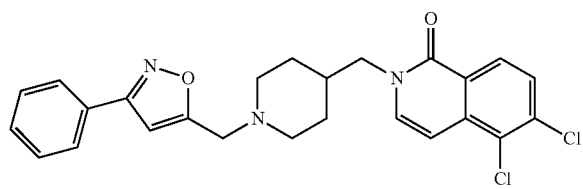 [SMILES: O=c1c2ccc(Cl)c(Cl)c2ccn1CC1CCN(Cc2cc(-c3ccccc3)no2)CC1]

The compound prepared in Example 77 (0.041 g), the compound prepared in Example 7 (0.026 g) and sodium triacetoxyborohydride (0.074 g) were suspended in dichloromethane (5 mL) and diisopropylethylamine (0.10 mL). The reaction mixture was stirred at room temperature overnight. The reaction mixture was diluted with dichloromethane and washed with a saturated aqueous sodium bicarbonate solution, dried over anhydrous magnesium sulfate and concentrated. The residue was purified by column chromatography on silica gel (ethyl acetate:hexane=3:1) to obtain the title compound (0.029 g) having the following physical data.

¹H NMR (CDCl₃): δ 8.28 (d, J=8.7 Hz, 1H), 7.82-7.76 (m, 2H), 7.52 (d, J=8.7 Hz, 1H), 7.48-7.41 (m, 3H), 7.13 (d, J=7.7 Hz, 1H), 6.84 (d, J=7.7 Hz, 1H), 6.47 (s, 1H), 3.88 (d, J=7.1 Hz, 2H), 3.72 (s, 2H), 3.01-2.94 (m, 2H), 2.16-2.06 (m, 2H), 1.98-1.87 (m, 1H), 1.74-1.66 (m, 2H), 1.50-1.38 (m, 2H);

Mass data (APCI, Pos.): m/z 468 (M+H)⁺.

Example 79

6-({1-[(3-phenyl-5-isoxazolyl)methyl]-4-piperidinyl}methyl)-1,6-dihydro-7H-pyrrolo[2,3-c]pyridin-7-one

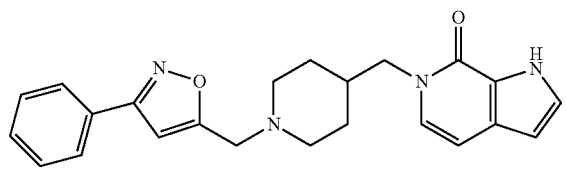 [SMILES: O=c1c2[nH]ccc2ccn1CC1CCN(Cc2cc(-c3ccccc3)no2)CC1]

According to the same procedures described in Examples 76→77→78, using the corresponding fused pyridinone instead of 5,6-dichloroisoquinolin-1(2H)-one, the title compound having the following physical data was obtained.

¹H NMR (CDCl₃): δ 9.96 (s, 1H), 7.84-7.76 (m, 2H), 7.49-7.41 (m, 3H), 7.25-7.21 (m, 1H), 6.85 (d, J=7.1 Hz, 1H), 6.52 (d, J=7.1 Hz, 1H), 6.78 (s, 1H), 6.39-6.35 (m, 1H), 3.93 (d, J=7.2 Hz, 2H), 3.72 (s, 2H), 3.02-2.95 (m, 2H), 2.16-2.06 (m, 2H), 1.99-1.87 (m, 1H), 1.75-1.65 (m, 2H), 1.52-1.38 (m, 2H);

Mass data (APCI, Pos.): m/z 389 (M+H)⁺.

Example 80

2-({1-[(3-phenyl-5-isoxazolyl)methyl]-4-piperidinyl}methyl)-1(2H)-isoquinolinone

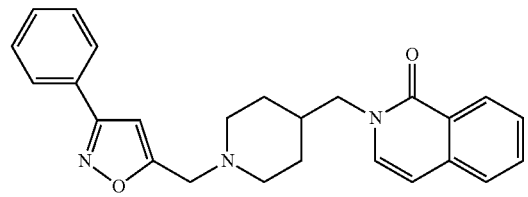 [SMILES: O=c1c2ccccc2ccn1CC1CCN(Cc2cc(-c3ccccc3)no2)CC1]

According to the same procedures described in Examples 76→77→78, using the corresponding fused pyridinone instead of 5,6-dichloroisoquinolin-1(2H)-one, the title compound having the following physical data was obtained.

¹H NMR (CDCl₃): δ 8.42 (d, J=8.2 Hz, 1H), 7.81-7.78 (m, 2H), 7.65-7.61 (m, 1H), 7.51-7.43 (m, 5H), 7.00 (d, J=7.7 Hz, 1H), 6.48-6.46 (m, 2H), 3.88 (d, J=7.1 Hz, 2H), 3.71 (s, 2H), 2.99-2.94 (m, 2H), 2.14-2.07 (m, 2H), 2.00-1.90 (m, 1H), 1.74-1.69 (m, 2H), 1.49-1.39 (m, 2H).

Mass data (APCI, Pos.): m/z 400 (M+H)⁺.

Example 81

4-chloro-7-hydrazino-3-phenylisoxazolo[4,5-d]pyridazine

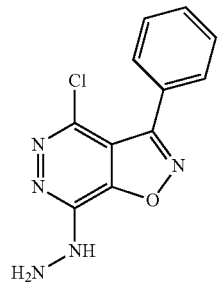 [SMILES: NNc1nnc(Cl)c2c(-c3ccccc3)noc12]

To 4,7-dichloro-3-phenylisoxazolo[4,5-d]pyridazine (25.5 g, Desimoni, G.; Et al. *Tetrahedron* 1967, 23, 681) in 1,4-dioxane (200 mL) and ethanol (50 mL) at 0° C. was added hydrazine (7.0 g) slowly. The reaction mixture was allowed to slowly warm to room temperature. After 20 hours, the reaction mixture was concentrated and the solid obtained was washed with water and filtered. The material was purified by column chromatography on silica gel (methanol:dichloromethane=5:95) to afford first the regioisomer of the title compound followed by the later eluting title compound (4.50 g) having the following physical data.
$^1$H NMR (DMSO-$d_6$): δ 9.33 (br s, 1H), 7.80 (d, J=7.0 Hz, 2H), 7.66-7.58 (m, 3H), 4.72 (br s, 2H);
Mass data (ESI, Pos.): m/z 262 (M+H)$^+$.

Example 82

4-chloro-3-phenylisoxazolo[4,5-d]pyridazine

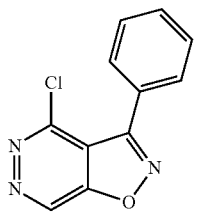 [SMILES: Clc1nncc2onc(-c3ccccc3)c12]

The compound prepared in Example 81 (4.40 g) was dissolved in benzene (500 mL)-ethanol (50 mL) and 1 mol/L aqueous sodium hydroxide (67.0 mL) was added. This mixture was cooled to 0° C. Oxygen was bubbled through the vigorously stirred mixture for 30 minutes. The mixture was separated and the aqueous portion was extracted with dichloromethane. The combined organics were washed with brine, dried over anhydrous magnesium sulfate and concentrated. The residue was purified by column chromatography on silica gel (hexane:ethyl acetate=4:1) to obtain the title compound (2.53 g) having the following physical data.
$^1$H NMR (CDCl$_3$): δ 9.71 (s, 1H), 7.83-7.80 (m, 2H), 7.67-7.57 (m, 3H).
Mass data (ESI, Pos.): m/z 232 (M+H)$^+$.

Example 83 tert-butyl 4-{[(3-phenylisoxazolo[4,5-d]pyridazin-4-yl)amino]methyl}-1-piperidinecarboxylate

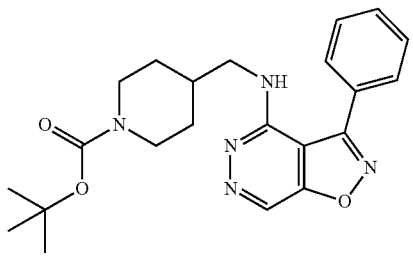 [SMILES: CC(C)(C)OC(=O)N1CCC(CNc2nncc3onc(-c4ccccc4)c23)CC1]

The compound prepared in Example 82 (202 mg), tert-butyl 4-(aminomethyl)piperidine-1-carboxylate (0.266 g) and triethylamine (0.607 mL) were combined in ethanol (1.5 mL) and heated at 80° C. for 17 hours. The reaction mixture cooled to room temperature, diluted with a saturated aqueous sodium bicarbonate solution and extracted with ethyl acetate. The combined organics were dried over anhydrous magnesium sulfate and concentrated. The residue was purified by column chromatography on silica gel (ethyl acetate:hexane=1:1 to 2:1) to obtain the title compound (316 mg) having the following physical data.
Mass data (ESI, Pos.): m/z 432 (M+Na)$^+$.

Example 84

3-phenyl-N-(4-piperidinylmethyl)isoxazolo[4,5-d]pyridazin-4-amine Hydrochloride

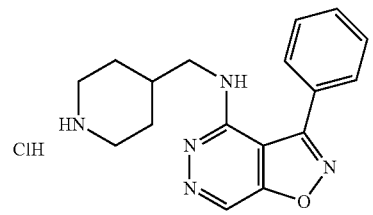 [SMILES: Cl ; c1ccc(-c2noc3cnnc(NCC4CCNCC4)c23)cc1]

According to the same procedure described in Example 77, using the compound obtained in Example 83 instead of the compound prepared in Example 76, the title compound having the following physical data was obtained.
$^1$H NMR (DMSO-$d_6$): δ 9.34 (s, 1H), 8.73 (br s, 1H), 8.54 (br s, 1H), 7.81-7.78 (m, 2H), 7.71-7.64 (m, 3H), 6.70 (br s, 1H), 3.49 (t, J=6.7 Hz, 2H), 3.31-3.25 (m, 2H), 2.84 (br q, J=11.7 Hz, 2H), 2.00 (m, 1 H), 1.90-1.83 (m, 2H), 1.45-1.34 (m, 2H);
Mass data (ESI, Pos.): m/z 310 (M+H)$^+$.

Example 85

3-phenyl-N-({1-[(3-phenyl-5-isoxazolyl)methyl]-4-piperidinyl}methyl)isoxazolo[4,5-d]pyridazin-4-amine

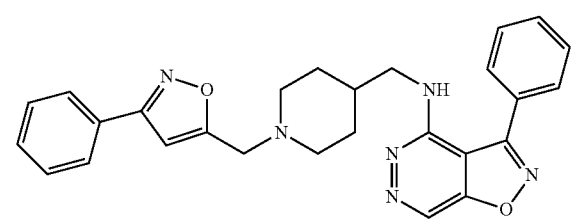 [SMILES: c1ccc(-c2cc(CN3CCC(CNc4nncc5onc(-c6ccccc6)c45)CC3)on2)cc1]

According to the same procedure described in Example 35, using the compound obtained in Example 84 instead of the compound obtained in Example 11 and the aldehyde obtained in Example 7 instead of 4-phenylthiophene-2-carbaldehyde, the title compound having the following physical data was obtained.
$^1$H NMR (CDCl$_3$): δ 9.14 (s, 1H), 7.82-7.80 (m, 2H), 7.72-7.70 (m, 2H), 7.66-7.61 (m, 3H), 7.48-7.44 (m, 3H), 6.49 (s, 1H), 4.97 (br t, J=5.1 Hz, 1H), 3.73 (s, 2H), 3.58 (t, J=5.9 Hz, 2H), 2.99-2.94 (m, 2H), 2.15-2.08 (m, 2H), 1.73-1.64 (m, 3H), 1.40-1.30 (m, 2H);
Mass data (APCI, Pos.): m/z 467 (M+H)$^+$.

Example 86

N-[(1-{[3-(4-chlorophenyl)-5-isoxazolyl]methyl}-4-piperidinyl)methyl]-3-phenylisoxazolo[4,5-d]pyridazin-4-amine

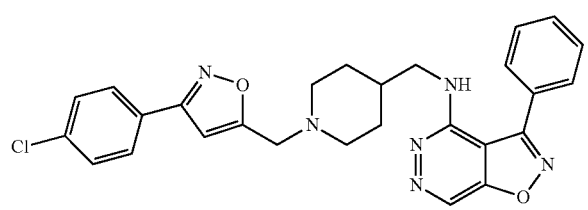 [SMILES: Clc1ccc(-c2cc(CN3CCC(CNc4nncc5onc(-c6ccccc6)c45)CC3)on2)cc1]

According to the same procedure described in Example 35, using the compound obtained in Example 84 instead of the compound obtained in Example 11 and 3-(4-chlorophenyl) isoxazole-5-carbaldehyde instead of 4-phenylthiophene-2-carbaldehyde, the title compound having the following physical data was obtained.

$^1$H NMR (CDCl$_3$): δ 9.14 (s, 1H), 7.76-7.69 (m, 4H), 7.67-7.61 (m, 3H), 7.45-7.42 (m, 2H), 6.46 (s, 1H), 4.97 (br t, J=5.5 Hz, 1H), 3.72 (s, 2H), 3.58 (t, J=6.3 Hz, 2H), 2.98-2.93 (m, 2H), 2.15-2.08 (m, 2H), 1.73-1.67 (m, 3H), 1.40-1.29 (m, 2H);

Mass data (ESI, Pos.): m/z 523 (M+Na)$^+$.

Example 87

N-[(1-{[3-(3-chlorophenyl)-5-isoxazolyl]methyl}-4-piperidinyl)methyl]-3-phenylisoxazolo[4,5-d]pyridazin-4-amine

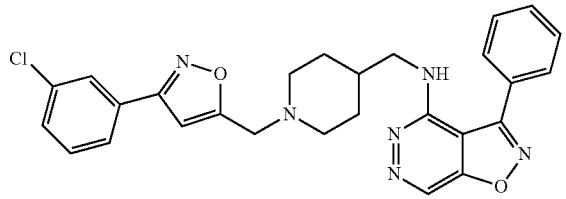 [SMILES: Clc1cccc(-c2cc(CN3CCC(CNc4nncc5onc(-c6ccccc6)c45)CC3)on2)c1]

According to the same procedure described in Example 35, using the compound obtained in Example 84 instead of the compound obtained in Example 11 and 3-(3-chlorophenyl) isoxazole-5-carbaldehyde instead of 4-phenylthiophene-2-carbaldehyde, the title compound having the following physical data was obtained.

$^1$H NMR (CDCl$_3$): δ 9.14 (s, 1H), 7.80 (m, 1H), 7.72-7.68 (m, 3H), 7.67-7.61 (m, 3H), 7.44-7.38 (m, 2H), 6.48 (s, 1H), 4.97 (br t, J=5.1 Hz, 1H), 3.73 (s, 2H), 3.58 (t, J=6.3 Hz, 2H), 2.98-2.93 (m, 2H), 2.15-2.08 (m, 2H), 1.73-1.65 (m, 3H), 1.40-1.30 (m, 2H);

Mass data (APCI, Pos.): m/z 501 (M+H)$^+$.

Example 88

N-[(1-{[3-(2-chlorophenyl)-5-isoxazolyl]methyl}-4-piperidinyl)methyl]-3-phenylisoxazolo[4,5-d]pyridazin-4-amine

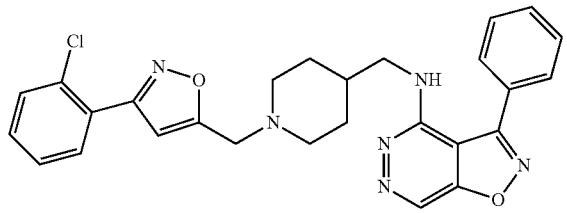 [SMILES: Clc1ccccc1-c1cc(CN2CCC(CNc3nncc4onc(-c5ccccc5)c34)CC2)on1]

According to the same procedure described in Example 35, using the compound obtained in Example 84 instead of the compound obtained in Example 11 and 3-(2-chlorophenyl) isoxazole-5-carbaldehyde instead of 4-phenylthiophene-2-carbaldehyde, the title compound having the following physical data was obtained.

$^1$H NMR (CDCl$_3$): δ 9.13 (s, 1H), 7.76-7.69 (m, 3H), 7.68-7.61 (m, 3H), 7.49 (m, 1H), 7.42-7.34 (m, 2H), 6.64 (s, 1H), 4.98 (br t, J=5.5 Hz, 1H), 3.76 (s, 2H), 3.58 (t, J=6.3 Hz, 2H), 3.00-2.95 (m, 2H), 2.16-2.09 (m, 2H), 1.74-1.66 (m, 3H), 1.41-1.30 (m, 2H);

Mass data (ESI, Pos.): m/z 523 (M+Na)$^+$.

Example 89

3-phenyl-4-(4-piperidinylmethoxy)isoxazolo[4,5-d]pyridazine

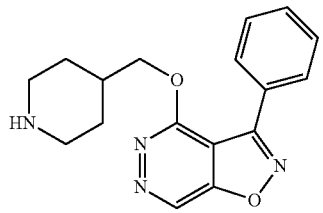 [SMILES: c1ccc(-c2noc3cnnc(OCC4CCNCC4)c23)cc1]

To sodium hydride (95% dispersion in mineral oil, 0.043 g) in N,N-dimethylformamide (6 mL) at 0° C. was added piperidin-4-ylmethanol (0.206 g). After stirring for 30 minutes, the compound prepared in Example 82 was added. The ice bath was removed and the reaction mixture was stirred at room temperature for two hours. The reaction mixture was then diluted with saturated a sodium bicarbonate solution and extracted with dichloromethane. The organics were dried over anhydrous magnesium sulfate and concentrated. The residue was purified by column chromatography on silica gel (methanol:concentrated aqueous ammonia:dichloromethane=6:1:94) to obtain the title compound (0.20 g) having the following physical data.

$^1$H NMR (DMSO-d$_6$): δ 9.73 (s, 1H), 8.08-8.05 (m, 2H), 7.67-7.58 (m, 3H), 4.48 (d, J=6.3 Hz, 2H), 2.97-2.92 (m, 2H), 2.51-2.43 (m, 2H), 2.15 (br s, 1H), 1.91 (m, 1H), 1.67-1.61 (m, 2H), 1.24-1.13 (m, 2H);

Mass data (ESI, Pos.): m/z 311 (M+H)$^+$.

Example 90

4-[(1-{[3-(2-chlorophenyl)-5-isoxazolyl]methyl}-4-piperidinyl)methoxy]-3-phenylisoxazolo[4,5-d]pyridazine

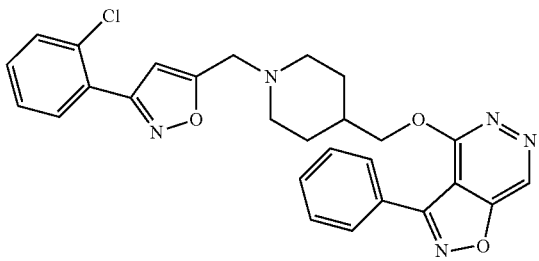 [SMILES: Clc1ccccc1-c1cc(CN2CCC(COc3nncc4onc(-c5ccccc5)c34)CC2)on1]

According to the same procedure described in Example 35, using the compound obtained in Example 89 instead of the compound obtained in Example 11 and 3-(2-chlorophenyl)isoxazole-5-carbaldehyde instead of 4-phenylthiophene-2-carbaldehyde, the title compound having the following physical data was obtained.

$^1$H NMR (DMSO-$d_6$): δ 9.74 (s, 1H), 8.07-8.03 (m, 2H), 7.74-7.47 (m, 7H), 6.83 (s, 1H), 4.54-4.49 (m, 2H), 3.78 (br s, 2H), 3.00-2.87 (m, 2H), 2.18-2.06 (m, 2H), 1.91-1.68 (m, 3H), 1.49-1.36 (m, 2H);

Mass data (ESI, Pos.): m/z 502 (M+H)$^+$.

Example 91

3-phenyl-4-({1-[(3-phenyl-5-isoxazolyl)methyl]-4-piperidinyl}methoxy)isoxazolo[4,5-d]pyridazine

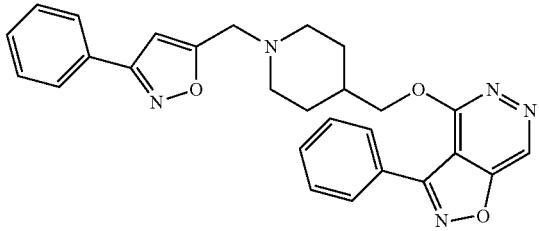 [SMILES: c1ccc(-c2cc(CN3CCC(COc4nncc5onc(-c6ccccc6)c45)CC3)on2)cc1]

According to the same procedure described in Example 35, using the compound obtained in Example 89 instead of the compound obtained in Example 11 and the compound obtained in Example 7 instead of 4-phenylthiophene-2-carbaldehyde, the title compound having the following physical data was obtained.

$^1$H NMR (CDCl$_3$): δ 9.40 (s, 1H), 8.09-8.06 (m, 2H), 7.83-7.80 (m, 2H), 7.60-7.51 (m, 3H), 7.49-7.42 (m, 3H), 6.50 (s, 1H), 4.61 (d, J=6.3 Hz, 2H), 3.76 (s, 2H), 3.03-2.99 (m, 2H), 2.22-2.15 (m, 2H), 1.93 (m, 1H), 1.85-1.79 (m, 2H), 1.56-1.46 (m, 2H);

Mass data (ESI, Pos.): m/z 468 (M+H)$^+$.

Example 92

4-anilino-2-(methylthio)-5-pyrimidinecarboxylic Acid

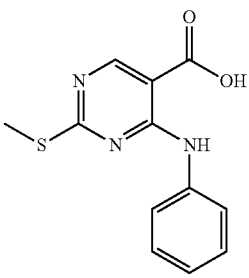 [SMILES: CSc1ncc(C(=O)O)c(Nc2ccccc2)n1]

A solution of ethyl 2-(methylthio)-4-(phenylamino)pyrimidine-5-carboxylate (4.0 g, prepared according to the reported preparation in Barvian, M.; et al. *J. Med. Chem.* 2000, 43, 4606) in ethanol (50 mL) was treated with 2 N lithium hydroxide (50 mL) at room temperature for 16 hours. The reaction mixture was washed with ether and then brought to pH 6 via the addition of 1 N hydrochloric acid. The resulting precipitate was collected by filtration, azeotroped with toluene and dried under vacuum to obtain the title compound (2.2 g) having the following physical data.

$^1$H NMR (DMSO-$d_6$): δ 10.62 (br s, 1H), 8.70 (s, 1H), 7.69 (d, J=7.8 Hz, 2H), 7.39 (t, J=7.8 Hz, 2H), 7.14 (t, J=7.8 Hz, 1H), 2.51 (s, 3H);

Mass data (APCI, Pos.): m/z 262 (M+H)$^+$.

Example 93

4-anilino-2-(methylthio)-5-pyrimidinecarboxamide

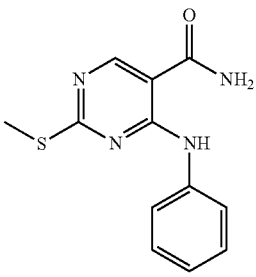 [SMILES: CSc1ncc(C(N)=O)c(Nc2ccccc2)n1]

The compound prepared in Example 92 (2.15 g), 1-ethyl-3-(3'-dimethylaminopropyl)carbodiimide (1.74 g) and 1-hydroxybenzotriazole hydrate (1.39 g) were combined in N,N-dimethylformamide (20 mL). The mixture was stirred for 2 hours at room temperature and then concentrated aqueous ammonium hydroxide (15 mL) was added slowly. The reaction was stirred for one hour and then was diluted with ethyl acetate and sequentially washed with water and brine. The organics were dried over anhydrous magnesium sulfate and concentrated to obtain the title compound (2.06 g) having the following physical data.

$^1$H NMR (DMSO-$d_6$): δ 11.51 (s, 1H), 8.72 (s, 1H), 8.29 (s, 1H), 7.74 (s, 1H), 7.67 (d, J=8.0 Hz, 2H), 7.37 (t, J=8.0 Hz, 2H), 7.11 (t, J=8.0 Hz, 1H), 2.49 (s, 3H).

Mass data (APCI, Pos.): m/z 261 (M+H)$^+$.

Example 94

4-anilino-2-[({1-[(3-phenyl-5-isoxazolyl)methyl]-4-piperidinyl}methyl)amino]-5-pyrimidinecarboxamide

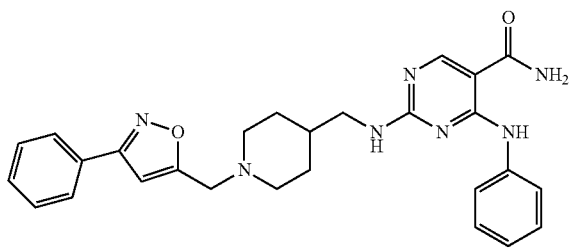 [SMILES: NC(=O)c1cnc(NCC2CCN(Cc3cc(-c4ccccc4)no3)CC2)nc1Nc1ccccc1]

3-Chloroperoxybenzoic acid (195 mg) was added to a 0° C. suspension of the compound prepared in Example 93 (100 mg) in dichloromethane (4 mL). The reaction was stirred one hour at room temperature. Diisopropylethylamine (0.669 mL) and the compound prepared in Example 9 (198 mg) were added and the mixture was stirred at room temperature for 18 hours. The reaction was diluted with ethyl acetate and sequentially washed with a saturated sodium bicarbonate solution and brine. The organics were dried over magnesium sulfate and concentrated. The residue was purified by column chromatography on silica gel (concentrated aqueous ammonia: methanol:ethyl acetate=0.1:0.9:25) to obtain the title compound (51 mg) having the following physical data.

$^1$H NMR (CDCl$_3$): δ 11.04 (s, 1H), 8.25 (s, 1H), 7.81-7.78 (m, 2H), 7.72-7.64 (m, 2H), 7.45-7.43 (m, 3H), 7.30 (t, J=7.5 Hz, 2H), 7.07 (t, J=7.5 Hz, 1H), 6.48 (s, 1H), 5.56-5.46 (m, 3H), 3.72 (s, 2H), 3.36-3.33 (m, 2H), 2.99-2.96 (m, 2H), 2.15-2.08 (m, 2H), 1.80-1.77 (m, 2H), 1.73-1.64 (m, 1H), 1.43-1.33 (m, 2H);

Mass data (APCI, Pos.): m/z 484 (M+H)$^+$.

Example 95 methyl 6-bromo-3-hydroxy-1-oxo-4-phenyl-2-({1-[(3-phenyl-5-isoxazolyl)methyl]-4-piperidinyl}methyl)-1,2,3,4-tetrahydro-3-isoquinolinecarboxylate

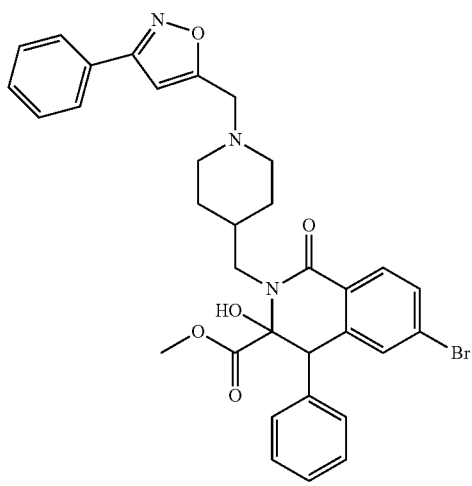 [SMILES: COC(=O)C1(O)C(c2ccccc2)c2cc(Br)ccc2C(=O)N1CC1CCN(Cc2cc(-c3ccccc3)no2)CC1]

Methyl 6-bromo-1-oxo-4-phenyl-1H-isochromene-3-carboxylate (0.319 g, prepared according to the reported preparation in US 2005/0148624) and the compound prepared in Example 9 (0.458 g) were suspended in methanol (10 mL) and diisopropylethylamine (0.772 mL) was added. Tetrahydrofuran (5 mL) was added and the reaction mixture was heated at 60° C. overnight. The reaction mixture was then cooled to room temperature and concentrated. The reaction mixture was partitioned between ethyl acetate and a saturated aqueous sodium bicarbonate solution. The organics were washed with brine, dried over anhydrous magnesium sulfate and concentrated. The residue was purified by column chromatography on silica gel (ethyl acetate) to obtain the title compound (0.560 g) having the following physical data.

$^1$H NMR (CDCl$_3$): δ 8.05 (d, J=8.4 Hz, 1H), 7.83-7.77 (m, 2H), 7.56-7.51 (m, 1H), 7.48-7.42 (m, 3H), 7.40-7.33 (m, 3H), 7.23-7.18 (m, 2H), 7.10 (s, 1H), 6.46 (s, 1H), 4.73 (s, 1H), 3.74 (s, 3H), 3.67 (s, 2H), 3.62-3.58 (m, 2H), 2.97-2.89 (m, 1H), 2.86-2.78 (m, 1H), 2.04-1.91 (m, 2H), 1.74-1.91 (m, 1H), 1.40-1.30 (m, 2H), 1.24-1.16 (m, 2H).

Example 96 methyl 6-bromo-1-oxo-4-phenyl-2-({1-[(3-phenyl-5-isoxazolyl)methyl]-4-piperidinyl}methyl)-1,2-dihydro-3-isoquinolinecarboxylate

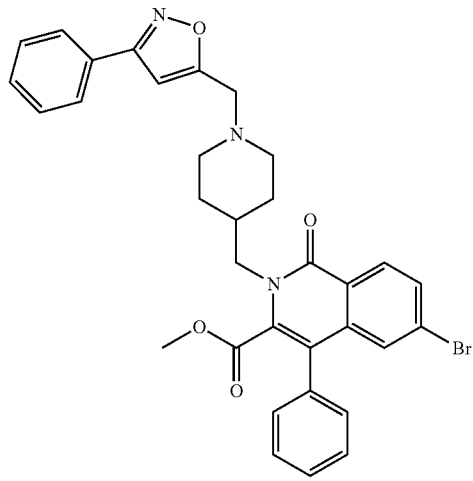 [SMILES: COC(=O)c1c(-c2ccccc2)c2cc(Br)ccc2c(=O)n1CC1CCN(Cc2cc(-c3ccccc3)no2)CC1]

p-Toluenesulfonic acid monohydrate (0.070 g) was added to a suspension of the compound prepared in Example 95 (0.56 g) in toluene (20 mL). The reaction mixture was heated at reflux under Dean-Stark conditions overnight. The reaction mixture was then cooled to room temperature and partitioned between dichloromethane and a saturated aqueous sodium bicarbonate solution. The combined organics were dried over anhydrous magnesium sulfate and concentrated. The residue was purified by column chromatography on silica gel (ethyl acetate:hexane=3:2) to obtain the title compound (0.35 g) having the following physical data.

¹H NMR (CDCl₃): δ 8.34 (d, J=8.6 Hz, 1H), 7.82-7.76 (m, 2H), 7.66-7.60 (m, 1H), 7.48-7.41 (m, 6H), 7.36-7.32 (m, 1H), 7.31-7.27 (m, 2H), 6.46 (s, 1H), 4.03-3.94 (m, 2H), 3.71 (s, 2H), 3.50 (s, 3H), 2.99-2.91 (m, 2H), 2.14-2.05 (m, 2H), 1.96-1.85 (m, 1H), 1.72-1.62 (m, 2H), 1.48-1.35 (m, 2H);

Mass data (APCI, Pos.): m/z 612 (M+H)⁺.

Example 97 methyl 1-oxo-4-phenyl-2-({1-[(3-phenyl-5-isoxazolyl)methyl]-4-piperidinyl}methyl)-1,2-dihydro-3-isoquinolinecarboxylate

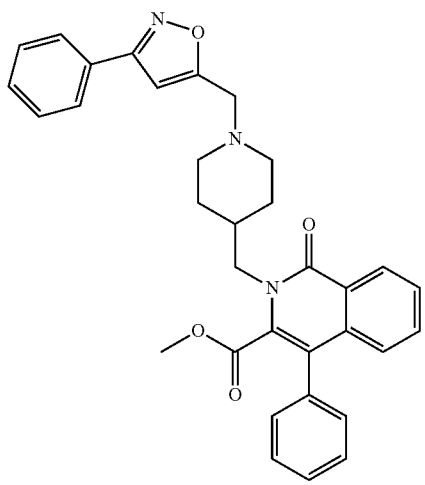 [SMILES: COC(=O)c1c(-c2ccccc2)c2ccccc2c(=O)n1CC1CCN(Cc2cc(-c3ccccc3)no2)CC1]

The compound prepared in Example 96 (0.050 g) was suspended in dry tetrahydrofuran (10 mL) and cooled to −78° C. n-Butyl lithium (2.5 mol/L solution in hexane, 0.03 mL) was added dropwise and the reaction was allowed to stirred at −78° C. for 5 minutes. A saturated aqueous ammonium chloride solution was added and the reaction mixture was warmed to room temperature. The mixture was partitioned between a saturated aqueous ammonium chloride solution and ethyl acetate. The organics were washed with brine, dried over anhydrous magnesium sulfate and concentrated. The residue was purified by column chromatography on silica gel to obtain the title compound (0.015 g) having the following physical data.

¹H NMR (CDCl₃): δ 8.50 (d, J=7.2 Hz, 1H) 7.85-7.75 (m, 2H), 7.61-7.50 (m, 2H), 7.49-7.37 (m, 6H), 7.34-7.30 (m, 2H), 7.23-7.19 (m, 1H), 6.47 (s, 1H), 4.08-3.96 (m, 2H), 3.70 (s, 2H), 3.45 (s, 3H), 3.00-2.90 (m, 2H), 2.16-2.05 (m 2H), 2.00-1.86 (m, 1H), 1.75-1.63 (m, 2H), 1.51-1.35 (m, 2H);

Mass data (APCI, Pos.): m/z 534 (M+H)⁺.

Example 98 methyl 6-chloro-1-oxo-4-phenyl-2-({1-[(3-phenyl-5-isoxazolyl)methyl]-4-piperidinyl}methyl)-1,2-dihydro-3-isoquinolinecarboxylate

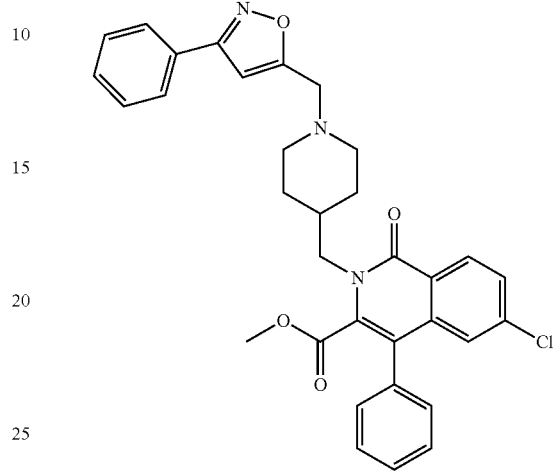

The compound prepared in Example 96 (0.10 g) was suspended in dry tetrahydrofuran (10 mL).

The reaction mixture was cooled to −78° C. and tert-butyl lithium (1.7 mol/L solution in pentane, 0.21 mL) added dropwise. The reaction mixture was stirred at −78° C. for 10 minutes and then hexachloroethane (0.08 g) was added in one portion and the reaction mixture allowed to warm to room temperature slowly. The reaction mixture was poured into a saturated aqueous ammonium chloride solution and extracted with ethyl acetate. The organics were washed with brine, dried over anhydrous magnesium sulfate and concentrated. The residue was purified by column chromatography on silica gel to obtain the title compound (0.032 g) having the following physical data.

¹H NMR (CDCl₃): δ 8.42 (d, J=8.6 Hz, 1H), 7.81-7.75 (m, 2H), 7.50-7.41 (m, 7H), 7.31-7.27 (m, 2H), 7.19-7.16 (m, 1H), 6.47 (s, 1H), 4.03-3.95 (m, 2H), 3.71 (s, 2H), 3.45 (s, 3H), 3.00-2.91 (m, 2H), 2.15-2.05 (m, 2H), 1.98-1.85 (m, 1H), 1.73-1.61 (m, 2H), 1.49-1.37 (m, 2H);

Mass data (APCI, Pos.): m/z 568 (M+H)⁺.

Example 101

4-Amino-5-cyano-6-ethoxy-N-((1-((2-phenylthiazol-5-yl)methyl)piperidin-4-yl)methyl)picolinamide

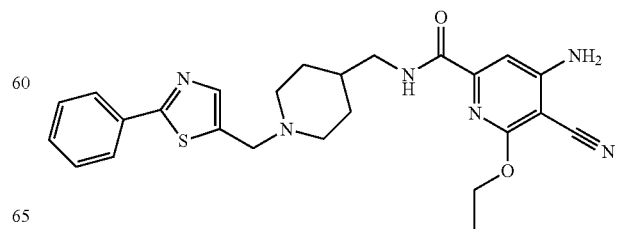

The compound prepared in Example 226 (0.050 g), 2-phenylthiazole-5-carbaldehyde (0.033 g), sodium triacetoxyborohydride (0.141 g) and triethylamine (0.093 mL) were suspended in 1,2-dichloroethane (5 mL) and stirred at room temperature overnight. The reaction mixture was partitioned between saturated aqueous sodium bicarbonate and dichloromethane. The organics were dried, magnesium sulfate and concentrated under reduced pressure to afford the crude material, which was purified by flash column chromatography (eluant: 50-100% ethyl acetate/hexane (0.5% triethylamine) to furnish the title compound (0.044 g) having the following physical data.

$^1$H NMR (CDCl$_3$): δ 7.94-7.90 (m, 2H), 7.83-7.77 (m, 1H), 7.61 (s, 1H), 7.44-7.40 (m, 3H), 7.19 (s, 1H), 5.10 (s, 2H), 4.43 (q, J=7.1 Hz, 2H), 3.74 (s, 2H), 3.34 (t, J=6.5 Hz, 2H), 3.01-2.93 (m, 2H), 2.10-2.00 (m, 2H), 1.77-1.68 (m, 2H), 1.67-1.57 (m, 1H), 1.44 (t, J=7.1 Hz, 3H), 1.41-1.31 (m, 2H);

Mass data (APCI, Pos.): m/z 477 (M+H)$^+$.

Example 102

4-Amino-5-cyano-6-ethoxy-N-((1-((4-methyl-2-phenylthiazol-5-yl)methyl)piperidin-4-yl)methyl)picolinamide

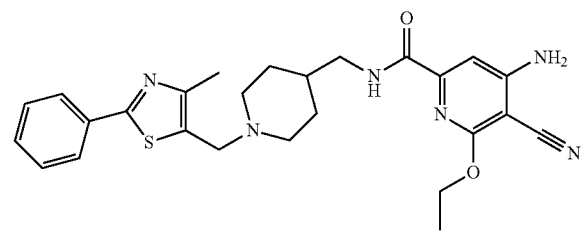 [SMILES: CCOc1nc(C(=O)NCC2CCN(Cc3sc(-c4ccccc4)nc3C)CC2)cc(N)c1C#N]

According to the same procedure described in Example 101, using the corresponding aldehyde instead of 2-phenylthiazole-5-carbaldehyde, the title compound having the following physical data was obtained.

$^1$H NMR (CDCl$_3$): δ 7.91-7.87 (m, 2H), 7.83-7.77 (m, 1H), 7.44-7.36 (m, 3H), 7.18 (s, 1H), 5.09 (s, 2H), 4.43 (q, J=7.1 Hz, 2H), 3.64 (s, 2H), 3.34 (t, J=6.5 Hz, 2H), 3.01-2.93 (m, 2H), 2.41 (s, 3H), 2.09-2.00 (m, 2H), 1.76-1.68 (m, 2H), 1.66-1.60 (m, 1H), 1.44 (t, J=7.1 Hz, 3H), 1.40-1.31 (m, 2H);

Mass data (APCI, Pos.): m/z 491 (M+H)$^+$.

Example 103

4-Amino-5-cyano-N-((1-(4-((dimethylamino)methyl)-2-phenylthiazol-5-yl)methyl)piperidin-4-yl)methyl)-6-ethoxypicolinamide

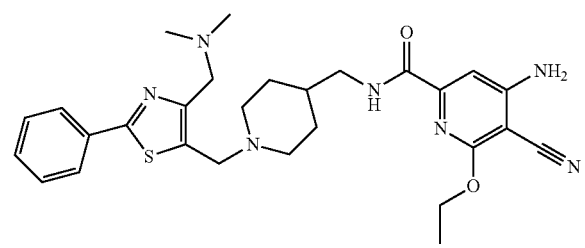 [SMILES: CCOc1nc(C(=O)NCC2CCN(Cc3sc(-c4ccccc4)nc3CN(C)C)CC2)cc(N)c1C#N]

According to the same procedure described in Example 101, using the corresponding aldehyde instead of 2-phenylthiazole-5-carbaldehyde, the title compound having the following physical data was obtained.

$^1$H NMR (CDCl$_3$): δ 7.95-7.91 (m, 2H), 7.83-7.78 (m, 1H), 7.42-7.37 (m, 3H), 7.19 (s, 1H), 5.10 (s, 2H), 4.43 (q, J=7.1 Hz, 2H), 3.73 (s, 2H), 3.57 (s, 2H), 3.35 (t, J=6.55 Hz, 2H), 3.02-2.95 (m, 2H), 2.30 (s, 6H), 2.10-2.00 (M, 2H), 1.76-1.69 (m, 2H), 1.68-1.58 (m, 1H), 1.44 (t, J=7.1 Hz, 3H), 1.41-1.32 (m, 2H);

Mass data (APCI, Pos.): m/z 534 (M+H)$^+$.

Example 104

4-Amino-5-cyano-6-ethoxy-N-((1-(3-(pyridin-2-yl)isoxazol-5-yl)methyl)piperidin-4-yl)methyl)picolinamide

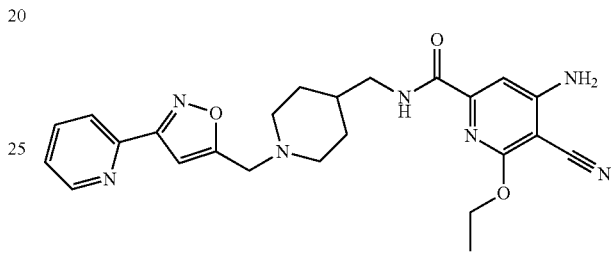

According to the same procedure described in Example 101, using the corresponding aldehyde instead of 2-phenylthiazole-5-carbaldehyde, the title compound having the following physical data was obtained.

$^1$H NMR (CDCl$_3$): δ 8.68 (d, J=4.3 Hz, 1H), 8.07 (d, J=7.9 Hz, 1H), 7.82-7.76 (m, 2H), 7.37-7.32 (m, 1H), 7.18 (s, 1H), 6.81 (s, 1H), 5.08 (s, 2H), 4.43 (q, J=7.1 Hz, 2H), 3.77 (s, 2H), 3.34 (t, J=6.5 Hz, 2H), 3.02-2.95 (m, 2H), 2.19-2.10 (m, 2H), 1.77-1.70 (m, 2H), 1.63-1.57 (m, 1H), 1.48-1.33 (m, 5H);

Mass data (APCI, Pos.): m/z 462 (M+H)$^+$.

Example 105

4-Amino-5-cyano-6-ethoxy-N-((1((2-phenyl-1H-imidazol-4-yl)methyl)piperidin-4-yl) methyl)picolinamide

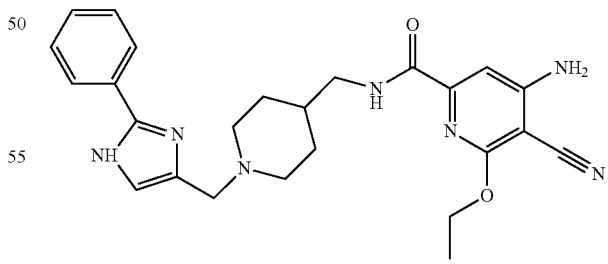

According to the same procedure described in Example 101, using the corresponding aldehyde instead of 2-phenylthiazole-5-carbaldehyde, the title compound having the following physical data was obtained.

$^1$H NMR (CDCl$_3$) δ 9.52 (s, 1H), 9.30 (s, 1H), 7.86-7.77 (m, 3H), 7.48-7.31 (m, 3H), 7.19 (s, 1H), 6.98 (s, 1H), 5.14 (s, 2H), 4.43 (q, J=7.1 Hz, 2H), 3.61-3.52 (m, 2H), 3.38-3.29 (m,

2H), 3.11-2.88 (m, 2H), 2.09-1.93 (m, 2H), 1.78-1.55 (m, 3H), 1.43- (t, J=7.1 Hz, 3H), 1.38-1.28 (m, 2H);

Mass data (APCI, Pos.): m/z 460 (M+H)+.

Example 106

4-Amino-5-cyano-6-ethoxy-N-((1-((1-methyl-2-phenyl-1H-imidazol-4-yl)methyl)piperidin-4-yl)methyl)picolinamide

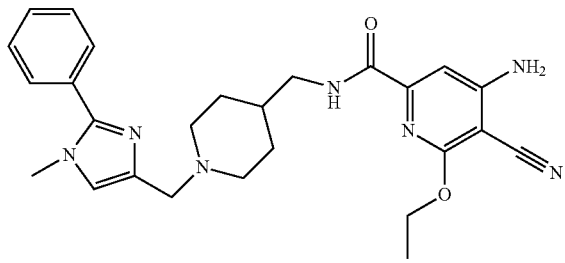 [SMILES: CCOc1nc(C(=O)NCC2CCN(Cc3cn(C)c(-c4ccccc4)n3)CC2)cc(N)c1C#N]

According to the same procedure described in Example 101, using the corresponding aldehyde instead of 2-phenylthiazole-5-carbaldehyde, the title compound having the following physical data was obtained.

1H NMR (CDCl3): δ 7.84-7.79 (m, 1H), 7.63-7.57 (m, 2H), 7.48-7.36 (m, 3H), 7.24 (s, 1H), 6.88 (s, 1H), 5.36 (s, 2H), 4.424 (q, J=7.1 Hz, 2H), 3.70 (s, 3H), 3.54 (s, 2H), 3.33 (t, J=6.5 Hz, 2H), 3.14-3.02 (m, 2H), 2.14-2.01 (m, 2H), 1.77-1.67 (m, 2H), 1.65-1.54 (m, 1H), 1.48-1.32 (m, 5H);

Mass data (APCI, Pos.): m/z 474 (M+H).

Example 107

4-Amino-5-cyano-6-ethoxy-N-((1-((1-methyl-2-phenyl-1H-imidazol-5-yl)methyl)piperidin-4-yl)methyl)picolinamide

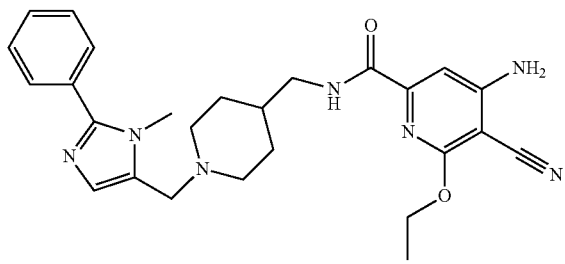 [SMILES: CCOc1nc(C(=O)NCC2CCN(Cc3cnc(-c4ccccc4)n3C)CC2)cc(N)c1C#N]

According to the same procedure described in Example 101, using the corresponding aldehyde instead of 2-phenylthiazole-5-carbaldehyde, the title compound having the following physical data was obtained.

1H NMR (CDCl3): δ 7.85-7.77 (m, 1H), 7.65-7.58 (m, 2H), 7.50-7.35 (m, 3H), 7.23 (s, 1H), 6.96 (s, 1H), 5.27 (s, 2H), 4.43 (q, J=7.1 Hz, 2H), 3.71 (s, 3H), 3.47 (s, 2H), 3.33 (t, J=6.6 Hz, 2H), 2.98-2.89 (m, 2H), 2.02-1.91 (m, 2H), 1.77-1.67 (m, 2H), 1.66-1.56 (m, 1H), 1.44 (t, J=7.1 Hz, 3H), 1.36-1.23 (m, 2H);

Mass data (APCI, Pos.): m/z 474 (M+H).

Example 108 tert-Butyl 2-(5-((4-amino-5-cyano-6-ethoxypicolinamido)methyl)piperidin-1-yl)methyl)-3-phenyl-1H-pyrazol-1-yl)ethylcarbamate

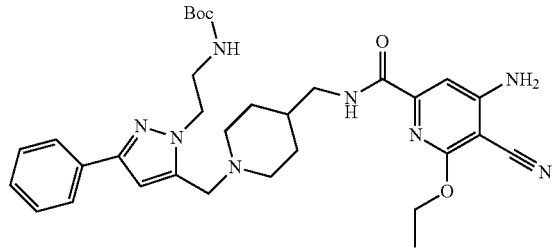 [SMILES: CCOc1nc(C(=O)NCC2CCN(Cc3cc(-c4ccccc4)nn3CCNC(=O)OC(C)(C)C)CC2)cc(N)c1C#N]

According to the same procedure described in Example 101, using the corresponding aldehyde instead of 2-phenylthiazole-5-carbaldehyde, the title compound having the following physical data was obtained.

1H NMR (CDCl3): δ 7.85-7.74 (m, 3H), 7.38 (t, J=7.5 Hz, 2H), 7.32-7.28 (m, 1H), 7.19 (s, 1H), 6.42 (s, 1H), 5.57 (s, 1H), 5.12 (s, 2H), 4.42 (q, J=7.1 Hz, 2H), 4.33-4.26 (m, 2H), 3.66-3.58 (m, 2H), 3.48 (s, 2H), 3.37-3.29 (m, 2H), 2.98-2.90 (m, 2H), 2.07-1.98 (m, 2H), 1.77-1.67 (m, 2H), 1.67-1.59 (m, 1H), 1.47-1.31 (m, 14H);

Mass data (APCI, Pos.): m/z 603 (M+H)+.

Example 109

4-amino-5-cyano-6-ethoxy-N-((1-((5-(pyridin-2-yl)-1,3,4-thiadiazol-2-yl)methyl)piperidin-4-yl) methyl)picolinamide

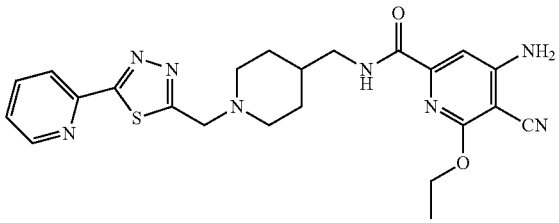 [SMILES: CCOc1nc(C(=O)NCC2CCN(Cc3nnc(-c4ccccn4)s3)CC2)cc(N)c1C#N]

According to the same procedure described in Example 101, using the corresponding aldehyde instead of 2-phenylthiazole-5-carbaldehyde, the title compound having the following physical data was obtained.

1H NMR (CDCl3): δ 8.65 (d, J=3.1 Hz, 1H), 8.33 (d, J=7.8 Hz, 1H), 7.87-7.80 (m, 2H), 7.40-7.37 (m, 1H), 7.23 (s, 1H), 5.21 (s, 2H), 4.44 (q, J=7.0 Hz, 2H), 3.98 (s, 2H), 3.35 (t, J=6.3 Hz, 2H), 3.01 (bd, J=11.0, 2H), 2.23 (t, J=11.7 Hz, 2H), 1.74 (bd, J=12.5 Hz, 2H), 1.68-1.62 (m, 1H), 1.45 (t, J=7.0 Hz, 3H), 1.42-1.35 (m, 2H).

Mass data (ESI, Pos.): m/z 501 (M+Na)+.

Example 110

4-amino-5-cyano-6-ethoxy-N-((1-((2-(pyrimidin-2-yl)thiazol-5-yl)methyl)piperidin-4-yl)methyl)picolinamide

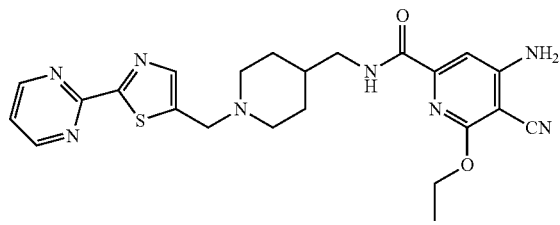 [SMILES: CCOc1nc(C(=O)NCC2CCN(Cc3cnc(-c4ncccn4)s3)CC2)cc(N)c1C#N]

According to the same procedure described in Example 101, using the corresponding aldehyde instead of 2-phenylthiazole-5-carbaldehyde, the title compound having the following physical data was obtained.

$^1$H NMR (CDCl$_3$): δ 8.83 (d, J=5.5 Hz, 2H), 7.81-7.79 (m, 2H), 7.29 (t, J=4.7 Hz, 1H), 7.19 (s, 1H), 5.12 (s, 2H), 4.44 (q, J=7.0 Hz, 2H), 3.79 (s, 2H), 3.34 (t, J=7.0 Hz, 2H), 2.97 (d, J=11.7 Hz, 2H), 2.11-2.05 (m, 2H), 1.72 (d, J=11.7 Hz, 2H), 1.67-1.57 (m, 1H), 1.45 (t, J=7.0 Hz, 3H), 1.42-1.32 (m, 2H);

Mass data (ESI, Pos.): m/z 501 (M+Na)$^+$.

Example 111

4-amino-5-cyano-6-ethoxy-N-((1-((2-(4-fluorophenyl)thiazol-5-yl)methyl)piperidin-4-yl)methyl)picolinamide

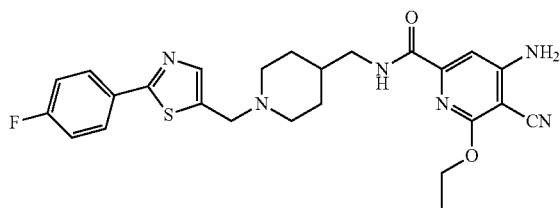 [SMILES: CCOc1nc(C(=O)NCC2CCN(Cc3cnc(-c4ccc(F)cc4)s3)CC2)cc(N)c1C#N]

According to the same procedure described in Example 101, using the corresponding aldehyde instead of 2-phenylthiazole-5-carbaldehyde, the title compound having the following physical data was obtained.

$^1$H NMR (DMSO-d$_6$): δ 8.45 (t, J=6.3 Hz, 1H), 7.97-7.94 (m, 2H), 7.71 (s, 1H), 7.35-7.26 (m, 4H), 7.03 (s, 1H), 4.47 (q, J=7.0 Hz, 2H), 3.71 (s, 2H), 3.16 (t, J=5.5 Hz, 2H), 2.86 (d, J=11 Hz, 2H), 1.96 (t, J=11.7 Hz, 2H), 1.62-1.51 (m, 3H), 1.31 (t, J=7.0 Hz, 3H), 1.23-1.13 (m, 2H);

Mass data (ESI, Pos.): m/z 517 (M+Na)$^+$.

Example 112

4-amino-5-cyano-6-ethoxy-N-((1-((2-(3-fluorophenyl)thiazol-5-yl)methyl)piperidin-4-yl) methyl)picolinamide

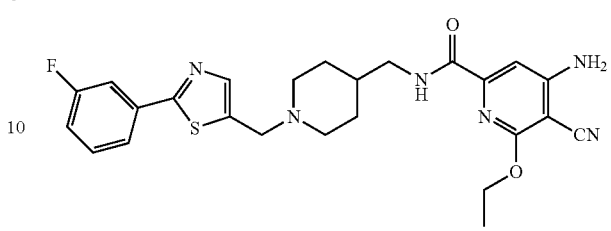

According to the same procedure described in Example 101, using the corresponding aldehyde instead of 2-phenylthiazole-5-carbaldehyde, the title compound having the following physical data was obtained.

$^1$H NMR (DMSO-d$_6$): δ 8.45 (t, J=6.3 Hz, 1H), 7.76 (s, 1H), 7.74-7.69 (m, 2H), 7.57-7.51 (m, 1H), 7.34-7.29 (m, 3H), 7.03 (s, 1H), 4.47 (q, J=7.0 Hz, 2H), 3.73 (s, 2H), 3.16 (t, J=5.5 Hz, 2H), 2.86 (d, J=11.0 Hz, 2H), 1.96 (t, J=11.7 Hz, 2H), 1.62-1.51 (m, 3H), 1.31 (t, J=7.0 Hz, 3H), 1.23-1.13 (m, 2H);

Mass data (ESI, Pos.): m/z 517 (M+Na)$^+$.

Example 113

4-amino-5-cyano-6-ethoxy-N-((1-((2-(2-fluorophenyl)thiazol-5-yl)methyl)piperidin-4-yl)methyl)picolinamide

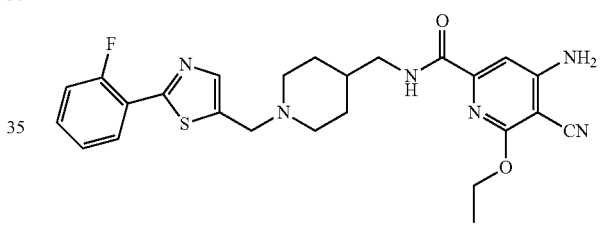

According to the same procedure described in Example 101, using the corresponding aldehyde instead of 2-phenylthiazole-5-carbaldehyde, the title compound having the following physical data was obtained.

$^1$H NMR (DMSO-d$_6$): δ 8.45 (t, J=5.5 Hz, 1H), 8.20 (t, J=7.8 Hz, 1H), 7.82 (s, 1H), 7.55-7.50 (m, 1H), 7.44-7.25 (m, 4H), 7.03 (s, 1H), 4.47 (q, J=7.0 Hz, 2H), 3.77 (s, 2H), 3.16 (t, J=5.5 Hz, 2H), 2.86 (d, J=11.0 Hz, 2H), 1.96 (t, J=11.7 Hz, 2H), 1.63-1.51 (m, 3H), 1.31 (t, J=7.0 Hz, 3H), 1.23-1.14 (m, 2H);

Mass data (ESI, Pos.): m/z 517 (M+Na)$^+$.

Example 114

4-amino-5-cyano-N-((1-((2-(3,5-difluoropyridin-2-yl)thiazol-5-yl)methyl)piperidin-4-yl)methyl)-6-ethoxypicolinamide

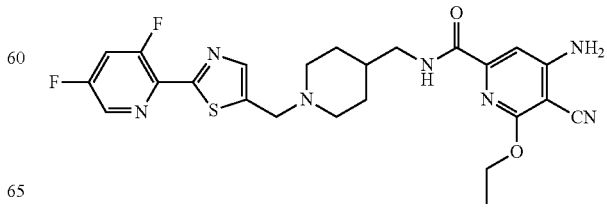

According to the same procedure described in Example 101, using the corresponding aldehyde instead of 2-phenylthiazole-5-carbaldehyde, the title compound having the following physical data was obtained.

¹H NMR (DMSO-d₆): δ 8.16 (d, J=2.3 Hz, 1H), 8.45 (t, J=6.3 Hz, 1H), 8.14 (dt, J=8.6, 2.3 Hz, 1H), 7.83 (s, 1H), 7.29 (bs, 1H), 7.03 (s, 1H), 4.47 (q, J=7.0 Hz, 2H), 3.75 (s, 2H), 3.16 (t, J=6.2 Hz, 2H), 2.86 (d, J=11.0 Hz, 2H), 1.97 (t, J=11.7 Hz, 2H), 1.63-1.51 (m, 3H), 1.31 (t, J=7.0 Hz, 3H), 1.23-1.14 (m, 2H);

Mass data (APCI, Pos.): m/z 514 (M+Na)⁺.

Example 115

4-amino-5-cyano-6-ethoxy-N-((1-((2-(pyridin-2-yl)thiazol-5-yl)methyl)piperidin-4-yl)methyl)picolinamide

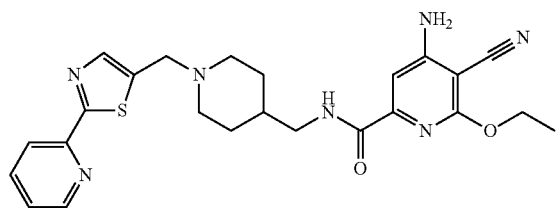 [SMILES: CCOc1nc(C(=O)NCC2CCN(Cc3cnc(-c4ccccn4)s3)CC2)cc(N)c1C#N]

According to the same procedure described in Example 101, using the corresponding aldehyde instead of 2-phenylthiazole-5-carbaldehyde, the title compound having the following physical data was obtained.

¹H NMR (CDCl₃): δ 8.63-8.56 (m, 1H), 8.20-8.11 (m, 1H), 7.85-7.75 (m, 2H), 7.67 (s, 1H), 7.33-7.28 (m, 1H), 7.19 (s, 1H), 5.12 (s, 2H), 4.43 (q, J=7.1 Hz, 2H), 3.78 (s, 2H), 3.30 (t, J=6.5 Hz, 2H), 3.01-2.93 (m, 2H), 2.12-2.02 (m, 2H), 1.76-1.72 (m, 2H), 1.66-1.53 (obs, 1H), 1.44 (t, J=7.1 Hz, 3H), 1.41-1.33 (m, 2H);

Mass data (ESI, Pos.): m/z 478 (M+H)⁺.

Example 116

4-Amino-5-cyano-6-ethoxy-N-((1-((2-phenyloxazol-4-yl)methyl)piperidin-4-yl)methyl)picolinamide

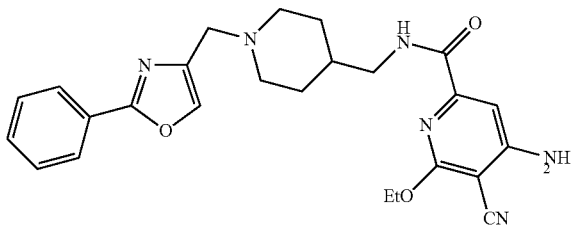 [SMILES: CCOc1nc(C(=O)NCC2CCN(Cc3coc(-c4ccccc4)n3)CC2)cc(N)c1C#N]

According to the same procedure described in Example 101, using the corresponding aldehyde instead of 2-phenylthiazole-5-carbaldehyde, the title compound having the following physical data was obtained.

¹H NMR (DMSO-d₆): δ 8.45 (t, J=6.2 Hz, 1H), 8.03 (br, 1H), 7.97-7.95 (m, 2H), 7.53-7.52 (m 2H), 7.30 (br, 2H), 7.03 (s, 1H), 5.76 (s, 1H), 4.47 (q, J=7.0 Hz, 2H), 3.42 (br, 2H), 3.18-3.14 (m, 2H), 2.89 (d, J=10.5 Hz, 2H), 1.96 (d, J=10.5 Hz, 2H), 1.62-1.55 (m, 3H), 1.31 (t, J=7.0, 3H), 1.24-1.15 (m, 2H);

Mass data (APCI, Pos.): nth 461 (M+H)⁺.

Example 117

4-Amino-5-cyano-6-ethoxy-N-((1-((5-phenyloxazol-2-yl)methyl)piperidin-4-yl)methyl)picolinamide

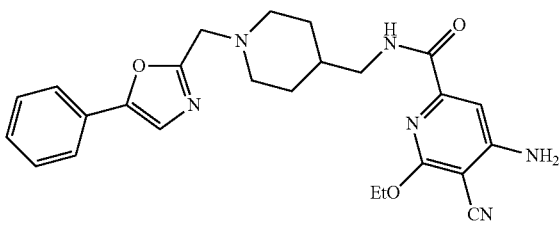 [SMILES: CCOc1nc(C(=O)NCC2CCN(Cc3ncc(-c4ccccc4)o3)CC2)cc(N)c1C#N]

According to the same procedure described in Example 101, using the corresponding aldehyde instead of 2-phenylthiazole-5-carbaldehyde, the title compound having the following physical data was obtained.

Mass data (APCI, Pos.): m/z 461 (M+H)⁺.

Example 118

4-amino-5-cyano-N-((1-((4-((dimethylamino)methyl)-2-(pyridin-2-yl)thiazol-5-yl)methyl)piperidin-4-yl)methyl)-6-ethoxypicolinamide

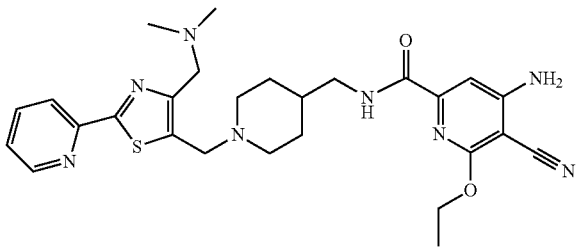 [SMILES: CCOc1nc(C(=O)NCC2CCN(Cc3sc(-c4ccccn4)nc3CN(C)C)CC2)cc(N)c1C#N]

According to the same procedure described in Example 101, using the corresponding aldehyde instead of 2-phenylthiazole-5-carbaldehyde, the title compound having the following physical data was obtained.

¹H NMR (CDCl₃): δ 8.63-8.54 (m, 1H), 8.19-8.10 (m, 1H), 8.09-8.02 (m, 1H), 7.88-7.77 (m, 1H), 7.41-7.32 (m, 1H), 7.09 (s, 1H), 4.82 (s, 2H), 4.43 (q, J=6.9, 2H), 4.24-4.14 (m, 2H), 3.96-3.86 (m, 2H), 3.43-3.32 (m, 2H), 3.17-3.07 (m, 2H), 2.74 (s, 2H), 2.50 (s, 6H), 2.36-2.24 (m 2H), 1.89-1.68 (m, 2H), 1.43 (t, J=6.9, 3H), 1.39-1.26 (m, 1H);

Mass data (ESI, Pos.): m/z 535 (M+H)⁺.

Example 119

4-Amino-N-((1-((1-(2-aminoethyl)-3-phenyl-1H-pyrazol-5-yl)methyl)piperidin-4-yl)methyl)-5-cyano-6-ethoxypicolinamide

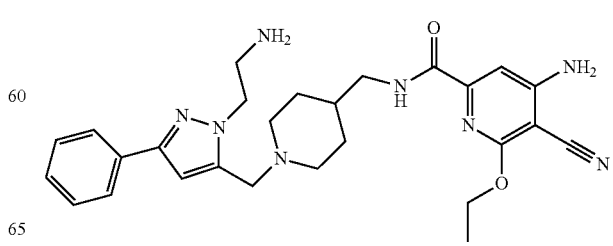

The compound prepared in Example 108 (0.074 g) was suspended in dichloromethane (5 mL) and trifluoroacetic acid (2.00 mL) added and the reaction mixture stirred at room temperature for 2 hours. The reaction mixture was diluted with toluene and concentrated under reduced pressure. The residue was partitioned between saturated aqueous sodium bicarbonate and ethyl acetate. The organics were washed with brine, dried over magnesium sulfate and concentrated under reduced pressure to afford the crude material, which was purified by flash column chromatography (eluant: gradient elution 1-20% (9:1 methanol/concentrated ammonium hydroxide)/ethyl acetate) to afford the title compound (0.035 g) having the following physical data.

$^1$H NMR (CDCl$_3$): δ 7.84-7.75 (m, 3H), 7.38 (t, J=7.6 Hz, 2H), 7.31-7.27 (m, 1H), 7.18 (s, 1H), 6.43 (s, 1H), 5.14 (s, 2H), 4.47-4.38 (m, 3H), 4.26 (t, J=5.8 Hz, 1H), 3.88-3.81 (m, 1H), 3.51 (s, 2H), 3.36-3.29 (m, 2H), 3.25-3.18 (m, 1H), 2.98-2.87 (m, 2H), 2.02-1.93 (m, 2H), 1.76-1.66 (m, 2H), 1.65-1.57 (m, 1H), 1.43 (t, J=7.1 Hz, 3H), 1.35-1.26 (m, 2H);

Mass data (APCI, Pos.): m/z 503 (M+H)$^+$.

Example 120

Methyl 3-phenyl-1H-pyrazole-5-carboxylate Hydrochloride

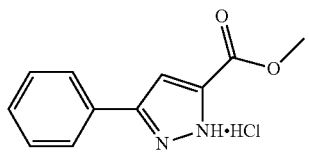

3-Phenyl-1H-pyrazole-5-carboxylic acid (4.96 g) was suspended in methanol (80 mL) and concentrated hydrochloric acid (22.0 mL) and the reaction mixture heated at reflux overnight. Upon cooling the title compound (3.00 g) precipitated from the reaction mixture, was filtered and dried under vacuum. The material was used without further purification having the following physical data.

$^1$H NMR (DMSO-d$_6$): δ 7.93-7.78 (m, 2H), 7.54-7.17 (m, 4H), 3.85 (s, 3H);

Mass data (APCI, Pos.): m/z 203 (M+H (free base))$^+$.

Example 121

Methyl 1-(2-(tert-butoxycarbonylamino)ethyl)-3-phenyl-1H-pyrazole-5-carboxylate

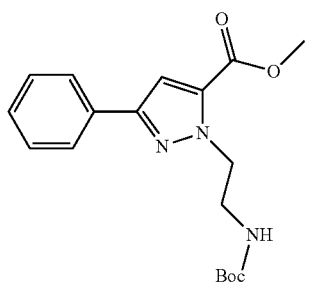 [SMILES: COC(=O)c1cc(-c2ccccc2)nn1CCNC(=O)OC(C)(C)C]

The compound prepared in Example 120 (0.500 g), tert-butyl 2-bromoethylcarbamate (0.704 g) and potassium carbonate (1.16 g) were suspended in acetonitrile (20 mL) and heated at reflux overnight. Another 0.5 equivalents of tert-butyl 2-bromoethylcarbamate was added and the reaction mixture heated at reflux overnight again. The reaction mixture was cooled to room temperature and partitioned between saturated aqueous sodium bicarbonate and ethyl acetate. The organics were washed with brine, dried over magnesium sulfate, filtered and concentrated under reduced pressure to afford the crude material, which was purified by flash column chromatography to furnish the title compound (0.624 g) having the following physical data.

$^1$H NMR (CDCl$_3$): δ 7.80 (d, J=7.8 Hz, 2H), 7.41 (t, J=7.5 Hz, 2H), 7.33 (t, J=7.3 Hz, 1H), 7.14 (s, 1H), 4.95 (s, 1H), 4.72 (t, J=4.0 Hz 2H), 3.91 (s, 3H), 3.69-3.59 (m, 2H), 1.40 (s, 9H);

Mass data (APCI, Pos.): m/z 346 (M+H)$^+$.

Example 122 tert-Butyl 2-(5-(hydroxymethyl)-3-phenyl-1H-pyrazol-1-yl)ethylcarbamate

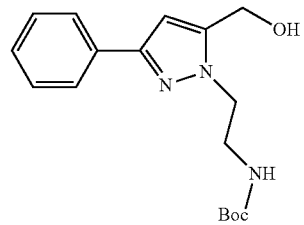 [SMILES: CC(C)(C)OC(=O)NCCn1nc(-c2ccccc2)cc1CO]

The compound prepared in Example 121 (0.620 g) was suspended in methanol (30 mL) and sodium borohydride (0.088 g) was added portion-wise to the stirred reaction mixture at room temperature. Excess sodium borohydride was added portion-wise to the reaction mixture and the system heated at reflux overnight. The reaction mixture was cooled to room temperature and concentrated under reduced pressure. The solids were partitioned between saturated aqueous ammonium chloride and ethyl acetate. The organics were washed with brine, dried, magnesium sulfate and concentrated under reduced pressure to afford the crude material, which was purified by flash column chromatography (pre-absorbed to silica) (eluant: 50-75% ethyl acetate/hexane 0.5% triethylamine) to furnish the title compound (0.253 g) having the following physical data.

$^1$H NMR (DMSO-d$_6$): δ 7.76 (d, J=7.1 Hz, 2H), 7.38 (t, J=7.6 Hz, 2H), 7.27 (t, J=7.4 Hz, 1H), 6.96-6.90 (m, 1H), 6.60 (s, 1H), 5.33 (t, J=5.4 Hz, 1H), 4.51 (d, J=5.4 Hz, 2H), 4.16 (t, J=6.6 Hz, 2H), 1.36 (s, 9H);

Mass data (APCI, Pos.): m/z 318 (M+H)$^+$.

Example 123 tert-butyl 2-(5-formyl-3-phenyl-1H-pyrazol-1-yl)ethylcarbamate

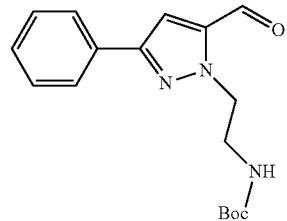 [SMILES: CC(C)(C)OC(=O)NCCn1nc(-c2ccccc2)cc1C=O]

The compound prepared in Example 122 (0.25 g) was suspended in tetrahydrofuran (20 mL) manganese (II) oxide (2.05 g) was added and the suspension stirred at room temperature overnight. The reaction mixture was then filtered through a pad of silica and celite (trade mark), eluting with ethyl acetate. The organics were concentrated under reduced pressure to afford the crude material, which was purified by flash column chromatography (eluant: 20% ethyl acetate/hexane) to afford the title compound (0.10 g) having the following physical data.

$^1$H NMR (CDCl$_3$): δ 9.90 (s, 1H), 7.82 (d, J=7.2 Hz, 2H), 7.43 (t, J=7.4 Hz, 2H), 7.36 (t, J=7.3 Hz, 1H), 7.19 (s, 1H), 4.85 (s, 1H), 4.69 (t, J=6 Hz, 2H), 3.67-3.59 (m, 2H), 1.39 (s, 9H);

Mass data (APCI, Pos.): m/z 316 (M+H)$^+$.

Example 124

(3-(Pyridin-2-yl)isoxazol-5-yl)methanol

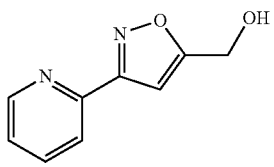 [SMILES: OCc1cc(-c2ccccn2)no1]

A solution of (E)-picolinaldehyde oxime (4 g) in N,N-dimethylformamide (20 mL) was treated with N-chlorosuccinimide (4.81 g) at 0° C., in portions. The mixture was stirred at 60° C. for 2 hours. The mixture was then cooled to 0° C. and treated with prop-2-yn-1-ol (7.59 mL) through a syringe. A solution of triethylamine (5.02 mL) in N,N-dimethylformamide (4 mL) was added slowly (30 minutes). The resulting mixture was stirred at 0° C. for 1 hour, and then at room temperature for 18 hs. The solvent was evaporated in vacuo and the residue partitioned between ethyl acetate and water. The organic layer was separated, dried and evaporated in vacuo to a yellow oil and purified by column chromatography on silica gel (2-10% methanol in dichloromethane) to obtain the title compound (4.25 g) having the following physical data.

$^1$H NMR (DMSO-d$_6$): δ 8.72 (d, J=4.8 Hz, 1H), 8.0 (d, J=7.7 Hz, 1H), 7.96 (td, J=1.7, 7.7 Hz, 1H), 7.53-7.50 (m, 1H), 6.88 (s, 1H), 5.72 (t, J=6.1 Hz, 1H), 4.64 (d, J=6.0 Hz, 2H);

Mass data (APCI, Pos.): m/z 177 (M+H)$^+$.

Example 125

3-(Pyridin-2-yl)isoxazole-5-carbaldehyde

Sulfur trioxide pyridine (10.0 g, 62.8 mmol) was dissolved in dimethylsulfoxide (50 mL) and cooled to near 0° C. A solution of the compound prepared in Example 124 (5.05 g, 28.7 mmol) and triethylamine (16.0 mL, 115 mmol) in dichloromethane (40 mL) was added to the solution over 45 minutes. The reaction was warmed to room temperature and stirred overnight. The reaction was diluted with ethyl acetate and washed with sodium hydrogen carbonate aqueous solution. The organic phase was washed with water and dried over magnesium sulfate. The crude mixture was purified by column chromatography using an eluant of 1 to 3% ethyl acetate/dichloromethane to provide the title compound (0.90 g) with the following physical data.

$^1$H NMR (CDCl$_3$): δ 10.05 (s, 1H), 8.72 (d, J=4.7 Hz, 1H), 8.15 (d, J=7.8 Hz, 1H), 7.85 (dt, J=7.8, 1.6 Hz, 1H), 7.65 (s, 1H), 7.43-7.40 (m, 1H).

Example 126

Ethyl 4-(bromomethyl)-2-phenylthiazole-5-carboxylate

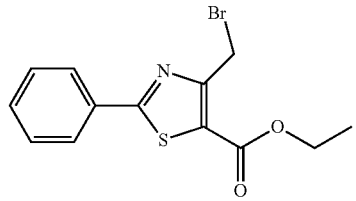 [SMILES: CCOC(=O)c1sc(-c2ccccc2)nc1CBr]

Ethyl 4-methyl-2-phenylthiazole-5-carboxylate (5.00 g), N-bromosuccinimide (3.78 g) and benzoyl peroxide (0.49 g) were suspended in carbon tetrachloride (50 mL) and heated at reflux overnight. The reaction mixture was cooled to room temperature and partitioned between dichloromethane and saturated aqueous sodium bicarbonate. The combined organics were dried over magnesium sulfate and concentrated under reduced pressure to afford the crude title compound (6.60 g), which was used without further purification possessing the following physical data.

$^1$H NMR (CDCl$_3$): δ 8.01-7.97 (m, 2H), 7.51-7.44 (m, 3H), 4.99 (s, 2H), 4.41 (q, J=7.1 Hz, 2H), 1.42 (t, J=7.1 Hz, 3H);

Mass data (APCI, Pos.): m/z 328 (M+H)$^+$.

Example 127

Ethyl 4-((dimethylamino)methyl)-2-phenylthiazole-5-carboxylate

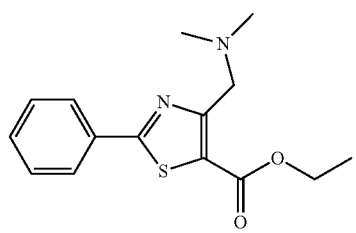 [SMILES: CCOC(=O)c1sc(-c2ccccc2)nc1CN(C)C]

The compound prepared in Example 126 (1.00 g) was suspended in tetrahydrofuran (20 mL) and dimethylamine (2 M) (7.66 mL) added and the reaction mixture stirred at room temperature for 3 hours. The reaction mixture was partitioned between saturated aqueous sodium bicarbonate and ethyl acetate. The organics were washed with brine, dried, magnesium sulfate and concentrated under reduced pressure to afford the crude material, which was purified by flash column chromatography to afford the title compound (0.65 g) having the following physical data.

$^1$H NMR (DMSO-d$_6$): δ 8.04-7.99 (m, 2H), 7.57-7.52 (m, 3H), 4.32 (q, J=7.1 Hz, 2H), 3.93 (s, 2H), 2.25 (s, 6H), 1.32 (t, J=7.1 Hz, 3H);

Mass data (APCI, Pos.): m/z 291 (M+H)$^+$.

Example 128

(4-((Dimethylamino)methyl)-2-phenylthiazol-5-yl)methanol

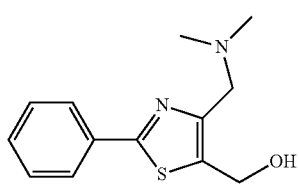 [SMILES: CN(C)Cc1nc(-c2ccccc2)sc1CO]

The compound prepared in Example 127 (0.65 g) was suspended in tetrahydrofuran (20 mL) and then lithium aluminum hydride solution (1 M; 4.44 mL) was added dropwise to the solution at room temperature and stirred overnight. The reaction mixture was transferred dropwise to a stirred room temperature saturated aqueous solution of Rochelle's salt (sodium potassium tartrate). The mixture was diluted with ethyl acetate and the biphasic mixture stirred rapidly for 30 minutes. The layers were separated and the organics washed with brine, dried over magnesium sulfate, filtered and concentrated under reduced pressure to afford the crude material (0.53 g), which was used without further purification possessing the following physical data.

Mass data (APCI, Pos.): m/z 249 (M+H)$^+$.

Example 129

4-((Dimethylamino)methyl)-2-phenylthiazole-5-carbaldehyde

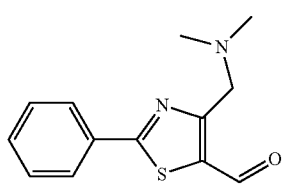 [SMILES: CN(C)Cc1nc(-c2ccccc2)sc1C=O]

According to the same procedure described in Example 123, using the corresponding alcohol instead of (tert-butyl 2-(5-(hydroxymethyl)-3-phenyl-1H-pyrazol-1-yl)ethylcarbamate, the title compound having the following physical data was obtained.

$^1$H NMR (CDCl$_3$): δ 10.38 (s, 1H), 8.04-8.00 (m, 2H), 7.52-7.43 (m, 3H), 3.95 (s, 2H), 2.37 (s, 6H);

Mass data (APCI, Pos.): m/z 247 (M+H)$^+$.

Example 130

Methyl 2-phenyl-1H-imidazole-4-carboxylate

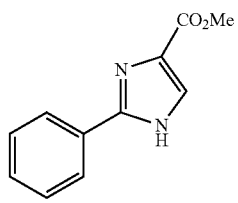 [SMILES: COC(=O)c1c[nH]c(-c2ccccc2)n1]

2-Phenyl-1H-imidazole-4-carboxylic acid mono hydrate (2.00 g) was suspended in methanol (30 mL) and concentrated hydrochloric acid (10.0 mL) was added and the reaction mixture heated at reflux overnight. The reaction mixture was cooled to room temperature and diluted with ethylacetate and the aqueous basified with 1 N sodium hydroxide. The organics were washed with brine, dried over magnesium sulfate, filtered and concentrated under reduced pressure to afford the title compound. The title compound was used without further purification, having the following physical data.

$^1$H NMR (CDCl$_3$): δ 10.41-10.11 (m, 1H), 7.98-7.86 (m, 2H), 7.84-7.77 (m, 1H), 7.52-7.36 (m, 3H), 3.92 (s, 3H);

Mass data (APCI, Pos.): m/z 203 (M+H)$^+$.

Example 131

(2-Phenyl-1H-imidazol-4-yl)methanol

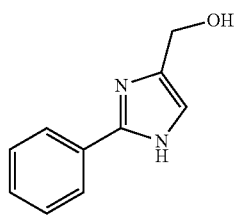 [SMILES: OCc1c[nH]c(-c2ccccc2)n1]

According to the same procedure described in Example 128, using the corresponding ester instead of ethyl 4-((dimethylamino)methyl)-2-phenylthiazole-5-carboxylate, the title compound having the following physical data was obtained.

$^1$H NMR (CDCl$_3$): δ 7.85-7.79 (m, 2H), 7.48-7.35 (m, 3H), 7.07 (s, 1H), 4.71 (s, 2H);

Mass data (APCI, Pos.): m/z 175 (M+H)$^+$.

Example 132

2-Phenyl-1H-imidazole-4-carbaldehyde

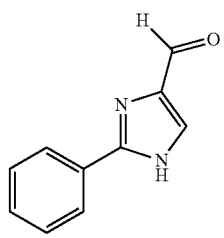 [SMILES: O=Cc1c[nH]c(-c2ccccc2)n1]

According to the same procedure described in Example 123, using the corresponding alcohol instead of (tert-butyl 2-(5-(hydroxymethyl)-3-phenyl-1H-pyrazol-1-yl)ethylcarbamate, the title compound having the following physical data was obtained.

¹H NMR (CDCl₃): δ 10.25 (s, 1H), 9.74 (s, 1H), 7.99-7.81 (m, 3H), 7.54-7.45 (m, 3);

Mass data (APCI, Pos.): m/z 173 (M+H)⁺.

Example 133

Methyl 1-methyl-2-phenyl-1H-imidazole-4-carboxylate

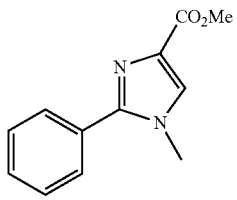 [SMILES: COC(=O)c1cn(C)c(-c2ccccc2)n1]

The compound prepared in Example 130 (0.204 g) was suspended in N,N-dimethyl formamide (4 mL) and cooled to 0° C. Potassium carbonate (0.279 g) was added and then iodomethane (0.069 mL). The reaction mixture was stirred at 0° C. for 30 minutes and then warmed to room temperature and stirred at room temperature for further 1 hour. The reaction mixture was diluted with ethyl acetate and washed sequentially with sodium bicarbonate aqueous solution and brine. The organics were dried over magnesium sulfate, filtered and concentrated under reduced pressure to afford the crude material, which was purified by flash column chromatography to furnish the title compound (0.130 g) having the following physical data.

¹H NMR (CDCl₃): δ 7.69 (s, 1H), 7.67-7.63 (m, 2H), 7.48-7.44 (m, 3H), 3.91 (s, 3H), 3.78 (s, 3H);

Mass data (APCI, Pos.): m/z 217 (M+H)⁺.

Example 134

(1-Methyl-2-phenyl-1H-imidazol-4-yl)methanol

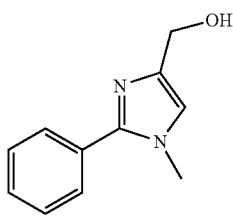

According to the same procedure described in Example 128, using the corresponding ester instead of ethyl 4-((dimethylamino)methyl)-2-phenylthiazole-5-carboxylate, the title compound having the following physical data was obtained.

Mass data (APCI, Pos.): m/z 189 (M+H)⁺.

Example 135

1-methyl-2-phenyl-1H-imidazole-4-carbaldehyde

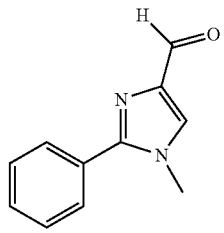

According to the same procedure described in Example 123, using the corresponding alcohol instead of (tert-butyl 2-(5-(hydroxymethyl)-3-phenyl-1H-pyrazol-1-yl)ethylcarbamate, the title compound having the following physical data was obtained.

Mass data (APCI, Pos.): m/z 187 (M+H)⁺.

Example 136

Methyl 1-methyl-2-phenyl-1H-imidazole-5-carboxylate

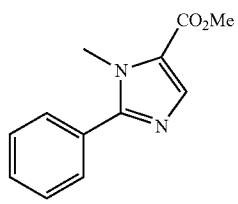 [SMILES: COC(=O)c1cnc(-c2ccccc2)n1C]

According to the same procedure described in Example 133, the title compound having the following physical data was obtained.

¹H NMR (CDCl₃): δ 7.84 (s, 1H), 7.65-7.60 (m, 2H), 7.52-7.46 (m, 3H), 3.96 (s, 3H), 3.88 (s, 3H);

Mass data (APCI, Pos.): m/z 217 (M+H)⁺.

Example 137

(1-Methyl-2-phenyl-1H-imidazol-5-yl)methanol

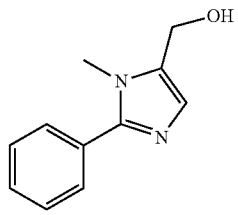

According to the same procedure described in Example 128, using the corresponding ester instead of ethyl 4-((dimethylamino)methyl)-2-phenylthiazole-5-carboxylate, the title compound having the following physical data was obtained.

Mass data (APCI, Pos.): m/z 189 (M+H)⁺.

Example 138

1-Methyl-2-phenyl-1H-imidazole-5-carbaldehyde

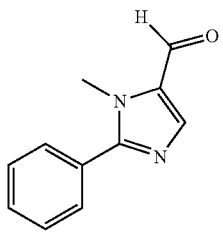

According to the same procedure described in Example 123, using the corresponding alcohol instead of (tert-butyl 2-(5-(hydroxymethyl)-3-phenyl-1H-pyrazol-1-yl)ethylcarbamate, the title compound having the following physical data was obtained.
Mass data (APCI, Pos.): m/z 187 (M+H)$^+$.

Example 139

2-(Pyridin-2-yl)thiazole-5-carbaldehyde

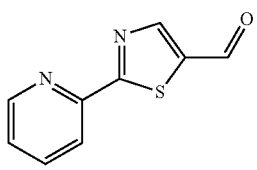 [SMILES: O=Cc1cnc(-c2ccccn2)s1]

Pyridine-2-carbothioamide (4.5 g) was dissolved in tetrahydrofuran (40 mL). Pyridine (7.9 mL) was added and the reaction was heated to reflux. 2-Bromomalonaldehyde (7.2 g) was added in dimethylsulfoxide (15 mL) dropwise over 10 minutes and the reaction was heated for 3 hours. The reaction was concentrated in vacuo and partitioned between ethyl acetate and sodium hydrogen carbonate aqueous solution. The aqueous layer was back extracted and the combined organic phase was washed with brine and concentrated. The crude reaction was purified by silica gel column chromatography using an eluant of 2% to 4% acetone/dichloromethane to obtain the title compound (2.4 g) with the following physical data.
$^1$H NMR (CDCl$_3$): δ 10.09 (s, 1H), 8.68 (d, J=4.7 Hz, 1H), 8.48 (s, 1H), 8.27 (d, J=7.8 Hz, 1H), 7.86 (dt, J=7.8, 1.6 Hz, 1H), 7.44-7.41 (m, 1H).

Example 140

2-(Pyrimidin-2-yl)thiazole-5-carbaldehyde

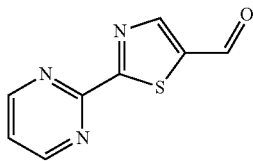 [SMILES: O=Cc1cnc(-c2ncccn2)s1]

According to the same procedure described in Example 139, using the corresponding thioamide instead of pyridine-2-carbothioamide, the title compound having the following physical data was obtained.
$^1$H NMR (CDCl$_3$): δ 10.14 (s, 1H), 8.92 (d, J=4.7 Hz, 2H), 8.61 (s, 1H), 7.42 (t, J=4.7 Hz, 1H).

Example 141

2-(3,5-difluoropyridin-2-yl)thiazole-5-carbaldehyde

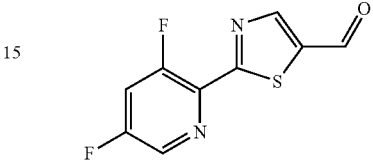

According to the same procedure described in Example 139, using the corresponding thioamide instead of pyridine-2-carbothioamide, the title compound having the following physical data was obtained.
$^1$H NMR (CDCl$_3$): δ 10.12 (s, 1H), 8.56 (s, 1H), 8.45 (d, J=2.3 Hz, 1H), 7.42 (dt, J=7.8, 2.3 Hz, 1H).

Example 142

2-(4-fluorophenyl)thiazole-5-carbaldehyde

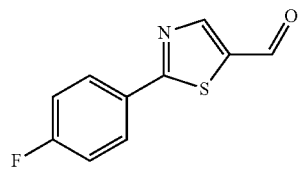 [SMILES: O=Cc1cnc(-c2ccc(F)cc2)s1]

According to the same procedure described in Example 139, using the corresponding thioamide instead of pyridine-2-carbothioamide, the title compound having the following physical data was obtained.
$^1$H NMR (CDCl$_3$): δ 10.05 (s, 1H), 8.42 (s, 1H), 8.06-8.02 (m, 2H), 7.21-7.16 (m, 2H).

Example 143

2-(3-fluorophenyl)thiazole-5-carbaldehyde

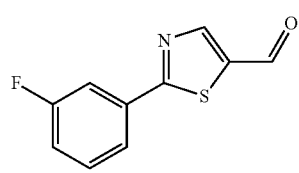 [SMILES: O=Cc1cnc(-c2cccc(F)c2)s1]

According to the same procedure described in Example 139, using the corresponding thioamide instead of pyridine-2-carbothioamide, the title compound having the following physical data was obtained.
$^1$H NMR (CDCl$_3$): δ 10.07 (s, 1H), 8.45 (s, 1H), 7.80-7.76 (m, 2H), 7.50-7.45 (m, 1H), 7.25-7.20 (m, 1H).

Example 144

2-(2-fluorophenyl)thiazole-5-carbaldehyde

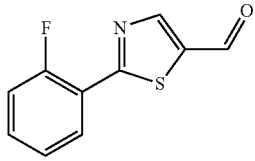 [SMILES: O=Cc1cnc(-c2ccccc2F)s1]

According to the same procedure described in Example 139, using the corresponding thioamide instead of pyridine-2-carbothioamide, the title compound having the following physical data was obtained.

$^1$H NMR (CDCl$_3$): δ 10.11 (s, 1H), 8.50 (d, J=2.3 Hz, 1H), 8.37 (dt, J=7.8, 2.3 Hz, 1H), 7.54-7.48 (m, 1H), 7.34-7.23 (m, 2H).

Example 145

3,5-difluoropyridine-2-carbothioamide

3,5-Difluoropicolinonitrile (1.00 g) was partially dissolved in methanol (5 mL) and cooled to 0° C. A solution of ammonium sulfide in water (1.1 mL, 45% weight) was added slowly and the reaction was stirred 14 hours. The reaction was decanted and this solution was concentrated and then purified by column chromatography using dichloromethane as the eluant to obtain the title compound (0.17 g) having the following physical data.

$^1$H NMR (DMSO-d$_6$): δ 10.26 (bs, 1H), 9.80 (bs, 1H), 8.48 (d, J=2.3 Hz, 1H), 8.03 (dt, J=10.2, 2.3 Hz, 1H).

Example 146

N'-(2-(benzyloxy)acetyl)picolinohydrazide

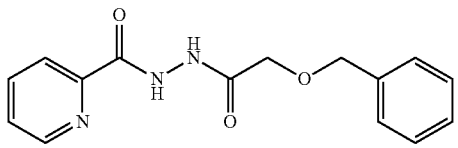 [SMILES: O=C(COCc1ccccc1)NNC(=O)c1ccccn1]

Picolinohydrazide (4.55 g) was dissolved in dichloromethane (40 mL) and 2-(benzyloxy)acetyl chloride (6.06 mL) was added slowly with cooling. Triethylamine (5.98 mL) was added slowly with a strong exotherm. Additional dichloromethane (45 mL) was added to aid stirring. The reaction was allowed to stir overnight. The reaction was partitioned between ethyl acetate and sodium hydrogen carbonate aqueous solution. The organic phase was washed with brine, dried and purified by column chromatography using an eluant of 10% ethyl acetate/dichloromethane to provide the title compound (4.1 g) having the following physical data.

$^1$H NMR (CDCl$_3$): δ 10.08 (d, J=5.5 Hz, 1H), 8.95 (d, J=5.5 Hz, 1H), 8.58 (d, J=3.9 Hz, 1H), 8.16 (d, J=7.8 Hz, 1H), (dt, J=7.8, 1.6 Hz, 1H), 7.49-7.46 (m, 1H), 7.41-7.33 (m, 5H), 4.66 (s, 2H), 4.18 (s, 2H);

Mass data (APCI, Pos.): m/z 286 (M+H)$^+$.

Example 147

2-(benzyloxymethyl)-5-(pyridin-2-yl)-1,3,4-thiadiazole

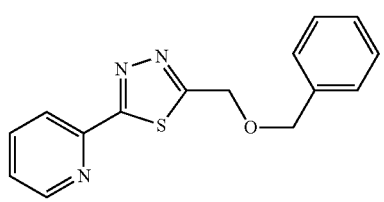 [SMILES: c1ccc(COCc2nnc(-c3ccccn3)s2)cc1]

The compound prepared in Example 46 (3.3 g) and Lawesson's reagent (2,4-bis-(4-methoxyphenyl)-[1,3,2,4]dithiadiphosphetane 2,4-dithion; 4.7 g) were heated in toluene (60 mL) at reflux for 4 hours. The reaction was concentrated and purified by column chromatography using an eluant of 10% ethyl acetate/dichloromethane to provide the title compound (2.4 g) having the following physical data.

$^1$H NMR (CDCl$_3$): δ 8.66 (d, J=5.5 Hz, 1H), 8.35 (d, J=7.8 Hz, 1H), 7.88-7.84 (m, 1H), 7.41-7.30 (m, 6H), 4.99 (s, 2H), 4.69 (s, 2H);

Mass data (APCI, Pos.): m/z 284 (M+H)$^+$.

Example 148

(5-(pyridin-2-yl)-1,3,4-thiadiazol-2-yl)methanol

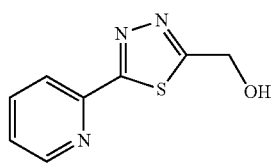 [SMILES: OCc1nnc(-c2ccccn2)s1]

The compound prepared in Example 147 (0.295 g) was dissolved in dichloromethane (7 mL) and cooled to 0° C. Tribromoborane (0.3 mL) was added slowly and the reaction was allowed to warm and then was stirred overnight. The reaction was quenched with ethyl acetate/sodium hydrogen carbonate aqueous solution and the organic phase was washed with brine, dried over magnesium sulfate and filtered. The solution was concentrated and purified by column chromatography using an eluant of 5% methanol/dichloromethane to provide the title compound (0.10 g) having the following physical data.

$^1$H NMR (CD$_3$OD): δ 8.66 (d, J=4.7 Hz, 1H), 8.28 (d, J=7.8 Hz, 1H), 7.98 (dt, J=7.8, 1.6 Hz, 1H), 7.53-7.50 (m, 1H), 4.99 (s, 2H);

Mass data (APCI, Pos.): m/z 194 (M+H)$^+$.

Example 149

5-(pyridin-2-yl)-1,3,4-thiadiazole-2-carbaldehyde

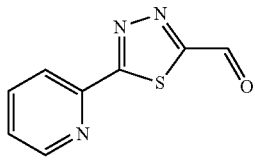 [SMILES: O=Cc1nnc(-c2ccccn2)s1]

The compound prepared in Example 148 (0.18 g) and IBX (o-iodoxybenzoic acid; 0.40 g) were stirred in ethyl acetate (8 mL) and heated at 85° C. for 14 hours. The reaction was cooled, filtered and washed with ethyl acetate. The solution was washed twice with sodium hydrogen carbonate aqueous solution and then brine, dried over magnesium sulfate, filtered and concentrated to provide the title compound (0.13 g) having the following physical data.

$^1$H NMR (CDCl$_3$): δ 10.26 (s, 1H), 8.70 (d, J=4.7 Hz, 1H), 8.45 (d, J=7.8 Hz, 1H), 7.92 (dt, J=7.8, 1.6 Hz, 1H), 7.50-7.46 (m, 1H).

Example 150

5-Phenyloxazole-2-carbaldehyde

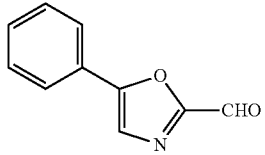 [SMILES: O=Cc1ncc(-c2ccccc2)o1]

A solution of 5-phenyloxazole (0.192 g) in 2:1 tetrahydrofuran/diethyl ether (7 mL) was cooled to −78° C., and treated with n-butyl lithium (0.582 mL) dropwise under Argon. The mixture was stirred for 30 minutes at −78° C., at this time a solution of N-methyl-N-(pyridin-2-yl) formamide (0.270 g) in tetrahydrofuran (2.6 mL) was added dropwise to the solution. After stirring at −78° C. for 30 minutes, the mixture was allowed to warm up to room temperature and stirring continued overnight. The mixture was quenched by the addition of water and extracted with ethyl acetate. The combined extracts were washed with 10% hydrochloric acid, saturated aqueous solution of sodium bicarbonate and brine, dried and concentrated in vacuo and purified by column chromatography on silica gel (10-50% ethyl acetate in hexane) to provide the title compound (0.016 g) with the following physical data.

$^1$H NMR (DMSO-d$_6$): δ 9.72 (s, 1H), 8.12 (s, 1H), 7.88 (d, J=7.02 Hz, 1H), 7.60-7.49 (m, 4H);

Mass data (APCI, Pos.): m/z 174 (M+H)$^+$.

Example 151 methyl 4-methyl-2-(pyridin-2-yl)thiazole-5-carboxylate

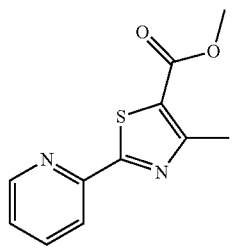 [SMILES: COC(=O)c1sc(-c2ccccn2)nc1C]

A mixture of pyridine-2-carbothioamide (5.00 g) and ethanol (15 mL) was heated at 50° C. Methyl 2-chloro-3-oxobutanoate (4.41 mL) was slowly added to this solution over 10 minutes. The solution was heated at 70° C. for 18 hours. The solution was cooled to room temperature and 50% ethanol (20 mL) was added. The solution was cooled to 0° C. and stirred for 1 hour. The solution was filtered and dried over vacuum to obtain the title compound (4.90 g) with the following physical data.

$^1$H NMR (CDCl$_3$): δ 8.68-8.58 (m, 1H), 8.27-8.17 (m, 1H), 7.87-7.77 (m, 1H), 7.41-7.33 (m, 1H), 3.90 (s, 3H), 2.80 (s, 3H);

Mass data (ESI, Pos.): m/z 235 (M+H)$^+$.

Example 152 methyl 4-(bromomethyl)-2-(pyridin-2-yl)thiazole-5-carboxylate

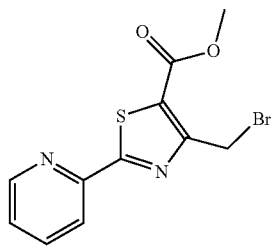 [SMILES: COC(=O)c1sc(-c2ccccn2)nc1CBr]

A mixture of the compound prepared in Example 151 (3.50 g) and N-bromosuccinimide (2.66 g) and benzoyl peroxide (0.362 g) in carbon tetrachloride (80 mL) was heated at 90° C. for 18 hours. The mixture was partitioned between a saturated aqueous sodium bicarbonate solution and dichloromethane. The organic layer was dried over anhydrous magnesium sulfate and concentrated to obtain the title compound (4.70 g) having the following physical data.

Mass data (ESI, Pos.): m/z 4 (M+H)$^+$.

Example 153 methyl 4-((dimethylamino)methyl)-2-(pyridin-2-yl)thiazole-5-carboxylate

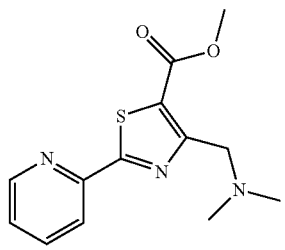 [SMILES: COC(=O)c1sc(-c2ccccn2)nc1CN(C)C]

A mixture of the compound prepared in Example 152 (500 mg) and dimethylamine (1.8 mL) in tetrahydrofuran (3 mL) was stirred at room temperature for 30 minutes. The mixture was partitioned between a saturated aqueous sodium bicarbonate solution and ethyl acetate. The organic layer was dried over anhydrous magnesium sulfate and concentrated. The residue was purified by column chromatography on silica gel (ethyl acetate:hexane=1:1 then ethyl acetate=1) to obtain the title compound (191 mg) having the following physical data.
$^1$H NMR (CDCl$_3$): δ 8.63-8.59 (m, 1H), 8.34-8.25 (m, 1H), 7.84-7.76 (m, 1H), 7.40-7.33 (m, 1H), 4.01 (s, 2H), 3.91 (m, 3H), 2.41 (s, 6H);
Mass data (ESI, Pos.): m/z 340 (M+H)$^+$.

Example 154 methyl 4-((4-(tert-butoxycarbonyl)piperazin-1-yl)methyl)-2-(pyridin-2-yl)thiazole-5-carboxylate

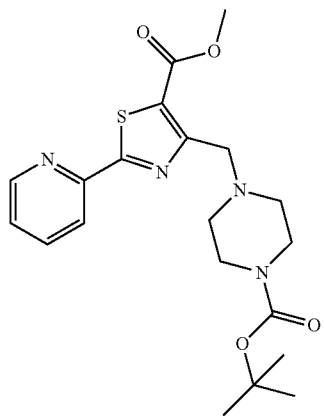 [SMILES: COC(=O)c1sc(-c2ccccn2)nc1CN1CCN(C(=O)OC(C)(C)C)CC1]

According to the same procedure described in Example 153, using the corresponding amine instead of dimethylamine, the title compound having the following physical data was obtained.
Mass data (ESI, Pos.): m/z 419 (M+H)$^+$.

Example 155

(4-((dimethylamino)methyl)-2-(pyridin-2-yl)thiazol-5-yl)methanol

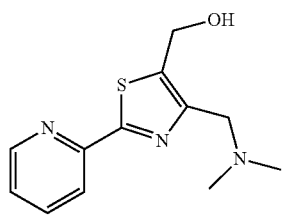 [SMILES: CN(C)Cc1nc(-c2ccccn2)sc1CO]

The compound prepared in Example 153 (180 mg) in tetrahydrofuran (2 mL) was stirred at 0° C. for 30 minutes. Lithium aluminum hydride (1.30 g) was added and the reaction was stirred for 18 hours. Rochelle's salt (sodium potassium tartrate; 10 g) was added and the solution was stirred for 30 minutes. The mixture was then partitioned between a saturated aqueous sodium bicarbonate solution and ethyl acetate. The organic layer was dried over anhydrous magnesium sulfate and concentrated to obtain the title compound (0.096 g) having the following physical data.
$^1$H NMR (CDCl$_3$): δ 8.64-8.53 (m, 1H), 8.16-8.07 (m, 1H), 7.82-7.70 (m, 1H), 7.35-7.25 (m, 1H), 4.79 (s, 2H), 3.76 (m, 2H), 2.32 (s, 6H);
Mass data (ESI, Pos.): m/z 250 (M+H)$^+$.

Example 156 tert-butyl 4-((5-(hydroxymethyl)-2-(pyridin-2-yl)thiazol-4-yl)methyl)piperazine-1-carboxylate

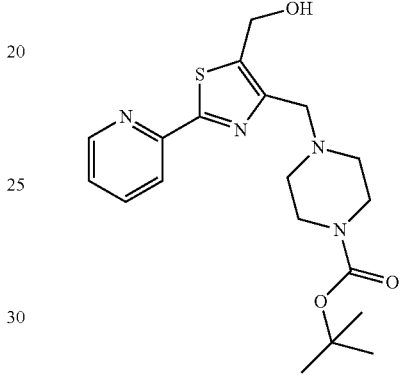

According to the same procedure described in Example 155, using the compound made in Example 154 instead of the compound prepared in Example 153, the title compound having the following physical data was obtained.
$^1$H NMR (CDCl$_3$): δ 8.64-8.57 (m, 1H), 8.13-8.07 (m, 1H), 7.82-7.73 (m, 1H), 7.33-7.25 (m, 1H), 4.82 (s, 2H), 3.84 (m, 2H), 3.53-3.34 (m, 4H), 2.60-2.44 (m, 4H), 1.45 (s, 9H);
Mass data (ESI, Pos.): m/z 391 (M+H)$^+$.

Example 157

4-((dimethylamino)methyl)-2-(pyridin-2-yl)thiazole-5-carbaldehyde

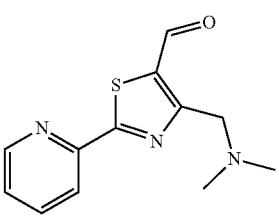 [SMILES: CN(C)Cc1nc(-c2ccccn2)sc1C=O]

According to the same procedure described in Example 123, using the compound made in Example 155 instead of the compound prepared in Example 122, the title compound having the following physical data was obtained.
Mass data (ESI, Pos.): m/z 248 (M+H)$^+$.

Example 158 tert-butyl 4-((5-formyl-2-(pyridin-2-yl)thiazol-4-yl)methyl)piperazine-1-carboxylate

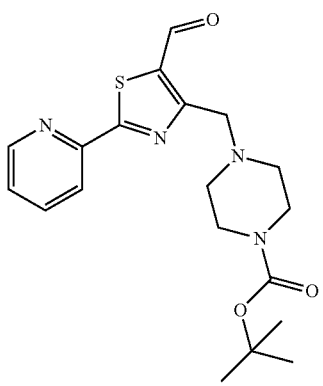 [SMILES: CC(C)(C)OC(=O)N1CCN(Cc2nc(-c3ccccn3)sc2C=O)CC1]

According to the same procedure described in Example 123, using the compound made in Example 156 instead of the compound prepared in Example 122, the title compound having the following physical data was obtained.

$^1$H NMR (CDCl$_3$): δ 10.44 (s, 1H), 8.68-8.63 (s, 1H), 8.28-8.20 (s, 1H), 7.88-7.78 (s, 1H), 7.44-7.35 (s, 1H), 4.04 (s, 2H), 3.50-3.42 (m, 4H), 2.61-2.51 (m, 4H), 1.45 (s, 9H);
Mass data (ESI, Pos.): m/z 389 (M+H)$^+$.

Example 159 tert-butyl 4-((5-((4-((4-amino-5-cyano-6-ethoxypicolinamido)methyl)piperidin-1-yl)methyl)-2-(pyridin-2-yl)thiazol-4-yl)methyl)piperazine-1-carboxylate

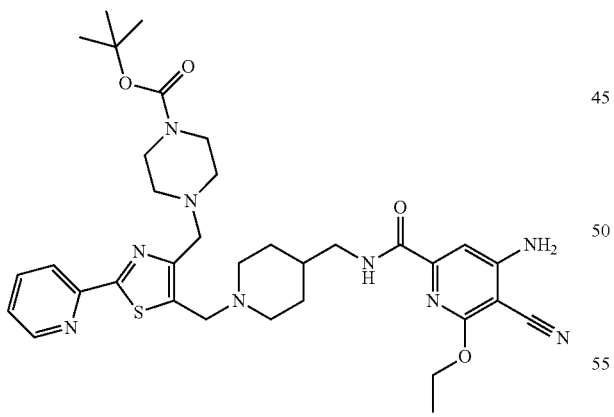

A mixture of the compound made in Example 158 (115 mg) and the compound made in Example 226 (90 mg) in methanol (1 mL) was stirred at room temperature for 18 hours. Sodium triacetoxyborohydride (13 mg) was added and the reaction was stirred for 18 hours. The solution was concentrated. The material was stirred in a saturated aqueous sodium bicarbonate solution for 10 minutes. The material was partitioned between a saturated aqueous sodium bicarbonate solution and ethyl acetate. The organic layer was dried over anhydrous magnesium sulfate and concentrated. The residue was purified by scavenging with silica supported amine silica gel and polystyrene supported isocyanate resin to obtain the title compound (100 mg) having the following physical data.

$^1$H NMR (CDCl$_3$): δ 8.62-8.53 (m, 1H), 8.19-8.14 (m, 1H), 7.85-7.72 (m, 2H), 7.33-7.26 (m, 1H), 7.19 (s, 1H), 5.14 (s, 2H), 4.44 (q, J=7.1 Hz, 2H), 3.72 (s, 2H), 3.69 (s, 2H), 3.53-3.38 (m, 8H), 3.37-3.29 (m, 2H), 3.01-2.92 (m, 2H), 2.58-2.42 (m, 3H), 2.08 (m, 2H), 1.75-1.58 (m, 2H), 1.45 (s, 9H), 1.41-1.26 (m, 3H);
Mass data (ESI, Pos.): m/z 676 (M+H)$^+$.

Example 160

4-amino-5-cyano-6-ethoxy-N-[(1-{[4-(1-piperazinylmethyl)-2-(2-pyridinyl)-1,3-thiazol-5-yl]methyl}-4-piperidinyl)methyl]-2-pyridinecarboxamide tris(trifluoroacetate)

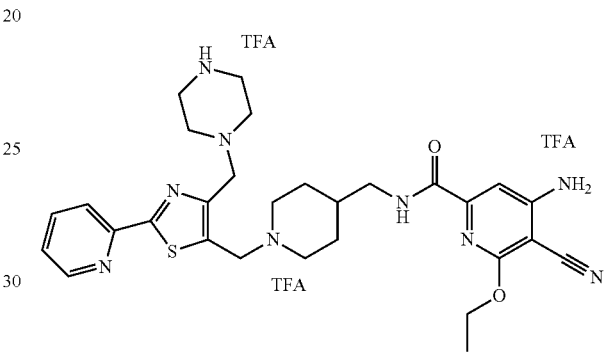

A solution of the compound prepared in Example 159 (100 mg) in dichloromethane (1 mL)-trifluoroacetic acid (228 mL) was stirred for 30 minutes. The reaction was concentrated and the excess trifluoroacetic acid was removed via azeotropic distillation from toluene and hexane to obtain the title compound (110 mg) having the following physical data.

$^1$H NMR (DMSO-d$_6$): δ 8.73-8.56 (m, 2H), 8.16-8.10 (m, 1H), 8.04-7.95 (m, 1H), 7.59-7.53 (m, 1H), 7.38-7.29 (m, 1H), 7.04 (s, 1H), 4.69 (s, 2H), 4.48 (q, J=7.1 Hz, 2H), 3.99-3.92 (m, 2H), 3.52-3.42 (m, 2H), 3.28-2.99 (m, 9H), 2.90-2.79 (m, 4H), 1.90-1.80 (m, 3H), 1.52-1.37 (m 2H), 1.32 (t, J=7.1 Hz, 3H);
Mass data (ESI, Pos.): m/z 576 (M+H)$^+$.

Example 161

4-Amino-5-cyano-6-morpholino-N4(1-((2-(pyridin-2-yl)thiazol-5-yl)methyl)piperidin-4-yl)methyl)picolinamide

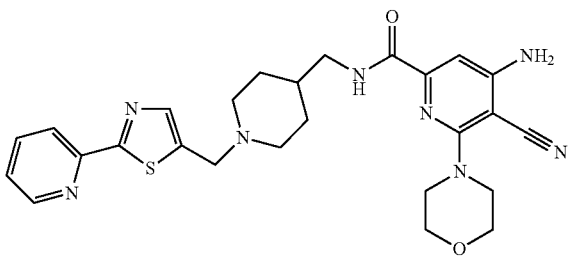 [SMILES: N#Cc1c(N)cc(C(=O)NCC2CCN(Cc3cnc(-c4ccccn4)s3)CC2)nc1N1CCOCC1]

The compound prepared in Example 215 (0.075 g) and morpholine (0.279 g) were suspended in N,N-dimethyl acetamide (1 mL) and heated at 160° C. in a microwave reactor for 10 minutes. The solution was diluted with ethyl acetate, washed sequentially with saturated aqueous sodium bicarbonate solution and brine. The organics were dried over magnesium sulfate and concentrated under reduced pressure to afford the crude material, which was purified by flash column chromatography (eluant: 2% (9:1 methanol/concentrated ammonium hydroxide)/ethyl acetate) to afford the title compound (0.065 g) having the following physical data.

$^1$H NMR (CDCl$_3$): δ 8.60-8.59 (m, 1H), 8.14 (d, J=7.9 Hz, 1H), 7.87-7.83 (m, 1H), 7.78-7.76 (m, 1H), 7.67 (s, 1H), 7.32-7.29 (m, 1H), 7.09 (s, 1H), 5.14 (s, 2H), 3.86-3.84 (m, 4H), 3.78 (s, 2H), 3.63-3.60 (m, 4H), 3.33 (t, J=6.5 Hz, 2H), 3.01-2.94 (m, 2H), 2.09-2.07 (m, 2H), 1.72-1.70 (m, 2H), 1.62-1.56 (m, 1H), 1.42-1.31 (m, 2H);

Mass data (APCI, Pos.): m/z 519 (M+H)$^+$.

Example 162

4-Amino-5-cyano-6-(piperazin-1-yl)-N-((1-((2-(pyridin-2-yl)thiazol-5-yl)methyl)piperidin-4-yl)methyl)picolinamide

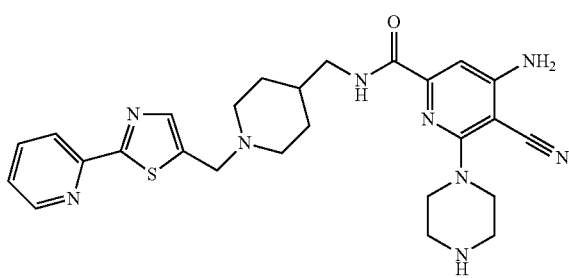 [SMILES: N#Cc1c(N)cc(C(=O)NCC2CCN(Cc3cnc(-c4ccccn4)s3)CC2)nc1N1CCNCC1]

According to the same procedure described in Example 161, using the corresponding amine instead of morpholine, the title compound having the following physical data was obtained.

$^1$H NMR (CDCl$_3$): δ 8.60-8.59 (m, 1H), 8.14 (d, J=7.9 Hz, 1H), 7.91-7.88 (m, 1H), 7.80-7.77 (m, 1H), 7.67 (s, 1H), 7.32-7.29 (m, 1H), 7.04 (s, 1H), 5.10 (s, 2H), 3.77 (s, 2H), 3.63-3.59 (m, 4H), 3.33 (t, J=6.5 Hz, 2H), 3.04-3.03 (m, 2H), 2.97-2.95 (m, 2H), 2.08-2.03 (m, 2H), 1.82 (br s, 1H) 1.73-1.70 (m, 2H), 1.64-1.54 (m, 1H), 1.41-1.32 (m, 2H), 1.28-1.24 (m, 2H);

Mass data (APCI, Pos.): m/z 518 (M+H)$^+$.

Example 163

4-Amino-5-cyano-6-(4-methylpiperazin-1-yl)-N-((1-((2-(pyridin-2-yl)thiazol-5-yl)methyl)piperidin-4-yl)methyl)picolinamide

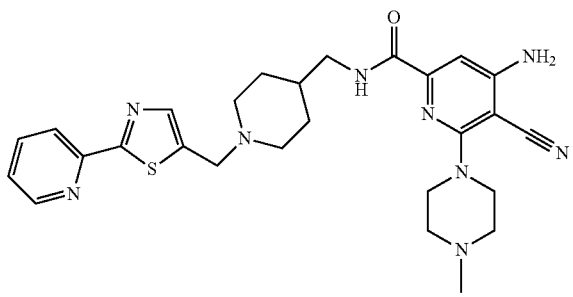 [SMILES: CN1CCN(c2nc(C(=O)NCC3CCN(Cc4cnc(-c5ccccn5)s4)CC3)cc(N)c2C#N)CC1]

According to the same procedure described in Example 161, using the corresponding amine instead of morpholine, the title compound having the following physical data was obtained.

$^1$H NMR (CDCl$_3$): δ 8.60-8.59 (m, 1H), 8.15-8.13 (m, 1H), 7.91-7.87 (m, 1H), 7.80-7.76 (m, 1H), 7.67 (s, 1H), 7.31-7.28 (m, 1H), 7.07 (s, 1H), 5.16 (s, 2H), 3.78 (s, 2H), 3.67-3.65 (m, 4H), 3.34-3.31 (m, 2H), 2.98-2.95 (m, 2H), 2.58-2.56 (m, 4H), 2.35 (s, 3H), 2.09-2.05, (m, 2H), 1.73-1.70 (m, 2H), 1.64-1.54 (m, 1H), 1.41-1.31 (m, 2H);

Mass data (APCI, Pos.): m/z 532 (M+H)$^+$.

Example 164

4-Amino-5-cyano-6-(cyclopropylamino)-N-((1-((2-(pyridin-2-yl)thiazol-5-yl)methyl)piperidin-4-yl)methyl)picolinamide

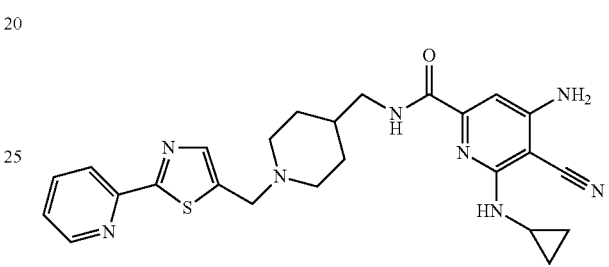

According to the same procedure described in Example 161, using the corresponding amine instead of morpholine, the title compound having the following physical data was obtained.

$^1$H NMR (CDCl$_3$): δ 8.60-8.59 (m, 1H), 8.20-8.17 (m, 1H), 8.15-8.13 (m, 1H), 7.67 (s, 1H), 7.31-7.28 (m, 1H), 6.96 (s, 1H), 5.26 (br s, 1H), 5.03 (br s, 2H), 3.77 (s, 2H), 3.34-3.31 (m, 2H), 3.01-2.94 (m, 3H), 2.82-2.75 (m, 1H), 2.08-2.05 (m, 2H), 1.75-1.71 (m, 2H), 1.63-1.53 (m, 1H), 1.42-1.33 (m, 2H), 0.84-0.83 (m, 2H), 0.62-0.58 (m, 2H);

Mass data (APCI, Pos.): m/z 489 (M+H)$^+$.

Example 165

4-Amino-5-cyano-6-(2-hydroxyethylamino)-N-((1-((2-(pyridin-2-yl)thiazol-5-yl)methyl)piperidin-4-yl)methyl)picolinamide

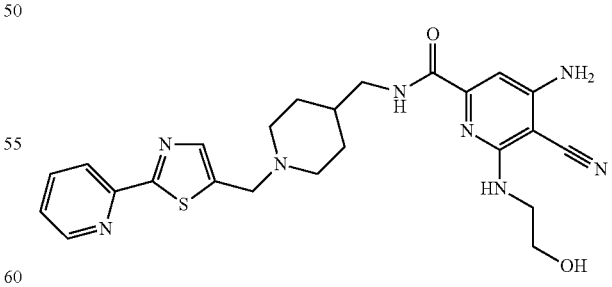

According to the same procedure described in Example 161, using the corresponding amine instead of morpholine, the title compound having the following physical data was obtained.

$^1$H NMR (CDCl$_3$): δ 8.59-8.58 (m, 1H), 8.16-8.14 (m, 1H), 7.95-7.92 (m, 1H), 7.80-7.77 (m, 1H), 7.67 (s, 1H), 7.32-7.29

(m, 1H), 6.94 (s, 1H), 5.45-5.42 (m, 1H), 5.11 (s, 2H), 3.88 (t, J=5.4 Hz, 2H), 3.77 (s, 2H), 3.69-3.67 (s, 2H), 3.34 (t, J=5.9 Hz, 2H), 2.98-2.95 (m, 2H), 2.10-2.05 (m, 3H), 1.71-1.58 (m, 3H), 1.45-1.35 (m, 1H);

Mass data (APCI, Pos.): m/z 493 (M+H)$^+$.

Example 166

4-Amino-5-cyano-6-(2-methoxyethylamino)-N-((1-((2-(pyridin-2-yl)thiazol-5-yl)methyl)piperidin-4-yl)methyl)picolinamide

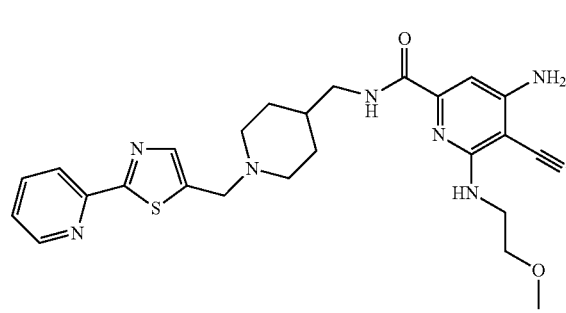

According to the same procedure described in Example 161, using the corresponding amine instead of morpholine, the title compound having the following physical data was obtained.

$^1$H NMR (CDCl$_3$): δ 8.60-8.59 (m, 1H), 8.15-8.13 (m, 1H), 7.96-7.93 (m, 1H), 7.80-7.77 (m, 1H), 7.67 (s, 1H), 7.31-7.29 (m, 1H), 6.94 (s, 1H), 5.36-5.33 (m, 1H), 1.97 (s, 2H), 3.77 (s, 2H), 3.67-3.64 (m, 2H), 3.59-3.57 (m, 2H), 3.39 (s, 3H), 3.31 (t, J=6.5 Hz, 2H), 3.01-2.94 (m, 3H), 2.08-2.04 (m, 1H), 1.73-1.70 (m, 2H), 1.63-1.53 (m, 1H), 1.41-1.32 (m, 2H);

Mass data (APCI, Pos.): m/z 507 (M+H)$^+$.

Example 167

4-Amino-5-cyano-6-(2-(dimethylamino)ethylamino)-N-((1-((2-(pyridin-2-yl)thiazol-5-yl)methyl)piperidin-4-yl)methyl)picolinamide

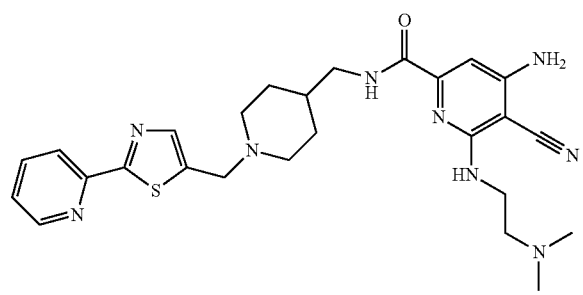 [SMILES: CN(C)CCNc1nc(C(=O)NCC2CCN(Cc3cnc(-c4ccccn4)s3)CC2)cc(N)c1C#N]

According to the same procedure described in Example 161, using the corresponding amine instead of morpholine, the title compound having the following physical data was obtained.

$^1$H NMR (CDCl$_3$): δ 8.60-8.59 (m, 1H), 8.15-8.13 (m, 1H), 7.96-7.93 (m, 1H), 7.80-7.76 (m, 1H), 7.67 (s, 1H), 7.31-7.26 (m, 1H), 6.91 (s, 1H), 5.69-5.65 (m, 1H), 5.00 (s, 2H), 3.77 (s, 2H), 3.51-3.49 (m, 2H), 3.31 (t, J=6.5 Hz, 2H), 2.98-2.95 (m, 2H), 2.55 (t, J=6.1 Hz, 2H), 2.28 (s, 6H), 2.06-2.04 (m, 2H), 1.74-1.71 (m, 2H), 1.63-1.53 (m, 1H), 1.41-1.31 (m, 2H);

Mass data (APCI, Pos.): m/z 520 (M+H)$^+$.

Example 168

4-Amino-5-cyano-6-((2-hydroxyethyl)(methyl)amino)-N-((1-((2-(pyridin-2-yl)thiazol-5-yl)methyl)piperidin-4-yl)methyl)picolinamide

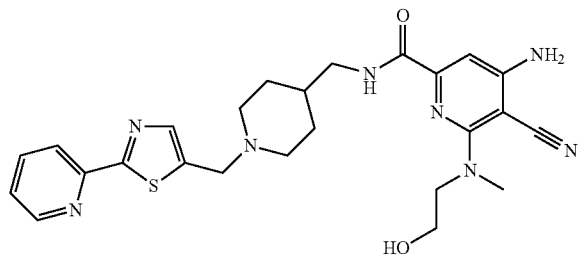 [SMILES: CN(CCO)c1nc(C(=O)NCC2CCN(Cc3cnc(-c4ccccn4)s3)CC2)cc(N)c1C#N]

According to the same procedure described in Example 161, using the corresponding amine instead of morpholine, the title compound having the following physical data was obtained.

$^1$H NMR (CDCl$_3$): δ 8.60-8.59 (m, 1H), 8.15-8.13 (m, 1H), 7.83-7.77 (m, 2H), 7.68 (s, 1H), 7.32-7.29 (m, 1H), 6.94 (s, 1H), 5.21 (s, 2H), 3.94-3.92 (m, 2H), 3.81-3.77 (m, 3H), 3.40 (s, 3H), 3.34 (t, J=5.7 Hz, 2H), 2.98-2.96 (m, 2H), 2.10-2.05 (m, 2H), 1.70-1.57 (m, 3H), 1.44-1.41 (m, 2H) 1.26 (t, J=7.1 Hz, 1H);

Mass data (APCI, Pos.): m/z 507 (M+H)$^+$.

Example 169

4-Amino-6-(bis(2-hydroxyethyl)amino)-5-cyano-N-((1-((2-(pyridin-2-yl)thiazol-5-yl)methyl)piperidin-4-yl)methyl)picolinamide

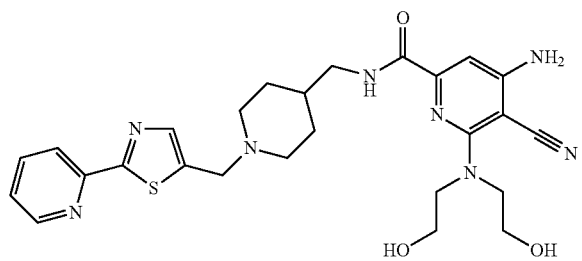 [SMILES: N#Cc1c(N)cc(C(=O)NCC2CCN(Cc3cnc(-c4ccccn4)s3)CC2)nc1N(CCO)CCO]

According to the same procedure described in Example 161, using the corresponding amine instead of morpholine, the title compound having the following physical data was obtained.

$^1$H NMR (CDCl$_3$): δ 8.56-8.54 (m, 1H), 8.17-8.15 (m, 1H), 7.83-7.78 (m, 2H), 7.67 (s, 1H), 7.35-7.21 (m, 1H), 6.94 (s, 1H), 5.17 (m, 2H), 4.58 (br s, 2H), 4.10-4.08 (m, 4H), 4.01-3.98 (m, 4H), 3.74 (s, 2H), 3.43-3.41 (m, 2H), 2.99-2.96 (m, 2H), 2.13-2.07 (m, 2H), 1.71-1.63 (m, 3H), 1.47-1.38 (m, 2H);

Mass data (APCI, Pos.): m/z 537 (M+H)$^+$.

Example 170

(S)-4-Amino-5-cyano-6-(1-hydroxypropan-2-ylamino)-N-((1-((2-(pyridin-2-yl)thiazol-5-yl)methyl)piperidin-4-yl)methyl)picolinamide

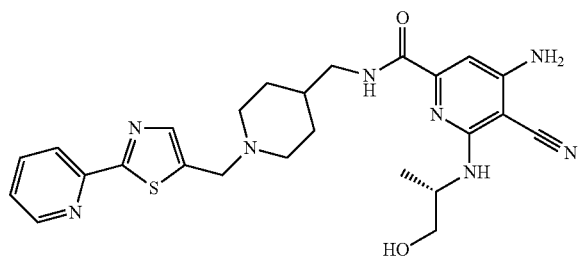 [SMILES: C[C@@H](CO)Nc1nc(C(=O)NCC2CCN(Cc3cnc(-c4ccccn4)s3)CC2)cc(N)c1C#N]

According to the same procedure described in Example 161, using the corresponding amine instead of morpholine, the title compound having the following physical data was obtained.

$^1$H NMR (CDCl$_3$): δ 8.60-8.58 (m, 1H), 8.16-8.14 (m, 1H), 7.92-7.90 (m, 1H), 7.81-7.77 (m, 1H), 7.68 (s, 1H), 7.33-7.29 (m, 1H), 6.91 (s, 1H), 5.03-5.01 (m, 3H), 4.31-4.25 (m, 1H), 3.77-3.73 (m, 4H), 3.46-3.40 (m, 1H), 3.29-3.22 (m, 1H), 2.99-2.94 (m, 1H), 2.11-2.02 (m, 3H), 1.72-1.58 (m, 3H), 1.46-1.37 (m, 2H), 1.32 (d, J=6.7 Hz, 3H), 1.26 (t, J=7.1 Hz, 1H);

Mass data (APCI, Pos.): m/z 507 (M+H)$^+$.

Example 171

4-Amino-5-cyano-6-(piperidin-1-yl)-N-((1-((2-(pyridin-2-yl)thiazol-5-yl)methyl)piperidin-4-yl)methyl)picolinamide

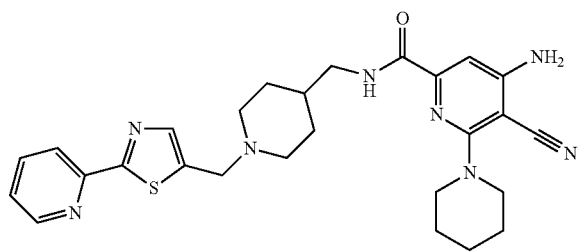 [SMILES: N#Cc1c(N)cc(C(=O)NCC2CCN(Cc3cnc(-c4ccccn4)s3)CC2)nc1N1CCCCC1]

According to the same procedure described in Example 161, using the corresponding amine instead of morpholine, the title compound having the following physical data was obtained.

$^1$H NMR (CDCl$_3$): δ 8.60-8.58 (m, 1H), 8.15-8.13 (m, 1H), 7.94-7.92 (m, 1H), 7.81-7.78 (m, 1H), 7.67 (s, 1H), 7.31-7.28 (m, 1H), 7.00 (s, 1H), 5.10 (s, 2H), 3.78 (s, 2H), 3.60-3.58 (m, 4H), 3.32 (t, J=6.5 Hz, 2H), 3.01-2.94 (m, 5H), 2.09-2.04 (m, 2H), 1.73-1.57, (m, 8H), 1.42-1.32 (m, 2H);

Mass data (APCI, Pos.): m/z 517 (M+H)$^+$.

Example 172

(R)-4-Amino-5-cyano-6-(1-hydroxypropan-2-ylamino)-N-((1-((2-(pyridin-2-yl)thiazol-5-yl)methyl)piperidin-4-yl)methyl)picolinamide

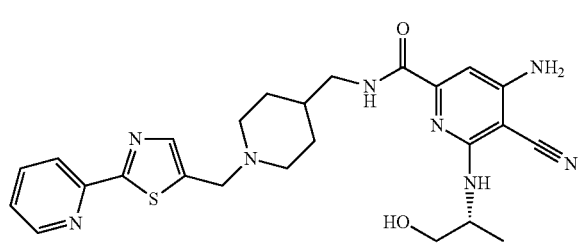 [SMILES: C[C@H](CO)Nc1nc(C(=O)NCC2CCN(Cc3cnc(-c4ccccn4)s3)CC2)cc(N)c1C#N]

According to the same procedure described in Example 161, using the corresponding amine instead of morpholine, the title compound having the following physical data was obtained.

$^1$H NMR (CDCl$_3$): δ 8.60-8.58 (m, 1H), 8.15-8.13 (m, 1H), 7.93-7.91 (m, 1H), 7.80-7.77 (m, 1H), 7.68 (s, 1H), 7.32-7.29 (m, 1H), 6.92 (s, 1H), 5.08 (s, 2H), 5.04-5.02 (m, 1H), 4.30-4.25 (m, 1H), 3.77-3.72 (m, 4H), 3.45-3.40 (m, 1H), 3.29-3.23 (m, 1H), 3.00-2.94 (m, 2H), 2.10-2.04 (m, 2H), 1.72-1.59 (m, 3H), 1.45-1.37 (m, 2H), 1.32 (d, J=6.7 Hz, 3H), 1.26 (t, J=7.1 Hz, 1H);

Mass data (APCI, Pos.): m/z 507 (M+H)$^+$.

Example 173

4-Amino-5-cyano-6-(3-hydroxyazetidin-1-yl)-N-((1-((2-(pyridin-2-yl)thiazol-5-yl)methyl)piperidin-4-yl)methyl)picolinamide

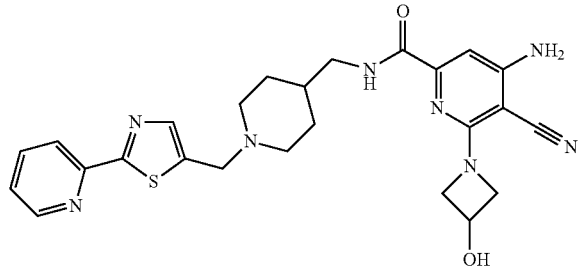 [SMILES: N#Cc1c(N)cc(C(=O)NCC2CCN(Cc3cnc(-c4ccccn4)s3)CC2)nc1N1CC(O)C1]

According to the same procedure described in Example 161, using the corresponding amine instead of morpholine, the title compound having the following physical data was obtained.

$^1$H NMR (CDCl$_3$): δ 8.58-8.56 (m, 1H), 8.21-8.19 (m, 1H), 8.10-8.06 (m, 1H), 7.83-7.80 (m, 1H), 7.68 (s, 1H), 7.35-7.32 (m, 1H), 6.85 (s, 1H), 4.98 (s, 2H), 4.88-4.82 (m, 1H), 4.61-4.57 (m, 2H), 4.25-4.21 (m, 2H), 3.74 (s, 2H), 3.37-3.34 (m, 2H), 2.98-2.95 (m, 2H), 2.08-2.03 (m, 2H), 1.67-1.64 (m, 2H), 1.52-1.43 (m, 2H), 1.26 (t, J=7.1 Hz, 2H);

Mass data (APCI, Pos.): m/z 505 (M+H)$^+$.

Example 174

4-Amino-6-(azetidin-1-yl)-5-cyano-N-((1-((2-(pyridin-2-yl)thiazol-5-yl)methyl)piperidin-4-yl)methyl)picolinamide

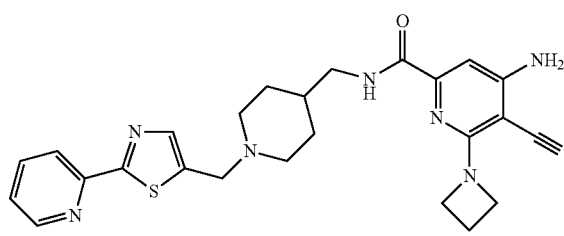

According to the same procedure described in Example 161, using the corresponding amine instead of morpholine, the title compound having the following physical data was obtained.

$^1$H NMR (CDCl$_3$): δ 8.60-8.58 (m, 1H), 8.15-8.13 (m, 1H), 7.96-7.94 (m, 1H), 7.80-7.76 (m, 1H), 7.67 (s, 1H), 7.31-7.28 (m, 1H), 6.85 (s, 1H), 4.94 (s, 2H), 4.34-4.30 (m, 4H), 3.77 (s, 2H), 3.30 (t, J=6.5 Hz, 2H), 2.97-2.94 (m, 2H), 2.42-2.36 (m, 2H), 2.09-2.04 (m, 2H), 1.71-1.69 (m, 2H), 1.61-1.52 (m, 1H), 1.39-1.32 (m, 2H);

Mass data (APCI, Pos.): m/z 489 (M+H)$^+$.

Example 175

(R)-4-Amino-5-cyano-6-(2-hydroxypropylamino)-N-((1-((2-(pyridin-2-yl)thiazol-5-yl)methyl)piperidin-4-yl)methyl)picolinamide

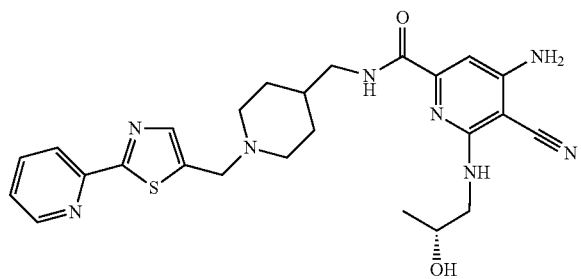 [SMILES: C[C@@H](O)CNc1nc(C(=O)NCC2CCN(Cc3cnc(-c4ccccn4)s3)CC2)cc(N)c1C#N]

According to the same procedure described in Example 161, using the corresponding amine instead of morpholine, the title compound having the following physical data was obtained.

$^1$H NMR (CDCl$_3$): δ 8.60-8.58 (m, 1H), 8.15-8.13 (m, 1H), 7.90-7.88 (m, 1H), 7.80-7.76 (m, 1H), 7.67 (s, 1H), 7.32-7.29 (m, 1H), 6.94 (s, 1H), 5.45-5.43 (m, 1H), 5.13 (s, 2H), 4.15-4.06 (m, 1H), 3.77 (s, 2H), 3.65-3.57 (m, 2H), 3.44-3.30 (m, 3H), 2.98-2.95 (m, 2H), 2.11-2.04 (m, 2H), 1.72-1.69 (m, 2H), 1.65-1.56 (m, 1H), 1.43-1.37 (m, 2H), 1.26 (d, J=6.2 Hz, 3H);

Mass data (APCI, Pos.): m/z 507 (M+H)$^+$.

Example 176

(S)-4-Amino-5-cyano-6-(2-hydroxypropylamino)-N-((1-((2-(pyridin-2-yl)thiazol-5-yl)methyl)piperidin-4-yl)methyl)picolinamide

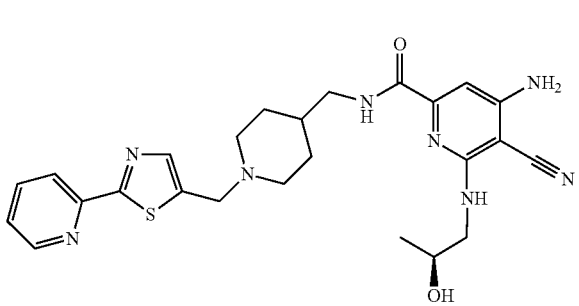 [SMILES: C[C@H](O)CNc1nc(C(=O)NCC2CCN(Cc3cnc(-c4ccccn4)s3)CC2)cc(N)c1C#N]

According to the same procedure described in Example 161, using the corresponding amine instead of morpholine, the title compound having the following physical data was obtained.

$^1$H NMR (CDCl$_3$): δ 8.60-8.58 (m, 1H), 8.15-8.13 (m, 1H), 7.90-7.88 (m, 1H), 7.80-7.77 (m, 1H), 7.67 (s, 1H), 7.32-7.29 (m, 1H), 6.95 (s, 1H), 5.45-5.43 (m, 1H), 5.14 (s, 2H), 4.15-4.06 (m, 1H), 3.77 (s, 2H), 3.65-3.57 (m, 2H), 3.44-3.30 (m, 3H), 2.98-2.95 (m, 2H), 2.11-2.04 (m, 2H), 1.72-1.69 (m, 2H), 1.65-1.56 (m, 1H), 1.43-1.37 (m, 2H), 1.25 (d, J=6.4 Hz, 3H);

Mass data (APCI, Pos.): m/z 507 (M+H)$^+$.

Example 177

4-Amino-5-cyano-6-(3-hydroxypropylamino)-N-((1-((2-(pyridin-2-yl)thiazol-5-yl)methyl)piperidin-4-yl)methyl)picolinamide

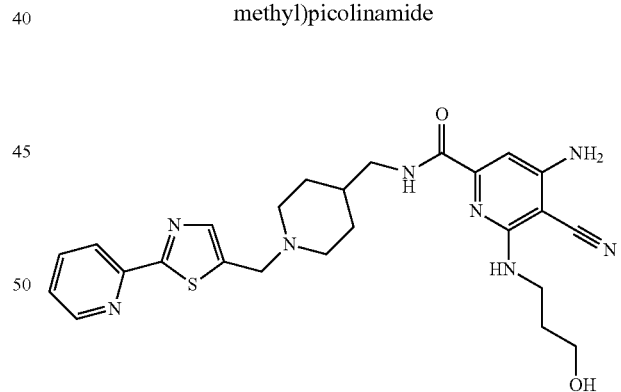

According to the same procedure described in Example 161, using the corresponding amine instead of morpholine, the title compound having the following physical data was obtained.

$^1$H NMR (CDCl$_3$): δ 8.60-8.58 (m, 1H), 8.16-8.14 (m, 1H), 8.04-8.06 (m, 1H), 7.80-7.77 (m, 1H), 7.68 (s, 1H), 7.32-7.29 (m, 1H), 6.89 (s, 1H), 5.43-5.40 (m, 1H), 5.00 (s, 2H), 3.79-3.76 (m, 4H), 3.68-3.65 (m, 2H), 3.35-3.33 (m, 2H), 2.99-2.97 (m, 2H), 2.75 (br s, 1H), 2.08-2.05 (m, 2H), 1.91-1.86 (m, 2H), 1.71-1.62 (m, 3H), 1.49-1.40 (m, 2H);

Mass data (APCI, Pos.): m/z 507 (M+H)$^+$.

Example 178

(S)-4-Amino-5-cyano-6-(1-hydroxybutan-2-ylamino)-N-((1-((2-(pyridin-2-yl)thiazol-5-yl)methyl)piperidin-4-yl)methyl)picolinamide

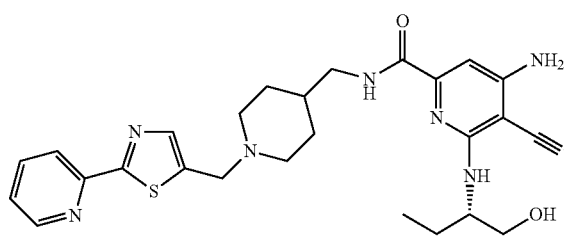

According to the same procedure described in Example 161, using the corresponding amine instead of morpholine, the title compound having the following physical data was obtained.

$^1$H NMR (CDCl$_3$): δ 8.59-8.57 (m, 1H), 8.15-8.13 (m, 1H), 7.90-7.88 (m, 1H), 7.81-7.77 (m, 1H), 7.68 (s, 1H), 7.32-7.29 (m, 1H), 6.90 (s, 1H), 5.01 (s, 2H), 4.15-4.05 (m, 1H), 3.77-3.76 (m, 3H), 3.46-3.39 (m, 1H), 3.33-3.21 (m, 1H), 2.99-2.93 (m, 2H), 2.10-2.05 (m, 2H), 1.83-1.58 (m, 6H), 1.45-1.36 (m, 2H), 1.28-1.23 (m, 2H), 1.01 (t, J=7.5 Hz, 2H);

Mass data (APCI, Pos.): m/z 521 (M+H)$^+$.

Example 179

(R)-4-Amino-5-cyano-6-(1-hydroxybutan-2-ylamino)-N-((1-((2-(pyridin-2-yl)thiazol-5-yl)methyl)piperidin-4-yl)methyl)picolinamide

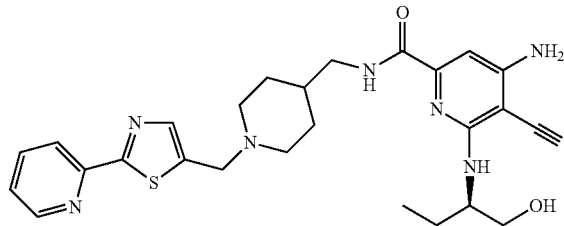

According to the same procedure described in Example 161, using the corresponding amine instead of morpholine, the title compound having the following physical data was obtained.

$^1$H NMR (CDCl$_3$): δ 8.59-8.57 (m, 1H), 8.16-8.14 (m, 1H), 7.90-7.88 (m, 1H), 7.81-7.77 (m, 1H), 7.68 (s, 1H), 7.33-7.29 (m, 1H), 6.90 (s, 1H), 5.00 (s, 2H), 4.15-4.05 (m, 1H), 3.77-3.76 (m, 3H), 3.46-3.39 (m, 1H), 3.33-3.22 (m, 1H), 2.99-2.93 (m, 2H), 2.10-2.05 (m, 2H), 1.82-1.58 (m, 6H), 1.45-1.36 (m, 2H), 1.28-1.24 (m, 2H), 1.01 (t, J=7.5 Hz, 2H);

Mass data (APCI, Pos.): m/z 521 (M+H)$^+$.

Example 180

4-Amino-5-cyano-6-(2-morpholinoethylamino)-N-((1-((2-(pyridin-2-yl)thiazol-5-yl)methyl)piperidin-4-yl)methyl)picolinamide

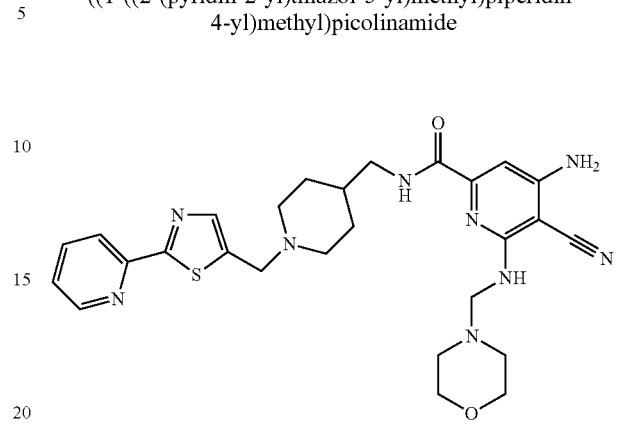

According to the same procedure described in Example 161, using the corresponding amine instead of morpholine, the title compound having the following physical data was obtained.

$^1$H NMR (CDCl$_3$): δ 8.60-8.58 (m, 1H), 8.15-8.13 (m, 1H), 7.98-7.96 (m, 1H), 7.81-7.77 (m, 1H), 7.67 (s, 1H), 7.33-7.29 (m, 1H), 6.90 (s, 1H), 5.80-5.78 (m, 1H), 4.95 (s, 2H), 3.77-3.73 (m, 7H), 3.53-3.50 (m, 2H), 3.32 (t, J=6.5 Hz, 2H), 2.98-2.95 (m, 2H), 2.64 (t, J=6.0 Hz, 2H), 2.52-2.49 (m, 4H), 2.09-2.04 (m, 2H), 1.74-1.70 (m, 2H), 1.39-1.33 (m, 2H);

Mass data (APCI, Pos.): m/z 562 (M+H)$^+$.

Example 181

(R)-4-Amino-5-cyano-6-(2,3-dihydroxypropylamino)-N-((1-((2-(pyridin-2-yl)thiazol-5-yl)methyl)piperidin-4-yl)methyl)picolinamide

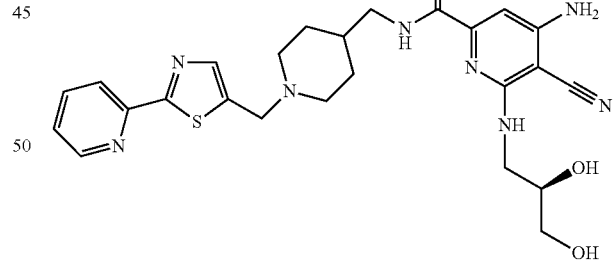

According to the same procedure described in Example 161, using the corresponding amine instead of morpholine, the title compound having the following physical data was obtained.

$^1$H NMR (CDCl$_3$): δ 8.60-8.58 (m, 1H), 8.15-8.13 (m, 1H), 7.92-7.90 (m, 1H), 7.81-7.76 (m, 1H), 7.69 (s, 1H), 7.33-7.30 (m, 1H), 6.90 (s, 1H), 5.46-5.44 (m, 1H), 4.99 (s, 2H), 4.02-3.97 (m, 1H), 3.78-3.73 (m, 3H), 3.67-3.62 (m, 2H), 3.39-3.34 (m, 3H), 3.02-2.98 (m, 2H), 2.12-2.04 (m, 2H), 1.68-1.65 (m, 3H), 1.58-1.53 (m, 3H);

Mass data (APCI, Pos.): m/z 523 (M+H)$^+$.

Example 182

(S)-4-Amino-5-cyano-6-(2,3-dihydroxypropy-lamino)-N-((1-((2-(pyridin-2-yl)thiazol-5-yl)methyl)piperidin-4-yl)methyl)picolinamide

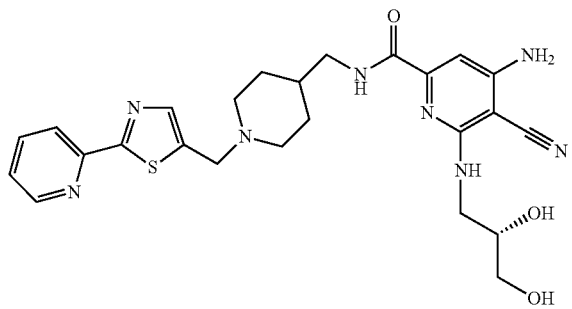 [SMILES: N#Cc1c(N)cc(C(=O)NCC2CCN(Cc3cnc(-c4ccccn4)s3)CC2)nc1NC[C@H](O)CO]

According to the same procedure described in Example 161, using the corresponding amine instead of morpholine, the title compound having the following physical data was obtained.

$^1$H NMR (CDCl$_3$): δ 8.60-8.58 (m, 1H), 8.16-8.14 (m, 1H), 7.92-7.90 (m, 1H), 7.81-7.77 (m, 1H), 7.69 (s, 1H), 7.33-7.30 (m, 1H), 6.90 (s, 1H), 5.46-5.44 (m, 1H), 4.99 (s, 2H), 4.02-3.98 (m, 1H), 3.78-3.73 (m, 3H), 3.67-3.62 (m, 2H), 3.40-3.35 (m, 3H), 3.02-2.99 (m, 2H), 2.12-2.04 (m, 2H), 1.68-1.66 (m, 3H), 1.57-1.53 (m, 3H);

Mass data (APCI, Pos.): m/z 523 (M+H)$^+$.

Example 183

4-Amino-5-cyano-6-(1-methylpiperidin-4-ylamino)-N-((1-((2-(pyridin-2-yl)thiazol-5-yl)methyl)piperidin-4-yl)methyl)picolinamide

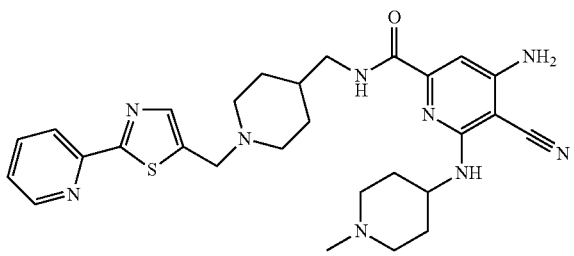 [SMILES: CN1CCC(Nc2nc(C(=O)NCC3CCN(Cc4cnc(-c5ccccn5)s4)CC3)cc(N)c2C#N)CC1]

According to the same procedure described in Example 161, using the corresponding amine instead of morpholine, the title compound having the following physical data was obtained.

$^1$H NMR (CDCl$_3$): δ 8.60-8.58 (m, 1H), 8.15-8.13 (m, 1H), 7.94-7.92 (m, 1H), 7.80-7.76 (m, 1H), 7.68 (s, 1H), 7.32-7.29 (m, 1H), 6.88 (s, 1H), 5.46-5.44 (m, 1H), 4.95 (s, 2H), 4.89-4.86 (m, 1H), 3.90 (br s, 1H), 3.78 (s, 2H), 3.32 (t, J=6.4 Hz, 2H), 2.99-2.96 (m, 2H), 2.82-2.80 (m, 2H), 2.28 (s, 3H), 2.17-2.02 (m, 6H), 1.72-1.70 (m, 2H), 1.64-1.56 (m, 2H), 1.41-1.36 (m, 2H);

Mass data (APCI, Pos.): m/z 546 (M+H)$^+$.

Example 184

4-Amino-5-cyano-6-(4-hydroxypiperidin-1-yl)-N-((1-((2-(pyridin-2-yl)thiazol-5-yl)methyl)piperidin-4-yl)methyl)picolinamide

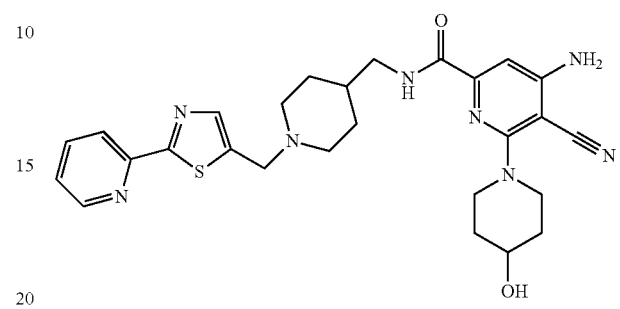

According to the same procedure described in Example 161, using the corresponding amine instead of morpholine, the title compound having the following physical data was obtained.

$^1$H NMR (CDCl$_3$): δ 8.60-8.58 (m, 1H), 8.17-8.15 (m, 1H), 7.95-7.93 (m, 1H), 7.81-7.78 (m, 1H), 7.67 (s, 1H), 7.33-7.29 (m, 1H), 7.04 (s, 1H), 5.16 (s, 2H), 4.07-4.02 (m, 3H), 3.76 (s, 2H), 3.42-3.33 (m, 4H), 2.99-2.96 (m, 2H), 2.28 (s, 1H), 2.10-2.02 (m, 4H), 1.77-1.58 (m, 5H), 1.47-1.35 (m, 2H);

Mass data (APCI, Pos.): m/z 533 (M+H)$^+$.

Example 185

4-Amino-5-cyano-6-(4-(hydroxymethyl)piperidin-1-yl)-N-((1-((2-(pyridin-2-yl)thiazol-5-yl)methyl)piperidin-4-yl)methyl)picolinamide

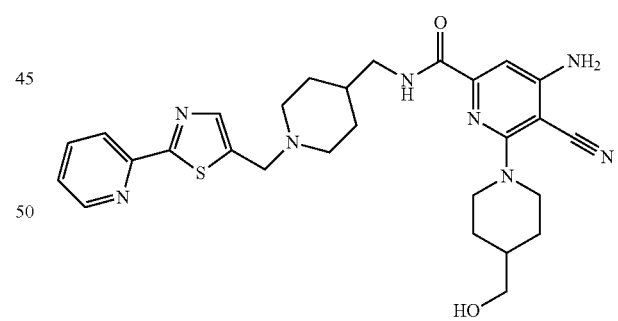

According to the same procedure described in Example 161, using the corresponding amine instead of morpholine, the title compound having the following physical data was obtained.

$^1$H NMR (CDCl$_3$): δ 8.60-8.58 (m, 1H), 8.16-8.14 (m, 1H), 7.95-7.93 (m, 1H), 7.81-7.77 (m, 1H), 7.68 (s, 1H), 7.33-7.29 (m, 1H), 7.01 (s, 1H), 5.09 (s, 2H), 4.32-4.29 (m, 2H), 3.77 (s, 2H), 3.57 (t, J=6.2 Hz, 4H), 3.34 (t, J=6.2 Hz, 3H), 3.06-2.94 (m, 3H), 2.10-2.03 (m, 2H), 1.89-1.78 (m, 2H), 1.72-1.69 (m, 2H), 1.65-1.55 (m, 1H), 1.47-1.35 (m, 4H);

Mass data (APCI, Pos.): m/z 547 (M+H)$^+$.

Example 186

4-Amino-5-cyano-6-(3-(dimethylamino)propylamino)-N-((1-((2-(pyridin-2-yl)thiazol-5-yl)methyl)piperidin-4-yl)methyl)picolinamide

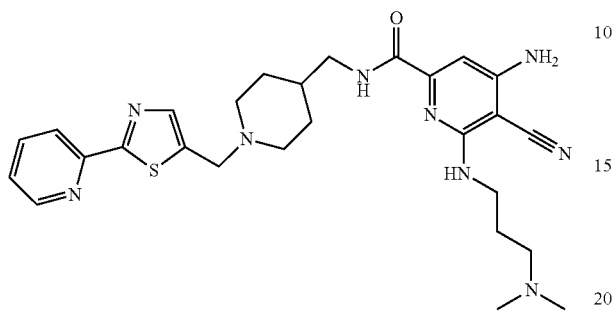

According to the same procedure described in Example 161, using the corresponding amine instead of morpholine, the title compound having the following physical data was obtained.

¹H NMR (CDCl₃): δ 8.60-8.58 (m, 1H), 8.15-8.13 (m, 1H), 8.05-8.02 (m, 1H), 7.80-7.76 (m, 1H), 7.67 (s, 1H), 7.58 (s, 1H), 7.32-7.28 (m, 1H), 6.84 (s, 1H), 4.88 (s, 2H), 3.77 (s, 2H), 3.56-3.53 (m, 2H), 3.31 (t, J=6.5 Hz, 3H), 2.97-2.95 (m, 2H), 2.50-2.47 (m, 2H), 2.29 (s, 6H), 2.09-2.04 (m, 2H), 1.79-1.71 (m, 3H), 1.63-1.54 (m, 1H), 1.40-1.32 (m, 2H);

Mass data (APCI, Pos.): m/z 534 (M+H)⁺.

Example 187

4-Amino-6-(3-aminopropylamino)-5-cyano-N-((1-((2-(pyridin-2-yl)thiazol-5-yl)methyl)piperidin-4-yl)methyl)picolinamide

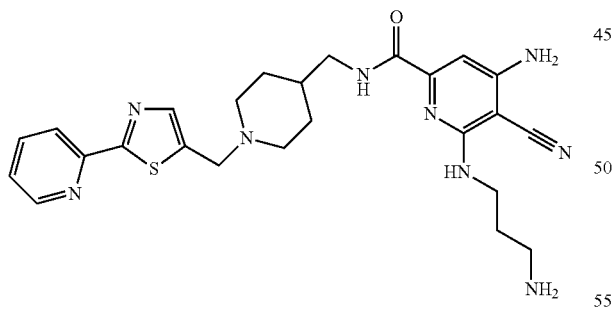

According to the same procedure described in Example 161, using the corresponding amine instead of morpholine, the title compound having the following physical data was obtained.

¹H NMR (CDCl₃): δ 8.61-8.59 (m, 1H), 8.15-8.13 (m, 1H), 8.09-8.04 (m, 1H), 7.81-7.77 (m, 1H), 7.67 (s, 1H), 7.32-7.28 (m, 1H), 6.86-6.84 (m, 1H), 4.95-4.87 (m, 2H), 3.77 (s, 2H), 3.65-3.56 (m, 4H), 3.34-3.29 (m, 2H), 2.97-2.91 (m, 2H), 2.09-2.02 (m, 4H), 1.83-1.74 (m, 4H), 1.39-1.32 (m, 4H);

Mass data (APCI, Pos.): m/z 506 (M+H)⁺.

Example 188

4-Amino-5-cyano-6-(4-(dimethylamino)piperidin-1-yl)-N-((1-((2-(pyridin-2-yl)thiazol-5-yl)methyl)piperidin-4-yl)methyl)picolinamide

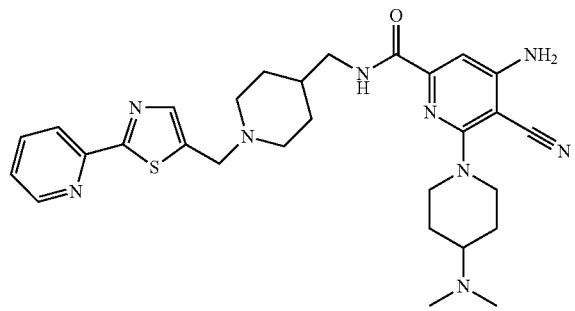 [SMILES: CN(C)C1CCN(c2nc(C(=O)NCC3CCN(Cc4cnc(-c5ccccn5)s4)CC3)cc(N)c2C#N)CC1]

According to the same procedure described in Example 161, using the corresponding amine instead of morpholine, the title compound having the following physical data was obtained.

¹H NMR (CDCl₃): δ 8.61-8.59 (m, 1H), 8.15-8.13 (m, 1H), 7.91-7.89 (m, 1H), 7.81-7.77 (m, 1H), 7.67 (s, 1H), 7.31-7.29 (m, 1H), 7.02 (s, 1H), 5.09 (s, 2H), 4.32-4.29 (m, 2H), 3.77 (s, 2H), 3.32 (t, J=6.5 Hz, 2H), 3.03-2.96 (m, 4H), 2.45-2.36 (m, 1H), 2.23 (s, 6H), 2.10-2.05 (m, 2H), 1.96-1.93 (m, 2H), 1.73-1.58 (m, 5H), 1.38-1.35 (m, 2H);

Mass data (APCI, Pos.): m/z 560 (M+H)⁺.

Example 189

4-Amino-5-cyano-6-(3-morpholinopropylamino)-N-((1-((2-(pyridin-2-yl)thiazol-5-yl)methyl)piperidin-4-yl)methyl)picolinamide

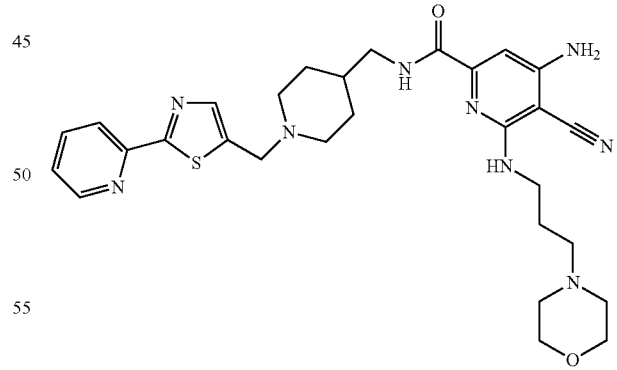

According to the same procedure described in Example 161, using the corresponding amine instead of morpholine, the title compound having the following physical data was obtained.

¹H NMR (CDCl₃): δ 8.61-8.59 (m, 1H), 8.15-8.13 (m, 1H), 8.00-7.98 (m, 1H), 7.81-7.77 (m, 1H), 7.67 (s, 1H), 7.32-7.29 (m, 1H), 6.87 (s, 1H), 6.68-6.66 (m, 1H), 4.93 (s, 2H), 3.84-3.81 (m, 4H), 3.77 (s, 2H), 3.57-3.54 (m, 2H), 3.32 (t, J=6.5

Hz, 2H), 2.98-2.95 (m, 2H), 2.54-2.49 (m, 6H), 2.09-2.04 (m, 2H), 1.86-1.79 (m, 2H), 1.74-1.70 (m, 2H), 1.64-1.56 (m, 1H), 1.41-1.32 (m, 2H);
Mass data (APCI, Pos.): m/z 576 (M+H)+.

Example 190

6-(3-(1H-Imidazol-1-yl)propylamino)-4-amino-5-cyano-N-((1-((2-(pyridin-2-yl)thiazol-5-yl)methyl)piperidin-4-yl)methyl)picolinamide

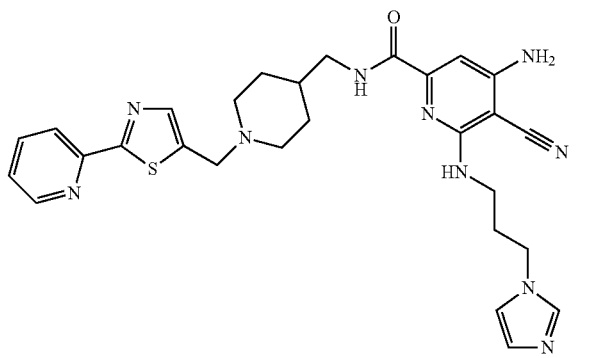 [SMILES: N#Cc1c(N)cc(C(=O)NCC2CCN(Cc3cnc(-c4ccccn4)s3)CC2)nc1NCCCn1ccnc1]

According to the same procedure described in Example 161, using the corresponding amine instead of morpholine, the title compound having the following physical data was obtained.
$^1$H NMR (CDCl$_3$): δ 8.60-8.58 (m, 1H), 8.15-8.13 (m, 1H), 7.79-7.77 (m, 1H), 7.75-7.71 (m, 1H) 7.68 (s, 1H), 7.08 (s, 1H), 6.92 (s, 2H), 5.01-4.97 (m, 1H), 4.95 (s, 2H), 4.07 (t, J=6.7 Hz, 2H), 3.77 (s, 2H), 3.52-3.45 (m, 2H), 3.37-3.33 (m, 2H), 2.98-2.95 (m, 2H), 2.10-2.04 (m, 2H), 1.72-1.67 (m, 2H), 1.57 (s, 4H), 1.42-1.33 (m, 2H);
Mass data (APCI, Pos.): m/z 557 (M+H)+.

Example 191

6-(2-(1H-Imidazol-1-yl)ethylamino)-4-amino-5-cyano-N-((1-((2-(pyridin-2-yl)thiazol-5-yl)methyl)piperidin-4-yl)methyl)picolinamide

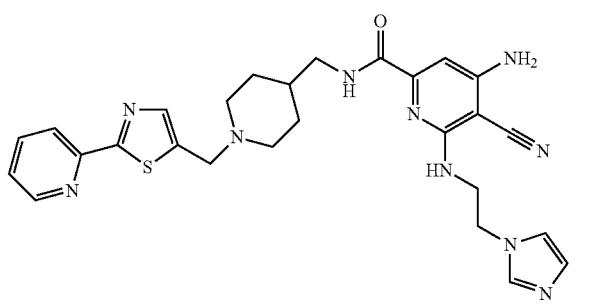 [SMILES: N#Cc1c(N)cc(C(=O)NCC2CCN(Cc3cnc(-c4ccccn4)s3)CC2)nc1NCCn1ccnc1]

According to the same procedure described in Example 161, using the corresponding amine instead of morpholine, the title compound having the following physical data was obtained.
$^1$H NMR (CDCl$_3$): δ 8.60-8.58 (m, 1H), 8.15-8.13 (m, 1H), 7.80-7.77 (m, 1H), 7.75-7.71 (m, 1H) 7.67 (s, 1H), 7.49 (s, 1H), 7.32-7.28 (m, 1H), 7.07 (s, 1H), 6.96 (s, 1H), 6.93 (s, 1H), 5.30-5.27 (m, 1H), 5.17 (s, 2H), 4.21 (t, J=5.9 Hz, 2H), 3.86-3.83 (m, 2H), 3.77 (s, 2H), 3.34 (t, J=6.3 Hz, 2H), 2.99-2.96 (m, 2H), 2.10-2.04 (m, 2H), 1.73-1.69 (m, 2H), 1.64-1.56 (m, 1H), 1.42-1.32 (m, 2H);
Mass data (APCI, Pos.): m/z 543 (M+H)+.

Example 192

4-Amino-6-(3-amino-3-oxopropylamino)-5-cyano-N-((1-((2-(pyridin-2-yl)thiazol-5-yl)methyl)piperidin-4-yl)methyl)picolinamide

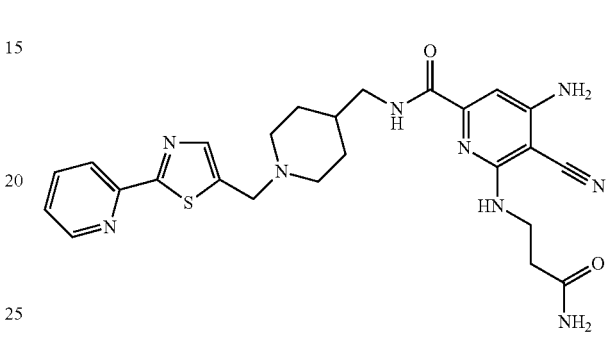

According to the same procedure described in Example 161, using the corresponding amine instead of morpholine, the title compound having the following physical data was obtained.
$^1$H NMR (CDCl$_3$): δ 8.60-8.58 (m, 1H), 8.15-8.13 (m, 1H), 8.08-8.06 (m, 1H), 7.81-7.76 (m, 1H), 7.67 (s, 1H), 7.32-7.28 (m, 1H), 6.90 (s, 1H), 5.64-5.59 (m, 2H), 5.40 (s, 1H), 4.95 (s, 2H), 3.85-3.80 (m, 2H), 3.76 (s, 2H), 3.34 (t, J=6.2 Hz, 2H), 2.98-2.95 (m, 2H), 2.56 (t, J=6.1 Hz, 2H), 2.10-2.04 (m, 2H), 1.74-1.69 (m, 2H), 1.65-1.58 (m, 1H), 1.44-1.35 (m, 2H);
Mass data (APCI, Pos.): m/z 520 (M+H)+.

Example 193

6-(2-(1H-Imidazol-4-yl)ethylamino)-4-amino-5-cyano-N-((1-((2-(pyridin-2-yl)thiazol-5-yl)methyl)piperidin-4-yl)methyl)picolinamide

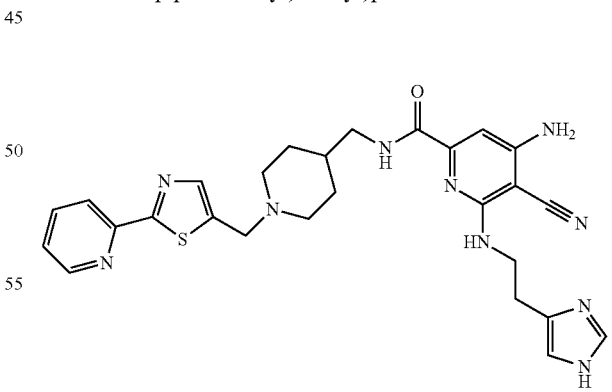

According to the same procedure described in Example 161, using the corresponding amine instead of morpholine, the title compound having the following physical data was obtained.
$^1$H NMR (CDCl$_3$): δ 8.60-8.59 (m, 1H), 8.16-8.14 (m, 2H), 7.82-7.78 (m, 1H), 7.67 (s, 1H), 7.59 (s, 1H), 7.33-7.30 (m, 1H), 6.87 (s, 1H), 6.84 (s, 1H), 5.59-5.57 (m, 1H), 5.03 (s, 2H), 3.78-3.74 (m, 5H), 3.32 (t, J=6.4 Hz, 2H), 2.94-2.92 (m, 4H), 2.08-2.03 (m, 2H), 1.72-1.70 (m, 2H), 1.64-1.56 (m, 1H), 1.39-1.34 (m, 2H);
Mass data (APCI, Pos.): m/z 543 (M+H)+.

Example 194

4-Amino-6-(3-amino-2-hydroxypropylamino)-5-cyano-N-((1-((2-(pyridin-2-yl)thiazol-5-yl)methyl)piperidin-4-yl)methyl)picolinamide

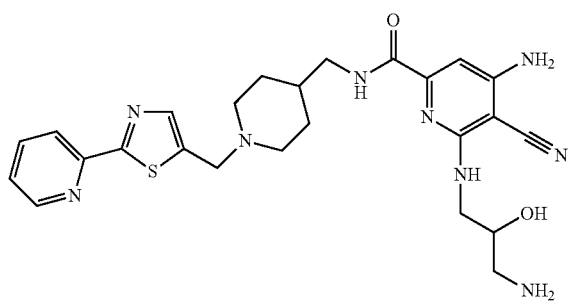 [SMILES: N#Cc1c(N)cc(C(=O)NCC2CCN(Cc3cnc(-c4ccccn4)s3)CC2)nc1NCC(O)CN]

According to the same procedure described in Example 161, using the corresponding amine instead of morpholine, the title compound having the following physical data was obtained.
$^1$H NMR (CDCl$_3$): δ 8.60-8.59 (m, 1H), 8.15-8.13 (m, 1H), 7.94-7.91 (m, 1H), 7.80-7.77 (m, 1H), 7.67 (s, 1H), 7.32-7.29 (m, 1H), 6.90 (s, 1H), 5.62 (s, 1H), 5.02 (s, 2H), 3.83-3.77 (m, 3H), 3.68-3.63 (m, 2H), 3.55-3.48 (m, 2H), 3.34-3.30 (m, 2H), 2.99-2.91 (m, 3H), 2.74-2.69 (m, 1H), 2.10-2.02 (m, 2H), 1.73-1.68 (m, 2H), 1.63-1.56 (m, 2H), 1.40-1.35 (m, 2H);
Mass data (APCI, Pos.): m/z 522 (M+H)+.

Example 195

4-Amino-5-cyano-6-(1,3-dihydroxypropan-2-ylamino)-N-((1-((2-(pyridin-2-yl)thiazol-5-yl)methyl)piperidin-4-yl)methyl)picolinamide

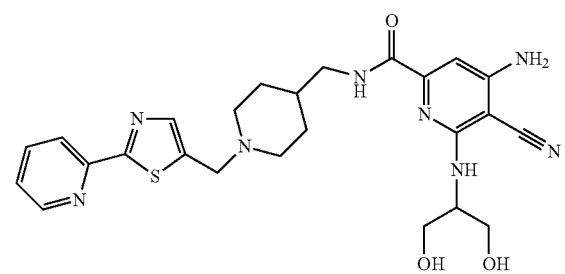 [SMILES: N#Cc1c(N)cc(C(=O)NCC2CCN(Cc3cnc(-c4ccccn4)s3)CC2)nc1NC(CO)CO]

According to the same procedure described in Example 161, using the corresponding amine instead of morpholine, the title compound having the following physical data was obtained.
$^1$H NMR (CD$_3$OD): δ 8.57 (d, J=4.8 Hz, 1H), 8.12 (d, J=8.0 Hz, 1H), 7.94-7.87 (m, 1H), 7.74 (s, 1H), 7.45-7.39 (m, 1H), 6.78 (s, 1H), 4.35-4.28 (m, 1H), 3.82 (s, 2H), 3.78-3.66 (m, 4H), 3.37-3.25 (m, 2H), 3.03-2.94 (m, 2H), 2.15-2.06 (m, 2H), 1.80-1.71 (m, 2H), 1.69-1.58 (m, 1H), 1.43-1.28 (m, 2H);
Mass data (APCI, Pos.): m/z 523 (M+H)+.

Example 196

4-Amino-6-(tert-butylamino)-5-cyano-N-((1-((2-(pyridin-2-yl)thiazol-5-yl)methyl)piperidin-4-yl)methyl)picolinamide

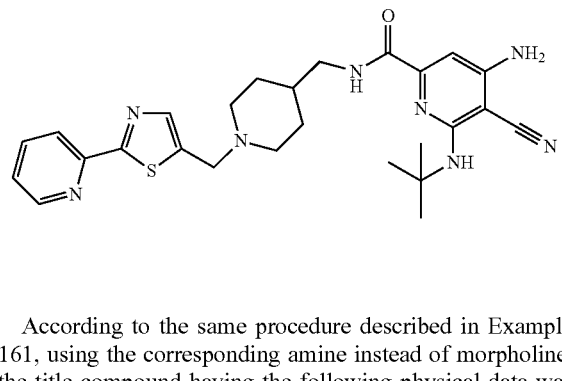

According to the same procedure described in Example 161, using the corresponding amine instead of morpholine, the title compound having the following physical data was obtained.
$^1$H NMR (CDCl$_3$): δ 8.60-8.59 (m, 1H), 8.15-8.13 (m, 1H), 7.88-7.85 (m, 1H), 7.81-7.76 (m, 1H), 7.67 (s, 1H), 7.32-7.29 (m, 1H), 6.85 (s, 1H), 4.92 (s, 1H), 4.84 (s, 2H), 3.77 (s, 2H), 3.33 (t, J=6.4 Hz, 2H), 2.98-2.95 (m, 2H), 2.09-2.03 (m, 2H), 1.75-1.71 (m, 1H), 1.49 (s, 9H), 1.41-1.35 (m, 2H), 1.24 (s, 2H);
Mass data (APCI, Pos.): m/z 505 (M+H)+.

Example 197

4-Amino-5-cyano-6-(isopropylamino)-N-((1-((2-(pyridin-2-yl)thiazol-5-yl)methyl)piperidin-4-yl)methyl)picolinamide

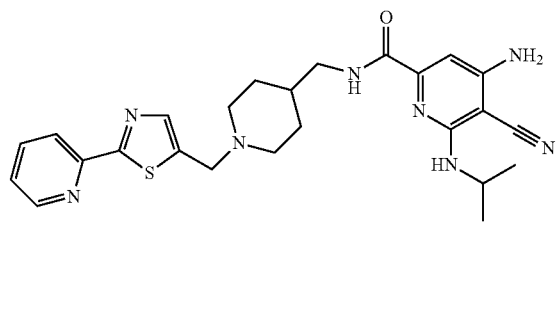 [SMILES: CC(C)Nc1nc(C(=O)NCC2CCN(Cc3cnc(-c4ccccn4)s3)CC2)cc(N)c1C#N]

According to the same procedure described in Example 161, using the corresponding amine instead of morpholine, the title compound having the following physical data was obtained.
$^1$H NMR (CDCl$_3$): δ 8.60-8.59 (m, 1H), 8.15-8.13 (m, 1H), 7.99-7.97 (m, 1H), 7.81-7.78 (m, 1H), 7.70 (s, 1H), 7.32-7.29 (m, 1H), 6.87 (s, 1H), 4.92 (s, 1H), 4.81-4.79 (m, 1H), 3.81 (s, 2H), 3.33 (t, J=6.5 Hz, 2H), 3.01-2.95 (m, 3H), 2.09-2.03 (m, 2H), 1.75-1.72 (m, 2H), 1.44-1.38 (m, 4H), 1.27 (d, J=6.5 Hz, 6H);
Mass data (APCI, Pos.): m/z 491 (M+H)+.

Example 198

4-Amino-5-cyano-6-(cyclopropylmethylamino)-N-((1-((2-(pyridin-2-yl)thiazol-5-yl)methyl)piperidin-4-yl)methyl)picolinamide

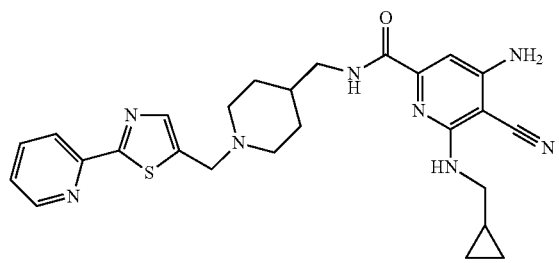 [SMILES: N#Cc1c(N)cc(C(=O)NCC2CCN(Cc3cnc(-c4ccccn4)s3)CC2)nc1NCC1CC1]

According to the same procedure described in Example 161, using the corresponding amine instead of morpholine, the title compound having the following physical data was obtained.

$^1$H NMR (CDCl$_3$): δ 8.61-8.59 (m, 1H), 8.15-8.13 (m, 1H), 7.97-7.95 (m, 1H), 7.81-7.77 (m, 1H), 7.67 (s, 1H), 7.33-7.29 (m, 1H), 6.88 (s, 1H), 5.13-5.11 (m, 1H), 4.92 (s, 2H), 3.77 (s, 2H), 3.33-3.29 (m, 4H), 2.97-2.94 (m, 2H), 2.09-2.05 (m, 2H), 1.74-1.70 (m, 2H), 1.42-1.33 (m, 2H), 1.14-1.05 (m, 1H), 0.92 (d, J=6.7 Hz, 1H), 0.60-0.54 (m, 2H), 0.29-0.26 (m, 2H);

Mass data (APCI, Pos.): m/z 503 (M+H)$^+$.

Example 199

4-Amino-5-cyano-6-(ethylamino)-N-((1-((2-(pyridin-2-yl)thiazol-5-yl)methyl)piperidin-4-yl)methyl)picolinamide

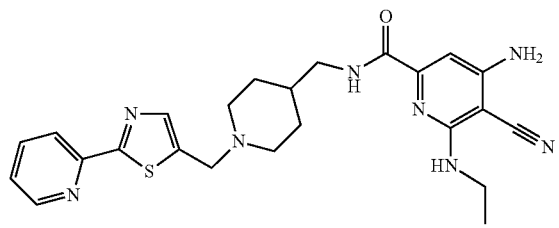 [SMILES: CCNc1nc(C(=O)NCC2CCN(Cc3cnc(-c4ccccn4)s3)CC2)cc(N)c1C#N]

According to the same procedure described in Example 161, using the corresponding amine instead of morpholine, the title compound having the following physical data was obtained.

$^1$H NMR (CDCl$_3$): δ 8.61-8.59 (m, 1H), 8.15-8.13 (m, 1H), 8.01-7.99 (m, 1H), 7.81-7.77 (m, 1H), 7.68 (s, 1H), 7.33-7.29 (m, 1H), 6.90 (s, 1H), 5.50 (s, 1H), 5.02 (s, 2H), 4.97-4.95 (m, 1H), 3.78 (s, 2H), 3.52-3.47 (m, 2H), 3.33-3.26 (m, 2H), 3.01-2.94 (m, 2H), 2.11-2.05 (m, 2H), 1.97 (s, 1H), 1.74-1.71 (m, 2H), 1.63-1.57 (m, 1H), 1.41-1.33 (m, 2H), 1.27 (t, J=7.2 Hz, 1H);

Mass data (APCI, Pos.): m/z 477 (M+H)$^+$.

Example 200

4-Amino-5-cyano-6-propoxy-N-((1-((2-(pyridin-2-yl)thiazol-5-yl)methyl)piperidin-4-yl)methyl)picolinamide

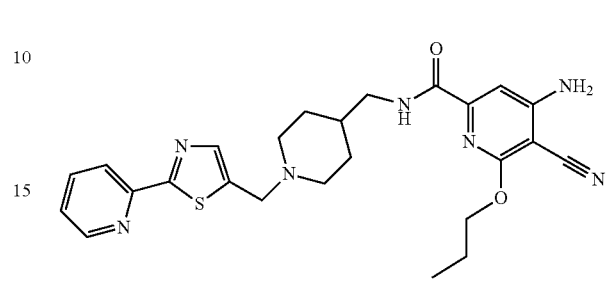

The compound prepared in Example 215 (0.097 g), 1,10-phenanthroline (0.022 g), Cu(I)I (0.012 g) and cesium carbonate (0.135 g) were suspended in n-propanol (1 mL) in a sealed reactor vial and heated at 110° C. for 4 hours. The reaction mixture was diluted with ethyl acetate, filtered through a pad of celite (trade mark) and concentrated under reduced pressure to afford the crude material, which was purified by flash column chromatography (eluant: 5% (9:1 methanol/concentrated ammonium hydroxide)/ethyl acetate) to afford the title compound (0.036 g) having the following physical data.

$^1$H NMR (CDCl$_3$): δ 8.60-8.59 (m, 1H), 8.15-8.13 (m, 1H), 7.80-7.76 (m, 2H), 7.67 (s, 1H), 7.31-7.26 (m, 1H), 7.20 (s, 1H), 5.13 (s, 2H), 4.32 (t, J=6.5 Hz, 2H), 3.78 (s, 2H), 3.34 (t, J=6.5 Hz, 2H), 2.98-2.95 (m, 2H), 2.10-2.05 (m, 2H), 1.88-1.80 (m, 2H), 1.74-1.70 (m, 2H), 1.63-1.58 (m, 1H), 1.42-1.34 (m, 2H), 1.05 (t, J=7.4 Hz, 3H);

Mass data (APCI, Pos.): m/z 492 (M+H)$^+$.

Example 201

4-Amino-5-cyano-6-(2-hydroxyethoxy)-N-((1-((2-(pyridin-2-yl)thiazol-5-yl)methyl)piperidin-4-yl)methyl)picolinamide

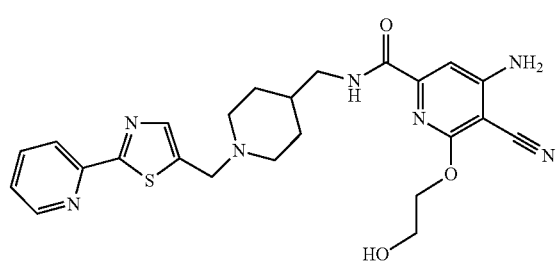 [SMILES: N#Cc1c(N)cc(C(=O)NCC2CCN(Cc3cnc(-c4ccccn4)s3)CC2)nc1OCCO]

According to the same procedure described in Example 200, using the corresponding alcohol instead of n-propanol, the title compound having the following physical data was obtained.

$^1$H NMR (CD$_3$OD): δ 8.57-8.56 (m, 1H), 8.13-8.11 (m, 1H), 7.93-7.88 (m, 1H), 7.75 (s, 1H), 7.44-7.41 (m, 1H), 7.09 (s, 1H), 4.53-4.51 (m, 3H), 3.90-3.87 (m, 2H), 3.83 (s, 2H), 3.31-3.29 (m, 4H), 3.01-2.98 (m, 2H), 2.15-2.10 (m, 2H), 1.77-1.73 (m, 2H), 1.70-1.62 (m, 1H), 1.41-1.33 (m, 2H);
Mass data (APCI, Pos.): m/z 494 (M+H)+.

Example 202

4-Amino-5-cyano-6-(3-hydroxypropoxy)-N-((1-((2-(pyridin-2-yl)thiazol-5-yl)methyl)piperidin-4-yl)methyl)picolinamide

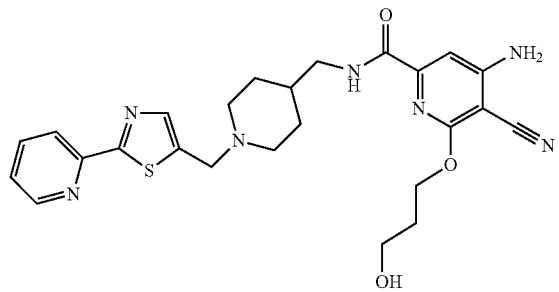 [SMILES: N#Cc1c(N)cc(C(=O)NCC2CCN(Cc3cnc(-c4ccccn4)s3)CC2)nc1OCCCO]

According to the same procedure described in Example 200, using the corresponding alcohol instead of n-propanol, the title compound having the following physical data was obtained.

$^1$H NMR (CD$_3$OD): δ 8.57-8.56 (m, 1H), 8.13-8.11 (m, 1H), 7.93-7.88 (m, 1H), 7.75 (s, 1H), 7.44-7.41 (m, 1H), 7.08 (s, 1H), 4.85-4.81 (m, 3H), 4.55 (t, J=6.3 Hz, 2H), 3.83 (s, 2H), 3.73 (t, J=6.2 Hz, 2H), 3.33-2.26 (m, 4H), 3.01-2.98 (m, 2H), 2.14-2.09 (m, 2H), 2.01-1.96 (m, 2H), 1.76-1.73 (m, 2H), 1.69-1.62 (m, 1H), 1.42-1.32 (m, 2H);
Mass data (APCI, Pos.): m/z 508 (M+H)+.

Example 203

4-Amino-5-cyano-6-isopropoxy-N-((1-((2-(pyridin-2-yl)thiazol-5-yl)methyl)piperidin-4-yl)methyl)picolinamide

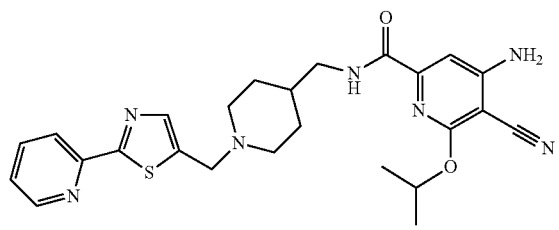 [SMILES: CC(C)Oc1nc(C(=O)NCC2CCN(Cc3cnc(-c4ccccn4)s3)CC2)cc(N)c1C#N]

According to the same procedure described in Example 200, using the corresponding alcohol instead of n-propanol, the title compound having the following physical data was obtained.

$^1$H NMR (CDCl$_3$): δ 8.60-8.59 (m, 1H), 8.15-8.13 (m, 1H), 7.80-7.77 (m, 1H), 7.67 (s, 1H), 7.33-7.29 (m, 1H), 7.17 (s, 1H), 5.31-5.26 (m, 1H), 5.12 (s, 2H), 3.78 (s, 2H), 3.68-3.63 (m, 2H), 3.33 (t, J=6.5 Hz, 2H), 2.99-2.96 (m, 2H), 2.11-2.05 (m, 2H), 1.73-1.70 (m, 2H), 1.65-1.56 (m, 2H), 1.40 (d, J=6.2 Hz, 6H);
Mass data (APCI, Pos.): m/z 592 (M+H)+.

Example 204

4-Amino-5-cyano-6-(1-cyclopropylethoxy)-N-((1((2-(pyridin-2-yl)thiazol-5-yl)methyl)piperidin-4-yl)methyl)picolinamide

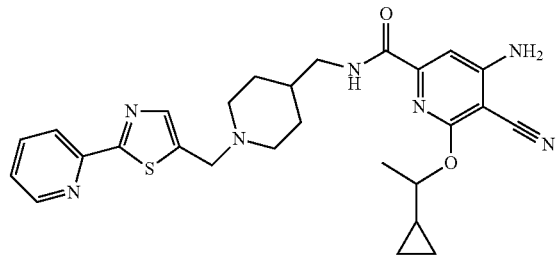 [SMILES: CC(Oc1nc(C(=O)NCC2CCN(Cc3cnc(-c4ccccn4)s3)CC2)cc(N)c1C#N)C1CC1]

The compound prepared in Example 215 (0.100 g), 1,10-phenanthroline (0.007 g) and cesium carbonate (0.209 g) were suspended in 1-cyclopropylethanol (3 mL) and purged with Argon. Tetrakis(acetonitrile) copper (I) hexafluorophosphate (0.003 g) was added in one portion and the system purged with Argon again. The reaction mixture was sealed in a reactor vial and heated at 120° C. overnight. The reaction mixture was cooled to room temperature and partitioned between saturated aqueous sodium bicarbonate and ethyl acetate. The organics were washed with brine, dried over magnesium sulfate, filtered and concentrated under reduced pressure to afford the crude material, which was purified by flash column chromatography (eluant: gradient 0-3% (9:1 methanol/concentrated ammonium hydroxide)/ethyl acetate) then preparative thin layer chromatography (eluant: 5% (9:1 methanol/concentrated ammonium hydroxide)/ethyl acetate) to furnish the title compound (0.038 g) having the following physical data.

$^1$H NMR (CDCl$_3$): δ 8.60 (d, J=4.4 Hz, 1H), 8.14 (d, J=7.9 Hz, 1H), 7.83-7.76 (m, 1H), 7.73 (t, J=6.2 Hz, 1H), 7.68 (s, 1H), 7.34-7.29 (m, 1H), 7.24 (s, 1H), 5.35 (s, 2H), 4.75-4.66 (m, 1H), 3.78 (s, 2H), 3.32 (t, J=6.5 Hz, 2H), 3.02-2.92 (m, 2H), 2.12-2.02 (m, 2H), 1.76-1.65 (m, 2H), 1.64-1.54 (m, 1H), 1.43 (d, J=6.3 Hz, 3H), 1.40-1.31 (m, 2H), 1.22-1.14 (m, 1H), 0.60-0.51 (m, 2H), 0.47-0.41 (m, 1H), 0.36-0.28 (m, 1H);
Mass data (APCI, Pos.): m/z 518 (M+H)+.

Example 205

4-Amino-5-cyano-N-((1-((2-(pyridin-2-yl)thiazol-5-yl)methyl)piperidin-4-yl)methyl)-6-(3,3,3-trifluoropropoxy)picolinamide

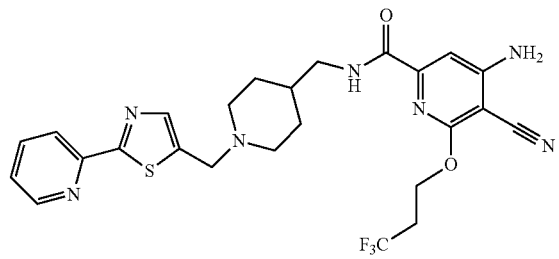 [SMILES: N#Cc1c(N)cc(C(=O)NCC2CCN(Cc3cnc(-c4ccccn4)s3)CC2)nc1OCCC(F)(F)F]

According to the same procedure described in Example 204, using the corresponding alcohol instead of 1-cyclopropylethanol, the title compound having the following physical data was obtained.

¹H NMR (CDCl₃): δ 8.60 (d, J=4.8 Hz, 1H), 8.14 (d, J=7.9 Hz, 1H), 7.82-7.75 (m, 1H), 7.74-7.66 (m, 2H), 7.33-7.28 (m, 1H), 7.24 (s, 1H), 5.18 (s, 2H), 4.63 (t, J=6.8 Hz, 2H), 3.78 (s, 2H), 3.34 (t, J=6.5 Hz, 2H), 3.02-2.92 (m, 2H), 2.74-2.63 (m, 2H), 2.13-2.02 (m, 2H), 1.77-1.67 (m, 2H), 1.65-1.58 (m, 1H), 1.44-1.31 (m, 2H);

Mass data (APCI, Pos.): m/z 546 (M+H)⁺.

Example 206

4-amino-5-cyano-N-((1-((2-(pyridin-2-yl)thiazol-5-yl)methyl)piperidin-4-yl)methyl)-6-(2,2,2-trifluoroethoxy)picolinamide

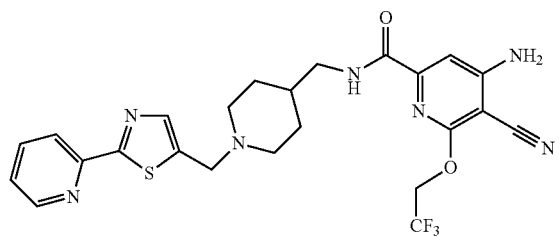 [SMILES: N#Cc1c(N)cc(C(=O)NCC2CCN(Cc3cnc(-c4ccccn4)s3)CC2)nc1OCC(F)(F)F]

According to the same procedure described in Example 204, using the corresponding alcohol instead of 1-cyclopropylethanol, the title compound having the following physical data was obtained.

¹H NMR (CDCl₃): δ 8.60 (d, J=4.4 Hz, 1H), 8.14 (d, J=7.9 Hz, 1H), 7.82-7.76 (m, 1H), 7.68 (s, 1H), 7.62 (t, J=6.3 Hz, 1H), 7.37 (s, 1H), 7.33-7.28 (m, 1H), 5.45 (s, 2H), 4.80 (q, J=8.2 Hz, 2H), 3.78 (s, 2H), 3.35 (t, J=6.5 Hz, 2H), 3.02-2.92 (m, 2H), 2.13-2.03 (m, 2H), 1.76-1.66 (m, 2H), 1.61-1.54 (m, 1H), 1.44-1.30 (m, 2H);

Mass data (APCI, Pos.): m/z 532 (M+H)⁺.

Example 207

(R)-4-amino-5-cyano-6-(3-hydroxybutoxy)-N-((1-((2-(pyridin-2-yl)thiazol-5-yl)methyl)piperidin-4-yl)methyl)picolinamide

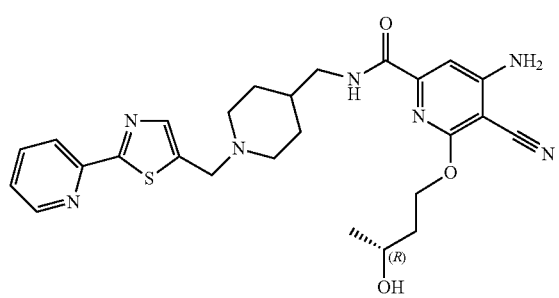

According to the same procedure described in Example 204, using the compound prepared in Example 216 instead of 1-cyclopropylethanol, the title compound having the following physical data was obtained.

¹H NMR (CDCl₃): δ 8.60 (d, J=4.8 Hz, 1H), 8.15 (d, J=7.9 Hz, 1H), 8.07-7.92 (m, 1H), 7.83-7.76 (m, 1H), 7.68 (s, 1H), 7.35-7.29 (m, 1H), 7.24-7.19 (m, 1H), 5.38-5.28 (m, 2H), 4.64-4.50 (m, 2H), 4.12-4.03 (m 1H), 3.64 (s, 2H), 3.34 (t, J=6.1 Hz, 2H), 3.03-2.93 (m, 2H), 2.13-1.81 (m, 4H), 1.74-1.57 (m, 3H), 1.49-1.37 (m, 2H), 1.28 (d, J=6.2 Hz, 3H);

Mass data (APCI, Pos.): m/z 522 (M+H)⁺.

Example 208

(S)-4-Amino-5-cyano-6-(3-hydroxybutoxy)-N-((1-(((2-(pyridin-2-yl)thiazol-5-yl)methyl)piperidin-4-yl)methyl)picolinamide

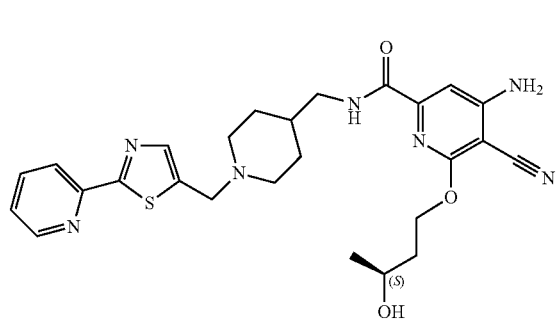

According to the same procedure described in Example 204, using the compound prepared in Example 217 instead of 1-cyclopropylethanol, the title compound having the following physical data was obtained.

¹H NMR (CDCl₃): δ 8.60 (d, J=4.8 Hz, 1H), 8.15 (d, J=7.9 Hz, 1H), 8.07-7.92 (m, 1H), 7.83-7.76 (m, 1H), 7.68 (s, 1H), 7.35-7.29 (m, 1H), 7.24-7.19 (m, 1H), 5.38-5.28 (m, 2H), 4.64-4.50 (m, 2H), 4.12-4.03 (m 1H), 3.64 (s, 2H), 3.34 (t, J=6.1 Hz, 2H), 3.03-2.93 (m, 2H), 2.13-1.81 (m, 4H), 1.74-1.57 (m, 3H), 1.49-1.37 (m, 2H), 1.28 (d, J=6.2 Hz, 3H);

Mass data (APCI, Pos.): m/z 522 (M+H)⁺.

Example 209

(R)-4-Amino-6-(1-(tert-butyldimethylsilyloxy)propan-2-yloxy)-5-cyano-N-((1-((2-(pyridin-2-yl)thiazol-5-yl)methyl)piperidin-4-yl)methyl)picolinamide

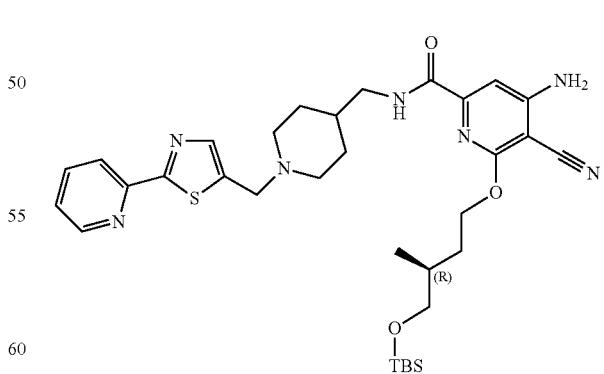

According to the same procedure described in Example 204, using the compound prepared in Example 218 instead of 1-cyclopropylethanol, the title compound having the following physical data was obtained.

Mass data (APCI, Pos.): m/z 622 (M+H)⁺.

Example 210

(S)-4-Amino-6-(1-(tert-butyldimethylsilyloxy)propan-2-yloxy)-5-cyano-N-((1-((2-(pyridin-2-yl)thiazol-5-yl)methyl)piperidin-4-yl)methyl)picolinamide

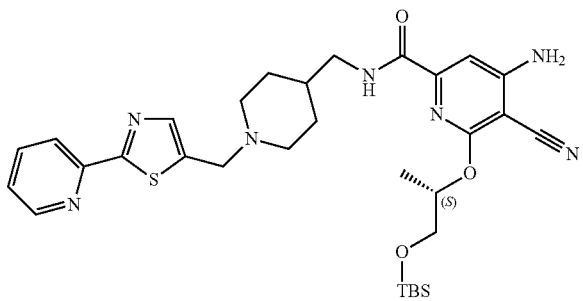

According to the same procedure described in Example 204, using the compound prepared in Example 219 instead of 1-cyclopropylethanol, the title compound having the following physical data was obtained.

Mass data (APCI, Pos.): m/z 622 (M+H)+.

Example 211

(R)-4-Amino-5-cyano-6-(1-hydroxypropan-2-yloxy)-N-((1-((2-(pyridin-2-yl)thiazol-5-yl)methyl)piperidin-4-yl)methyl)picolinamide

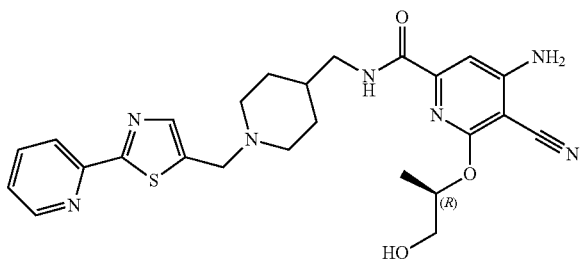

The compound prepared in Example 209 (0.032 g) was suspended in tetrahydrofuran (10 mL) and aqueous tetrabutylammonium fluoride solution (1 mol/L; 0.103 mL) added dropwise to the reaction mixture. The reaction mixture was stirred at room temperature for 2 hours. The reaction mixture was partitioned between ethyl acetate and saturated aqueous sodium bicarbonate. The combined organics were washed with brine, dried over magnesium sulfate, filtered and concentrated under reduced pressure to afford the crude material, which was purified by preparative TLC, (eluant: 10% (9:1 methanol/concentrated ammonium hydroxide)/ethyl acetate) to furnish the title compound (0.020 g) having the following physical properties.

$^1$H NMR (CDCl$_3$): δ 8.59 (d, J=4.4 Hz, 1H), 8.14 (d, J=7.9 Hz, 1H), 7.82-7.73 (m, 2H), 7.67 (s, 1H), 7.34-7.25 (m, 2H), 5.41-5.32 (m, 2H), 4.36-4.21 (m, 2H), 3.89-3.78 (m, 3H), 3.37-3.32 (m, 2H), 3.01-2.92 (m, 2H), 2.13-2.02 (m, 2H), 1.76-1.66 (m, 2H), 1.65-1.55 (m, 1H), 1.45-1.28 (m, 5H);

Mass data (APCI, Pos.): m/z 508 (M+H)+.

Example 212

(S)-4-Amino-5-cyano-6-(1-hydroxypropan-2-yloxy)-N-((1-((2-(pyridin-2-yl)thiazol-5-yl)methyl)piperidin-4-yl)methyl)picolinamide

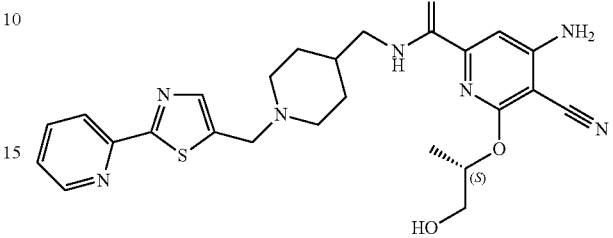

According to the same procedure described in Example 211, using the corresponding silyl ether instead of (R)-4-Amino-6-(1-(tert-butyldimethylsilyloxy)propan-2-yloxy)-5-cyano-N4((1-((2-(pyridin-2-yl)thiazol-5-yl)methyl)piperidin-4-yl)methyl)picolinamide, the title compound having the following physical data was obtained.

$^1$H NMR (CDCl$_3$): δ 8.60 (d, J=4.4 Hz, 1H), 8.14 (d, J=7.9 Hz, 1H), 7.82-7.76 (m, 1H), 7.68 (s, 1H), 7.62 (t, J=6.3 Hz, 1H), 7.37 (s, 1H), 7.33-7.28 (m, 1H), 5.45 (s, 2H), 4.80 (q, J=8.2 Hz, 2H), 3.78 (s, 2H), 3.35 (t, J=6.5 Hz, 2H), 3.02-2.92 (m, 2H), 2.13-2.03 (m, 2H), 1.76-1.66 (m, 2H), 1.61-1.54 (m, 1H), 1.44-1.30 (m, 2H);

Mass data (APCI, Pos.): m/z 532 (M+H)+.

Example 213 tert-Butyl ((1-((2-(pyridin-2-yl)thiazol-5-yl)methyl)piperidin-4-yl)methylcarbamate

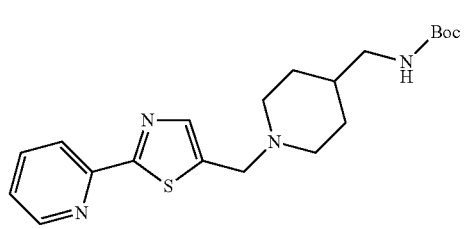 [SMILES: CC(C)(C)OC(=O)NCC1CCN(Cc2cnc(-c3ccccn3)s2)CC1]

The compound prepared in Example 139 (2.4 g) and tert-butyl piperidin-4-ylmethylcarbamate (4.06 g) were combined in dichloromethane (80 mL) and sodium triacetoxyborohydride (4.3 g) was added using an ice bath to keep the reaction cool. The bath was removed and the reaction was allowed to stir for 24 hours. The reaction was concentrated and then partitioned between ethyl acetate and sodium hydrogen carbonate aqueous solution. The organic phase was washed with brine, dried over magnesium sulfate, filtered and concentrated. The crude reaction was purified by column chromatography using an eluant of 1-4% methanol/dichloromethane to provide the title compound (4.7 g) with the following physical data.

$^1$H NMR (CDCl$_3$): δ 8.60 (d, J=4.7 Hz, 1H), 8.14 (d, J=7.8 Hz, 1H), 7.78 (dt, J=7.8, 1.6 Hz, 1H), 7.67 (s, 1H), 7.31-7.28 (m, 1H), 4.58 (bs, 1H), 3.77 (s, 2H), 3.03-3.00 (m, 2H), 2.96-2.93 (m, 2H), 2.05 (dt, J=11.7, 2.3 Hz, 2H), 1.67 (d, J=12.5 Hz, 2H), 1.43 (s, 9H), 1.29 (dt, J=11.7, 3.1 Hz, 2H);
Mass data (ESI, Pos.): m/z 411 (M+Na)+.

Example 214

((1-((2-(Pyridin-2-yl)thiazol-5-yl)methyl)piperidin-4-yl)methanamine Trihydrochloride

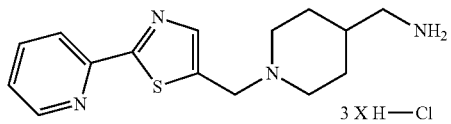

The compound prepared in Example 213 (4.75 g) was partially dissolved in methanol (70 mL). A solution of 4 mol/L hydrogen chloride in dioxane (18 mL) was added to the solution with cooling. The reaction was allowed to stir at room temperature for 14 hours. The reaction was then concentrated and heated under vacuum to provide the title compound (4.85 g) with the following physical data.
$^1$H NMR (DMSO-$d_6$): δ 11.35 (bs, 1H), 8.66 (d, J=4.7 Hz, 1H), 8.14 (d, J=7.8 Hz, 1H), 8.13 (s, 1H), 8.08 (bs, 3H), 8.00 (dt, J=7.8, 1.6 Hz, 1H), 7.56-7.53 (m, 1H), 4.61 (d, J=4.7 Hz, 2H), 3.45-3.42 (m, 2H), 3.17 (bs, 1H), 2.98-2.90 (m, 2H), 2.73-2.68 (m, 2H), 1.97-1.93 (m, 2H), 1.86 (bs, 1H), 1.62-1.53 (m, 2H);
Mass data (ESI, Pos.): m/z 289 (M+H)+.

Example 215

4-Amino-6-chloro-5-cyano-N-((1-((2-(pyridin-2-yl)thiazol-5-yl)methyl)piperidin-4-yl)methyl)picolinamide

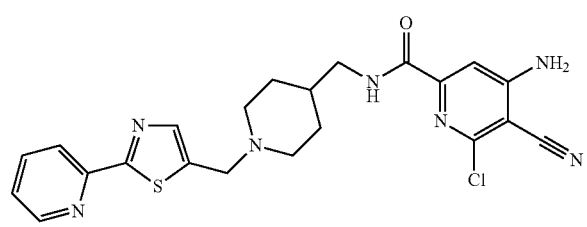 [SMILES: N#Cc1c(N)cc(C(=O)NCC2CCN(Cc3cnc(-c4ccccn4)s3)CC2)nc1Cl]

4-Amino-6-chloro-5-cyanopicolinic acid (1.053 g, prepared according to the reported preparation in Zhao, Hongyu, et al.; J. Med. Chem. 2006, 49(15), 4455-4458), the compound prepared in Example 214 (2.12 g), (benzotriazol-1-yloxy)tripyrrolidinophosphonium hexafluorophosphate (3.33 g) and triethylamine (7.43 mL) were suspended in N,N-dimethylformamide (100 mL) and stirred at room temperature over weekend. The reaction mixture was poured onto saturated aqueous sodium bicarbonate solution and ethyl acetate. The organics were washed with brine, dried over magnesium sulfate, filtered and concentrated under reduced pressure to afford the crude material. The crude material was slurried with dichloromethane and the desired material precipitated out of solution. The solids was filtered and washed with dichloromethane to afford clean material. The filtrate was concentrated under reduced pressure and purified by flash column chromatography (gradient elution: 100% ethyl acetate to 96.5% ethyl acetate, 2.5% triethylamine 1% methanol) to afford pure material, which was combined with the triturated material to give the title compound (1.69 g), with the following physical data.
$^1$H NMR (DMSO-$d_6$): δ 8.61 (d, J=4.8 Hz, 1H), 8.57 (t, J=6.0 Hz, 1H), 8.09 (d, J=7.9 Hz, 1H), 7.97-7.91 (m, 1H), 7.78 (s, 1H), 7.74 (s, 2H), 7.49-7.44 (m 1H), 7.35 (s, 1H), 3.73 (s, 2H), 3.18-3.12 (m, 2H), 2.89-2.81 (m, 2H), 2.00-1.90 (m 2H), 1.64-1.50 (m, 3H), 1.23-1.11 (m, 2H);
Mass data (APCI, Pos.): m/z 468 (M+H)+.

Example 216

(R)-4-(tert-Butyldimethylsilyloxy)butan-2-ol

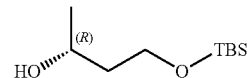

(R)-Butane-1,3-diol (5.00 mL), tert-butylchlorodimethylsilane (8.82 g), N,N-dimethylpyridin-4-amine (0.34 g) and triethylamine (23.2 mL) were suspended in dichloromethane (60 mL) and stirred at room temperature overnight. The reaction mixture was partitioned between saturated aqueous sodium bicarbonate and dichloromethane. The organics were dried over magnesium sulfate and concentrated under reduced pressure to afford the crude material, which was purified by flash column chromatography (eluant: 5-10% ethyl acetate/hexane) to furnish to afford the title compound (8.33 g) having the following physical properties.
$^1$H NMR (CDCl$_3$): δ 4.06-3.98 (m, 1H), 3.93-3.87 (m, 1H), 3.84-3.77 (m, 1H), 3.36 (d, J=2.4 Hz, 1H), 1.71-1.59 (m, 2H), 1.19 (d, J=6.2 Hz, 3H), 0.90 (s, 9H), 0.08 (s, 6H).

Example 217

(S)-4-(tert-Butyldimethylsilyloxy)butan-2-ol

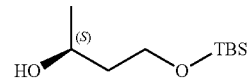

According to the same procedure described in Example 216, using the corresponding diol instead of (R)-butane-1,3-diol, the title compound having the following physical data was obtained.
$^1$H NMR (CDCl$_3$): δ 4.06-3.98 (m, 1H), 3.92-3.87 (m, 1H), 3.84-3.78 (m, 1H), 3.36 (d, J=2.4 Hz, 1H), 1.72-1.59 (m, 2H), 1.19 (d, J=6.2 Hz, 3H), 0.90 (s, 9H), 0.08 (s, 6H).

Example 218

(R)-1-(tert-Butyldimethylsilyloxy)propan-2-ol

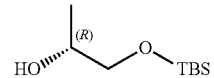

According to the same procedure described in Example 216, using the corresponding diol instead of (R)-butane-1,3-diol, the title compound having the following physical data was obtained.

¹H NMR (CDCl₃): δ 3.86-3.78 (m, 1H), 3.59 (dd, J=3.4, 9.9 Hz, 1H), 3.35 (dd, J=7.8 9.9 Hz, 1H), 2.45 (d, J=3.2 Hz), 1.12 (d, J=6.3 Hz), 0.91 (s, 9H), 0.08 (s, 6H).

Example 219

(S)-1-(tert-Butyldimethylsilyloxy)propan-2-ol

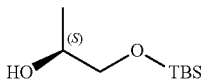

According to the same procedure described in Example 216, using the corresponding diol instead of (R)-butane-1,3-diol, the title compound having the following physical data was obtained.

¹H NMR (CDCl₃): δ 3.86-3.78 (m, 1H), 3.60 (dd, J=3.4, 9.9 Hz, 1H), 3.35 (dd, J=7.8 9.9 Hz, 1H), 2.45 (d, J=3.2 Hz), 1.12 (d, J=6.3 Hz), 0.91 (s, 9H), 0.08 (s, 6H).

Example 220

(1-((2-(Pyridin-2-yl)thiazol-5-yl)methyl)piperidin-4-yl)methanol

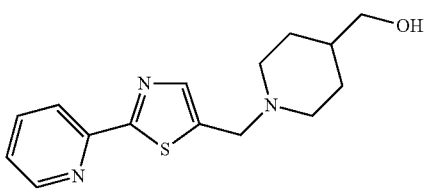 [SMILES: OCC1CCN(Cc2cnc(-c3ccccn3)s2)CC1]

The compound prepared in Example 139 (0.569 g), piperidin-4-ylmethanol (0.689 g) and sodium triacetoxyborohydride (1.902 g) were suspended in 1,2-dichloroethane (15 mL) and stirred at room temperature overnight. The reaction mixture was diluted with ethyl acetate and washed sequentially with saturated aqueous sodium bicarbonate solution, ammonium chloride solution and brine. The organics were then dried over magnesium sulfate, filtered and concentrated under reduced pressure and to afford the crude material, which was purified by flash column chromatography (eluant: 10% (9:1 methanol/concentrated ammonium hydroxide)/ethyl acetate) to furnish the title compound (0.571 g) having the following physical properties.

¹H NMR (CDCl₃): δ 8.60 (d, J=4.1 Hz, 1H), 8.15 (d, J=7.9 Hz, 1H), 7.82-7.74 (m, 1H), 7.69 (s, 1H), 7.34-7.28 (m, 1H), 3.79 (s, 2H), 3.55-3.45 (m, 2H), 3.03-2.92 (m, 2H), 2.12-2.00 (m, 2H), 1.78-1.68 (m, 2H), 1.55-1.44 (m, 1H), 1.39-1.22 (m, 3H);

Mass data (APCI, Pos.): m/z 29 (M+H)⁺.

Example 221

Methyl 5-(tert-butoxycarbonylamino)-4-cyano-3-methylthiophene-2-carboxylate

Methyl 5-amino-4-cyano-3-methylthiophene-2-carboxylate (0.790 g), N,N-diisopropylethylamine (1.40 mL), 4-dimethylaminopyridine (0.049 g) and di-tert-butyl dicarbonate (1.318 g) were suspended in N,N-dimethylformamide (10 mL) and heated at 60° C. for 1 hr. The reaction mixture was cooled to room temperature and partitioned between saturated aqueous ammonium chloride solution and ethyl acetate. The organics were washed with sodium bicarbonate aqueous solution and brine. The organics were then dried over magnesium sulfate, filtered and concentrated under reduced pressure and to afford the crude material, which was purified by flash column chromatography (eluant: 8:2 dichloromethane/hexane) to furnish the title compound (0.840 g) having the following physical properties.

¹H NMR (CDCl₃): δ 7.70 (s, 1H), 3.84 (s, 3H), 2.59 (s, 3H), 1.49 (s, 9H);

Mass data (APCI, Neg.): m/z 295 (M−H)⁻.

Example 222

5-(tert-Butoxycarbonylamino)-4-cyano-3-methylthiophene-2-carboxylic Acid

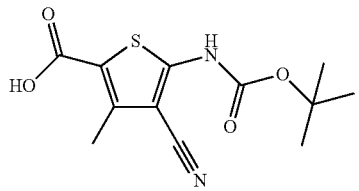 [SMILES: Cc1c(C(=O)O)sc(NC(=O)OC(C)(C)C)c1C#N]

The compound prepared in Example 221 (0.200 g) was suspended in methanol (10 mL) and aqueous sodium hydroxide solution (2 mol/L; 3.375 mL) was added and the reaction mixture stirred at 50° C. overnight. The reaction mixture was cooled to room temperature and concentrated under reduced pressure to afford a solid, which was dissolved in water, acidified to pH 1 and filtered to furnish the title compound (0.177 g) with the following physical properties.

¹H NMR (DMSO-d₆): δ 13.13 (s, 1H), 11.64 (s, 1H), 2.46 (s, 3H), 1.50 (s, 9H);

Mass data (APCI, Neg.): m/z 281 (M−H)⁻.

Example 223

(1-((2-(Pyridin-2-yl)thiazol-5-yl)methyl)piperidin-4-yl)methyl 5-(tert-butoxycarbonylamino)-4-cyano-3-methylthiophene-2-carboxylate

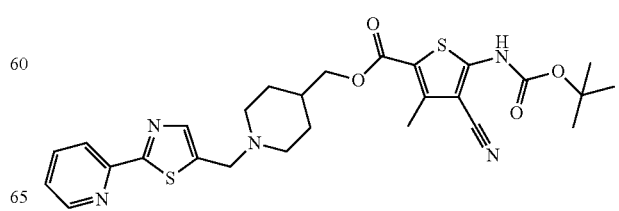

The compound prepared in Example 222 (0.100 g), the compound prepared in Example 220 (0.123 g), N-(3-dimethylaminopropyl)-N'-ethylcarbodiimide hydrochloride (0.102 g), N,N-diisopropylethylamine (0.185 mL) and 4-dimethylaminopyridine (0.011 g) were suspended in N,N-dimethylacetamide (10 mL) and heated at 60° C. overnight. The reaction mixture was cooled to room temperature and suspended between ethyl acetate and saturated aqueous sodium bicarbonate solution. The organics were washed with brine, dried over magnesium sulfate, filtered and concentrated under reduced pressure to afford the crude material, which was purified by flash column chromatography (eluant: 25 to 50% ethyl acetate/hexane/1% (9:1 methanol/concentrated ammonium hydroxide) to furnish the title compound (0.049 g) with the following physical properties.

$^1$H NMR (CDCl$_3$): δ 8.60 (d, J=4.6 Hz, 1H), 8.15 (d, J=7.9 Hz, 1H), 7.79 (t, J=7.7 Hz, 1H), 7.71 (s, 1H), 7.69 (s, 1H), 7.34-7.29 (m 1H), 4.10 (d, J=6.1 Hz, 2H), 3.79 (s, 2H), 3.04-2.91 (m, 2H), 2.58 (s, 3H), 2.14-2.02 (m, 2H), 1.82-1.66 (m, 3H), 1.56 (s, 9H), 1.45-1.30 (m, 2H);

Mass data (APCI, Pos.): m/z 554 (M+H)$^+$.

Example 224

(1-((2-(Pyridin-2-yl)thiazol-5-yl)methyl)piperidin-4-yl)methyl 5-amino-4-cyano-3-methylthiophene-2-carboxylate trihydrochloride

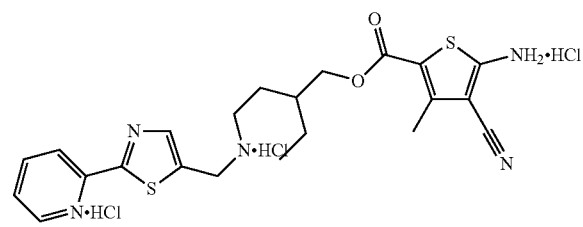

The compound prepared in Example 223 (0.026 g) was suspended in methanol (2 mL) and dichloromethane (2 mL). Hydrogen chloride solution (4 M in 1,4-dioxane) (3.0 mL) was added and the reaction mixture stirred at room temperature overnight. The reaction mixture was concentrated under reduced pressure to afford the title compound (0.027 g), which was used without further purification possessing the following physical data.

$^1$H NMR (DMSO-d$_6$): δ 10.71 (s, 1H), 8.70-8.63 (m, 1H), 8.18-7.96 (m, 4H), 7.58-7.51 (m, 1H), 5.24 (s, 3H), 4.73-4.63 (m, 2H), 4.20-4.05 (m, 2H), 3.54-3.41 (m, 2H), 3.05-2.90 (m, 2H), 2.38 (s, 3H), 2.01-1.78 (m, 3H), 1.67-1.51 (m, 2H);

Mass data (APCI, Pos.): m/z 454 (M+H (free base))$^+$.

Example 225 tert-Butyl 4-((4-amino-5-cyano-6-ethoxypicolinamido)methyl)piperidine-1-carboxylate

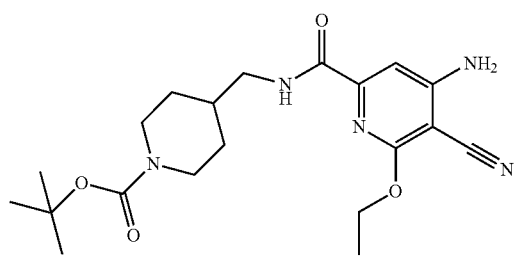 [SMILES: CCOc1nc(C(=O)NCC2CCN(C(=O)OC(C)(C)C)CC2)cc(N)c1C#N]

To a solution of 4-amino-5-cyano-6-ethoxypicolinic acid (193 mg) in dichloromethane (4 mL) was added 1-ethyl-3-(3'-dimethylaminopropyl)carbodiimide (215 mg), 1-hydroxybenzotriazole hydrate (164 mg), and diisopropylethylamine (813 μL). The mixture was stirred at room temperature for 5 minutes and then tert-butyl 4-(aminomethyl)piperidine-1-carboxylate (200 mg) was added. The reaction mixture was stirred at room temperature for 16 hours. The organic phase was diluted with ethyl acetate, washed with a saturated aqueous sodium bicarbonate solution, dried over anhydrous magnesium sulfate, filtered and concentrated. The residue was purified by column chromatography on silica gel (ethyl acetate:hexane=1:1) to obtain the title compound (252 mg) having the following physical data.

$^1$H NMR (CDCl$_3$): δ ppm 7.85-7.78 (m, 1H), 7.20 (s, 1H), 5.18-5.09 (m, 2H), 4.44 (q, J=7.1 Hz, 2H), 4.22-4.03 (m, 2H), 3.41-3.28 (m, 2H), 2.8-2.6 (m, 2H), 1.82-1.74 (m, 1H), 1.73-1.65 (m, 2H), 1.45 (s, 9H), 1.29-1.12 (m, 3H);

Mass data (ESI, Pos.): m/z 404 (M+H)$^+$.

Example 226

4-Amino-5-cyano-6-ethoxy-N-(piperidin-4-ylmethyl)picolinamide Dihydrochloride

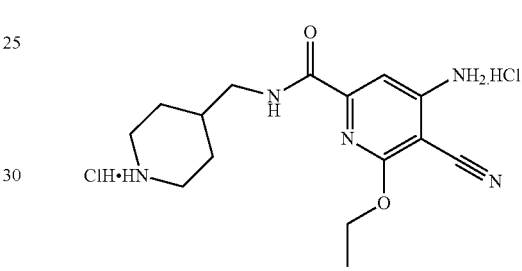

The compound prepared in Example 225 (0.603 g) was suspended in dichloromethane (30 mL) and methanol (10 mL). Hydrogen chloride solution (4 mol/L in 1,4-dioxane) (10.0 mL) was added and the reaction mixture stirred at room temperature for 6 hours. The reaction mixture was concentrated under reduced pressure to afford the title compound (0.547 g), which was used without further purification, possessing the following physical data.

$^1$H NMR (DMSO-d$_6$): δ 8.79-8.68 (m, 1H), 8.63-8.55 (m, 1H), 8.49-8.36 (m, 1H), 7.39-7.26 (m, 2H), 7.05 (s, 1H), 4.49 (q, J=7.1 Hz, 2H), 3.28-3.14 (m, 4H), 2.88-2.75 (m, 2H), 1.89-1.70 (m, 3H), 1.42-1.27 (m, 5H);

Mass data (APCI, Pos.): m/z 304 (M+H (free base))$^+$.

Example 227

5-amino-4-cyano-3-methylthiophene-2-carboxylic Acid

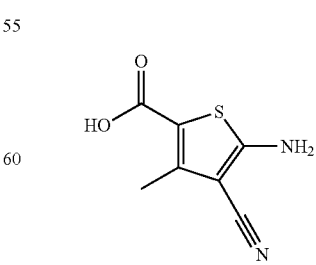

According to the same procedure described in Example 222, using the corresponding ester instead of Methyl 5-(tert-butoxycarbonylamino)-4-cyano-3-methylthiophene-2-carboxylate, the title compound (1.8 g) having the following physical data was obtained.

$^1$H NMR (DMSO-d$_6$): δ 12.55 (bs, 1H), 8.45 (s, 2H), 2.35 (s, 3H);

Mass data (ESI, Neg.): m/z 181 (M−H)$^-$.

Example 228

5-amino-4-cyano-3-methyl-N-((1-((3-phenylisoxazol-5-yl)methyl)piperidin-4-yl)methyl)thiophene-2-carboxamide

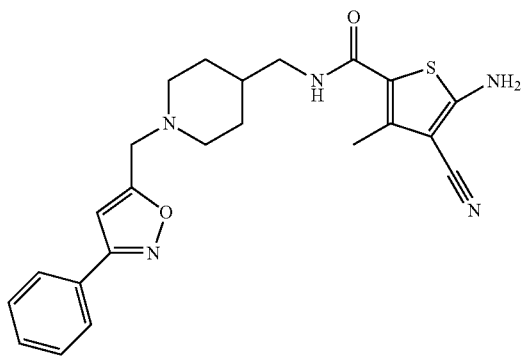 [SMILES: Cc1c(C(=O)NCC2CCN(Cc3cc(-c4ccccc4)no3)CC2)sc(N)c1C#N]

According to the same procedure described in Example 225, using the compound prepared in Example 227 instead of 4-amino-5-cyano-6-ethoxypicolinic acid, and using the compound prepared in Example 9 instead of tert-butyl 4-(aminomethyl)piperidine-1-carboxylate, the title compound having the following physical data was obtained.

$^1$H NMR (CDCl$_3$): δ 7.72-7.78 (m, 2H), 7.48-7.42 (m, 3H), 6.48 (s, 1H), 5.63 (br t, 1H), 5.10 (s, 2H), 3.74 (s, 2H), 3.29 (t, 2H), 3.29 (br d, 2H), 2.45 (s, 3H), 2.21-2.08 (m, 2H), 1.74 (br d, 2H), 1.58 (m, 1H), 1.42-1.31 (m, 2H);

Mass Data (ESI, Pos.): m/z 436 (M+H)$^+$.

Example 229 ethyl 2-chloro-6-ethoxyisonicotinate

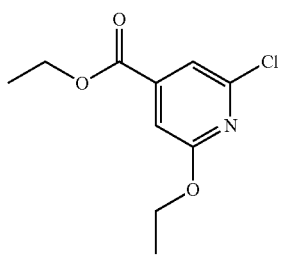

Methyl 2,6-dichloroisonicotinate (2.62 g) was partially dissolved in ethanol (50 mL) and a freshly prepared solution of 0.72 mol/L solution of sodium ethanolate (17.7 mL) was added at room temperature and then heated at 70° C. for 3 hours. The reaction was neutralized by the addition of 2N hydrochloric acid (6.5 mL) and then concentrated. The resulting solid was partitioned between ethyl acetate and water. The organic phase was washed with brine, dried over magnesium sulfate, filtered and concentrated. The crude reaction was purified by column chromatography using an eluant of 2-4% ethyl acetate/hexane to provide the title compound (1.7 g) with the following physical data.

$^1$H NMR (CDCl$_3$): δ 7.41 (s, 1H), 7.21 (s, 1H), 4.38 (q, J=7.0, 4H), 1.40 (t, J=7.0, 3H), 1.39 (t, J=7.0 Hz, 3H);

Mass data (ESI, Pos.): m/z 230 (M+H; Cl)$^+$.

Example 230 ethyl 2-(diphenylmethyleneamino)-6-ethoxyisonicotinate

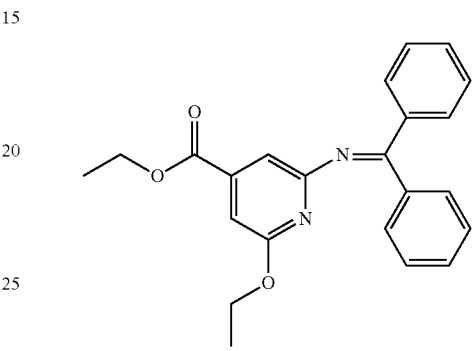

The compound prepared in Example 229 (0.26 g), diphenylmethanimine (0.24 g), cesium carbonate (1.8 g), racemic-2,2'-bis(diphenylphosphino)-1,1'-binaphthyl (0.070 g) and Pd(OAc)$_2$ (0.013 g) were dissolved in degassed toluene (4.5 mL) and then heated under argon at 110° C. for 1 hr. The reaction was cooled, diluted with ethyl acetate and filtered through celite (trade mark) with an ethyl acetate wash. The combined organic solutions were purified by column chromatography using an eluant of 0-2% ethyl acetate/dichloromethane to provide the title compound (0.40 g) with the following physical data.

$^1$H NMR (CDCl$_3$): δ 7.82-7.78 (m, 2H), 7.52-7.47 (m, 1H), 7.43-7.39 (m, 2H), 7.30-7.24 (m, 3H), 7.18-7.16 (m, 2H), 6.86 (s, 1H), 6.79 (s, 1H), 4.30 (q, J=7.0 Hz, 2H), 4.14 (q, J=7.0 Hz, 2H), 1.33 (t, J=7.0 Hz, 3H), 1.24 (t, J=7.0 Hz, 3H);

Mass data (ESI, Pos.): m/z 375 (M+H)$^+$.

Example 231

2-amino-6-ethoxy-N-((1-((3-phenylisoxazol-5-yl)methyl)piperidin-4-yl)methyl)isonicotinamide

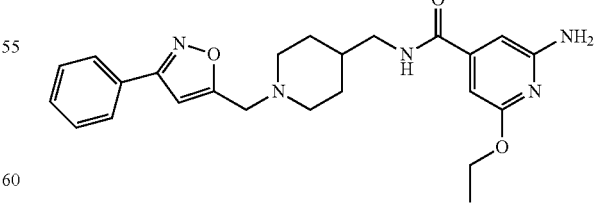

The compound prepared in Example 230 (0.090 g) and lithium hydroxide hydrate (0.011 g) were combined in methanol (1 mL), tetrahydrofuran (1 mL) and water (0.1 mL) and allowed to stir for 48 hours. The reaction was concentrated, pumped to dryness and used without further purification. The crude acid was combined with the compound prepared in Example 9 (0.11 g, 0.31 mmol), 1-ethyl-3-(3'-dimethylaminopropyl)carbodiimide (0.069 g, 0.36 mmol), diisopropylethylamine (0.16 g, 1.2 mmol) and 1-hydroxybenzotriazole hydrate (0.049 g, 0.36 mmol) in dichloromethane (2.5 mL). The reaction was sonicated briefly to aid dissolution and then stirred for 24 hours. The crude reaction was concentrated and then dissolved in methanol and treated with 2N hydrochloric acid. After stirring for 15 minutes, this solution was concentrated and then partitioned between ethyl acetate and sodium hydrogen carbonate aqueous solution. The organic phase was dried over magnesium sulfate, filtered, concentrated and purified by column chromatography using an eluant of 4% methanol/dichloromethane to provide the title compound (0.023 g) with the following physical data.

$^1$H NMR (CDCl$_3$): δ 7.82-7.79 (m, 2H), 7.48-7.44 (m, 3H), 6.49 (s, 1H), 6.38 (s, 1H), 6.26 (s, 1H), 6.17 (bt, 1H), 4.45 (bs, 2H), 4.26 (q, J=7.0 Hz, 2H), 3.73 (s, 2H), 3.31 (t, J=6.3 Hz, 2H), 2.99-2.96 (m, 2H), 2.16-2.10 (m, 2H), 1.76-1.72 (m, 2H), 1.65-1.56 (m, 1H), 1.43-1.37 (m, 2H), 1.35 (t, J=7.0 Hz, 3H);

Mass data (ESI, Pos.): m/z 458 (M+Na)$^+$.

Example 232

Dimethyl 4-amino-3-cyanopyridine-2,6-dicarboxylate

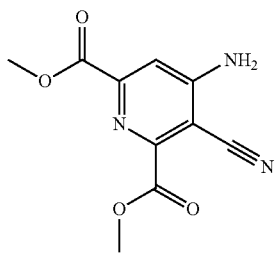 [SMILES: COC(=O)c1cc(N)c(C#N)c(C(=O)OC)n1]

4-Amino-6-chloro-5-cyanopyridin-2-yl trifluoromethanesulfonate (4.53 g, prepared according to the reported preparation in Zhao, Hongyu; et al.; *J. Med. Chem.* 2006, 49(15), 4455-4458), triethylamine (4.61 mL) and [1,1'-bis(diphenylphosphino)ferrocene]dichloropalladium (II) complex with dichloromethane (0.62 g) were suspended in methanol (150 mL) in a pressure bomb and the system purged with carbon monoxide gas. The reaction vessel was charged to 150 psi with carbon monoxide gas and heated at 100° C. overnight. The reaction mixture was concentrated under reduced pressure and dissolved in ethyl acetate. The organics were washed sequentially with saturated aqueous sodium bicarbonate, and brine. The organics were then dried over magnesium sulfate, and concentrated under reduced pressure to afford the crude material, which was purified by flash column chromatography (eluant: ethyl acetate) to furnish the title compound (1.50 g) having the following physical properties.

$^1$H NMR (CDCl$_3$): δ 7.64 (s, 1H), 5.41 (s, 2H), 4.05 (s, 3H), 4.01 (s, 3H);

Mass data (APCI, Pos.): m/z 236 (M+H)$^+$.

Example 233 methyl 4-amino-3-cyano-6-((1-((2-(pyridin-2-yl)thiazol-5-yl)methyl)piperidin-4-yl)methylcarbamoyl)picolinate

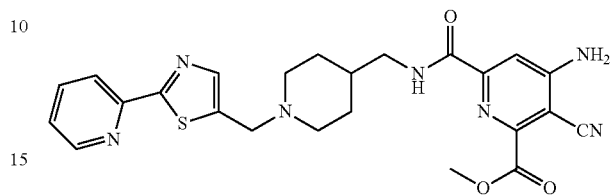

The compound prepared in Example 232 (0.042 g) was dissolved in tetrahydrofuran (20 mL) and methanol (5 mL) and then 1N lithium hydroxide solution (0.2 mL) was added followed by water (1 mL). After stirring for 4 hours, the crude material contains about equal amounts of diacid, two monoacids and starting material by HPLC analysis. The reaction was concentrated to dryness. To the crude acid (1-((2-(pyridin-2-yl)thiazol-5-yl)methyl)piperidin-4-yl)methanamine trihydrochloride (0.14 g), 1-hydroxybenzotriazole hydrate (0.055 g), N1-((ethylimino)methylene)-N3,N3-dimethylpropane-1,3-diamine hydrochloride (0.087 g), N-ethyl-N-isopropylpropan-2-amine (0.16 g) and N,N-dimethylacetamide (2.5 mL) were added and the mixture was sonicated for 2 minutes. The reaction was then stirred overnight. The reaction was partitioned between ethyl acetate and aqueous sodium hydrogen carbonate aqueous solution. The organic phase was dried over magnesium sulfate, filtered, concentrated and purified by column chromatography using an eluant of 5 to 10% methanol/dichloromethane followed by a second purification using 5 to 10% methanol/toluene to provide the title compound (0.008 g) with the following physical data.

$^1$H NMR (CDCl$_3$): δ 8.60 (d, J=4.7 Hz, 1H), 8.15-8.10 (m, 2H), 7.84 (s, 1H), 7.78 (t, J=7.8 Hz, 1H), 7.67 (s, 1H), 7.32-7.25 (m, 1H), 5.73 (bs, 2H), 4.04 (s, 3H), 3.78 (s, 2H), 3.36 (t, J=6.3 Hz, 2H), 2.96 (bd, J=11.7 Hz, 2H), 2.07 (t, J=10.5 Hz, 2H), 1.73 (bd, J=12.5 Hz, 2H), 1.68-1.58 (m, 1H), 1.45-1.34 (m, 2H);

Mass data (APCI, Pos.): m/z 492 (M+H)$^+$.

Example 234

4-amino-5-cyano-N2-((1-((2-(pyridin-2-yl)thiazol-5-yl)methyl)piperidin-4-yl)methyl)pyridine-2,6-dicarboxamide

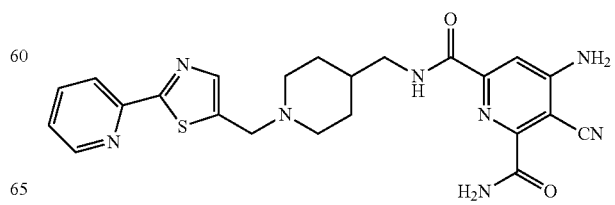

The compound prepared in Example 233 (0.057 g) was suspended in methanol (4 mL) and 7 M ammonia solution in methanol (4 mL) was added. After stirring overnight at room temperature, the reaction was concentrated to provide the title compound (0.053 g) with the following physical data.

$^1$H NMR (DMSO-d$_6$): δ 10.60 (s, 1H), 8.72 (s, 1H), 8.61 (d, J=3.9 Hz, 1H), 8.57 (t, J=6.3 Hz, 1H), 8.08 (d, J=7.8 Hz, 1H), 7.95 (dt, J=7.8, 1.6 Hz, 1H), 7.78 (s, 1H), 7.73 (bs, 2H), 7.50 (s, 1H), 7.48-7.45 (m, 1H), 3.73 (s, 2H), 3.22-3.19 (m, 2H), 2.87 (d, J=11.0 Hz, 2H), 1.97 (t, J=11.0 Hz, 2H), 1.64-1.56 (m, 3H), 1.24-1.15 (m, 2H);

Mass data (ESI, Pos.): m/z 499 (M+Na)$^+$.

Example 235 tert-butyl (1-(cyano(2-(pyridin-2-yl)thiazol-5-yl)methyl)piperidin-4-yl)methylcarbamate

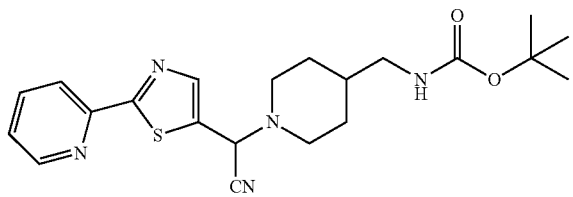 [SMILES: CC(C)(C)OC(=O)NCC1CCN(C(C#N)c2cnc(-c3ccccn3)s2)CC1]

Sodium metabisulfite (0.157 g) was added to degassed water (2.4 mL) followed the compound prepared in Example 139 (0.286 g) and methanol (0.05 mL). After stirring for 15 minutes, sodium cyanide (0.0737 g) was added. A thick white precipitate forms. Methanol (3.2 mL) was added to the reaction mixture. After stirring for 20 minutes, tert-butyl piperidin-4-ylmethylcarbamate (0.322 g) was added to the reaction mixture. After stirring for 2 days the reaction was partitioned between ethyl acetate and water. The organic phase was washed with water and brine, dried over magnesium sulfate and filtered. The organic phase was concentrated and purified by column chromatography using an eluant of 15-25% ethyl acetate/dichloromethane to provide the title compound (0.15 g) with the following physical data.

$^1$H NMR (CDCl$_3$): δ 8.61 (d, J=4.7 Hz, 1H), 8.17 (d, J=8.6 Hz, 1H), 7.97 (d, J=1.6 Hz, 1H), 7.82 (dt, J=7.8, 1.6 Hz, 1H), 5.02 (s, 1H), 4.57 (bs, 1H), 3.05-2.99 (m, 3H), 2.81-2.77 (m, 1H), 2.56 (dt, J=11.7, 3.1 Hz, 1H), 2.19 (dt, J=11.7, 3.1 Hz, 1H), 1.83-1.78 (m, 1H), 1.71-1.66 (m, 1H), 1.54-1.51 (m, 1H), 1.44 (s, 9H), 1.42-1.36 (m, 1H), 1.27-1.17 (m, 1H);

Mass data (APCI, Pos.): m/z 414 (M+Na)$^+$.

Example 236

2-(4-(aminomethyl)piperidin-1-yl)-2-(2-(pyridin-2-yl)thiazol-5-yl)acetonitrile

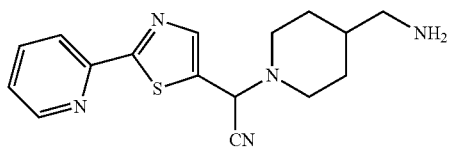 [SMILES: N#CC(c1cnc(-c2ccccn2)s1)N1CCC(CN)CC1]

The compound prepared in Example 235 (0.14 g) was dissolved in dichloromethane (2 mL) and trifluoroacetic acid (0.4 mL). The reaction was stirred for 1 hour and then concentrated and pumped to dryness. The amine salt was dissolved in tetrahydrofuran (5 mL) and Macroporous triethylammonium methylpolystyrene carbonate (MP-carbonate: Argonaut Technologies catalog number 80,026-9; 0.65 g) (2.5-3.5 mmol/g) 1.6-2.2 mmol was added. After 2 hours of stirring the reaction was filtered, washed with tetrahydrofuran, concentrated and used without further purification.

Example 237

4-amino-5-cyano-N-((1-(cyano(2-(pyridin-2-yl)thiazol-5-yl)methyl)piperidin-4-yl)methyl)-6-ethoxynicolinamide

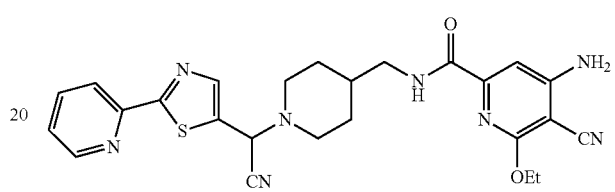

The compound prepared in Example 236 (0.0308 g), 4-amino-5-cyano-6-ethoxypicolinic acid (0.0224 g), 1-ethyl-3-(3'-dimethylaminopropyl)carbodiimide (0.0226 g) and 1-hydroxybenzotriazole hydrate (0.0181 g) were partially dissolved in dichloromethane (2.2 mL) and diisopropylethylamine (0.0599 mL) was then added. The reaction was allowed to stir for 24 hours. The reaction was then partitioned between ethyl acetate and sodium hydrogen carbonate aqueous solution, washed with brine, dried over magnesium sulfate and filtered. The organic phase was concentrated and purified by column chromatography using an eluant of 1-10% methanol/dichloromethane to provide the title compound (0.018 g) with the following physical data.

$^1$H NMR (CDCl$_3$): δ 8.61 (d, J=4.7 Hz, 1H), 8.17 (d, J=7.8 Hz, 1H), 7.97 (s, 1H), 7.84-7.78 (m, 2H), 7.37-7.34 (m, 1H), 7.18 (s, 1H), 5.08 (s, 2H), 5.03 (s, 1H), 4.44 (q, J=7.0 Hz, 2H), 3.41-3.30 (m, 2H), 3.04-3.01 (m, 1H), 2.82-2.80 (m, 1H), 2.61-2.56 (m, 1H), 2.24-2.19 (m, 1H), 1.86-1.83 (m, 1H), 1.75-1.66 (m, 2H), 1.50-1.42 (obs, 1H), 1.45 (t, J=7.0 Hz, 3H), 1.36-1.26 (m, 1H);

Mass data (ESI, Pos.): m/z 476 (M−CN)$^+$.

Example 238

2-amino-6-chloro-5-nitronicotinic Acid

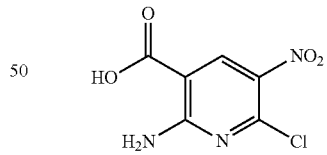

2-Amino-6-chloronicotinic acid (0.479 g) [Helvetica Chimica Acta (1976), 59(1), 222-9] was dissolved in concentrated sulfuric acid (5 mL) and cooled in an ice-saltwater bath and 2.5 mL of fuming nitric acid was then added dropwise with stirring. The ice bath was removed and the reaction mixture was stirred at ambient temperature for 8 hours. The mixture was then added dropwise to a saturated sodium bicarbonate solution (200 mL). The mixture was acidified with 9M aqueous sulfuric acid to pH 2. The solid that formed was filtered and rinsed with water to obtain the title compound (0.340 g) having the following physical data.

$^1$H NMR (d$_6$-DMSO): δ 13.4 (br s, 1H), 8.71 (br s, 1H), 8.70 (s, 1H), 8.46 (br s, 1H);

Mass data (ESI, Neg.): m/z 216 (M−H)$^−$.

Example 239

2-amino-6-cyano-5-nitronicotinic Acid

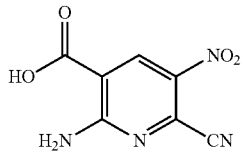 [SMILES: N#Cc1nc(N)c(C(=O)O)cc1[N+](=O)[O-]]

The compound prepared in Example 238 (0.130 g) and potassium cyanide (0.195 g) were combined in N,N-dimethylformamide (3 mL) and water (0.5 mL) was added. The reaction mixture was heated at 90° C. for 3 hours. The mixture was diluted with water and extracted with ethyl acetate. The aqueous layer was cautiously acidified with 1N hydrochloric acid to pH 1 to 2. It was then extracted with ethyl acetate. These extracts were combined, washed with brine, dried over magnesium sulfate, filtered and concentrated to obtain the title compound (0.105 g) having the following physical data.

$^1$H NMR ($d_6$-DMSO): δ 8.97 (br s, 1H), 8.70 (s, 1H), 8.39 (br s, 1H);

Mass data (ESI, Neg.): m/z 207 (M−H)$^-$.

Example 240

2,5-diamino-6-cyanonicotinic Acid

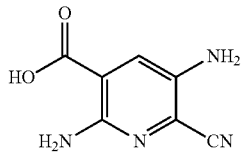

A mixture of the compound prepared in Example 239 (0.063 g) and 10% Pd on charcoal (0.0161 g) in ethyl acetate (2 mL) and ethanol (0.5 mL) was placed under hydrogen for 15 hours. The reaction mixture was filtered and concentrated to obtain the title compound (0.0238 g) having the following physical data. $^1$H NMR ($d_6$-DMSO): δ 9.4-8.2 (br m, 3H), 7.78 (s, 1H), 5.40 (br s, 2H).

Example 241

6-amino-5-cyano-N-((1-((2-(pyridin-2-yl)thiazol-5-yl)methyl)piperidin-4-yl)methyl)imidazo[1,2-a]pyridine-8-carboxamide

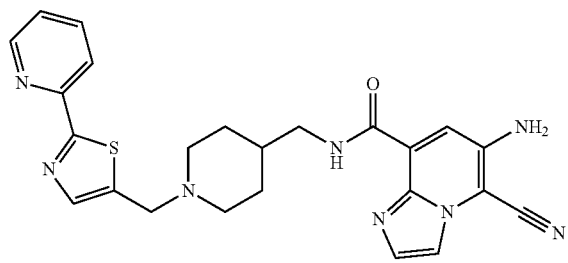 [SMILES: N#Cc1c(N)cc(C(=O)NCC2CCN(Cc3cnc(-c4ccccn4)s3)CC2)c2nccn12]

To a solution of the compound prepared in Example 240 (0.011 g) in ethanol (0.5 mL) was added a 50% aqueous solution of 2-chloroacetaldehyde (0.0088 mL). The reaction mixture was heated at 90° C. for 2.5 hours. The reaction mixture was allowed to cool to room temperature, and then filtered and concentrated to afford 15.3 mg of a brown powder.

This material was then combined with 1H-benzo[d][1,2,3]triazol-1-ol (0.012 g), and triethylamine (0.0613 mL) in N,N-dimethylformamide (0.5 mL). 1-ethyl-3-(3'-dimethylaminopropyl)carbodiimide (0.0145 g) was then added to the reaction mixture. After stirring for 30 minutes, the compound prepared in Example 214 (0.030 g) was added to the reaction mixture. The reaction mixture was allowed to stir at room temperature for 3 hours. Equivalent amounts of 1H-benzo[d][1,2,3]triazol-1-ol, triethylamine, and the compound prepared in Example 214 were added to the reaction mixture, and then heated at 40° C. for 17 hours. The reaction mixture was diluted with saturated sodium hydrogen carbonate aqueous solution and extracted with ethyl acetate. The combined organics were then washed with water and brine, dried over magnesium sulfate and concentrated. The residue was purified by column chromatography on silica gel (dichloromethane:methanol=19:1) to obtain the title compound (0.0085 g) having the following physical data.

$^1$H NMR (CDCl$_3$): δ 10.33 (br t, J=4.7 Hz, 1H), 8.60 (d, J=3.9 Hz, 1H), 8.14 (d, J=8.6 Hz, 1H), 7.80-7.76 (m, 2H), 7.74 (s, 1H), 7.68 (s, 1H), 7.61 (s, 1H), 7.30 (dd, J=4.7, 7.8 Hz, 1H), 4.61 (s, 2H), 3.78 (s, 2H), 3.45 (t, J=6.26 Hz, 2H), 3.01-2.95 (m, 2H), 2.14-2.05 (m, 2H), 1.85-1.38 (m, 5H);

Mass data (ESI, Pos.): m/z 495 (M+Na)$^+$.

Example 242

6-amino-5-cyano-2-ethyl-N-((1-((2-(pyridin-2-yl)thiazol-5-yl)methyl)piperidin-4-yl)methyl)imidazo[1,2-a]pyridine-8-carboxamide

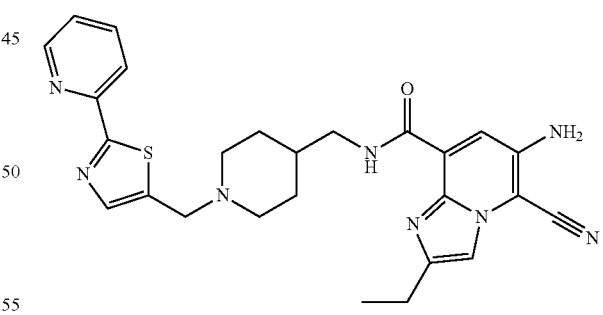

According to the same procedure described in example 241, using 1-bromobutan-2-one instead of 2-chloroacetaldehyde, the title compound having the following physical data was obtained.

$^1$H NMR (CDCl$_3$): δ 10.46 (m, 1H), 8.60 (d, J=3.1 Hz, 1H), 8.14 (d, J=8.6 Hz, 1H), 7.80-7.76 (m, 2H), 7.68 (s, 1H), 7.66 (s, 1H), 7.30 (dd, J=4.7, 8.6 Hz, 1H), 4.45 (s, 2H), 3.78 (s, 2H), 3.47-3.27 (m, 2H), 3.04-2.77 (m, 4H), 2.14-2.03 (m, 2H), 1.86-1.30 (m, 8H);

Mass data (APCI, Pos.): m/z 501 (M+H)$^+$.

Example 243 tert-Butyl (1-(5-(pyridin-2-yl)thiophen-2-ylsulfonyl)piperidin-4-yl)methylcarbamate

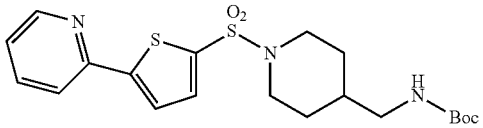 [SMILES: CC(C)(C)OC(=O)NCC1CCN(S(=O)(=O)c2ccc(-c3ccccn3)s2)CC1]

tert-Butyl piperidin-4-ylmethylcarbamate (0.100 g) in dichloromethane (2.3 mL) was treated with 5-(pyridin-2-yl)thiophene-2-sulfonyl chloride (0.133 g), followed by triethylamine (0.325 mL) at room temperature. After stirring the mixture at room temperature overnight, it was washed with 1N hydrochloric acid, the organic layer was separated and filtered. Evaporation of the solvent and purification by column chromatography on silica gel (1-4% methanol in dichloromethane) provide the title compound (0.088 g) having the following physical data.
$^1$H NMR (DMSO-$d_6$): δ 8.58 (d, J=5.0 Hz, 1H), 8.08 (d, J=8.0 Hz, 1H), 7.95-7.90 (m, 2H), 7.63 (d, J=4.0 Hz, 1H), 7.40 (dd, J=4.9, 7.5 Hz, 1H), 6.88 (t, J=5.8 Hz, 1H), 3.63 (d, J=11.5 Hz, 2H), 2.79 (t, J=6.1 Hz, 2H), 2.36 (t, J=10.5 Hz, 2H), 1.70 (d, J=10.8 Hz, 2H), 1.33-1.30 (m, 10H), 1.2-1.13 (m, 2H);
Mass data (APCI, Pos.): m/z 438 (M+H)$^+$.

Example 244

(1-(5-(Pyridin-2-yl)thiophen-2-ylsulfonyl)piperidin-4-yl)methanamine Dihydrochloride

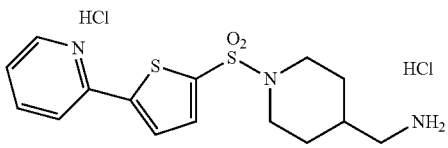 [SMILES: Cl ; NCC1CCN(S(=O)(=O)c2ccc(-c3ccccn3)s2)CC1 ; Cl]

A solution of the compound prepared in Example 243 (0.088 g) in dichloromethane (1 mL) was treated with 4N hydrogen chloride in dioxane (0.151 mL) at room temperature. The mixture was stirred at room temperature for 18 hours. The solvent was evaporated in vacuo to provide the title compound (0.072 g) having the following physical data.
Mass data (APCI, Pos.): m/z 338 (M+H)$^+$.

Example 245

4-Amino-5-cyano-6-ethoxy-N-((1-(5-(pyridin-2-yl)thiophen-2-ylsulfonyl)piperidin-4-yl)methyl)picolinamide

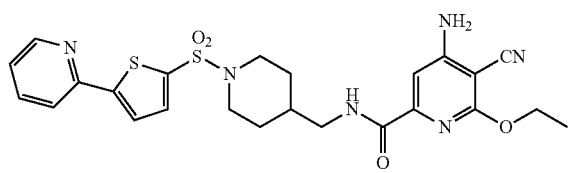 [SMILES: CCOc1nc(C(=O)NCC2CCN(S(=O)(=O)c3ccc(-c4ccccn4)s3)CC2)cc(N)c1C#N]

A solution of 4-amino-5-cyano-6-ethoxypicolinic acid (0.038 g) in N,N-dimethylformamide (2 mL) was treated with 1-ethyl-3-(3'-dimethylaminopropyl)carbodiimide hydrochloride (0.039 g), 1-hyroxybenzotriazole hydrate (0.031 g), followed by diisopropylethylamine (0.096 mL) at room temperature. After stirring for 15 minutes, the compound prepared in Example 244 (0.079 g) was added. Stirring was continued overnight, and the resulting mixture was washed with water, and the product extracted with ethyl acetate. The organic layer was separated, filtered, evaporated in vacuo and the residue triturated in 1:1 hexane-diethyl ether. The precipitated solids were collected by filtration to provide the title compound (0.041 g) having the following physical data.
$^1$H NMR (DMSO-$d_6$): δ 8.58 (d, J=4.6 Hz, 1H), 8.49 (t, J=6.2 Hz, 1H), 8.07 (d, J=8.0 Hz, 1H), 7.95-7.90 (m, 2H), 7.63 (d, J=3.9 Hz, 1H), 7.45-7.39 (m, 1H), 7.31 (br, 2H), 7.01 (s, 1H), 4.45 (q, J=7.0 Hz, 2H), 3.64 (d, J=11.6 Hz, 2H), 3.14 (t, J=7.2 Hz, 2H), 2.41 (t, J=10.7 Hz, 2H), 1.73 (d, J=13.7 Hz, 2H), 1.60-1.56 (m, 1H), 1.29 (t, J=7.0 Hz, 3H), 1.26-1.20 (m, 2H);
Mass data (APCI, Pos.): m/z 527 (M+H)$^+$.

Example 246

4-Amino-5-cyano-6-ethoxy-N-((1-((3-(pyridin-2-yl)-1,2,4-oxadiazol-5-yl)methyl)piperidin-4-yl)methyl)Picolinamide

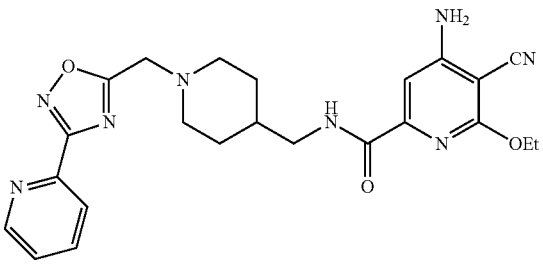 [SMILES: CCOc1nc(C(=O)NCC2CCN(Cc3nc(-c4ccccn4)no3)CC2)cc(N)c1C#N]

A solution of the compound prepared in Example 226 (0.050 g) in N,N-dimethylformamide (0.65 mL) was treated with the compound prepared in Example 247 (0.028 g), followed by triethylamine (0.074 mL) at room temperature. The mixture was heated at 80° C. with stirring overnight. The solvent was evaporated in vacuo, the residue was taken in dichloromethane and purified by column chromatography on silica gel (2-10% hexane in dichloromethane) to obtain the title compound (0.044 g) having the following physical data.
$^1$H NMR (CD$_3$OD): δ 8.71 (d, J=4.66 Hz, 1H), 8.18 (d, J=7.86 Hz, 1H), 8.02 (d, J=7.77 Hz, 1H), 7.98 (br, 1H), 7.60-7.57 (m, 1H), 7.30 (br, 2H), 7.08 (s, 1H), 4.48 (q, J=7.07 Hz, 2H), 4.00 (s, 1H), 3.07-3.03 (m, 2H), 2.30 (t, J=10.78 Hz, 2H), 1.76 (d, J=13.16 Hz, 2H), 1.69-1.63 (m, 1H), 1.44-1.28 (m, 5H);
Mass data (APCI, Pos.): m/z 463 (M+H)$^+$.

Example 247

5-(Chloromethyl)-3-(pyridin-2-yl)-1,2,4-oxadiazole

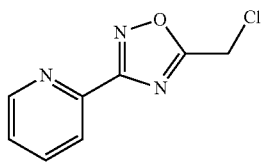 [SMILES: ClCc1nc(-c2ccccn2)no1]

A solution of 2-chloroacetyl chloride (0.209 mL) in dichloromethane (3 mL) was added dropwise to a solution of (Z)—N'-hydroxypicolinamidine (0.300 g) in dichloromethane (7 mL). Triethylamine (0.366 mL) was added dropwise to the reaction solution and stirring at room temperature continued for 18 hours. The mixture was purified by column chromatography on silica gel (10-50% ethyl acetate in hexane). Desired fractions were evaporated in vacuo to a pale pink residue (0.21 g). This material was taken in toluene and refluxed for 18 hours. The solvent was evaporated in vacuo and the residue purified by column chromatography on silica gel (1-3% methanol in dichloromethane) to provide the title compound (0.085 g) having the following physical data.

$^1$H NMR (DMSO-$d_6$): δ 8.78 (d, J=4.7 Hz, 1H), 8.11-8.02 (m, 2H), 7.65-7.62 (m, 1H), 5.21 (s, 2H);

Mass data (APCI, Pos.): m/z 196 (M+H)$^+$.

Example 248

1-Benzyl-4-hydroxypiperidine-4-carbonitrile

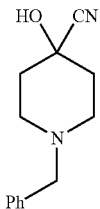

A solution of 1-benzylpiperidin-4-one (7.00 g) in 1:1 diethyl ether-water (30 mL) was cooled to 0° C. and treated with potassium cyanide (6.02 g), followed by hydrochloric acid (7.71 mL). The ice bath was removed and the mixture was stirred at room temperature for 18 hours. The phases were separated, and the aqueous layer was extracted with diethyl ether, dried and evaporated in vacuo to provide the title compound (4.08 g) having the following physical data.

$^1$H NMR (DMSO-$d_6$): δ 7.30 (m, 5H), 6.56 (br, 1H), 3.38 (q, J=7.0 Hz, 2H), 2.62-2.59 (m, 2H), 2.26-2.21 (m, 2H), 1.99-194 (m, 2H), 1.76-1.70 (m, 2H).

Example 249

4-(Aminomethyl)-1-benzylpiperidin-4-ol

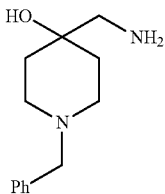

A suspension of the compound prepared in Example 248 (4.00 g) in tetrahydrofuran (90 mL) was treated with lithium aluminum hydride (1.75 g) slowly at 0° C. The mixture was allowed to stir at room temperature overnight, cooled to 0° C. and treated with Rochelle's salt (sodium potassium tartrate; 400 g). After stirring at room temperature for 3 hours, the organic phase was separated and the aqueous layer extracted with ethyl acetate. The combined organic extracts were dried and evaporated in vacuo to obtain the title compound (3.76 g) having the following physical data.

$^1$H NMR (DMSO-$d_6$): δ 7.29 (m, 5H), 6.56 (br, 1H), 4.52 (br, 1H), 3.93 (br, 2H), 4.03 (q, J=7.1 Hz, 2H), 3.44 (m, 2H), 2.65-2.62 (m, 2H), 2.44-2.41 (m, 2H), 2.31-2.25 (m, 2H), 2.03-1.99 (m, 2H), 1.71-1.66 (m, 1H), 1.43-1.36 (m, 6H);

Mass data (APCI, Pos.): m/z 221 (M+H)$^+$.

Example 250 tert-Butyl (1-benzyl-4-hydroxypiperidin-4-yl)methylcarbamate

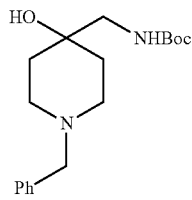

A solution of the compound prepared in Example 249 (3.76 g) in dichloromethane (23 mL) was cooled to 0° C. and treated with di-tert-butyl dicarbonate (3.91 g). The mixture was then stirred at room temperature overnight, washed with aqueous potassium carbonate, dried and evaporated in vacuo to obtain the title compound (6.07 g) having the following physical data.

$^1$H NMR (DMSO-$d_6$): δ 7.29 (m, 5H), 6.56 (br, 1H), 4.16 (br, 1H), 4.09 (q, J=5.3 Hz, 2H), 2.90 (d, J=6.1 Hz, 2H), 2.45-2.23 (m, 4H), 2.62-2.59 (m, 2H), 1.38 (s, 9H), 1.65-1.31 (m, 13H);

Mass data (APCI, Pos.): m/z 321 (M+H)$^+$.

Example 251 tert-Butyl (4-hydroxypiperidin-4-yl)methylcarbamate

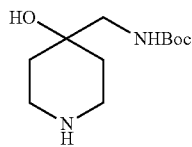

A solution the compound prepared in Example 250 (0.68 g) in ethanol (11 mL) was treated with hydrazine monohydrate (0.208 mL), followed by 10% palladium-carbon (0.238 g). The mixture was refluxed for 18 hours. After allowing mixture to cool to room temperature, the catalyst was filtered off and washed with methanol. The filtrate was evaporated in vacuo to obtain the title compound (0.510 g) having the following physical data.

$^1$H NMR (DMSO-$d_6$): δ 6.52 (br, 1H), 4.17 (br, 1H), 2.75-2.69 (m, 2H), 2.62-2.59 (m, 2H), 1.38 (s, 9H), 1.34-1.25 (m, 4H);

Mass data (APCI, Pos.): m/z 231 (M+H)$^+$.

Example 252 tert-Butyl (4-hydroxy-1-((2-(pyridin-2-yl)thiazol-5-yl)methyl)piperidin-4-yl)methylcarbamate

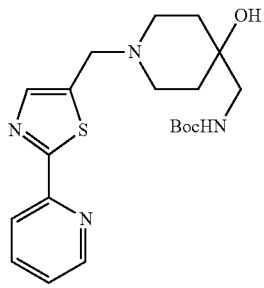 [SMILES: CC(C)(C)OC(=O)NCC1(O)CCN(Cc2cnc(-c3ccccn3)s2)CC1]

According to the same procedure described in Example 101, starting with the compound prepared in Example 251 instead of the compound prepared in Example 226 and the compound prepared in Example 139 instead of 2-phenylthiazole-5-carbaldehyde, the title compound having the following physical data was obtained.

$^1$H NMR (DMSO-d$_6$): δ 8.61 (d, J=4.8 Hz, 1H), 8.109 (d, J=7.9 Hz, 1H), 7.97-7.92 (m, 1H), 7.79 (s, 1H), 7.48-7.44 (m, 1H), 6.58 (br, 1H), 4.19 (br, 1H), 3.73 (s, 1H), 2.91 (d, J=6.1 Hz, 2H), 2.58 (m, 2H), 2.34 (t, J=10.0 Hz, 2H), 1.51-1.34 (m, 1H), 1.44-1.28 (m, 12H);

Mass data (APCI, Pos.): m/z 405 (M+H)$^+$.

Example 253

4-(aminomethyl)-1-{[2-(2-pyridinyl)-1,3-thiazol-5-yl]methyl}-4-piperidinol bis(trifluoroacetate)

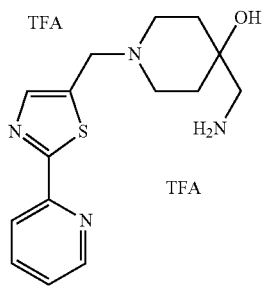 [SMILES: NCC1(O)CCN(Cc2cnc(-c3ccccn3)s2)CC1]

A solution of the compound prepared in Example 252 (0.108 g) in dichloromethane (1.3 mL) was treated with trifluoroacetic acid (0.3 mL) at room temperature for 18 hours. The solvent was evaporated in vacuo and the residue was azeotroped from toluene twice to obtain the title compound (0.104 g) having the following physical data.

Mass data (APCI, Pos.): m/z 305 (M+H)$^+$.

Example 254

4-Amino-5-cyano-6-ethoxy-N-((4-hydroxy-1-((2-(pyridin-2-yl)thiazol-5-yl)methyl)piperidin-4-yl)methyl)picolinamide

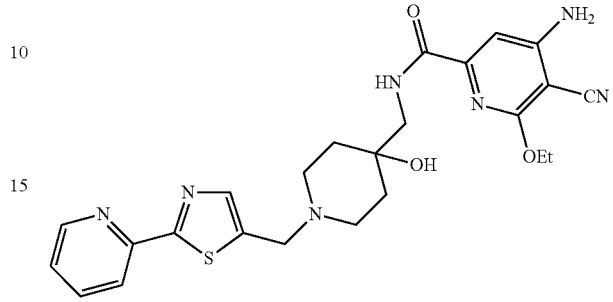

According to the same procedure described in Example 245, using the compound prepared in Example 253 instead of (1-(5-(pyridin-2-yl)thien-2-ylsulfonyl)piperidin-4-yl)methanamine dihydrochloride, the title compound having the following physical data was obtained.

$^1$H NMR (DMSO-d$_6$): δ 8.61 (d, J=4.8 Hz, 1H), 8.23 (d, J=6.1 Hz, 1H), 8.09 (d, J=7.9 Hz, 1H), 7.94 (td, J=1.7, 7.7 Hz, 1H), 7.79 (s, 1H), 7.48-7.44 (m, 1H), 7.34 (br, 2H), 7.06 (s, 1H), 4.59 (br, 1H), 4.42 (q, J=7.0 Hz, 2H), 3.75 (s, 1H), 3.28 (d, J=5.8 Hz, 2H), 2.56 (m, 2H), 2.42-2.37 (m, 2H), 1.52-1.46 (m, 4H), 1.33 (t, J=7.0 Hz, 2H);

Mass data (APCI, Pos.): m/z 494 (M+H)$^+$.

Example 255 tert-Butyl 1-oxa-6-azaspiro[2.5]octane-6-carboxylate

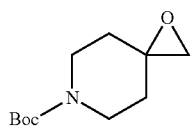 [SMILES: CC(C)(C)OC(=O)N1CCC2(CC1)CO2]

A solution of tert-butyl 4-oxopiperidine-1-carboxylate (2.00 g), trimethylsulfoxonium iodide (2.43 g) and tetrabutylammomium bromide (0.048 g) in toluene (20 mL) was added a solution of sodium hydroxide (5.02 mL) in water (6.3 mL) dropwise at room temperature. The resulting mixture was heated at 80° C. for 4 hours. The organic phase was separated and the aqueous layer was extracted with toluene. The combined extracts were washed with water, brine, dried and evaporated in vacuo and further dried under high vacuum to obtain the title compound (1.85 g) having the following physical data.

$^1$H NMR (DMSO-d$_6$): δ 3.53-3.47 (m, 2H), 3.41-3.34 (m, 2H), 2.65 (s, 1H), 1.67-1.61 (m, 2H), 1.41-1.35 (m, 11H).

Example 256 tert-Butyl 4-(azidomethyl)-4-hydroxypiperidine-1-carboxylate

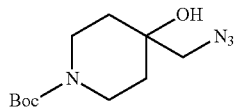

To a solution of the compound prepared in Example 255 (0.500 g) in dioxane (31 mL) and water (3 mL) was treated with sodium azide (0.143 g) at room temperature. The mixture was refluxed overnight. The solvent was evaporated in vacuo and the residue was distributed between ethyl acetate and water. The aqueous layer was extracted with more ethyl acetate, dried and evaporated in vacuo to obtain the title compound (0.534 g) having the following physical data.

$^1$H NMR (DMSO-$d_6$): δ 4.85 (br, 1H), 3.64 (d, J=12.9 Hz, 2H), 3.17 (s, 2H), 3.05 (br, 2H), 1.51-1.32 (m, 13H).

Example 257 tert-Butyl 4-(azidomethyl)-4-methoxypiperidine-1-carboxylate

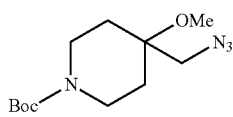

To a solution of the compound prepared in Example 256 (0.123 g) in tetrahydrofuran (1.5 mL) was added sodium hydride (0.057 g) and iodomethane (0.089 mL) at room temperature. The mixture was stirred at room temperature overnight and then diluted with water and ethyl acetate. The organic layer was dried, evaporated in vacuo and purified by column chromatography on silica gel (5% methanol in dichloromethane) to obtain the title compound (0.071 g) having the following physical data.

$^1$H NMR (DMSO-$d_6$): δ 3.62 (br, 2H), 3.37 (s, 3H), 3.16 (s, 2H), 2.95 (br, 2H), 1.70 (d, J=12.7 Hz, 2H), 1.41-1.32 (m, 11H);

Mass data (APCI, Pos.): m/z 171 (M+H−Boc)$^+$.

Example 258 tert-Butyl 4-(aminomethyl)-4-methoxypiperidine-1-carboxylate

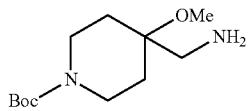

A solution of the compound prepared in Example 257 (0.071 g) in ethanol (1.3 mL) was purged with Argon, treated with 10% palladium-carbon (0.010 g), and attached to a hydrogen balloon. Stirring was continued at room temperature for 14 hours. The mixture was filtered. The solvent was evaporated to obtain the title compound (0.059 g) having the following physical data.

Mass data (APCI, Pos.): m/z 245 (M+H)$^+$.

Example 259 tert-Butyl 4-(4-amino-5-cyano-6-ethoxypicolinamido)methyl)-4-methoxypiperidine-1-carboxylate

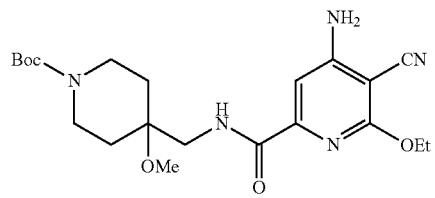 [SMILES: CCOc1nc(C(=O)NCC2(OC)CCN(C(=O)OC(C)(C)C)CC2)cc(N)c1C#N]

According to the same procedure described in Example 245, using the compound prepared in Example 258 instead of (1-(5-(pyridin-2-yl)thiophen-2-ylsulfonyl)piperidin-4-yl)methanamine dihydrochloride, the title compound having the following physical data was obtained.

$^1$H NMR (DMSO-$d_6$): δ 8.11 (t, J=6.3 Hz, 1H), 7.36 (br, 2H), 7.06 (s, 1H), 4.43 (q, J=7.0 Hz, 2H), 3.64 (d, J=12.7 Hz, 2H), 3.38 (d, J=6.3 Hz, 2H), 3.18 (s, 3H), 2.96 (br, 2H), 1.65 (d, J=13.3 Hz, 2H), 1.38-1.32 (m, 14H);

Mass data (APCI, Pos.): m/z 434 (M+H)$^+$.

Example 260

4-Amino-5-cyano-6-ethoxy-N-((4-methoxypiperidin-4-yl)methyl)picolinamide

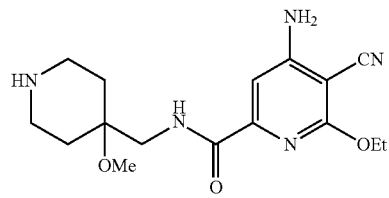 [SMILES: CCOc1nc(C(=O)NCC2(OC)CCNCC2)cc(N)c1C#N]

According to the same procedure described in Example 253, using the compound prepared in Example 259 instead of tert-butyl (4-hydroxy-1-((2-(pyridin-2-yl)thiazol-5-yl)methyl)piperidin-4-yl)methylcarbamate, the title compound having the following physical data was obtained.

Mass data (APCI, Pos.): m/z 334 (M+H)$^+$.

Example 261

4-Amino-5-cyano-6-ethoxy-N-((4-methoxy-1-((2-(pyridin-2-yl)thiazol-5-yl)methyl)piperidin-4-yl)methyl)picolinamide

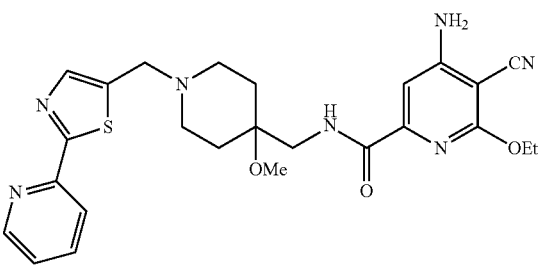 [SMILES: CCOc1nc(C(=O)NCC2(OC)CCN(Cc3cnc(-c4ccccn4)s3)CC2)cc(N)c1C#N]

According to the same procedure described in Example 101, starting with the compound prepared in Example 260 instead of the compound prepared in Example 226 and the compound prepared in Example 139 instead of 2-phenylthiazole-5-carbaldehyde, the title compound having the following physical data was obtained.

$^1$H NMR (DMSO-d$_6$): δ 8.61 (d, J=4.6 Hz, 1H), 8.1-8.06 (m, 2H), 7.97-7.92 (m, 1H), 7.70 (s, 1H), 7.49-7.45 (m, 1H), 7.36 (br, 1H), 7.05 (s, 1H), 4.42 (q, J=7.1 Hz, 2H), 3.75 (s, 2H), 3.37 (d, J=6.2 Hz, 2H), 3.14 (s, 3H), 2.58-2.54 (m, 2H), 2.33-2.25 (m, 2H), 1.71-1.68 (m, H), 1.53-1.46 (m, 2H), 1.73 (t, J=7.0 Hz, 3H);

Mass data (APCI, Pos.): m/z 508 (M+H)$^+$.

Example 262

1-Benzyl-1-4-(hydroxymethyl)piperidin-3-ol

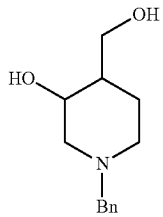

To a solution of ethyl 1-benzyl-3-oxopiperidine-4-carboxylate (10.00 g) in ethanol (75 mL) was added sodium borohydride (4.34 g) at 0° C. The mixture was stirred at room temperature overnight and then diluted with water and extracted with chloroform. The combined extracts were washed with brine, dried and evaporated in vacuo to an oil that was purified by column chromatography on silica gel (1-10% ethanol in dichloromethane) to obtain the title compound (2.66 g, cis-isomer; 2.28 g, trans-isomer) having the following physical data.

(Cis)-Isomer $^1$H NMR (DMSO-d$_6$): δ 7.32-7.24 (m, 5H), 4.27 (t, J=5.3 Hz, 1H), 3.94 (d, J=6.9 Hz, 1H), 3.73-3.69 (m, 1H), 3.49-3.46 (m, 1H), 3.32 (s, 2H), 3.28-3.23 (m, 1H), 2.72-2.67 (m, 2H), 2.04 (d, J=10.3 Hz, 1H), 1.97-1.92 (m, 1H), 1.56-1.35 (m, 3H).

(Trans)-Isomer $^1$H NMR (DMSO-d$_6$): δ 7.31-7.23 (m, 5H), 4.27 (t, J=5.3 Hz, 1H), 4.55 (d, J=5.2 Hz, 1H), 4.32 (t, J=5.2 Hz, 1H), 3.64-3.59 (m, 1H), 3.49 (d, J=13.1 Hz, 1H), 3.38 (d, J=13.1 Hz, 1H), 3.26-3.20 (m, 2H), 2.83 (dd, J=3.5, 10.40 Hz, 1H), 2.75 (d, J=10.9 Hz, 2H), 1.82 (t, J=11.2 Hz, 1H), 1.69-1.61 (m, 1H), 1.24-1.18 (m, 3H).

Mass data (APCI, Pos.): m/z 508 (M+H)$^+$.

Example 263

(trans)-4-(Hydroxymethyl)piperidin-3-ol

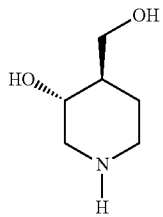

According to the same procedure described in Example 251, using the corresponding amine instead of tert-butyl (1-benzyl-4-hydroxypiperidin-4-yl)methylcarbamate, the title compound having the following physical data was obtained.

$^1$H NMR (DMSO-d$_6$): δ 4.53 (br, 1H), 4.33 (br, 1H), 3.59 (dd, J=10.3, 4.4 Hz, 1H), 3.44 (q, J=7.0 Hz, 1H), 3.32 (dd, J=10.0 Hz, 1H), 3.17-3.10 (m, 1H), 2.92 (dd, J=4.5, 11.5 Hz, 1H), 2.83-2.78 (m, 1H), 2.32 (td, J=2.7, 12.1 Hz, 1H), 2.15 (dd, J=10.0, 11.5 Hz, 1H), 1.64 (ddd, J=2.6, 6.3, 13.1 Hz, 1H), 1.32-1.23 (m, 1H), 1.09-1.02 (m, 1H);

Mass data (APCI, Pos.): m/z 132 (M+H)$^+$.

Example 264

(trans)-tert-Butyl 3-hydroxy-4-(hydroxymethyl)piperidine-1-carboxylate

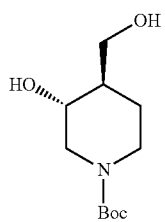

The compound prepared in Example 263 (1.35 g) was dissolved in N,N-dimethylformamide (35 mL) and di-tert-butyl dicarbonate (2.25 g) was added at room temperature and was stirred 14 hours. The solvent was evaporated in vacuo and the residue purified by column chromatography on silica gel (1-10% methanol in dichloromethane) to obtain the title compound (2.15 g) having the following physical data.

$^1$H NMR (DMSO-d$_6$): δ 4.85 (d, J=5.0 Hz, 1H), 4.37 (t, J=5.2 Hz, 1H), 3.97-3.84 (m, 2H), 3.62-3.57 (m, 1H), 3.36-3.34 (m, 2H), 3.14-3.03 (m, 1H), 1.71-1.65 (m, 1H), 1.38-1.31 (m, 11H), 1.15-1.05 (m, 1H);

Mass data (APCI, Pos.): m/z 132 (M+H−Boc)$^+$.

Example 265

(trans)-tert-Butyl 4-(azidomethyl)-3-hydroxypiperidine-1-carboxylate

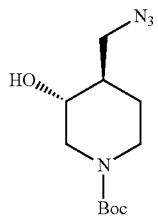 [SMILES: CC(C)(C)OC(=O)N1CC[C@H](CN=[N+]=[N-])[C@@H](O)C1]

To a solution of the compound prepared in Example 264 (2.15 g) and triethylamine (1.94 mL) in dichloromethane (33 mL) was added methanesulfonyl chloride (0.79 mL) at room temperature. The mixture was stirred at room temperature overnight, diluted with water, and extracted with chloroform. The combined organic extracts were washed with brine, dried and evaporated in vacuo to a clear oil, taken in N,N-dimethylformamide (40 mL) and treated with sodium azide (0.906 g), followed by ammonium chloride (0.746 g) at room temperature. This mixture was heated at 60° C. for 6 hours. The mixture was cooled to room temperature, concentrated in vacuo, diluted with water, extracted with chloroform. The combined extracts were washed with brine, dried and evaporated in vacuo to a pale yellow oil, which was purified by column chromatography on silica gel (1-10% methanol in dichloromethane) to obtain the title compound (1.08 g) having the following physical data.

$^1$H NMR (DMSO-$d_6$): δ 5.11 (d, J=5.3 Hz, 1H), 4.06-3.83 (m, 2H) 3.58 (dd, J=3.4, 12.1 Hz, 1H), 3.38-3.34 (m, 2H), 3.14-3.07 (m, 1H), 1.71-1.65 (m, 1H), 1.54-1.46 (m, 1H), 1.39 (s, 11H), 1.23-1.10 (m, 1H).

Example 266

(trans)-tert-Butyl 4-(aminomethyl)-3-hydroxypiperidine-1-carboxylate

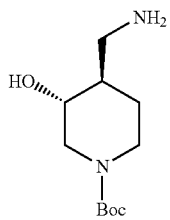 [SMILES: CC(C)(C)OC(=O)N1CC[C@H](CN)[C@@H](O)C1]

According to the same procedure described in Example 258, using the corresponding azide instead of tert-butyl 4-(azidomethyl)-4-methoxypiperidine-1-carboxylate, the title compound having the following physical data was obtained.

$^1$H NMR (DMSO-$d_6$): δ 5.76 (s, 1H), 3.95-3.83 (m, 2H), 3.20-3.1 (m, 3H), 2.72-2.58 (m, 2H), 2.43-2.33 (m, 1H), 1.76-1.54 (m, 1H), 1.38 (s, 9H), 1.32-0.93 (m, 2H);

Mass data (APCI, Pos.): m/z 231 (M+H)$^+$.

Example 267

(trans)-tert-Butyl 4-((4-amino-5-cyano-6-ethoxypicolinamido)methyl)-3-hydroxypiperidine-1-carboxylate

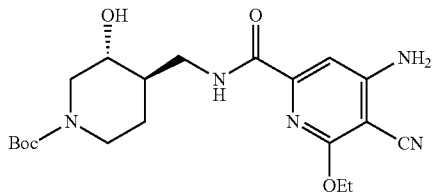 [SMILES: CCOc1nc(C(=O)NC[C@H]2CCN(C(=O)OC(C)(C)C)C[C@@H]2O)cc(N)c1C#N]

According to the same procedure described in Example 245, using the corresponding amine instead of (1-(5-(pyridin-2-yl)thiophen-2-ylsulfonyl)piperidin-4-yl)methanamine dihydrochloride, the title compound having the following physical data was obtained.

$^1$H NMR (DMSO-$d_6$): δ 6.79 (br, 1H), 7.31 (br, 2H), 7.01 (s, 1H), 5.33 (d, J=4.5 Hz, 1H), 4.45-4.40 (m, 3H), 4.03-3.81 (m, 2H), 3.42-3.36 (m, 2H), 3.27-3.16 (m, 2H), 2.45-2.38 (m, 2H), 2.43-2.33 (m, 1H), 1.76-1.54 (m, 1H), 1.38 (s, 9H), 1.33-1.29 (m, 2H), 1.09 (t, J=7.0 Hz, 3H);

Mass data (APCI, Pos.): m/z 420 (M+H)$^+$.

Example 268

4-Amino-5-cyano-6-ethoxy-N-(((trans)-3-hydroxypiperidin-4-yl)methyl)picolinamide

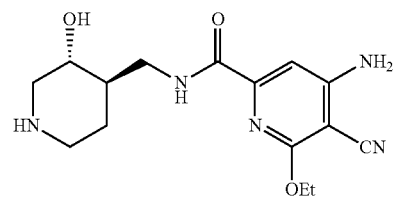 [SMILES: CCOc1nc(C(=O)NC[C@H]2CCNC[C@@H]2O)cc(N)c1C#N]

According to the same procedure described in Example 253, using the corresponding amine instead of tert-butyl (4-hydroxy-1-((2-(pyridin-2-yl)thiazol-5-yl)methyl)piperidin-4-yl)methylcarbamate, the title compound having the following physical data was obtained.

Mass data (APCI, Pos.): m/z 320 (M+H)$^+$.

Example 269

4-Amino-5-cyano-6-ethoxy-N-(((trans)-3-hydroxy-1-((2-(pyridin-2-yl)thiazol-5-yl)methyl)piperidin-4-yl)methyl)picolinamide

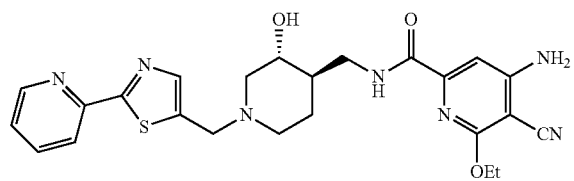 [SMILES: CCOc1nc(C(=O)NC[C@H]2CCN(Cc3cnc(-c4ccccn4)s3)C[C@@H]2O)cc(N)c1C#N]

According to the same procedure described in Example 101, starting with the compound prepared in Example 268 and the compound prepared in Example 139, the title compound having the following physical data was obtained.

$^1$H NMR (DMSO-$d_6$): δ 8.84 (br, 1H), 8.61 (d, J=4.2 Hz, 1H), 8.09 (d, J=7.9 Hz, 1H), 7.95 (td, J=1.7, 7.7 Hz, 1H), 7.80 (s, 1H), 7.47 (ddd, J=1.1, 4.8, 7.5 Hz, 1H), 7.30 (br, 2H), 7.04 (s, 1H), 5.09 (d, J=4.7 Hz, 1H), 4.41 (q, J=7.0 Hz, 2H), 3.82 (d, J=14.2 Hz, 1H), 3.73 (d, J=14.2 Hz, 1H), 3.48-3.40 (m, 1H), 3.29-3.21 (m, 2H), 2.96-2.82 (m, 2H), 1.97-1.92 (m, 1H), 1.78 (t, J=10.1 Hz, 1H), 1.62 (d, J=9.7 Hz, 1H), 1.41-1.31 (m, 1H), 1.29 (t, J=7.0 Hz, 3H), 1.25-1.21 (m, 1H);

Mass data (APCI, Pos.): m/z 494 (M+H)$^+$.

Example 270

4-Amino-5-cyano-6-ethoxy-N-(((cis)-3-hydroxy-1-((2-(pyridin-2-yl)thiazol-5-yl)methyl)piperidin-4-yl)methyl)picolinamide

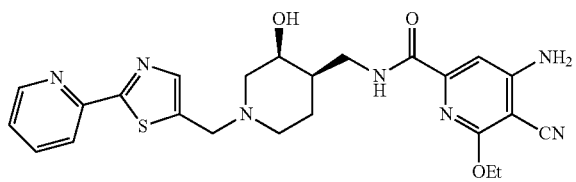 [SMILES: CCOc1nc(C(=O)NC[C@H]2CCN(Cc3cnc(-c4ccccn4)s3)C[C@H]2O)cc(N)c1C#N]

According to the same procedures described in Examples 263→264→265→266→267→268→269, starting with (cis)-1-benzyl-4-(hydroxymethyl)piperidin-3-ol instead of (trans)-1-benzyl-4-(hydroxymethyl)piperidin-3-ol, the title compound having the following physical data was obtained.

$^1$H NMR (CD$_3$OD): δ 8.62-8.58 (m, 2H), 8.09 (d, J=7.9 Hz, 1H), 7.95 (td, J=1.7, 7.8 Hz, 1H), 7.80 (s, 1H), 7.49-7.45 (m, 1H), 7.31 (br, 2H), 7.04 (s, 1H), 4.50 (d, J=5.6 Hz, 1H), 4.45 (q, J=7.0 Hz, 2H), 3.76 (br, 2H), 3.72-3.68 (m, 1H), 3.28-3.21 (m, 2H), 2.79-2.73 (m, 2H), 2.22-2.18 (m, 1H), 2.09 (t, J=9.4 Hz, 1H), 1.71-1.58 (m, 1H), 1.40-1.32 (m, 2H), 1.31 (t, J=7.1 Hz, 3H);

Mass data (APCI, Pos.): m/z 494 (M+H)$^+$.

Example 271

Dimethyl 2-(phenylamino)maleate

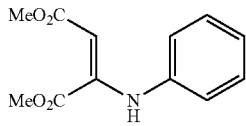 [SMILES: COC(=O)/C=C(/Nc1ccccc1)C(=O)OC]

To a solution of dimethyl but-2-ynedioate (1.452 mL) in methanol (20 mL) was added aniline (0.98 mL) at room temperature. The mixture was stirred at room temperature overnight. The mixture was purified by column chromatography on silica gel (20-50% ethyl acetate in hexane) to obtain the title compound (1.73 g) having the following physical data.

$^1$H NMR (DMSO-d$_6$): δ 9.61 (br, 1H), 7.30 (t, J=7.8 Hz, 1H), 7.14 (d, J=7.7 Hz, 1H), 7.08 (t, J=7.4 Hz, 1H), 6.94 (d, J=8.0 Hz, 1H), 5.28 (s, 1H), 3.67 (s, 6H);

Mass data (APCI, Pos.): m/z 236 (M+H)$^+$.

Example 272

Methyl 4-oxo-1,4-dihydroquinoline-2-carboxylate

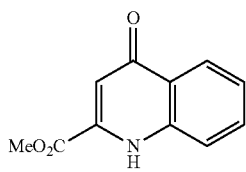 [SMILES: COC(=O)c1cc(=O)c2ccccc2[nH]1]

A mixture of the compound prepared in Example 271 (0.980 g) in Dowtherm A (trade mark; 1 mL) was heated at 250° C. for 15 minutes. The mixture was cooled to room temperature and shaken between dichloromethane and water. The organic layer was dried, concentrated in vacuo and purified by column chromatography on silica gel (1-5% methanol in dichloromethane) to obtain the title compound (0.036 g) having the following physical data.

$^1$H NMR (CD$_3$OD): δ 8.24 (d, J=8.3 Hz, 1H), 7.85 (d, J=8.5 Hz, 1H), 7.76 (t, J=7.7 Hz, 1H), 7.46 (t, J=7.6 Hz, 1H), 6.94 (s, 1H), 5.49 (s, 1H), 4.04 (s, 3H);

Mass data (APCI, Neg.): m/z 202 (M–H)$^-$.

Example 273

Methyl 4-azidoquinoline-2-carboxylate

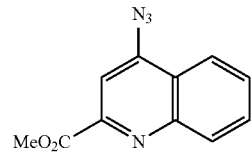 [SMILES: COC(=O)c1cc(N=[N+]=[N-])c2ccccc2n1]

A solution of the compound prepared in Example 272 (0.032 g) in N,N-dimethylformamide (1 mL) was treated with diphenyl phosphoryl azide (0.037 mL), followed by triethylamine (0.028 mL) at room temperature. The mixture was heated at 100° C. overnight. The solvent was evaporated in vacuo and the resulting oil was purified by column chromatography on silica gel (1-10% diethyl ether in dichloromethane) to obtain the title compound (0.016 g) having the following physical data.

$^1$H NMR (CD$_3$OD): δ 8.18 (dd, J=8.3, 4.7 Hz, 1H), 7.99 (s, 1H), 7.88 (m, 1H), 7.72 (m, 1H), 7.40-7.16 (m, 1H), 4.07 (s, 3H);

Mass data (APCI, Pos.): m/z 229 (M+H)$^+$.

Example 274

Methyl 4-aminoquinoline-2-carboxylate

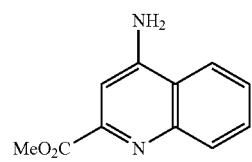 [SMILES: COC(=O)c1cc(N)c2ccccc2n1]

A solution of the compound prepared in Example 273 (0.031 g) in methanol (3 mL) was degassed and treated with 10% palladium-carbon (0.003 g), degassed again and then attached to a hydrogen balloon. Stirring at room temperature was continued overnight. The mixture was filtered, washed with methanol and evaporated in vacuo to obtain the title compound (0.028 g) having the following physical data.

$^1$H NMR (DMSO-d$_6$): δ 8.20 (d, J=8.3 Hz, 1H), 7.87 (d, J=8.4 Hz, 1H), 7.68 (t, J=7.6 Hz, 1H), 7.50 (t, J=7.5 Hz, 1H), 5.46 (br, 2H), 3.86 (s, 3H);

Mass data (APCI, Pos.): m/z 203 (M+H)$^+$.

Example 275

4-Aminoquinoline-2-carboxylic Acid

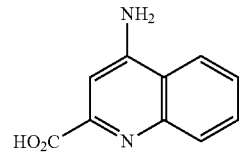 [SMILES: Nc1cc(C(=O)O)nc2ccccc12]

A solution of the compound prepared in Example 274 (0.028 g) in ethanol (0.7 mL) was treated with sodium hydroxide (0.069 mL) at room temperature. Stirring was continued at room temperature for 3 days. The solvent was evaporated in vacuo, the residue suspended in water and acidified to pH3 with 2N hydrochloric acid. The aqueous layer was extracted with ethyl acetate, dried and evaporated in vacuo to a brown solid to obtain the title compound (0.006 g). In addition, the aqueous layer was evaporated in vacuo, shaken in small amount of water and collected by filtration to obtain the title compound (0.015 g) having the following physical data.

Mass data (APCI, Neg.): m/z 187 (M−H)⁻.

Example 275

4-Amino-N-((1-((3-phenylisoxazol-5-yl)methyl)piperidin-4-yl)methyl)quinoline-2-carboxamide

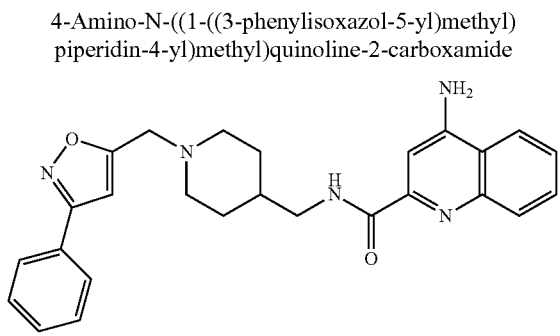

According to the same procedure described in Example 225, using the compound prepared in Example 275 instead of 4-amino-5-cyano-6-ethoxypicolinic acid, and using 1-{1-[(3-phenyl-5-isoxazolyl)methyl]-4-piperidinyl}methanaminethe compound prepared in Example 9 instead of tert-butyl 4-(aminomethyl)piperidine-1-carboxylate the title compound having the following physical data was obtained.

$^1$H NMR (CD$_3$OD): δ 8.07 (d, J=8.4 Hz, 1H), 7.91 (d, J=8.5 Hz, 1H), 7.84-7.81 (m, 2H), 7.66 (t, J=7.7 Hz, 1H), 7.48-7.41 (m, 4H), 7.30 (s, 1H), 6.78 (s, 1H), 3.77 (s, 2H), 3.35 (d, J=6.8 Hz, 2H), 3.01 (d, J=11.5 Hz, 2H), 2.19 (t, J=10.8 Hz, 2H), 1.82 (d, J=12.4 Hz, 2H), 1.71-1.67 (m, 1H), 1.47-1.38 (m, 2H);

Mass data (APCI, Pos.): m/z 442 (M+H)⁺.

Example 277

4-Amino-8-methoxy-N-((1-((3-phenylisoxazol-5-yl)methyl)piperidin-4-yl)methyl)quinoline-2-carboxamide

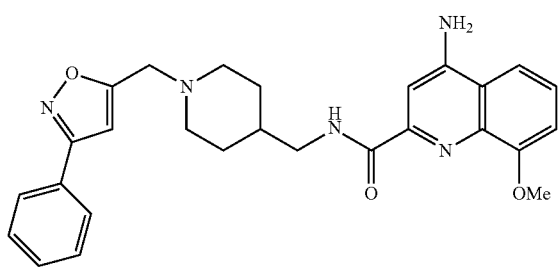 [SMILES: COc1cccc2c(N)cc(C(=O)NCC3CCN(Cc4cc(-c5ccccc5)no4)CC3)nc12]

According to the same procedures described in Examples 271→272→273→274→275→276, starting with 2-methoxyaniline instead of aniline, the title compound having the following physical data was obtained.

$^1$H NMR (CD$_3$OD): δ 7.84-7.81 (m, 2H), 7.64 (d, J=8.6 Hz, 1H), 7.46-7.38 (m, 5H), 7.18 (d, J=7.7 Hz, 1H), 6.79 (s, 1H), 4.07 (s, 3H), 3.78 (s, 2H), 3.35 (d, J=6.8 Hz, 2H), 3.01 (d, J=11.7 Hz, 2H), 2.21 (t, J=11.7 Hz, 2H), 1.85 (d, J=12.1 Hz, 2H), 1.74-1.67 (m, 1H), 1.47-1.38 (m, 2H);

Mass data (APCI, Pos.): m/z 442 (M+H)⁺.

Example 278

2-Bromo-6-ethoxypyridine

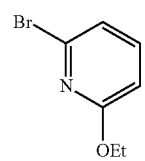

A mixture of 2,6-dibromopyridine (1.5 g) in ethanol (6 mL) was treated with sodium ethoxide (3.55 mL) solution dropwise and resulting mixture was refluxed for 18 hours. The mixture was allowed to cool to room temperature and poured into a beaker containing 5% sodium bicarbonate, extracted with diethyl ether. The combined organics were washed with brine, dried, evaporated in vacuo and purified by column chromatography on silica gel (1-3% methanol in dichloromethane) to obtain the title compound (0.840 g) having the following physical data.

$^1$H NMR (CDCl$_3$): δ 7.40 (t, J=7.8 Hz, 1H), 7.03 (d, J=7.5 Hz, 1H), 6.66 (d, J=8.2 Hz, 1H), 4.35 (q, J=7.1 Hz, 2H), 1.38 (t, J=7.1 Hz, 3H).

Example 279

2-Bromo-6-ethoxy-3-nitropyridine

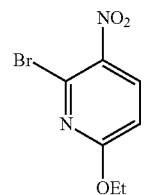 [SMILES: CCOc1ccc([N+](=O)[O-])c(Br)n1]

Potassium nitrate (0.625 g) was added with stirring to a solution of the compound prepared in Example 278 (0.500 g) in sulfuric acid (2.47 mL) at 0° C. The mixture was allowed to warm up to room temperature and then heated slowly to 75° C. After heating for 2 hours, the mixture was cooled to room temperature, poured into ice, pH adjusted to 4 with 10% aqueous sodium hydroxide, and the precipitated to obtain the title compound (0.440 g) having the following physical data.

$^1$H NMR (DMSO-d$_6$): δ 8.41 (d, J=8.8 Hz, 1H), 7.05 (d, J=8.8 Hz, 1H), 4.41 (q, J=7.0 Hz, 2H), 1.35 (t, J=7.1 Hz, 3H);

Mass data (APCI, Pos.): m/z 245 (M+H)⁺.

Example 280

6-Ethoxy-3-nitropicolinonitrile

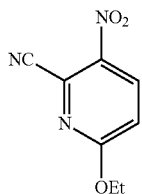

To a solution of the compound prepared in Example 279 (0.317 g) in N,N-dimethylformamide (6 mL) was added potassium cyanide (0.100 g) at room temperature. The mixture was heated at 80° C. for 18 hours and then cooled to room temperature. The solids were filtered, and the filtrate diluted with ethyl acetate, washed with 1N hydrochloric acid and water. The organic layer was filtered, evaporated in vacuo and purified by column chromatography on silica gel (10-50% ethyl acetate in hexane) to obtain the title compound (0.096 g) having the following physical data.

$^1$H NMR (DMSO-$d_6$): δ 8.62 (d, J=9.2 Hz, 1H), 7.36 (d, J=9.2 Hz, 1H), 4.47 (q, J=7.1 Hz, 2H), 1.37 (t, J=7.1 Hz, 3H).

Example 281

3-Amino-6-ethoxypicolinonitrile

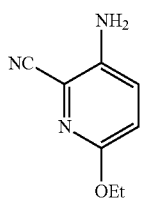

To a suspension of the compound prepared in Example 280 (0.672 g) in hydrochloric acid (2.3 mL) and methanol (7 mL) was added portionwise iron (0.680 g) slowly. After addition was complete, the mixture was stirred at room temperature for 1 hour. The mixture was evaporated in vacuo, diluted with dichloromethane, filtered, and purified by column chromatography on silica gel (5-70% ethyl acetate in hexane) to obtain the title compound (0.460 g) having the following physical data.

$^1$H NMR (DMSO-$d_6$): δ 7.26 (d, J=9.1 Hz, 1H), 6.89 (d, J=9.0 Hz, 1H), 5.84 (br, 2H), 4.14 (q, J=7.0 Hz, 2H), 1.26 (t, J=7.1 Hz, 3H);

Mass data (APCI, Pos.): m/z 164 (M+H)$^+$.

Example 282

3-Amino-6-ethoxypicolinic Acid

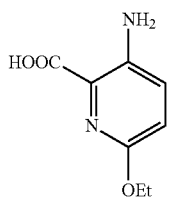 [SMILES: CCOc1ccc(N)c(C(=O)O)n1]

A solution of the compound prepared in Example 281 (0.075 g) in ethanol (2.3 mL) was treated with 2M potassium hydroxide (1.1 mL) and the mixture refluxed overnight. The solvent was evaporated in vacuo, the residue taken in water, acidified with 1N hydrochloric acid, extracted with ethyl acetate, dried and evaporated in vacuo to obtain the title compound (0.074 g) having the following physical data.

$^1$H NMR (DMSO-$d_6$): δ 8.16 (br, 2H), 7.26 (d, J=8.9 Hz, 1H), 6.86 (d, J=8.9 Hz, 1H), 4.25 (q, J=7.0 Hz, 2H), 1.26 (t, J=7.1 Hz, 3H);

Mass data (APCI, Neg.): m/z 181 (M−H)$^−$.

Example 283

3-Amino-6-ethoxy-N-((1-((3-phenylisoxazol-5-yl)methyl)piperidin-4-yl)methyl)picolinamide

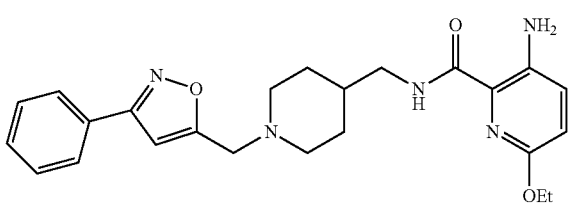 [SMILES: CCOc1ccc(N)c(C(=O)NCC2CCN(Cc3cc(-c4ccccc4)no3)CC2)n1]

According to the same procedure described in Example 225, using the compound prepared in Example 282 instead of 4-amino-5-cyano-6-ethoxypicolinic acid, and using the compound prepared in Example 9 instead of tert-butyl 4-(aminomethyl)piperidine-1-carboxylate, the title compound having the following physical data was obtained.

$^1$H NMR (DMSO-$d_6$): δ 8.22 (t, J=6.2 Hz, 1H), 7.89-7.86 (m, 2H), 7.52-7.50 (m, 3H), 7.18 (d, J=8.8 Hz, 1H), 6.95 (s, 1H), 6.88 (d, J=8.8 Hz, 1H), 6.41 (br, 2H), 4.24 (q, J=7.0 Hz, 2H), 3.70 (s, 2H), 3.16-3.14 (m, 2H), 2.87 (s, J=11.2 Hz, 2H), 2.03 (t, J=10.7 Hz, 2H), 1.63 (d, J=13.3 Hz, 2H), 1.54-1.49 (m, 1H), 1.29-1.20 (m, 5H);

Mass data (APCI, Pos.): m/z 436 (M+H)$^+$.

Example 284

2-Ethoxynicotinic Acid

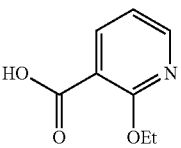

A solution of sodium ethoxide (14.2 mL) was added to a solution of 2-chloronicotinic acid (2.00 g) in ethanol (13 mL). The mixture was heated in a sealed vessel at 170° C. for 2 days. After cooling, the mixture was concentrated in vacuo and the residue taken in water and acidified with hydrochloric acid to pH 3. The precipitated solids were collected by filtration and washed with water to obtain the title compound (1.32 g) having the following physical data.

¹H NMR (DMSO-d₆): δ 12.94 (br, 1H), 8.31 (dd, J=1.6, 4.6 Hz, 1H), 8.07 (m, 1H), 7.05 (dd, J=4.9, 7.4 Hz, 1H), 4.39 (q, J=7.0 Hz, 2H), 1.32 (t, J=7.0 Hz, 3H);

Mass data (APCI, Pos.): m/z 168 (M+H)⁺.

Example 285

Ethyl 2-ethoxynicotinate

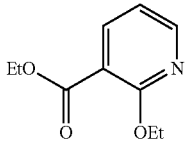 [SMILES: CCOc1ncccc1C(=O)O]

A suspension of the compound prepared in Example 284 (1.3 g) and cesium carbonate (2.53 g) in N,N-dimethylformamide (15 mL) was stirred at room temperature for 2 hours and then treated with ethyl iodide (0.62 mL) at room temperature, and stirring continued for 18 hours. The solvent was evaporated in vacuo and the residue partitioned between ethyl acetate and saturated aqueous solution of sodium bicarbonate. The combined organic extracts were washed with brine, dried and evaporated in vacuo to a yellow oil and purified by column chromatography on silica gel (10-50% ethyl acetate in hexane) to obtain the title compound (0.904 g) having the following physical data.

¹H NMR (DMSO-d₆): δ 8.34 (dd, J=1.7, 4.8 Hz, 1H), 8.09 (dd, J=1.7, 7.6 Hz, 1H), 7.08 (dd, J=4.9, 7.4 Hz, 1H), 4.38 (q, J=7.0 Hz, 2H), 4.27 (q, J=7.1 Hz, 2H), 1.33 (t, J=5.5 Hz, 3H), 1.29 (t, J=5.6 Hz, 3H);

Mass data (APCI, Pos.): m/z 196 (M+H)⁺.

Example 286

Ethyl 2-ethoxy-5-nitronicotinate

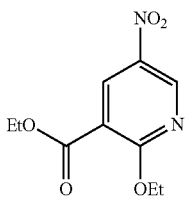

Ammonium nitrate (1.11 g) was added portionwise to an ice-cooled solution of the compound prepared in Example 285 (0.900 g) in trifluoroacetic anhydride (11.5 mL). The mixture was stirred at room temperature overnight and then carefully poured into ice-water and the resulting suspension stirred for an hour. The precipitate was collected by filtration and washed with water. The solids were dried under vacuo to obtain the title compound (0.624 g) having the following physical data.

¹H NMR (DMSO-d₆): δ 9.23 (s, 1H), 8.75 (s, 1H), 4.55 (q, J=7.0 Hz, 2H), 4.33 (q, J=7.0 Hz, 2H), 1.37 (t, J=7.0 Hz, 3H), 1.32 (t, J=7.1 Hz, 3H).

Example 287

Ethyl 5-amino-2-ethoxynicotinate

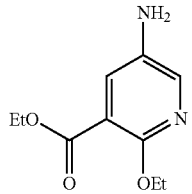 [SMILES: CCOC(=O)c1cc(N)cnc1OCC]

A solution of the compound prepared in Example 286 (0.624 g) in methanol (13 mL) was degassed with nitrogen, treated with 10% palladium-carbon (0.094 g), degassed again and then attached to a hydrogen balloon. The mixture was stirred at room temperature overnight. The catalyst was filtered out and washed with methanol. The filtrate was evaporated in vacuo to obtain the title compound (0.574 g) having the following physical data.

¹H NMR (DMSO-d₆): δ 7.69 (s, 1H), 7.40 (s, 1H), 4.99 (br, 2H), 4.26-4.19 (m, 4H), 1.29-1.24 (m, 6H);

Mass data (APCI, Pos.): m/z 211 (M+H)⁺.

Example 288

5-Amino-2-ethoxynicotinic Acid

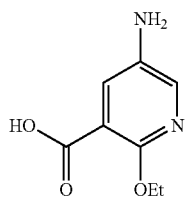 [SMILES: CCOc1ncc(N)cc1C(=O)O]

According to the same procedure described in Example 275, using the corresponding ester instead of methyl 4-aminoquinoline-2-carboxylate, the title compound having the following physical data was obtained.

¹H NMR (DMSO-d₆): δ 12.62 (br, 1H), 7.66 (s, 1H), 7.40 (s, 1H), 4.91 (br, 2H), 4.23 (d, J=7.0 Hz, 2H), 1.26 (t, J=7.0 Hz, 3H);

Mass data (APCI, Neg.): m/z 181 (M–H)⁻.

Example 289

5-Amino-2-ethoxy-N-((1-((3-phenylisoxazol-5-yl)methyl)piperidin-4-yl)methyl)nicotinamide

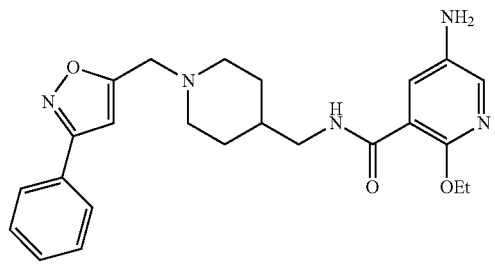 [SMILES: CCOc1ncc(N)cc1C(=O)NCC1CCN(Cc2cc(-c3ccccc3)no2)CC1]

According to the same procedure described in Example 225, using the compound prepared in Example 288 instead of 4-amino-5-cyano-6-ethoxypicolinic acid, and using the compound prepared in Example 9 instead of tert-butyl 4-(aminomethyl)piperidine-1-carboxylate, the title compound having the following physical data was obtained.

$^1$H NMR (CD$_3$OD): δ 7.85-7.81 (m, 2H), 7.72 (dd, J=13.8, 2.7 Hz, 1H), 7.48-7.46 (m, 3H), 6.78 (s, 1H), 4.41 (q, J=7.0 Hz, 2H), 3.78 (s, 2H), 3.35 (s, 2H), 3.01 (d, J=11.6 Hz, 2H), 2.20 (t, J=11.6 Hz, 2H), 1.81 (d, J=12.6 Hz, 2H), 1.65-1.61 (m, 1H), 1.45-1.35 (m, 5H);

Mass data (APCI, Pos.): m/z 436 (M+H)$^+$.

Example 290

5-Amino-2-ethoxy-6-methyl-N-((1-((3-phenylisoxazol-5-yl)methyl)piperidin-4-yl)methyl)nicotinamide

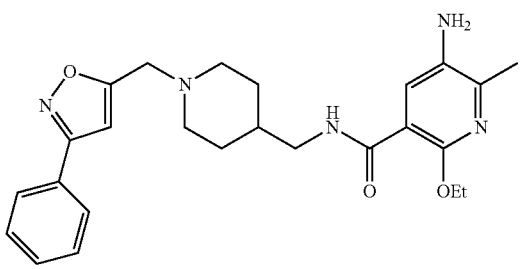 [SMILES: CCOc1nc(C)c(N)cc1C(=O)NCC1CCN(Cc2cc(-c3ccccc3)no2)CC1]

According to the same procedures described in Examples 284→285→286→287→288→289, starting with 2-ethoxy-6-methylnicotinic acid instead of 2-ethoxynicotinic acid, the title compound having the following physical data was obtained.

$^1$H NMR (CD$_3$OD): δ 8.46 (br, 1H), 7.84-7.82 (m, 2H), 7.67 (s, 1H), 7.48-7.46 (m, 3H), 4.45 (q, J=7.0 Hz, 2H), 3.81 (s, 2H), 3.35 (s, 2H), 3.04 (d, J=11.5 Hz, 2H), 2.33 (s, 3H), 2.23 (t, J=11.5 Hz, 2H), 1.81 (d, J=12.6 Hz, 2H), 1.69-1.61 (m, 1H), 1.46-1.37 (m, 5H);

Mass data (APCI, Pos.): m/z 450 (M+H)$^+$.

Example 291

Ethyl 5-amino-6-chloro-2-ethoxynicotinate

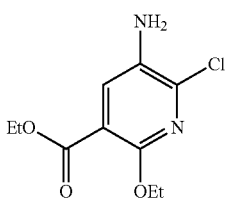 [SMILES: CCOC(=O)c1cc(N)c(Cl)nc1OCC]

To a solution of the compound prepared in Example 287 (0.217 g) in N,N-dimethylformamide (2 mL) was added N-chlorosuccinimide (0.138 g) at room temperature. The mixture was stirred at room temperature overnight and then diluted with water. The resulting greenish mixture was extracted with dichloromethane, dried over, evaporated in vacuo, and purified by column chromatography on silica gel (1-10% diethyl ether in dichloromethane) to obtain the title compound (0.097 g) having the following physical data.

$^1$H NMR (DMSO-d$_6$): δ 7.64 (s, 1H), 5.21 (br, 2H), 4.27-4.18 (m, 4H), 1.28 (t, J=7.0 Hz, 3H);

Mass data (APCI, Pos.): m/z 245 (M+H)$^+$.

Example 292

5-Amino-6-chloro-2-ethoxynicotinic Acid

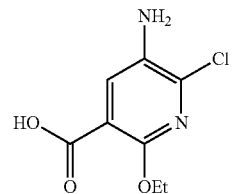 [SMILES: CCOc1nc(Cl)c(N)cc1C(=O)O]

According to the same procedure described in Example 275, using the corresponding ester instead of methyl 4-aminoquinoline-2-carboxylate, the title compound having the following physical data was obtained.

$^1$H NMR (DMSO-d$_6$): δ 12.82 (br, 1H), 7.63 (s, 1H), 5.16 (br, 2H), 4.21 (q, J=7.0 Hz, 2H), 1.27 (t, J=7.0 Hz, 3H);

Mass data (APCI, Neg.): m/z 215 (M−H)$^-$.

Example 293

5-Amino-6-chloro-2-ethoxy-N-((1-((3-phenylisoxazol-5-yl)methyl)piperidin-4-yl)methyl)nicotinamide

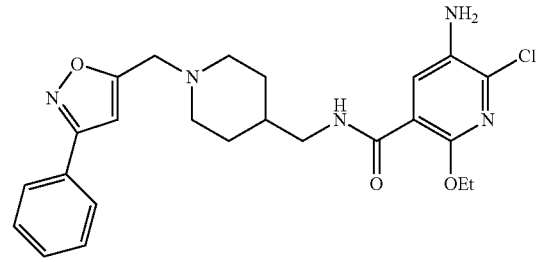 [SMILES: CCOc1nc(Cl)c(N)cc1C(=O)NCC1CCN(Cc2cc(-c3ccccc3)no2)CC1]

According to the same procedure described in example 225, using the compound prepared in Example 292 instead of 4-amino-5-cyano-6-ethoxypicolinic acid, and using the compound prepared in Example 9 instead of tert-butyl 4-(aminomethyl)piperidine-1-carboxylate, the title compound having the following physical data was obtained.

$^1$H NMR (CD$_3$OD): δ 7.83-7.81 (m, 2H), 7.76 (s, 1H), 7.48-7.46 (m, 3H), 6.78 (s, 1H), 4.40 (q, J=7.0 Hz, 2H), 3.78 (s, 2H), 3.31 (s, 2H), 3.01 (d, J=11.6 Hz, 2H), 2.19 (t, J=10.8 Hz, 2H), 1.79 (d, J=12.5 Hz, 2H), 1.65-1.61 (m, 1H), 1.43-1.37 (m, 5H);

Mass data (APCI, Pos.): m/z 470 (M+H)$^+$.

Example 294

2,6-Diethoxynicotinic Acid

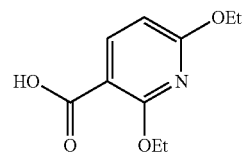 [SMILES: CCOc1ccc(C(=O)O)c(OCC)n1]

A solution of sodium ethoxide (23.3 mL) was added to a solution of 2,6-dichloronicotinic acid (2.00 g) in ethanol (10 mL). The mixture was heated in a sealed vessel at 170° C. for 1 day. After cooling, the mixture was concentrated in vacuo and the residue taken in water and acidified with hydrochloric acid to pH 3. The precipitated solids were collected by filtration and washed with water to obtain the title compound (1.75 g) having the following physical data.

$^1$H NMR (DMSO-d$_6$): δ 12.33 (br, 1H), 8.06 (d, J=8.3 Hz, 1H), 6.38 (d, J=8.3 Hz, 1H), 4.40 (q, 7.0 Hz, 2H), 4.21 (q, J=7.0 Hz, 2H), 1.33 (t, J=7.0 Hz, 3H).

Example 295

Ethyl 2,6-diethoxynicotinate

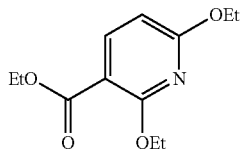 [SMILES: CCOC(=O)c1ccc(OCC)nc1OCC]

A suspension of the compound prepared in Example 294 (1.75 g) and cesium carbonate (2.70 g) in N,N-dimethylformamide (21 mL) was stirred at room temperature for 2 hours. Ethyl iodide (0.663 mL) was added and stirring continued at room temperature for 18 hours. The solvent was evaporated in vacuo and the residue partitioned between a saturated aqueous solution of sodium bicarbonate and ethyl acetate. The combined organic extracts were washed with brine, dried and evaporated in vacuo to a yellow oil and purified by column chromatography on silica gel (10-50% ethyl acetate in hexane) to obtain the title compound (1.6 g) having the following physical data.

$^1$H NMR (DMSO-d$_6$): δ 8.07 (d, J=8.4 Hz, 1H), 6.40 (d, J=8.4 Hz, 1H), 4.42-4.33 (m, 4H), 4.21 (q, J=7.1 Hz, 2H), 1.35-1.31 (m, 6H), 1.27 (t, J=7.1 Hz, 3H);

Mass data (APCI, Pos.): m/z 240 (M+H)$^+$.

Example 296

Ethyl 2,6-diethoxy-5-nitronicotinate

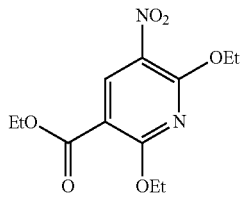 [SMILES: CCOC(=O)c1cc([N+](=O)[O-])c(OCC)nc1OCC]

According to the same procedure described in Example 286, using the corresponding substrate instead of ethyl 2-ethoxynicotinate, the title compound having the following physical data was obtained.

$^1$H NMR (DMSO-d$_6$): δ 8.78 (s, 1H), 4.59 (q, J=7.0 Hz, 2H), 4.52 (q, J=7.0 Hz, 2H), 4.27 (q, 7.1 Hz, 2H), 1.35-1.31 (m, 6H), 1.29 (t, 7.1 Hz, 3H).

Example 297

Ethyl 5-amino-2,6-diethoxynicotinate

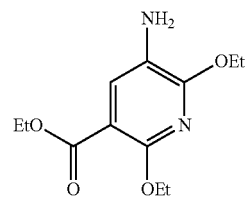 [SMILES: CCOC(=O)c1cc(N)c(OCC)nc1OCC]

According to the same procedure described in Example 287, using the corresponding substrate instead of ethyl 2-ethoxy-5-nitronicotinate, the title compound having the following physical data was obtained.

$^1$H NMR (DMSO-d$_6$): δ 7.42 (s, 1H), 4.51 (br, 2H), 4.38 (q, J=7.0 Hz, 2H), 4.27 (q, J=7.0 Hz, 2H), 4.18 (q, 7.1 Hz, 2H), 1.35 (t, J=7.0 Hz, 3H), 1.29 (t, J=6.6 Hz, 3H), 1.26 (t, 6.9 Hz, 3H);

Mass data (APCI, Pos.): m/z 255 (M+H)$^+$.

Example 298

5-Amino-2,6-diethoxynicotinic Acid

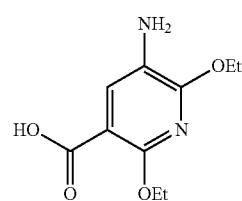 [SMILES: CCOc1nc(OCC)c(C(=O)O)cc1N]

According to the same procedure described in Example 275, using the corresponding ester instead of methyl 4-aminoquinoline-2-carboxylate, the title compound having the following physical data was obtained.

$^1$H NMR (DMSO-d$_6$): δ 12.08 (br, 1H), 7.43 (s, 1H), 4.63 (br, 2H), 4.38 (q, J=7.0 Hz, 2H), 4.29 (q, J=7.0 Hz, 2H), 1.35 (t, J=7.0 Hz, 3H), 1.29 (t, J=7.0 Hz, 3H);

Mass data (APCI, Neg.): m/z 225 (M−H)$^−$.

Example 299

5-Amino-2,6-diethoxy-N-((1-((3-phenylisoxazol-5-yl)methyl)piperidin-4-yl)methyl)nicotinamide

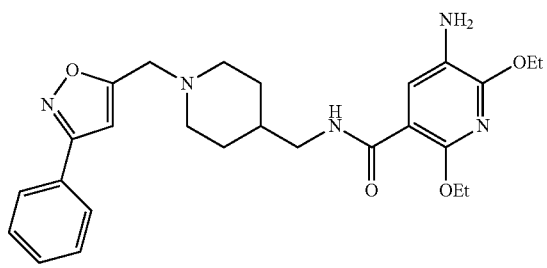 [SMILES: CCOc1nc(OCC)c(C(=O)NCC2CCN(Cc3cc(-c4ccccc4)no3)CC2)cc1N]

According to the same procedure described in Example 225, using the compound prepared in Example 298 instead of 4-amino-5-cyano-6-ethoxypicolinic acid, and using the compound prepared in Example 9 instead of tert-butyl 4-(aminomethyl)piperidine-1-carboxylate, the title compound having the following physical data was obtained.
¹H NMR (CD₃OD): δ 8.33 (br, 1H), 7.84-7.81 (m, 2H), 7.65 (s, 1H), 7.49-7.46 (m, 3H), 6.80 (s, 1H), 4.46 (q, J=7.2 Hz, 4H), 3.83 (s, 2H), 3.31 (s, 2H), 3.04 (d, J=11.5 Hz, 2H), 2.25 (t, J=10.9 Hz, 2H), 1.81 (d, J=13.0 Hz, 2H), 1.65-1.59 (m, 1H), 1.44-1.40 (m, 5H);
Mass data (APCI, Pos.): m/z 480 (M+H)⁺.

Example 300

4-Amino-6-ethoxy-N-((1-((3-phenylisoxazol-5-yl)methyl)piperidin-4-yl)methyl)picolinamide

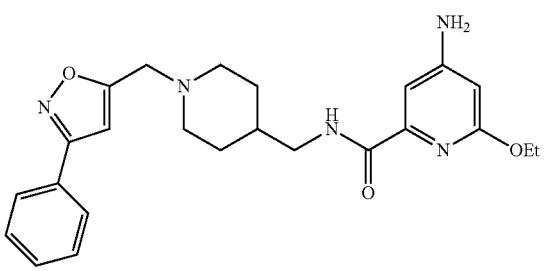 [SMILES: CCOc1cc(N)cc(C(=O)NCC2CCN(Cc3cc(-c4ccccc4)no3)CC2)n1]

According to the same procedure described in example 225, using 4-amino-6-ethoxypicolinic acid (prepared according to the reported preparation in *J. Med. Chem.* 2006, 49(15), 4455-4458), instead of 4-amino-5-cyano-6-ethoxypicolinic acid, and the compound prepared in Example 9 instead of tert-butyl 4-(aminomethyl)piperidine-1-carboxylate, the title compound having the following physical data was obtained.
¹H NMR (DMSO-d₆): δ 7.84-7.81 (m, 2H), 7.48-7.45 (m, 3H), 6.97 (s, 1H), 6.78 (s, 1H), 4.29 (q, J=7.1 Hz, 2H), 3.77 (s, 2H), 3.34 (s, 2H), 3.0 (d, J=11.3 Hz, 2H), 2.18 (t, J=11.3 Hz, 2H), 1.77 (d, J=13.4 Hz, 2H), 1.79-1.63 (m, 1H), 1.40-1.29 (m, 5H).

Example 301

(Z)-tert-Butyl 4-(3-(2-nitrophenyl)-3-oxoprop-1-enyl)piperidine-1-carboxylate

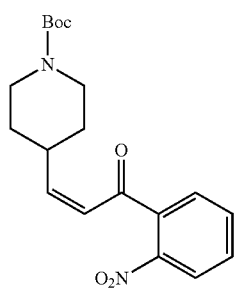 [SMILES: CC(C)(C)OC(=O)N1CCC(/C=C\C(=O)c2ccccc2[N+](=O)[O-])CC1]

1-(2-Nitrophenyl)ethanone (1.04 g) and tert-butyl 4-formylpiperidine-1-carboxylate (1.47 g) were suspended in dry tetrahydrofuran (20 mL) and 20 drops of sodium ethoxide in ethanol (21% by weight) was added. The reaction mixture was stirred at room temperature for 18 hours and concentrated under reduced pressure to afford the crude material, which was purified by flash column chromatography (eluant: 15% ethyl acetate/hexane) to furnish the title compound (1.30 g) with the following physical properties.
¹H NMR (CDCl₃): δ 8.13-8.10 (m, 1H), 7.75-7.71 (m, 1H), 7.65-7.60 (m, 1H), 7.45-7.42 (m, 1H), 6.39-6.37 (m, 2H), 2.78-2.71 (m, 2H), 2.37-2.28 (m, 1H), 1.72-1.68 (m, 2H), 1.46-1.44 (m, 11H), 1.36-1.25 (m, 2H);
Mass data (APCI, Pos.): m/z 361 (M+H)⁺.

Example 302 tert-Butyl 4-(3-(2-aminophenyl)-3-oxopropyl)piperidine-1-carboxylate

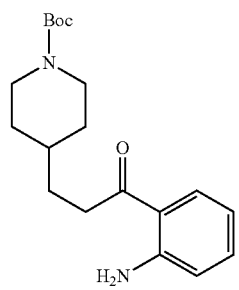 [SMILES: CC(C)(C)OC(=O)N1CCC(CCC(=O)c2ccccc2N)CC1]

The compound prepared in Example 301 (1.30 g) was suspended in ethyl acetate (4.0 mL) and platinum (IV) oxide (81.9 mg, 0.361 mmol) added. The reaction mixture was stirred at room temperature under a balloon of hydrogen for 18 hours and then concentrated under reduced pressure to afford the crude material, which was purified by flash column chromatography (eluant: 10% ethyl acetate/hexane) to furnish the title compound (1.00 g) with the following physical properties.
¹H NMR (CDCl₃): δ 7.74-7.72 (m, 1H), 7.28-7.24 (m, 1H), 6.67-6.62 (m, 2H), 6.27 (br s, 2H), 4.15-4.09 (m, 2H), 2.96 (t, J=7.0 Hz, 3H), 2.72-2.65 (m, 2H), 1.73-1.65 (m, 4H), 1.51-1.44 (m, 10H), 1.20-1.09 (m, 2H);
Mass data (APCI, Pos.): m/z 333 (M+H)⁺.

Example 303 tert-Butyl 4-(3-oxo-3-(2-(phenylamino)phenyl)propyl)piperidine-1-carboxylate

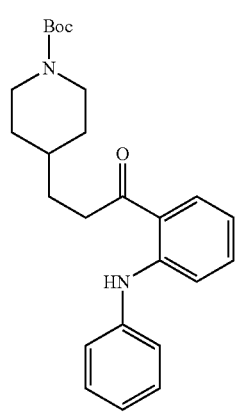 [SMILES: CC(C)(C)OC(=O)N1CCC(CCC(=O)c2ccccc2Nc2ccccc2)CC1]

A flask was charged with the compound prepared in Example 302 (0.533 g), 1-bromobenzene (0.252 g), potassium tert-butoxide (0.252 g), 4,5-bis(diphenylphosphino)-9,9-dimethyl-9H-xanthene (0.056 mg), and bis(dibenzylideneacetone)palladium (0.037 g) and flushed with nitrogen gas. Toluene (30 mL) which was thoroughly purged with nitrogen gas was added and the reaction mixture heated at 105° C. for 18 hours. The reaction mixture was concentrated under reduced pressure to afford the crude material, which was purified by flash column chromatography (eluant: 10% ethyl acetate/hexane) to furnish the title compound (0.365 g) with the following physical properties.

$^1$H NMR (CDCl$_3$): δ 10.56 (br s, 1H), 7.84-7.82 (m, 1H), 7.37-7.24 (m, 6H), 7.12-7.08 (m, 1H), 6.75-6.71 (m, 1H), 4.10 (br s, 2H), 3.03 (t, J=7.6 Hz, 2H), 2.73-2.66 (m, 2H), 1.74-1.68 (m, 4H), 1.54-1.48 (m, 1H), 1.46 (s, 9H), 1.21-1.11 (m, 2H);

Mass data (APCI, Pos.): m/z 409 (M+H)$^+$.

Example 304 tert-Butyl 4-(3-(2-(2-methoxy-2-oxo-N-phenylacetamido)phenyl)-3-oxopropyl)piperidine-1-carboxylate

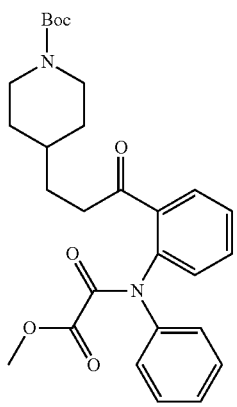 [SMILES: COC(=O)C(=O)N(c1ccccc1)c1ccccc1C(=O)CCC1CCN(C(=O)OC(C)(C)C)CC1]

To a solution of the compound prepared in Example 303 (350 mg) in dichloromethane (3.0 mL) at 0° C. was added diisopropylethylamine (0.746 mL) followed by methyl 2-chloro-2-oxoacetate (262 mg). The reaction was allowed to warm to room temperature and then stirred for 2 hours. The solution was diluted with ethyl acetate, washed with saturated aqueous ammonium chloride, saturated aqueous sodium bicarbonate and brine. The organics were dried over magnesium sulfate, and concentrated under reduced pressure to afford the crude material, which was purified by flash column chromatography (eluant: 10% ethyl acetate/hexane) to furnish the title compound (374 mg) with the following physical properties.

Mass data (APCI, Pos.): m/z 495 (M+H)$^+$.

Example 305

Methyl 3-((1-(tert-butoxycarbonyl)piperidin-4-yl)methyl)-4-oxo-1-phenyl-1,4-dihydroquinoline-2-carboxylate

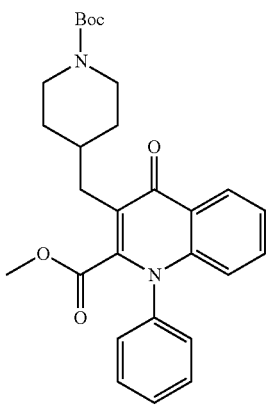 [SMILES: COC(=O)c1c(CC2CCN(C(=O)OC(C)(C)C)CC2)c(=O)c2ccccc2n1-c1ccccc1]

To a solution of the compound prepared in Example 304 (365 mg) in methanol (10 mL) was added potassium carbonate (102 mg). The reaction mixture was stirred at room temperature for 1 hour and then filtered. The organics were concentrated under reduced pressure to afford the crude material, which was purified by flash column chromatography (eluant: 20% ethyl acetate/hexane) to furnish the title compound (314 mg) with the following physical properties.

$^1$H NMR (CDCl$_3$): δ 8.47-8.44 (m, 1H), 7.58-7.55 (m, 3H), 7.49-7.45 (m, 1H), 7.40-7.34 (m, 3H), 6.81-6.78 (m, 1H), 4.07 (br s, 2H), 3.48 (s, 3H), 2.79-2.62 (m, 2H), 2.47 (br s, 2H), 2.04-1.97 (m, 1H), 1.70-1.67 (m, 2H), 1.44 (s, 9H), 1.19-1.08 (m, 2H);

Mass data (APCI, Pos.): m/z 477 (M+H)$^+$.

Example 306

Methyl 4-oxo-1-phenyl-3-(piperidin-4-ylmethyl)-1,4-dihydroquinoline-2-carboxylate Hydrochloride

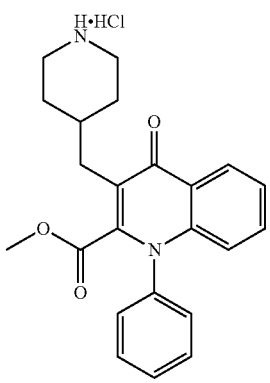

To a solution of the compound prepared in Example 305 (292 mg) in methanol (5.0 mL) was added hydrogen chloride solution in 1,4-dioxane (4 mol/L; 4.60 mL). The reaction was stirred at room temperature for 18 hours and then concentrated under reduced pressure to afford the title compound (253 mg), which was used without further purification, possessing the following physical data.

Mass data (APCI, Pos.): m/z 377 (M+H (free base))$^+$.

Example 307

Methyl 4-oxo-1-phenyl-3-((1-(3-(pyridin-2-yl)isoxazol-5-yl)methyl)piperidin-4-yl)methyl)-1,4-dihydroquinoline-2-carboxylate

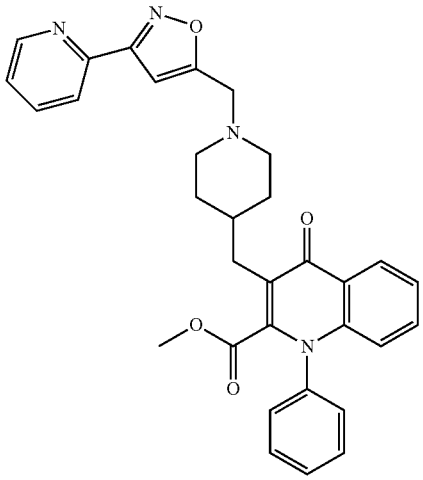 [SMILES: COC(=O)c1c(CC2CCN(Cc3cc(-c4ccccn4)no3)CC2)c(=O)c2ccccc2n1-c1ccccc1]

To a solution of the compound prepared in Example 306 (52 mg) and the compound prepared in Example 125 (44 mg) in dichloromethane (3.0 mL) was added diisopropylethylamine (0.09 mL) and sodium triacetoxyborohydride (80 mg). The reaction mixture was stirred at room temperature for 18 hours. The mixture was diluted with ethyl acetate, washed with saturated aqueous sodium bicarbonate solution and brine. The organics were dried over magnesium sulfate, filtered and concentrated under reduced pressure to afford the crude material, which was purified by flash column chromatography (eluant: 2% (9:1 methanol/concentrated ammonium hydroxide)/ethyl acetate) to furnish the title compound (52 mg) with the following physical properties.

$^1$H NMR (CDCl$_3$): δ 8.68-8.67 (m, 1H), 8.45-8.44 (m, 1H), 8.06-8.04 (m, 1H), 7.80-7.76 (m, 1H), 7.56-7.54 (m, 3H), 7.47-7.44 (m, 1H), 7.36-7.31 (m, 4H), 6.79-6.77 (m, 2H), 3.73 (s, 2H), 3.47 (s, 3H), 2.95-2.92 (m, 2H), 2.47 (d, J=7.0 Hz, 2H), 2.13-2.08 (m, 2H), 1.95-1.86 (m, 1H), 1.74-1.71 (m, 2H), 1.34-1.27 (m, 2H);

Mass data (APCI, Pos.): m/z 535 (M+H)$^+$.

Example 308

1-(2-Aminophenyl)-3-(piperidin-4-yl)propan-1-one dihydrochloride

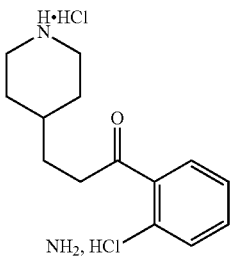

A solution of the compound prepared in Example 303 (1.00 g) in methanol (10 mL) was treated with hydrogen chloride solution in 1,4-dioxane (4 mol/L; 7.52 mL) and stirred at room temperature for 18 hours. The solution was concentrated under reduced pressure and azeotropped from methanol several times to furnish the title compound (0.76 g), which was used without further purification, possessing the following physical data.

$^1$H NMR (DMSO-d$_6$): 9.20 (s, 1H), 8.78 (s, 1H), 7.80-7.78 (m, 1H), 7.28-7.24 (m, 1H), 6.82-6.80 (m, 1H), 6.61-6.58 (m, 1H), 6.35 (s, 2H), 3.23-3.17 (m, 2H), 2.97-2.95 (m, 2H), 2.82-2.78 (m, 2H), 1.85-1.82 (m, 2H), 1.56-1.54 (2H), 1.37-1.33 (m, 2H);

Mass data (APCI, Pos.): m/z 233 (M+(free base))$^+$.

Example 309

1-(2-Aminophenyl)-3-(1-((2-(pyridin-2-yl)thiazol-5-yl)methyl)piperidin-4-yl)propan-1-one

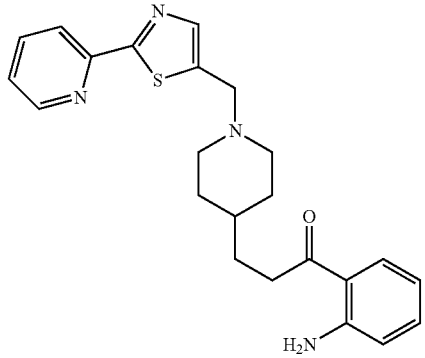 [SMILES: Nc1ccccc1C(=O)CCC1CCN(Cc2cnc(-c3ccccn3)s2)CC1]

To a suspension of the compound prepared in Example 308 (323 mg) and the compound prepared in Example 139 (267 mg) in 1,2-dichloroethane (10 mL) and N,N-dimethylformamide (4 mL) was added diisopropylethylamine (0.89 mL) and sodium triacetoxyborohydride (813 mg). The reaction mixture was stirred at room temperature for 18 hours. The mixture was diluted with ethyl acetate, washed with saturated aqueous sodium bicarbonate and brine. The organics were dried over magnesium sulfate, filtered and concentrated under reduced pressure to afford the crude material, which was purified by flash column chromatography (eluant: 50-75% ethyl acetate/hexane) to furnish the title compound (222 mg) with the following physical properties.

$^1$H NMR (CDCl$_3$): δ 8.61-8.60 (m, 1H), 8.15-8.13 (m, 1H), 7.80-7.72 (m, 2H), 7.68 (s, 1H), 7.31-7.23 (m, 2H), 6.66-6.63 (m, 2H), 6.25 (s, 2H), 3.77 (s, 2H), 2.96-2.92 (m, 4H), 2.05-2.03 (m, 2H), 1.71-1.60 (m, 6H), 1.32-1.28 (m, 1H);

Mass data (APCI, Pos.): m/z 407 (M+H)$^+$.

Example 310

1-(2-(Phenylamino)phenyl)-3-((1-((2-(pyridin-2-yl)thiazol-5-yl)methyl)piperidin-4-yl)propan-1-one

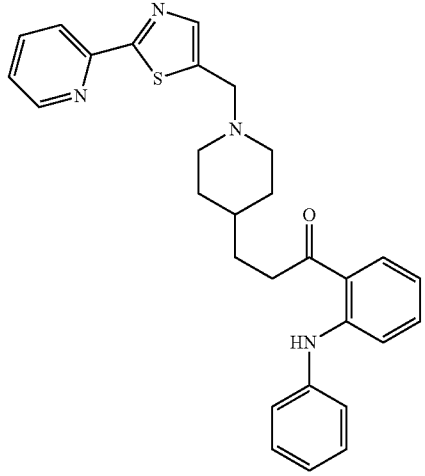 [SMILES: O=C(CCC1CCN(Cc2cnc(-c3ccccn3)s2)CC1)c1ccccc1Nc1ccccc1]

A flask was charged with the compound prepared in Example 309 (0.220 g), 1-bromobenzene (0.094 g), potassium tert-butoxide (0.085 g), 4,5-bis(diphenylphosphino)-9,9-dimethyl-9H-xanthene (0.019 mg), and bis(dibenzylideneacetone)palladium (0.013 g) and flushed with nitrogen gas. Toluene (25 mL) which was thoroughly purged with nitrogen gas was added and the reaction mixture heated at 105° C. for 18 hours. The reaction mixture was concentrated under reduced pressure to afford the crude material, which was purified by flash column chromatography (eluant: 80% ethyl acetate/hexane with 1% (9:1 methanol/concentrated ammonium hydroxide)) to furnish the title compound (0.070 g) with the following physical properties.

$^1$H NMR (CDCl$_3$): δ 10.57 (s, 1H), 8.61-8.60 (m, 1H), 7.84-7.77 (m, 2H), 7.68 (s, 1H), 7.36-7.23 (m, 5H), 7.11-7.08 (m, 1H), 6.74-6.71 (m, 1H), 3.80-3.75 (m, 3H), 3.03-2.94 (m, 4H), 2.63 (s, 2H), 2.18 (s, 2H), 2.08-2.04 (m, 2H), 1.75-1.67 (m, 2H), 1.33-1.25 (m, 4H);

Mass data (APCI, Pos.): m/z 483 (M+H)$^+$.

Example 311

2-(Dimethylamino)ethyl 2-oxo-2-(phenyl(2-(3-((1-((2-(pyridin-2-yl)thiazol-5-yl)methyl)piperidin-4-yl)propanoyl)phenyl)amino)acetate

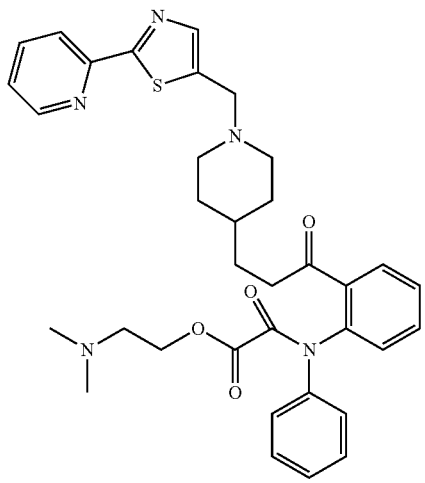 [SMILES: CN(C)CCOC(=O)C(=O)N(c1ccccc1)c1ccccc1C(=O)CCC1CCN(Cc2cnc(-c3ccccn3)s2)CC1]

A solution of the compound prepared in Example 310 (70 mg) in toluene (7 mL) was treated with oxalyl chloride (0.05 mL) for 1 hour at room temperature. 2-(dimethylamino)ethanol (517 mg) was added and the reaction was stirred for 1 hour at room temperature. The solution was diluted with ethyl acetate, washed with saturated aqueous sodium bicarbonate solution and brine. The organics were dried over magnesium sulfate, filtered and concentrated under reduced pressure to afford the crude material, which was purified by flash column chromatography (eluant: 10% (9:1 methanol/concentrated ammonium hydroxide)/ethyl acetate) to furnish the title compound (52 mg) with the following physical properties.

Mass data (APCI, Pos.): m/z 626 (M+H)$^+$.

Example 312

2-(Dimethylamino)ethyl 4-oxo-1-phenyl-3-((1-((2-(pyridin-2-yl)thiazol-5-yl)methyl)piperidin-4-yl)methyl)-1,4-dihydroquinoline-2-carboxylate

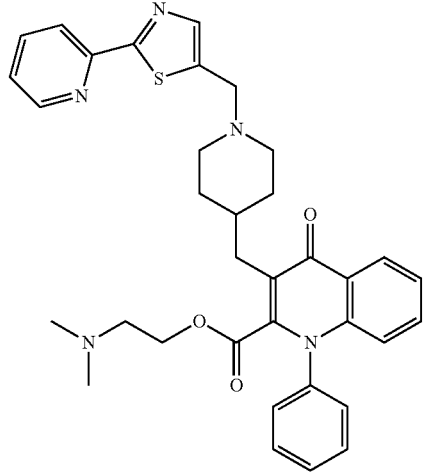 [SMILES: CN(C)CCOC(=O)c1c(CC2CCN(Cc3cnc(-c4ccccn4)s3)CC2)c(=O)c2ccccc2n1-c1ccccc1]

To a solution of the compound prepared in Example 311 (52 mg) in methanol (3 mL) was added potassium carbonate (11 mg). The reaction mixture was stirred at room temperature for 1 hour and then filtered. The organics were concentrated under reduced pressure. The residue was diluted with ethyl acetate, washed with saturated aqueous sodium bicarbonate and brine. The organics were dried over magnesium sulfate, and concentrated under reduced pressure to afford the crude material, which was purified by flash column chromatography (eluant: 10% (9:1 methanol/concentrated ammonium hydroxide)/ethyl acetate) to furnish the title compound (11 mg) with the following physical properties.

$^1$H NMR (CDCl$_3$): δ 8.59-8.58 (m, 1H), 8.45-8.43 (m, 1H), 8.14-8.12 (m, 1H), 7.79-7.76 (m, 1H), 7.66 (s, 1H), 7.57-7.54 (m, 2H), 7.46-7.39 (m, 3H), 7.35-7.26 (m, 3H), 6.78-6.76 (m, 1H), 3.95 (t, J=6.1 Hz, 2H), 3.73 (s, 2H), 2.92-2.90 (m, 2H), 2.50 (d, J=6.9 Hz, 2H), 2.28 (t, J=6.2 Hz, 2H), 2.17 (s, 6H), 2.05-2.02 (m, 2H), 1.72-1.69 (m, 2H), 1.59-1.49 (m, 1H), 1.39-1.32 (m, 2H);

Mass data (APCI, Pos.): m/z 608 (M+H)$^+$.

Example 313

2-Morpholinoethyl 2-oxo-2-(phenyl(2-(3-((1-((2-(pyridin-2-yl)thiazol-5-yl)methyl)piperidin-4-yl)propanoyl)phenyl)amino)acetate

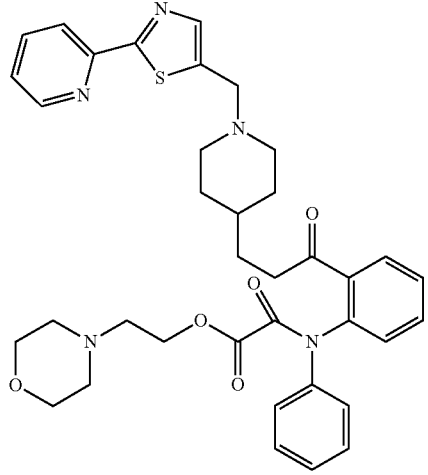 [SMILES: O=C(OCCN1CCOCC1)C(=O)N(c1ccccc1)c1ccccc1C(=O)CCC1CCN(Cc2cnc(-c3ccccn3)s2)CC1]

According to the same procedure described in Example 311, using the corresponding alcohol instead of 2-(dimethylamino)ethanol, the title compound having the following physical data was obtained.

Mass data (APCI, Pos.): m/z 668 (M+H)+.

Example 314

2-Morpholinoethyl 4-oxo-1-phenyl-3-((1-((2-(pyridin-2-yl)thiazol-5-yl)methyl)piperidin-4-yl)methyl)-1,4-dihydroquinoline-2-carboxylate

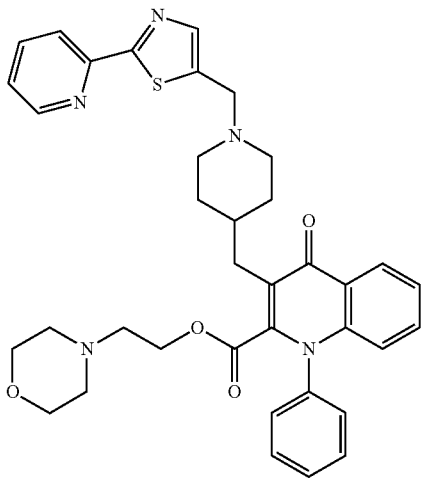 [SMILES: O=C(OCCN1CCOCC1)c1c(CC2CCN(Cc3cnc(-c4ccccn4)s3)CC2)c(=O)c2ccccc2n1-c1ccccc1]

According to the same procedure described in Example 312, using the corresponding starting material instead of 2-(dimethylamino)ethyl 2-oxo-2-(phenyl(2-(3-((1-((2-(pyridin-2-yl)thiazol-5-yl)methyl)piperidin-4-yl)propanoyl)phenyl)amino)acetate, the title compound having the following physical data was obtained.

$^1$H NMR (CDCl$_3$): δ 8.59-8.58 (m, 1H), 8.46-8.44 (m, 1H), 8.14-8.12 (m, 1H), 7.78-7.76 (m, 1H), 7.66 (s, 1H), 7.56-7.54 (m, 3H), 7.46-7.44 (m, 1H), 7.40-7.27 (m, 4H), 6.78-6.75 (m, 1H), 3.99-3.97 (m, 2H), 3.73 (s, 2H), 3.68-3.66 (m, 3H), 2.92-2.90 (m, 2H), 2.50-2.49 (m, 2H), 2.40-2.32 (m, 6H), 2.05-2.00 (m, 2H), 1.92-1.85 (m, 1H), 1.72-1.69 (m, 2H), 1.35-1.25 (m, 3H);

Mass data (APCI, Pos.): m/z 650 (M+H)+.

Example 315 tert-Butyl 4-(3-(2-(2-(2-(dimethylamino)ethoxy)-2-oxo-N-phenylacetamido)phenyl)-3-oxopropyl)piperidine-1-carboxylate

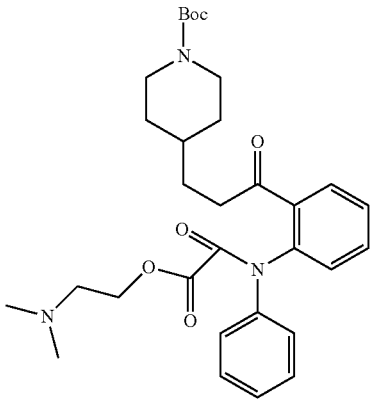 [SMILES: CN(C)CCOC(=O)C(=O)N(c1ccccc1)c1ccccc1C(=O)CCC1CCN(C(=O)OC(C)(C)C)CC1]

A solution of the compound prepared in Example 303 (100 mg) in toluene (20 mL) was treated with oxalyl chloride (0.09 mL) for 2 hours at room temperature. 2-(dimethylamino)ethanol (873 mg) was added and the reaction was stirred for 1 hour at room temperature. The solution was diluted with ethyl acetate, washed with saturated aqueous sodium bicarbonate solution and brine. The organics were dried over magnesium sulfate, filtered and concentrated under reduced pressure to afford the title material (120 mg), which was used without further purification.

Example 316

2-(Dimethylamino)ethyl 3-((1-(tert-butoxycarbonyl)piperidin-4-yl)methyl)-4-oxo-1-phenyl-1,4-dihydroquinoline-2-carboxylate

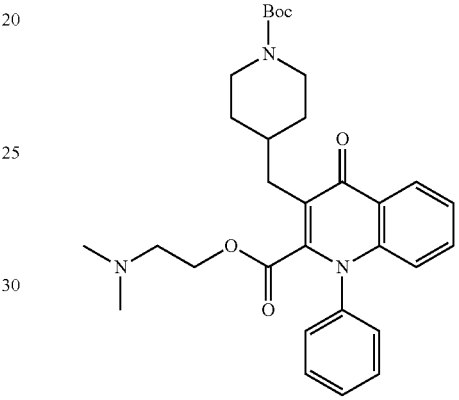

According to the same procedure described in Example 312, using the corresponding starting material instead of 2-(dimethylamino)ethyl 2-oxo-2-(phenyl(2-(3-(1-((2-(pyridin-2-yl)thiazol-5-yl)methyl)piperidin-4-yl)propanoyl)phenyl)amino)acetate, the title compound having the following physical data was obtained.

Mass data (APCI, Pos.): m/z 534 (M+

Example 317

2-(Dimethylamino)ethyl 4-oxo-1-phenyl-3-(piperidin-4-ylmethyl)-1,4-dihydroquinoline-2-carboxylate Hydrochloride

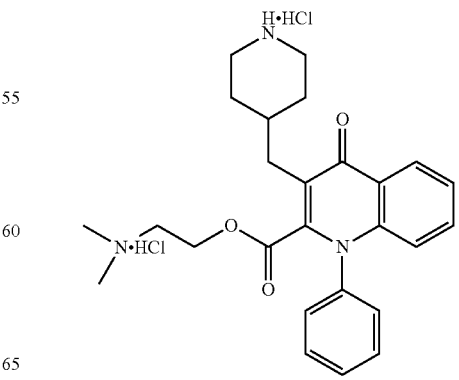

According to the same procedure described in Example 306, using the corresponding protected amine instead of methyl 3-((1-(tert-butoxycarbonyl)piperidin-4-yl)methyl)-4-oxo-1-phenyl-1,4-dihydroquinoline-2-carboxylate, the title compound was obtained.

Example 318

2-(Dimethylamino)ethyl 4-oxo-1-phenyl-3-((1-((3-phenylisoxazol-5-yl)methyl)piperidin-4-yl)methyl)-1,4-dihydroquinoline-2-carboxylate

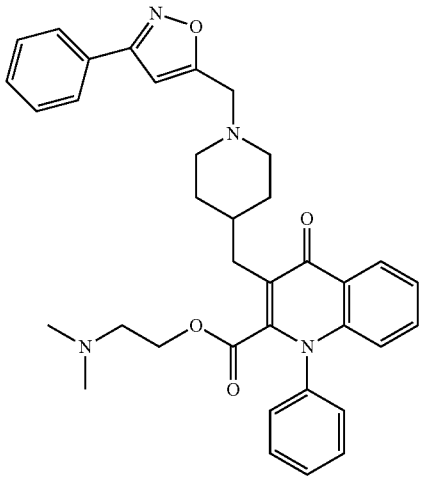 [SMILES: CN(C)CCOC(=O)c1c(CC2CCN(Cc3cc(-c4ccccc4)no3)CC2)c(=O)c2ccccc2n1-c1ccccc1]

According to the same procedure described in Example 307, using the corresponding amine instead of methyl 4-oxo-1-phenyl-3-(piperidin-4-ylmethyl)-1,4-dihydroquinoline-2-carboxylate hydrochloride, using the compound prepared in Example 7 instead of the compound prepared in Example 125, the title compound having the following physical data was obtained.

$^1$H NMR (CDCl$_3$): δ 8.45-8.43 (m, 1H), 7.80-7.78 (m, 2H), 7.56-7.54 (m, 4H), 7.45-7.40 (m, 5H), 7.34-7.31 (m, 1H), 6.78-6.76 (m, 1H), 6.47 (s, 1H), 3.94 (t, J=6.1 Hz, 2H), 3.70 (s, 2H), 2.52-2.50 (m, 2H), 2.27 (t, J=6.1 Hz, 2H), 2.17 (s, 6H), 2.13-2.08 (m, 2H), 1.92-1.83 (m, 1H), 1.76-1.65 (m, 4H), 1.41-1.35 (m, 2H);
Mass data (APCI, Pos.): m/z 591 (M+H)$^+$.

Example 319 tert-butyl 4-(3-(2-(2-(methylamino)-2-oxo-N-phenylacetamido)phenyl)-3-oxopropyl)piperidine-1-carboxylate

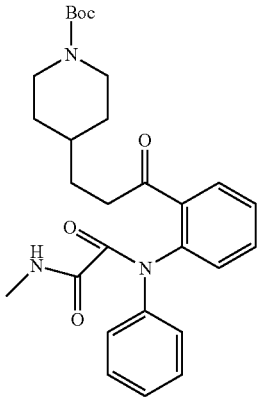 [SMILES: CNC(=O)C(=O)N(c1ccccc1)c1ccccc1C(=O)CCC1CCN(C(=O)OC(C)(C)C)CC1]

The compound prepared in Example 303 (0.100 g) was suspended in toluene (10 mL) and oxalyl chloride (0.085 mL) added. The reaction mixture was stirred at room temperature for 2 hours. Methylamine solution (2 mol/L; 3.672 mL) was added and the reaction mixture stirred at room temperature for 1 hour. The reaction mixture was then partitioned between saturated aqueous sodium bicarbonate solution and ethyl acetate. The organics were washed with brine, dried over magnesium sulfate, filtered and concentrated under reduced pressure to afford the crude material (0.173 g), which was used without further purification possessing the following physical data.
Mass data (APCI, Pos.): m/z 494 (M+H)$^+$.

Example 320 tert-butyl 4-((2-(methylcarbamoyl)-4-oxo-1-phenyl-1,4-dihydroquinolin-3-yl)methyl)piperidine-1-carboxylate

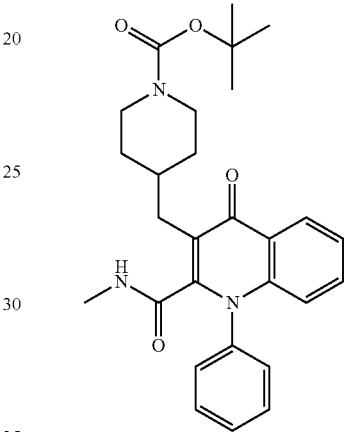

The compound prepared in Example 319 (0.121 g) was suspended in methanol (10 mL) and potassium carbonate (0.051 g) added. The reaction mixture was stirred at room temperature overnight. The reaction mixture was concentrated under reduced pressure to afford the crude material, which was partitioned between ethyl acetate and water. The organics were washed with brine, dried over magnesium sulfate, filtered and concentrated under reduced pressure to afford the crude product, which was purified by flash column chromatography to furnish the title compound (0.005 g) having the following physical properties.
Mass data (APCI, Pos.): ink 476 (M+H)$^+$.

Example 321

N-Methyl-4-oxo-1-phenyl-3-(piperidin-4-ylmethyl)-1,4-dihydroquinoline-2-carboxamide Hydrochloride

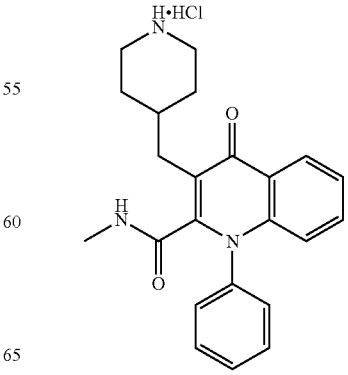

According to the same procedure described in Example 306, using the corresponding protected amine instead of methyl 3-((1-(tert-butoxycarbonyl)piperidin-4-yl)methyl)-4-oxo-1-phenyl-1,4-dihydroquinoline-2-carboxylate, the title compound was obtained.

Example 322

N-Methyl-4-oxo-1-phenyl-3-((1-((2-(pyridin-2-yl)thiazol-5-yl)methyl)piperidin-4-yl)methyl)-1,4-dihydroquinoline-2-carboxamide

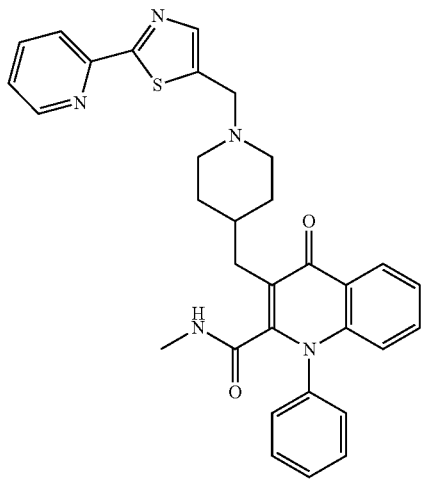 [SMILES: CNC(=O)c1c(CC2CCN(Cc3cnc(-c4ccccn4)s3)CC2)c(=O)c2ccccc2n1-c1ccccc1]

According to the same procedure described in Example 309, using the corresponding amine instead of methyl 4-oxo-1-phenyl-3-(piperidin-4-ylmethyl)-1,4-dihydroquinoline-2-carboxylate hydrochloride, the title compound having the following physical data was obtained.

$^1$H NMR (CDCl$_3$): δ 8.59-8.58 (m, 1H), 8.26-8.24 (m, 1H), 8.13-8.11 (m, 1H), 7.79-7.75 (m, 1H), 7.64 (s, 1H), 7.56-7.52 (m, 4H), 7.42-7.38 (m, 1H), 7.30-7.20 (m, 3H), 6.75-6.73 (m, 1H), 4.23-4.19 (m, 2H), 3.70 (s, 2H), 2.85-2.82 (m, 2H), 2.64 (d, J=4.7 Hz, 3H), 2.05-1.96 (m, 2H), 1.59-1.53 (m, 2H), 1.32-1.22 (m, 2H), 0.94-0.88 (m, 2H);

Mass data (APCI, Pos.): m/z 550 (M+H)$^+$.

Example 323

1-(2-(2,2-Dimethoxyethylamino)phenyl)-3-(1-((2-(pyridin-2-yl)thiazol-5-yl)methyl)piperidin-4-yl)propan-1-one

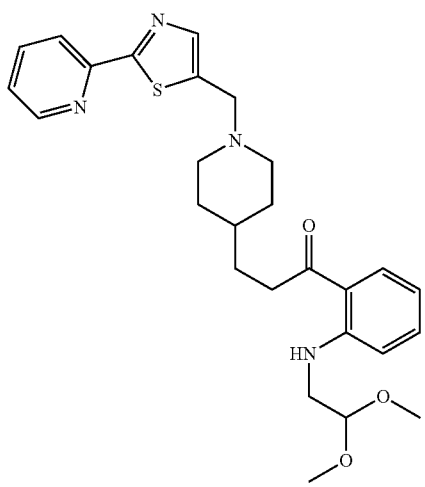 [SMILES: COC(CNc1ccccc1C(=O)CCC1CCN(Cc2cnc(-c3ccccn3)s2)CC1)OC]

The compound prepared in Example 309 (0.613 g) was suspended in 1,2-dichloroethane (30 mL). 2,2-Dimethoxyacetaldehyde solution in water (60% by weight) (2.28 mL) and beaded molecular sieves were added and the reaction mixture stirred at room temperature for 4 hours. Sodium triacetoxyborohydride (2.62 g) was added and the reaction mixture stirred at room temperature overnight. The reaction mixture was diluted with ethyl acetate, washed with saturated aqueous sodium bicarbonate solution and brine. The organics were dried over magnesium sulfate, filtered and concentrated under reduced pressure to afford the crude material, which was purified by flash column chromatography (eluant: 2% (9:1 methanol/concentrated ammonium hydroxide)/dichloromethane) to furnish the title compound (0.555 g) with the following physical properties.

Mass data (APCI, Pos.): m/z 495 (M+H)$^+$.

Example 324

Methyl 2-((2,2-dimethoxyethyl)(2-(3-(1-((2-(pyridin-2-yl)thiazol-5-yl)methyl)piperidin-4-yl)propanoyl)phenyl)amino)-2-oxoacetate

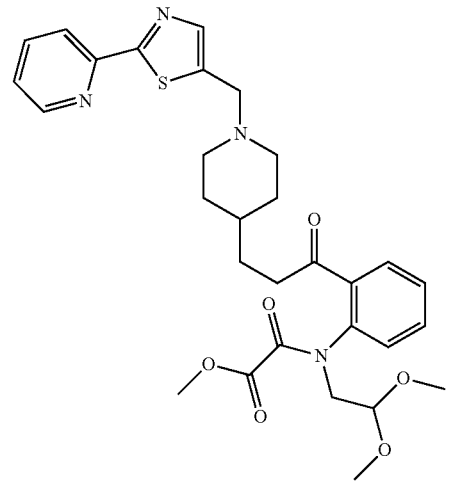 [SMILES: COC(=O)C(=O)N(CC(OC)OC)c1ccccc1C(=O)CCC1CCN(Cc2cnc(-c3ccccn3)s2)CC1]

To a solution of the compound prepared in Example 323 (555 mg) in dichloromethane (7.0 mL) at 0° C. was added diisopropylethylamine (0.59 mL) followed by methyl 2-chloro-2-oxoacetate (0.16 mL). The reaction was allowed to warm to room temperature and then stirred for 2 hours. The solution was diluted with ethyl acetate, washed with saturated aqueous sodium bicarbonate solution and brine. The organics were dried over magnesium sulfate, filtered and concentrated under reduced pressure to afford the crude material, which was purified by flash column chromatography (eluant: 80% ethyl acetate/hexane with 3% (9:1 methanol/concentrated ammonium hydroxide)) to furnish the title compound (392 mg) with the following physical properties.

Mass data (APCI, Pos.): m/z 581 (M+H)$^+$.

Example 325

Methyl 1-(2,2-dimethoxyethyl)-4-oxo-3-((1-((2-(pyridin-2-yl)thiazol-5-yl)methyl)piperidin-4-yl)methyl)-1,4-dihydroquinoline-2-carboxylate

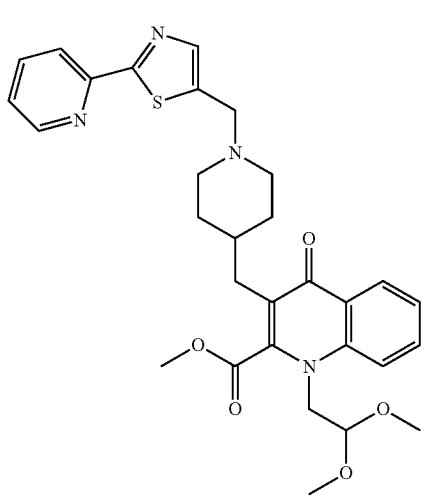 [SMILES: COC(=O)c1c(CC2CCN(Cc3cnc(-c4ccccn4)s3)CC2)c(=O)c2ccccc2n1CC(OC)OC]

The compound prepared in Example 324 (0.390 g) was suspended in methanol (7 mL) and potassium carbonate (0.093 g) added. The reaction mixture was stirred at room temperature overnight. The reaction mixture was concentrated under reduced pressure to afford the crude material, which was partitioned between ethyl acetate and water. The organics were washed with brine, dried over magnesium sulfate, filtered and concentrated under reduced pressure to afford the crude product, which was purified by flash column chromatography (eluant: 5% (9:1 methanol/concentrated ammonium hydroxide)/ethyl acetate) to furnish the title compound (0.340 g) having the following physical properties.

$^1$H NMR (CDCl$_3$): δ 8.60-8.59 (m, 1H), 8.44-8.42 (m, 1H), 8.14-8.12 (m, 1H), 7.79-7.75 (m, 1H), 7.66-7.62 (m, 3H), 7.39-7.35 (m, 1H), 7.31-7.27 (m, 1H), 4.61 (t, J=5.0 Hz, 1H), 4.21 (s, 1H), 4.15-4.06 (m, 1H), 4.01 (s, 3H), 3.73 (s, 2H), 3.34 (s, 6H), 2.92-2.90 (m, 2H), 2.43 (d, J=6.9 Hz, 2H), 2.04-2.02 (t, J=5.0 Hz, 2H), 1.90-1.81 (m, 1H), 1.67-1.63 (m, 2H), 1.28-1.24 (m, 2H);

Mass data (APCI, Pos.): m/z 563 (M+H)$^+$.

Example 326 tert-Butyl 4-(3-(2-(3-(benzyloxycarbonylamino)propylamino)phenyl)-3-oxopropyl)piperidine-1-carboxylate The compound prepared in Example 302 (0.455 g) was suspended in 1,2-dichloroethane (10 mL). Benzyl 3-oxopropylcarbamate (0.425 g) and beaded molecular sieves were added and the reaction mixture stirred at room temperature for 1 hour. Sodium triacetoxyborohydride (0.870 g) was added and the reaction mixture stirred at room temperature overnight. The reaction mixture was diluted with ethyl acetate, washed with saturated aqueous sodium bicarbonate solution and brine. The organics were dried over magnesium sulfate, filtered and concentrated under reduced pressure to afford the crude material, which was purified by flash column chromatography (eluant: 20-30% ethyl acetate/hexane) to furnish the title compound (0.629 g) with the following physical properties.

Mass data (APCI, Pos.): m/z 524 (M+H)$^+$.

Example 327 tert-Butyl 4-(3-(2-(N-(3-(benzyloxycarbonylamino)propyl)-2-methoxy-2-oxoacetamido)phenyl)-3-oxopropyl)piperidine-1-carboxylate

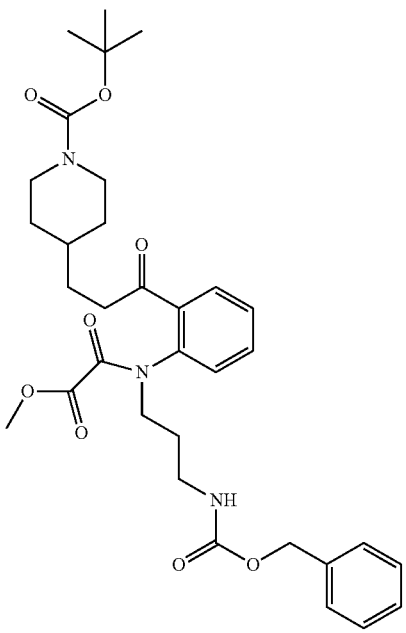 [SMILES: COC(=O)C(=O)N(CCCNC(=O)OCc1ccccc1)c1ccccc1C(=O)CCC1CCN(C(=O)OC(C)(C)C)CC1]

To a solution of the compound prepared in Example 326 (620 mg) in dichloromethane (10.0 mL) at 0° C. was added diisopropylethylamine (0.82 mL) followed by methyl 2-chloro-2-oxoacetate (0.22 mL). The reaction was allowed to warm to room temperature and then stirred for 2 hours. The solution was diluted with ethyl acetate, washed with saturated aqueous sodium bicarbonate solution and brine. The organics were dried over magnesium sulfate, filtered and concentrated under reduced pressure to afford the crude material, which was purified by flash column chromatography (eluant: 50% ethyl acetate/hexane) to furnish the title compound (722 mg) with the following physical properties.

Mass data (ESI, Pos.): m/z 632 (M+Na)$^+$.

Example 328

Methyl 1-(3-(benzyloxycarbonylamino)propyl)-3-(1-(tert-butoxycarbonyl)piperidin-4-yl)methyl)-4-oxo-1,4-dihydroquinoline-2-carboxylate

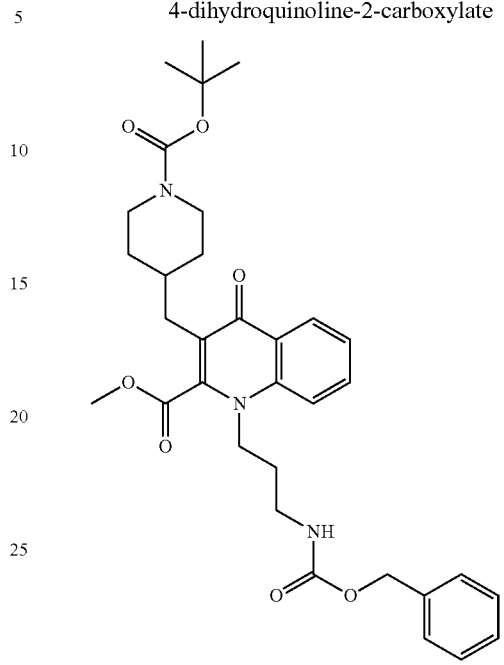

The compound prepared in Example 327 (0.720 g) was suspended in methanol (10 mL) and potassium carbonate (0.326 g) added. The reaction mixture was stirred at room temperature overnight. The reaction mixture was concentrated under reduced pressure to afford the crude material, which was partitioned between ethyl acetate and water. The organics were washed with brine, dried over magnesium sulfate, filtered and concentrated under reduced pressure to afford the title compound (0.588 g), which was used without further purification having the following physical properties.

Mass data (APCI, Pos.): m/z 524 (M+H)$^+$.

Example 329

Methyl 1-(3-(benzyloxycarbonylamino)propyl)-4-oxo-3-(piperidin-4-ylmethyl)-1,4-dihydroquinoline-2-carboxylate Hydrochloride

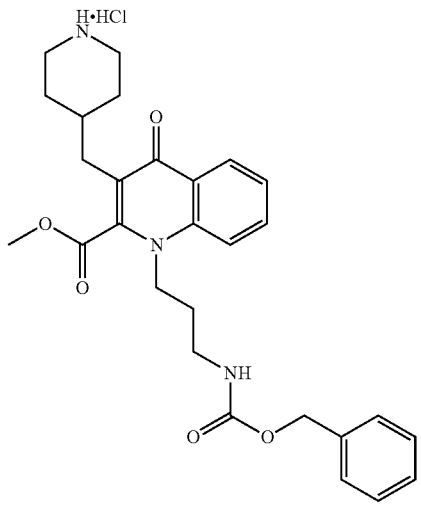

According to the same procedure described in Example 306, using the corresponding protected amine instead of methyl 3-((1-(tert-butoxycarbonyl)piperidin-4-yl)methyl)-4-oxo-1-phenyl-1,4-dihydroquinoline-2-carboxylate, the title compound was obtained.

Example 330

Methyl 1-(3-(benzyloxycarbonylamino)propyl)-4-oxo-3-((1-((2-(pyridin-2-yl)thiazol-5-yl)methyl)piperidin-4-yl)methyl)-1,4-dihydroquinoline-2-carboxylate

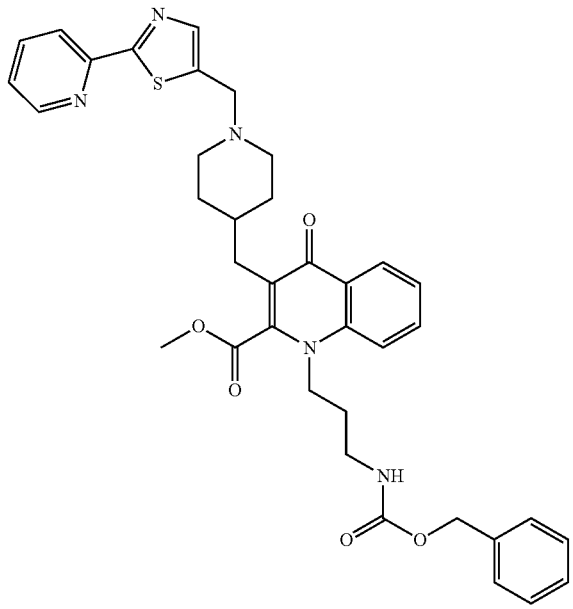 [SMILES: COC(=O)c1c(CC2CCN(Cc3cnc(-c4ccccn4)s3)CC2)c(=O)c2ccccc2n1CCCNC(=O)OCc1ccccc1]

According to the same procedure described in Example 309, using the corresponding amine instead of methyl 4-oxo-1-phenyl-3-(piperidin-4-ylmethyl)-1,4-dihydroquinoline-2-carboxylate hydrochloride, the title compound having the following physical data was obtained.

$^1$H NMR (CDCl$_3$): δ 8.60-8.59 (m, 1H), 8.46-8.43 (m, 1H), 8.14-8.13 (m, 1H), 7.79-7.75 (m, 1H), 7.66-7.62 (m, 2H), 7.42-7.35 (m, 6H), 7.31-7.27 (m, 2H), 5.12 (s, 2H), 4.96-4.92 (m, 2H), 4.05-4.02 (m, 2H), 3.93 (s, 3H), 3.72 (s, 2H), 3.31-3.27 (m, 2H), 2.91-2.88 (m, 2H), 2.36 (d, J=6.9 Hz, 2H), 2.10-1.97 (m, 3H), 1.87-1.81 (m, 1H), 1.65-1.62 (m, 2H), 1.30-1.21 (m, 2H);

Mass data (APCI, Pos.): m/z 666 (M+H)$^+$.

Example 331

Methyl 1-(3-aminopropyl)-4-oxo-3-((1-((2-(pyridin-2-yl)thiazol-5-yl)methyl)piperidin-4-yl)methyl)-1,4-dihydroquinoline-2-carboxylate

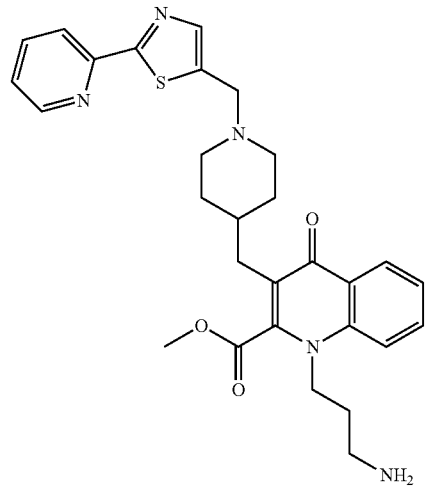 [SMILES: COC(=O)c1c(CC2CCN(Cc3cnc(-c4ccccn4)s3)CC2)c(=O)c2ccccc2n1CCCN]

A solution of the compound prepared in Example 330 (37 mg) in acetonitrile (1 mL) was treated with iodotrimethylsilane (0.015 mL) for 30 minutes at room temperature. The solution was diluted with ethyl acetate, washed with saturated aqueous sodium bicarbonate solution and brine. The organics were dried over magnesium sulfate, filtered and concentrated under reduced pressure to afford the crude material, which was purified by preparative thin layer chromatography (eluant: 20% (9:1 methanol/concentrated ammonium hydroxide)/ethyl acetate) to furnish the title compound (5 mg) with the following physical properties.

$^1$H NMR (CDCl$_3$): δ 8.60-8.59 (m, 1H), 8.46-8.44 (m, 1H), 8.14-8.12 (m, 1H), 7.79-7.75 (m, 1H), 7.68-7.64 (m, 2H), 7.56-7.54 (m, 1H), 7.39-7.35 (m, 1H), 7.30-7.27 (m, 1H), 4.115-4.11 (m, 1H), 4.01 (s, 3H), 3.74 (s, 2H), 2.93-2.90 (m, 2H), 2.81 (t, J=6.4 Hz, 2H), 2.39 (d, J=6.9 Hz, 2H), 2.05-1.95 (m, 5H), 1.90-1.82 (m, 1H), 1.67-1.64 (m, 2H), 1.26-1.24 (m, 4H);

Mass data (APCI, Pos.): m/z 532 (M+H)$^+$.

Example 332

Methyl 4-oxo-1-phenyl-3-({1-[(3-phenyl-5-isoxazolyl)methyl]-4-piperidinyl}methyl)-1,4-dihydro-2-quinolinecarboxylate

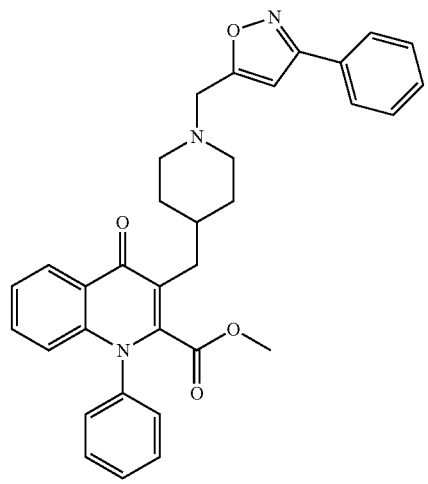 [SMILES: COC(=O)c1c(CC2CCN(Cc3cc(-c4ccccc4)no3)CC2)c(=O)c2ccccc2n1-c1ccccc1]

To a solution of the compound prepared in Example 306 (83.0 mg) and the compound prepared in Example 7 (52.2 mg) in dichloromethane (5.0 mL) was added diisopropylethylamine (0.105 mL) and sodium triacetoxyborohydride (85.2 mg). The reaction mixture was stirred at room temperature for 18 hours. The mixture was diluted with ethyl acetate, washed with saturated aqueous solution of sodium hydrogen carbonate, brine, dried over anhydrous magnesium sulfate and concentrated. The residue was purified by column chromatography on silica gel (ethyl acetate:hexane=9:1) to obtain the title compound (72.0 mg) having the following physical data.

$^1$H NMR (CDCl$_3$): δ 8.46-8.44 (m, 1H), 7.81-7.72 (m, 2H), 7.56-5.54 (m, 3H), 7.46-7.42 (m, 4H), 7.38-7.33 (m, 3H), 6.80-6.77 (m, 1H), 6.47 (s, 1H), 3.69 (s, 2H), 3.47 (s, 3H), 2.95-2.91 (m, 2H), 2.48 (d, J=3.9 Hz, 2H), 2.13-2.07 (m, 2H), 1.94-1.86 (m, 1H), 1.76-1.71 (m, 2H), 1.39-1.29 (m, 2H);

Mass data (APCI, Pos.): m/z 534 (M+H)$^+$.

Example 333

2-(thiophen-2-yl)thiazole-5-carbaldehyde

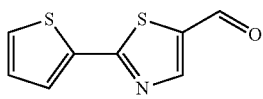 [SMILES: O=Cc1cnc(-c2cccs2)s1]

According to the same procedure described in Example 139, using the corresponding thioamide instead of pyridine-2-carbothioamide, the title compound having the following physical data was obtained.

$^1$H NMR (CDCl$_3$): δ 10.02 (s, 1H), 8.33 (s, 1H), 7.69 (d, J=3.9 Hz, 1H), 7.56 (d, J=4.7 Hz, 1H), 7.15 (m, 1H);

Mass data (ESI, Pos.): m/z 501 (M+H)$^+$.

Example 334

4-amino-5-cyano-6-ethoxy-N-(piperidin-4-ylmethyl)picolinamide

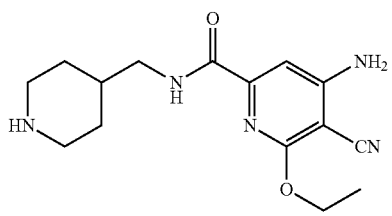 [SMILES: CCOc1nc(C(=O)NCC2CCNCC2)cc(N)c1C#N]

The compound prepared in Example 225 (3.579 g) was suspended in dichloromethane (50 mL) and trifluoroacetic acid (10.00 mL) added and the reaction mixture stirred at room temperature for 2 hours. The reaction mixture was poured onto saturated aqueous sodium bicarbonate and ethyl acetate. The aqueous layer was saturated with sodium chloride. The desired material crystallized from the aqueous and was isolated by filtration to obtain the title compound (2.752 g) with the following physical data.

Mass data (APCI, Pos.): m/z 304 (M+H)$^+$.

Example 335

4-amino-5-cyano-6-ethoxy-N-((1-((2-(thiophen-2-yl)thiazol-5-yl)methyl)piperidin-4-yl)methyl)picolinamide

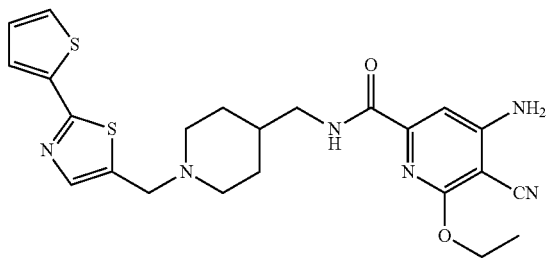 [SMILES: CCOc1nc(C(=O)NCC2CCN(Cc3cnc(-c4cccs4)s3)CC2)cc(N)c1C#N]

The compound prepared in Example 333 (31 mg) and the compound prepared in Example 334 (48 mg) were combined in dichloroethane (1.6 mL) and acetic acid (0.054 mL) was added. Sodium triacetoxyborohydride (0.101 g) was then added. The reaction mixture was stirred at ambient temperature for 17 hours. It was then treated with saturated sodium bicarbonate and extracted with dichloromethane. The combined organics were dried over magnesium sulfate and concentrated. The residue was purified by column chromatography on silica gel (ethyl acetate:methanol=98:2) to obtain the title compound (24 mg) having the following physical data.

$^1$H NMR (CDCl$_3$): δ 7.80 (brt, J=6.3 Hz, 1H), 7.51 (s, 1H), 7.45 (d, J=4.7 Hz, 1H), 7.37 (d, J=6.3 Hz, 1H), 7.18 (s, 1H), 7.07 (m, 1H), 5.09 (br s, 2H), 4.43 (q, J=7.0 Hz, 2H), 3.71 (s, 2H), 3.34 (t, J=6.6 Hz, 2H), 2.98-2.93 (m, 2H), 2.07-2.00 (m, 2H), 1.76-1.70 (m, 2H), 1.62 (m, 1H), 1.44 (t, J=7.0 Hz, 3H), 1.41-1.31 (m, 2H);

Mass data (APCI, Pos.): m/z 483 (M+H)$^+$.

Example 336

4-amino-N-((1-((2-bromothiazol-5-yl)methyl)piperidin-4-yl)methyl)-5-cyano-6-ethoxypicolinamide

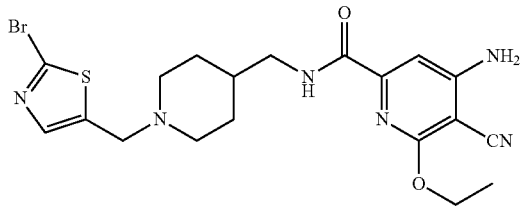 [SMILES: CCOc1nc(C(=O)NCC2CCN(Cc3cnc(Br)s3)CC2)cc(N)c1C#N]

According to the same procedure described in Example 335, using the corresponding aldehyde instead of 2-(thiophen-2-yl)thiazole-5-carbaldehyde, the title compound having the following physical data was obtained.

$^1$H NMR (CDCl$_3$): δ 7.81 (brt, J=6.3 Hz, 1H), 7.35 (s, 1H), 7.19 (s, 1H), 5.14 (br s, 2H), 4.43 (q, J=7.0 Hz, 2H), 3.65 (s, 2H), 3.34 (t, J=6.7 Hz, 2H), 2.93-2.89 (m, 2H), 2.05-1.98 (m, 2H), 1.75-1.69 (m, 2H), 1.61 (m, 1H), 1.45 (t, J=7.0 Hz, 3H), 1.38-1.28 (m, 2H);

Mass data (APCI, Pos.): m/z 479, 481 (M+H)$^+$.

Example 337

4-amino-5-cyano-6-ethoxy-N-((1-((2-(2-oxopyridin-1(2H)-yl)thiazol-5-yl)methyl)piperidin-4-yl)methyl)picolinamide

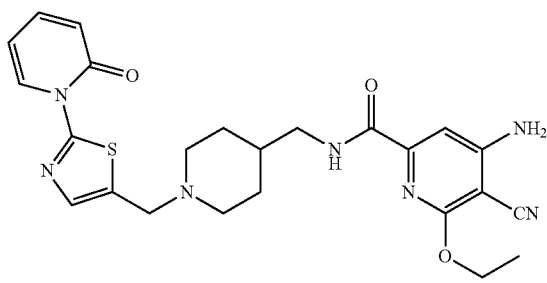 [SMILES: CCOc1nc(C(=O)NCC2CCN(Cc3cnc(-n4ccccc4=O)s3)CC2)cc(N)c1C#N]

The compound prepared in Example 336 (30 mg), pyridin-2-ol (0.0124 g), copper(I) iodide (0.0068 g), trans-N1,N2-dimethylcyclohexane-1,2-diamine (0.0113 mL), and potassium carbonate (0.0173 g) were combined in N,N-dimethylformamide (0.5 mL). The reaction mixture was purged with argon for 5 minutes and then heated at 110° C. for 4 hours. The reaction mixture was diluted with ethyl acetate (15 mL) and passed through a plug of silica gel, eluting with ethyl acetate. The eluent was concentrated and the residue was purified by column chromatography on silica gel (ethyl acetate:methanol=19:1) to obtain the title compound (11 mg) having the following physical data.
$^1$H NMR (CDCl$_3$): δ 8.77 (m, 1H), 7.81 (br t, J=6.3 Hz, 1H), 7.45 (s, 1H), 7.42 (m, 1H), 7.20 (s, 1H), 6.76 (d, J=9.7 Hz, 1H), 6.41 (m, 1H), 5.14 (br s, 2H), 4.43 (q, J=7.0 Hz, 2H), 3.75 (s, 2H), 3.33 (t, J=6.6 Hz, 2H), 2.99-2.93 (m, 2H), 2.10-2.02 (m, 2H), 1.71 (m, 2H), 1.60 (m, 1H), 1.44 (t, J=7.0 Hz, 3H), 1.42-1.32 (m, 2H);
Mass data (APCI, Pos.): m/z 494 (M+H)$^+$.

Example 338

N-((1-((2-(1H-pyrazol-3-yl)thiazol-5-yl)methyl)piperidin-4-yl)methyl)-4-amino-5-cyano-6-ethoxypicolinamide

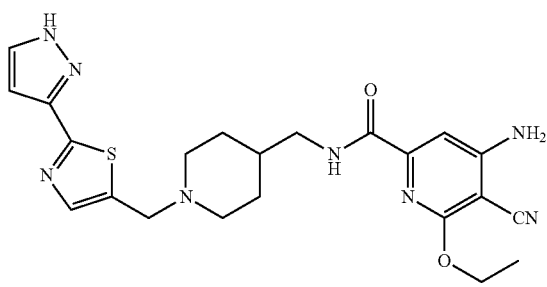 [SMILES: CCOc1nc(C(=O)NCC2CCN(Cc3cnc(-c4cc[nH]n4)s3)CC2)cc(N)c1C#N]

To a mixture of the compound prepared in Example 336 (0.028 g), 1H-pyrazol-3-ylboronic acid (0.013 g) and tetrakis(triphenylphosphine)palladium (0.003 g) in dimethyl ether (0.3 mL) was added a solution of sodium carbonate (0.016 g) in water (0.1 mL). Argon was bubbled through the mixture for 10 minutes. The mixture was then heated at 95° C. for 8 hours. An additional tetrakis(triphenylphosphine)palladium (4.5 mg) and 1H-pyrazol-3-ylboronic acid (13 mg) were added, and the reaction mixture was again purged with argon for 10 minutes and then heated at 110° C. for 6 hours. An additional tetrakis(triphenylphosphine)palladium (10 mg) was added, and the reaction mixture was again purged with argon and then heated at 110° C. for another 38 hours. The reaction mixture was diluted with water and then filtered. The solid was purified by column chromatography on silica gel (dichloromethane:methanol=94:6) to obtain the title compound (2 mg) having the following physical data.
$^1$H NMR (CDCl$_3$): δ 10.3 (br s, 1H), 7.80 (br t, J=6.7 Hz, 1H), 7.63 (d, J=2.3 Hz, 1H), 7.59 (s, 1H), 7.19 (s, 1H), 6.83 (d, J=2.3 Hz, 1H), 5.11 (br s, 2H), 4.43 (q, J=7.0 Hz, 2H), 3.75 (s, 2H), 3.34 (t, J=6.7 Hz, 2H), 2.99-2.92 (m, 2H), 2.10-2.00 (m, 2H), 1.76-1.68 (m, 2H), 1.61 (m, 1H), 1.47-1.31 (m, 5H);
Mass data (APCI, Pos.): m/z 467 (M+H)$^+$.

Example 339

2-oxo-1,2-dihydropyridine-3-carbothioamide

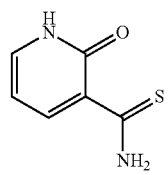

To a suspension of 2-oxo-1,2-dihydropyridine-3-carbonitrile (0.211 g) in methanol (14 mL) was added a 40% aqueous solution of ammonium sulfide (0.50 mL). The reaction mixture was heated at 130° C. in a microwave reactor for 2 hours. The reaction mixture was concentrated. The residue obtained was triturated with methanol and the solid filtered to obtain the title compound (0.174 g) having the following physical data.
$^1$H NMR (DMSO-d$_6$): δ 12.64 (br s, 1H), 11.33 (br s, 1H), 10.01 (br s, 1H), 8.95 (dd, J=7.8, 2.3 Hz, 1H), 7.79 (m, 1H), 6.54 (t, J=7.0 Hz, 1H);
Mass data (APCI, Pos.): m/z 155 (M+H)$^+$.

Example 340

2-(2-oxo-1,2-dihydropyridin-3-yl)thiazole-5-carbaldehyde

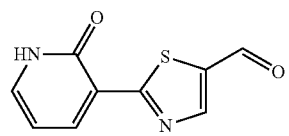 [SMILES: O=Cc1cnc(-c2ccc[nH]c2=O)s1]

According to the same procedure described in Example 139, using the compound prepared in Example 339 instead of pyridine-2-carbothioamide, the title compound having the following physical data was obtained.
$^1$H NMR (DMSO-d$_6$): δ 12.72 (br s, 1H), 10.09 (s, 1H), 8.75 (s, 1H), 8.66 (dd, J=7.4, 2.0 Hz, 1H), 7.82 (dd, J=5.8, 2.0 Hz, 1H), 6.54 (m, 1H);
Mass data (APCI, Pos.): m/z 207 (M+H)$^+$.

Example 341

4-amino-5-cyano-6-ethoxy-N-((1-((2-(2-oxo-1,2-dihydropyridin-3-yl)thiazol-5-yl)methyl)piperidin-4-yl)methyl)picolinamide

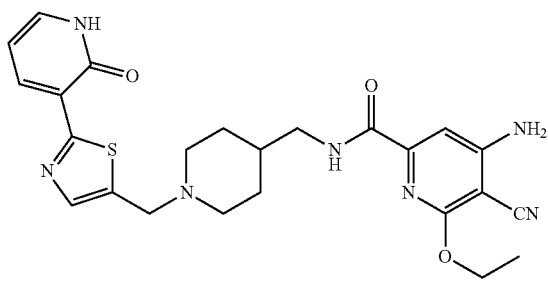 [SMILES: CCOc1nc(C(=O)NCC2CCN(Cc3cnc(-c4ccc[nH]c4=O)s3)CC2)cc(N)c1C#N]

According to the same procedure described in Example 335, using the compound prepared in Example 340 instead of 2-(thiophen-2-yl)thiazole-5-carbaldehyde, the title compound having the following physical data was obtained.

$^1$H NMR (DMSO-d$_6$): δ 12.06 (br s, 1H), 8.52 (dd, J=7.0, 2.3 Hz, 1H), 7.85 (br t, J=6.7 Hz, 1H), 7.66 (s, 1H), 7.37 (m, 1H) 7.22 (s, 1H), 6.39 (t, J=7.0 Hz, 1H) 6.18 (br s, 2H), 4.43 (q, J=7.0 Hz, 2H), 3.79 (s, 2H), 3.31 (t, J=6.3 Hz, 2H), 2.97-2.92 (m, 2H), 2.09-2.01 (m, 2H), 1.73-1.67 (m, 2H), 1.58 (m, 1H), 1.43 (t, J=7.0 Hz, 3H), 1.40-1.29 (m, 2H);

Mass data (ESI, Pos.): m/z 494 (M+H)$^+$.

Example 342

4-amino-5-cyano-6-ethoxy-N-((1-((1-phenyl-1H-imidazol-2-yl)methyl)piperidin-4-yl)methyl)picolinamide

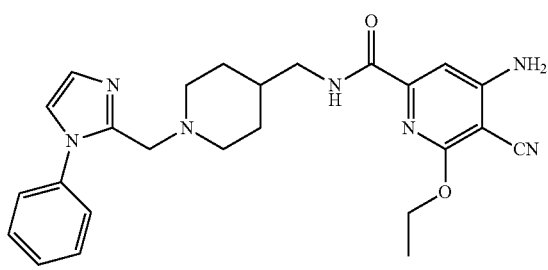 [SMILES: CCOc1nc(C(=O)NCC2CCN(Cc3nccn3-c3ccccc3)CC2)cc(N)c1C#N]

According to the same procedure described in Example 335, using the corresponding aldehyde instead of 2-(thiophen-2-yl)thiazole-5-carbaldehyde, the title compound having the following physical data was obtained.

$^1$H NMR (CDCl$_3$): δ 7.80 (m, 1H), 7.70 (d, J=7.0 Hz, 2H), 7.57 (s, 1H), 7.46-7.41 (m, 2H), 7.40-7.34 (m, 2H), 7.19 (s, 1H), 5.14 (br s, 2H) 4.42 (q, J=7.0 Hz, 2H), 3.46 (s, 2H), 3.33 (t, J=6.3 Hz, 2H), 3.01-2.93 (m, 2H), 1.99-1.90 (m, 2H), 1.74-1.67 (m, 2H), 1.60 (m, 1H), 1.43 (t, J=7.0 Hz, 3H), 1.40-1.28 (m, 2H);

Mass data (APCI, Pos.): m/z 460.1 (M+H)$^+$.

Example 343

4-amino-5-cyano-6-ethoxy-N((1-((1-(pyrimidin-2-yl)-1H-imidazol-2-yl)methyl)piperidin-4-yl)methyl)picolinamide

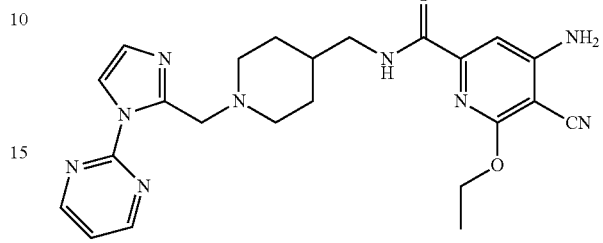

According to the same procedure described in Example 335, using the corresponding aldehyde instead of 2-(thiophen-2-yl)thiazole-5-carbaldehyde, the title compound having the following physical data was obtained.

$^1$H NMR (CDCl$_3$): δ 8.75 (d, J=4.7 Hz, 2H), 7.91 (m, 1H), 7.86 (d, J=1.6 Hz, 1H), 7.27 (t, J=4.7 Hz, 1H), 7.07 (s, 1H), 7.01, (d, J=1.6 Hz, 1H), 4.39, (q, J=7.0 Hz, 2H), 4.15 (s, 2H), 3.24 (t, J=6.3 Hz, 2H), 2.98-2.92 (m, 2H), 2.16-2.07 (m, 2H), 1.66-1.59 (m, 2H), 1.54 (m, 1H), 1.42 (t, J=7.0 Hz, 3H), 1.18-1.06 (m, 2H);

Mass data (APCI, Pos): m/z 462.2 (M+H)$^+$.

Example 344

2,6-difluorobenzothioamide

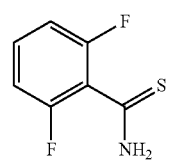

According to the same procedure described in Example 145, using the corresponding nitrile instead of 3,5-difluoropicolinitrile, the title compound having the following physical data was obtained.

$^1$H NMR (CDCl$_3$): δ 7.82 (s, 2H), 7.33 (m, 1H), 6.98-6.92 (m, 2H);

Mass data (APCI, Neg): m/z 172.0 (M−H)$^-$.

Example 345

2-(2,6-difluorophenyl)thiazole-5-carbaldehyde

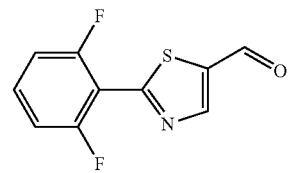 [SMILES: O=Cc1cnc(-c2c(F)cccc2F)s1]

According to the same procedure described in Example 139, using the corresponding thioamide instead of pyridine-2-carbothioamide, the title compound having the following physical data was obtained.

¹H NMR (CDCl₃): δ 10.14 (s, 1H), 8.59 (s, 1H), 7.48 (m, 1H), 7.14-7.08 (m, 2H).

Example 346

4-amino-5-cyano-N-((1-((2-(2,6-difluorophenyl)thiazol-5-yl)methyl)piperidin-4-yl)methyl)-6-ethoxypicolinamide

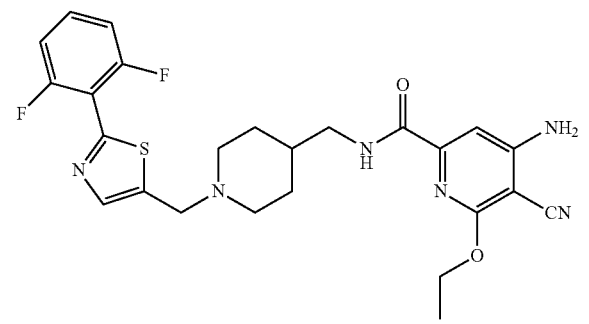 [SMILES: CCOc1nc(C(=O)NCC2CCN(Cc3cnc(-c4c(F)cccc4F)s3)CC2)cc(N)c1C#N]

According to the same procedure described in Example 335, using the corresponding aldehyde instead of 2-(thiophen-2-yl)thiazole-5-carbaldehyde, the title compound having the following physical data was obtained.

¹H NMR (CDCl₃): δ 7.84 (t, J=6.3 Hz, 1H), 7.78 (s, 1H), 7.36 (m, 1H), 7.27 (s, 1H), 7.07-7.01 (m, 2H), 5.36 (br s, 2H), 4.43 (q, J=7.0 Hz, 2H), 3.80 (s, 2H), 3.34 (t, J=6.3 Hz, 2H), 3.01-2.95 (m, 2H), 2.10-2.02 (m, 2H), 1.76-1.68 (m, 2H), 1.62 (m, 1H), 1.44 (t, J=7.0 Hz, 3H), 1.42-1.32 (m, 2H);

Mass data (APCI, pos) m/z 513.0 (M+H)⁺.

Example 347

3-fluoropyridine-2-carbothioamide

According to the same procedure described in Example 145, using the corresponding nitrile instead of 3,5-difluoropicolinitrile, the title compound having the following physical data was obtained.

¹H NMR (CDCl₃): δ 8.99 (s, 2H), 8.39 (m, 1H), 7.63-7.45 (m, 2H);

Mass data (APCI, pos) m/z 157.0 (M+H)⁺.

Example 348

2-(3-fluoropyridin-2-yl)thiazole-5-carbaldehyde

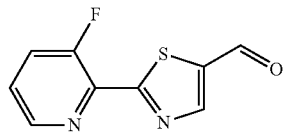 [SMILES: O=Cc1cnc(-c2ncccc2F)s1]

According to the same procedure described in Example 139, using the corresponding thioamide instead of pyridine-2-carbothioamide, the title compound having the following physical data was obtained.

¹H NMR (CDCl₃): δ 10.12 (s, 1H), 8.58 (s, 1H), 8.54 (m, 1H), 7.64 (m, 1H), 7.49 (m, 1H).

Example 349

4-amino-5-cyano-6-ethoxy-N-((1-((2-(3-fluoropyridin-2-yl)thiazol-5-yl)methyl)piperidin-4-yl)methyl)picolinamide

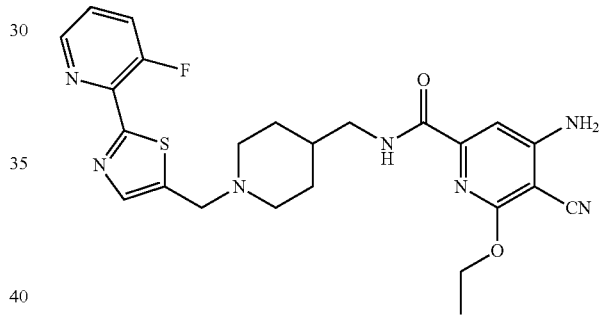

According to the same procedure described in Example 335, using the corresponding aldehyde instead of 2-(thiophen-2-yl)thiazole-5-carbaldehyde, the title compound having the following physical data was obtained.

¹H NMR (CDCl₃): δ 8.47 (m, 1H), 7.82 (t, J=6.3 Hz, 1H), 7.79 (s, 1H), 7.57 (m, 1H), 7.35 (m, 1H), 7.23 (s, 1H), 5.25 (br s, 2H), 4.43 (q, J=7.0 Hz, 2H), 3.79 (s, 2H), 3.34 (t, J=6.3 Hz, 2H), 3.0-2.94 (m, 2H), 2.11-2.03 (m, 2H), 1.75-1.69 (m, 2H), 1.60 (m, 1H), 1.44 (t, J=7.0 Hz, 3H), 1.42-1.32 (m, 2H);

Mass data (APCI, pos) m/z 496.0 (M+H)⁺.

Example 350

Thiazole-2-carbonitrile

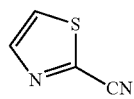

2-(trimethylsilyl)thiazole (1.50 g) and 4-methylbenzenesulfonyl cyanide (2.07 g) were combined neat and then heated at 150° C. in a microwave reactor for 30 minutes. The crude mixture was purified by column chromatography on silica gel (acetone:hexanes=9:1) to provide the title compound (0.25 g) with the following physical data.

$^1$H NMR (CDCl$_3$): δ 9.05 (s, 1H), 8.43 (s, 1H).

Example 351

Thiazole-2-carbothioamide

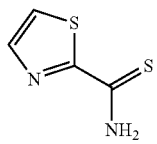

According to the same procedure described in Example 145, using the corresponding nitrile instead of 3,5-difluoropicolinitrile, the title compound having the following physical data was obtained.

$^1$H NMR (CDCl$_3$): δ 8.87 (s, 1H), 8.22 (s, 1H);
Mass data (APCI, pos) m/z 145.1 (M+H)$^+$.

Example 352

2,2-bithiazole-5-carbaldehyde

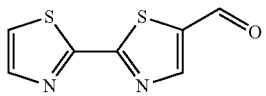 [SMILES: O=Cc1cnc(-c2nccs2)s1]

According to the same procedure described in Example 139, using the corresponding thioamide instead of pyridine-2-carbothioamide, the title compound having the following physical data was obtained.

$^1$H NMR (CDCl$_3$): δ 10.06 (s, 1H), 8.96 (s, 1H), 8.46 (s, 1H), 8.39 (s, 1H).

Example 353

N-((1-(2,2-bithiazol-5-ylmethyl)piperidin-4-yl)methyl-4-amino-5-cyano-6-ethoxypicolinamide

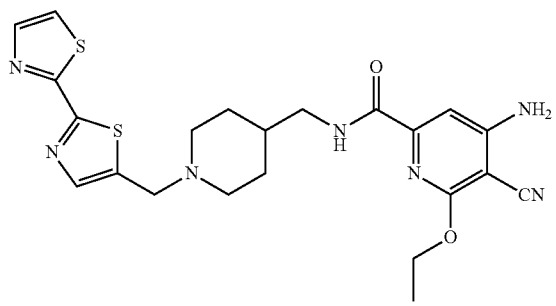 [SMILES: CCOc1nc(C(=O)NCC2CCN(Cc3cnc(-c4nccs4)s3)CC2)cc(N)c1C#N]

According to the same procedure described in Example 335, using the corresponding aldehyde instead of 2-(thiophen-2-yl)thiazole-5-carbaldehyde, the title compound having the following physical data was obtained.

$^1$H NMR (CDCl$_3$): δ 8.81 (s, 1H), 8.23 (s, 1H), 7.81 (t, J=6.3 Hz, 1H), 7.57 (s, 1H), 7.20 (s, 1H), 5.14 (br s, 2H), 4.43 (q, J=7.0 Hz, 2H), 3.73 (s, 2H), 3.34 (t, J=6.3 Hz, 2H), 2.98-2.93 (m, 2H), 2.09-2.01 (m, 2H), 1.77-1.70 (m, 2H), 1.63 (m, 1H), 1.44 (t, J=7.0 Hz, 3H), 1.43-1.32 (m, 2H);
Mass data (APCI, pos) m/z 483.9 (M+H)$^+$.

Example 354

3-chlorothiophene-2-carbothioamide

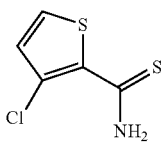

According to the same procedure described in Example 145, using the corresponding nitrile instead of 3,5-difluoropicolinitrile, the title compound having the following physical data was obtained.

$^1$H NMR (CDCl$_3$): δ 8.31 (s, 2H), 7.76 (s, 1H), 7.57 (d, J=5.4 Hz, 1H), 7.06 (d, J=5.4 Hz, 1H).

Example 355

2-(3-chlorothiophe-2-yl)thiazole-5-carbaldehyde

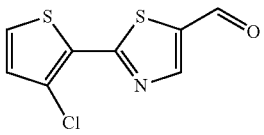 [SMILES: O=Cc1cnc(-c2sccc2Cl)s1]

According to the same procedure described in Example 139, using the corresponding thioamide instead of pyridine-2-carbothioamide, the title compound having the following physical data was obtained.

$^1$H NMR (CDCl$_3$): δ 10.09 (s, 1H), 8.40 (s, 1H), 7.53 (d, J=5.4 Hz, 1H), 7.10 (d, J=5.4 Hz, 1H).

Example 356

4-amino-N-((1-((2-(3-chlorothiophen-2-yl)thiazol-5-yl)methyl)piperidin-4-yl)methyl)-5-cyano-6-ethoxypicolinamide

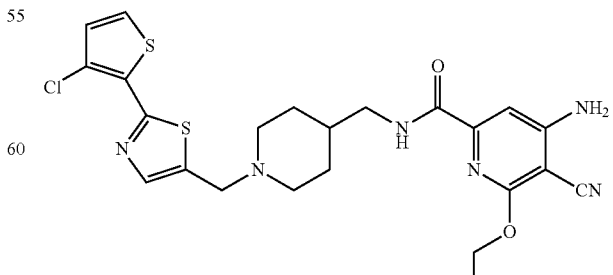

According to the same procedure described in Example 335, using the corresponding aldehyde instead of 2-(thiophen-2-yl)thiazole-5-carbaldehyde, the title compound having the following physical data was obtained.

$^1$H NMR (DMSO-d$_6$): δ 8.45 (t, J=6.3 Hz, 1H), 7.79 (d, J=5.5 Hz, 1H), 7.72 (s, 1H), 7.29 (s, 2H), 7.23 (d, J=5.5 Hz, 1H), 7.03 (s, 1H), 4.47 (q, J=7.0 Hz, 2H), 3.75 (s, 2H), 3.18-3.14 (m, 2H), 2.89-2.83 (m, 2H), 2.00-1.92 (m, 2H), 1.64-1.58 (m, 2H), 1.54 (m, 1H), 1.31 (t, J=7.0 Hz, 3H), 1.26-1.14 (m, 2H);

Mass data (APCI, pos) m/z 516.9 (M+H)$^+$.

Example 357

1-(2-(pyridin-2-yl)thiazol-5-yl)ethanol

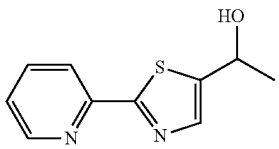

The compound prepared in Experiment 139 (3.0 g) was dissolved in 40 mL of tetrahydrofuran and cooled to −20° C. before methyl magnesium bromide in diethyl ether (3 mol/L; 6.3 mL) was added. The reaction was allowed to warm to room temperature and stirred overnight. The reaction was poured onto ice and extracted with ethyl acetate. The organics were dried over magnesium sulfate and concentrated under reduced pressure to afford the crude material, which was purified by column chromatography on silica gel (ethyl acetate:hexanes=1:1) to afford the title compound (2.5 g) having the following physical data.

$^1$H NMR (CDCl$_3$): δ 8.57 (d, J=4.6 Hz, 1H), 8.11 (d, J=7.9 Hz, 1H), 7.76 (m, 1H), 7.68 (s, 1H), 7.29 (m, 1H), 5.19 (m, 1H), 3.29 (s, 1H), 1.62 (d, J=6.4 Hz, 3H).

Example 358

1-(2-(pyridin-2-yl)thiazol-5-yl)ethanone

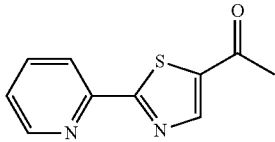

The compound prepared in Example 357 (2.5 g) was dissolved in 80 mL of dichloromethane and manganese (IV) oxide (21 g) was added stirred overnight at room temperature. The reaction mixture was filtered through a plug of Celite (trade mark), washed with dichloromethane, and concentrated under reduced pressure to afford the title compound (2.35 g) having the following physical data. $^1$H NMR (CDCl$_3$): δ 8.64 (d, J=4.5 Hz, 1H), 8.39 (s, 1H), 8.22 (d, J=7.9 Hz, 1H), 7.83 (m, 1H), 7.39 (m, 1H), 2.62 (s, 3H).

Example 359

Tert-butyl (1-(1-(2-(pyridin-2-yl)thiazol-5-yl)ethyl)piperidin-4-yl)methyl Carbamate

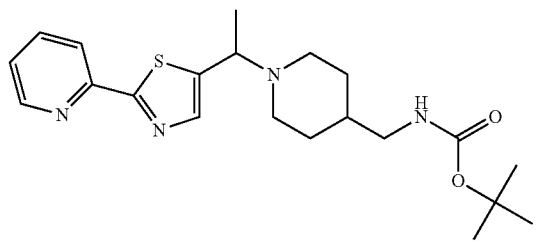 [SMILES: CC(c1cnc(-c2ccccn2)s1)N1CCC(CNC(=O)OC(C)(C)C)CC1]

The compound prepared in Example 358 (0.050 g), tert-butyl piperidin-4-ylmethylcarbamate (0.525 g), acetic acid (0.029 g), and sodium triacetoxyborohydride (0.519 g) were suspended in 2 mL of dichloroethane and stirred at 50° C. for 16 hr. The reaction was partitioned between ethyl acetate and saturated aqueous sodium bicarbonate. The organics were dried over magnesium sulfate and concentrated under reduced pressure to afford the crude material, which was purified by column chromatography on silica gel (ethyl acetate:hexanes=1:1) to afford the title compound (0.020 g) having the following physical data.

$^1$H NMR (CDCl$_3$): δ 8.60 (d, J=4.7 Hz, 1H), 8.15 (d, J=8.6 Hz, 1H), 7.78 (m, 1H), 7.63 (s, 1H), 7.30 (m, 1H), 4.57 (s, 1H), 4.02 (q, J=7.0 Hz, 1H), 3.00 (t, J=5.4 Hz, 2H), 2.93 (m, 1H), 2.86 (m, 1H), 2.18-2.07 (m, 2H), 1.70-1.63 (m, 2H), 1.47 (d, J=7.0 Hz, 3H), 1.43 (s, 9H), 1.37 (m, 1H), 1.31-1.21 (m, 2H).

Example 360

(1-(1-(2-(pyridin-2-yl)thiazol-5-yl)ethyl)piperidin-4-yl)methanamine Trihydrochloride

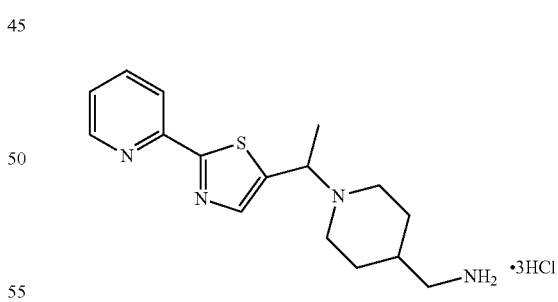

According to the same procedure described in Example 244, using the corresponding carbamate instead of tert-Butyl (1-(5-(pyridin-2-yl)thiophen-2-ylsulfonyl)piperidin-4-yl)methylcarbamate, the title compound (0.020 g) having the following physical data was obtained.

$^1$H NMR (10:1 CDCl$_3$: MeOD-d$_3$): δ 8.71 (d, J=3.9 Hz, 1H), 8.30 (d, J=7.8 Hz, 1H), 8.16 (s, 1H), 8.06 (m, 1H), 7.58 (m, 1H), 4.96 (m, 1H), 3.54-3.49 (m, 2H), 3.08-2.96 (m, 2H), 2.89-2.84 (m, 2H), 2.16 (m, 1H), 2.08-2.00 (m, 2H), 1.96 (d, J=6.3 Hz, 3H);

Mass data (APCI, pos) m/z 302.9 (M+H)$^+$.

Example 361

4-amino-5-cyano-6-ethoxy-N-((1-(1-(2-(pyridin-2-yl)thiazol-5-yl)ethyl)piperidin-4-yl)methyl)picolinamide

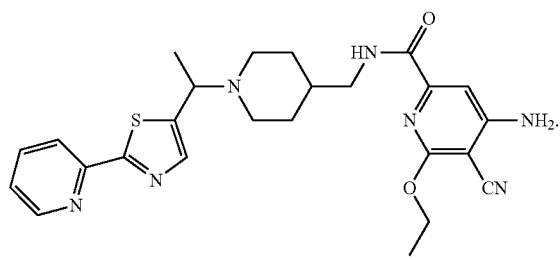 [SMILES: CCOc1nc(C(=O)NCC2CCN(C(C)c3cnc(-c4ccccn4)s3)CC2)cc(N)c1C#N]

According to the same procedure described in Example 245, using the corresponding amine instead of (1-(5-(Pyridin-2-yl)thiophen-2-ylsulfonyl)piperidin-4-yl)methanamine dihydrochloride, the title compound having the following physical data was obtained.

$^1$H NMR (CDCl$_3$): δ 8.60 (d, J=4.7 Hz, 1H), 8.15 (d, J=7.8 Hz, 1H), 7.82-7.76 (m, 2H), 7.62 (s, 1H), 7.30 (m, 1H), 7.22 (s, 1H), 5.22 (br s, 2H), 4.43 (q, J=7.0 Hz, 2H), 4.30 (m, 1H), 3.32 (t, J=6.3 Hz, 2H), 2.95 (m, 1H), 2.87 (m, 1H), 2.22-2.09 (m, 2H), 1.76-1.67 (m, 2H), 1.55 (m, 1H), 1.48 (d, J=7.0 Hz, 3H), 1.43 (t, J=7.0 Hz, 3H), 1.40-1.30 (m, 2H);

Mass data (ESI, pos) m/z 492.1 (M+H)$^+$.

Example 362

4-amino-N-((1-(biphenyl-2-ylmethyl)piperidin-4-yl)methyl)-5-cyano-6-ethoxypicolinamide

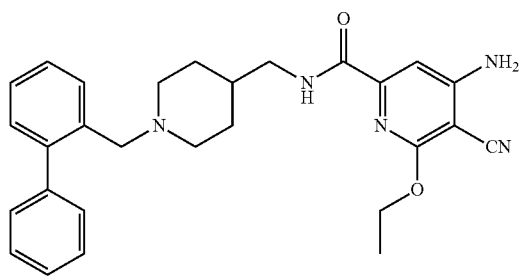 [SMILES: CCOc1nc(C(=O)NCC2CCN(Cc3ccccc3-c3ccccc3)CC2)cc(N)c1C#N]

According to the same procedure described in Example 335, using the corresponding aldehyde instead of 2-(thiophen-2-yl)thiazole-5-carbaldehyde, the title compound having the following physical data was obtained.

$^1$H NMR (CDCl$_3$): δ 7.80 (m, 1H), 7.53 (m, 1H), 7.40-7.36 (m, 4H), 7.35 (m, 1H), 7.34-7.29 (m, 2H), 7.25-7.22 (m, 2H), 5.28 (br s, 2H), 4.42 (q, J=7.0 Hz, 2H), 3.38 (s, 2H), 3.30 (t, J=6.3 Hz, 2H), 2.84-2.78 (m, 2H), 1.89-1.81 (m, 2H), 1.66-1.61 (m, 2H), 1.52 (m, 1H), 1.43 (t, J=7.0 Hz, 3H), 1.34-1.24 (m, 2H);

Mass data (APCI, pos) m/z 470.2 (M+H)$^+$.

Example 363 tert-butyl (1-(1-(biphenyl-4-yl)-1-cyanoethyl)piperidin-4-yl)methylcarbamate

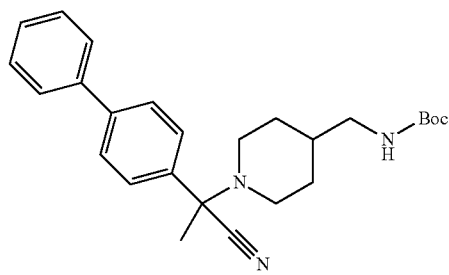 [SMILES: CC(C)(C)OC(=O)NCC1CCN(C(C)(C#N)c2ccc(-c3ccccc3)cc2)CC1]

To tert-butyl piperidin-4-ylmethylcarbamate (0.527 g) and 1-(biphenyl-4-yl)ethanone (0.483 g) in dichloromethane (6.2 mL) was added titanium (IV) isopropoxide (0.720 mL). The reaction mixture was stirred at room temperature for 24 hours. A 1.0 mol/L solution of cyanodiethylaluminum (2.46 mL) in toluene was then added dropwise and the reaction mixture was stirred at ambient temperature for another 24 hours. It was then quenched with saturated sodium bicarbonate and diluted with dichloromethane. The biphasic mixture was filtered, and the layers of the filtrate were separated. The aqueous layer was extracted with dichloromethane, and the combined organics were dried over magnesium sulfate and concentrated. The residue was purified by column chromatography on silica gel (ethyl acetate:hexanes=85:15) to obtain the title compound (0.565 g) having the following physical data.

$^1$H NMR (CDCl$_3$): δ 7.66-7.62 (m, 2H), 7.61-7.57 (m, 4H), 7.48-7.42 (m, 2H), 7.36 (m, 1H), 4.56 (br s, 1H), 3.27 (m, 1H), 3.04 (br t, J=6.3 Hz, 2H), 2.62 (m, 1H), 2.29 (dt, J=11.0, 3.1 Hz, 1H), 2.08 (br dt, J=11.0, 2.3 Hz, 1H), 1.85 (m, 1H), 1.74 (s, 3H), 1.63-1.32 (m, 12H), 1.17 (dq, J=12.0, 3.9 Hz, 1H);

Mass data (APCI, Pos.): m/z 420 (M+H)$^+$.

Example 364 tert-butyl (1-(2-(biphenyl-4-yl)propan-2-yl)piperidin-4-yl)methylcarbamate

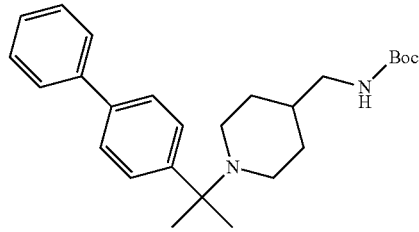 [SMILES: CC(C)(C)OC(=O)NCC1CCN(C(C)(C)c2ccc(-c3ccccc3)cc2)CC1]

To a solution of the compound prepared in Example 363 (0.112 g) in tetrahydrofuran (3 mL) at 0° C. was added a 3.0 M solution of methylmagnesium bromide in diethyl ether (0.27 mL), and the reaction mixture was stirred at room temperature for 3 hours. The reaction mixture was poured onto cold saturated ammonium chloride, and the mixture was extracted with ethyl acetate. The combined organics were washed with brine, dried over magnesium sulfate and concentrated. The residue was purified by column chromatography on silica gel (ethyl acetate:hexanes:triethylamine=80:20:1) to obtain the title compound (0.035 g) having the following physical data.

¹H NMR (CDCl₃): δ 7.61-7.57 (m, 4H), 7.54-7.51 (m, 2H), 7.45-7.40 (m, 2H), 7.32 (m, 1H), 4.56 (br s, 1H), 3.03-2.99 (m, 2H), 2.88-2.83 (m, 2H), 2.11-2.05 (m, 2H), 1.66-1.61 (m, 2H), 1.45-1.38 (m, 10H), 1.36 (s, 6H), 1.26-1.16 (m, 2H);
Mass data (ESI, Pos.): m/z 409 (M+H)⁺.

Example 365

4-amino-N-((1-(2-(biphenyl-4-yl)propan-2-yl)piperidin-4-yl)methyl)-5-cyano-6-ethoxypicolinamide

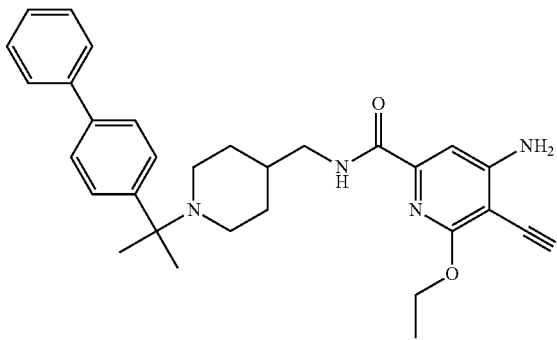

To the compound prepared in Example 364 (0.034 g) in dioxane (1 mL) was added 4 mol/L hydrogen chloride (2.0 mL) in dioxane. The reaction solution was stirred at room temperature for 1 hour and then concentrated to obtain a solid residue (34 mg).

A portion of this solid (0.014 g), 1-ethyl-3-(3'-dimethylaminopropyl)carbodiimide hydrochloride (0.018 g), and 4-amino-5-cyano-6-ethoxypicolinic acid were combined in tetrahydrofuran (0.8 mL). Triethylamine (0.058 mL) was then added, and the reaction mixture was stirred at room temperature for 18 hours. The reaction mixture was diluted with saturated sodium bicarbonate and extracted with ethyl acetate. The combined organics were washed with brine, dried over magnesium sulfate and concentrated. The residue was purified by column chromatography on silica gel (ethyl acetate:hexanes=9:1) to obtain the title compound (0.015 g) having the following physical data.

¹H NMR (CDCl₃): δ 7.80 (br t, J=5.9 Hz, 1H), 7.61-7.56 (m, 4H), 7.53-7.51 (m, 2H), 7.45-7.41 (m, 2H), 7.32 (m, 1H), 7.18 (s, 1H), 5.07 (br s, 2H), 4.43 (q, J=7.0 Hz, 2H), 3.33 (t, J=6.7 Hz, 2H), 2.91-2.85 (m, 2H), 2.14-2.07 (m, 2H), 1.71-1.66 (m, 2H), 1.57 (m, 1H), 1.44 (t, J=7.0 Hz, 3H), 1.37-1.25 (m, 8H);
Mass data (ESI, Pos.): m/z 498 (M+H)⁺.

Example 366

4-amino-5-cyano-6-ethoxy-N-((1-(4-(pyridin-2-yl)benzyl)piperidin-4-yl)methyl)picolinamide

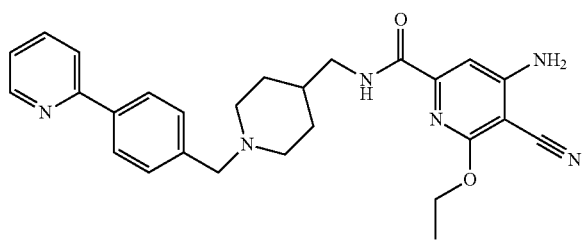 [SMILES: CCOc1nc(C(=O)NCC2CCN(Cc3ccc(-c4ccccn4)cc3)CC2)cc(N)c1C#N]

According to the same procedure described in Example 101, using 4-(pyridin-2-yl)benzaldehyde instead of 2-phenylthiazole-5-carbaldehyde, the title compound having the following physical data was obtained.

¹H NMR (CDCl₃): δ 8.68 (d, J=4.6 Hz, 1H), 7.93 (d, J=8.2 Hz, 2H), 7.80-7.79 (m, 1H), 7.75-7.71 (m, 2H), 7.41 (d, J=8.2 Hz, 2H), 7.23-7.21 (m, 1H), 7.19 (s, 1H), 5.10 (s, 1H), 4.43 (q, J=7.1 Hz, 2H), 3.55 (s, 2H), 3.34 (t, J=6.5 Hz, 2H), 2.94-2.91 (m, 2H), 2.01-1.96 (m, 2H), 1.69-1.56 (m, 4H), 1.44 (t, J=7.1 Hz, 3H), 1.42-1.39 (m, 2H);
Mass data (ESI, Pos.): m/z 471 (M+H)⁺.

Example 367

4-amino-5-cyano-6-ethoxy-N-((1-(4-(pyrazin-2-yl)benzyl)piperidin-4-yl)methyl)picolinamide

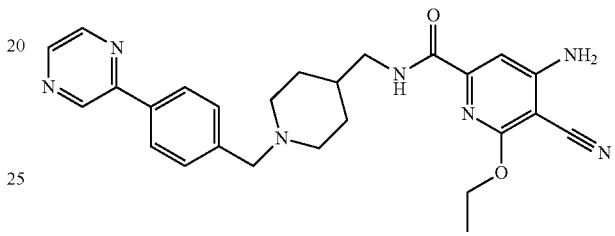

According to the same procedure described in Example 101, using 4-(pyrazin-2-yl)benzaldehyde instead of 2-phenylthiazole-5-carbaldehyde, the title compound having the following physical data was obtained.

¹H NMR (CDCl₃): δ 9.02 (d, J=1.5 Hz, 1H), 8.65-8.60 (m, 1H), 8.50 (d, J=2.5 Hz, 1H), 7.96 (d, J=8.2 Hz, 2H), 7.86-7.77 (m, 1H), 7.46 (d, J=8.2 Hz, 2H), 7.19 (s, 1H), 5.11 (s, 2H), 4.43 (q, J=7.1 Hz, 2H), 3.56 (s, 2H), 3.34 (t, J=6.5 Hz, 2H), 2.97-2.88 (m, 2H), 2.06-1.94 (m, 2H), 1.76-1.67 (m, 2H), 1.66-1.54 (m, 2H), 1.44 (t, J=7.1 Hz, 3H), 1.40-1.31 (m, 1H);
Mass data (ESI, Pos.): m/z 472 (M+H)⁺.

Example 368

4-amino-5-cyano-6-ethoxy-N-((1-(4-(pyrimidin-5-yl)benzyl)piperidin-4-yl)methyl)picolinamide

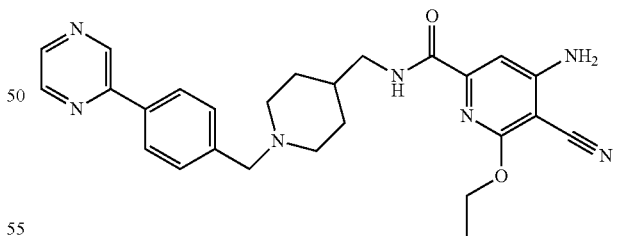

According to the same procedure described in Example 101, using 4-(pyrimidin-5-yl)benzaldehyde instead of 2-phenylthiazole-5-carbaldehyde, the title compound having the following physical data was obtained.

¹H NMR (CDCl₃): δ 9.20 (s, 1H), 8.95 (s, 2H), 7.85-7.76 (m, 1H), 7.55-7.50 (m, 2H), 7.49-7.45 (m, 2H), 7.19 (s, 1H), 5.11 (s, 2H), 4.43 (q, J=7.1 Hz, 2H), 3.56 (s, 2H), 3.35 (t, J=6.5 Hz, 2H), 2.97-2.87 (m, 2H), 2.02-2.00 (m, 2H), 1.77-1.67 (m, 2H), 1.68-1.58 (m, 1H), 1.44 (t, J=7.1 Hz, 3H), 1.41-1.35 (m, 2H);
Mass data (ESI, Pos.): m/z 472 (M+H)⁺.

Example 369

4-amino-5-cyano-6-ethoxy-N-((1-(3-(pyrazin-2-yl)benzyl)piperidin-4-yl)methyl)picolinamide

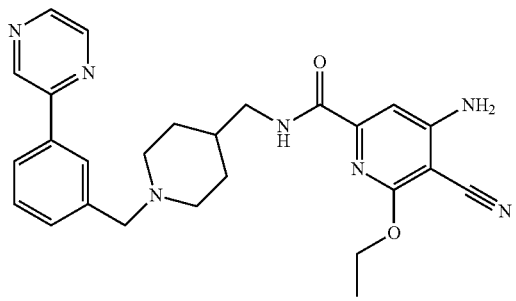 [SMILES: CCOc1nc(C(=O)NCC2CCN(Cc3cccc(-c4cnccn4)c3)CC2)cc(N)c1C#N]

According to the same procedure described in Example 101, using 3-(pyrazin-2-yl)benzaldehyde instead of 2-phenylthiazole-5-carbaldehyde, the title compound having the following physical data was obtained.

$^1$H NMR (CDCl$_3$): δ 9.03 (d, J=1.5 Hz, 1H), 8.65-8.62 (m, 1H), 8.51 (d, J=2.5 Hz, 1H), 7.96 (s, 1H), 7.90-7.87 (m, 1H), 7.83-7.77 (m, 1H), 7.47-7.43 (m, 2H), 7.19 (s, 1H), 5.12 (s, 2H), 4.42 (q, J=7.1 Hz, 2H), 3.59 (s, 2H), 3.34 (t, J=6.5 Hz, 2H), 2.97-2.90 (m, 2H), 2.05-1.97 (m, 2H), 1.75-1.67 (m, 2H), 1.65-1.58 (m, 1H), 1.43 (t, J=7.1 Hz, 3H), 1.40-1.34 (m, 2H);

Mass data (ESI, Pos.): m/z 472 (M+H)$^+$.

Example 370

4-amino-N-((1-(biphenyl-4-ylmethyl)piperidin-4-yl)methyl)-5-cyano-6-ethoxypicolinamide

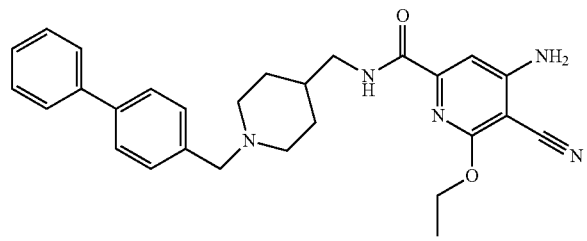 [SMILES: CCOc1nc(C(=O)NCC2CCN(Cc3ccc(-c4ccccc4)cc3)CC2)cc(N)c1C#N]

According to the same procedure described in Example 101, using biphenyl-4-carbaldehyde instead of 2-phenylthiazole-5-carbaldehyde, the title compound having the following physical data was obtained.

$^1$H NMR (CDCl$_3$): δ 7.85-7.78 (m, 1H), 7.59 (d, J=7.3 Hz, 2H), 7.54 (d, J=8.1 Hz, 2H), 7.43 (t, J=7.6 Hz, 2H), 7.39-7.31 (m, 3H), 7.21 (s, 1H), 5.17 (s, 2H), 4.43 (q, J=7.1 Hz, 2H), 3.53 (s, 2H), 3.34 (t, J=6.5 Hz, 2H), 2.98-2.91 (m, 2H), 2.04-1.95 (m, 2H), 1.75-1.68 (m, 2H), 1.66-1.60 (m, 1H), 1.44 (t, J=7.1 Hz, 3H), 1.40-1.35 (m, 2H);

Mass data (ESI, Pos.): m/z 470 (M+H)$^+$.

Example 371

4-amino-5-cyano-6-ethoxy-N-((4-(pyridin-4-yl)benzyl)piperidin-4-yl)methyl)picolinamide

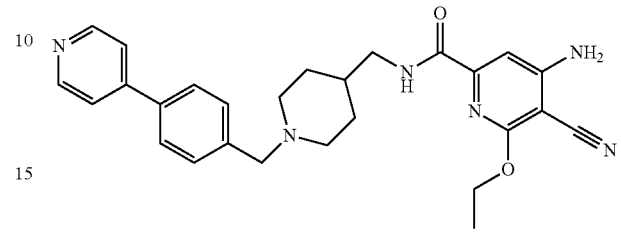

According to the same procedure described in Example 101, using 4-(pyridin-4-yl)benzaldehyde instead of 2-phenylthiazole-5-carbaldehyde, the title compound having the following physical data was obtained.

$^1$H NMR (CDCl$_3$): δ 8.65 (d, J=6.1 Hz, 2H), 7.83-7.78 (m, 1H), 7.59 (d, J=8.1 Hz, 2H), 7.50 (d, J=6.1 Hz, 2H), 7.43 (d, J=8.1 Hz, 2H), 7.19 (s, 1H), 5.13 (s, 2H), 4.43 (q, J=7.1 Hz, 2H), 3.55 (s, 2H), 3.35 (t, J=6.5 Hz, 2H), 2.95-2.89 (m, 2H), 2.04-1.96 (m, 2H), 1.76-1.68 (m, 2H), 1.66-1.59 (m, 1H), 1.44 (t, J=7.1 Hz, 3H), 1.40-1.34 (m, 2H);

Mass data (ESI, Pos.): m/z 471 (M+H)$^+$.

Example 372

4-amino-N-((1-(biphenyl-3-ylmethyl)piperidin-4-yl)methyl)-5-cyano-6-ethoxypicolinamide

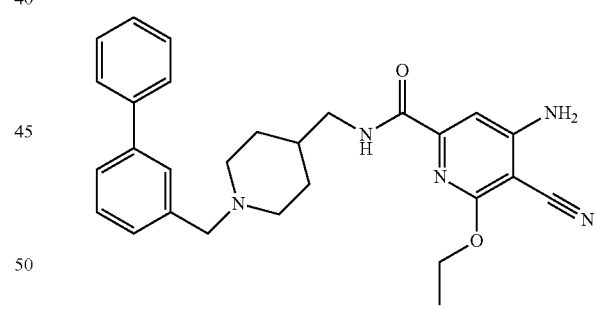

According to the same procedure described in Example 101, using biphenyl-3-carbaldehyde instead of 2-phenylthiazole-5-carbaldehyde, the title compound having the following physical data was obtained.

$^1$H NMR (CDCl$_3$): δ 7.84-7.76 (m, 1H), 7.62-7.57 (m, 2H), 7.53 (s, 1H), 7.50-7.27 (m, 6H), 7.20 (s, 1H), 5.14 (s, 2H), 4.42 (q, J=7.1 Hz, 2H), 3.56 (s, 2H), 3.34 (t, J=6.5 Hz, 2H), 2.98-2.90 (m, 2H), 2.04-1.94 (m, 2H), 1.74-1.67 (m, 2H), 1.65-1.59 (m, 1H), 1.43 (t, J=7.1 Hz, 3H), 1.39-1.33 (m, 2H);

Mass data (ESI, Pos.): m/z 470 (M+H)$^+$.

Example 373

4-amino-5-cyano-6-ethoxy-N-((1-(3-(pyridin-2-yl)benzyl)piperidin-4-yl)methyl)picolinamide

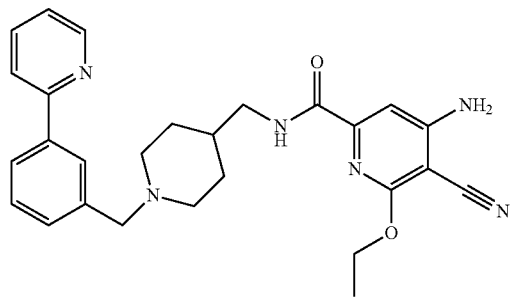 [SMILES: CCOc1nc(C(=O)NCC2CCN(Cc3cccc(-c4ccccn4)c3)CC2)cc(N)c1C#N]

According to the same procedure described in Example 101, using 3-(pyridin-2-yl)benzaldehyde instead of 2-phenylthiazole-5-carbaldehyde, the title compound having the following physical data was obtained.

$^1$H NMR (CDCl$_3$): δ 8.69 (d, J=4.9 Hz, 1H), 7.92 (s, 1H), 7.86 (d, J=7.4 Hz, 1H), 7.83-7.70 (m, 3H), 7.45-7.35 (m, 2H), 7.24-7.20 (m, 1H), 7.18 (s, 1H), 5.10 (s, 2H), 4.42 (q, J=7.1 Hz, 2H), 3.58 (s, 2H), 3.33 (t, J=6.5 Hz, 2H), 2.99-2.89 (m, 2H), 2.05-1.94 (m, 2H), 1.74-1.66 (m, 2H), 1.65-1.59 (m, 1H), 1.43 (t, J=7.1 Hz, 3H), 1.39-1.33 (m, 2H);

Mass data (ESI, Pos.): m/z 471 (M+H)$^+$.

Example 374

4-amino-5-cyano-6-ethoxy-N-((1-(3-(pyridin-3-yl)benzyl)piperidin-4-yl)methyl)picolinamide

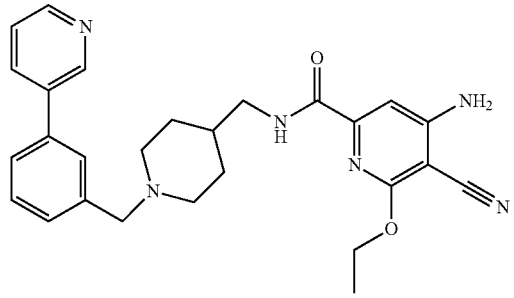 [SMILES: CCOc1nc(C(=O)NCC2CCN(Cc3cccc(-c4cccnc4)c3)CC2)cc(N)c1C#N]

According to the same procedure described in Example 101, using 3-(pyridin-3-yl)benzaldehyde instead of 2-phenylthiazole-5-carbaldehyde, the title compound having the following physical data was obtained.

$^1$H NMR (CDCl$_3$): δ 8.85 (d, J=1.7 Hz, 1H), 8.60-8.57 (m, 1H), 7.90-7.86 (m, 1H), 7.84-7.79 (m, 1H), 7.54 (s, 1H), 7.49-7.39 (m, 2H), 7.38-7.33 (m, 2H), 7.22 (s, 1H), 5.22 (s, 2H), 4.42 (q, J=7.1 Hz, 2H), 3.57 (s, 2H), 3.34 (t, J=6.5 Hz, 2H), 2.97-2.90 (m, 2H), 2.05-1.96 (m, 2H), 1.75-1.68 (m, 2H), 1.66-1.57 (m, 2H), 1.43 (t, J=7.1 Hz, 3H), 1.40-1.34 (m, 1H);

Mass data (ESI, Pos.): m/z 471 (M+H)$^+$.

Example 375

4-amino-5-cyano-6-ethoxy-N-((1-(3-(pyridin-4-yl)benzyl)piperidin-4-yl)methyl)picolinamide

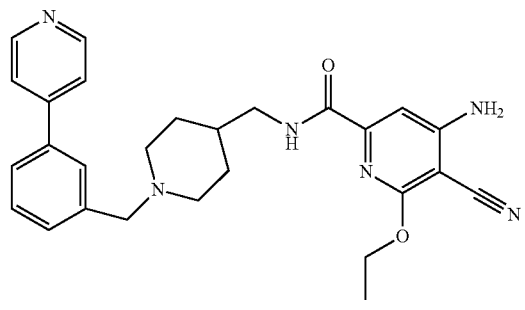 [SMILES: CCOc1nc(C(=O)NCC2CCN(Cc3cccc(-c4ccncc4)c3)CC2)cc(N)c1C#N]

According to the same procedure described in Example 101, using 3-(pyridin-4-yl)benzaldehyde instead of 2-phenylthiazole-5-carbaldehyde, the title compound having the following physical data was obtained.

$^1$H NMR (CDCl$_3$): δ 8.66 (d, J=6.1 Hz, 2H), 7.85-7.78 (m, 1H), 7.59 (s, 1H), 7.55-7.49 (m, 3H), 7.46-7.36 (m, 2H), 7.21 (s, 1H), 5.17 (s, 2H), 4.42 (q, J=7.1 Hz, 2H), 3.57 (s, 2H), 3.34 (t, J=6.5 Hz, 2H), 2.96-2.89 (m, 2H), 2.04-1.96 (m, 2H), 1.76-1.67 (m, 2H), 1.67-1.56 (m, 1H), 1.43 (t, J=7.1 Hz, 3H), 1.40-1.33 (m, 2H);

Mass data (ESI, Pos.): m/z 471 (M+H)$^+$.

Example 376

N-((1-(4-(1H-pyrazol-1-yl)benzyl)piperidin-4-yl)methyl)-4-amino-5-cyano-6-ethoxypicolinamide

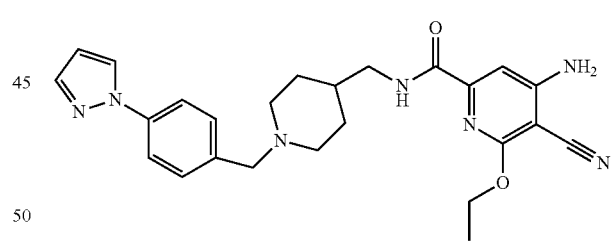

According to the same procedure described in Example 101, using 4-(1H-pyrazol-1-yl)benzaldehyde instead of 2-phenylthiazole-5-carbaldehyde, the title compound having the following physical data was obtained.

$^1$H NMR (CDCl$_3$): δ 7.91 (d, J=2.4 Hz, 1H), 7.85-7.80 (m, 1H), 7.72 (d, J=1.6 Hz, 1H), 7.63 (d, J=8.4 Hz, 2H), 7.39 (d, J=8.3 Hz, 2H), 7.25 (s, 1H), 6.46 (t, J=2.1 Hz, 1H), 5.26 (s, 2H), 4.43 (q, J=7.1 Hz, 2H), 3.52 (s, 2H), 3.34 (t, J=6.5 Hz, 2H), 2.94-2.88 (m, 2H), 2.03-1.94 (m, 2H), 1.75-1.67 (m, 2H), 1.66-1.55 (m, 1H), 1.44 (t, J=7.1 Hz, 3H), 1.39-1.32 (m, 2H);

Mass data (ESI, Pos.): m/z 460 (M+H)$^+$.

Example 377

N-((1-(4-(1H-1,2,4-triazol-1-yl)benzyl)piperidin-4-yl)methyl)-4-amino-5-cyano-6-ethoxypicolinamide

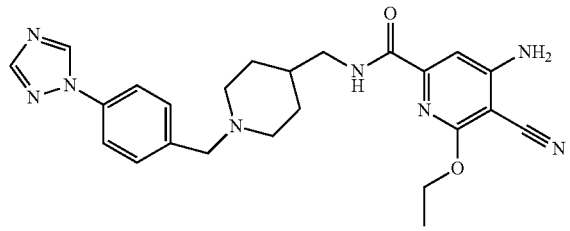 [SMILES: CCOc1nc(C(=O)NCC2CCN(Cc3ccc(-n4cncn4)cc3)CC2)cc(N)c1C#N]

According to the same procedure described in Example 101, using 4-(1H-1,2,4-triazol-1-yl)benzaldehyde instead of 2-phenylthiazole-5-carbaldehyde, the title compound having the following physical data was obtained.

$^1$H NMR (CDCl$_3$): δ 8.53 (s, 1H), 8.10 (s, 1H), 7.85-7.78 (m, 1H), 7.61 (d, J=8.4 Hz, 2H), 7.46 (d, J=8.4 Hz, 2H), 7.21 (s, 1H), 5.17 (s, 2H), 4.43 (q, J=7.1 Hz, 2H), 3.54 (s, 2H), 3.34 (t, J=6.5 Hz, 2H), 2.93-2.85 (m, 2H), 2.03-1.95 (m, 2H), 1.76-1.68 (m, 2H), 1.67-1.59 (m, 1H), 1.44 (t, J=7.1 Hz, 3H), 1.39-1.33 (m, 2H);

Mass data (ESI, Pos.): m/z 461 (M+H)$^+$.

Example 378

N-((1-(4-(1H-imidazol-1-yl)benzyl)piperidin-4-yl)methyl)-4-amino-5-cyano-6-ethoxypicolinamide

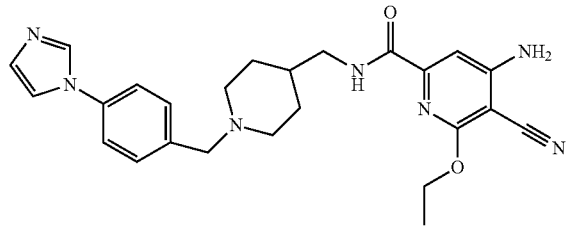 [SMILES: CCOc1nc(C(=O)NCC2CCN(Cc3ccc(-n4ccnc4)cc3)CC2)cc(N)c1C#N]

According to the same procedure described in Example 101, using 4-(1H-imidazol-1-yl)benzaldehyde instead of 2-phenylthiazole-5-carbaldehyde, the title compound having the following physical data was obtained.

$^1$H NMR (CDCl$_3$): δ 7.84 (s, 1H), 7.83-7.79 (m, 1H), 7.45-7.40 (m, 2H), 7.35-7.31 (m, 2H), 7.28-7.26 (m, 1H), 7.22-7.19 (m, 2H), 5.19 (s, 2H), 4.43 (q, J=7.1 Hz, 2H), 3.54 (s, 2H), 3.35 (t, J=6.5 Hz, 2H), 2.95-2.87 (m, 2H), 2.04-1.96 (m, 2H), 1.77-1.69 (m, 2H), 1.68-1.58 (m, 1H), 1.44 (t, J=7.1 Hz, 3H), 1.41-1.34 (m, 2H);

Mass data (ESI, Pos.): m/z 460 (M+H)$^+$.

Example 379

4-amino-5-cyano-6-ethoxy-N-((1-(4-morpholinobenzyl)piperidin-4-yl)methyl)picolinamide

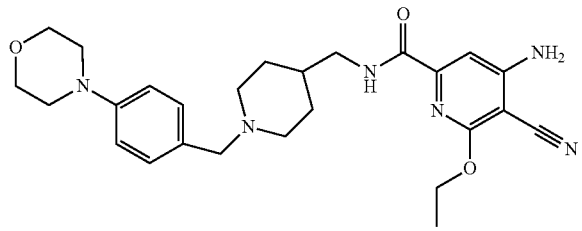 [SMILES: CCOc1nc(C(=O)NCC2CCN(Cc3ccc(N4CCOCC4)cc3)CC2)cc(N)c1C#N]

According to the same procedure described in Example 101, using 4-morpholinobenzaldehyde instead of 2-phenylthiazole-5-carbaldehyde, the title compound having the following physical data was obtained.

$^1$H NMR (CDCl$_3$): δ 7.82-7.76 (m, 1H), 7.22-7.17 (m, 3H), 6.86 (d, J=8.6 Hz, 2H), 5.09 (s, 2H), 4.42 (q, J=7.1 Hz, 2H), 3.88-3.82 (m, 4H), 3.42 (s, 2H), 3.32 (t, J=6.5 Hz, 2H), 3.17-3.11 (m, 4H), 2.93-2.85 (m, 2H), 1.97-1.88 (m, 2H), 1.73-1.64 (m, 2H), 1.57 (s, 1H), 1.44 (t, J=7.1 Hz, 3H), 1.35 (s, 2H);

Mass data (ESI, Pos.): m/z 479 (M+H)$^+$.

Example 380

4-amino-5-cyano-6-ethoxy-N-((1-(4-(4-methylpiperazin-1-yl)benzyl)piperidin-4-yl)methyl)picolinamide

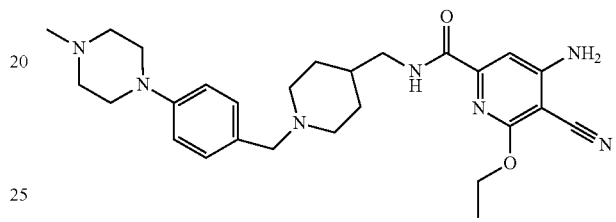

According to the same procedure described in Example 101, using 4-(4-methylpiperazin-1-yl)benzaldehyde instead of 2-phenylthiazole-5-carbaldehyde, the title compound having the following physical data was obtained.

$^1$H NMR (CDCl$_3$): δ 7.80 (d, J=6.2 Hz, 1H), 7.25 (s, 1H), 7.18 (d, J=8.5 Hz, 2H), 6.87 (d, J=8.6 Hz, 2H), 5.30 (s, 2H), 4.42 (q, J=7.1 Hz, 2H), 3.41 (s, 2H), 3.32 (t, J=6.5 Hz, 2H), 3.23-3.16 (m, 4H), 2.94-2.86 (m, 2H), 2.61-2.53 (m, 4H), 2.35 (s, 3H), 1.98-1.88 (m, 2H), 1.72-1.65 (m, 2H), 1.63-1.52 (m, 1H), 1.43 (t, J=7.1 Hz, 3H), 1.39-1.29 (m, 2H);

Mass data (ESI, Pos.): m/z 492 (M+H)$^+$.

Example 381

4-amino-5-cyano-6-ethoxy-N-((1-((2'-methylbiphenyl-4-yl)methyl)piperidin-4-yl)methyl)picolinamide

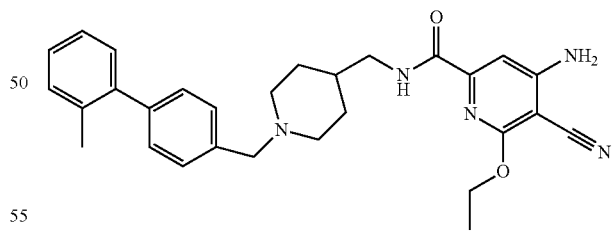

According to the same procedure described in Example 101, using 2'-methylbiphenyl-4-carbaldehyde instead of 2-phenylthiazole-5-carbaldehyde, the title compound having the following physical data was obtained.

$^1$H NMR (CDCl$_3$): δ 7.85-7.78 (m, 1H), 7.36-7.31 (m, 2H), 7.29-7.21 (m, 6H), 7.20 (s, 1H), 5.12 (s, 2H), 4.43 (q, J=7.1 Hz, 2H), 3.54 (s, 2H), 3.35 (t, J=6.5 Hz, 2H), 2.99-2.92 (m, 2H), 2.27 (s, 3H), 2.05-1.95 (m, 2H), 1.76-1.68 (m, 2H), 1.67-1.57 (m, 1H), 1.44 (t, J=7.1 Hz, 3H), 1.41-1.33 (m, 2H);

Mass data (ESI, Pos.): m/z 484 (M+H)$^+$.

Example 382

4-amino-5-cyano-6-ethoxy-N-1-((4'-methylbiphenyl-4-yl)methyl)piperidin-4-yl)methyl)picolinamide

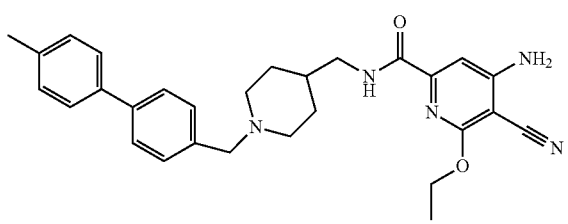 [SMILES: CCOc1nc(C(=O)NCC2CCN(Cc3ccc(-c4ccc(C)cc4)cc3)CC2)cc(N)c1C#N]

According to the same procedure described in Example 101, using 4'-methylbiphenyl-4-carbaldehyde instead of 2-phenylthiazole-5-carbaldehyde, the title compound having the following physical data was obtained.

$^1$H NMR (CDCl$_3$): δ 7.84-7.77 (m, 1H), 7.54-7.45 (m, 4H), 7.35 (d, J=8.0 Hz, 2H), 7.24 (d, J=8.0 Hz, 2H), 7.18 (s, 1H), 5.08 (s, 2H), 4.43 (q, J=7.1 Hz, 2H), 3.52 (s, 2H), 3.34 (t, J=6.5 Hz, 2H), 2.98-2.89 (m, 2H), 2.39 (s, 3H), 2.04-1.94 (m, 2H), 1.75-1.67 (m, 2H), 1.66-1.57 (m, 1H), 1.44 (t, J=7.1 Hz, 3H), 1.40-1.32 (m, 2H);

Mass data (ESI, Pos.): m/z 484 (M+H)$^+$.

Example 383

4-amino-5-cyano-6-ethoxy-N-((1-(4-(pyrimidin-2-yl)benzyl)piperidin-4-yl)methyl)picolinamide

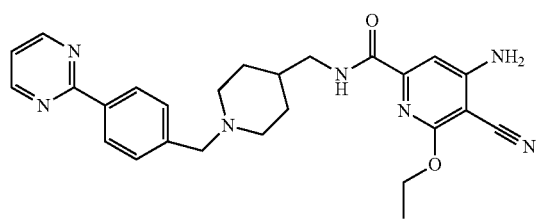 [SMILES: CCOc1nc(C(=O)NCC2CCN(Cc3ccc(-c4ncccn4)cc3)CC2)cc(N)c1C#N]

According to the same procedure described in Example 101, using 4-(pyrimidin-2-yl)benzaldehyde (prepared according to the reported preparation in *Bioorganic and Medicinal Chemistry Letters*, 2005 15(3), 631-634) instead of 2-phenylthiazole-5-carbaldehyde, the title compound having the following physical data was obtained.

$^1$H NMR (CDCl$_3$): δ 8.80 (d, J=4.8 Hz, 2H), 8.38 (d, J=7.9 Hz, 2H), 7.85-7.76 (m, 1H), 7.48-7.40 (m, 2H), 7.18 (s, 2H), 5.08 (s, 2H), 4.43 (q, J=7.1 Hz, 2H), 3.57 (s, 2H), 3.34 (t, J=6.5 Hz, 2H), 2.97-2.86 (m, 2H), 2.03-1.93 (m, 2H), 1.76-1.67 (m, 2H), 1.66-1.57 (m, 1H), 1.44 (t, J=7.1 Hz, 3H), 1.40-1.30 (m, 2H);

Mass data (ESI, Pos.): m/z 472 (M+H)$^+$.

Example 384

4-amino-5-cyano-6-ethoxy-N-((1-(4-(2-methylthiazol-4-yl)benzyl)piperidin-4-yl)methyl)picolinamide

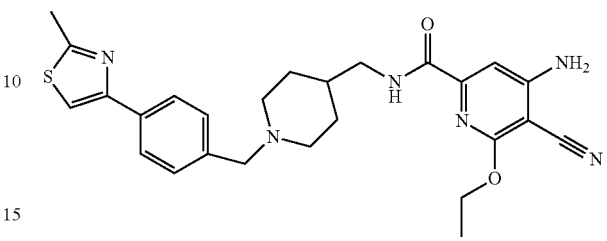

According to the same procedure described in Example 101, using 4-(2-methylthiazol-4-yl)benzaldehyde instead of 2-phenylthiazole-5-carbaldehyde, the title compound having the following physical data was obtained.

$^1$H NMR (CDCl$_3$): δ 7.81 (d, J=8.1 Hz, 2H), 7.34 (d, J=8.1 Hz, 2H), 7.28 (s, 1H), 7.19 (s, 1H), 5.11 (s, 2H), 4.43 (q, J=7.1 Hz, 2H), 3.52 (s, 2H), 3.49 (s, 1H), 3.33 (t, J=6.5 Hz, 2H), 2.95-2.87 (m, 2H), 2.77 (s, 3H), 2.01-1.93 (m, 2H), 1.74-1.66 (m, 2H), 1.65-1.58 (m, 1H), 1.44 (t, J=7.1 Hz, 3H), 1.39-1.33 (m, 2H);

Mass data (ESI, Pos.): m/z 491 (M+H)$^+$.

Example 385

4-amino-5-cyano-6-ethoxy-N-((1-((3'-methylbiphenyl-4-yl)methyl)piperidin-4-yl)methyl)picolinamide

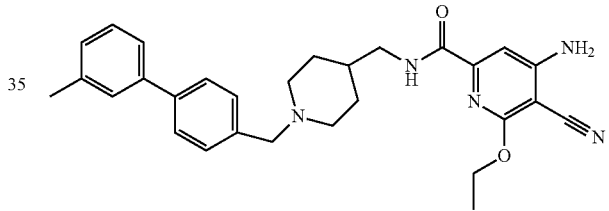

According to the same procedure described in Example 101, using 3'-methylbiphenyl-4-carbaldehyde instead of 2-phenylthiazole-5-carbaldehyde, the title compound having the following physical data was obtained.

$^1$H NMR (CDCl$_3$): δ 7.85-7.77 (m, 1H), 7.53 (d, J=8.0 Hz, 2H), 7.41-7.29 (m, 5H), 7.19 (s, 1H), 7.15 (d, J=7.4 Hz, 1H), 5.11 (s, 2H), 4.43 (q, J=7.1 Hz, 2H), 3.53 (s, 2H), 3.34 (t, J=6.4 Hz, 2H), 2.98-2.90 (m, 2H), 2.42 (s, 3H), 2.05-1.93 (m, 2H), 1.76-1.67 (m, 2H), 1.67-1.58 (m, 1H), 1.44 (t, J=7.1 Hz, 3H), 1.41-1.32 (m, 2H);

Mass data (ESI, Pos.): m/z 484 (M+H)$^+$.

Example 386 methyl 3'-((dimethylamino)methyl)biphenyl-4-carboxylate

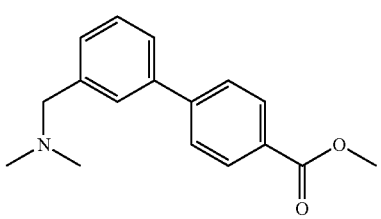

A solution of methyl 3'-formylbiphenyl-4-carboxylate (0.338 g) was dissolved in 2 mol/L dimethylamine in tetrahydrofuran (20 mL) and stirred at room temperature for 1 hour. Sodium triacetoxyborohydride (0.895 g) was added. The reaction was stirred at room temperature for 5 days and then partitioned between saturated aqueous sodium bicarbonate and ethyl acetate. The organics were dried over magnesium sulfate and concentrated under reduced pressure to afford the crude material, which was purified by flash column chromatography (eluant: 0-5% methanol/dichloromethane (0.5% triethylamine) to furnish the title compound (0.112 g) having the following physical data.

$^1$H NMR(CDCl$_3$): δ 8.13-8.07 (m, 2H), 7.70-7.63 (m, 2H), 7.60-7.39 (m, 3H), 7.36-7.32 (m, 1H), 3.94 (s, 3H), 3.50 (s, 2H), 2.28 (s, 6H).

Example 387

(3'-dimethylamino)methylbiphenyl-4-yl)methanol

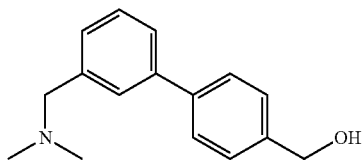 [SMILES: CN(C)Cc1cccc(-c2ccc(CO)cc2)c1]

The compound prepared in Example 386 (0.112 g) was dissolved in tetrahydrofuran (5 mL) and cooled to 0° C. Lithium aluminum hydride (0.032 g) was added and the reaction was allowed to warm to room temperature overnight. The reaction mixture was partitioned between saturated aqueous sodium bicarbonate and ethyl acetate. The organics were dried over magnesium sulfate and concentrated under reduced pressure to furnish the title compound (0.089 g) having the following physical data.

Mass data (ESI, Pos.): m/z 242 (M+H)$^+$.

Example 388

3'-((dimethylamino)methyl)biphenyl-4-carbaldehyde

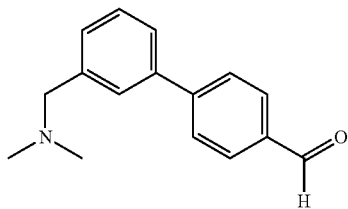 [SMILES: CN(C)Cc1cccc(-c2ccc(C=O)cc2)c1]

The compound prepared in Example 387 (0.089 g) was dissolved in tetrahydrofuran (5 mL) and treated with manganese oxide (0.962 g) for 2 hours at room temperature. The reaction mixture was diluted with ethyl acetate and filtered through celite (trade mark) to furnish the title compound (0.062 g) having the following physical data.

Mass data (ESI, Pos.): m/z 240 (M+H)$^+$.

Example 389

4-amino-5-cyano-N-((1-((3'-((dimethylamino)methyl)biphenyl-4-yl)methyl)piperidin-4-yl)methyl)-6-ethoxypicolinamide

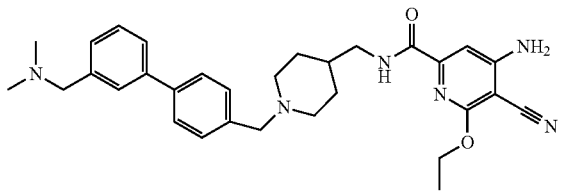 [SMILES: CCOc1nc(C(=O)NCC2CCN(Cc3ccc(-c4cccc(CN(C)C)c4)cc3)CC2)cc(N)c1C#N]

According to the same procedure described in Example 101, using the compound prepared in Example 388 instead of 2-phenylthiazole-5-carbaldehyde, the title compound having the following physical data was obtained.

$^1$H NMR (CDCl$_3$): δ 7.84-7.77 (m, 1H), 7.57-7.46 (m, 3H), 7.41-733 (m, 3H), 7.30-7.26 (m, 2H), 7.18 (s, 1H), 5.09 (s, 2H), 4.43 (q, J=7.1 Hz, 2H), 3.53 (s, 2H), 3.49 (s, 2H), 3.37-3.31 (m, 2H), 2.97-2.89 (m, 2H), 2.27 (s, 6H), 2.03-1.94 (m, 2H), 1.77-1.67 (m, 2H), 1.66-1.56 (m, 1H), 1.44 (t, J=7.1 Hz, 3H), 1.40-1.33 (m, 2H);

Mass data (ESI, Pos.): m/z 527 (M+H)$^+$.

Example 390

N-((1-(2,2'-bipyridin-5-ylmethyl)piperidin-4-yl)methyl)-4-amino-5-cyano-6-ethoxypicolinamide

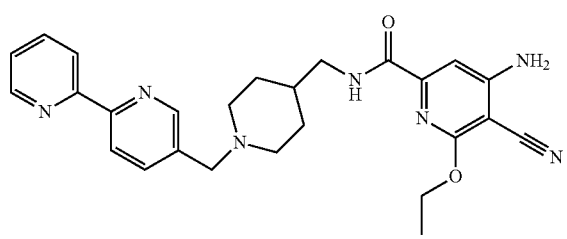 [SMILES: CCOc1nc(C(=O)NCC2CCN(Cc3ccc(-c4ccccn4)nc3)CC2)cc(N)c1C#N]

The compound prepared in Example 334 (0.009 g), 5-(bromomethyl)-2,2'-bipyrdine (0.008 g, prepared according to the reported preparation in *Journal of the American Chemical Society*, 2006, 128(1), 250-256) and cesium carbonate (0.019 g) were heated to 80° C. for 16 hours in N,N-dimethylformamide (2 mL). The reaction mixture was partitioned between saturated aqueous sodium bicarbonate and ethyl acetate. The organics were washed with brine, dried over magnesium sulfate and concentrated under reduced pressure to afford the crude material, which was purified by flash column chromatography (eluant: 1-4% (9:1 methanol:ammonium hydroxide)/ethyl acetate) to furnish the title compound (0.006 g) having the following physical data.

$^1$H NMR (CDCl$_3$): δ 8.68 (d, J=4.6 Hz, 1H), 8.59 (s, 1H), 8.41-8.32 (m, 2H), 7.84-7.76 (m, 3H), 7.34-7.27 (m, 1H), 7.19 (s, 1H), 5.13 (s, 2H), 4.43 (q, J=7.1 Hz, 2H), 3.57 (s, 2H), 3.34 (t, J=6.5 Hz, 2H), 2.95-2.86 (m, 2H), 2.07-1.97 (m, 2H), 1.76-1.68 (m, 2H), 1.67-1.59 (m, 1H), 1.44 (t, J=7.1 Hz, 3H), 1.40-1.32 (m, 2H);

Mass data (ESI, Pos.): m/z 472 (M+H)$^+$.

Example 391 tert-Butyl (1-((2-(2-fluorophenyl)thiazol-5-yl)methyl)piperidin-4-yl)methylcarbamate

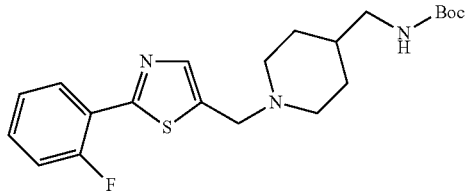 [SMILES: CC(C)(C)OC(=O)NCC1CCN(Cc2cnc(-c3ccccc3F)s2)CC1]

According to the same procedure described in Example 213, using the compound prepared in Example 144 instead of 2-(pyridin-2-yl)thiazole-5-carbaldehyde, the title compound having the following physical data was obtained.

$^1$H NMR (CDCl$_3$): δ 8.27-8.21 (m, 1H), 7.69 (s, 1H), 7.41-7.34 (m, 1H), 7.25-7.16 (m, 2H), 4.59 (bs, 1H), 3.78 (s, 2H), 3.06-3.00 (m, 2H), 2.95 (d, J=10.2 Hz, 2H), 2.03 (t, J=11.7 Hz, 2H), 1.68 (d, J=11.7 Hz, 2H), 1.51-1.40 (m, 10H), 1.34-1.24 (m, 2H);
Mass data (ESI, Pos.): m/z 428 (M+Na)$^+$.

Example 392

(1-((2-(2-Fluorophenyl)thiazol-5-yl)methyl)piperidin-4-yl)methanamine Trihydrochloride

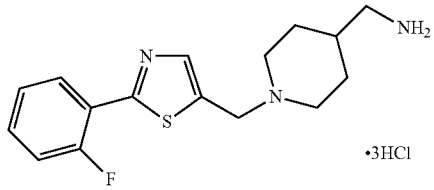 [SMILES: NCC1CCN(Cc2cnc(-c3ccccc3F)s2)CC1]

According to the same procedure described in Example 214, using the compound prepared in Example 391 instead of the compound prepared in Example 213, the title compound having the following physical data was obtained.

$^1$H NMR (DMSO-d$_6$): δ 11.45 (s, 1H), 8.30-8.14 (m, 4H), 7.63-7.56 (m, 1H), 7.50-7.39 (m, 2H), 6.85 (bs, 2H), 4.65 (d, J=4.7 Hz, 2H), 3.44 (d, J=11.7 Hz, 2H), 3.00-2.89 (m, 2H), 2.74-2.67 (m, 2H), 2.01-1.83 (m, 3H), 1.64-1.51 (m, 2H);
Mass data (ESI, Pos.): m/z 306 (M+H)$^+$.

Example 393

4-Amino-6-chloro-5-cyano-N-((1-((2-(2-fluorophenyl)thiazol-5-yl)methyl)piperidin-4-yl)methyl)picolinamide

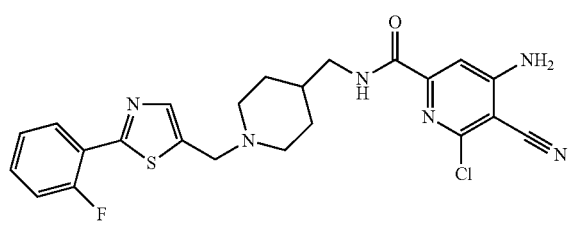 [SMILES: N#Cc1c(N)cc(C(=O)NCC2CCN(Cc3cnc(-c4ccccc4F)s3)CC2)nc1Cl]

A solution of 1,1'-carbodiimidazole (0.15 g) and 4-amino-6-chloro-5-cyanopicolinic acid (0.14 g, prepared according to the reported preparation in Zhao, Hongyu, et al.; *J. Med. Chem.* 2006, 49(15), 4455-4458) in N,N-dimethylformamide (3.5 mL) was stirred one hour at room temperature. The compound prepared in Example 392 (0.30 g) and triethylamine (0.60 mL) were added and the reaction was stirred for one hour more. A saturated sodium bicarbonate solution was added and the mixture was vigorously stirred overnight. The mixture was diluted with water and then filtered. The solids were evaporated from acetone and then a 1:1 dichloromethane:toluene solution. The solids were triturated with dichloromethane to furnish the title compound (0.22 g) having the following physical data.

$^1$H NMR (DMSO-d$_6$): δ 8.57 (t, J=5.9 Hz, 1H), 8.20 (t, J=7.8 Hz, 1H), 7.82 (s, 1H), 7.81-7.67 (bs, 1H), 7.56-7.49 (m, 1H), 7.45-7.34 (m, 4H), 3.76 (s, 2H), 3.15 (t, J=6.3 Hz, 2H), 2.86 (d, J=11.0 Hz, 2H), 1.96 (t, J=11.0 Hz, 2H), 1.65-1.53 (m, 3H), 1.24-1.10 (m, 2H);
Mass data (APCI, Pos.): m/z 485 (M+H)$^+$.

Example 394

4-Amino-5-cyano-6-(cyclopropylmethoxy)-N-((1-((2-(2-fluorophenyl)thiazol-5-yl)methyl)piperidin-4-yl)methyl)picolinamide

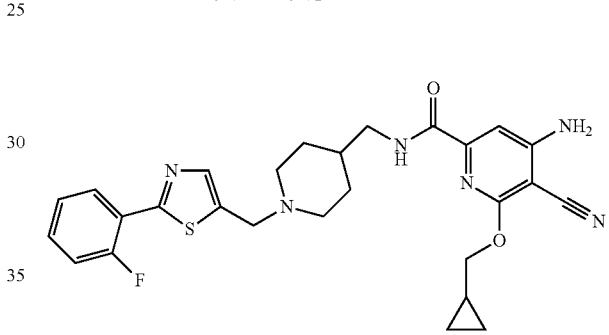

According to the same procedure described in Example 204, using the compound prepared in Example 393 instead of the compound prepared in Example 215 and cyclopropylmethanol instead of 1-cyclopropylethanol, the title compound having the following physical data was obtained.

$^1$H NMR (CDCl$_3$): δ 8.27-8.20 (m, 1H), 7.82-7.75 (m, 1H), 7.69 (s, 1H), 7.42-7.35 (m, 1H), 7.25-7.16 (m, 3H), 5.16 (s, 2H), 4.21 (d, J=7.0 Hz, 2H), 3.78 (s, 2H), 3.34 (t, J=6.3 Hz, 2H), 2.97 (d, J=11 Hz, 2H), 2.10-2.01 (m, 2H), 1.73 (d, J=12.5 Hz, 2H), 1.67-1.57 (m, 1H), 1.43-1.24 (m, 3H), 0.66-0.60 (m, 2H), 0.40-0.35 (m, 2H);
Mass data (ESI, Pos.): m/z 543 (M+Na)$^+$.

Example 395

4-Amino-5-cyano-N-((1-((2-(2-fluorophenyl)thiazol-5-yl)methyl)piperidin-4-yl)methyl)-6-isopropoxypicolinamide

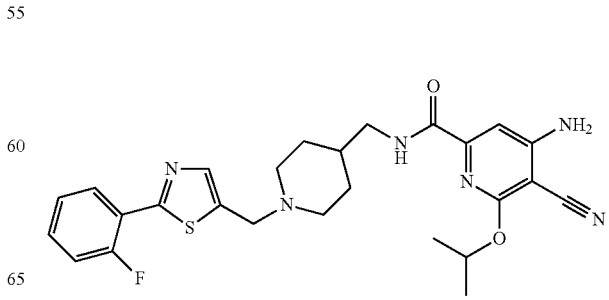

According to the same procedure described in Example 204, using the compound prepared in Example 393 instead of the compound prepared in Example 215 and isopropanol instead of 1-cyclopropylethanol, the title compound having the following physical data was obtained.

¹H NMR (CDCl₃): δ 8.26-8.20 (m, 1H), 7.85-7.78 (m, 1H), 7.69 (s, 1H), 7.41-7.35 (m, 1H), 7.27-7.15 (m, 3H), 5.37 (s, 2H), 5.32-5.24 (m, 1H), 3.78 (s, 2H), 3.34 (t, J=6.7 Hz, 2H), 2.97 (d, J=11.0 Hz, 2H), 2.11-2.01 (m, 2H), 1.72 (d, J=12.5 Hz, 2H), 1.66-1.55 (m, 1H), 1.45-1.33 (m, 8H);

Mass data (ESI, Pos.): m/z 531 (M+Na)⁺.

Example 396

4-Amino-5-cyano-6-(neopentyloxy)-N-((1-((2-(pyridin-2-yl)thiazol-5-yl)methyl)piperidin-4-yl)methyl)picolinamide

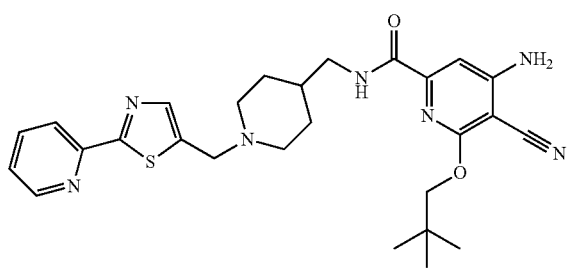 [SMILES: CC(C)(C)COc1nc(C(=O)NCC2CCN(Cc3cnc(-c4ccccn4)s3)CC2)cc(N)c1C#N]

According to the same procedure described in Example 204, using 2,2-dimethylpropan-1-ol instead of 1-cyclopropylethanol, the title compound having the following physical data was obtained.

¹H NMR (CDCl₃): δ 8.60 (d, J=4.7 Hz, 1H), 8.14 (d, J=7.8 Hz, 1H), 7.84-7.76 (m, 2H), 7.67 (s, 1H), 7.32-7.28 (m, 1H), 7.25 (m, 1H), 5.29 (s, 2H), 4.00 (s, 2H), 3.78 (s, 2H), 3.34 (t, J=6.3 Hz, 2H), 2.97 (d, J=11.0 Hz, 2H), 2.12-2.05 (m, 2H), 1.72 (d, J=12.5 Hz, 2H), 1.67-1.56 (m, 1H), 1.43-1.32 (m, 2H), 1.06 (s, 9H);

Mass data (ESI, Pos.): m/z 542 (M+Na)⁺.

Example 397 tert-Butyl (1-((2-(2,6-difluorophenyl)thiazol-5-yl)methyl)piperidin-4-yl)methylcarbamate

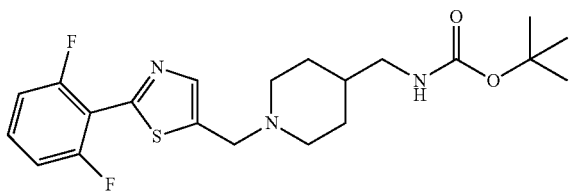 [SMILES: CC(C)(C)OC(=O)NCC1CCN(Cc2cnc(-c3c(F)cccc3F)s2)CC1]

According to the same procedure described in Example 213, using the compound prepared in Example 345 instead of 2-(pyridin-2-yl)thiazole-5-carbaldehyde, the title compound having the following physical data was obtained.

¹H NMR (CDCl₃): δ 7.78 (2, 1H), 7.38-7.33 (m, 1H), 7.06-7.02 (m, 2H), 4.59 (bs, 1H), 3.79 (s, 2H), 3.04-2.94 (m, 4H), 2.04 (t, J=11.7 Hz, 2H), 1.68 (d, J=11.7 Hz, 2H), 1.51-1.40 (m, 10H), 1.31-1.25 (m, 2H);

Mass data (ESI, Pos.): m/z 446 (M+Na)⁺.

Example 398

(1-((2-(2,6-Difluorophenyl)thiazol-5-yl)methyl)piperidin-4-yl)methanamine Dihydrochloride

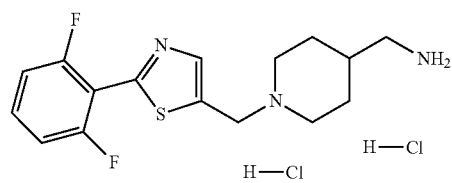

According to the same procedure described in Example 214, using the compound prepared in Example 397 instead of the compound prepared in Example 213, the title compound which was used without further purification.

Example 399

4-Amino-6-chloro-5-cyano-N-((1-((2-(2,6-difluorophenyl)thiazol-5-yl)methyl)piperidin-4-yl)methyl)picolinamide

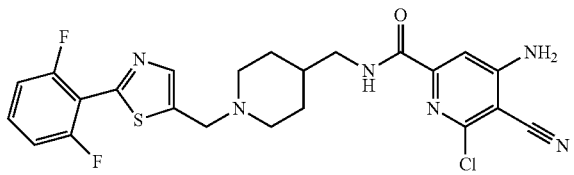 [SMILES: N#Cc1c(N)cc(C(=O)NCC2CCN(Cc3cnc(-c4c(F)cccc4F)s3)CC2)nc1Cl]

According to the same procedure described in Example 215, using the compound prepared in Example 398 instead of the compound prepared in Example 214, the title compound having the following physical data was obtained.

¹H NMR (CDCl₃): δ 7.88-7.85 (m, 1H), 7.78 (s, 1H), 7.53 (s, 1H), 7.40-7.32 (m, 1H), 7.04 (t, J=8.6 Hz, 2H), 5.50 (bs, 2H), 3.80 (s, 2H), 3.34 (t, J=6.3 Hz, 2H), 2.98 (bd, J=10.2 Hz, 2H), 2.06 (t, J=11.0 Hz, 2H), 1.75 (bd, J=12.5 Hz, 2H), 1.68-1.52 (m, 1H), 1.42-1.33 (m, 2H);

Mass data (APCI, Pos.): m/z 503 (M+H)⁺.

Example 400

4-Amino-5-cyano-N-((1-((2-(2,6-difluorophenyl)thiazol-5-yl)methyl)piperidin-4-yl)methyl)-6-isopropoxypicolinamide

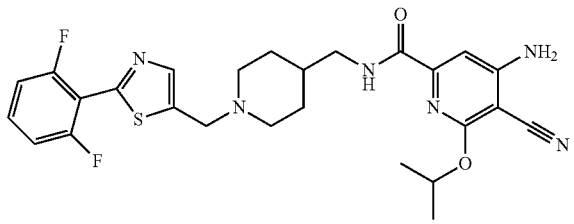 [SMILES: CC(C)Oc1nc(C(=O)NCC2CCN(Cc3cnc(-c4c(F)cccc4F)s3)CC2)cc(N)c1C#N]

According to the same procedure described in Example 204, using the compound prepared in Example 399 instead of the compound prepared in Example 215 and isopropanol instead of 1-cyclopropylethanol, the title compound having the following physical data was obtained.

$^1$H NMR. (CDCl$_3$): δ 7.78 (bs, 2H), 7.40-7.33 (m, 1H), 7.17 (s, 1H), 7.04 (t, J=8.6 Hz, 2H), 5.32-5.26 (m, 1H), 5.09 (bs, 2H), 3.80 (s, 2H), 3.34 (t, J=6.3 Hz, 2H), 2.98 (bd, J=11.0 Hz, 2H), 2.07 (t, J=11.0 Hz, 2H), 1.73 (bd, J=11.7 Hz, 2H), 1.65-1.55 (m, 1H), 1.42-1.37 (m, 8H);

Mass data (APCI, Pos.): m/z 527 (M+H)$^+$.

Example 401

4-amino-5-cyano-6-(cyclopropylmethoxy)-N-((1-((2-(2,6-difluorophenyl)thiazol-5-yl)methyl)piperidin-4-yl)methyl)picolinamide

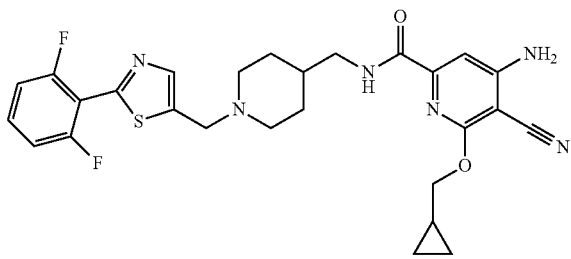 [SMILES: N#Cc1c(N)cc(C(=O)NCC2CCN(Cc3cnc(-c4c(F)cccc4F)s3)CC2)nc1OCC1CC1]

According to the same procedure described in Example 204, using the compound prepared in Example 399 instead of the compound prepared in Example 215 and cyclopropylmethanol instead of 1-cyclopropylethanol, the title compound having the following physical data was obtained.

$^1$H NMR (CDCl$_3$): δ 7.78 (bs, 2H), 7.40-7.32 (m, 1H), 7.20 (s, 1H), 7.04 (t, J=8.6 Hz, 2H), 5.16 (bs, 2H), 4.21 (d, J=7.0 Hz, 2H), 3.80 (s, 2H), 3.34 (t, J=6.3 Hz, 2H), 2.97 (bd, J=11.7 Hz, 2H), 2.06 (t, J=11.0 Hz, 2H), 1.72 (bd, J=11.7 Hz, 2H), 1.66-1.57 (m, 1H), 1.42-1.35 (m, 2H), 1.33-1.28 (m, 1H), 0.66-0.61 (m, 2H), 0.40-0.36 (m, 2H);

Mass data (APCI, Pos.): m/z 539 (M+H)$^+$.

Example 402

4-Amino-6-chloropyridin-2(1H)-one

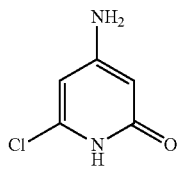

2-Chloro-6-ethoxypyridin-4-amine (10.0 g, prepared according to the reported preparation in J. Med. Chem., (2006), 49 (12), 3563-3580) and aluminum trichloride (19.3 g) were suspended in toluene (300 mL) and heated at reflux under a nitrogen atmosphere. The reaction mixture was cooled to room temperature and partitioned between saturated aqueous Rochelle's salt and ethyl acetate and vigorously stirred overnight. The biphasic mixture was filtered. The aqueous was repeatedly extracted with ethyl acetate. The combined organics were dried, magnesium sulfate and concentrated under reduced pressure to furnish the title compound (4.23 g), which was used without further purification, possessing the following physical data.

$^1$H NMR (DMSO-d$_6$): δ 10.53 (br s, 1H), 6.18 (s, 2H), 6.05 (s, 1H), 5.59 (s, 1H);

Mass data (APCI, Pos.): m/z 145 (M+H)$^+$.

Example 403

4-Amino-6-chloropyridin-2-yl trifluoromethanesulfonate

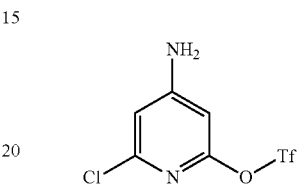

The compound prepared in Example 402 (4.190 g) was suspended in dimethyl formamide (150 mL) and triethylamine (12.12 mL). 1,1,1-Trifluoro-N-phenyl-N-(trifluoromethylsulfonyl)methanesulfonamide (10.87 g) was added in one portion and stirred at room temperature overnight. The reaction mixture was partitioned between saturated aqueous sodium bicarbonate and ethyl acetate. The organics were washed with brine, dried, magnesium sulfate and concentrated under reduced pressure to afford the crude material, which was purified by flash column chromatography (eluant 10-30% ethyl acetate/hexanes) to furnish the title compound (7.428 g), possessing the following physical data.

$^1$H NMR (CDCl$_3$): δ 7.26 (s, 1H), 6.58 (d, J=1.6 Hz, 1H), 6.28 (d, J=1.6 Hz, 1H), 4.61 (br, s, 2H);

Mass data (APCI, Neg.): m/z 275 (M−H)$^-$.

Example 404

Methyl 4-amino-6-chloropicolinate

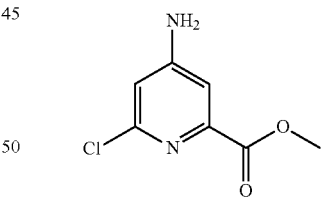

The compound prepared in Example 403 (8.086 g), 1,1'-bis(diphenylphosphino)ferrocenedichlrorpalladium (II) (0.7374 g) and triethyl amine (12.22 mL) were suspended in methanol (300 mL) in a steel bomb. The reaction mixture was charged with 80 psi of carbon monoxide and heated at 80° C. overnight. The reaction mixture was cooled to room temperature and concentrated under reduced pressure to afford the crude material, which was purified by flash column chromatography (eluant 30-50% ethyl acetate/hexanes) to furnish the title compound (3.120 g), possessing the following physical data.

$^1$H NMR (DMSO-d$_6$): δ 7.21 (s, 1H), 6.75 (s, 2H), 6.65 (s, 1H), 3.82 (s, 3H);

Mass data (APCI, Pos.): m/z 187 (M+H)$^+$.

Example 405

Methyl 4-amino-5,6-dichloropicolinate

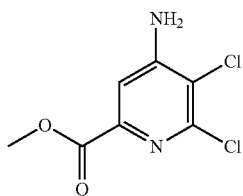

The compound prepared in Example 404 (3.120 g) and N-chlorosuccinimide (2.456 g) were suspended in dimethyl formamide (100 mL) and stirred at 50° C. overnight. The reaction mixture was heated at 70° C. for a further 3 hours. The reaction mixture was added drop-wise to a stirred solution of 1:1 saturated aqueous sodium bicarbonate and water. The slurry was filtered and the solids dried under high vacuum to furnish the title compound (2.438 g), possessing the following physical data.

$^1$H NMR (DMSO-$d_6$): δ 7.41 (s, 1H), 7.09 (br s, 2H), 3.83 (s, 3H);

Mass data (APCI, Pos.): m/z 221 (M+H)$^+$.

Example 406

4-Amino-5,6-dichloropicolinic Acid

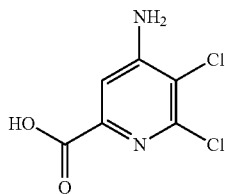 [SMILES: Nc1cc(C(=O)O)nc(Cl)c1Cl]

The compound prepared in Example 405 (2.438 g) and potassium trimethylsilanolate (2.971 g) were suspended in tetrahydrofuran (100 mL) and stirred at reflux for 4 hours. The reaction mixture was dissolved in water and added to 1 N hydrochloric acid. Ethyl acetate was added and the system stirred at room temperature. The organics were dried, magnesium sulfate and concentrated under reduced pressure to furnish the title compound (2.250 g), which was used without further purification, possessing the following physical data.

$^1$H NMR (DMSO-$d_6$): δ 13.22 (br, s, 1H), 7.39 (s, 1H), 7.03 (br s, 2H);

Mass data (APCI, Neg.): m/z 205 (M−H)$^−$.

Example 407

4-amino-5,6-dichloro-N-((1-((2-(pyridin-2-yl)thiazol-5-yl)methyl)piperidin-4-yl)methyl)picolinamide

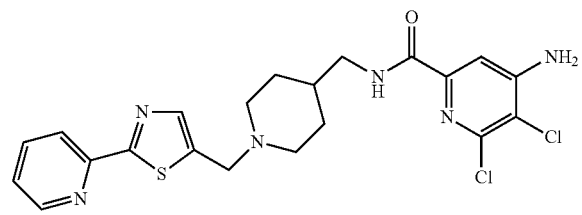 [SMILES: Nc1cc(C(=O)NCC2CCN(Cc3cnc(-c4ccccn4)s3)CC2)nc(Cl)c1Cl]

The compound prepared in Example 406 (0.533 g), benzotriazole-1-yl-oxy-tris-(dimethylamino)-phosphonium hexafluorophosphate (2.0098 g), the compound prepared in Example 214 (1.3315 g) and triethyl amine were suspended in dimethyl formamide (40 mL) and stirred at room temperature overnight. The reaction mixture was poured onto saturated aqueous sodium bicarbonate and ethyl acetate. The organics were washed with brine, dried over with magnesium sulfate and concentrated under reduced pressure to afford the crude material. The crude material was purified by flash column chromatography (eluant gradient elution 1-5% (9:1=methanol:ammonium hydroxide)/ethyl acetate) to furnish the title compound (0.902 g), possessing the following physical data.

$^1$H NMR (CDCl$_3$): δ 8.60 (d, J=4.8 Hz, 1H), 8.14 (d, J=8.0, 1H) 7.87-7.75 (m, 2H), 7.68 (s, 1H), 7.48 (s, 1H), 7.33-7.28 (m, 1H), 4.97 (s, 2H), 3.78 (s, 2H), 3.32 (t, J=6.6 Hz, 2H), 3.01-2.93 (m, 2H), 2.13-2.01 (m, 2H), 1.79-1.68 (m, 2H), 1.67-1.62 (m, 1H), 1.44-1.30 (m, 2H);

Mass data (APCI, Pos.): m/z 447 (M+H)$^+$.

Example 408

4-Amino-5-chloro-6-(2-hydroxyethylamino)-N-((1-((2-(pyridin-2-yl)thiazol-5-yl)methyl)piperidin-4-yl)methyl)picolinamide

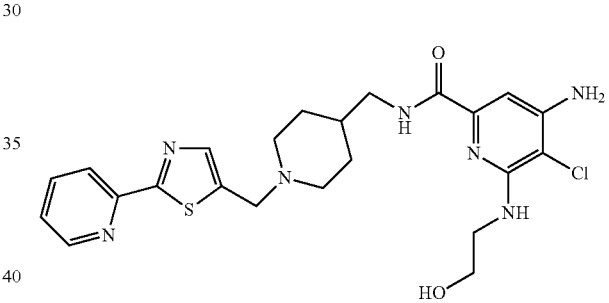

The compound prepared in Example 407 (0.065 g) and 2-aminoethanol (0.008 g) were suspended in dimethyl acetamide (3 mL) and heated at 160° C. for 30 minutes. The reaction mixture was heated at 200° C. for 1 hour. The reaction mixture was cooled to room temperature and partitioned between saturated aqueous sodium bicarbonate and ethyl acetate. The organics were washed with brine, dried, magnesium sulfate and concentrated under reduced pressure to afford the crude material. The crude material was purified by flash column chromatography (eluant: 1-4% (9:1=methanol: ammonium hydroxide)/ethyl acetate) to furnish the title compound (0.037 g), possessing the following physical data.

$^1$H NMR (CDCl$_3$): δ 8.58 (d, J=4.3 Hz, 1H), 8.14 (d, J=7.9 Hz, 1H), 7.93 (t, J=6.0 Hz, 1H), 7.80-7.76 (M, 1H), 7.67 (s, 1H), 7.31-7.28 (m, 1H), 7.02 (s, 1H), 5.30 (t, J=5.6 Hz, 1H), 4.69 (s, 2H), 3.87 (t, J=5.3 Hz, 2H), 3.76 (s, 2H), 3.65 (q, J=5.5, 2H), 3.32 (t, J=6.1 Hz, 2H), 3.00-2.89 (m, 2H), 2.12-2.01 (m, 2H), 1.75-1.65 (m, 2H), 1.64-1.53 (m, 1H), 1.46-1.32 (m, 2H);

Mass data (APCI, Pos.): m/z 502 (M+H)$^+$.

Example 409

4-Amino-6-(3-aminopropylamino)-5-chloro-N-((1-((2-(pyridin-2-yl)thiazol-5-yl)methyl)piperidin-4-yl)methyl)picolinamide

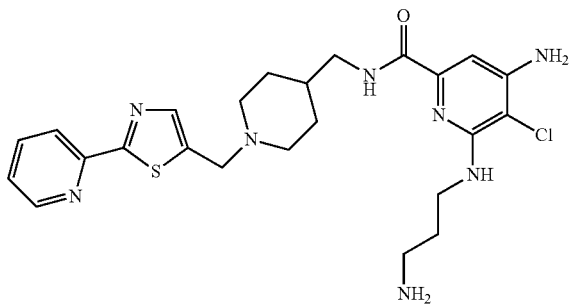 [SMILES: NCCCNc1nc(C(=O)NCC2CCN(Cc3cnc(-c4ccccn4)s3)CC2)cc(N)c1Cl]

According to the same procedure described in Example 408, using propane-1,3-diamine instead of 2-aminoethanol, the title compound having the following physical data was obtained.

$^1$H NMR (CDCl$_3$): δ 8.59 (d, J=4.5 Hz, 1H), 8.18-8.02 (m, 2H), 7.81-7.74 (m, 1H), 7.67 (s, 1H), 7.33-7.27 (m, 1H), 6.98 (s, 1H), 5.47-5.34 (m, 1H), 4.61 (s, 1H), 4.55 (s, 1H), 3.76 (d, J=3.3 Hz, 2H), 3.61-3.45 (m, 3H), 3.30 (d, J=4.5 Hz, 2H), 3.00-2.84 (m, 2H), 2.46 (s, 2H), 2.11-2.00 (m, 2H), 1.98-1.90 (m, 2H), 1.86-1.78 (m, 1H), 1.77-1.65 (m, 2H), 1.65-1.50 (m, 1H), 1.43-1.29 (m, 2H);

Mass data (APCI, Pos.): m/z 515 (M+H)$^+$.

Example 410

(R)-4-amino-5-chloro-6-(1-hydroxypropan-2-ylamino)-N-((1-((2-(pyridin-2-yl)thiazol-5-yl)methyl)piperidin-4-yl)methyl)picolinamide

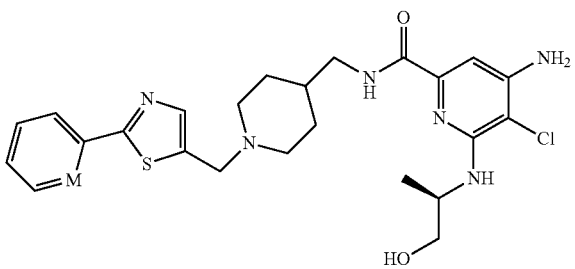

According to the same procedure described in Example 408, using (R)-2-aminopropan-1-ol instead of 2-aminoethanol, the title compound having the following physical data was obtained.

$^1$H NMR (CD$_3$OD): δ 8.57 (d, J=4.7 Hz, 1H), 8.12 (d, J=7.9 Hz, 1H), 7.93-7.87 (m, 1H), 7.75 (s, 1H), 7.46-7.39 (m, 1H), 6.86 (s, 1H), 4.33-4.22 (m, 1H), 3.84 (s, 2H), 3.68-3.60 (m, 1H), 3.58-3.51 (m, 1H), 3.40 (d, J=5.6 Hz, 1H), 3.30-3.26 (m, 2H), 3.04-2.97 (m, 2H), 2.19-2.09 (m, 2H), 1.80-1.71 (m, 2H), 1.70-1.59 (m, 1H), 1.44-1.31 (m, 2H), 1.25 (d, J=6.7 Hz, 2H);

Mass data (ESI, Pos.): m/z 516 (M+H)$^+$.

Example 411

(R)-4-amino-5-chloro-6-(2,3-dihydroxypropylamino)-N-((1-((2-(pyridin-2-yl)thiazol-5-yl)methyl)piperidin-4-yl)methyl)picolinamide

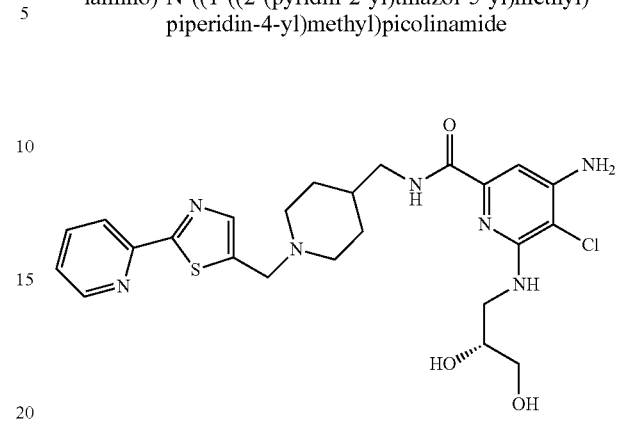

According to the same procedure described in Example 408, using (R)-3-aminopropane-1,2-diol instead of 2-aminoethanol, the title compound having the following physical data was obtained.

$^1$H NMR (CD$_3$OD): δ 8.58 (d, J=4.7 Hz, 1H), 8.14 (d, J=7.9 Hz, 1H), 7.96-7.87 (m, 1H), 7.81 (s, 1H), 7.47-7.40 (m, 1H), 6.85 (s, 1H), 4.01 (s, 2H), 3.87-3.69 (m, 2H), 3.54 (d, J=5.4 Hz, 2H), 3.47-3.38 (m, 1H), 3.29-3.24 (m, 2H), 3.18-3.07 (m, 2H), 2.42-2.25 (m, 2H), 1.87-1.77 (m, 2H), 1.77-1.65 (m, 1H), 1.49-1.33 (m, 2H);

Mass data (ESI, Pos.): m/z 532 (M+H)$^+$.

Example 412

(S)-4-amino-5-chloro-6-(2,3-dihydroxypropylamino)-N-((1-((2-(pyridin-2-yl)thiazol-5-yl)methyl)piperidin-4-yl)methyl)picolinamide

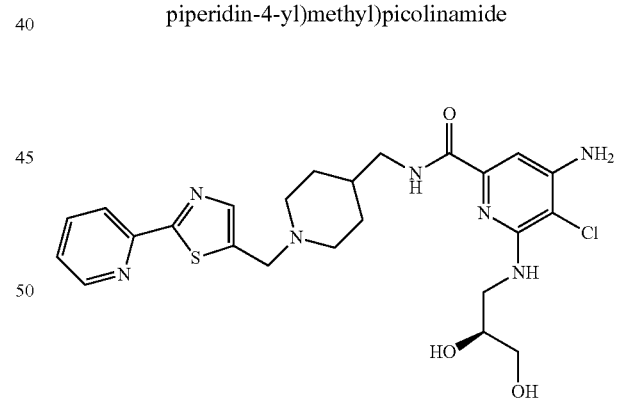

According to the same procedure described in Example 408, using (S)-3-aminopropane-1,2-diol instead of 2-aminoethanol, the title compound having the following physical data was obtained.

$^1$H NMR (CD$_3$OD): δ 8.57 (d, J=4.7 Hz, 1H), 8.13 (d, J=7.9 Hz, 1H), 7.95-7.87 (m, 1H), 7.80 (s, 1H), 7.46-7.39 (m, 1H), 6.85 (s, 1H), 3.98 (s, 2H), 3.86-3.70 (m, 2H), 3.55 (d, J=5.3 Hz, 2H), 3.46-3.38 (m, 1H), 3.30-3.26 (m, 2H), 3.14-3.05 (m, 2H), 2.37-2.22 (m, 2H), 1.86-1.76 (m, 2H), 1.76-1.62 (m, 1H), 1.47-1.33 (m, 2H);

Mass data (ESI, Pos.): m/z 532 (M+H)$^+$.

Example 413

4-Amino-5-cyano-6-(2-(6-fluoro-1H-indol-3-yl)ethylamino)-N-((1-((2-(pyridin-2-yl)thiazol-5-yl)methyl)piperidin-4-yl)methyl)picolinamide

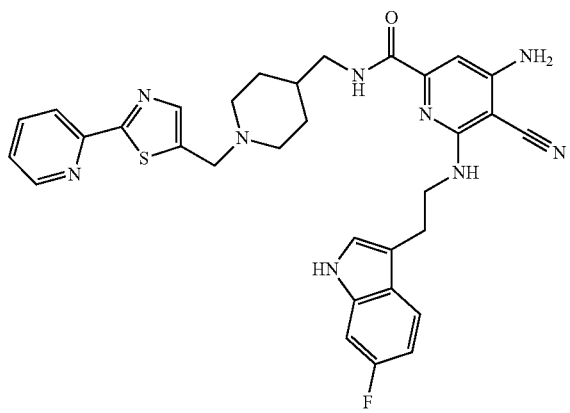 [SMILES: N#Cc1c(N)cc(C(=O)NCC2CCN(Cc3cnc(-c4ccccn4)s3)CC2)nc1NCCc1c[nH]c2cc(F)ccc12]

According to the same procedure described in Example 161, using 2-(6-fluoro-1H-indol-3-yl)ethanamine instead of morpholine, the title compound having the following physical data was obtained.

$^1$H NMR (DMSO-d$_6$): δ 10.88 (s, 1H), 8.64-8.58 (m, 1H), 8.23-8.16 (m, 1H), 8.11-8.06 (m, 1H), 7.98-7.90 (m, 1H), 7.77 (s, 1H), 7.55-7.43 (m, 2H), 7.16 (s, 1H), 7.11-7.05 (m, 1H), 6.90 (s, 2H), 6.84-6.76 (m, 1H), 6.75-6.69 (m, 1H), 6.66 (s, 1H), 5.76 (s, 1H), 3.70 (s, 3H), 3.18-3.08 (m, 2H), 2.97-2.90 (m, 2H), 2.82-2.74 (m, 2H), 1.94-1.83 (m, 2H), 1.61-1.50 (m, 2H), 1.49-1.35 (m, 1H), 1.21-1.07 (m, 2H);

Mass data (APCI, Pos.): m/z 610 (M+H)$^+$.

Example 414

4-Amino-N-((1-((2-(pyridin-2-yl)thiazol-5-yl)methyl)piperidin-4-yl)methyl)picolinamide

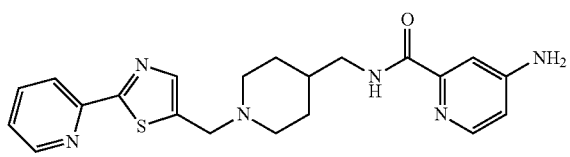 [SMILES: Nc1ccnc(C(=O)NCC2CCN(Cc3cnc(-c4ccccn4)s3)CC2)c1]

The compound prepared in Example 214 (0.44 g), 1-ethyl-3-(3'-dimethylaminopropyl)carbodiimide hydrochloride (0.25 g), 4-aminopicolinic acid (0.18 g), 1-hyroxybenzotriazole hydrate (0.20 g) and N-ethyl-N-isopropylpropan-2-amine (1.2 ml) were combined in dimethylacetamide (8 mL) and the reaction was allowed to stir 2 days. The reaction was diluted with ethyl acetate and washed with aqueous sodium bicarbonate and brine. The organic phase was dried over magnesium sulfate, filtered, concentrated and purified by column chromatography using an eluant (2 to 6% methanol/dichloromethane) to provide the title compound (0.05 g) with the following physical data.

$^1$H NMR (CDCl$_3$): δ 8.60 (d, J=3.9 Hz, 1H), 8.15-8.12 (m, 3H), 7.78 (dt, J=7.8, 2.3, 1H), 7.67 (s, 1H), 7.43 (d, J=2.3 Hz, 1H), 7.31-7.28 (m, 1H), 6.59 (dd, J=5.5, 2.3 Hz, 1H), 5.30 (bs, 2H), 3.77 (s, 2H), 3.34 (t, J=6.3 Hz, 2H), 2.96 (bd, J=11.0 Hz, 2H), 2.06 (dt, J=11.7, 2.3 Hz, 2H), 1.76 (bd, J=12.5 Hz, 2H), 1.65-1.62 (m, 1H), 1.43-1.36 (m, 2H);

Mass data (APCI, Pos.): m/z 409 (M+H)$^+$.

Example 415 tert-Butyl 4-carbamoyl-4-methylpiperidine-1-carboxylate

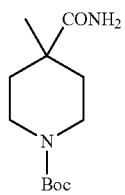

1-Ethyl-3-(3'-dimethylaminopropyl)carbodiimide hydrochloride (0.284 g) was added to a mixture of 1-hyroxybenzotriazole hydrate (0.227 g) and 1-(tert-butoxycarbonyl)-4-methylpiperidine-4-carboxylic acid (0.300 g) in dichloromethane (6 mL). Diisopropylethylamine (0.644 mL) was added and the reaction was stirred overnight. Ammonia (7 mol/L; 5.28 mL) in methanol was syringed in and the reaction was stirred for 2 hours at room temperature. The volatiles were removed in vacuo. The residue was suspended in ethyl acetate (500 mL) and stirred for 15 minutes with a saturated ammonium chloride solution (250 mL). The layers were separated and the organic layer was washed with a saturated aqueous sodium bicarbonate solution (300 mL). The aqueous phase was extracted once with ethyl acetate (200 mL). The combined organics were dried with magnesium sulfate, and then concentrated to afford the title compound as a tan solid (0.299 g) with the following physical data.

$^1$H NMR (DMSO-d$_6$): δ 3.49-3.59 (m, 2H), 2.98-3.06 (br, 2H), 1.86-1.92 (m, 2H), 1.38 (s, 9H), 1.18-1.25 (m, 4H), 1.06 (s, 3H);

Mass data (APCI, Pos.): m/z 143 (M+H−Boc)$^+$.

Example 416 tert-Butyl 4-(aminomethyl)-4-methylpiperidine-1-carboxylate

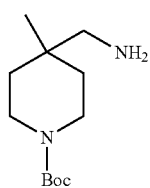 [SMILES: CC1(CN)CCN(C(=O)OC(C)(C)C)CC1]

Borane-tetrahydrofuran complex (10 mL) was added to a cold (0° C.) solution of the compound prepared in Example 415 (0.309 g) in tetrahydrofuran (6 mL) at room temperature. The mixture was refluxed overnight, cooled to 0° C., treated with methanol (13 mL), and evaporated in vacuo. The residue was diluted with methanol (5 mL) and refluxed for 1 hour. The solvent was evaporated in vacuo, taken in ethyl acetate, washed with saturated aqueous solution of sodium bicarbonate, brine, dried, evaporated in vacuo to an oil that was purified by column chromatography on silica gel (1-10% methanol in dichloromethane) to afford the title compound as a clear oil (0.119 g) with the following physical data.

$^1$H NMR (DMSO-$d_6$): δ 4.52 (t, J=5.2 Hz, 2H), 3.48-3.54 (m, 2H), 3.14 (d, J=4.7 Hz, 2H), 3.04-3.09 (m, 2H), 1.38 (s, 9H), 1.31-1.36 (m, 2H), 1.11-1.19 (m, 2H), 0.86 (s, 3H);

Mass data (APCI, Pos.): m/z 229 (M+H)$^+$.

Example 417 tert-Butyl 4-((4-amino-5-cyano-6-ethoxypicolinamido)methyl)-4-methylpiperidine-1-carboxylate

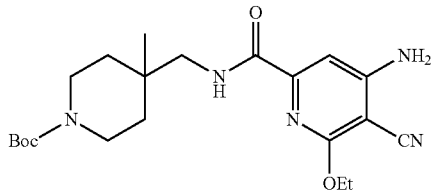 [SMILES: CCOc1nc(C(=O)NCC2(C)CCN(C(=O)OC(C)(C)C)CC2)cc(N)c1C#N]

A solution of 4-amino-5-cyano-6-ethoxypicolinic acid (0.100 g) in N,N-dimethylformamide (2.5 mL) was treated with 1-ethyl-3-(3'-dimethylaminopropyl)carbodiimide hydrochloride (0.102 g), 1-hyroxybenzotriazole hydrate (0.0813 g), followed by diisopropylethylamine (0.252 mL) at room temperature. After stirring for 15 minutes, the compound prepared in Example 416 (0.116 g) was added. Stirring was continued overnight, the mixture diluted with water, organic layer separated and washed with brine, dried, evaporated in vacuo to a beige paste that was triturated in ether and solids collected by filtration (0.584 g) with the following physical data.

$^1$H NMR (DMSO-$d_6$): δ 7.31 (br, 2H), 7.11 (s, 1H), 4.51 (t, J=5.5 Hz, 1H), 4.37 (dd, J=7.1, 14.1 Hz, 2H), 3.48-3.56 (m, 2H), 3.13-3.19 (m, 2H), 1.38 (s, 9H), 1.28-1.34 (m, 9H), 0.86 (s, 3H);

Mass data (APCI, Pos.): m/z 419 (M+

Example 418

4-Amino-5-cyano-6-ethoxy-N-((4-methylpiperidin-4-yl)methyl)picolinamide bis-trifluoroacetate

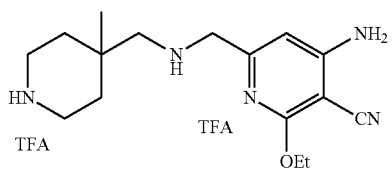 [SMILES: CCOc1nc(CNCC2(C)CCNCC2)cc(N)c1C#N]

According to the same procedure described in Example 11, using the compound prepared in Example 417 instead of the compound prepared in Example 10, the title compound having the following physical data was obtained.

$^1$H NMR (DMSO-$d_6$): δ 8.41 (br, 1H), 7.35 (br, 2H), 7.32 (s, 1H), 4.38 (q, J=7.0 Hz, 2H), 4.13 (br, 2H), 4.25 (br, 2H), 3.03-3.17 (m, 4H), 1.63-1.71 (m, 2H), 1.48-1.56 (m, 2H), 1.32 (t, J=7.0 Hz, 3H), 1.06 (s, 3H);

Mass data (APCI, Pos.): m/z 319 (M+H)$^+$.

Example 419

4-Amino-5-cyano-6-ethoxy-N-((4-methyl-1-((2-(pyridin-2-yl)thiazol-5-yl)methyl)piperidin-4-yl)methyl)picolinamide

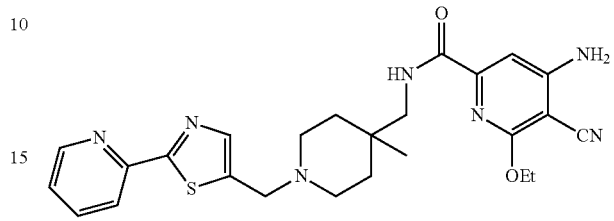

According to the same procedure described in Example 35, using the compound prepared in Example 418 instead of the compound prepared in Example 11 and the compound prepared in Example 139 instead of 4-phenylthiophene-2-carbaldehyde, the title compound having the following physical data was obtained.

$^1$H NMR (DMSO-$d_6$): δ 8.61-8.63 (m, 1H), 8.08-8.10 (m, 1H), 7.92-7.97 (m, 1H), 7.80 (s, 1H), 7.45-7.48 (m, 1H), 7.37-7.32 (br, 2H), 7.11 (s, 1H), 4.71 (br, 1H), 4.39 (q, J=7.0 Hz, 2H), 4.04 (s, 2H), 3.78 (s, 2H), 2.54-2.59 (m, 2H), 2.34-2.40 (m, 2H), 1.56-1.61 (m, 2H), 1.37-1.41 (m, 2H), 1.32 (t, J=7.0 Hz, 3H), 1.01 (s, 3H);

Mass data (APCI, Pos.): m/z 493 (M+H)$^+$.

Example 420

4-Amino-5-chloro-6-ethoxy-N-((1-((2-(pyridin-2-yl)thiazol-5-yl)methyl)piperidin-4-yl)methyl)picolinamide

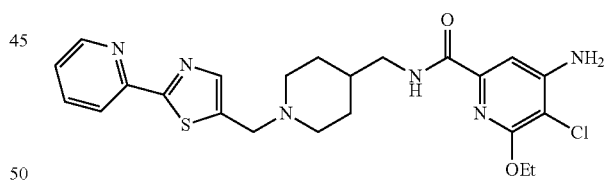

According to the same procedure described in Example 16 and starting with 4-amino-5-chloro-6-ethoxypicolinic acid (prepared according to the reported preparation in J. Med. Chem. 2006, 49, 4455) instead of 4-chloro-3-methoxybenzoic acid and the compound prepared in Example 214 instead of the compound prepared in Example 9, the title compound having the following physical data was obtained. $^1$H NMR (DMSO-$d_6$): δ 8.61 (d, J=4.7 Hz, 1H), 8.33 (t, J=6.4 Hz, 1H), 8.09 (d, J=7.9 Hz, 1H), 7.94 (td, J=1.7, 7.7 Hz, 2H), 7.78 (s, 1H), 7.47 (ddd, J=1.1, 4.8, 7.5 Hz, 1H), 7.09 (s, 1H), 6.50 (s, 1H), 4.45 (q, J=7.0 Hz, 2H), 3.73 (s, 2H), 3.16 (t, J=6.5 Hz, 2H), 2.85-2.88 (m, 2H), 1.97 (t, J=10.7 Hz, 2H), 1.60-1.63 (m, 2H), 1.50-1.55 (m, 1H), 1.31 (t, J=7.0 Hz, 3H), 1.15-1.24 (m, 2H);

Mass data (APCI, Pos.): m/z 487 (M+H)$^+$.

Example 421

6-ethoxy-2-methyl-3-nitropyridine

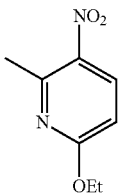

To a stirred solution of 6-chloro-2-methyl-3-nitropyridine (2.15 g) in ethanol (25 mL) was added sodium ethoxide (4.88 mL) solution at room temperature. The reaction mixture immediately turned dark purple and was refluxed for 2 hours. The reaction mixture was allowed to cool down to room temperature, concentrated in vacuo, and poured into ice. The precipitated solids were collected by filtration to provide the title compound (1.88 g) having the following physical data.

$^1$H NMR (DMSO-d$_6$): δ 8.36 (d, J=9.0 Hz, 1H), 6.85 (d, J=9.0 Hz, 1H), 4.42 (q, J=7.1 Hz, 2H), 2.71 (s, 3H), 1.34 (t, J=7.1 Hz, 3H).

Example 422

(E)-2-(6-ethoxy-3-nitropyridin-2-yl)-N,N-dimethyl-ethenamine

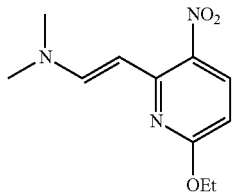 [SMILES: CCOc1ccc([N+](=O)[O-])c(/C=C/N(C)C)n1]

To a stirred solution of the compound prepared in Example 421 (1.88 g) in N,N-dimethylformamide (25 mL) was added N,N-dimethylformamide dimethylacetal (1.61 mL) at room temperature. The resulting purple solution was placed in an oil bath and heating was started to 140° C. The mixture was heated for 30 minutes, cooled to room temperature, the solvent evaporated in vacuo, coevaporated from methanol and dried further under high vacuum for 2 hours. This material was triturated in 1:1 hexane-ether and collected by filtration to afford the title compound as red solids (2.2 g) with the following physical data.

$^1$H NMR (DMSO-d$_6$): δ 8.19 (d, J=9.1 Hz, 1H), 8.14 (d, J=12.3 Hz, 1H), 6.31 (d, J=12.3 Hz, 1H), 6.24 (d, J=9.1 Hz, 1H), 4.41 (q, J=7.0 Hz, 2H), 3.04 (br, 6H), 1.33 (t, J=7.1 Hz, 3H).

Example 423

6-ethoxy-3-nitropicolinaldehyde

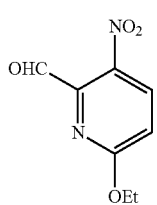 [SMILES: CCOc1ccc([N+](=O)[O-])c(C=O)n1]

To a stirred solution of the compound prepared in Example 422 (2.2 g) in tetrahydrofuran (40 mL) was added sodium periodate (5.95 g) in water (40 mL). The mixture was stirred at room temperature overnight. The suspended inorganic solids were filtered out, washed with tetrahydrofuran and the filtrate evaporated in vacuo. The residue was taken in small amount of water and extracted with chloroform, dried, evaporated in vacuo to a brown oil and further dried under high vacuum to afford the title compound (1.6 g) with the following physical data.

$^1$H NMR (CDCl$_3$): δ 10.32 (s, 1H), 8.27 (d, J=9.0 Hz, 1H), 6.96 (d, J=9.0 Hz, 1H), 4.55 (q, J=7.1 Hz, 2H), 1.44 (t, J=7.1 Hz, 3H);

Mass data (APCI, Pos.): m/z 196 (M+H)$^+$.

Example 424

6-ethoxy-3-nitropicolinic Acid

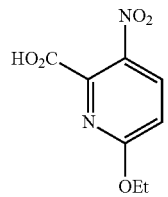 [SMILES: CCOc1ccc([N+](=O)[O-])c(C(=O)O)n1]

To a stirred solution of the compound prepared in Example 423 (1.66 g) in dioxane (40 mL) at room temperature was added 2-methyl-2-butene (2.0 mol/L; 25.811 mL) in tetrahydrofuran. To the resulting stirred solution was added a solution of sodium chlorite (4.2095 g) and sodium phosphate monobasic monohydrate (4.2039 g) in water (28 mL). The resulting two-phase mixture was vigorously stirred at room temperature. The color of the reaction mixture lightened considerably over the first 30 minutes. After 18 hours, the reaction mixture was diluted with ethyl acetate (50 mL) and transferred to a separatory funnel. The aqueous layer was acidified with concentrated hydrochloric acid to about pH 1.5, and the resulting mixture was extracted with ethyl acetate. The organic layer was dried, evaporated and dried further under high vacuo to provide the title compound (2.2 g) as a pale orange oil with the following physical data.

$^1$H NMR (DMSO-d$_6$): δ 12.95 (br, 1H), 8.47 (d, J=9.1 Hz, 1H), 7.10 (d, J=9.1 Hz, 1H), 4.43 (q, J=7.0 Hz, 2H), 1.38 (t, J=6.9 Hz, 3H);

Mass data (APCI, Pos.): m/z 211 (M−H)$^−$.

Example 425 methyl 6-ethoxy-3-nitropicolinate

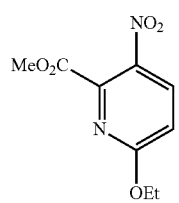 [SMILES: CCOc1ccc([N+](=O)[O-])c(C(=O)OC)n1]

A mixture of the compound prepared in Example 424 (1.8 g) in N,N-dimethylformamide (25 mL) was treated with potassium carbonate (1.76 g), followed by iodomethane (2.65 mL). The mixture was stirred at room temperature overnight. The solvent was concentrated in vacuo and the residue diluted with water, crude precipitated solids were collected by filtration, 2.14 g. These solids were taken in dichloromethane and purified by column chromatography on silica gel (5-25% ethyl acetate in hexanes) to provide the title compound (1.16 g) having the following physical data.

$^1$H NMR (DMSO-$d_6$): δ 8.52 (d, J=9.2 Hz, 1H), 7.17 (d, J=9.2 Hz, 1H), 4.42 (q, J=7.0 Hz, 2H), 3.98 (s, 3H), 1.35 (t, J=7.0 Hz, 3H);

Mass data (APCI, Pos.): m/z 527 (M+H)$^+$.

Example 426 methyl 3-amino-6-ethoxypicolinate

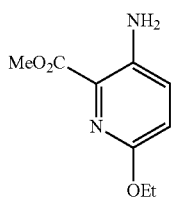 [SMILES: CCOc1ccc(N)c(C(=O)OC)n1]

To a stirred solution of the compound prepared in Example 425 (0.200 g,) in tetrahydrofuran (4.5 mL) was added zinc dust (0.5782 g), followed by saturated aqueous ammonium chloride (4.5 mL). The mixture was stirred at room temperature for 2 hours. The mixture was diluted with water-ethyl acetate and then filtered through paper. The phases were separated, organic layer dried, concentrated in vacuo and the bright yellow oil purified by column chromatography on silica gel (1-2% methanol in dichloromethane) to provide the title compound (0.132 g) as a yellow oil having the following physical data.

$^1$H NMR (DMSO-$d_6$): δ 7.26 (d, J=8.9 Hz, 1H), 6.85 (d, J=8.9 Hz, 1H), 6.39 (br, 2H), 4.18 (q, J=7.0 Hz, 2H), 3.78 (s, 3H), 1.27 (t, J=7.1 Hz, 3H).

Example 427 methyl 3-amino-4-chloro-6-ethoxypicolinate

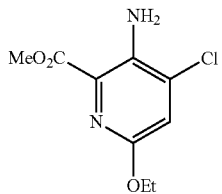 [SMILES: CCOc1cc(Cl)c(N)c(C(=O)OC)n1]

To a stirred solution of the compound prepared in Example 426 (0.048 g) in N,N-dimethylformamide (1.2 mL) was added N-chlorosuccinimide (0.0343 g). The resulting mixture was heated at 80° C. for 18 hours. The solvent was evaporated and the residue dissolved in dichloromethane and purified by column chromatography on silica gel (20% ethyl acetate in hexanes) to obtain the title compound (0.003 g) having the following physical data.

Mass data (APCI, Pos.): m/z 231 (M+H)$^+$.

Example 428

3-amino-4-chloro-6-ethoxypicolinic Acid

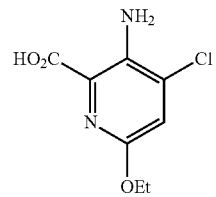 [SMILES: CCOc1cc(Cl)c(N)c(C(=O)O)n1]

A solution of the compound prepared in Example 427 (0.025 g) in methanol (1 mL) was treated with sodium hydroxide (0.11 mL) and refluxed for 18 hours. This material was evaporated in vacuo and residue dissolved in water and acidified with 1N hydrochloric acid. The product was extracted with ethyl acetate, dried, and evaporated in vacuo to provide the title compound (0.003 g) having the following physical data.

Mass data (APCI, Pos.): m/z 215 (M−H)$^-$.

Example 429

3-amino-4-chloro-6-ethoxy-N-((1-((2-(pyridin-2-yl)thiazol-5-yl)methyl)piperidin-4-yl)methyl)picolinamide

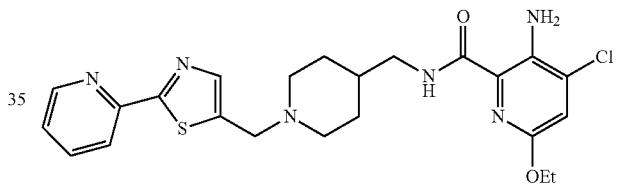

According to the same procedure described in Example 16, using the compound prepared in Example 428 instead of 4-chloro-3-methoxybenzoic acid and the compound prepared in Example 214 instead of the compound prepared in Example 9, the title compound having the following physical data was obtained.

$^1$H NMR (CDCl$_3$): δ 8.60 (d, J=4.7 Hz, 1H), 8.14 (d, J=7.9 Hz, 1H), 7.78 (br, 1H), 7.67 (s, 1H), 7.31-7.27 (m, 2H), 6.89 (s, 1H), 6.09 (br, 2H), 4.23 (q, J=7.0 Hz, 2H), 3.78 (s, 2H), 3.30 (d, J=6.6 Hz, 2H), 2.97 (d, J=11.5 Hz, 2H), 2.07 (t, J=10.6 Hz, 2H), 1.74 (d, J=12.2 Hz, 2H), 1.58-1.61 (m, 1H), 1.38 (t, J=7.1 Hz, 3H), 1.26 (br, 2H);

Mass data (APCI, Pos.): m/z 487 (M+H)$^+$.

Example 430 methyl 3-amino-4,5-dichloro-6-ethoxypicolinate

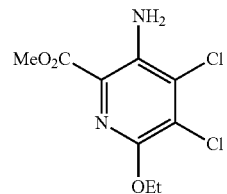 [SMILES: CCOc1nc(C(=O)OC)c(N)c(Cl)c1Cl]

To a stirred solution of the compound prepared in Example 426 (0.050 g) in a mixture of tetrahydrofuran (3 mL) and carbon tetrachloride (3 mL) was added n-chlorosuccinimide (0.068 g). The resulting mixture was heated at 60° C. for 4 hours. The solvent was evaporated and the insoluble solids filtered out and washed with ether. The filtrate was taken in dichloromethane and purified by column chromatography on silica gel (20% ether in hexanes) to provide the title compound (0.008 g) which was used without further characterization.

Example 431

3-amino-4,5-dichloro-6-ethoxypicolinic Acid

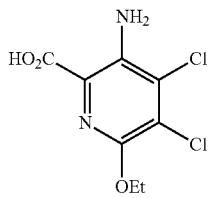 [SMILES: CCOc1nc(C(=O)O)c(N)c(Cl)c1Cl]

A solution of the compound prepared in Example 430 (0.025 g) in methanol (1 mL) was treated with sodium hydroxide (0.094 mL) and refluxed for 3 hours. This material was evaporated in vacuo and residue dissolved in water and acidified with 1 mol/L hydrochloric acid. The product was extracted with ethyl acetate, dried, and evaporated in vacuo to provide the title compound (0.011 g) with the following physical data.

Mass data (APCI, Pos.): m/z 249 (M–H)⁻.

Example 432

3-amino-4,5-dichloro-6-ethoxy-N-((1-((2-(pyridin-2-yl)thiazol-5-yl)methyl)piperidin-4-yl)methyl)picolinamide

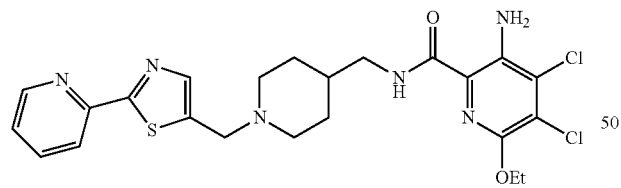

According to the same procedure described in Example 16, using the compound prepared in Example 431 instead of 4-chloro-3-methoxybenzoic acid and the compound prepared in Example 214 instead of the compound prepared in Example 9, the title compound having the following physical data was obtained.

1H NMR (CD$_3$OD): δ 8.57 (d, J=4.8 Hz, 1H), 8.26-8.35 (br, 1H), 8.13 (d, J=7.9 Hz, 1H), 7.791 (t, J=7.3 Hz, 1H), 7.79 (s, 1H), 7.43 (dd, J=5.1, 7.4 Hz, 1H), 4.38 (q, J=7.0 Hz, 2H), 3.94 (s, 2H), 3.33-3.29 (m, 2H), 3.08 (d, J=11.6 Hz, 2H), 2.24 (t, J=11.5 Hz, 2H), 1.80 (d, J=13.1 Hz, 2H), 1.67-1.73 (m, 1H), 1.35-1.39 (m, 5H);

Mass data (APCI, Pos.): m/z 523 (M+H)⁺.

Example 433

4-methoxy-2-phenoxynicotinonitrile

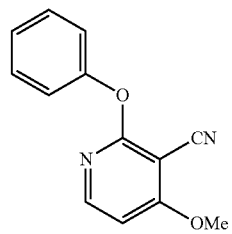 [SMILES: COc1ccnc(Oc2ccccc2)c1C#N]

A solution of 2-chloro-4-methoxynicotinonitrile (1.02 g) in dimethylacetamide (30 mL) was treated with cesium carbonate (2.96 g) followed by phenol (0.683 g) at room temperature. The mixture was heated to 75° C. overnight. The mixture was cooled to room temperature, diluted with water (100 mL) and the precipitated solids collected by filtration, to provide the title compound (0.964 g) with the following physical data.

¹H NMR (DMSO-d$_6$): δ 8.23 (d, J=6.1 Hz, 1H), 7.47-7.43 (m, 2H), 7.27 (t, J=7.4 Hz, 2H), 7.21 (d, J=7.6 Hz, 1H), 7.09 (d, J=6.1 Hz, 1H), 4.01 (s, 3H);

Mass data (APCI, Pos.): m/z 227 (M+H)⁺.

Example 434

4-phenoxy-1H-pyrazolo[4,3-c]pyridin-3-amine

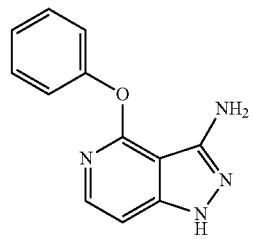 [SMILES: Nc1n[nH]c2ccnc(Oc3ccccc3)c12]

A suspension of the compound prepared in Example 433 (0.964 g) in ethanol (21 mL) was treated with hydrazine monohydrate (2.073 mL) and refluxed overnight. A solution was obtained upon heating. The mixture was cooled to room temperature and diluted with water. The precipitated solids were collected by filtration. This material was taken in 10% methanol in dichloromethane, insoluble solids filtered out and the filtrate purified by column chromatography on silica gel (1-3% methanol in dichloromethane) to provide the title compound (0.415 g) as a beige solid having the following physical data.

¹H NMR (DMSO-d$_6$): δ 12.0 (br, 1H), 8.59 (br, 2H), 7.73 (d, J=6.2 Hz, 1H), 7.43-7.39 (m, 2H), 7.23 (dd, J=6.5, 13.8 Hz, 2H), 7.13 (d, J=7.6 Hz, 1H), 6.81-6.69 (m, 1H);

Mass data (APCI, Pos.): m/z 227 (M+H)⁺.

Example 435 tert-butyl 4-((4-phenoxy-1H-pyrazolo[4,3-c]pyridin-3-ylamino)methyl)piperidine-1-carboxylate

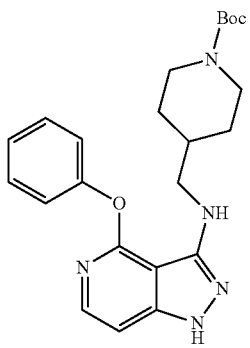 [SMILES: CC(C)(C)OC(=O)N1CCC(CNc2n[nH]c3ccnc(Oc4ccccc4)c23)CC1]

To a stirred solution of the compound prepared in Example 434 (0.217 g,) in toluene (12 mL) was added tert-butyl 4-formylpiperidine-1-carboxylate (0.205 g). The mixture was evaporated in vacuo to remove water from imine formed. Sodium triacetoxyborohydride (0.244 g) was added, followed by acetic acid (0.4 mL). After stirring at room temperature for 1 hour, the reaction mixture was quenched with methanol slowly, to decompose excess borohydride, and then concentrated in vacuo. Ethyl acetate, was added to the residue and then washed with aqueous saturated sodium bicarbonate, dried, evaporated in vacuo to provide the title compound (0.262 g) with the following physical data.

$^1$H NMR (DMSO-$d_6$): δ 8.59 (br, 1H), 7.44-7.40 (m, 2H), 7.32 (d, J=6.4 Hz, 1H), 7.25-7.22 (m, 2H), 6.70 (d, J=6.4 Hz, 1H), 6.44 (br, 1H), 4.02 (d, J=7.3 Hz, 2H), 3.95-3.91 (m, 2H), 2.71-2.64 (m, 2H), 2.13-2.07 (m, 1H), 1.52-1.49 (m, 2H), 1.39 (s, 12H), 1.19-1.11 (m, 2H);

Mass data (APCI, Pos.): m/z 424 (M+H)$^+$.

Example 436

4-phenoxy-N-(piperidin-4-ylmethyl)-1H-pyrazolo[4,3-c]pyridin-3-amine bis(2,2,2-trifluoroacetate)

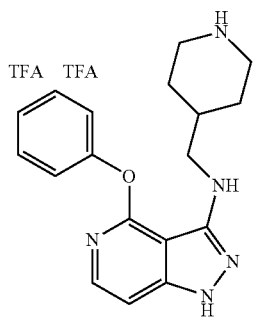 [SMILES: c1ccc(Oc2nccc3[nH]nc(NCC4CCNCC4)c23)cc1]

A solution of the compound prepared in Example 435 (0.262 g) in dichloromethane (3 mL) was treated with trifluoroacetic acid (0.6 mL) at room temperature. After stirring at room temperature for 4 hours, the mixture was shaken in dichloromethane and washed with aqueous saturated sodium bicarbonate, dried, and evaporated in vacuo to provide the title compound (0.065 g) with the following physical data.

$^1$H NMR (DMSO-$d_6$): δ 8.55 (br, 1H), 8.26 (br, 1H), 7.50-7.46 (m, 2H), 7.36 (d, J=6.5 Hz, 1H), 7.31-7.28 (m, 3H), 6.81 (d, J=6.5 Hz, 1H), 4.10 (d, J=6.9 Hz, 2H), 3.29-3.26 (m, 2H), 2.90-2.82 (m, 2H), 2.23-2.19 (m, 1H), 1.75-1.72 (m, 2H), 1.47-1.39 (m, 2H);

Mass data (APCI, Pos.): m/z 324 (M+H)$^+$.

Example 437

4-phenoxy-N-((1-((2-(pyridin-2-yl)thiazol-5-yl)methyl)piperidin-4-yl)methyl)-1H-pyrazolo[4,3-c]pyridin-3-amine

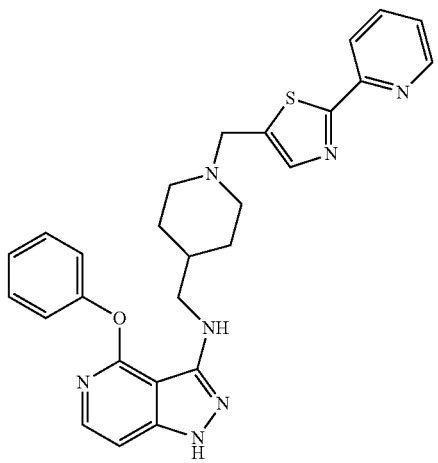 [SMILES: c1ccc(Oc2nccc3[nH]nc(NCC4CCN(Cc5cnc(-c6ccccn6)s5)CC4)c23)cc1]

A solution of the compound prepared in Example 436 (0.053 g) and the compound prepared in Example 214 (0.039 g) in acetonitrile (1 mL) was stirred at room temperature for 30 minutes. Tetramethylammoniumtriacetoxy borohydride (0.094 g) was added and stirring at room temperature continued for 1 hour. The reaction mixture was quenched with aqueous saturated sodium bicarbonate. After stirring at room temperature for 20 minutes, hopeful product was extracted with ethyl acetate, washed with aqueous saturated sodium bicarbonate, dried, evaporated in vacuo to an oil that was purified by column chromatography on silica gel (1-5% methanol in dichloromethane) to provide the title compound (0.008 g) with the following physical data.

$^1$H NMR (DMSO-$d_6$): δ 11.98 (br, 1H), 8.61 (d, J=4.3 Hz, 1H), 8.09 (d, J=7.9 Hz, 1H), 7.97-7.92 (m, 1H), 7.78 (s, 1H), 7.49-7.40 (m, 3H), 7.32 (d, J=6.4 Hz, 1H), 7.25-7.20 (m, 3H), 6.70 (d, J=6.4 Hz, 1H), 6.42 (br, 1H), 4.02 (d, J=7.2 Hz, 2H), 3.74 (s, 2H), 3.17 (d, =5.2 Hz, 2H), 2.89-2.87 (m, 2H), 1.99-1.93 (m, 2H), 1.54-1.51 (m, 1H), 1.38-1.28 (m, 2H);

Mass data (APCI, Pos.): m/z 498 (M+H)$^+$.

Example 438 ethyl 2-(2,6-difluorophenyl)-4-methylthiazole-5-carboxylate

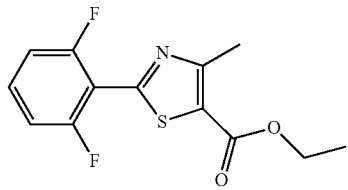 [SMILES: CCOC(=O)c1sc(-c2c(F)cccc2F)nc1C]

To a solution of the compound prepared in Example 344 (50 g) in ethanol (250 mL) was added ethyl 2-chloroacetoacetate (42 mL) at room temperature. The mixture was heated to reflux for 12 hours, cooled and concentrated. The residue was stirred with hexane (250 mL) for 30 minutes, filtered and then washed with hexane (50 mL). The solid was dried to obtain the title compound (48.6 g) having the following physical data.

$^1$H NMR (CDCl$_3$): δ 7.42 (m, 1H), 7.05 (m, 2H), 4.38 (q, J=7.1 Hz, 2H), 2.82 (s, 3H), 1.40 (t, J=7.1 Hz, 3H);

Example 439 ethyl 2-(2,6-difluorophenyl)-4-((dimethylamino)methyl)thiazole-5-carboxylate

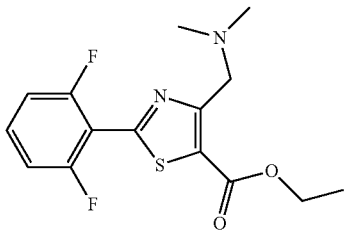 [SMILES: CCOC(=O)c1sc(-c2c(F)cccc2F)nc1CN(C)C]

A solution of the compound prepared in Example 438 (5.0 g), N-bromosuccinimide (3.48 g) and benzoyl peroxide (0.428 g) in carbon tetrachloride (50 mL) was stirred at reflux overnight. The mixture was cooled, and saturated aqueous sodium bicarbonate was added. The mixture was extracted with ethyl acetate. The combined organics were washed with water, dried over sodium sulfate and concentrated. The residue was purified by column chromatography on silica gel (petroleum ether:ethyl acetate=10:1) to obtain the brominated compound (5.75 g).

To a solution of this compound (5.75 g) in tetrahydrofuran (50 mL) was added a 2M solution of dimethylamine in tetrahydrofuran (45 mL). The mixture was stirred at room temperature for 3 hours. The mixture was then diluted with saturated sodium bicarbonate and extracted with ethyl acetate. The combined organics were dried over sodium sulfate and concentrated. The residue was purified by column chromatography on silica gel (petroleum ether:ethyl acetate=5:1) to obtain the title compound (2.5 g) having the following physical data.

$^1$H NMR (d$_6$-DMSO): δ 7.67 (m, 1H), 7.38-7.33 (m, 2H), 4.33 (q, J=7.0 Hz, 2H), 3.96 (s, 2H), 2.24 (s, 6H), 1.32 (t, J=7.0 Hz, 3H);

Mass data (APCI, Pos.): m/z 327 (M+H)$^+$.

Example 440

2-(2,6-difluorophenyl)-4-((dimethylamino)methyl)thiazole-5-carbaldehyde

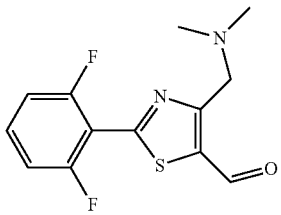 [SMILES: CN(C)Cc1nc(-c2c(F)cccc2F)sc1C=O]

To a solution of the compound prepared in Example 439 (12.5 g) in dichloromethane (300 mL) at −95° C. was added a 1 mol/L solution of diisobutylaluminium hydride (48.5 mL) in hexanes dropwise slowly. The mixture was stirred for 3 hours and then quenched with methanol (50 mL). A solution of Rochelle's salt was then added dropwise. The mixture was warmed to room temperature and extracted with ethyl acetate. The combined extracts were washed with water and then concentrated. The residue was purified by column chromatography on silica gel (petroleum ether:ethyl acetate=5:1) to obtain the title compound (4.3 g) having the following physical data.

$^1$H NMR (d$_6$-DMSO): δ 10.37 (s, 1H), 7.69 (m, 1H), 7.40-7.33 (m, 2H), 3.98 (s, 2H), 2.26 (s, 6H);

Mass data (APCI, Pos.): m/z 283 (M+H)$^+$.

Example 441

4-amino-5-cyano-N-((1-((2-(2,6-difluorophenyl)-4-((dimethylamino)methyl)thiazol-5-yl)methyl)piperidin-4-yl)methyl)-6-ethoxypicolinamide

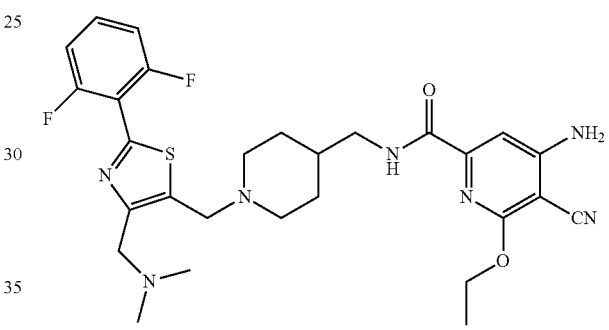

According to the same procedure described in Example 101, using the corresponding aldehyde instead of 2-phenylthiazole-5-carbaldehyde, the title compound having the following physical data was obtained.

$^1$H NMR (DMSO-d$_6$): δ 8.46 (t, J=6.3 Hz, 1H), 7.61-7.54 (m, 1H), 7.29 (s, 2H), 7.28 (t, J=8.6 Hz, 2H), 7.04 (s, 1H), 4.47 (q, J=7.0 Hz, 2H), 3.76 (s, 2H), 3.54 (s, 2H), 3.17 (t, J=6.3 Hz, 2H), 2.92-2.86 (m, 2H), 2.16 (s, 6H), 2.05-1.98 (m, 2H), 1.64-1.59 (m, 2H), 1.58-1.52 (m, 1H), 1.31 (t, J=7.0, 3H), 1.20-1.15 (m, 2H);

Mass data (APCI, Pos.): m/z 570.1 (M+H)$^+$.

Example 442

2-hydroxy-6-methyl-5-nitronicotinonitrile

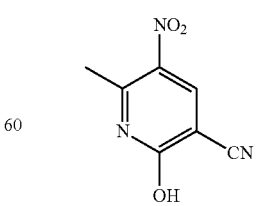

A suspension of 2-hydroxy-6-methylnicotinonitrile (16.5 g) in acetic anhydride (60 mL) was stirred and cooled in an ice-salt bath. Separately, acetic anhydride (16 mL) containing a crystal of urea (21 mg) was cooled in an ice-salt bath to 2° C. To the latter mixture was added fuming nitric acid (8.6 mL). The mixture evolved nitrogen dioxide gas and became hot. Cooling in the bath was continued until the temperature reached 8° C. This solution was then added to the nitrile suspension, which was at −2° C. The temperature rose to 0° C., and the cooling bath was removed. The temperature rose slowly as the mixture was stirred, and the rate of temperature rise increased as the temperature rose. When the temperature reached 35° C., the flask was cooled in the bath until the temperature fell to 25° C. The bath was again removed. The temperature rose more slowly this time, and reached a maximum of 34° C. The reaction was allowed to cool on its own, and did not reach ambient temperature for about 3 hours. The resulting mixture was allowed to stir at ambient temperature overnight. The mixture was poured into a beaker containing crushed ice (300 g). The mixture was stirred until the ice melted, and the resulting precipitate was collected by filtration, washed with ice water, and air-dried to give about 13 g of light yellow solid. This material was recrystallized from boiling glacial acetic acid (130 mL). The resulting mixture was allowed to cool to ambient temperature and stirred overnight. The precipitate was collected by filtration, washed with a small amount of glacial acetic acid, and dried under vacuum to provide the title compound (8.2 g) with the following physical data.

$^1$H NMR (DMSO-$d_6$): δ 13.39 (s, 1H), 8.89 (s, 1H), 3.69 (s, 3H);

Mass data (ESI, Neg.): m/z 178 (M−H)$^-$.

Example 443

2-chloro-6-methyl-5-nitronicotinonitrile

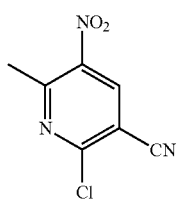

A suspension of the compound prepared in Example 442 (5.00 g) and phosphorus pentachloride (6.97 g) in phosphorus oxychloride (25 mL) was stirred and heated in an oil bath set to 110° C. for 30 minutes. The resulting solution was cooled to ambient temperature and concentrated. The residual liquid was cooled in an ice bath, whereupon a solid formed. This solid was carefully treated with 50% aqueous ethanol (10 mL), and then the mixture was stirred and heated in the 110° C. oil bath for 5 minutes. This redissolved the solid, and then the flask was again placed in the ice bath. The solid reappeared on cooling, and it was collected by filtration, washed with water, and air-dried. The solid was then recrystallized by stirring it with methanol (20 mL), and heating to boiling until all solid dissolved. On cooling to ambient temperature crystallization began, and the mixture was stored in the refrigerator overnight. The crystals were collected by filtration, washed with cold methanol, and dried under vacuum to provide the title compound (2.09 g) with the following physical data.

1H NMR (DMSO-$d_6$): δ 9.21 (s, 1H), 2.81 (s, 3H);
Mass data (ESI, Neg.): m/z 197 (M−H)$^-$.

Example 444

2-ethoxy-6-methyl-5-nitronicotinonitrile

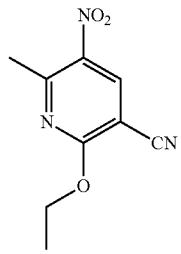

To a stirred solution of the compound prepared in Example 443 (2.04 g) in ethanol (50 mL) at ambient temperature was added a 21% solution of sodium ethoxide in denatured ethanol (4.24 mL). The reaction mixture immediately turned dark purple and was stirred at ambient temperature for 2.5 hours, then diluted with water (250 mL), and the resulting mixture was stirred at ambient temperature for 3 days. The mixture was poured into a separatory funnel and diluted with water (250 mL) and ethyl acetate (500 mL). The organic layer was dried over sodium sulfate and concentrated to give about 9 g of a dark semisolid. This material was partitioned between dichloromethane (200 mL) and water (100 mL). The organic layer was dried over sodium sulfate and concentrated. The residue was purified by chromatography on silica gel, eluting with 4/1 hexanes/ethyl acetate, to provide the title compound (0.87 g) with the following physical data.

$^1$H NMR (CDCl$_3$): δ 8.60 (s, 1H), 4.62 (q, J=7.2 Hz, 2H), 2.85 (s, 3H), 1.50 (t, J=7.2 Hz, 3H);

Mass data (ESI, Neg.): m/z 206 (M−H)$^-$.

Example 445

6-(2-(dimethylamino)vinyl)-2-ethoxy-5-nitronicotinonitrile

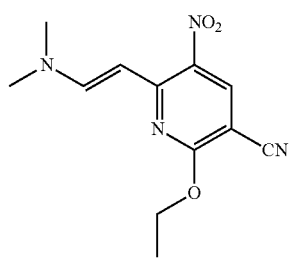 [SMILES: CCOc1nc(/C=C/N(C)C)c([N+](=O)[O-])cc1C#N]

To a stirred solution of the compound prepared in Example 444 (0.86 g) in N,N-dimethylformamide (10 mL) at ambient temperature was added N,N-dimethylformamide dimethyl acetal (94%, 0.65 mL). The resulting solution was stirred and heated to reflux for 30 minutes. After cooling to ambient temperature, the solution was concentrated to provide the title compound (1.07 g) with the following physical data.

1H NMR (CDCl$_3$): δ 8.52 (s, 1H), 8.08 (d, J=12.4 Hz, 1H), 6.44 (d, J=12.4 Hz, 1H), 4.50 (q, J=7.2 Hz, 2H), 3.23 (broad s, 3H), 3.03 (broad s, 3H), 1.46 (t, J=7.2 Hz, 3H);

Mass data (ESI, Pos.): m/z 263 (M+H)$^+$.

Example 446

2-ethoxy-6-formyl-5-nitronicotinonitrile

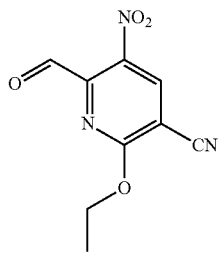 [SMILES: CCOc1nc(C=O)c([N+](=O)[O-])cc1C#N]

To a stirred solution of the compound prepared in Example 445 (1.07 g) in tetrahydrofuran (20 mL) at ambient temperature was added water (20 mL), and to the resulting mixture was added sodium periodate (2.62 g). The resulting mixture was stirred at ambient temperature for 18 hours. There was a significant amount of precipitate present in the reaction mixture, and it was collected by filtration and washed with 50% aqueous tetrahydrofuran. The combined filtrate and wash were concentrated to remove most of the tetrahydrofuran, and the residue was extracted with chloroform. The organic layers were combined and dried over sodium sulfate and concentrated. The residue was purified by chromatography on silica gel, eluting with 1/1 hexanes/ethyl acetate, to provide the title compound (0.61 g) with the following physical data.

1H NMR (CDCl$_3$): δ 10.35 (s, 1H), 8.68 (d, J=23.2 Hz, 1H), 4.72 (q, J=7.2 Hz, 2H), 1.57 (t, J=7.2 Hz, 3H);

Mass data (ESI, Neg.): m/z 221 my.

Example 447

5-cyano-6-ethoxy-3-nitropicolinic Acid

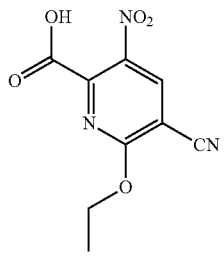 [SMILES: CCOc1nc(C(=O)O)c([N+](=O)[O-])cc1C#N]

To a stirred solution of the compound prepared in Example 446 (0.61 g) in dioxane (10 mL) at ambient temperature was added of a 2 mol/L solution of 2-methyl-2-butene in tetrahydrofuran (8.4 mL). To the resulting stirred solution was added a solution of sodium chlorite (80%, 1.37 g) and sodium dihydrogen phosphate monohydrate (1.37 g) in water (8 mL). The resulting mixture was vigorously stirred at ambient temperature for 18 hours. The reaction mixture was diluted with ethyl acetate (15 mL), and after stirring for 10 minutes, the mixture was transferred to a separatory funnel. The aqueous layer was acidified with 6M hydrochloric acid to pH 1.5, and then extracted with chloroform (20 mL). The organic layer was dried over sodium sulfate and concentrated to provide the title compound (0.16 g) with the following physical data.

1H NMR (DMSO-d$_6$): δ 9.19 (s, 1H), 4.58 (q, J=7.2 Hz, 2H), 1.40 (t, J=7.2 Hz, 3H);

Mass data (ESI, Neg.): m/z 237 my.

Example 448

5-cyano-6-ethoxy-3-nitro-N-((1-((2-(pyridin-2-yl)thiazol-5-yl)methyl)piperidin-4-yl)methyl)picolinamide

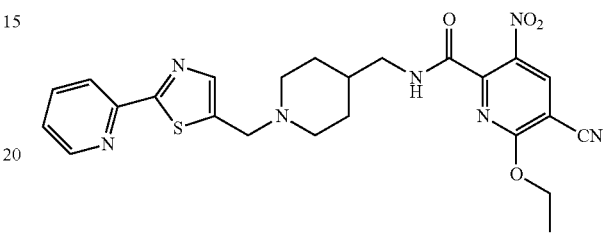

To a stirred solution of the compound prepared in Example 447 (94 mg) and 1-hydroxybenzotriazole hydrate (67 mg) in N,N-dimethylformamide (2.5 mL) at ambient temperature was added 1-ethyl-(3-dimethylaminopropyl)carbodiimide hydrochloride (84 mg). The resulting solution was stirred at ambient temperature for 40 minutes, and then the compound prepared in Example 214 (189 mg) was added, followed immediately by N,N-diisopropylethylamine (0.35 mL). The resulting mixture was stirred at ambient temperature for 1 hr 50 minutes, and then diluted with water (25 mL). After stirring for 30 minutes, the resulting precipitate was collected by filtration, washed with a small amount of water, and dried under vacuum to provide the title compound (95 mg) with the following physical data.

1H NMR (DMSO-d$_6$): δ 9.15 (s, 1H), 8.78 (t, J=5.2 Hz, 1H), 8.61 (d, J=4.4 Hz, 1H), 8.12 (d, J=8.0 Hz, 1H), 7.95 (t, J=8.0 Hz, 1H), 7.79 (s, 1H), 7.49 (t, J=5.2 Hz, 1H), 4.60 (q, J=7.2 Hz, 2H), 3.75 (s, 2H), 3.17 (t, J=6.0 Hz, 2H), 2.89 (t, J=8.0 Hz, 2H), 2.00 (t, J=10.8 Hz, 2H), 1.66 (d, J=11.6 Hz, 2H), 1.57 (broad s, 1H), 1.41 (t, J=7.2 Hz, 3H), 1.23 (m, 2H);

Mass data (ESI, Pos.): m/z 508 (M+H)$^+$.

Example 449

3-amino-5-cyano-6-ethoxy-N-((1-((2-(pyridin-2-yl)thiazol-5-yl)methyl)piperidin-4-yl)methyl)picolinamide

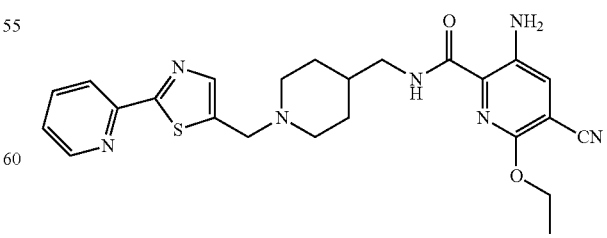

To a stirred solution of the compound prepared in Example 448 (48 mg) in tetrahydrofuran (1 mL) at ambient temperature was added zinc dust (120 mg), and to the resulting stirred mixture added saturated ammonium chloride (0.5 mL). The resulting mixture was stirred at ambient temperature for 17 hours. The reaction mixture was diluted with tetrahydrofuran (5 mL) and filtered through a glass microfibre filter. The flask and filter were rinsed with additional tetrahydrofuran. The combined filtrate and rinses were concentrated to remove most of the tetrahydrofuran, and the residue was partitioned between ethyl acetate and water, with addition of 10% sodium carbonate. The organic layer was dried over sodium sulfate and concentrated. The residue was purified by chromatography on silica gel, eluting with 99/1 chloroform/methanol to provide the title compound (20 mg) with the following physical data. 1H NMR (CDCl$_3$): δ 8.60 (d, J=4.4 Hz, 1H), 8.15 (d, J=8.0 Hz, 1H), 7.79 (m, 2H), 7.68 (s, 1H), 7.32 (m, 2H), 5.77 (broad s, 2H), 4.35 (q, J=7.2 Hz, 2H), 3.80 (broad s, 2H), 3.33 (t, J=6.8 Hz, 2H), 2.99 (d, J=10.8 Hz, 2H), 2.11 (t, J=10.8 Hz, 2H), 1.76 (d, J=12.0 Hz, 2H), 1.60 (broad s, 1H), 1.41 (m, 5H);

Mass data (ESI, Pos.): m/z 478 (M+H)$^+$.

Example 450

5-Cyano-6-ethoxy-3-nitro-N-((1-((3-phenylisoxazol-5-yl)methyl)piperidin-4-yl)methyl)picolinamide

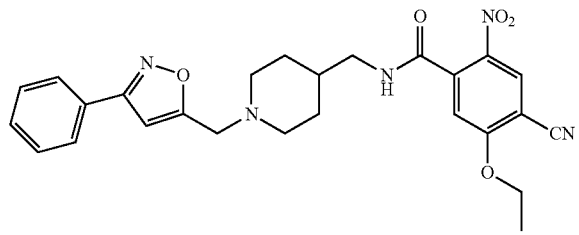 [SMILES: CCOc1cc(C(=O)NCC2CCN(Cc3cc(-c4ccccc4)no3)CC2)c([N+](=O)[O-])cc1C#N]

According to the same procedure described in Example 448, using the compound prepared in Example 9 instead of the compound prepared in Example 214, the title compound having the following physical data was obtained.

1H NMR (DMSO-d$_6$): δ 9.13 (s, 1H), 8.81 (m, 1H), 7.90 (m, 2H), 7.53 (m, 2H), 6.95 (s, 1H), 4.61 (q, J=7.2 Hz, 2H), 3.73 (broad s, 2H), 3.17 (m, 2H), 2.92 (m, 2H), 2.03 (t, J=10.8 Hz, 2H), 1.71 (d, J=12.0 Hz, 2H), 1.55 (broad s, 1H), 1.39 (t, J=7.2 Hz, 3H), 1.22 (q, J=10.8 Hz, 2H), 0.95 (d, J=6.4 Hz, 1H);

Mass data (ESI, Pos.): m/z 491 (M+H)$^+$.

Example 451

3-amino-5-cyano-6-ethoxy-N-((1-((3-phenylisoxazol-5-yl)methyl)piperidin-4-yl)methyl)picolinamide Hydrochloride

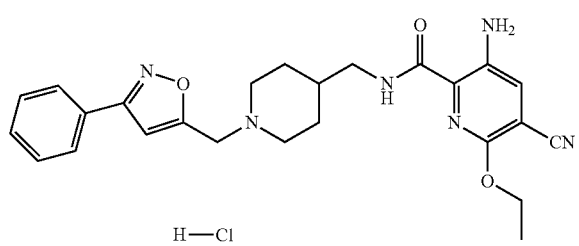 [SMILES: CCOc1nc(C(=O)NCC2CCN(Cc3cc(-c4ccccc4)no3)CC2)c(N)cc1C#N ; Cl]

To a stirred solution of the compound prepared in Example 450 (120 mg) in tetrahydrofuran (2 mL) at ambient temperature was added zinc dust (160 mg), followed by saturated ammonium chloride (1 mL). The resulting mixture was stirred at ambient temperature for 17 hours. The reaction mixture was diluted with ethyl acetate and water, and then filtered through a glass filter. The filter was washed with ethyl acetate. The combined two-phase filtrate and wash were transferred to a separatory funnel and the organic layer was dried over sodium sulfate and concentrated. The residue was dissolved in methanol, and to convert to the hydrochloride salt, a 4 mol/L solution of hydrogen chloride in dioxane (0.1 mL) was added. The solvent was concentrated to provide the title compound (102 mg) with the following physical data.

1H NMR (DMSO-d$_6$): δ 10.82 (broad s, 1H), 8.55 (t, J=6.4 Hz, 1H), 7.89 (d, J=6.4 Hz, 2H), 7.67 (s, 1H), 7.56 (d, J=4.4 Hz, 3H), 4.61 (broad s, 2H), 4.50 (broad s, 3H), 4.42 (q, J=7.2 Hz, 2H), 3.49 (d, J=11.6 Hz, 2H), 3.18 (t, J=6.0 Hz, 2H), 3.02 (q, J=10.8 Hz, 2H), 1.83 (d, J=11.6 Hz, 3H), 1.57 (q, J=11.6 Hz, 2H), 1.33 (t, J=7.2 Hz, 3H);

Mass data (ESI, Pos.): m/z 461 (M+H)$^+$.

Pharmacological Activities

The compound of the present invention of the formula (I) possesses an anti-diabetic effect and a neuroprotective effect, for example, such an effect of the compound of the present invention of the formula (I) was confirmed by following tests.

All the procedures were conducted by conventionally used method on the basis of basic biological methods. Furthermore, the measuring method of the present invention was modified to improve the accuracy and/or sensitivity of measurement for evaluating the compound of the present invention. The detailed experimental method was as follows.

Experimental Method (1) Assay of an Anti-Diabetic Effect of the Compounds in DIO (Diet-Induced Obese) Mice The anti-diabetic effect of the compounds of the present invention was proved by the following methods.

Male, 12-weeks old high fat-fed obese mice (C57BL/6-DIO, Charles River Japan) were orally administered with the compounds of the present invention twice a day for 15 days. During the experiment, mice were provided high fat pellet diet (D12492, Research Diets) and tap water from bottle of feed water ad libitum. On the first day of the experiment, blood samples were collected from tail vein using a microcapillary to measure plasma glucose concentration. Based on plasma glucose concentration, mice were divided into some groups (five mice per group) and started dosing. The dosing was carried out by oral gavage, after suspending the compounds of the present invention in the previously described vehicle. The control group received only the vehicle. After 15 days from starting the dosing, plasma samples were collected from tail vein at overnight fasting state. Plasma glucose and insulin levels were measured with commercial kits (glucose, Glucose CII-Test Wako®, Wako Pure Chemical Industries, Ltd.; insulin, Rat Insulin ELISA Kit, Morinaga Institute of Biological Science Inc.).

For example, in the assay described above, the compound of Example 115 significantly decreased fasted plasma glucose and insulin levels dose-dependently without any effects on body weight and food intake, at a dose of 30 or 100 mg/kg b.i.d.

As a result, the compounds of the present invention showed the anti-diabetic effect in the assays.

(2) Assay of a Neuroprotective Effect of the Compound in the Rat Transient Focal Cerebral Ischemia Model.

Transient focal cerebral ischemia (120 min) was induced by intraluminal middle cerebral artery (hereinafter abbreviated to MCA) occlusion using the method of Koizumi et al., (in Japanese Journal of Stroke 1986; 8:1-8). Male Sprague Dawley rats (7 weeks old; Charles River Japan) were used.

Under conditions of 30% oxygen and 70% air, the animals inhaled 2.5% halothane (Takeda Chemical Industries, Ltd.) through a halothane vaporizer (Shinano Works). Under the anesthesia, the left common carotid artery (hereinafter abbreviated to CCA), the external carotid artery (hereinafter abbreviated to ECA) and the internal carotid artery (hereinafter abbreviated to ICA) were isolated from surrounding connective tissue, then the CCA and the ECA were ligated with surgical thread. Silicon-coated [mixture of XANTOPREN VL plus, (Heraeus Dental Material, Co., LTD) and OPTO-SIL-XANTOPREN ACTIVATOR (Heraeus Dental Material, Co., LTD)] nylon suture (approx. 25 mm length, 4-0, Niccho Industries, Co., Ltd.) was inserted via the CCA into the ICA, then clamped with Sugita aneurysm clip (Mizuho Co., LTD) to occluded the left MCA. Two hours after MCA occlusion, a nylon suture was removed for reperfusion under anesthesia. Immediately before MCA reperfusion neurological score of animals were observed using the method of Yonemori et al., (in J Cereb Blood Flow Metab 1996; 16: 973-80.) and animals that scored less than 5 were excluded due to insufficient occlusion. Neurological score were observed based on cumulative scores of rotation posture in the tail suspension test (0: normal; 1: mild; 2: moderate; 3: severe) and decrease in traction of the right lower limb (0: normal; 1: mild; 2: moderate; 3: severe). The compounds of the present invention or vehicle (0.5% Methyl Cellulose) were administered orally 1 hour before MCA occlusion and 12 hours after MCA occlusion at a dose of 100 mg/kg. The compounds of the present invention were suspended with 0.5% Methyl Cellulose.

(2-1) An Evaluation Method of the Cerebral Infarct Volume

At 24 hours after MCA occlusion, neurological score were evaluated. Then the brain was removed and sliced into 2 mm-thick sections from the interaural line, using a handy brain-slicer (BrainScience idea. Co., LTD.), in order to prepare 6 cross-sectional slices. The slices were stained with 2% 2,3,5-triphenyltetrazolium chloride solution for 20 to 30 minutes, fixed with formalin, and then stored until image analysis was performed. The images of samples were scanned using an image analyzer (MCID, Imaging Research). The cerebral infarct area was identified in scanned images and measured using image analysis software (Photoshop 5.5/NIH image 1.63) to determine the infarct area per slice. The cerebral infarct volume was then estimated using the following formula:

The cerebral infarct volume (mm$^3$)=(Total cerebral infarct area in six 2-mm slices)×2

The cerebral infarct volume was estimated separately for the cortex and subcortex regions. The total volume in both regions was considered to be the total cerebral infarct volume (hemisphere).

For example, the compound of Example 115 showed significant preventive effect against the neurological score and the cerebral infarct volume at 24 hours after MCA occlusion in this model.

As a result, the compounds of the present invention showed a neuroprotective effect in the assays.

(3) Evaluation of Hepatic Damage by the Compounds in Rats

The compounds of the present invention were administered orally to male Crl: CD(SD) rats with four animals per group once daily for 4 days at dose levels of 0 (control) and 100 mg/kg to investigate hepatotoxicity. The compounds of the present invention were dissolved in 70% Wellsolve (solubilizer, Celeste Corporation) containing 30% DMSO (dimethyl sulfoxide) and administered orally at a dose volume of 10 mL/kg. The control group was treated with the vehicle at the same dosing volume.

Blood was drawn from the abdominal vein of each animal at the day after the final dosing. The plasma was separated by centrifugation at 13,684×g for 5 min at 4° C. The plasma concentration of aspartate aminotransferase (AST) and alanine aminotransferase (ALT), biochemical markers of hepatic damage, were measured.

For example, in the assay, the compound of Example 115 and Example 118 were not increased in the plasm AST and ALT levels, respectively.

As a result, the compounds of the present invention showed to avoid undesirable side effects such as hepatotoxicity in the assays.

Therefore, the results indicated that these compounds of the present invention possess an anti-diabetic effect and a neuroprotective effect, but not undesirable side effects such as hepatotoxicity.

Formulation Example 1

The following components were admixed in conventional method and punched out to obtain 10,000 tablets each containing 10 mg of active ingredient.

4-chloro-3-methoxy-N-({1-[(3-phenyl-5-isoxazolyl)methyl]-4-piperidinyl}methyl)benzamide . . . 100 g
Carboxymethylcellulose calcium (disintegrating agent) . . . 20 g
Magnesium stearate (lubricating agent) . . . 10 g
Microcrystalline cellulose . . . 870 g Formulation Example 2

The following components were admixed in conventional method. The solution was sterilized in conventional manner, filtered through dust removal equipment, placed 5 ml portions into ampoules and sterilized by autoclave to obtain 10,000 ampoules each containing 20 mg of the active ingredient.

4-chloro-3-methoxy-N-({1-[(3-phenyl-5-isoxazolyl)methyl]-4-piperidinyl}methyl)benzamide . . . 200 g
mannitol . . . 20 g
distilled water . . . 50 L

INDUSTRIAL APPLICABILITY

Since the compound represented by the formula (I), a salt thereof, a N-oxide thereof, a solvate thereof, or a prodrug thereof, has an anti-diabetic effect and a neuroprotective effect, and are furthermore safe, it is useful in a preventive and/or therapeutic agent for, for example, a metabolic disease such as diabetes, cerebrovascular disease such as stroke, etc.

The invention claimed is:
1. A compound of the formula (I-1-5):

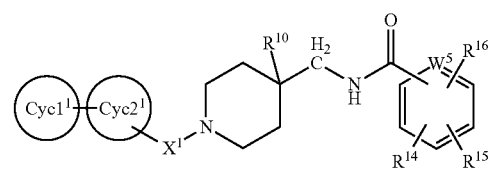

(I-1-5)

wherein Cyc1$^1$ is pyrrolidinyl, phenyl, N-morpholinyl or pyridyl which may have an oxo, alkyl or halogen;
Cyc2$^1$ is thiazolyl, isoxazolyl, thienyl or oxadiazolyl which may have an alkyl which may have an amino, mono- or di-(C1-6 alkyl)amino or heterocyclic ring;

$X^1$ is —CH$_2$—, —CO— or —SO$_2$—;
$R^{10}$ is hydrogen, C1-4 alkyl, hydroxy, phenyl or cyano;
$W^5$ is CH or N;
$R^{14}$ is cyano or amino;
$R^{15}$ is halogen, cyano or amino; and
$R^{16}$ is halogen, hydroxy, C1-4 alkoxy which may have a halogen, alkyl, hydroxy or carbocyclic ring, C1-4 alkyl which may have an oxo, amino or alkoxy, cyano or amino, a salt thereof, an N-oxide thereof or a solvate thereof.

2. The compound according to claim 1, wherein

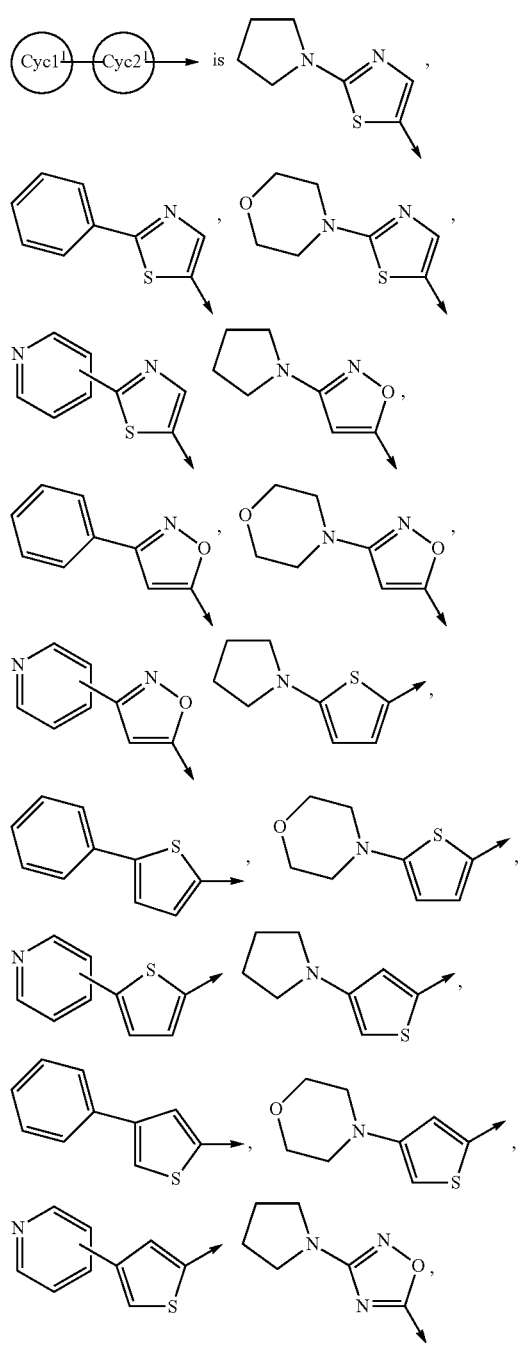

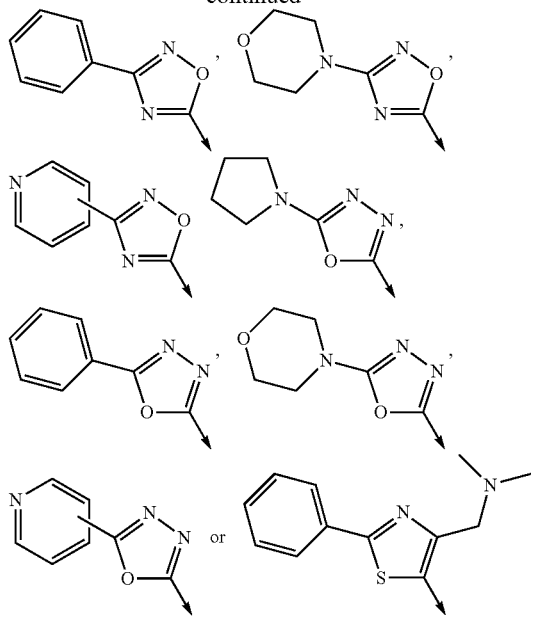

wherein the arrow represents a bonding position to $X^1$.

3. The compound according to claim 1, wherein

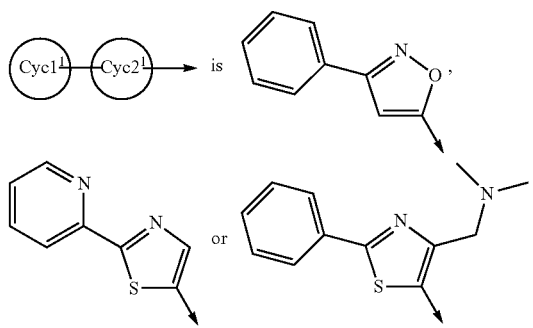

wherein the arrow represents a bonding position to $X^1$;

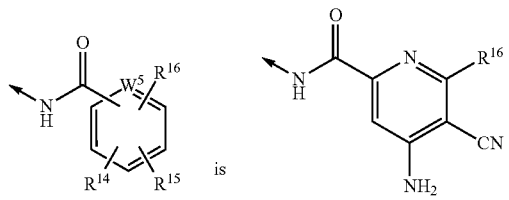

wherein the arrow represents a bonding position to methylene carbon;

$X^1$ is —CH$_2$—;
$R^{10}$ is hydrogen; and
$R^{16}$ is chlorine, hydroxy, methoxy or ethoxy which may have halogen, alkyl, hydroxy or carbocyclic ring, methyl or ethyl which may have a oxo, amino or alkoxy, cyano or amino; and the other symbols have the same meanings as described in claim 1.

4. The compound according to claim 1, which is selected from the group consisting of
   (1) 4-amino-5-chloro-6-ethoxy-N-({1-[(3-phenyl-5-isoxazolyl)methyl]-4-piperidinyl}methyl)-2-pyridinecarboxamide,
   (2) 4-amino-5-cyano-6-ethoxy-N-({1-[(3-phenyl-5-isoxazolyl)methyl]-4-piperidinyl}methyl)-2-pyridinecarboxamide,
   (3) 4-amino-5-cyano-6-ethoxy-N-((1-(2-(pyridin-2-yl)thiazol-5-yl)methyl)piperidin-4-yl)methyl)picolinamide, and
   (4) 4-Amino-5-cyano-N-((1-(4-(((dimethylamino)methyl)-2-phenylthiazol-5-yl)methyl)piperidin-4-yl)methyl)-6-ethoxypicolinamide.

5. A pharmaceutical composition which comprises the compound of the formula (I-1-5) according to claim 1, a salt thereof, an N-oxide thereof or a solvate thereof.

6. A method for treating insulin-resistant diabetes mellitus, which comprises administering to a mammal in need of treatment an effective amount of the compound of claim 1.

\* \* \* \* \*